(12) United States Patent
Van Der Werf et al.

(10) Patent No.: US 7,736,850 B2
(45) Date of Patent: Jun. 15, 2010

(54) STRAIN OF SARS-ASSOCIATED CORONAVIRUS AND APPLICATIONS THEREOF

(75) Inventors: Sylvie Van Der Werf, Gif-sur-Yvette (FR); Nicolas Escriou, Paris (FR); Bernadette Crescenzo-Chaigne, Neuilly-sur-Seine (FR); Jean-Claude Manuguerra, Paris (FR); Frederick Kunst, Paris (FR); Benoît Callendret, Nanterre (FR); Jean-Michel Betton, Paris (FR); Valérie Lorin, Montrouge (FR); Sylvie Gerbaud, Saint-Maur-des-Fosses (FR); Ana Maria Burguiere, Clamart (FR); Saliha Azebi, Vitry-sur-Seine (FR); Pierre Charneau, Paris (FR); Frédéric Tangy, Les Lilas (FR); Chantal Combredet, Paris (FR); Jean-François Delagneau, La Celle Saint Cloud (FR); Monique Martin, Chatenay Malabry (FR)

(73) Assignees: Institute Pasteur, Paris (FR); Centre National de la Recherche Scientifique, Paris (FR); Universite Paris 7, Paris (FR)

( * ) Notice: Subject to any disclaimer, the term of this patent is extended or adjusted under 35 U.S.C. 154(b) by 798 days.

(21) Appl. No.: 10/581,356

(22) PCT Filed: Dec. 2, 2004

(86) PCT No.: PCT/FR2004/003106

§ 371 (c)(1),
(2), (4) Date: Feb. 8, 2007

(87) PCT Pub. No.: WO2005/056584

PCT Pub. Date: Jun. 23, 2005

(65) Prior Publication Data
US 2007/0128224 A1 Jun. 7, 2007

(30) Foreign Application Priority Data
Dec. 2, 2003 (FR) .................................. 03 14151
Dec. 2, 2003 (FR) .................................. 03 14152

(51) Int. Cl.
*C12Q 1/68* (2006.01)

(52) U.S. Cl. .................. 435/6; 435/91.1; 435/91.2; 536/23.1; 536/24.33

(58) Field of Classification Search .............. None
See application file for complete search history.

(56) References Cited

OTHER PUBLICATIONS

Database EMBL, XP002294758, Database accession No. AY278489, "EMBL Sequence Version Archive", pp. 1-7, (Apr. 22, 2003).
Database EMBL, XP002294760, Database accession No. AY290752, "EMBL Sequence Version Archive", pp. 1-2, (Jun. 10, 2003).
Database UNIPROT, XP002294761, Database accession No. P59595, pp. 1-4, "Human Coronavirus", (Oct. 10, 2003).
Marra, et al., "The Genome Sequence of the SARS-Associated Coronavirus", Science, American Association for the Advancement of Science, vol. 300, No. 5624, pp. 1399-1404, (May 30, 2003).
Che, et al., "Rapid and Efficient Preparation of Monoclonal Antibodies Against SARS-Associated Coronavirus Nucleocapsid Protein by Immunizing Mice", Di Yi Junyi Daxue Xuebao—Academic Journal of First Medical College of PLA, Gain Kan Bianjishi, Guangzhou, CN, vol. 23, No. 7, pp. 640-642, (Jul. 2003).
Wang, et al., "Assessment of Immunoreactive Synthetic Peptides from the Structural Proteins of Severe Acute Respiratory Syndrome Coronavirus", Clinical Chemistry, American Association for Clinical Chemistry, Winston, US, vol. 49, No. 12, pp. 1989-1996, (Nov. 13, 2003).
Shi, et al., "Diagnosis of Severe Acute Respiratory Syndrome (SARS) by Detection of SARS Coronavirus Nucleocapsid Antibodies in an Antigen-Capturing Enzyme-Linked Immunosorbent Assay", Journal of Clinical Microbiology, Washington, DC, US, vol. 41, No. 12, pp. 5781-5782, (Dec. 2003).
Liu, et al., "The C-Terminal Portion of the Nucleocapsid Protein Demonstrates SARS-CoV Antigenicity", Genomics, Proteomics and Bioinformatics, vol. 1, No. 3, pp. 193-197, (Aug. 2003).
Poon, et al., "Rapid Diagnosis of a Coronavirus Associated with Severe Acute Respiratory Syndrome (SARS)", Clinical Chemistry, American Association for Clinical Chemistry, Winston, US, vol. 49, No. 6, Pt. 1, pp. 953-955, (Jun. 2003).

*Primary Examiner*—Heather G Calamita
(74) *Attorney, Agent, or Firm*—Finnegan, Henderson, Farabow, Garrett & Dunner, L.L.P.

(57) ABSTRACT

The invention relates to a novel strain of severe acute respiratory syndrome (SARS)-associated coronavirus, resulting from a sample collected in Hanoi (Vietnam), reference number 031589, nucleic acid molecules originating from the genome of same, proteins and peptides coded by said nucleic acid molecules and, more specifically, protein N and the applications thereof, for example, as diagnostic reagents and/or as a vaccine.

5 Claims, 116 Drawing Sheets

A.

SRAS-CoV   M   10⁻¹   M   10⁻¹

```
                              — 220
                              — 130
                              — 90
                              — 70
55 kDa ⟶                      — 60
35 kDa ⟶                      — 40

— 30
                              — 20
         I.S.      p.i.
         anti-N
```

B.

SRAS-CoV   M   10⁻¹   M   10⁻¹

```
         220 —
         130 —                ⟵ 200 kDa
         90 —
         70 —
         60 —
         40 —

30 —
         20 —
              I.S.      p.i.
              anti-S
```

FIGURE 8

A
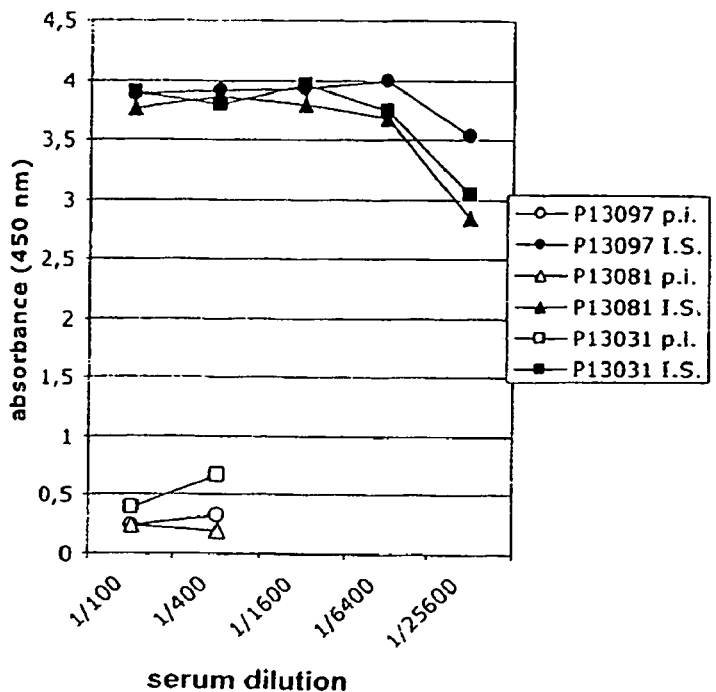
B
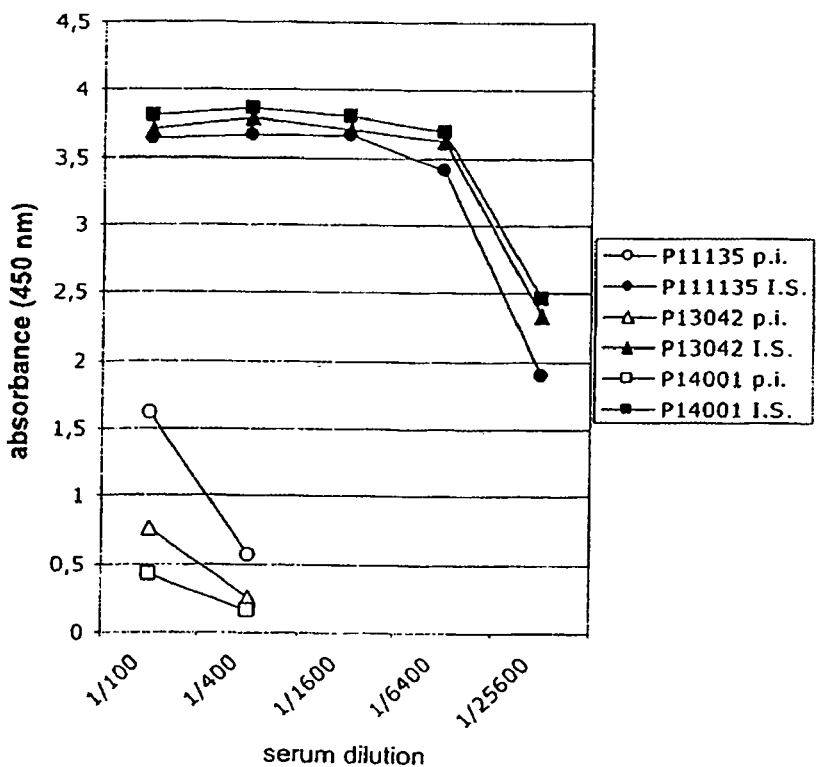
FIGURE 9

```
                                                      >< XhoII
                     >< ScrFI                         >< Sau3AI
                     >< MvaI        > < TthHB8I       >< NdeII
                   >< EcoRII        > < TaqI          >< MflI
                     >< Ecl136I       >< Sau3AI       >< MboI
                  >< DsaV             >< NdeII        >< DpnII
                     >< BstOI         >< MboI >< MnlI >< DpnI
                     >< BstNI         >< DpnII        >< BstYI
                     >< BsiLI           >< DpnI       >< BspAI
                  >< BsaJI             >< BspAI         >< Bsp143I
                     >< ApyI             >< Bsp143I >< BglII
ATATTAGGTT TTTACCTACC CAGGAAAAGC CAACCAACCT CGATCTCTTG TAGATCTGTT CTCTAAACGA
    10         20         30         40         50         60         70

>< VneI
                                  >< SphI
                                     >< SnoI
                                  >< RmaI
                                  >< PaeI    >< SduI
                                  >< NspI    >< NspII
                                  >< NspHI   >< HgiAI
                                  >< NlaIII  >< Bsp1286I
                                     >< MaeI >< BmyI
>< Tru9I                                  >< ApaLI
>< MseI          >< BbvI                  >< Alw44I
>< DraI          >< AluI    > < Fnu4HI    >< Alw21I
ACTTTAAAAT CTGTGTAGCT GTCGCTCGGC TGCATGCCTA GTGCACCTAC GCAGTATAAA CAATAATAAA
    80         90        100        110        120        130        140

>< SfcI
                                             >< PstI
                                             >< MnlI
                                             >< Ksp632I
           >< HindII        > < MboII        >< EarI
           >< HincII      >< MaeIII          >< Eam1104I
TTTTACTGTC GTTGACAAGA AACGAGTAAC TCGTCCCTCT TCTGCAGACT GCTTACGGTT TCGTCCGTGT
   150        160        170        180        190        200        210

>< TthHB8I      >< StyI
>< TaqI         >< RmaI       >< ScrFI
>< Sau3AI       >< MaeI       >< NciI
>< NdeII        >< EcoT14I
>< MboI         >< Eco130I
>< DpnII        >< BssT1I     >< HpaII       >< MaeIII
  >< DpnI       >< BsaJI      >< HapII
>< BspAI        >< BlnI       >< DsaV
  >< Bsp143I    >< AvrII      >< BcnI
TGCAGTCGAT CATCAGCATA CCTAGGTTTC GTCCGGGTGT GACCGAAAGG TAAGATGGAG AGCCTTGTTC
   220        230        240        250        260        270        280

>< RmaI
                                                   >< Esp3I  >< MaeII
           >< HindII    >< MaeII > < Eco57I        >< BsmAI          >< MaeI
           >< HincII    > < AflIII > < DdeI        >< Alw26I         >< BsmBI
TTGGTGTCAA CGAGAAAACA CACGTCCAAC TCAGTTTGCC TGTCCTTCAG GTTAGAGACG TGCTAGTGCG
   290        300        310        320        330        340        350
```

FIGURE 13.1

```
                                    >< Sau96I
                                         >< PssI
                                      >< PalI
                                    >< NspIV
                                      >< MnlI
                                      >< HaeIII
                                    >< EcoO109I
                                    >< DraII>< MboII    >< PmlI
                  >< MnlI         >< Cfr13I             >< PmaCI
                  >< Ksp632I      >< BsuRI           >  < MaeII
             >< HinfI          >< BsiZI>< EcoNI    >< Eco72I
                  >< EarI         >< BshI    >< BslI >< BsaAI
     >< PleI    >< Eam1104I>< AsuI    >< BsiYI>< BbrPI            >< MnlI
  TGGCTTCGGG GACTCTGTGG AAGAGGCCCT ATCGGAGGCA CGTGAACACC TCAAAAATGG CACTTGTGGT
         360        370        380        390        400        410        420

>< Tru9I
                       >< RsaI                                >< SfaNI
  >< RmaI              >< Csp6I          >< BspWI             >< MseI
  >< MaeI >< AluI      >< AfaI    >< AluI                     >  < MaeII
  CTAGTAGAGC TGGAAAAAGG CGTACTGCCC CAGCTTGAAC AGCCCTATGT GTTCATTAAA CGTTCTGATG
         430        440        450        460        470        480        490

>< PalI
                 >< HaeIII                                    >< RsaI
  >< Tru9I       >< GdiII                                   McrI ><
  >< MseI        >< EaeI                                      >< Csp6I
  >< Esp4I       >< BsuRI                             >< BsmI BsiEI ><
  >< AflII       >< BshI        >< AluI               >< BscCI     >< AfaI
  CCTTAAGCAC CAATCACGGC CACAAGGTCG TTGAGCTGGT TGCAGAAATG GACGGCATTC AGTACGGTCG
         500        510        520        530        540        550        560

>< NspI
                       >< ScaI     >< NspHI
                       >< RsaI     >< NlaIII
                    >  < Csp6I     >< BslI                    >< MboII
                       >< BsrI     >< BsiYI                   >< MboII
  >< AciI              >< AfaI     >< AflIII    >< MunI       >< AciI
  TAGCGGTATA ACACTGGGAG TACTCGTGCC ACATGTGGGC GAAACCCCAA TTGCATACCG CAATGTTCTT
         570        580        590        600        610        620        630

>< TthHB8I
                                                              >< TaqI
                                                              >< Sau3AI
                                                              >< NdeII
                                                              >< MboI
                                                              >< DpnII
                                                            >  < DpnI
                                                              >< ClaI
                                                              >< Bsu15I
                                                              >< BspDI
                                 >< NlaIV                     >< BspAI
                                 >< MspI                    >  < Bsp143I
                                 >< HpaII                     >< Bsp106I
                                 >< HapII                     >< BsiXI           MaeIII >
                                 >< Cfr10I                    >< BscI>< SfaNI    DdeI ><
                                 >< BscBI     >< AluI         >< BanIII          BfrI ><
  CTTCGTAAGA ACGGTAATAA GGGAGCCGGT GGTCATAGCT ATGGCATCGA TCTAAAGTCT TATGACTTAG
         640        650        660        670        680        690        700
```

FIGURE 13.2

```
                           >< Sau3AI
                           >< NdeII
                           >< MboI
                  >< HphI                                                  VneI ><
                      >< DpnII                                             SnoI ><
                      >< BspAI                                          > < NlaIII
               >< AlwI>< DpnI                              >< DdeI      ApaLI ><
         >< AluI       >< Bsp143I       >< MboII  >< BsrI        Alw44I ><
         GTGACGAGCT TGGCACTGAT CCCATTGAAG ATTATGAACA AAACTGGAAC ACTAAGCATG GCAGTGGTGC
            710        720        730        740        750        760        770

>< SstI
                                   >< SduI
                                   >< SacI
                                   >< NspII
                                   >< MnlI                                 Sau96I ><
                                   >< HgiAI               >< TthHB8I       PalI ><
         >< SduI                   >< Eco24I              >< TaqI          NspIV ><
         >< NspII                  >< Ecl136II           > < SalI          HaeIII ><
         >< HgiAI                  >< Bsp1286I           > < RtrI          Cfr13I ><
            >< DraIII              >< BmyI                  >< HindII      BsuRI ><
         >< Bsp1286I               >< BanII                 >< HincII      BsiZI ><
         >< BmyI                   >< Alw21I                   >< BsgI     BshI ><
         >< Alw21I        >< AluI          >< MaeIII        >< AccI        AsuI ><
         ACTCCGTGAA CTCACTCGTG AGCTCAATGG AGGTGCAGTC ACTCGCTATG TCGACAACAA TTTCTGTGGC
            780        790        800        810        820        830        840

>< ThaI
                                           >< ThaI
                                             >< MvnI
                                           >< MvnI
                                           >< HinPlI
            > < RsaI                         >< Hin6I            > < VneI
            > < NlaIV                        >< HhaI             > < SnoI
               >< KpnI                       >< CfoI                >< SduI
         >< Eco64I                           >< BstUI        NspII ><
         >< Csp6I                          >< BstUI          HgiAI ><
            > < BscBI                        >< Bsp50I       Bsp1286I ><
         >< BanI                           >< Bsp50I              >< BmyI
         >< Asp718                           >< AciI           > < ApaLI
            > < AfaI                         >< AccII          > < Alw44I
         >< AccBlI                        >< AccII          Alw21I ><
         >< Acc65I        >< MnlI   >< SfaNI    >< AccII
         CCAGATGGGT ACCCTCTTGA TTGCATCAAA GATTTTCTCG CACGCGCGGG CAAGTCAATG TGCACTCTTT
            850        860        870        880        890        900        910

>< TthHB8I
                        >< TthHB8I
                              >< TaqI
                           >< TaqI
                              >< MnlI
                           >< Ksp632I                                NlaIII ><
                           >< HinfI>< PleI                           >< NlaIII
                           >< Eam1104I       >< MboII  >< MaeIII       EcoRII ><
                           >< EarI   > < BbvI>< AccI >< Fnu4HI         DsaV ><
         CCGAACAACT TGATTACATC GAGTCGAAGA GAGGTGTCTA CTGCTGCCGT GACCATGAGC ATGAAATTGC
            920        930        940        950        960        970        980

>< TthHB8I
                                                               >< TaqI
                                                               >< SfuI
                                                               >< NspV>< Tru9I
         >< ScrFI       >< HinPlI                               >< LspI>< MseI
```

FIGURE 13.3

```
>< MvaI         >< Hin6I                    >< SduI          >< Csp45I
>< Ecl136I      >< HhaI                     >< NspII         >< BstBI
>< BstOI        >< HaeII                    >< HgiAI         >< Bsp119I
>< BstNI        >< Eco47III                 >< Bsp1286I      >< BsiCI
>< BsiLI        >< CfoI                     >< BmyI          >< Bpu14I
>< ApyI  >< DdeI >< Bsp143II  >< AluI       >< Alw21I        >< AsuII
CTGGTTCACT GAGCGCTCTG ATAAGAGCTA CGAGCACCAG ACACCCTTCG AAATTAAGAG TGCCAAGAAA
    990        1000        1010       1020       1030       1040       1050

>< Tru9I
                         >< BsmI                      >< MseI
                       >< BscCI                        > < MnlI
TTTGACACTT TCAAAGGGGA ATGCCCAAAG TTTGTGTTTC CTCTTAACTC AAAAGTCAAA GTCATTCAAC
   1060        1070       1080       1090       1100       1110       1120

>< PmlI
>< PmaCI
>< MaeII
>< Eco72I
>< BsaAI                             >< NlaIII              >< RsaI
>< BbrPI                                  >< Bst1107I >< Csp6I
>< AflIII      >< MnlI>< DdeI             >< AccI        >< AfaI
CACGTGTTGA AAAGAAAAAG ACTGAGGGTT TCATGGGGCG TATACGCTCT GTGTACCCTG TTGCATCTCC
   1130        1140       1150       1160       1170       1180       1190

>< SfaNI
    >< MaeIII             >< AccI                                 NlaIII ><
ACAGGAGTGT AACAATATGC ACTTGTCTAC CTTGATGAAA TGTAATCATT GCGATGAAGT TTCATGGCAG
   1200        1210       1220       1230       1240       1250.      1260

>< SinI
                                                                   >< Sau96I
                                                             PssI ><
                                                                  >< Psp5II
                                                                   >< PpuMI
                                                                   >< NspIV
                                                                    >< NspHII
                                                                   >< Eco47I
                                                                   >< DraII
                                                                   >< Cfr13I
                                                                   >< BsiZI
                                                                   >< Bme18I
                                                                   >< AvaII
                                                                   >< AsuI
>< MaeII                                                 EcoO109I ><AflIII >
ACGTGCGACT TTCTGAAAGC CACTTGTGAA CATTGTGGCA CTGAAAATTT AGTTATTGAA GGACCTACTA
   1270        1280       1290       1300       1310       1320       1330

Van91I ><
                                                                 SinI ><
        >< RsaI                                                Sau96I ><
>< NspI                                                        PflMI ><
    >< NlaIV                                                   NspIV ><
>< NlaIII                                                      NspHII >
>< NspHI>< KpnI                                                Eco47I ><
    >< Eco64I                                                  Cfr13I ><
      >< Csp6I                                                   BslI ><
      >< BscBI                                                  BsiZI ><
    >< BanI                                                     BsiYI ><
    >< Asp718                                                  Bme18I ><
      >< AfaI                                                   AvaII ><
    >< AccBlI                                                    AsuI ><
```

FIGURE 13.4

```
              >< Acc65I              >< SfcI              >< NlaIII           AccB7I ><
    CATGTGGGTA CCTACCTACT AATGCTGTAG TGAAAATGCC ATGTCCTGCC TGTCAAGACC CAGAGATTGG
        1340       1350       1360       1370       1380       1390       1400

>< TthHB8I
                                                              >< TaqI>< MnlI
                                                                 >< HinfI
    >< DdeI                                           >< PleI      >< AciI
    ACCTGAGCAT AGTGTTGCAG ATTATCACAA CCACTCAAAC ATTGAAACTC GACTCCGCAA GGGAGGTAGG
        1410       1420       1430       1440       1450       1460       1470

>< RmaI                                                      NlaIV ><
       >< MnlI                                                         >< BsrI
    >< MaeI              >< BbvI       >< Fnu4HI              BscBI ><
    ACTAGATGTT TTGGAGGCTG TGTGTTTGCC TATGTTGGCT GCTATAATAA GCGTGCCTAC TGGGTTCCTC
        1480       1490       1500       1510       1520       1530       1540

XhoII ><
                                                                       Sau3AI ><
                                                                       NdeII ><
                                                                       MflI ><
                                            >< MaeIII                  MboI ><
                        >< PalI                 >< Eco31I              DpnII ><
                        >< HaeIII              >< BsrI          >< MnlI DpnI >
    >< RmaI             >< BsuRI   >< BsrI     >< BsmAI            BstYI ><
       >< MnlI         > < DdeI   >< BspWI     >< BsaI>< HphI     BspAI ><
    >< MaeI              >< BshI>< BglI         >< Alw26I          Bspl43I >
    GTGCTAGTGC TGATATTGGC TCAGGCCATA CTGGCATTAC TGGTGACAAT GTGGAGACCT TGAATGAGGA
        1550       1560       1570       1580       1590       1600       1610

> < Tru9I
                                 > < MseI
                              >< MaeII     >< Tru9I
                                     >< HpaI                      > < MnlI
                                     >< HindII                    > < Ksp632I
                            >< HinfI >< PleI >< HincII            > < EarI
    >< AlwI   >< DdeI         >< AflIII     >< MseI               > < Eam1104I
    TCTCCTTGAG ATACTGAGTC GTGAACGTGT TAACATTAAC ATTGTTGGCG ATTTTCATTT GAATGAAGAG
        1620       1630       1640       1650       1660       1670       1680

>< MboII                                                        PleI ><
         >< BstXI     >< SfaNI                                    > < HinfI
    GTTGCCATCA TTTTGGCATC TTTCTCTGCT TCTACAAGTG CCTTTATTGA CACTATAAAG AGTCTTGATT
        1690       1700       1710       1720       1730       1740       1750

>< StyI
                                                         >< MaeIII
                                                         >< EcoT14I
                                 >< PleI                 >< Eco130I
                                 >< MaeIII              >< BssT1I      BslI ><
                             >< HinfI>< AciI            >< BsaJI      BsiYI ><
    ACAAGTCTTT CAAAACCATT GTTGAGTCCT GCGGTAACTA TAAAGTTACC AAGGGAAAGC CCGTAAAAGG
        1760       1770       1780       1790       1800       1810       1820

>< Sau3AI            >< Van91I
                     >< NdeII             >< PflMI
                     >< MboI              >< DraIII
                     >< DpnII             >< BslI
                       >< DpnI >< Tru9I   >< BsiYI
                     >< BspAI  >< MseI         >< BbvI           >< MnlI
                     >< Bspl43I            >< AccB7I      Fnu4HI ><
```

FIGURE 13.5

```
TGCTTGGAAC ATTGGACAAC AGAGATCAGT TTTAACACCA CTGTGTGGTT TTCCCTCACA GGCTGCTGGT
   1830       1840       1850       1860       1870       1880       1890
                           >< ThaI
                           >< SfaNI
                           >< MvnI
                           >< HinPlI
                        >< HinPlI
                        >< Hin6I
                        >< Hin6I
                           >< HhaI
   >< Sau3AI          >< HhaI
   >< NdeII           >< CfoI                                        PvuII >
   >< MboI            >< CfoI                                        Psp5I >
   >< DpnII           >< BstUI                                       NspBII >
     >< DpnI       >< BssHII                                         HphI ><
   >< BspAI          >< Bsp50I                                       Fnu4HI ><
     >< Bspl43I      >< AccII       >< Fnu4HI   >< BbvI              AluI >
GTTATCAGAT CAATTTTTGC GCGCACACTT GATGCAGCAA ACCACTCAAT TCCTGATTTG CAAAGAGCAG
   1900       1910       1920       1930       1940       1950       1960
                                                   >< TthHB8I
                                                      >< StyI
                                                      >< NcoI
                                                   >< HindII
                                                   >< HincII
                                                      >< HinlI
                                                         >< EcoT14I
                                                      >< Eco57I
                                                   >< TaqI>< Eco130I
                                                   >< SalI >< DsaI
                                                   >< RtrI >< BssT1I
                                                      >< BsaHI
                                                      >< BbiII>< NlaIII
>< MaeIII                                             >< AcyI  >< HgaI
     >< BbvI                   >< MaeII >< AccI>< BsaJI      HphI ><
CTGTCACCAT ACTTGATGGT ATTTCTGAAC AGTCATTACG TCTTGTCGAC GCCATGGTTT ATACTTCAGA
   1970       1980       1990       2000       2010       2020       2030
                                                      >< RsaI
                        >< NdeI                       > < Csp6I
   >< BspMI             >< MaeIII >< BsrI  >< AfaI       >< DdeI
CCTGCTCACC AACAGTGTCA TTATTATGGC ATATGTAACT GGTGGTCTTG TACAACAGAC TTCTCAGTGG
   2040       2050       2060       2070       2080       2090       2100
                           >< StuI
                           >< PalI
                           >< HaeIII
                           >< Ecol47I
              >< SduI      >< DdeI
              >< NspII     >< BsuRI
              >< Bsp1286I  >< BshI                              DdeI ><
              >< BmyI      >< AatI      > < MnlI                BfrI ><
TTGTCTAATC TTTTGGGCAC TACTGTTGAA AAACTCAGGC CTATCTTTGA ATGGATTGAG GCGAAACTTA
   2110       2120       2130       2140       2150       2160       2170
                           >< TfiI
                           >< HinfI                          Tth111I ><
              >< SfaNI >< BsgI  >< FokI                      AspI ><
GTGCAGGAGT TGAATTTCTC AAGGATGCTT GGGAGATTCT CAAATTTCTC ATTACAGGTG TTTTTGACAT
   2180       2190       2200       2210       2220       2230       2240
```

FIGURE 13.6

```
                                                                 Tru9I ><
                                                                  MseI ><
                                                                  HpaI >
                                                                 HindII >
          >< Eco57I                                              HincII >
CGTCAAGGGT CAAATACAGG TTGCTTCAGA TAACATCAAG GATTGTGTAA AATGCTTCAT TGATGTTGTT
   2250       2260       2270       2280       2290       2300       2310

>< Sau3AI
                       >< NdeII
                       >< MboI
                         > < MaeIII                   >< Sau3AI
                       >< FbaI                        >< NdeII
                       >< DpnII                       >< DpnII
                       >< DpnI                              >< DpnIMboII ><
                       >< BspAI          >< HinPlI              DdeI ><
                       >< Bsp143I        >< Hin6I           >< Bsp143I
          >< TthHB8I   >< BsiQI          >< HhaI           >< MboIBfrI ><
          >< TaqI      >< BclI           >< CfoI          >< BspAI   BbsI ><
AACAAGGCAC TCGAAATGTG CATTGATCAA GTCACTATCG CTGGCGCAAA GTTGCGATCA CTCAACTTAG
   2320       2330       2340       2350       2360       2370       2380

>< PvuII
                                             >< MaeII             >< Psp5I
                                             >< Bst1107I          >< NspBII
                                             >< BsaAI     Fnu4HI ><
                                             >< BbvI     > < Fnu4HI
          >< HphI                 >< DrdI  >< AccI                >< AluI
GTGAAGTCTT CATCGCTCAA AGCAAGGGAC TTTACCGTCA GTGTATACGT GGCAAGGAGC AGCTGCAACT
   2390       2400       2410       2420       2430       2440       2450

>< Tru9I
            >< NlaIV
          >< MseI
            >< MnlI
          >< Esp4I                                               >< ScaI
            >< Eco64I                                            >< RsaI
            >< BscBI                                        >< NlaIIIMnlI ><
>< NlaIII >< BanI                                                MnlI ><
          >< AflII                             >< TfiI           >< Csp6I
>< BbvI   >< AccBlI  >< MaeIII                 >< HinfI  >< HphI >< AfaI
ACTCATGCCT CTTAAGGCAC CAAAAGAAGT AACCTTTCTT GAAGGTGATT CACATGACAC AGTACTTACC
   2460       2470       2480       2490       2500       2510       2520

> < XhoI
                                         >< TthHB8I
                                  >< TthHB8I >< TaqI
                                         > < SlaI
                                         > < PaeR7I
                                         > < NspIII
                                       >< HphI    >< HinlI
                                         > < Eco88I
                                         > < CcrI
                                       >< Esp3I   >< BsaHI
                                         > < BcoI
                                       >< BsmAI   >< BbiII
                                         > < AvaI        >< HgaI
                                       >< TaqI > < Ama87I >< BsmBI
>< DdeI >< MnlI                            >< Alw26I >< AcyI    >< AluI
TCTGAGGAGG TTGTTCTCAA GAACGGTGAA CTCGAAGCAC TCGAGACGCC CGTTGATAGC TTCACAAATG
   2530       2540       2550       2560       2570       2580       2590
```

FIGURE 13.7

```
                                        >< PalI >< NlaIII
                                        >< HaeIII    >< MnlI
                                        >< BsuRI    >< DdeI   >< Tru9I
    >< AluI         >< BsrI             >< BshI      >< BfrI  >< MseI
 GAGCTATCGT TGGCACACCA GTCTGTGTAA ATGGCCTCAT GCTCTTAGAG ATTAAGGACA AAGAACAATA
     2600       2610       2620       2630       2640       2650       2660

>< VneI
                                                                  Tru9I ><
                    >< ScrFI                                    >< SnoI
                    >< MvaI                                     >< SduI
                    >< EcoRII                                   >< NspII
   >< MstI          >< Ecl136I                                    MseI ><
   >< HinP1I        >< DsaV                                     >< HgiAI
   >< Hin6I         >< BstOI                           Bsp1286I ><BslI ><
    >< HhaI         >< BstNI                                      BsiYI ><
   >< FspI          >< BsmAI                                    >< BmyI
   >< FdiII         >< BsiLI                                    >< ApaLI
    >< CfoI         >< ApyI                   >< Tru9I          >< Alw44I
    >< AviII        >< Alw26I    >< BsrI      >< MseI           >< Alw21I
 CTGCGCATTG TCTCCTGGTT TACTGGCTAC AAACAATGTC TTTCGCTTAA AAGGGGGTGC ACCAATTAAA
     2670       2680       2690       2700       2710       2720       2730

>< TfiI
   >< MaeIII                    >< MboII   > < MaeIII  >< HinfI AluI ><
 GGTGTAACCT TTGGAGAAGA TACTGTTTGG GAAGTTCAAG GTTACAAGAA TGTGAGAATC ACATTTGAGC
     2740       2750       2760       2770       2780       2790       2800

>< RsaI
                                                                >< NlaIV
                                                                MaeIII ><
                                                               >< MspI>< KpnI
                                                               >< HpaII
                                                               >< HapII
                                                                > < Eco64I
                                               >< SduI          >< Csp6I
                                               >< NspII         >< TfiI >< BscBI
                                               >< HgiAI          > < BanI
   >< MaeII                                    >< Bsp1286I       > < Asp718
         >< HindII                             >< BmyI          >< HinfI >< AfaI
         >< HincII    >< Tru9I                 >< Alw21I         > < AccBII
   >< AflIII          >< MseI                  >< AccI           > < Acc65I
 TTGATGAACG TGTTGACAAA GTGCTTAATG AAAAGTGCTC TGTCTACACT GTTGAATCCG GTACCGAAGT
     2810       2820       2830       2840       2850       2860       2870

>< Sau3AI
                                                                >< NdeII
                                                                >< MboI
                                                                >< DpnII
                                                                 > < DpnI
         >< NspI
         >< NspHI
         >< NlaIII                                   >< MboII >< BspAI
   >< DdeI      >< MnlI       >< AlwNI      >< BbsI         >< AlwNI  > < Bsp143I
 TACTGAGTTT GCATGTGTTG TAGCAGAGGC TGTTGTGAAG ACTTTACAAC CAGTTTCTGA TCTCCTTACC
     2880       2890       2900       2910       2920       2930       2940

>< Sau3AI
         >< NdeII
         >< MboI
         >< DpnII
          >< DpnI
         >< BspAI
```

FIGURE 13.8

```
           >< NlaIII>< Bsp143I            >< AluI     >< SfaNI
         AACATGGGTA TTGATCTTGA TGAGTGGAGT GTAGCTACAT TCTACTTATT TGATGATGCT GGTGAAGAAA
           2950       2960       2970       2980       2990       3000       3010

>< SfaNI
                                                         >< MnlI
         >< MboII     >< GsuI                            >< Ksp632I               >< MnlI
                 >< BsaAI                                >< EarI             > < MboII
         >< HphI >< MaeII>< BpmI          >< MnlI        >< Eam1104I      >< MboII
         ACTTTTCATC ACGTATGTAT TGTTCCTTTT ACCCTCCAGA TGAGGAAGAA GAGGACGATG CAGAGTGTGA
           3020       3030       3040       3050       3060       3070       3080

> < RsaI
                                                  >< RsaI
                                                  >< NlaIII
                                                  >< MnlI                 >< FokI
                                                     >< Csp6I               Eco31I ><
                                           >< Csp6I               >< MamI BsmAI ><
                             >< MboII             > < AfaI        >< BsiBI BsaI ><
                             >< MboII             >< AfaI         >< BsaBIAlw26I ><
         GGAAGAAGAA ATTGATGAAA CCTGTGAACA TGAGTACGGT ACAGAGGATG ATTATCAAGG TCTCCCTCTG
           3090       3100       3110       3120       3130       3140       3150

>< NlaIV>< PvuII>< XmnI
           >< Eco64I >< Psp5I    >< TthHB8I
         >< MnlI >< DdeI       >< TaqI      >< MnlI                   >< MboII
              >< BscBI>< NspBI  >< MnlI     >< Ksp632I        >< MboII    >< MboII
         >< BanI       >< MnlI             >< EarI                      >< BsrI
         >< AccBlI >< AluI >< Asp700I      >< Eam1104I >< MboII>< BbsI
         GAATTTGGTG CCTCAGCTGA AACAGTTCGA GTTGAGGAAG AAGAAGAGGA AGACTGGCTG GATGATACTA
           3160       3170       3180       3190       3200       3210       3220

>< Tru9I
         >< FokI                                                     >< MseI   >< Eco57I
         >< DdeI                                              >< BsrI>< MboII BsrI ><
         CTGAGCAATC AGAGATTGAG CCAGAACCAG AACCTACACC TGAAGAACCA GTTAATCAGT TTACTGGTTA
           3230       3240       3250       3260       3270       3280       3290

>< Tru9I                              >< MnlI
         >< MseI              >< Tru9I       >< HindII>< Tru9I       >< DraIII
         >< DraI              >< MseI        >< HincII>< MseI        >< BspWI
         TTTAAAACTT ACTGACAATG TTGCCATTAA ATGTGTTGAC ATCGTTAAGG AGGCACAAAG TGCTAATCCT
           3300       3310       3320       3330       3340       3350       3360

>< VneI
                                                                       >< SnoI
                                                                       > < SduI
                                                                       > < NspII
                                                                       > < HgiAI
                                                                       > < Bsp1286I
                                                                       > < BmyI
                                                                       >< ApaLI
                              >< HphI                 > < NlaIII      >< Alw44I
         >< BbvI         >< Fnu4HI                    >< BspMI        > < Alw21I
         ATGGTGATTG TAAATGCTGC TAACATACAC CTGAAACATG GTGGTGGTGT AGCAGGTGCA CTCAACAAGG
           3370       3380       3390       3400       3410       3420       3430

>< Sau96I
                                                                       >< PalI
                                                                       >< NspIV
                                                                       >< HaeIII
                      >< NlaIV                                         >< Cfr13I
```

FIGURE 13.9

```
                    >< Eco64I                                      >< BsuRI
                      >< BscBI              > < Tru9I       >< BsiZI
                    >< BanI                 > < MseI        >< BshI         >< MnlI
                    >< AccBlI >< NlaIII             >< AluI >< AsuI >< MnlI
           CAACCAATGG TGCCATGCAA AAGGAGAGTG ATGATTACAT TAAGCTAAAT GGCCCTCTTA CAGTAGGAGG
               3440       3450       3460       3470       3480       3490       3500

>< SinI
                                                                  >< Sau96I
                                                                  >< NspIV
                                                        >< NspHI >< NspHII
                                                                  >< Eco47I
                                                                  >< Cfr13I
                                                       >< NlaIII      >< BspMI
                                                                  >< BsiZI
                                                                  >< Bme18I
                                                                  >< AvaII  MnlI ><
                                 > < DdeI            >< NspI >< AsuI FokI ><
           GTCTTGTTTG CTTTCTGGAC ATAATCTTGC TAAGAAGTGT CTGCATGTTG TTGGACCTAA CCTAAATGCA
               3510       3520       3530       3540       3550       3560       3570

> < Tru9I
                   >< HphI> < MseI
                      >< Esp4I
                    >< AluI       > < NdeI
                       >< AflII >< Fnu4HI    >< BbvI
           GGTGAGGACA TCCAGCTTCT TAAGGCAGCA TATGAAAATT TCAATTCACA GGACATCTTA CTTGCACCAT
               3580       3590       3600       3610       3620       3630       3640

RsaI ><
                                                                           Csp6I ><
                             >< Eco57I                     >< BcgI         AfaI ><
           TGTTGTCAGC AGGCATATTT GGTGCTAAAC CACTTCAGTC TTTACAAGTG TGCGTGCAGA CGGTTCGTAC
               3650       3660       3670       3680       3690       3700       3710

>< BsgI                      >< BspMI
                   >< BcgI/a             >< AluI                   >< NlaIII
           ACAGGTTTAT ATTGCAGTCA ATGACAAAGC TCTTTATGAG CAGGTTGTCA TGGATTATCT TGATAACCTG
               3720       3730       3740       3750       3760       3770       3780

>< MnlI
                >< RmaI      > < MnlI       >< NlaIV        >< TfiI      >< MboII
                >< MaeI      >< Eco57I      >< BscBI        >< HinfI     >< DdeI
           AAGCCTAGAG TGGAAGCACC TAAACAAGAG GAGCCACCAA ACACAGAAGA TTCCAAAACT GAGGAGAAAT
               3790       3800       3810       3820       3830       3840       3850

>< Tru9I
                                                        >< StuI
                                                        >< PalI
                                                >< MseI      >< MnlI     >< MaeIII
                                                       >< HaeIII         >< Eco0651
                                                       >< Ecol47I        >< Eco91I
                >< RsaI                                >< BsuRI                BstXI ><
                >< Csp6I       >< TthHB8I              >< BshI        >< BstPI
                >< AfaI        >< TaqI                 >< AatI        >< BstEII
           CTGTCGTACA GAAGCCTGTC GATGTGAAGC CAAAAATTAA GGCCTGCATT GATGAGGTTA CCACAACACT
               3860       3870       3880       3890       3900       3910       3920

TfiI ><
                                                                           NlaIII ><
                                                                            HinfI ><
                >< DdeI                                        >< EcoRV   >< HindIII
```

FIGURE 13.10

```
         >< BsrI        >< MboII       >< MaeIII                >< Eco321      >< AluI
       GGAAGAAACT    AAGTTTCTTA    CCAATAAGTT   ACTCTTGTTT    GCTGATATCA    ATGGTAAGCT    TTACCATGAT
          3930          3940          3950          3960          3970          3980          3990

>< NspI
                      >< NspHI
                      >< NlaIII                    >< SfaNI
             >< MnlI                               > < EcoNI
                      >< DdeI        >< MboII >< BslI                         > < NlaIII
       >< DdeI        >< BfrI        >< HphI       >< BsiYI                   >< FokI
       TCTCAGAACA    TGCTTAGAGG    TGAAGATATG    TCTTTCCTTG    AGAAGGATGC    ACCTTACATG    GTAGGTGATG
          4000          4010          4020          4030          4040          4050          4060

>< SpeI
             >< RmaI
             >< MaeI        >< EcoRV>< HphI                                  >< SfaNI
             >< HphI        >< Eco32I                           >< MnlI                    >< DdeI
       TTATCACTAG    TGGTGATATC    ACTTGTGTTG    TAATACCCTC    CAAAAAGGCT    GGTGGCACTA    CTGAGATGCT
          4070          4080          4090          4100          4110          4120          4130

>< ScrFI
                                                                            >< RsaI
                                                                                >< MvaI
                                                                                >< EcoRII
                                                                                >< Ecl136I
                                                                            >< DsaV
                                                                            >< Csp6I >< EcoNI
                                                                                >< BstOI
                                                                                >< BstNI
                                                                                >< BsiLI
                                                                            >< BsaJI
                                                                            >< BsaAI      >< BslI
                                    >< MboII                                >< MaeII>< ApyI
       >< AluI                      >< BsrI                                 >< AfaI       >< BsiYI
       CTCAAGAGCT    TTGAAGAAAG    TGCCAGTTGA    TGAGTATATA    ACCACGTACC    CTGGACAAGG    ATGTGCTGGT
          4140          4150          4160          4170          4180          4190          4200

>< Tru9I
                                   >< MseI
                      >< DdeI      >< Esp4I                                 >< RsaI
       >< MnlI                     >< BspWI                                 >< Csp6I
       >< FokI        >< AluI      >< AflII                   >< Eco57I    >< AfaI
       TATACACTTG    AGGAAGCTAA    GACTGCTCTT    AAGAAATGCA    AATCTGCATT    TTATGTACTA    CCTTCAGAAG
          4210          4220          4230          4240          4250          4260          4270

>< ScrFI
                                                 >< MvaI
                                                 >< EcoRII
                                   >< XmnI       >< Ecl136I                 NlaIII ><
             > < Ksp632I      >< RmaI            >< DsaV                    Ksp632I ><
             > < EarI     > < TfiI>< MboII       >< BstOI                              >< EarI
             > < Eam1104I     >< MaeI            >< BstNI                   Eam1104I ><
             > < DdeI     > < HinfI              >< BsiLI                   BsmAI ><
       >< BspWI         >< Asp700I               >< ApyI                    Alw26I ><
       CACCTAATGC    TAAGGAAGAG    ATTCTAGGAA    CTGTATCCTG    GAATTTGAGA    GAAATGCTTG    CTCATGCTGA
          4280          4290          4300          4310          4320          4330          4340

>< VspI           >< Zsp2I
                      >< Tru9I          >< Ppu10I
                      >< MseI           >< NsiI
             >< MboII                   >< NlaIII            >< FokI
                      >< Eco57I         >< Mph1103I          >< FokI
```

FIGURE 13.11

```
              >< AsnI         >< EcoT22I        >< BspWI
              >< AseI         >< AvaIII         >< BglI         >< MaeII
   AGAGACAAGA AAATTAATGC CTATATGCAT GGATGTTAGA GCCATAATGG CAACCATCCA ACGTAAGTAT
        4350       4360       4370       4380       4390       4400       4410

>< SfaNI
      >< Tru9I          > < HindII       >< TfiI         >< SpeI
      >< MseI           > < HincII>< MboII                >< RmaI
        >< MnlI                     >< DrdI >< HinfI      >< MaeI
   AAAGGAATTA AAATTCAAGA GGGCATCGTT GACTATGGTG TCCGATTCTT CTTTTATACT AGTAAAGAGC
        4420       4430       4440       4450       4460       4470       4480

>< MaeIII
   >< SfcI                                     >< Fnu4HI       >< MunI
      >< AluI           >< AluI                >< AciI             MaeIII ><
   CTGTAGCTTC TATTATTACG AAGCTGAACT CTCTAAATGA GCCGCTTGTC ACAATGCCAA TTGGTTATGT
        4490       4500       4510       4520       4530       4540       4550

>< ThaI
                              >< MvnI
                               >< MboII
                               >< HinPlI
                              >< HinPlI
                               >< Hin6I
                              >< Hin6I
                                >< HhaI
               >< Tru9I        >< HhaI
      >< NlaIII            >< Fnu4HI
         >< MseI              >< CfoI
           >< MnlI             >< CfoI
           >< Ksp632I          >< BstUI
           >< EarI          >< BssHII>< BspWI       >< Tru9I
           >< Eam1104I         >< Bsp50I            >< MseI
           >< BbvI             >< AccII                   >< AluI      Hph1 ><
   GACACATGGT TTTAATCTTG AAGAGGCTGC GCGCTGTATG CGTTCTCTTA AAGCTCCTGC CGTAGTGTCA
        4560       4570       4580       4590       4600       4610       4620

>< MaeIII
   >< SfaNI       >< AlwNI                           >< MnlI >< MnlI>< DdeI
   GTATCATCAC CAGATGCTGT TACTACATAT AATGGATACC TCACTTCGTC ATCAAAGACA TCTGAGGAGC
        4630       4640       4650       4660       4670       4680       4690

>< SinI
                                               >< Sau96I
                                              >< NspIV
                                               >< NspHII
   >< SduI                                    >< Eco47I
   >< NspII                                   >< Cfr13I
   >< HgiAI                                   >< BsiZI
   >< Bsp1286I                                >< Bme18I            >< RsaI
   >< BmyI                                    >< AvaII             >< Csp6I
   >< Alw21I                                  >< AsuI              >< AfaI
   ACTTTGTAGA AACAGTTTCT TTGGCTGGCT CTTACAGAGA TTGGTCCTAT TCAGGACAGC GTACAGAGTT
        4700       4710       4720       4730       4740       4750       4760

> < TthHB8I
                                                                  > < TaqI
                                                                 >< SduI
                                                   >< Van91I     >< NspII
              >< Tru9I                  >< RsaI    >< PflMI       >< Eco24I
              >< MseI                   >< HphI    >< BslI        >< Bsp1286I
              >< Esp4I                  >< Csp6I   >< BsiYI       >< BmyI GsuI ><
```

FIGURE 13.12

```
                  >< AflII   >< MaeIII        >< AfaI   >< AccB7I   >< BanIIBpmI ><
     AGGTGTTGAA TTTCTTAAGC GTGGTGACAA AATTGTGTAC CACACTCTGG AGAGCCCCGT CGAGTTTCAT
           4770       4780       4790       4800       4810       4820       4830

>< Tru9I
                                                     >< PleI  >< EcoNI
                                                     >< MnlI  >< BslI
                                                  >< BsmAI       >< BsiYI
     >< MnlI         >< HphI         >< Hinfl>< Alw26I>< AciI  >< MseI
     CTTGACGGTG AGGTTCTTTC ACTTGACAAA CTAAAGAGTC TCTTATCCCT GCGGGAGGTT AAGACTATAA
           4840       4850       4860       4870       4880       4890       4900

>< AluI                  >< NdeI
     AAGTGTTCAC AACTGTGGAC AACACTAATC TCCACACACA GCTTGTGGAT ATGTCTATGA CATATGGACA
           4910       4920       4930       4940       4950       4960       4970

>< SinI
     >< Sau96I
     >< NspIV
      >< NspHII
     >< Eco47I
     >< Cfr13I                                                       NlaIII ><
     >< BsiZI                                                        >< NlaIII
     >< Bme18I                                                      > < Mnll
     >< AvaII                      >< MaeIII   >< Tru9I    >< MnlI
     >< AsuI                       >< FokI     >< MseI              >< BspHI
     GCAGTTTGGT CCAACATACT TGGATGGTGC TGATGTTACA AAAATTAAAC CTCATGTAAA TCATGAGGGT
           4980       4990       5000       5010       5020       5030       5040

> < TthHB8I
                >< RsaI                           > < TaqI
                  > < RmaI              >< SnaBI              >< ScaI
                  > < MaeI              >< MaeII >< HindIII   >< RsaI
               >< Csp6I                 >< Eco105I            >< Csp6I
               >< AfaI                  >< BsaAI >< AluI      >< AfaI
     AAGACTTTCT TTGTACTACC TAGTGATGAC ACACTACGTA GTGAAGCTTT CGAGTACTAC CATACTCTTG
           5050       5060       5070       5080       5090       5100       5110

>< RsaI
                           >< NspI
                           >< NspHI
                           >< NlaIII
                     > < Csp6I     >< Tru9I                             MnlI >
                        >< AflIII  >< MseI                           BslI ><
                        >< AfaI    >< DraI                           BsiYI ><
     ATGAGAGTTT TCTTGGTAGG TACATGTCTG CTTTAAACCA CACAAAGAAA TGGAAATTTC CTCAAGTTGG
           5120       5130       5140       5150       5160       5170       5180

>< Tru9I   >< Tru9I                         >< RmaI
     >< MseI    >< MseI              >< MunI     >< MaeI              AluI >
     TGGTTTAACT TCAATTAAAT GGGCTGATAA CAATTGTTAT TTGTCTAGTG TTTTATTAGC ACTTCAACAG
           5190       5200       5210       5220       5230       5240       5250

>< SfaNI
                                                            >< SduI
                                                            >< NspII
                                                            >< Eco24I
                                                            >< Bsp1286I
                                                            >< BmyI        HphI >
                                                            >< BbvI Fnu4HI ><
                                     >< MnlI                >< BanII   >< BspWI
```

FIGURE 13.13

```
                CTTGAAGTCA AATTCAATGC ACCAGCACTT CAAGAGGCTT ATTATAGAGC CCGTGCTGGT GATGCTGCTA
                    5260       5270       5280       5290       5300       5310       5320

>< VneI
                    >< SnoI
                        >< SduI
                        >< NspII
                        >< HgiAI
                        >< Bsp1286I
                        >< BmyI
                    >< ApaLI
                    >< Alw44I                                                      MboII ><
                        >< Alw21I                            >< AluI              >< HphI
                ACTTTTGTGC ACTCATACTC GCTTACAGTA ATAAAACTGT TGGCGAGCTT GGTGATGTCA GAGAAACTAT
                    5330       5340       5350       5360       5370       5380       5390

> < SphI
                               > < PaeI
                               > < NspI
                               > < NspHI >< TfiI           >< Tru9I
                        >< SfcI > < NlaIII>< HinfI          >< MseI
                GACCCATCTT CTACAGCATG CTAATTTGGA ATCTGCAAAG CGAGTTCTTA ATGTGGTGTG TAAACATTGT
                    5400       5410       5420       5430       5440       5450       5460

>< RsaI
                               >< Tru9I                              > < Csp6I        Esp4I >
                               >< MseI             >< AluI             >< AfaI        AflII >
                GGTCAGAAAA CTACTACCTT AACGGGTGTA GAAGCTGTGA TGTATATGGG TACTCTATCT TATGATAATC
                    5470       5480       5490       5500       5510       5520       5530

>< RsaI
                                                                                   >< MboII
                                                                          >< RmaIHinfI ><
                                                                                   >< Csp6I
                >< Tru9I                  >< SfaNI                        >< MaeI >< BbsI
                >< MseI                   >< NlaIII                                >< AfaI
                TTAAGACAGG TGTTTCCATT CCATGTGTGT GTGGTCGTGA TGCTACACAA TATCTAGTAC AACAAGAGTC
                    5540       5550       5560       5570       5580       5590       5600

>< RsaI
                >< PleI                    > < DdeI                    >< Csp6I
                >< BsgI                    >< BspWI >< BspMI            >< AfaI
                TTCTTTTGTT ATGATGTCTG CACCACCTGC TGAGTATAAA TTACAGCAAG GTACATTCTT ATGTGCGAAT
                    5610       5620       5630       5640       5650       5660       5670

>< Eco31I
                >< RsaI                                                >< DdeI
                    > < MaeIII                                         >< BsmAI
                >< Csp6I                                               >< BsaI         MnlI ><
                >< AfaI    >< BsrI                                     >< Alw26I       HphI >
                GAGTACACTG GTAACTATCA GTGTGGTCAT TACACTCATA TAACTGCTAA GGAGACCCTC TATCGTATTG
                    5680       5690       5700       5710       5720       5730       5740

>< SstI                    >< SinI
                    >< SduI                    >< Sau96I
                    >< SacI                    >< NspIV
                    >< NspII                   >< NspHII
                    >< HgiAI             > < RsaI      >< MaeIII
                    >< Eco24I                  >< Eco47I
                    >< Ecl136II                >< Cfr13I
                    >< Bsp1286I                >< BsiZI
                    >< BmyI                    >< Bme18I
                                        FIGURE 13. 14
```

```
               >< BanII                         >< AvaII
               >< Alw21I                 >< Csp6I>< AsuI
               >< AluI                      >   < AfaI  >< BsrI>< AlwNI
       ACGGAGCTCA CCTTACAAAG ATGTCAGAGT ACAAAGGACC AGTGACTGAT GTTTTCTACA AGGAAACATC
           5750       5760       5770       5780       5790       5800       5810

>< TthHB8I
                                                    >< TaqI  >< MaeIII
       TTACACTACA ACCATCAAGC CTGTGTCGTA TAAACTCGAT GGAGTTACTT ACACAGAGAT TGAACCAAAA
           5820       5830       5840       5850       5860       5870       5880

>< RsaI
                                                                              >< Csp6I
                                                              >< SfcI  >< BbvI
                        >< FokI                              >< Fnu4HI       >< AfaI
       TTGGATGGGT ATTATAAAAA GGATAATGCT TACTATACAG AGCAGCCTAT AGACCTTGTA CCAACTCAAC
           5890       5900       5910       5920       5930       5940       5950

Tru9I ><
                                                                         SwaI ><
                                                                         MseI ><
                                                 >  < NspI               MamI ><
                                                 >  < NspHI              DraI ><
                                                 >  < NlaIII             BsiBI ><
                                          >< AflIII                      BsaBI ><
       CATTACCAAA TGCGAGTTTT GATAATTTCA AACTCACATG TTCTAACACA AAATTTGCTG ATGATTTAAA
           5960       5970       5980       5990       6000       6010       6020

>< MboII
                         >< AluI       >< AluI>< MaeIII
       TCAAATGACA GGCTTCACAA AGCCAGCTTC ACGAGAGCTA TCTGTCACAT TCTTCCCAGA CTTGAATGGC
           6030       6040       6050       6060       6070       6080       6090

>< SfcI
       GATGTAGTGG CTATTGACTA TAGACACTAT TCAGCGAGTT TCAAGAAAGG TGCTAAATTA CTGCATAAGC
           6100       6110       6120       6130       6140       6150       6160

>< Tru9I
                       >< ScrFI
                       >< MvaI
                   >< MseI
                       >< EcoRII
                           >< Ecl136I
                       >< DsaV
                           >< BstOI
                           >< BstNI                                Maell ><
       >< MunI             >< BsiLI                                >< DraIII
           >< BstXI        >< ApyI            >< MaeII       >< BstXI
       CAATTGTTTG GCACATTAAC CAGGCTACAA CCAAGACAAC GTTCAAACCA AACACTTGGT GTTTACGTTG
           6170       6180       6190       6200       6210       6220       6230

>  < RsaI
             >< Csp6I                                                     MboII ><
             >   < AfaI>< BsrI                                            >< BbsI
       TCTTTGGAGT ACAAAGCCAG TAGATACTTC AAATTCATTT GAAGTTCTGG CAGTAGAAGA CACACAAGGA
           6240       6250       6260       6270       6280       6290       6300

>< HindII                       >< MboII
                        >< HincII          >< MnlI       >< Eco57I
       ATGGACAATC TTGCTTGTGA AAGTCAACAA CCCACCTCTG AAGAAGTAGT GGAAAATCCT ACCATACAGA
           6310       6320       6330       6340       6350       6360       6370
```

FIGURE 13.15

```
                  >< MaeIII                                                    >< Tru9I
                    >< MaeII                                                   >< MseI
        AGGAAGTCAT AGAGTGTGAC GTGAAAACTA CCGAAGTTGT AGGCAATGTC ATACTTAAAC CATCAGATGA
           6380       6390       6400       6410       6420       6430       6440

>< XhoII
                                           >< Sau3AI
                                          >< NlaIII
                                            >< NdeII
                                            >< MflI
                                            >< MboI
                                            >< DpnII
                                             >< DpnI
                                            >< BstYI
        >< Tru9I                            >< BspAI
        >< MseI                >< BspHI  >< Bsp143I>< Fnu4HI
         > < MaeIII    >< MnlI >< BbvI       >< AlwI
        AGGTGTTAAA GTAACACAAG AGTTAGGTCA TGAGGATCTT ATGGCTGCTT ATGTGGAAAA CACAAGCATT
           6450       6460       6470       6480       6490       6500       6510

>< SauI
                             >< RmaI
                                >< MstII
                             >< MaeI
                                >< Eco81I
                                >< DdeI
                                >< CvnI
                                >< Bsu36I
                                >< Bse21I
                                >< BfrI  > < Tru9I
        >< Tru9I                >< AxyI> < MseI>< MunI              >< NlaIII
        >< MseI       >< AluI   >< AocI >< DraI       >< BbvI  Fnu4HI ><
        ACCATTAAGA AACCTAATGA GCTTTCACTA GCCTTAGGTT TAAAAACAAT TGCCACTCAT GGTATTGCTG
           6520       6530       6540       6550       6560       6570       6580

>< VspI      >< StyI
        >< Tru9I     >< EcoT14I                      > < DdeI
        >< MseI      >< Eco130I                       >< BslI
        >< AsnI      >< BssT1I                        >< BsiYI
        >< AseI      >< BsaJI                       > < BfrI   >< Fnu4HI
        CAATTAATAG TGTTCCTTGG AGTAAAATTT TGGCTTATGT CAAACCATTC TTAGGACAAG CAGCAATTAC
           6590       6600       6610       6620       6630       6640       6650

>< HinP1I
                    >< Hin6I                  >< Tru9I
                     >< HhaI         >< MaeII>< MseI
                     >< DdeI           >< DraIII
        >< BbvI      >< CfoI         >< AflIII
        AACATCAAAT TGCGCTAAGA GATTAGCACA ACGTGTGTTT AACAATTATA TGCCTTATGT GTTTACATTA
           6660       6670       6680       6690       6700       6710       6720

>< RsaI       > < RsaI>< XbaI
                    >< Csp6I      >< Csp6I >< RmaI
        >< MunI >< AfaI         > < AfaI >< MaeI       >< AluI
        TTGTTCCAAT TGTGTACTTT TACTAAAAGT ACCAATTCTA GAATTAGAGC TTCACTACCT ACAACTATTG
           6730       6740       6750       6760       6770       6780       6790

>< VspI
                                                               >< Tru9I
                                                              >< NaeI
                                                             >< MspI
                                                                >< MseI
                              FIGURE 13_16
```

```
                                          >< HpaII
                                          >< HapII
                              >< Cfr10I   >< FokI
         >< Tru9I                         >< AsnI
         >< MseI      >< SfaNI            >< AseI>< HphI>< MaeIII
CTAAAAATAG TGTTAAGAGT GTTGCTAAAT TATGTTTGGA TGCCGGCATT AATTATGTGA AGTCACCCAA
   6800      6810      6820      6830       6840      6850       6860

>< Tru9I       >< DdeI       MaeIII >
                              >< MseI        >< BfrI       >< BbvI
ATTTTCTAAA TTGTTCACAA TCGCTATGTG GCTATTGTTG TTAAGTATTT GCTTAGGTTC TCTAATCTGT
   6870      6880      6890      6900       6910       6920        6930

>< SduI
                                    >< NspII
                                    >< HgiAI
                    > < RsaI        >< Bsp1286I
                    >< Csp6I        >< BmyI
      >< Fnu4HI     > < AfaI        >< Alw21I
GTAACTGCTG CTTTTGGTGT ACTCTTATCT AATTTTGGTG CTCCTTCTTA TTGTAATGGC GTTAGAGAAT
   6940      6950      6960       6970        6980       6990       7000

Tru9I ><
                                                             MseI ><
      >< Tru9I     > < MaeIII                             >< Fnu4HI
      >< MseI      >< MaeII                                      BbvI >
TGTATCTTAA TTCGTCTAAC GTTACTACTA TGGATTTCTG TGAAGGTTCT TTTCCTTGCA GCATTTGTTT
   7010      7020      7030       7040       7050       7060       7070

> < TfiI                                    RsaI ><
                   >< MamI                                       >< HphI
                > < HinfI                                    Csp6I ><
                   >< BsiBI           >< XmnI>< MaeIII          AluI >
 >< PleI>< HinfI   >< BsaBI >< AluI   >< Asp700I             AfaI ><
AAGTGGATTA GACTCCCTTG ATTCTTATCC AGCTCTTGAA ACCATTCAGG TGACGATTTC ATCGTACAAG
   7080      7090       7100       7110       7120       7130       7140

>< PalI
              >< NspBII
              >< HaeIII
              >< GdiII
               >< Fnu4HI
               >< EaeI
                 >< DdeI
                 >< BsuRI
 >< RmaI         >< BshI  >< BslI
 >< MaeI         >< AciI>< BsiYI
CTAGACTTGA CAATTTTAGG TCTGGCCGCT GAGTGGGTTT TGGCATATAT GTTGTTCACA AAATTCTTTT
   7150      7160       7170       7180       7190       7200       7210

>< BspMI                              >< RmaI
         >< AluI                               >< MaeI
ATTATTAGG TCTTTCAGCT ATAATGCAGG TGTTCTTTGG CTATTTTGCT AGTCATTTCA TCAGCAATTC
   7220      7230      7240       7250       7260       7270       7280

RsaI ><
                                                              >< MboII
                                        >< NlaIV            MamI ><
                                        >< Eco64I           Csp6I ><
                                > < RsaI   >< BscBI         BsiBI ><
                                >< Csp6I >< BanI            BsaBI ><
          > < NlaIII            > < AfaI>< AccBI             AfaI ><
                           FIGURE 13.17
```

```
TTGGCTCATG TGGTTTATCA TTAGTATTGT ACAAATGGCA CCCGTTTCTG CAATGGTTAG GATGTACATC
   7290       7300       7310       7320       7330       7340       7350

TthHB8I ><
                                                                       >< TaqI
                                                                      MnlI ><
                            >< NdeI                              Ksp632I ><
                            >< Ksp632I                                >< FokI
                            >< EarI                              >< MboII EarI ><
 >< FokI                    >< Eam1104I>< AluI>< MboII   >< NlaIII Eam1104I ><
TTCTTTGCTT CTTTCTACTA CATATGGAAG AGCTATGTTC ATATCATGGA TGGTTGCACC TCTTCGACTT
   7360       7370       7380       7390       7400       7410       7420

XhoII ><
                                                                  Sau3AI ><
                                                                  NlaIII ><
                                                                   NdeII ><
                                                                    MflI ><
                                                                    MboI ><
                                  >< ThaI                        > < Ksp632I
                                  >< MvnI                        > < EarI
                  >< HinP1I       >< MluI                        > < Eam1104I
                  >< Hin6I        >< BstUI                          DpnII ><
                  >< HhaI         >< Bsp50I   >< RsaI               BstYI ><
   >< NlaIII      >< CfoI         >< AflIII   >< Csp6I       >< Tru9I BspAI ><
   >< BspWI  >< BspWI             >< AccII    >< AfaI        >< MseI  BglII ><
GCATGATGTG CTATAAGCGC AATCGTGCCA CACGCGTTGA GTGTACAACT ATTGTTAATG GCATGAAGAG
  .7430       7440       7450       7460       7470       7480       7490

>< PalI
                        >< HaeIII
                        >< DsaI
     >< MboII           >< BsuRI                                     >< MunI
 >< DpnI                >< BshI                      >< MunI        MaeIII ><
 >< Bsp143I    >< MnlI  >< BsaJI    >< PleI>< HinfI                 BsmAI ><
                                                                    Alw26I ><
ATCTTTCTAT GTCTATGCAA ATGGAGGCCG TGGCTTCTGC AAGACTCACA ATTGGAATTG TCTCAATTGT
   7500       7510       7520       7530       7540       7550       7560

>< RsaI                                          Tru9I ><
                > < Csp6I                                          MseI ><
               >< BsrI                     >< GsuI         >< MaeIIIDraI ><
                  >< AfaI                  >< BpmI               > < BsrI
GACACATTTT GCACTGGTAG TACATTCATT AGTGATGAAG TTGCTCGTGA TTTGTCACTC CAGTTTAAAA
   7570       7580       7590       7600       7610       7620       7630

>< ThaI
                                                                     >< MvnI
                                                                   > < HphI
                                                                 HinP1I ><
                                                                     >< HinP1I
                                                                     >< Hin6I
                                                                     >< Hin6I
                                                                  HhaI ><
                                                                     >< HhaI
                                                                  CfoI ><
                                                                     >< CfoI
                                                                     >< BstUI
                                                                     >< BssHII
                                                                 Bsp50I ><
                     > < BsrI                                        >< AccII
GACCAATCAA CCCTACTGAC CAGTCATCGT ATATTGTTGA TAGTGTTGCT GTGAAAAATG GCGCGCTTCA
   7640       7650       7660       7670       7680       7690       7700
```

FIGURE 13. 18

```
                              >< FokI
                              >< BsmAI
         >< MnlI              >< Alw26I      >< AciI
CCTCTACTTT GACAAGGCTG GTCAAAAGAC CTATGAGAGA CATCCGCTCT CCCATTTTGT CAATTTAGAC
   7710       7720       7730       7740       7750       7760       7770

>< VspI
                                   >< Tru9I
                                   >< MseI
                                   >< AsnI
         > < AluI                  >< AseI                        >< BcgI/a
AATTTGAGAG CTAACAACAC TAAAGGTTCA CTGCCTATTA ATGTCATAGT TTTTGATGGC AAGTCCAAAT
   7780       7790       7800       7810       7820       7830       7840

>< SfcI   >< PvuII
                                >< RsaI   >< Psp5I
              >< PleI           >< Csp6I  >< NspBII
   >< HinfI   >< DdeI  >< BcgI  >< AfaI   >< AluI
GCGACGAGTC TGCTTCTAAG TCTGCTTCTG TGTACTACAG TCAGCTGATG TGCCAACCTA TTCTGTTGCT
   7850       7860       7870       7880       7890       7900       7910

TthHB8I ><
                                                                TaqI ><
                                                                SalI ><
                                                                RtrI ><
                                   >< ScaI                     HindII >
                                   >< RsaI       >< Tru9I      HincII >
                                   >< Csp6I      >< SfaNI  >< Eco57I
   >< AluI    >< MaeII  >< AfaI                  >< MseI                AccI ><
TGACCAAGCT CTTGTATCAG ACGTTGGAGA TAGTACTAA GTTTCCGTTA AGATGTTTGA TGCTTATGTC
   7920       7930       7940       7950       7960       7970       7980

>< Tru9I
                                   >< MseI
                                 > < Esp4I         >< SfcI
                                 > < AflII         >< BspWI   >< AiuI
GACACCTTTT CAGCAACTTT TAGTGTTCCT ATGGAAAAAC TTAAGGCACT TGTTGCTACA GCTCACAGCG
   7990       8000       8010       8020       8030       8040       8050

>< PvuII
                                                   >< Psp5I
                                                   >< NspBII
                                                   >< Fnu4HI
              >< AluI              >< BbvI         >< AluI
AGTTAGCAAA GGGTGTAGCT TTAGATGGTG TCCTTTCTAC ATTCGTGTCA GCTGCCCGAC AAGGTGTTGT
   8060       8070       8080       8090       8100       8110       8120

MaeIII ><
              >< HindII             >< BsmAI                    >< DdeI
              >< HincII             >< FokI>< Alw26I            >< BfrI
TGATACCGAT GTTGACACAA AGGATGTTAT TGAATGTCTC AAACTTTCAC ATCACTCTGA CTTAGAAGTG
   8130       8140       8150       8160       8170       8180       8190

>< XhoII
                                                           Sau3AI ><
                                                                  >< NdeII
                                                                  >< MflI
                                                                  >< MboI
                                                      >< NlaIII >< HgaI
                                                      >< HinlI  >< DpnII
                                                           DpnI ><
```

FIGURE 13.19

```
                                                              Bsp143I ><
                                                          >< BsaHI >< BstYI
                >< MaeIII>< HphI                          >< BbiII >< BspAI
   >< MaeIII    >< HphI      >< NlaIII                    >< AcyI  >< BglII
ACAGGTGACA GTTGTAACAA TTTCATGCTC ACCTATAATA AGGTTGAAAA CATGACGCCC AGAGATCTTG
    8200       8210       8220       8230       8240       8250       8260

>< NspI
       >< NspHI
       >< NlaIII
>< HinP1I
>< Hin6I
  >< HhaI
  >< CfoI                                      >< BspWI    >< MaeIII
GCGCATGTAT TGACTGTAAT GCAAGGCATA TCAATGCCCA AGTAGCAAAA AGTCACAATG TTTCACTCAT
    8270       8280       8290       8300       8310       8320       8330

>< NspI
                    >< NspHI        >< PvuII
                    >< NlaIII       >< Psp5I
               >< Eam1105I          >< NspBII
                      >< BbvI       >< Fnu4HI
               >< AflIII            >< AluI    >< BbvI     >  < Fnu4HI
CTGGAATGTA AAAGACTACA TGTCTTTATC TGAACAGCTG CGTAAACAAA TTCGTAGTGC TGCCAAGAAG
    8340       8350       8360       8370       8380       8390       8400

>< RmaI
    >< MboII                           >< MaeI  >< Eam1105I
AACAACATAC CTTTTAGACT AACTTGTGCT ACAACTAGAC AGGTTGTCAA TGTCATAACT ACTAAAATCT
    8410       8420       8430       8440       8450       8460       8470

>< Tru9I
                                                    >< PalI
                                             >< MseI
                                                    >< HaeIII
                       >< ScaI               >< Esp4I
                       >< RsaI  >< Tru9I          >< BsuRI
                       >< Csp6I >< MseI           >< BshI
                       >< AfaI  >< DraI  >< AflII      >< BbvI
CACTCAAGGG TGGTAAGATT GTTAGTACTT GTTTAAACT TATGCTTAAG GCCACATTAT TGTGCGTTCT
    8480       8490       8500       8510       8520       8530       8540

>< RsaI
                          >< Csp6I
                >< BsrI                                >< NlaIII
   >< Fnu4HI              >< AfaI                      >< MaeIII
TGCTGCATTG GTTTGTTATA TCGTTATGCC AGTACATACA TTGTCAATCC ATGATGGTTA CACAAATGAA
    8550       8560       8570       8580       8590       8600       8610

>< MaeIII
                          >  < MaeIII
   >< MaeIII                 >< FokI
ATCATTGGTT ACAAAGCCAT TCAGGATGGT GTCACTCGTG ACATCATTTC TACTGATGAT TGTTTTGCAA
    8620       8630       8640       8650       8660       8670       8680

SfcI >
   >< NspI                                                   Fnu4HI ><
   >< NspHI                                                   BbvI ><
   >< NlaIII    >< NlaIII    >< HgaI     >< BstXI    >< BbvI     >< AluI
ATAAACATGC TGGTTTTGAC GCATGGTTTA GCCAGCGTGG TGGTTCATAC AAAAATGACA AAAGCTGCCC
    8690       8700       8710       8720       8730       8740       8750
```

FIGURE 13. 20

```
                                                        >< ScrFI
                                           >< ScrFI     >< RsaI
                                           >< MvaI  >< MspI
                                           >< EcoRII   >< HpaII
                                           >< Ecl136I>< NciI
                                           >< DsaV     >< HapII
                                           >< BstOI>< DsaV
                                           >< BstNI    >< Csp6I
         >< Fnu4HI                          >< BsiLI >< BcnIDdeI ><
         >< AluI                            >< ApyI     >< AfaI
TGTAGTAGCT GCTATCATTA CAAGAGAGAT TGGTTTCATA GTGCCTGGCT TACCGGGTAC TGTGCTGAGA
    8760       8770       8780       8790       8800       8810       8820

> < MaeIII  >< HphI               >< MnlI                >< BspWI
GCAATCAATG GTGACTTCTT GCATTTTCTA CCTCGTGTTT TTAGTGCTGT TGGCAACATT TGCTACACAC
    8830       8840       8850       8860       8870       8880       8890

Tru9I >
                                                              SfaNI ><
                                                                  >< RsaI
                                                                     MseI >
                                      >< BspWI         >< Fnu4HI >< Csp6I
                                         >< BbvI>< MnlI   >< DdeI >< AfaI
CTTCCAAACT CATTGAGTAT AGTGATTTTG CTACCTCTGC TTGCGTTCTT GCTGCTGAGT GTACAATTTT
    8900       8910       8920       8930       8940       8950       8960

> < RmaI
                                           >< MnlI
         >< FokI                           > < MaeI
TAAGGATGCT ATGGGCAAAC CTGTGCCATA TTGTTATGAC ACTAATTTGC TAGAGGGTTC TATTTCTTAT
    8970       8980       8990       9000       9010       9020       9030

ScrFI >
                                                                    MvaI >
                                                                    MnlI ><
                                                                   EcoRII ><
                                                                   Ecl136I >
                                                                   DsaV ><
                                                                   BstOI >
                                                  >< NlaIV         BstNI >
                                                        >< FokI    BsiLI >
>< AluI                                           >< BscBI         ApyI >
AGTGAGCTTC GTCCAGACAC TCGTTATGTG CTTATGGATG GTTCCATCAT ACAGTTTCCT AACACTTACC
    9040       9050       9060       9070       9080       9090       9100

>< RsaI
                                           >< SfcI              >< NspI
                                           >< ScaI              >< NspHI
                >< SfaNI                   >< RsaI       >< NlaIII
                > < MaeII                  >< Csp6I
                >< GsuI                    >< AfaI       >< Csp6I
                >< BpmI         >< DdeI    >< AccI       >< AfaI
TGGAGGGTTC TGTTAGAGTA GTAACAACTT TTGATGCTGA GTACTGTAGA CATGGTACAT GCGAAAGGTC
    9110       9120       9130       9140       9150       9160       9170

>< SstI
                                                                  >< SduI
                                                                  >< SacI
                                                           NspII ><
                                                           HgiAI ><
                                                           Eco24I ><
                                                           Bsp1286I ><

FIGURE 13.21
```

```
                                                     Ecl136II ><>< BmyI
                                                        BanII ><
                                    >< Tru9I            Alw21I ><
                      >< BsrI       >< MseI                    >< AluI
AGAAGTAGGT ATTTGCCTAT CTACCAGTGG TAGATGGGTT CTTAATAATG AGCATTACAG AGCTCTATCA
   9180       9190       9200       9210       9220       9230       9240

>< TfiI
      >< SfaNI        >< HinfI   >< AluI                       >< MnlI
GGAGTTTTCT GTGGTGTTGA TGCGATGAAT CTCATAGCTA ACATCTTTAC TCCTCTTGTG CAACCTGTGG
   9250       9260       9270       9280       9290       9300       9310

>< MaeIII
                                                 HphI ><
   >< Eco57I                                > < BbvI Fnu4HI ><
GTGCTTTAGA TGTGTCTGCT TCAGTAGTGG CTGGTGGTAT TATTGCCATA TTGGTGACTT GTGCTGCCTA
   9320       9330       9340       9350       9360       9370       9380

>< RsaI
                              >< Csp6I    >< NlaIII
              >< MaeII          >< BbvI       >< Fnu4HI
              >< AflIII       >< AfaI>< HphI      >< BspWI
CTACTTTATG AAATTCAGAC GTGTTTTTGG TGAGTACAAC CATGTTGTTG CTGCTAATGC ACTTTTGTTT
   9390       9400       9410       9420       9430       9440       9450

>< RsaI
                      >< NlaIV
                      >< KpnI
                      >< Eco64I            > < ScrFI
                      >< Csp6I             > < NciI
                      >< BscBI             >< MspI
                      >< Asp718            >< HpaII
                      >< BanI >< AluI         >< HinfI
                      >< AfaI            >< HapII      >< PleI
                      >< AccB1I         > < BcnI    > < DdeI
                      >< Acc65I    >< AluI>< DsaV   >< AccI
TTGATGTCTT TCACTATACT CTGTCTGGTA CCAGCTTACA GCTTTCTGCC GGGAGTCTAC TCAGTCTTTT
   9460       9470       9480       9490       9500       9510       9520

>< RsaI
   >< Csp6I
   >< AfaI   >< HphI              >< HphI                 NlaIII ><
ACTTGTACTT GACATTCTAT TTCACCAATG ATGTTTCATT CTTGGCTCAC CTTCAATGGT TGCCATGTT
   9530       9540       9550       9560       9570       9580       9590

TTCTCCTATT GTGCCTTTTT GGATAACAGC AATCTATGTA TTCTGTATTT CTCTGAAGCA CTGCCATTGG
   9600       9610       9620       9630       9640       9650       9660

>< TthHB8I
                                                         >< RsaI
                                                           >< MnlI
                                                         >< MnlI
                                    >< Tru9I             >< Csp6I
   >< Tru9I                         >< PleI      >< BcgI/a >< TaqI
   >< MseI     >< DdeI              >< NlaIII             >< BbvI
   >< Eco57I   >< BfrI    >< HinfI  >< MseI >< MaeIII     >< AfaI Fnu4HI ><
TTCTTTAACA ACTATCTTAG GAAAAGAGTC ATGTTTAATG GAGTTACATT TAGTACCTTC GAGGAGGCTG
   9670       9680       9690       9700       9710       9720       9730

>< RsaI
   >< Csp6I          >< RsaI
        >< BcgI      >< Csp6I      >< BsmAI
```

FIGURE 13.22

```
              >< AfaI                          >< AfaI      >< Alw26I
CTTTGTGTAC CTTTTTGCTC AACAAGGAAA TGTACCTAAA ATTGCGTAGC GAGACACTGT TGCCACTTAC
   9740       9750       9760       9770       9780       9790       9800

>< NlaIV
                                    >< RsaI                   >< DdeI
                                    >< Csp6I                  >< BscBI
                                    >< AfaI                   >< BfrI    AluI ><
ACAGTATAAC AGGTATCTTG CTCTATATAA CAAGTACAAG TATTTCAGTG GAGCCTTAGA TACTACCAGC
   9810       9820       9830       9840       9850       9860       9870

>< Fnu4HI
                   >< DdeI
         >< Fnu4HI >< BfrI
>< BbvI  >< AluI   >< BbvI                          >< DdeI >< AlwNI
TATCGTGAAG CAGCTTGCTG CCACTTAGCA AAGGCTCTAA ATGACTTTAG CAACTCAGGT GCTGATGTTC
   9880       9890       9900       9910       9920       9930       9940

>< SfcI                   >< BsmI
                                   >< PstI           >< BscCI
TCTACCAACC ACCACAGACA TCAATCACTT CTGCTGTTCT GCAGAGTGGT TTTAGGAAAA TGGCATTCCC
   9950       9960       9970       9980       9990      10000      10010

>< RsaI
                          >< NlaIII
                             >< MaeIII
                          >< Csp6I              >< Tru9I
                          >< AfaI               >< MseI
GTCAGGCAAA GTTGAAGGGT GCATGGTACA AGTAACCTGT GGAACTACAA CTCTTAATGG ATTGTGGTTG
   10020      10030      10040      10050      10060      10070      10080

XhoII ><
                                                                    Sau3AI ><
                                                         >< Tru9I   NdeII ><
                                                 >< NspI            MflI ><
                                                 >< NspHI           MboI ><
                                    >< NspI      >< NlaIII          DpnII ><
                    >< FokI         >< NspHI     >< MseI            BstYI ><
                    >< Bst1107I     >< NlaIII    >< MboII           BspAI ><
                    >< AccI         >< AflIII    > < BbsI           BglII ><
GATGACACAG TATACTGTCC AAGACATGTC ATTTGCACAG CAGAAGACAT GCTTAATCCT AACTATGAAG
   10090      10100      10110      10120      10130      10140      10150

PalI >
                                                                    MscI >
                                                                    HaeIII >
                                                                    EaeI ><
                                                                    BsuRI >
>< DpnI >< MboII                                                    BshI >
>< Bsp143I                    >< AluI                               BalI >
ATCTGCTCAT TCGCAAATCC AACCATAGCT TTCTTGTTCA GGCTGGCAAT GTTCAACTTC GTGTTATTGG
   10160      10170      10180      10190      10200      10210      10220

>< DdeI> < Tru9I
              >< BfrI> < MseI              >< DdeI
CCATTCTATG CAAAATTGTC TGCTTAGGCT TAAAGTTGAT ACTTCTAACC CTAAGACACC CAAGTATAAA
   10230      10240      10250      10260      10270      10280      10290

>< ScrFI
            >< MvaI
            >< EcoRII
            >< Ecl136I                        >< SphI
```

FIGURE 13.23

```
                    >< DsaV                              >< PaeI
                    >< BstOI                             >< NspI
                    >< BstNI                             >< NspHI
                    >< BsiLI                   >< RmaI   >< NlaIII
                    >< ApyI                    >< MaeI   >< HphI
         TTTGTCCGTA TCCAACCTGG TCAAACATTT TCAGTTCTAG CATGCTACAA TGGTTCACCA TCTGGTGTTT
         10300      10310      10320      10330      10340      10350      10360

>< Sau3AI
                                                              >< NdeII
                                                              >< MboI>< NlaIII
              >< Eco31I                                       >< DpnII
              >< BsmAI                                 >< Tru9I>< DpnI
              >< BsaI>< NlaIII        >< Tru9I         >< MseI >< Bsp143I
              >< Alw26I               >< MseI                  >< BspAI>< AlwI
         ATCAGTGTGC CATGAGACCT AATCATACCA TTAAAGGTTC TTTCCTTAAT GGATCATGTG GTAGTGTTGG
         10370      10380      10390      10400      10410      10420      10430

>< Zsp2I
                                          >< Ppu10I
                                          >< NsiI>< SfaNI
                                              >< NdeI
                                          >< Mph1103I            RsaI ><
    >< Tru9I                               >< EcoT22I            Csp6I ><
    >< MseI                               > < AvaIII  >< AluI    AfaI ><
         TTTTAACATT GATTATGATT GCGTGTCTTT CTGCTATATG CATCATATGG AGCTTCCAAC AGGAGTACAC
         10440      10450      10460      10470      10480      10490      10500

>< SinI
                                >< Sau96I
                                >< NspIV
                                 >< NspHII                         >< SfcI
                                >< Eco47I                          RsaI ><
                                >< Cfr13I                          PstI ><
                                >< BsiZI                           >< Fnu4HI
    >< RsaI                      >< Bme18I   >< HindII             Csp6I ><
    >< Csp6I>< DdeI              >< AvaII    >< HincII             >< BspWI
    >< AfaI>< BfrI              >< AsuI>< BsgI    >< BbvI >< BspMI AfaI ><
         GCTGGTACTG ACTTAGAAGG TAAATTCTAT GGTCCATTTG TTGACAGACA AACTGCACAG GCTGCAGGTA
         10510      10520      10530      10540      10550      10560      10570

>< Tru9I         >< NlaIII
                    >< MseI    >< BbvI        >< Fnu4HI            HphI ><
         CAGACACAAC CATAACATTA AATGTTTTGG CATGGCTGTA TGCTGCTGTT ATCAATGGTG ATAGGTGGTT
         10580      10590      10600      10610      10620      10630      10640

>< Tru9I
         >< TfiI
    >< MseI                                                    >< RsaI
    >< HphI                             >< Tru9I               >< Csp6I
         >< HinfI                       >< MseI                >< AfaI
         TCTTAATAGA TTCACCACTA CTTTGAATGA CTTTAACCTT GTGGCAATGA AGTACAACTA TGAACCTTTG
         10650      10660      10670      10680      10690      10700      10710

>< SinI
                              >< Sau96I
                                >< PssI
                              >< Psp5II
                              >< PpuMI
                              >< NspIV
                               >< NspHII
                              >< NlaIV
```

FIGURE 13. 24

```
                          >< EcoO109I
                          >< Eco47I
      >< Sau3AI           >< DraII
      >< NdeII            >< Cfr13I
      >< MboI             >< BsiZI
      >< DpnII>< NlaIII   >< BscBI
        >< DpnI >< HindII >< Bme18I                              >< DdeI
      >< BspAI  >< HincII >< AvaII                               >< BfrI
        >< Bsp143I        >< AsuI      >< MnlI                   >< BbvI
      ACACAAGATC ATGTTGACAT ATTGGGACCT CTTTCTGCTC AAACAGGAAT TGCCGTCTTA GATATGTGTG
         10720      10730      10740      10750      10760      10770      10780

>< StyI
                                                    >< RsaI
                                                    >< EcoT14I
                                                    >< Eco130I
                  >< SfcI                  > < Csp6I
      >< Fnu4HI   >< Fnu4HI                           >< BssTlI
       >< BbvI    >< Fnu4HI                           >< BsaJI
       >< BbvI    >< AluI   >< PstI        >< AfaI
      CTGCTTTGAA AGAGCTGCTG CAGAATGGTA TGAATGGTCG TACTATCCTT GGTAGCACTA TTTTAGAAGA
         10790      10800      10810      10820      10830      10840      10850

>< StyI
                                                    >< EcoT14I
                                                    >< Eco130I
                                                    >< BssTlI
      >< MboII                            > < MaeIII>< BsaJI
      TGAGTTTACA CCATTTGATG TTGTTAGACA ATGCTCTGGT GTTACCTTCC AAGGTAAGTT CAAGAAAATT
         10860      10870      10880      10890      10900      10910      10920

>< SfaNI
                  > < SduI
                  > < NspII      >< Tru9I                        RsaI ><
      >< Tru9I> < Bsp1286I       >< MseI             >< TfiI    Csp6I ><
      >< MseI  > < BmyI          >< FokI             >< HinfI   AfaI ><
      GTTAAGGGCA CTCATCATTG GATGCTTTTA ACTTCTTGA CATCACTATT GATTCTTGTT CAAAGTACAC
         10930      10940      10950      10960      10970      10980      10990

>< XmnI                                >< MunI
                                 >< BsmI                                Fnu4HI >
                                 >< BscCI                               BspWI ><
      >< MaeIII                  >< Asp700I                   >< BbvI   BbvI >
      AGTGGTCACT GTTTTTCTTT GTTTACGAGA ATGCTTTCTT GCCATTTACT CTTGGTATTA TGGCAATTGC
         11000      11010      11020      11030      11040      11050      11060

>< NspI
      >< NspHI
      >< NlaIII               >< Tru9I
      >< BspWI  >< Fnu4HI>< BspWI >< BscCI                   >< MaeIII
      TGCATGTGCT ATGCTGCTTG TTAAGCATAA GCACGCATTC TTGTGCTTGT TTCTGTTACC TTCTCTTGCA
         11070      11080      11090      11100      11110      11120      11130

>< SfaNI
                                     >< RmaI
                             > < NspI              >< MamI
                             > < NlaIII            >< HphI
                                     >< NheI      >< BspHI
                  >< Tru9I           >< MaeI      >< BsiBI    >< NlaIII
      >< BspWI    >< MseI   >< AccI> < NspHI>< AluI >< BsaBI >< NlaIII
      ACAGTTGCTT ACTTTAATAT GGTCTACATG CCTGCTAGCT GGGTGATGCG TATCATGACA TGGCTTGAAT
         11140      11150      11160      11170      11180      11190      11200
```

FIGURE 13.25

```
                                      >< Tru9I
                                      >< MseI
         > < RmaI              > < Esp4I
         > < MaeI                        >< Eco57I
             >< AluI         > < AflII                           >< AluI
TGGCTGACAC TAGCTTGTCT GGTTATAGGC TTAAGGATTG TGTTATGTAT GCTTCAGCTT TAGTTTTGCT
   11210      11220      11230      11240      11250      11260      11270

>< RmaI
                                             >< MaeII
                                   >< MaeI
         > < NlaIII   >< SfaNI     >< Fnu4HI
     >< BspHI >< AluI   >< BbvI              >< AflIII
TATTCTCATG ACAGCTCGCA CTGTTTATGA TGATGCTGCT AGACGTGTTT GGACACTGAT GAATGTCATT
   11280      11290      11300      11310      11320      11330      11340

>< Sau96I
                                                          >< PalI
                                                          >< NspIV
                                                          >< NlaIII
                                               >< Sau3AI  >< HaeIII
                                               >< NdeII        > < DdeI
                                               >< MboI    >< Cfr13I
                                               >< DpnII   >< BsuRI
                                               >< DpnI    >< BsiZI
                                                 >< DpnI  >< BshI
                                                 >< Bsp143I
             >< AccI                   >< BspAI>< AluI    >< AsuI     > < BfrI
ACACTTGTTT ACAAAGTCTA CTATGGTAAT GCTTTAGATC AAGCTATTTC CATGTGGGCC TTAGTTATTT
   11350      11360      11370      11380      11390      11400      11410

>< RmaI
                                   >< NlaIII
                                             >< MaeI>< SfcI
>< MaeIII    >< MnlI    >< MaeIII            >< AluI>< AluI
CTGTAACCTC TAACTATTCT GGTGTCGTTA CGACTATCAT GTTTTTAGCT AGAGCTATAG TGTTTGTGTG
   11420      11430      11440      11450      11460      11470      11480

DdeI >
                            >< BsrI                    >< NlaIII BfrI >
TGTTGAGTAT TACCCATTGT TATTTATTAC TGGCAACACC TTACAGTGTA TCATGCTTGT TTATTGTTTC
   11490      11500      11510      11520      11530      11540      11550

>< PalI
                         >< HaeIII
             >< Fnu4HI   >< BsuRI
   >< BbvI   >< Fnu4HI   >< BspWI
   >< BbvI   >< BspWI        >< BshI      >< Eco57I  >< MaeIII
TTAGGCTATT GTTGCTGCTG CTACTTTGGC CTTTTCTGTT TACTCAACCG TTACTTCAGG CTTACTCTTG
   11560      11570      11580      11590      11600      11610      11620

>< ScrFI
                                                           >< MvaI
                                                       >< EcoRII
                                                           >< Ecl136I
                                                       >< DsaV
                                                           >< BstOI
                                                           >< BstNI
                                          >< Eco31I        >< BsiLI
                                          >< BsmAI      > < BsaJI
                                          >< BsaI         >< BsaJI
```

FIGURE 13.26

```
                    >< DrdI    >< Alw26I                              >< ApyI    DdeI ><
             GTGTTTATGA CTACTTGGTC TCTACACAAG AATTTAGGTA TATGAACTCC CAGGGGCTTT TGCCTCCTAA
                11630      11640      11650      11660      11670      11680      11690

>< Tru9I
                                  >< MseI
>< SfaNI              > < HindIII> < Tru9I
>< MnlI                  >< AluI > < MseI   > < MnlI                 > < NlaIII
GAGTAGTATT GATGCTTTCA AGCTTAACAT TAAGTTGTTG GGTATTGGAG GTAAACCATG TATCAAGGTT
   11700      11710      11720      11730      11740      11750      11760

>< VneI
                                 >< SnoI
                                    >< SduI
                                    >< NspII
                                    >< HgiAI
                                    >< Bsp1286I
                                    >< BmyI     >< RsaI
      >< RsaI                     >< ApaLI              >< MboII
      >< Csp6I                    >< Alw44I   >< Csp6I              DdeI >
      >< AfaI          >< MaeII   >< Alw21I   >< AfaI               BfrI >
GCTACTGTAC AGTCTAAAAT GTCTGACGTA AAGTGCACAT CTGTGGTACT GCTCTCGGTT CTTCAACAAC
   11770      11780      11790      11800      11810      11820      11830

>< NspII> < RsaI
                                 >< DraIII
                              >< SduI>< Csp6I
      >< MboII                 >< Bsp1286I
        >< HinfI >< PleI       >< BmyI > < AfaI     >< MboII
TTAGAGTAGA GTCATCTTCT AAATTGTGGG CACAATGTGT ACAACTCCAC AATGATATTC TTCTTGCAAA
   11840      11850      11860      11870      11880      11890      11900

>< TthHB8I
              >< TaqI
      >< HindIII           >< MboII                        SfcI ><
        >< AluI         > < Eco57I                       >< NlaIII
                                                         >< BspWI  AccI ><
AGACACAACT GAAGCTTTCG AGAAGATGGT TTCTCTTTTG TCTGTTTTGC TATCCATGCA GGGTGCTGTA
   11910      11920      11930      11940      11950      11960      11970

>< VspI
    >< Tru9I                                       > < Ksp632I
    >< MseI                  >< TthHB8I            > < EarI
    >< AsnI                  >< TaqI  >< MboII
    >< AseI>< MnlI >< BcgI/a    >< Eco57I    >< Eco57I >< BcgI
GACATTAATA GGTTGTGCGA GGAAATGCTC GATAACCGTG CTACTCTTCA GGCTATTGCT TCAGAATTTA
   11980      11990      12000      12010      12020      12030      12040

>< StuI
                                >< ScrFI
                                   >< PalI
                                >< MvaI>< HaeIII
                              >< EcoRII>< Eco147I
                                >< Ecl136I
                                >< DsaV   >< BsuRI
                                   >< BstOI
                                   >< BstNI
                                      >< BspWI
                                      >< PsiLI
                 >< Fnu4HI      >< BsaJI >< BshI            TfiI ><
      >< NdeI    >< BspWI>< MnlI >< BglI            >< SfcI  HinfI ><
                 >< AciI          >< ApyI>< AatI              > < AluI
```

FIGURE 13. 27

```
                                                                                      >< SfaNI
       >< XmnI         >< Tru9I                                                       >< DdeI
       >< HphI         >< MseI
       >< Asp700I      >< Eco57I                                                      >< BbvI Fnu4HI ><
GTTCTTTACC ATCATATGCC GCTTATGCCA CTGCCCAGGA GGCCTATGAG CAGGCTGTAG CTAATGGTGA
     12050      12060      12070      12080      12090      12100      12110

TTCTGAAGTC GTTCTCAAAA AGTTAAAGAA ATCTTTGAAT GTGGCTAAAT CTGAGTTTGA CCGTGATGCT
     12120      12130      12140      12150      12160      12170      12180
                                                                           XhoII ><
                                                                           Sau3AI ><
                                                                           NdeII ><
                                                                               MnlI >
                                                                               >< MnlI
                                                                               >< MflI
                                  > < Sau3AI                                   >< MboI
                                  > < NdeII                              DpnII ><
                                  > < MboI                                 DpnI ><
                                  > < DpnII                                DdeI ><
                                      >< DpnI                             BstYI ><
                                         >< BspWI                     >< RsaIBspAI ><
                                  > < BspAI                           >< Csp6IBsp143I ><
     >< NlaIII                        >< Bsp143I                          >< AfaIBglII ><
GCCATGCAAC GCAAGTTGGA AAAGATGGCA GATCAGGCTA TGACCCAAAT GTACAAACAG GCAAGATCTG
     12190      12200      12210      12220      12230      12240      12250

>< SpeI                           >< Ksp632I   > < HindIII
                         >< RmaI                               >< DdeI  >< SfaNI
                      >< MaeIII        >< MboII         >< Eam1104I >< BspWI
                        >< MaeI         >< BspWI         >< EarI>< BfrI  >< AluI
AGGACAAGAG GGCAAAAGTA ACTAGTGCTA TGCAAACAAT GCTCTTCACT ATGCTTAGGA AGCTTGATAA
     12260      12270      12280      12290      12300      12310      12320

>< ThaI
                                 >< MvnI
                                >< HinP1I
                                >< Hin6I
                                 >< HhaI
                                 >< CfoI
                                 >< BstUI
       >< Tru9I                  >< Bsp50I
       >< MseI                   >< AccII                                 SfcI ><
TGATGCACTT AACAACATTA TCAACAATGC GCGTGATGGT TGTGTTCCAC TCAACATCAT ACCATTGACT
     12330      12340      12350      12360      12370      12380      12390

>< RsaI
                                           >< NlaIV
                                          >< Eco64I
                                          >< Csp6I
                                        >< BslI
                                        >< BsiYI>< KpnI
                                          >< BscBI
                                           >< BanI
                                           >< Asp718
                       >< NlaIII           >< AfaI
                       >< BstXI            >< AccBlI                   >< MaeIII
       >< Fnu4HI   >< BbvI                 >< Acc65I                    BsgI ><
ACAGCAGCCA AACTCATGGT TGTTGTCCCT GATTATGGTA CCTACAAGAA CACTTGTGAT GGTAACACCT
     12400      12410      12420      12430      12440      12450      12460

>< Zsp2I
     >< Ppu10I
```

FIGURE 13.28

```
                           >< NsiI
                           >< Mph1103I
          >< NdeI>< EcoT22I                                              DdeI ><
             >< AvaIII >< SfaNI           >< SfaNI       >< AciI         BfrI ><
          TTACATATGC ATCTGCACTC TGGGAAATCC AGCAAGTTGT TGATGCGGAT AGCAAGATTG TTCAACTTAG
             12470      12480      12490      12500      12510      12520      12530

>< PalI
                                              >< HaeIII   >< MnlI   >< DdeIDdeI ><
             >< Tru9I>< NlaIII                >< BsuRI    >< MaeIII      >< BspWI
             >< MseI>< HphI        > < XcmI>< BshI                >< AluI   BspWI ><
          TGAAATTAAC ATGGACAATT CACCAAATTT GGCTTGGCCT CTTATTGTTA CAGCTCTAAG AGCCAACTCA
             12540      12550      12560      12570      12580      12590      12600

RsaI ><
                                                                         NlaIV ><
                                                                          KpnI ><
                                                                       >< Fnu4HI
                                                                       Eco64I ><
                                                                        Csp6I ><
             >< Tru9I                                                   BscBI ><
          >< PvuII                                                      Asp718 ><
          >< Psp5I                                                        AfaI ><
          >< NspBII                                                    >< AciI>< BanI
             >< MseI          >< HinfI >< PleI                          AccBlI ><
          >< AluI   > < SfcI         >< DdeI>< BsrI          >< PshAI   Acc65I ><
          GCTGTTAAAC TACAGAATAA TGAACTGAGT CCAGTAGCAC TACGACAGAT GTCCTGTGCG GCTGGTACCA
             12610      12620      12630      12640      12650      12660      12670

>< TthHB8I
                                                         >< TaqI
                                                         >< SfuI
                                                         >< NspV
                                                        >< MnlI
                                                         >< LspI
                                                         >< Csp45I
                                                         >< BstBI
                     >< RsaI                             >< Bsp119I
                     >< Csp6I                            >< BsiCI
                  >< AluI                                >< Bpu14I
                     >< AfaI                             >< AsuII
          CACAAACAGC TTGTACTGAT GACAATGCAC TTGCCTACTA TAACAATTCG AAGGGAGGTA GGTTTGTGCT
             12680      12690      12700      12710      12720      12730      12740

>< XhoII
                     >< Sau3AI
                     >< NdeII
                     >< MflI
                     >< MboI
                     >< DpnII
                      >< DpnI
                     >< BstYI         >< TfiI              >< RsaI
                     >< BspAI         >< RmaI                       >< Csp6I
                        >< Bsp143I       >< HinfI              >< Csp6I>< RsaI
                     >< BglII        >< MaeI   >< DdeI         >< AfaI>< AfaI
          GGCATTACTA TCAGACCACC AAGATCTCAA ATGGGCTAGA TTCCCTAAGA GTGATGGTAC AGGTACAATT
             12750      12760      12770      12780      12790      12800      12810

>< Sau96I
                                                           >< PssI
                                                          >< PalI
                                                          >< NspIV
                                 FIGURE 13.29
```

```
                                                              >< HaeIII
                                                              >< EcoO109I
                                                              >< DraII
                                                              >< Cfr13I
                                                              >< BsuRI
              >< NlaIV                                        >< BsiZI         RsaI >
              >< BsrI                                         >< BshI          Csp6I ><
              >< BscBI           > < MaeIII                   >< AsuI          AfaI >
 TACACAGAAC TGGAACCACC TTGTAGGTTT GTTACAGACA CACCAAAAGG GCCTAAAGTG AAATACTTGT
    12820      12830      12840      12850      12860      12870      12880

>< SfcI
                                                                   > < MboII
                                                                    MaeII ><
                                                                   >< Fnu4HI >< RsaI
                                                                   >< Eco57I >< Csp6I
              >< Tru9I                                                      > < BbsI
              >< MseI    >< MnlI              >< BbvI         >< AluI       >< AfaI
 ACTTCATCAA AGGCTTAAAC AACCTAAATA GAGGTATGGT GCTGGGCAGT TTAGCTGCTA CAGTACGTCT
    12890      12900      12910      12920      12930      12940      12950

>< RsaI
              >< SfcI  >< Csp6I
              >< BspWI >< AfaI   >< BspMI                           AccI ><
 TCAGGCTGGA AATGCTACAG AAGTACCTGC CAATTCAACT GTGCTTTCCT TCTGTGCTTT TGCAGTAGAC
    12960      12970      12980      12990      13000      13010      13020

>< RmaI
                        >< MnlI
                        >< MaeI        >< HphI
 CCTGCTAAAG CATATAAGGA TTACCTAGCA AGTGGAGGAC AACCAATCAC CAACTGTGTG AAGATGTTGT
    13030      13040      13050      13060      13070      13080      13090

>< SinI
                                                              >< Sau96I
                                                              >< NspIV
                                                               >< NspHII
                                                              >< NlaIII
                                                              >< Eco47I
                                                                   >< Eam1105I
                                                              >< Cfr13I
 >< RsaI     >< RsaI                                          >< BsiZI
 >< MboII    >< Csp6I                                         >< Bme18I  >< XcmI
 >< Csp6I    >< BsrI                                          >< AvaII   PleI ><
 >< AfaI     >< AfaI            >< MaeIII         >< AluI     >< AsuI> < HinfI
 GTACACACAC TGGTACAGGA CAGGCAATTA CTGTAACACC AGAAGCTAAC ATGGACCAAG AGTCCTTTGG
    13100      13110      13120      13130      13140      13150      13160

>< TfiI
              >< SfaNI                                                  >< MaeIII
              >< NlaIII   >< FokI                                  >< HinfI
 TGGTGCTTCA TGTTGTCTGT ATTGTAGATG CCACATTGAC CATCCAAATC CTAAAGGATT CTGTGACTTG
    13170      13180      13190      13200      13210      13220      13230

> < RsaI
              >< MaeII
              >< Csp6I                                             >< DdeI
              > < AfaI                          >< BsrI            >< BfrI
 AAAGGTAAGT ACGTCCAAAT ACCTACCACT TGTGCTAATG ACCCAGTGGG TTTTACACTT AGAAACACAG
    13240      13250      13260      13270      13280      13290      13300

>< ThaI
```

FIGURE 13.30

```
                                                      >< SfaNI
                                                      >< MvnI
                                                      >< BstUI
        >< RsaI                                       >< Bsp50I
        >< Csp6I                                      >< AciI
        >< AfaI    >< AciI              >< SfcI >< MaeIII    >< AccIISfaNI ><
        TCTGTACCGT CTGCGGAATG TGGAAAGGTT ATGGCTGTAG TTGTGACCAA CTCCGCGAAC CCTTGATGCA
        13310      13320      13330      13340      13350      13360      13370

>< Zsp2I
                        > < SfaNI
                   >< Mph1103I>< Tru9I
              >< Ppu10I>< MaeII                              Fnu4HI ><
                   >< NsiI> < FokI                           BsgI   ><
                   >< EcoT22I >< MseI                        >< BbvI
        >< AciI>< AvaIII    >< DraI      >< AciI      >< Fnu4HI    AciI ><
        GTCTGCGGAT GCATCAACGT TTTTAAACGG GTTTGCGGTG TAAGTGCAGC CCGTCTTACA CCGTGCGGCA
        13380      13390      13400      13410      13420      13430      13440

>< SpeI
             >< ScaI
             >< RsaI
        >< RmaI
        >< MaeI
             > < Csp6I       >< SfcI                                    >< BspWI
        >< BspWI   >< AfaI    >< AccI      >< BcgI/a                    BcgI >
        CAGGCACTAG TACTGATGTC GTCTACAGGG CTTTTGATAT TTACAACGAA AAAGTTGCTG GTTTTGCAAA
        13450      13460      13470      13480      13490      13500      13510

>< ScrFI
                                       >< MvaI
                                           >< MnlI
                                   >< EcoRII
                                   >< Ecl136I
                                   >< BstOI
                                   >< BstNI
                                       >< BslI
                                   >< DsaV >< BsiYI
                                       >< BsiLI              >< PleI
                                       >< ApyI           > < FokI  >< HinfI
        GTTCCTAAAA ACTAATTGCT GTCGCTTCCA GGAGAAGGAT GAGGAAGGCA ATTTATTAGA CTCTTACTTT
        13520      13530      13540      13550      13560      13570      13580

>< NlaIII
                                   >< Ksp632I
                                   >< EarI
        >< Tru9I                   >< Eam1104I
        >< MseI                    >< BsmAI                        >< Tru9I
        >< MnlI                    >< Alw26I        >< MboII       >< MseI
        GTAGTTAAGA GGCATACTAT GTCTAACTAC CAACATGAAG AGACTATTTA TAACTTGGTT AAAGATTGTC
        13590      13600      13610      13620      13630      13640      13650

>< RsaI
                                                            >< NlaIV
                                                          > < NlaIII
                                                               >< KpnI
                                                               >< HphI
                                                          >  < Eco64I
                                                            >< Csp6I
                                                            >< BscBI
                                                          >  < BanI
                                                          >  < Asp718
                                      FIGURE 13.31
```

```
                                              >< MaeIII   >< AfaI
        >< NspBII                                     > < AccBlI MaeII ><
        >< AciI          >< NlaIII                    > < Acc65I  > < HgaI
    CAGCGGTTGC TGTCCATGAC TTTTTCAAGT TTAGAGTAGA TGGTGACATG GTACCACATA TATCACGTCA
        13660      13670      13680      13690      13700      13710      13720

>< MnlI
                                              >< MaeII
    GCGTCTAACT AAATACACAA TGGCTGATTT AGTCTATGCT CTACGTCATT TTGATGAGGG TAATTGTGAT
        13730      13740      13750      13760      13770      13780      13790

>< Tru9I
        >< MseI          >< MaeIII >< MunI
    ACATTAAAAG AAATACTCGT CACATACAAT TGCTGTGATG ATGATTATTT CAATAAGAAG GATTGGTATG
        13800      13810      13820      13830      13840      13850      13860

>< ThaI
                                  >< MvnI
                                  >< MluI
                                  >< BstUI                    >< RsaI
                                  >< Bsp50I                   >< HphI
              >< TfiI     >< AflIII    >< DdeI     >< Csp6I   Tru9I ><
              >< HinfI    >< AccII     >< BfrI     >< AfaI    MseI ><
    ACTTCGTAGA GAATCCTGAC ATCTTACGCG TATATGCTAA CTTAGGTGAG CGTGTACGCC AATCATTATT
        13870      13880      13890      13900      13910      13920      13930

XhoII >
                                                                        Sau3AI >
                                                                         NdeII >
                                                                          MflI >
              > < SfaNI                            >< RsaI                MboI >
              >< RsaI                           > < Csp6I                DpnII >
              >< Csp6I                           >< BspWI                BstYI >
              >< AfaI     >< SfaNI                            >< AfaI   BspAI >
    AAAGACTGTA CAATTCTGCG ATGCTATGCG TGATGCAGGC ATTGTAGGCG TACTGACATT AGATAATCAG
        13940      13950      13960      13970      13980      13990      14000

> < ScrFI
                                                     > < MvaI
                                                           >< Fnu4HI
                                                  >< EcoRII
                                                     > < Ecl136I
                                                     > < BstOI
                                                     > < BstNI
        >< Tru9I                        >< RsaI                >< BslI
        >< MseI       >< RsaI         > < HphI                 >< BsiYI
        >< DpnI       >< Csp6I          >< Csp6I     > < BsiLI
        >< Bspl43I    >< BsrI         > < BbvI       > < ApyI
           >< AlwI    >< AfaI            >< AfaI     >< DsaV  >< AciI
    GATCTTAATG GAACTGGTA CGATTTCGGT GATTTCGTAC AAGTAGCACC AGGCTGCGGA GTTCCTATTG
        14010      14020      14030      14040      14050      14060      14070

>< SfaNI
                                              >< RmaI                    > < HinfI
                                  >< MamI     >< MnlI           >< Fnu4HIPleI ><
        >< TfiI    >< SfaNI       >< BsiBI    >< MaeI           >< DdeI
        >< HinfI   >< FokI        >< BsaBI    >< BbvI           >< BspWI NdeI ><
    TGGATTCATA TTACTCATTG CTGATGCCCA TCCTCACTTT GACTAGGGCA TTGGCTGCTG AGTCCCATAT
        14080      14090      14100      14110      14120      14130      14140

>< Sau3AI
        >< NdeII
```

FIGURE 13.32

```
                      >< MboI
                      >< MamI
                         >< DpnII                                                      Tth111I ><
                            >< DpnI                                                     MboII ><
                               >< BspWI                                              >< Ksp632I
                   >< BspAI                                                          >< Eam1104I
                      >< Bsp143I      >< XcmI                                           >< BsmAI
                   >< BsiBI           >< Tru9I                                       >< EarI   AspI ><
                   >< BsaBI >< FokI   >< MseI                                           >< Alw26I
              GGATGCTGAT CTCGCAAAAC CACTTATTAA GTGGGATTTG CTGAAATATG ATTTTACGGA AGAGAGACTT
                  14150      14160      14170      14180      14190      14200      14210

>  < SinI
                                                >  < Sau96I
                                                >  < NspIV
                                                   >< NspHII
                   >< TthHB8I                      >< NlaIV
                   >< TaqI                      >< FokI
                      >< McrI                   >  < Eco47I
                   >  < Ksp632I                 >  < Cfr13I
                   >  < EarI                    >  < BsiZI
                   >  < Eam1104I           >< SspI>< BscBI
              >< BsmAI          >  < Tru9I  >  < Bme18I
     >< MboII      >< BsiEI>  < MseI   >  < AvaII                              >< Tru9I
        >< Alw26I       >< DraI    >  < AsuI            >< MunI  >< MseI
              TGTCTCTTCG ACCGTTATTT TAAATATTGG GACCAGACAT ACCATCCCAA TTGTATTAAC TGTTTGGATG
                  14220      14230      14240      14250      14260      14270      14280

SinI ><
                                                                                Sau96I ><
                                                                                NspIV ><
                                                                                NspHII >
                                                                                Eco47I ><
                                                                                Cfr13I ><
                                                                                BsiZI ><
                                                                                Bme18I ><
                                             >< Tru9I                           AvaII ><
              >< FokI                        >< MseI                            AsuI ><
              ATAGGTGTAT CCTTCATTGT GCAAACTTTA ATGTGTTATT TTCTACTGTG TTTCCACCTA CAAGTTTTGG
                  14290      14300      14310      14320      14330      14340      14350

>< SpeI
     >< RmaI
     >< MaeI         >< SspI                                         >< BsrI
              ACCACTAGTA AGAAAAATAT TTGTAGATGG TGTTCCTTTT GTTGTTTCAA CTGGATACCA TTTTCGTGAG
                  14360      14370      14380      14390      14400      14410      14420

>< ThaI>< Esp3I
                                                       >< DdeI
                                                    >< BstUI
                   >< RsaI                          >< Bsp50I   >< BsmBI
     >< HinfI >< PleI                               >< MvnI>< BsmAI
              >  < Csp6I             >< HgaI>< AluI        >< Alw26I
                 >< AfaI             >< FokI >< AccII           >  < BbvI
              TTAGGAGTCG TACATAATCA GGATGTAAAC TTACATAGCT CGCGTCTCAG TTTCAAGGAA CTTTTAGTGT
                  14430      14440      14450      14460      14470      14480      14490

>< Zsp2I
                            >< SphI
                      >< Ppu10I
                            >< PaeI
                            >< NspI
```

FIGURE 13.33

```
            >< Sau3AI          >< NspHI
            >< NdeII           >< NsiI
            >< MboI            >< NlaIII
            >< DpnII           >< Mph1103I                                      >< NspI
             > < DpnI          >< Fnu4HI                             NspHI ><
     >< Fnu4HI>< BspWI         >< EcoT22I                            NlaIII ><
            >< BspAI           >< BspWI                                      >< BspWI
             > < Bsp143I>    < AvaIII >  < AlwNI          >< RmaI            >< BsgI
     >< AlwI         >< AluI         >< AluI    >< BbvI    >< MaeI           >< BbvI
     ATGCTGCTGA TCCAGCTATG CATGCAGCTT CTGGCAATTT ATTGCTAGAT AAACGCACTA CATGCTTTTC
     14500      14510      14520      14530      14540      14550      14560

>< ScrFI
                                                 >< NciI
                                                 >< MspI
                                                 >< HpaII
       >< Fnu4HI                                  >< HapII
       >< AlwNI                                  >< DsaV      >< Tru9I
       >< AluI                                   >< BcnI      >< MseI
     AGTAGCTGCA CTAACAAACA ATGTTGCTTT TCAAACTGTC AAACCCGGTA ATTTAATAA AGACTTTTAT
     14570      14580      14590      14600      14610      14620      14630

>< Tru9I                                           DdeI ><
                      >< MseI                       >< MboII             BbvI ><
     GACTTTGCTG TGTCTAAAGG TTTCTTTAAG GAAGGAAGTT CTGTTGAACT AAAACACTTC TTCTTTGCTC
     14640      14650      14660      14670      14680      14690      14700

>< FokI                                            EcoRV ><
                 >< Fnu4HI                                          Eco32I ><
     AGGATGGCAA CGCTGCTATC AGTGATTATG ACTATTATCG TTATAATCTG CCAACAATGT GTGATATCAG
     14710      14720      14730      14740      14750      14760      14770

>< VspI
                                                                    >< Tru9I
                                                                    >< MseI
                                                                    >< AsnI
                                              >< MaeIII             >< AseI
     ACAACTCCTA TTCGTAGTTG AAGTTGTTGA TAAATACTTT GATTGTTACG ATGGTGGCTG TATTAATGCC
     14780      14790      14800      14810      14820      14830      14840

>< Tru9I
                >< MseI                >< PvuII
                >< HpaI                >< Psp5I           > < XcmI
                >< HindII              >< NspBII    >< Tru9I         RmaI ><
                >< HincII              >< AluI      >< MseI          MaeI ><
     AACCAAGTAA TCGTTAACAA TCTGGATAAA TCAGCTGGTT TCCCATTTAA TAAATGGGGT AAGGCTAGAC
     14850      14860      14870      14880      14890      14900      14910

>< SfaNI             >< ThaI
                           >< Sau3AI            >< MvnI
                           >< NdeII             >< BstUI
                           >< MboI                 >< Bst1107I
                           >< DpnII             >< BspWI  >< FokI
                           >< DpnI              >< Bsp50I
     >< PleI               >< Bsp143I           >< AccII>< DdeI
          >< HinfI>< MnlI  >< BspAI >< AlwI        >< AccI
     TTTATTATGA CTCAATGAGT TATGAGGATC AAGATGCACT TTTCGCGTAT ACTAAGCGTA ATGTCATCCC
     14920      14930      14940      14950      14960      14970      14980

>< SstI
                                                            >< SduI
                                                            >< SacI
```

FIGURE 13.34

```
                                                    >< NspII
                                                    >< HgiAI
                                                    >< Eco24I
              >< Tru9I                             > < Ecl136II
           >< TfiI                                  >< Bsp1286I
              >< MseI                               >< BmyI
           >< HinfI                                 >< BanII
               > < Esp4I                            >< Alw21I
                > < AflII        >< BspWI       > < AluI      >< AluI
TACTATAACT CAAATGAATC TTAAGTATGC CATTAGTGCA AAGAATAGAG CTCGCACCGT AGCTGGTGTC
    14990      15000      15010      15020      15030      15040      15050

RmaI ><
           >< ScaI                                           > < MnlI
        >< SfcI>< RsaI                                       MaeI ><
     >< BsmAI >< Csp6I                                       >< Fnu4HI
     >< Alw26I >< AfaI                                       >< AciI
TCTATCTGTA GTACTATGAC AAATAGACAG TTTCATCAGA AATTATTGAA GTCAATAGCC GCCACTAGAG
    15060      15070      15080      15090      15100      15110      15120

>< Tru9I
     >< AluI                                         >< MseI
GAGCTACTGT GGTAATTGGA ACAAGCAAGT TTTACGGTGG CTGGCATAAT ATGTTAAAAA CTGTTTACAG
    15130      15140      15150      15160      15170      15180      15190

NspI ><
                                                              NspHI ><
                                                              NlaIII ><
                                                            >< NlaIII
                                                              DdeI ><
                                                           BspWI ><
                                      >< MaeIII             BfrI ><
TGATGTAGAA ACTCCACACC TTATGGGTTG GGATTATCCA AAATGTGACA GAGCCATGCC TAACATGCTT
    15200      15210      15220      15230      15240      15250      15260

> < PalI
       > < HaeIII
       > < BsuRI
       > < BshI        >< MnlI                     >< MaeIII      SfcI ><
AGGATAATGG CCTCTCTTGT TCTTGCTCGC AAACATAACA CTTGCTGTAA CTTATCACAC CGTTTCTACA
    15270      15280      15290      15300      15310      15320      15330

Tru9I ><
                                                                 ScrFI >
                                                                 MvaI >
                                                                >< MseI
                      >< MstI                                    FokI ><
                      >< HinP1I                                  EcoRII ><
                      >< Hin6I                                   Ecl136I >
                       > < HhaI                                  DsaV ><
                      >< FspI                                    BstOI >
                      >< FdiII          >< NlaIII                BstNI >
                       > < CfoI>< Tru9I          > < Fnu4HI      BsiLI >
    >< AluI            >< AviII >< MseI          >< AciI         ApyI >
GGTTAGCTAA CGAGTGTGCG CAAGTATTAA GTGAGATGGT CATGTGTGGC GGCTCACTAT ATGTTAAACC
    15340      15350      15360      15370      15380      15390      15400

> < SfaNI
          >< MspI
          >< HpaII       >< HphI                         >< Tru9I    MaeIII ><
          >< HapII       >< BspWI                        >< MseI     AluI ><
```

FIGURE 13.35

```
AGGTGGAACA TCATCCGGTG ATGCTACAAC TGCTTATGCT AATAGTGTCT TTAACATTTG TCAAGCTGTT
    15410      15420      15430      15440      15450      15460      15470

>< DrdI
>< BspWI                                        >< AluI      > < AciI
ACAGCCAATG TAAATGCACT TCTTTCAACT GATGGTAATA AGATAGCTGA CAAGTATGTC CGCAATCTAC
    15480      15490      15500      15510      15520      15530      15540

>< Sau3AI
                                          >< NdeII
                                          >< MboI
                                         > < MamI
                                            >< FbaI
                                          >< DpnII
                                           >< DpnI
                                            >< BspHI
                                          >< BspAI
                                            >< Bsp143I
                                          >< BsiQI
                         >< SfcI         > < BsiBI>< NlaIII
                         >< BsmAI         > < BsaBI>< FokI
                         >< Alw26I          >< BclI>< EcoRI          FokI ><
AACACAGGCT CTATGAGTGT CTCTATAGAA ATAGGGATGT TGATCATGAA TTCGTGGATG AGTTTTACGC
    15550      15560      15570      15580      15590      15600      15610

>< TfiI
                          >< SfaNI
                         >< NlaIII
           >< BspMI       >< HinfI                                  >< MaeIII
TTACCTGCGT AAACATTTCT CCATGATGAT TCTTTCTGAT GATGCCGTTG TGTGCTATAA CAGTAACTAT
    15620      15630      15640      15650      15660      15670      15680

> < RmaI
             >< NheI >< Tru9I
>< Fnu4HI     > < MaeI       >< Tru9I
>< AciI       >< AluI >< MseI  >< MseI                               MnlI ><
GCGGCTCAAG GTTTAGTAGC TAGCATTAAG AACTTTAAGG CAGTTCTTTA TTATCAAAAT AATGTGTTCA
    15690      15700      15710      15720      15730      15740      15750

>< SinI
                                          >< Sau96I
                                            >< PssI
                                           >< Psp5II
                                          >< PpuMI
                                          >< NspIV
                                           >< NspHII
                                          >< EcoO109I
                                          >< Eco47I
                                          >< DraII
                                          >< Cfr13I
                                          >< BsiZI
                         >< DdeI          >< Bme18I
><-NlaIII                >< BsmAI         >< AvaII
  >< DdeI                >< Alw26I          >< AsuI           >< MnlI
TGTCTGAGGC AAAATGTTGG ACTGAGACTG ACCTTACTAA AGGACCTCAC GAATTTTGCT CACAGCATAC
    15760      15770      15780      15790      15800      15810      15820

>< XhoII
                                          >< Sau3AI
                                          >< NdeII
                                          >< MflI
                                          >< MboI

FIGURE 13.36
```

```
                                    >< RsaI       >< DpnII
                                    >< MaeII      >< DpnI        > < SspI
              >< Tru9I               >< Csp6I      >< BstYI       HinPlI ><
              >< RmaI                >< BsaAI      >< BspMI       Hin6I ><
              >< MaeI                >< AflIII     >< BspAI       HhaI ><
    >< BspWI>< MseI                  >< AfaI       >< AlwI>< Bsp143I    CfoI ><
    AATGCTAGTT AAACAAGGAG ATGATTACGT GTACCTGCCT TACCCAGATC CATCAAGAAT ATTAGGCGCA
         15830      15840      15850      15860      15870      15880      15890

>< RsaI                               >< SfaNI
              >< TthHB8I             >< Csp6I                             >< MaeIII
              >< TaqI                >< AfaI                              BsrI ><
    GGCTGTTTTG TCGATGATAT TGTCAAAACA GATGGTACAC TTATGATTGA AAGGTTCGTG TCACTGGCTA
         15900      15910      15920      15930      15940      15950      15960

> < FokI
    >< BspWI
    TTGATGCTTA CCCACTTACA AAACATCCTA ATCAGGAGTA TGCTGATGTC TTTCACTTGT ATTTACAATA
         15970      15980      15990      16000      16010      16020      16030

>< Van91I
                                              >< PflMI
                                              >< NspI
                                    > < PalI>< NspHI
                                    > < MscI>< NlaIII
                                    > < HaeIII
                                    > < BsuRI
                                    >< BsrI
                         >< EaeI     >< BslI       >< NspI
                         > < BshI>< BsiYI       >< NspHI
              >< NlaIII              >< AflIII >< AflIII
    >< MaeIII          >< AluI  > < BalI>< AccB7I >< NlaIII
    CATTAGAAAG TTACATGATG AGCTTACTGG CCACATGTTG GACATGTATT CCGTAATGCT AACTAATGAT
         16040      16050      16060      16070      16080      16090      16100

>< RsaI> < NlaIV
              >< MnlI
              >< Csp6I    >< DdeI               >< RsaI
                         >< BsrI >< MnlI       >< Csp6I
              >< AfaI> < BscBI                  >< AfaI               SfcI ><
    AACACCTCAC GGTACTGGGA ACCTGAGTTT TATGAGGCTA TGTACACACC ACATACAGTC TTGCAGGCTG
         16110      16120      16130      16140      16150      16160      16170

>< NlaIV
                                                        >< EcoNI
                                                        >< Eco31I
                                              >< Eco64I>< BsmAI
                                              >< BscBI >< BslI
                                              >< BanI      >< BsiYI
                                              >< AciI     >< BsaI
    >< BspWI                                           >< AccB1I>< Alw26I     BbvI ><
    TAGGTGCTTG TGTATTGTGC AATTCACAGA CTTCACTTCG TTGCGGTGCC TGTATTAGGA GACCATTCCT
         16180      16190      16200      16210      16220      16230      16240

>< Tth111I
              >< Fnu4HI   >< NlaIII                              > < Tru9I
              >< BspWI >< AspI                                   > < MseI
    ATGTTGCAAG TGCTGCTATG ACCATGTCAT TTCAACATCA CACAAATTAG TGTTGTCTGT TAATCCCTAT
         16250      16260      16270      16280      16290      16300      16310

>< ScrFI
              >< MvaI
```

FIGURE 13.37

```
                        >< EcoRII
                           >< Ecl136I
                        >< DsaV
                           >< BstOI
                           >< BstNI
                           >< BsiLI                              >< RmaI
                        >< BsaJI                          >< MnlI            BspWI ><
                           >< ApyI    >< MaeIII >< MaeIII     >< MaeI        >< AluI
GTTTGCAATG CCCCAGGTTG TGATGTCACT GATGTGACAC AACTGTATCT AGGAGGTATG AGCTATTATT
   16320      16330      16340      16350      16360      16370      16380

>< MaeIII             >< MnlI
GCAAGTCACA TAAGCCTCCC ATTAGTTTTC CATTATGTGC TAATGGTCAG GTTTTTGGTT TATACAAAAA
   16390      16400      16410      16420      16430      16440      16450

>< NspI                                              >< NspI
      >< NspHI      > < Tth111I                            >< NspHI
      >< NlaIII>< MaeIII>< MaeIII                          >< NlaIII
   >< AflIII       >< AspI                        >< AflIII
CACATGTGTA GGCAGTGACA ATGTCACTGA CTTCAATGCG ATAGCAACAT GTGATTGGAC TAATGCTGGC
   16460      16470      16480      16490      16500      16510      16520

>< RsaI
                       >< PleI
                       >< DdeI
                    >< Csp6I
                    >< BsmAI  >< HinfI                           >< MnlI
                    >< Alw26I    >< HindIII                   DdeI ><
                    >< AfaI      >< AluI  >< Fnu4HI     >< BbvI
GATTACATAC TTGCCAACAC TTGTACTGAG AGACTCAAGC TTTTCGCAGC AGAAACGCTC AAAGCCACTG
   16530      16540      16550      16560      16570      16580      16590

> < ThaI
                                              >< ScaI
                                  >< RsaI    >< RsaI
                                  > < MvnI
                                  >< Csp6I  >< Csp6I
                                     > < BstUI
         > < Tru9I                    > < Bsp50I
         > < MseI    > < NdeI      >< AfaI   >< AfaI
               >< AluI             > < AccII                 MnlI >
AGGAAACATT TAAGCTGTCA TATGGTATTG CCACTGTACG CGAAGTACTC TCTGACAGAG AATTGCATCT
   16600      16610      16620      16630      16640      16650      16660

MaeIII ><
                                                               >< MaeIII
                                                               >< EcoO65I
                                                               >< Eco91I
                                                               >< BstPI
      >< SfaNI              >< RmaI                            >< BstEII
      >< NlaIII             >< MaeI                              >< BsrI
TTCATGGGAG GTTGGAAAAC CTAGACCACC ATTGAACAGA AACTATGTCT TTACTGGTTA CCGTGTAACT
   16670      16680      16690      16700      16710      16720      16730

RsaI ><
                                                                 >< MnlI
                                                                 >< HphI
          >< RsaI      >< RsaI                                 Csp6I ><
          >< Csp6I     >< Csp6I          >< SfaNI
          >< AfaI      >< AfaI           >< MaeIII     >< HphI AfaI ><
AAAAATAGTA AAGTACAGAT TGGAGAGTAC ACCTTTGAAA AAGGTGACTA TGGTGATGCT GTTGTGTACA
   16740      16750      16760      16770      16780      16790      16800
```

FIGURE 13.38

```
                    >< RsaI                                                  >< HphI
                    >< Csp6I                                                 >< HindII                      DdeI ><
                    >< AfaI                                                  >< HincII                      BfrI ><
          GAGGTACTAC GACATACAAG TTGAATGTTG GTGATTACTT TGTGTTGACA TCTCACACTG TAATGCCACT
              16810      16820      16830      16840      16850      16860      16870

>< VneI
                    >< SnoI
                      >< SduI
                      >< NspII
                      >< HgiAI                   > < SduI
                    >< DraIII                    > < NspII
                      >< Bsp1286I                > < HgiAI
                      >< BmyI           >< BspWI >< DraIII              >< RsaI
          >< ApaLI   >< RmaI            > < Bsp1286I                    >< Csp6I
          >< Alw44I  >< MaeI            > < BmyI              >< BsrI
                     >< Alw21I          > < Alw21I                      >< AfaI           DdeI >
          TAGTGCACCT ACTCTAGTGC CACAAGAGCA CTATGTGAGA ATTACTGGCT TGTACCCAAC ACTCAACATC
              16880      16890      16900      16910      16920      16930      16940

StyI ><
                                                                            SinI >
                                                                          Sau96I >
                                                                           NspIV >
                                                                        EcoT14I ><
                                                                          Eco47I >
                                                                         Eco130I ><
                                                                   >< ScaI  Cfr13I >
                                                                            BssTII ><
                                                                >< SphI >< RsaI   BsiZI >
                                                                >< PaeI         BsaJI ><
                                                                >< NlaIII         Bme18I >
                               >< RmaI                          >< NspI>< Csp6I   AvaII >
                               >< MaeI                          >< NspHI>< AfaI    AsuI >
          TCAGATGAGT TTTCTAGCAA TGTTGCAAAT TATCAAAAGG TCGGCATGCA AAAGTACTCT ACACTCCAAG
              16950      16960      16970      16980      16990      17000      17010

>< ScrFI
                          >< RsaI
                    >< MvaI
                    >< EcoRII
                    >< Ecl136I
                      > < Csp6I
                    >< BstOI
                    >< BstNI
          >< XcmI    >< BslI
          >< NspHII  >< BsiYI
                     >< BsiLI
                     >< ApyI       >< BsrI
                   >< DsaV>< AfaI    > < HinfI>< PleI
          GACCACCTGG TACTGGTAAG AGTCATTTTG CCATCGGACT TGCTCTCTAT TACCCATCTG CTCGCATAGT
              17020      17030      17040      17050      17060      17070      17080

>< SfaNI
                     >< SphI      >< PvuII
                     >< PaeI      >< Psp5I
                     >< NspI      >< NspBII
                     >< NspHI  >< Fnu4HI                          > < Tru9I
          >< Bst1107I        > < NlaIII>< BspWI                      >< SspI
          >< AccI    >< NlaIII   >< AluI    >< BbvI             > < MseI
          GTATACGGCA TGCTCTCATG CAGCTGTTGA TGCCCTATGT GAAAAGGCAT TAAAATATTT GCCCATAGAT
              17090      17100      17110      17120      17130      17140      17150
```

FIGURE 13.39

```
                                    > < ThaI
                                  >< ThaI
                                    > < MvnI
                                  >< MvnI      >< ThaI
                                    > < HinP1I
                                  >< HinP1I
                              >< HinP1I  >< MvnI
                                    > < Hin6I
                                  >< Hin6I
                                    > < HhaI
                                  >< HhaI  >< HhaI
                                    > < CfoI
                                 >< CfoI   >< CfoI
                                    > < BstUI
                                  >< BstUI >< BstUI
                                     >< BssHII
                                     >< BspMI
                                    > < Bsp50I
                                 >< Bsp50I>< Bsp50I                        RmaI >
              >< TfiI       >< Hin6I> < AccII                              MaeI >
              >< HinfI        >< AccII >< AccII                    > < EcoRI
AAATGTAGTA GAATCATACC TGCGCGTGCG CGCGTAGAGT GTTTTGATAA ATTCAAAGTG AATTCAACAC
   17160      17170      17180      17190      17200      17210      17220

>< Zsp2I
                                  >< Ppu10I
                                     >< NsiI
                                     >< Mph1103I
                                     >< EcoT22I
   >< BsgI                 > < AvaIII                           >< DrdI
TAGAACAGTA TGTTTTCTGC ACTGTAAATG CATTGCCAGA AACAACTGCT GACATTGTAG TCTTTGATGA
   17230      17240      17250      17260      17270      17280      17290

>< RmaI
                                             >< MaeI                    >< MaeII
AATCTCTATG GCTACTAATT ATGACTTGAG TGTTGTCAAT GCTAGACTTC GTGCAAAACA CTACGTCTAT
   17300      17310      17320      17330      17340      17350      17360

>< Sau3AI
          >< NdeII
          >< MboI
          >< DpnII
           >< DpnI
          >< BspAI                                             >< RmaI
>< AlwI>< Bsp143I                                              >< MaeI SspI ><
ATTGGCGATC CTGCTCAATT ACCAGCCCCC CGCACATTGC TGACTAAAGG CACACTAGAA CCAGAATATT
   17370      17380      17390      17400      17410      17420      17430

>< SinI
                              >< Sau96I
                              >< NspIV         >< StyI
                               >< NspHII  >< NspI
                              >< Eco47I   >< NspHI
                              >< Cfr13I   >< NlaIII
                              >< Bsi2I        >< EcoT14I
                             >< BsgI           >< Eco130I
                              >< Bme18I        >< BssT1I
   >< Tru9I                   >< AvaII         >< BsaJI
   >< MseI                    >< AsuI> < AflIII
TTAATTCAGT GTGCAGACTT ATGAAAACAA TAGGTCCAGA CATGTTCCTT GGAACTTGTC GCCGTTGTCC
   17440      17450      17460      17470      17480      17490      17500
```

FIGURE 13.40

```
                        >< HindII
                        >< HincII                      >< AluI
        TGCTGAAATT  GTTGACACTG  TGAGTGCTTT  AGTTTATGAC  AATAAGCTAA  AAGCACACAA  GGATAAGTCA
           17510       17520       17530       17540       17550       17560       17570

>< AluI                                         >< NlaIII
        GCTCAATGCT  TCAAAATGTT  CTACAAAGGT  GTTATTACAC  ATGATGTTTC  ATCTGCAATC  AACAGACCTC
           17580       17590       17600       17610       17620       17630       17640

>< MnlI
        >< EcoNI
          >< BslI                                                   >< HphI
          >< BsiYI                                                  >< AluI
        AAATAGGCGT  TGTAAGAGAA  TTTCTTACAC  GCAATCCTGC  TTGGAGAAAA  GCTGTTTTTA  TCTCACCTTA
           17650       17660       17670       17680       17690       17700       17710

>< SfcI       >< DdeI                  >< TfiI
                      > < AluI     >< BfrI                  >< HinfI
        TAATTCACAG  AACGCTGTAG  CTTCAAAAAT  CTTAGGATTG  CCTACGCAGA  CTGTTGATTC  ATCACAGGGT
           17720       17730       17740       17750       17760       17770       17780

> < HindII
                     >< Tth111I                                              > < HincII
                     >< AspI                                                    >< AciI
        TCTGAATATG  ACTATGTCAT  ATTCACACAA  ACTACTGAAA  CAGCACACTC  TTGTAATGTC  AACCGCTTCA
           17790       17800       17810       17820       17830       17840       17850

>< XhoII
                                                                    >< Sau3A
                                                                    >< NdeII
                                                                    >< MflI
                                                                    >< MboI
                                                                    >< MamI
                                                                    >< DpnII
                                                                      >< DpnI
                                                                    >< BstYI
                                                                    >< BspAI
                                                                      >< Bsp143I
                                                                    >< BsiBI
                                                                    >< BsaBI
                                                 >< BspWI            >< BglII
        ATGTGGCTAT  CACAAGGGCA  AAAATTGGCA  TTTTGTGCAT  AATGTCTGAT  AGAGATCTTT  ATGACAAACT
           17860       17870       17880       17890       17900       17910       17920

>< XbaI
                    >< RmaI
                    >< MaeI      >< MaeII                           >< MaeIII
         GCAATTTACA AGTCTAGAAA  TACCACGTCG  CAATGTGGCT  ACATTACAAG  CAGAAAATGT  AACTGGACTT
           17930       17940       17950       17960       17970       17980       17990

>< Sau3AI
                     >< NdeII
                          >< MboII
                     >< MboI
                      > < FokI
                     >< DpnII                         >< NlaIV
                       >< DpnI                        >< Eco64I
                     >< BspAI                         >< BscBI
        >< Tru9I     >< Bsp143I                       >< BanI             MnlI ><
        >< MseI>< SfcI      >< BbsI  > < BsrI         >< AccBII           >< DdeI
```

FIGURE 13.41

```
TTTAAGGACT GTAGTAAGAT CATTACTGGT CTTCATCCTA CACAGGCACC TACACACCTC AGCGTTGATA
    18000      18010      18020      18030      18040      18050      18060
                                              >< ScrFI
                                              >< MvaI
                                           >< EcoRII
                                           >< Eco57I
                                              >< Ecl136I
                                           >< DsaV
                                              >< BstOI                    >< PleI
                                              >< BstNI                 >< NlaIII
                                 >< HindII >< BsiLI                    HinfI ><
                                 >< HincII >< ApyI                      AccI ><
TAAAGTTCAA GACTGAAGGA TTATGTGTTG ACATACCAGG CATACCAAAG GACATGACCT ACCGTAGACT
    18070      18080      18090      18100      18110      18120      18130

>< MaeIII               ThaI ><
                                    >< Eco0651             MvnI ><
                                    >< Eco91I              BstUI ><
                             >< BstXI                      Bsp50I ><
                                    >< BstPI                      >< AciI
                                    >< BstEII    >< HphI   AccII ><
CATCTCTATG ATGGGTTTCA AAATGAATTA CCAAGTCAAT GGTTACCCTA ATATGTTTAT CACCCGCGAA
    18140      18150      18160      18170      18180      18190      18200

>< XmnI
   > < MboII                                              >< SfaNI
   > < MaeIII                                                >< RmaI
>< Asp700I                                                >< NlaIII
>< AluI    >< MaeII           >< MnlI                        >< MaeI
GAAGCTATTC GTCACGTTCG TGCGTGGATT GGCTTTGATG TAGAGGGCTG TCATGCAACT AGAGATGCTG
    18210      18220      18230      18240      18250      18260      18270

>< Tru9I
                                   >< MseI
>< RsaI                            >< HpaI
>< GsuI          >< RmaI           >< HindII       >< RsaI
>< Csp6I         >< MnlI           >< HincII       >< Csp6I
>< BpmI          >< MaeI                      >< DdeI >< AluI   BsrI ><
>< AfaI          >< AluI    >< SfcI        >< BfrI       >< AfaI
TGGGTACTAA CCTACCTCTC CAGCTAGGAT TTTCTACAGG TGTTAACTTA GTAGCTGTAC CGACTGGTTA
    18280      18290      18300      18310      18320      18330      18340

>< ScrFI
                                                              >< MvaI
                                                                >< MnlI
                                                                >< MaeII
                                                           >< EcoRII
                                                              >< Eco0651
                                                           >< EcoNI
                                                              >< Ecc91I
                                                           >< Ecl136I
                                                           >< DsaV  Tru9I ><
                                                              >< DraIII
                                                              >< BstPI
                                                           >< BstOI
                                                              >< BstNI  PmeI ><
                                                              >< BstEII
                                                           >< BslI   MseI ><
                                                           >< BsiYI    HphI ><
>< HindII    >< HphI              >< Tru9I                 >< BsiLI  DraI ><
>< HincII         >< EcoRI        >< MseI                  >< ApyI >< BsrI
```

FIGURE 13.42

```
TGTTGACACT GAAAATAACA CAGAATTCAC CAGAGTTAAT GCAAAACCTC CACCAGGTGA CCAGTTTAAA
     18350      18360      18370      18380      18390      18400      18410
                                      >< ScrFI
                                      >< MvaI
                                      >< EcoRII
                                       >< Ecl136I
                                      >< DsaV
                                        >< BstOI
                                         >< BstNI                         >< RsaI
                                         >< BsiLI                             DdeI ><
                                         >< BsaJI            >  < Tru9I>< Csp6I
                    >< NlaIII            >< ApyI             >  < MseI  >< AfaI
CATCTTATAC CACTCATGTA TAAAGGCTTG CCCTGGAATG TAGTGCGTAT TAAGATAGTA CAAATGCTCA
     18420      18430      18440      18450      18460      18470      18480

>< NlaIII
                                                   >< HinP1I
                       >< Tth111I                  >< Hin6I
                       >< HinfI                    >  < HhaI
                       >< AspI        >< PleI      >  < CfoI         >< AluI
GTGATACACT GAAAGGATTG TCAGACAGAG TCGTGTTCGT CCTTTGGGCG CATGGCTTTG AGCTTACATC
     18490      18500      18510      18520      18530      18540      18550

>< SinI
                       >< Sau96I
                       >< NspIV
                        >< NspHII
                       >< Eco47I
                       >< Cfr13I
         >< ScaI       >< BsiZI
         >< RsaI       >< Bme18I
         >< Csp6I      >< AvaII   >< MaeII
         >< AfaI       >< AsuI    >< AflIII    >< MaeIII>< MaeII
AATGAAGTAC TTTGTCAAGA TTGGACCTGA AAGAACGTGT TGTCTGTGTG ACAAACGTGC AACTTGCTTT
     18560      18570      18580      18590      18600      18610      18620

>  < TfiI                  >< Tth111I
                              >  < HinfI                 >  < AspI
TCTACTTCAT CAGATACTTA TGCCTGCTGG AATCATTCTG TGGGTTTTGA CTATGTCTAT AACCCATTTA
     18630      18640      18650      18660      18670      18680      18690

>< ScrFI
                                                                   RsaI ><
                                                                      >< MvaI
                                                                      >< EcoRII
                                                                  Ecl136I ><
                                                                      >< DsaV
                                                                   Csp6I ><
                                                                       BstXI ><
                                            >  < MaeIII                 >< BstOI
                                            >  < EcoO65I                >< BstNI
                                            >  < Eco91I                 >< BsiLI
                                            >  < BstPI                  >< ApyI
                      >< Eco57I> < BstEII    >< MaeIII >< NlaIII     AfaI ><
TGATTGATGT TCAGCAGTGG GGCTTTACGG GTAACCTTCA GAGTAACCAT GACCAACATT GCCAGGTACA
     18700      18710      18720      18730      18740      18750      18760
         >< SfaNI
          >< RmaI
         >< NspI
         >< NspHI
```

FIGURE 13.43

```
                      >< NlaIII                  >< RmaI
                        >< MaeI                  >< NlaIII                  Tru9I ><
  >< NlaIII      >< BspWI                   >< MaeI                  >< NlaIII
       > < AflIII                  >< BspHI                                   MseI ><
  TGGAAATGCA CATGTGGCTA GTTGTGATGC TATCATGACT AGATGTTTAG CAGTCCATGA GTGCTTTGTT
     18770      18780      18790      18800      18810      18820      18830

>< ThaI
        >< MvnI
     >< HinPlI
      >< Hin6I
        >< HhaI
        >< CfoI
        >< BstUI                          >< EcoNI> < MnlI
        >< Bsp50I                         >< BslI                >< Tru9I
        >< AccII                          >< BsiYI      >< DdeI >< MseI
  AAGCGCGTTG ATTGGTCTGT TGAATACCCT ATTATAGGAG ATGAACTGAG GGTTAATTCT GCTTGCAGAA
     18840      18850      18860      18870      18880      18890      18900

>< RsaI
        >< Csp6I                                          >< MboII        > < NlaIII
        >< AfaI    >< NlaIII       >< BspWI                >< BsrI >< BspHI
  AAGTACAACA CATGGTTGTG AAGTCTGCAT TGCTTGCTGA TAAGTTTCCA GTTCTTCATG ACATTGGAAA
     18910      18920      18930      18940      18950      18960      18970

>< SauI
                              >< MstII
                              >< Eco81I
                              >< DdeI                                 NlaIII ><
                              >< CvnI                                 >< EspI
                              >< Bsu36I                        >< Eco57I MaeIII ><
                              >< Bse21I                                 >< DdeI
                              >< AxyI                                   >< CelII
                              >< AocI     >< MnlI      >< SfaNI      >< Bpu1102I
  TCCAAAGGCT ATCAAGTGTG TGCCTCAGGC TGAAGTAGAA TGGAAGTTCT ACGATGCTCA GCCATGTAGT
     18980      18990      19000      19010      19020      19030      19040

>< MnlI              >< Ksp632I
        >< HindIII                 >< EarI
           >< AluI    >< MboII     >< Eam1104I
  GACAAAGCTT ACAAAATAGA GGAACTCTTC TATTCTTATG CTACACATCA CGATAAATTC ACTGATGGTG
     19050      19060      19070      19080      19090      19100      19110

>< Sau3AI
                              >< NdeII
                              >< MboI
                            : MaeII> < MaeIII
                              >< DpnII
                                >< DpnI
                              >< BspAI                                     HinfI >
                  >< MaeIII  >< Bsp143I         >< MunI              DrdI ><
  TTTGTTTGTT TTGGAATTGT AACGTTGATC GTTACCCAGC CAATGCAATT GTGTGTAGGT TTGACACAAG
     19120      19130      19140      19150      19160      19170      19180

Zsp2I ><
                                                                      >< SphI
                                                                   > < Ppu10I
                                                                      >< PaeI
                                                                      >< NspI
                        >< ScrFI                                      >< NspHI
                        >< MvaI                                       >< NlaIII
                        >< EcoRII                                 Mph1103I ><
```

FIGURE 13.44

```
                        >< Ecl136I                      >< GsuI
                        >< DsaV                         EcoT22I ><
                        >< BstOI                               >< BsmI
                        >< BstNI                        >< BscCI
                        >< BsiLI                        >< BpmI >< NsiI
        >< PleI         >< ApyI                                 >< AvaIII
AGTCTTGTCA AACTTGAACT TACCAGGCTG TGATGGTGGT AGTTTGTATG TGAATAAGCA TGCATTCCAC
     19190      19200      19210      19220      19230      19240      19250

>< Tru9I
                                     > < MunI
            >< TthHB8I               >< MseI
>< BcgI/a   >< TaqI                  >< DraI
        >< AluI                      >< BcgI
ACTCCAGCTT TCGATAAAAG TGCATTTACT AATTTAAAGC AATTGCCTTT CTTTTACTAT TCTGATAGTC
     19260      19270      19280      19290      19300      19310      19320

>< PleI                                   SfaNI ><
              >< NlaIII                                        >< MaeII
              >< BsmAI                                  BsaAI ><
        >< HinfI>< Alw26I                               AflIII ><
CTTGTGAGTC TCATGGCAAA CAAGTAGTGT CGGATATTGA TTATGTTCCA CTCAAATCTG CTACGTGTAT
     19330      19340      19350      19360      19370      19380      19390

Zsp2I >
                                                               >< ScaI
                                                         Ppu10I ><
                                                               >< RsaINsiI >
                                                          Mph1103I >
                                                         >< SfaNIEcoT22I >
                                                      > < RsaI >< Csp6I
                                                        >< Csp6I        AvaIII ><
                                              >< NlaIII> < AfaI  >< AfaI
TACACGATGC AATTTAGGTG GTGCTGTTTG CAGACACCAT GCAAATGAGT ACCGACAGTA CTTGGATGCA
     19400      19410      19420      19430      19440      19450      19460

>< FokI
TATAATATGA TGATTTCTGC TGGATTTAGC CTATGGATTT ACAAACAATT TGATACTTAT AACCTGTGGA
     19470      19480      19490      19500      19510      19520      19530

>< ScrFI
            >< MvaI
              >< MaeIII
        >< EcoRII
        >< Ecl136I
     >< DsaV
        >< BstOI
        >< BstNI
        >< BsiLI                                        >< Tru9I
        >< ApyI                                         >< MseI
ATACATTTAC CAGGTTACAC                         TAATGTTGTT AATAAAGGAC ACTTTGATGG
     19540      19550      19560      19570      19580      19590      19600

>< SgrAI
 >< NaeI
  >< MspI                              > < VspI
  >< HpaII                             > < Tru9I
  >< HapII                             > < MseI
  >< Cfr10I                            > < AsnI
        >< BspWI                       > < AseI
ACACGCCGGC GAAGCACCTG TTTCCATCAT TAATAATGCT GTTTACACAA AGGTAGATGG TATTGATGTG
     19610      19620      19630      19640      19650      19660      19670
```

FIGURE 13. 45

```
                     >< XhoII
                     >< Sau3AI
                     >< NdeII
                     >< MflI
                     >< MboI
                     >< DpnII
                       >< DpnI                                                            >< MaeIII
                     >< BstYI                                                             >< EspI
                     >< BspAI                                                             >< DdeITru9I ><
                       >< Bsp143I                 >< Tru9I                                >< CelIIMseI ><
                     >< BglII                     >< MseI             >< AluI  >< Bpu102I
          GAGATCTTTG AAAATAAGAC AACACTTCCT GTTAATGTTT CATTTGAGCT TTGGGCTAAG CGTAACATTA
               19680      19690      19700      19710      19720      19730      19740

>< Fnu4HI
                                  >< Tru9I                    >< EcoRV
             >< BsrI              >< MseI           >< BbvI   >< Eco32I
          AACCAGTGCC AGAGATTAAG ATACTCAATA ATTTGGGTGT TGATATCGCT GCTAATACTG TAATCTGGGA
               19750      19760      19770      19780      19790      19800      19810

>< NspI
                                            >< NspHI
                                            >< NlaIII
                                            >< BsgI
                                 >< AflIII
          CTACAAAAGA GAAGCCCCAG CACATGTATC TACAATAGGT GTCTGCACAA TGACTGACAT TGCCAAGAAA
               19820      19830      19840      19850      19860      19870      19880

>< DdeI>< MboII                                                       >< AccI
          CCTACTGAGA GTGCTTGTTC TTCACTTACT GTCTTGTTTG ATGGTAGAGT GGAAGGACAG GTAGACCTTT
               19890      19900      19910      19920      19930      19940      19950

SinI ><
                                                                                 Sau96I ><
                                                                                  NspIV ><
                                                                                 NspHII ><
                                                                                  NlaIV ><
                                                                                  Eco47I ><
                                                                                  Cfr13I ><
                                                                                   >< BslI
                                                                                  BsiZI ><
                                                                                   >< BsiYI
                                                                                  BscBI ><
                                                                                  Bme18I ><
                                  >< Tru9I                                         AvaII ><
                                  >< MseI                                          AsuI ><
          TTAGAAACGC CCGTAATGGT GTTTTAATAA CAGAAGGTTC AGTCAAAGGT CTAACACCTT CAAAGGGACC
               19960      19970      19980      19990      20000      20010      20020

>< VspI
                                  >< Tru9I
                                  >< PleI
             >< RmaI              >< MseI                                         Tru9I ><
             >< NheI              >< MaeIII                                       >< Tru9I
             >< MaeI              >< AsnI   >< TfiI                               MseI ><
          >< HgaI>< AluI          >< HinfI>< AseI   >< HinfI                      >< MseI
          AGCACAAGCT AGCGTCAATG GAGTCACATT AATTGGAGAA TCAGTAAAAA CACAGTTTAA CTACTTTAAG
               20030      20040      20050      20060      20070      20080      20090

>< DdeI    >< MnlI   Tru9I ><
                                                                 >< BsmAI   >< DdeI
```

FIGURE 1346

```
                    >< AccI                                               >< Alw26I   >< BfrIMseI ><
           AAAGTAGACG GCATTATTCA ACAGTTGCCT GAAACCTACT TTACTCAGAG CAGAGACTTA GAGGATTTTA
              20100      20110      20120      20130      20140      20150      20160
                                          >< TthHB8I
                                          >< TaqI
                                                  >< SstI
                                                  >< SduI                           XhoI ><
                                                  >< SacI                        TthHB8I >
                                            > < PaeR7I                              TaqI >
                                            > < NspIII                              SlaI ><
                                                  >< NspII                        PaeR7I ><
                                                  >< HgiAI                        NspIII ><
                                            > < Eco88I                              >< MnlI
                    >< XcmI              > < XhoI>< Eco24I                        Eco88I ><
           >< Sau3AI                         >< Ecl136II                            CcrI ><
           >< NdeII                      > < SlaI>< Bsp1286I                      BspWI ><
           >< MboI                       > < CcrI>< BmyI                            BcoI ><
           >< DpnII                      > < BcoI>< BanII                        > < BcgI/a
              >< DpnI                    > < Ama87I                                  AvaI ><
           >< BspAI                      > < AvaI>< Alw21I                         Ama87I ><
             >< Bsp143I                          >< AluI       >< EcoRI   >< FokIAluI ><
           AGCCCAGATC ACAAATGGAA ACTGACTTTC TCGAGCTCGC TATGGATGAA TTCATACAGC GATATAAGCT
              20170      20180      20190      20200      20210      20220      20230
                          >< TthHB8I
                          >< TaqI
                          >< SfuI
                          >< NspV
                          >< LspI
                          >< Csp45I
                          >< BstBI
                          >< Bsp119I
                          >< BsiCI                                        >< MboII
                          >< Bpu14I                                       >< BbsI     Tru9I ><
                          >< AsuII   >< BcgI            >< NlaIII   >< AciIMseI ><
           CGAGGGCTAT GCCTTCGAAC ACATCGTTTA TGGAGATTTC AGTCATGGAC AACTTGGCGG TCTTCATTTA
              20240      20250      20260      20270      20280      20290      20300
                           >< HphI
                       >< HinP1I
                       >< Hin6I
              >< EspI       > < HhaI >< TfiI
              >< DdeI           >< HaeII
              >< CelII    >< Eco47III        >< Tru9I
              >< Bpu1102I > < CfoI >< HinfI  >< MseI
              >< BfrI        >< Bsp143II     >< MnlI
           ATGATAGGCT TAGCCAAGCG CTCACAAGAT TCACCACTTA AATTAGAGGA TTTTATCCCT ATGGACAGCA
              20310      20320      20330      20340      20350      20360      20370
                              >< MstI
                          >< HinP1I                                       Sau3AI ><
                          >< Hin6I                                        NdeII ><
                            >< HhaI                                       MboI ><
                            >< FspI                                       DpnII ><
                            >< FdiII                                       DpnI ><
                            >< CfoI                                       BspAI ><
                >< SfaNI    >< AviII                                     Bsp143I ><
           CAGTGAAAAA TTACTTCATA ACAGATGCGC AAACAGGTTC ATCAAAATGT GTGTGTTCTG TGATTGATCT
              20380      20390      20400      20410      20420      20430      20440
                   >< TthHB8I
```

FIGURE 13.47

```
                    >< Tth111I
                    >< TaqI
            >< AspI              > < MaeIII                     MaeIII ><
TTTACTTGAT  GACTTTGTCG  AGATAATAAA  GTCACAAGAT  TTGTCAGTGA  TTTCAAAAGT  GGTCAAGGTT
   20450       20460       20470       20480       20490       20500       20510

>< NspI
                                                              >< NspHI
                                                              >< NlaIII
                                                              >< FokI
>< MunI                             > < NlaIII             >< AflIII
ACAATTGACT  ATGCTGAAAT  TTCATTCATG  CTTTGGTGTA  AGGATGGACA  TGTTGAAACC  TTCTACCCAA
   20520       20530       20540       20550       20560       20570       20580

>< SfaNI
                         >< ScrFI
                         >< MvaI
                         >< EcoRII
                         >< Ecl136I
                         >< DsaV
                         >< BstOI              >< SfaNI
                         >< BstNI                   >< RsaI    BspWI ><
                         >< BsiLI              > < Csp6I            BsmI >
            >< BspWI     >< ApyI               >< AfaI    BscCI ><
AACTACAAGC  AAGTCAAGCG  TGGCAACCAG  GTGTTGCGAT  GCCTAACTTG  TACAAGATGC  AAAGAATGCT
   20590       20600       20610       20620       20630       20640       20650

>< Eco57I  >< MaeIII                >< HphI
TCTTGAAAAG  TGTGACCTTC  AGAATTATGG  TGAAAATGCT  GTTATACCAA  AAGGAATAAT  GATGAATGTC
   20660       20670       20680       20690       20700       20710       20720

> < RsaI
                                                >< Csp6I
>< Bst1107I             >< Tru9I                >< AluI
>< AccI                 >< MseI                 > < AfaINlaIII ><
GCAAAGTATA  CTCAACTGTG  TCAATACTTA  AATACACTTA  CTTTAGCTGT  ACCCTACAAC  ATGAGAGTTA
   20730       20740       20750       20760       20770       20780       20790

>< ScrFI
                                    >< RsaI
                                    >< MvaI
                                    >< EcoRII   >< NspBII
                                    >< Ecl136I           >< SduI
                                    > < Csp6I           >< NspII
                                    >< BstOI  >< PvuII>< HgiAI
                                    >< BstNI            >< DdeI
                                    >< BsiLI  >< Psp5I>< Bsp1286
                                    >< ApyI   >< AluI  >< BmyI
                                    >< DsaV>< AfaI       >< Alw21I
TTCACTTTGG  TGCTGGCTCT  GATAAAGGAG  TTGCACCAGG  TACAGCTGTG  CTCAGACAAT  GGTTGCCAAC
   20800       20810       20820       20830       20840       20850       20860

>< XhoII
                >< Tru9I
            >< Sau3AI
            >< NdeII
>< TthHB8I      >< MseI
            >< MflI
            >< MboI
            >< MamI
            >< DpnII
>< TfiI  >< DpnI
```

FIGURE 13. 48

```
                    >< BstYI                              > < TfiI
                    >< BspAI                              > < HinfI
             >< HinfI>< Bsp143I          >< Esp3I              >< Tru9I
                    >< BsiBI      >< Tth111I  >< BsmBI         >< MseI
                    >< BsaBI                  >< BsmAI         > < BsmAI
   >< BsrI    >< TaqI >< BglII  >< AspI   >< Alw26I  >< HgaI> < Alw26I
   TGGCACACTA CTTGTCGATT CAGATCTTAA TGACTTCGTC TCCGACGCAG ATTCTACTTT AATTGGAGAC
       20870      20880      20890      20900      20910      20920      20930

>< StyI
                                                                   >< SinI
                                                                   >< Sau96I
                              > < SinI                          >< RmaI
                              > < Sau96I                           >< NspIV
                                >< PssI                      NspHII ><
                                >< Psp5II                       >< MaeI
                              > < PpuMI                         >< EcoT14I
                              > < NspIV                            >< Eco47I
                                >< NspHII                       >< Eco130I
                                >< NlaIV                           >< Cfr13I
                              > < EcoO109I                      >< BssTlI
                              > < Eco47I                           >< BsiZI
                              > < DraII                         >< BsaJI
                              > < Cfr13I                           >< Bme18I
                              > < Bsi2I                         >< BlnI
                                >< BscBI                        >< AvrII
                >< RsaI       > < Bme18I                           >< AvaII
             > < Csp6I        > < AvaII                         >< AsuI
                >< AfaI       > < AsuI                       AflIII ><
   TGTGCAACAG TACATACGGC TAATAAATGG GACCTTATTA TTAGCGATAT GTATGACCCT AGGACCAAAC
       20940      20950      20960      20970      20980      20990      21000

>< NspI
   >< NspHI
   >< NlaIII  >< PleI                                                RmaI ><
   >< MaeIII        >< HinfI                                         MaeI ><
   ATGTGACAAA AGAGAATGAC TCTAAAGAAG GGTTTTTCAC TTATCTGTGT GGATTTATAA AGCAAAAACT
       21010      21020      21030      21040      21050      21060      21070

>< ScrFI
   >< MvaI
   >< EcoRII
   >< Ecl136I
   >< DsaV
     >< BstOI                                                       Sau96I >
     >< BstNI                                                       NspIV >
     >< BsiLI                                                       Cfr13I >
     >< BsaJI                                                       BsiZI >
     >< BsaJI  >< SfcI              >< BsmI        >< BsmI          AsuI >
     >< ApyI      > < AluI       >< BscCI       >< BscCIHindIII ><>< AluI
   AGCCCTGGGT GGTTCTATAG CTGTAAAGAT AACAGAGCAT TCTTGGAATG CTGACCTTTA CAAGCTTATG
       21080      21090      21100      21110      21120      21130      21140

>< Zsp2I
                                      >< Ppu10I
   >< PalI                            >< NsiI
   >< HaeIII                          >< Mph1103I       Tru9I ><
   >< BsuRI           >< MaeIII       >< EcoT22I              >< MseI
   >< BshI    >< NlaIII>< AluI  >< BcgI   >< AvaIII >< SfaNIBcgI/a ><
   GGCCATTTCT CATGGTGGAC AGCTTTTGTT ACAAATGTAA ATGCATCATC ATCGGAAGCA TTTTTAATTG
       21150      21160      21170      21180      21190      21200      21210
```

FIGURE 13.49

```
                                                          >< Zsp2I
                                                          >< SphI
                                                       >< Ppu10I
                                                          >< PaeI
                                                          >< NspI
                                                          >< NspHI
                                                         >< NsiI
                                                          >< NlaIII
                                                      >  < NlaIII
                                                          >< Mph1103I
                                                          >< EcoT22I
                                                      > <. AvaIII        >< MnlI
GGGCTAACTA TCTTGGCAAG CCGAAGGAAC AAATTGATGG CTATACCATG CATGCTAACT ACATTTCTG
   21220       21230      21240      21250      21260      21270      21280

Tru9I ><
            >< MboII                                                  >< Tru9I
            >< GsuI                                                   MseI ><
            >< BsrI                                                   >< MseI
            >< BpmI                                                   MnlI ><
            >< BbsI                                >< NlaIII           >< MnlI
GAGGAACACA AATCCTATCC AGTTGTCTTC CTATTCACTC TTTGACATGA GCAAATTTCC TCTTAAATTA
   21290       21300      21310      21320      21330      21340      21350

>< Tru9I
               >< MseI
               >< Esp4I> < TfiI
               >< BsmAI
               >< Alw26I                                 Ksp632I ><
               >< AflII> < HinfI               >< MboII           >< EarI
                                                          Eam1104I ><
AGAGGAACTG CTGTAATGTC TCTTAAGGAG AATCAAATCA ATGATATGAT TTATTCTCTT CTGGAAAAAG
   21360       21370      21380      21390      21400      21410      21420

>< Tru9I
                                                          >< MseI
                                                          >< HindII
                                                          >< HincII
                                                          >< HpaI AflIII >
GTAGGCTTAT CATTAGAGAA AACAACAGAG TTGTGGTTTC AAGTGATATT CTTGTTAACA ACTAAACGAA
   21430       21440      21450      21460      21470      21480      21490

>< VneI
                                                          >< SnoI
                                                             >< SduI
                                                             >< NspII
                                                         >< HpaII
                                                             >< HgiAI
                                                          >< HapII
                                                         >< Cfr10I
                                                             >< Bsp1286I
                                                          >< MspI>< BmyI
   >< NspI              >< SpeI                           >< ApaLI
   >< NspHI             >< RmaI                           >< Alw44I
   >< NlaIII            >< MaeI   >< MaeIII  >< AgeI  >< Alw21I
CATGTTTATT TTCTTATTAT TTCTTACTCT CACTAGTGGT AGTGACCTTG ACCGGTGCAC CACTTTTGAT
   21500       21510      21520      21530      21540      21550      21560

>  < AluI                     >< MnlI
GATGTTCAAG CTCCTAATTA CACTCAACAT ACTTCATCTA TGAGGGGGGT TTACTATCCT GATGAAATTT
   21570       21580      21590      21600      21610      21620      21630

>< Sau3AI
```

FIGURE 13. 50

```
              >< NdeII
              >< MboI
              >< DpnII
               >< DpnI          >< Tru9I
              >< BspAI          >< MseI    > < MboII
               >< Bsp143I          >< DdeI                              >< MaeIII
           TTAGATCAGA CACTCTTTAT TTAACTCAGG ATTTATTTCT TCCATTTTAT TCTAATGTTA CAGGGTTTCA
              21640      21650      21660      21670      21680      21690      21700

>< VspI
               >< Tru9I
               >< MseI
               >< AsnI                                 >< Tru9I         >< FokI
               >< AseI  >< MaeII                       >< MseI >< BbvI       > < Fnu4HI
           TACTATTAAT CATACGTTTG GCAACCCTGT CATACCTTTT AAGGATGGTA TTTATTTTGC TGCCACAGAG
              21710      21720      21730      21740      21750      21760      21770

>< BsII
                   >< DsaI >< BsiYI          >< NlaIII
                     >< BsaJI                     > < MaeIII
           AAATCAAATG TTGTCCGTGG TTGGGTTTTT GGTTCTACCA TGAACAACAA GTCACAGTGG GTGATTATTA
              21780      21790      21800      21810      21820      21830      21840

>< NspI
           >< Tru9I                    >< NspHI
           >< MseI                     >< NlaIII
           >< HphI                     >< MaeIII         >< MaeIII
           TTAACAATTC TACTAATGTT GTTATACGAG CATGTAACTT TGAATTGTGT GACAACCCTT TCTTTGCTGT
              21850      21860      21870      21880      21890      21900      21910

>< StyI                            >< Zsp2I
                       >< NlaIII                          >< Tru9I
                   >< NcoI  >< RsaI                >< Ppu10I    TthHB8I ><
                   >< EcoT14I                            >< NsiI        >< TaqI
                   >< Eco130I                                >< MseI    SfaNI ><
                   >< DsaI >< Csp6I                          >< Mph1103I  Rsal ><
                   >< BssT1I                      >< TthHB8I >< EcoT22I   Csp6I ><
                   >< BsaJI >< AfaI                   >< TaqI  >< AvaIII    AfaI ><
           TTCTAAACCC ATGGGTACAC AGACACATAC TATGATATTC GATAATGCAT TTAATTGCAC TTTCGAGTAC
              21920      21930      21940      21950      21960      21970      21980

>< Tru9I
                                                                    >< MseI
                                                                    >< DraI
           ATATCTGATG CCTTTTCGCT TGATGTTTCA GAAAAGTCAG GTAATTTTAA ACACTTACGA GAGTTTGTGT
              21990      22000      22010      22020      22030      22040      22050

>< Sau3AI
                                                                              >< NdeII
                                                                              >< MboI
                                                                              >< DpnII
           >< Tru9I                                                            >< DpnI
           >< MseI                                                             >< BspAI
           >< DraI                                            >< SfcI      Bsp143I ><
           TTAAAAATAA AGATGGGTTT CTCTATGTTT ATAAGGGCTA TCAACCTATA GATGTAGTTC GTGATCTACC
              22060      22070      22080      22090      22100      22110      22120

>< Tru9I
                  >< Tru9I       > < Tru9I     >< MseI
                     >< MseI        > < MseI        >< MnlI
           TTCTGGTTTT AACACTTTGA AACCTATTTT TAAGTTGCCT CTTGGTATTA ACATTACAAA TTTTAGAGCC
              22130      22140      22150      22160      22170      22180      22190
```

FIGURE 13.51

```
                                                      > < SduI >< SfcI
                                                              >< PvuII
                                                              >< Psp5I
                                                      > < NspII
                                                              >< NspBII
                                                      > < MaeII  > < Fnu4HI
                                                       > < Bsp1286I >< PstI          Tru9I >
                              >< BspMI              > < BmyI >< Fnu4HI              MseI >
  >< HphI                                  >< BbvI         >< AluI              >< BbvI
ATTCTTACAG CCTTTTCACC TGCTCAAGAC ATTTGGGGCA CGTCAGCTGC AGCCTATTTT GTTGGCTATT
   22200      22210      22220      22230      22240      22250      22260

>< SfaNI
                                                 >< RsaI
                                              > < Csp6I
  >< DraI                                        >< AfaI         >< AlwNI
TAAAGCCAAC TACATTTATG CTCAAGTATG ATGAAAATGG TACAATCACA GATGCTGTTG ATTGTTCTCA
   22270      22280      22290      22300      22310      22320      22330

> < Tru9I
                              > < MseI
                                     >< AluI
AAATCCACTT GCTGAACTCA AATGCTCTGT TAAGAGCTTT GAGATTGACA AAGGAATTTA CCAGACCTCT
   22340      22350      22360      22370      22380      22390      22400

>< SauI
                   >< MstII
                   >< Eco81I
                   >< DdeI
                   >< CvnI
                   >< Bsu36I
                   >< Bse21I
                   >< AxyI              >< TfiI
  >< MnlI   >< AocI    >< MnlI  >< HinfI    >< SspI              >< MnlI
AATTTCAGGG TTGTTCCCTC AGGAGATGTT GTGAGATTCC CTAATATTAC AAACTTGTGT CCTTTTGGAG
   22410      22420      22430      22440      22450      22460      22470

>< Zsp2I
                                   >< Ppu10I
                                      >< NsiI
                                    > < NlaIII
                                      >< Mph1103I
  >< Tru9I                            >< EcoT22I
  >< MseI                             >< AvaIII
AGGTTTTTAA TGCTACTAAA TTCCCTTCTG TCTATGCATG GGAGAGAAAA AAAATTTCTA ATTGTGTTGC
   22480      22490      22500      22510      22520      22530      22540

>< SduI
             >< NspII
             >< HgiAI
             >< Bsp1286I
             >< BmyI                        >< Tru9I
             >< Alw21I                      >< MseI            DdeI ><
TGATTACTCT GTGCTCTACA ACTCAACATT TTTTCAACC TTAAGTGCT ATGGCGTTTC TGCCACTAAG
   22550      22560      22570      22580      22590      22600      22610

>< Sau3AI
  >< NdeII
  >< MboI
  >< DpnII
   >< DpnI
```

FIGURE 13.52

```
             >< BspAI                        >< TfiI
                >< Bsp143I                   >< HinfI
        TTGAATGATC TTTGCTTCTC CAATGTCTAT GCAGATTCTT TTGTAGTCAA GGGAGATGAT GTAAGACAAA
             22620      22630      22640      22650      22660      22670      22680

>< ScrFI
                >< MvaI
           >< HinP1I
           >< Hin6I
             >< HhaI
              >< HaeII
              >< EcoRII
                 >< Ecl136I
             >< DsaV
             >< CfoI
                >< BstOI
                >< BstNI
                >< Bsp143II
                 >< BsiLI
                 >< ApyI       > < BsrI                                        >< NlaIII
        TAGCGCCAGG ACAAACTGGT GTTATTGCTG ATTATAATTA TAAATTGCCA GATGATTTCA TGGGTTGTGT
             22690      22700      22710      22720      22730      22740      22750

>< SfaNI
                   >< RmaI
                   >< MaeI                   >< BsrI                    DdeI ><
                                                                        BfrI ><
        CCTTGCTTGG AATACTAGGA ACATTGATGC TACTTCAACT GGTAATTATA ATTATAAATA TAGGTATCTT
             22760      22770      22780      22790      22800      22810      22820

>< Sau96I
                       >< PalI
                       >< NspIV
              > < HindIII
                         >< HaeIII
                         >< EcoO109I
                         >< DraII
                   >< DdeI
                      >< Cfr13I
                         >< BsuRI
                         >< Bsi2I
                         >< BshI
                 >< BfrI   >< PssI
           >< NlaIII  >< AsuI>< BsmAI
                 >< AluI      >< Alw26I                              BspWI ><
        AGACATGGCA AGCTTAGGCC CTTTGAGAGA GACATATCTA ATGTGCCTTT CTCCCCTGAT GGCAAACCTT
             22830      22840      22850      22860      22870      22880      22890

>< Tru9I
                               >< PalI
                               >< MscI
                               >< HaeIII
                            >< EaeI>< MseI
                   >< Tru9I      >< BsuRI
                   >< MseI       >< BshI
                   >< BspMI      >< BalI                              BsrI ><
        GCACCCCACC TGCTCTTAAT TGTTATTGGC CATTAAATGA TTATGGTTTT TACACCACTA CTGGCATTGG
             22900      22910      22920      22930      22940      22950      22960

Sau96I ><
                                                                   >< PalINspIV ><
                                                               > < MspI   NspHII ><
                                                                   >< HaeIII
```

FIGURE 13.53

```
                                                       > < HpaII Eco47I ><
                                                             >< DsaI
                                                       > < HapII Cfr13I ><
                                                             >< BsuRISinI ><
                                                             >< GdiII BsiZI ><
                         >< ScaI                             >< BsaJI
                         >< RsaI            >< Tru9I    >< EaeI BmeI8I ><
                         >< Csp6I           >< MseI >< Cfr10I    AvaII ><
                         >< AfaI            >< DraI        >< BshI AsuI ><
CTACCAACCT TACAGAGTTG TAGTACTTTC TTTTGAACTT TTAAATGCAC CGGCCACGGT TTGTGGACCA
    22970      22980      22990      23000      23010      23020      23030

>< Tru9I             >< RsaI
                                     >< Tru9I                         >< Csp6I
                                     >< PleI                       BsrI ><
                  > < Tru9I          >< MseI                       >< BsrI
                  > < MseI>< BsrI    >< MseI         >< HinfI      >< AfaI
AAATTATCCA CTGACCTTAT TAAGAACCAG TGTGTCAATT TTAATTTTAA TGGACTCACT GGTACTGGTG
    23040      23050      23060      23070      23080      23090      23100

>< Tru9I                                 >< PalI
>< MseI                                  >< HaeIII
>< MboII                                 >< GdiII
>< HpaI                                  >< EaeI
>< HindII                                >< BsuRI                  TfiI ><
>< HincII                                >< BshI                  HinfI ><
TGTTAACTCC TTCTTCAAAG AGATTTCAAC CATTTCAACA ATTTGGCCGT GATGTTTCTG ATTTCACTGA
    23110      23120      23130      23140      23150      23160      23170

> < XhoII
      >< TthHB8I
      >< TaqI
        > < Sau3AI
        > < NdeII
        > < MfII
        > < MboI
        > < DpnII
           >< DpnI
        > < BstYI
        > < BspAI               > < SspI
>< AlwI >< Bsp143I              >< HphI
TTCCGTTCGA GATCCTAAAA CATCTGAAAT ATTAGACATT TCACCTTGCT CTTTTGGGGG TGTAAGTGTA
    23180      23190      23200      23210      23220      23230      23240

>< ScrFI
>< MvaI
>< EcoRII
   >< Ecl136I                                           >< Tru9I
>< DsaV                                                 >< MseI
   >< BstOI                                             >< HpaI
   >< BstNI                                             >< HindII
   >< BsiLI                                       >< Eco57I
   >< ApyI                                  >< BsgI          >< HincII
ATTACACCTG GAACAAATGC TTCATCTGAA GTTGCTGTTC TATATCAAGA TGTTAACTGC ACTGATGTTT
    23250      23260      23270      23280      23290      23300      23310

>< Sau3AI
        >< NlaIII
          >< NdeII
          >< MboI
          >< DpnII
             >< DpnI                        >< HinP1I
```

FIGURE 13. 54

```
                ><  BspWI                              ><  Hin6I
                    ><  BspAI                           >  <  HhaI                  PleI  ><
><  SfcI            ><  Bsp143I        ><  AluI>  <  CfoI              ><  BsrI
CTACAGCAAT  TCATGCAGAT  CAACTCACAC  CAGCTTGGCG  CATATATTCT  ACTGGAAACA  ATGTATTCCA
   23320       23330       23340       23350       23360       23370       23380

><  TthHB8I
                                          ><  TaqI
                                          ><  SalI
                                          ><  RtrI
                                          ><  NspI
                            ><  EspI      ><  NspHI
                            ><  DdeI      ><  NlaIII
                            ><  CelII     ><  HindII
                            ><  Bpu1102I><  HincII
><  HinfI                   ><  AluI      ><  AccI
GACTCAAGCA  GGCTGTCTTA  TAGGAGCTGA  GCATGTCGAC  ACTTCTTATG  AGTGCGACAT  TCCTATTGGA
   23390       23400       23410       23420       23430       23440       23450

>  <  SnaBI
                                                ><  ScaI
                                                ><  RsaI
                                                   ><  RmaI
                                          ><  MaeII  ><  MaeI
                                          >  <  Eco105I
                 ><  RmaI                         ><  Csp6I
                    ><  MaeIII           >  <  BsaAI
><  AluI         ><  MaeI                         ><  AfaI
GCTGGCATTT  GTGCTAGTTA  CCATACAGTT  TCTTTATTAC  GTAGTACTAG  CCAAAAATCT  ATTGTGGCTT
   23460       23470       23480       23490       23500       23510       23520

><  MunI
ATACTATGTC  TTTAGGTGCT  GATAGTTCAA  TTGCTTACTC  TAATAACACC  ATTGCTATAC  CTACTAACTT
   23530       23540       23550       23560       23570       23580       23590

RsaI  ><
                                                                       ><  MnlI
                                                                        Csp6I  ><
                       ><  SfcI                                          AfaI  ><
TTCAATTAGC  ATTACTACAG  AAGTAATGCC  TGTTTCTATG  GCTAAAACCT  CCGTAGATTG  TAATATGTAC
   23600       23610       23620       23630       23640       23650       23660

>  <  TfiI
               >  <  HinfI
          ><  AciI                                                 >  <  AluI
ATCTGCGGAG  ATTCTACTGA  ATGTGCTAAT  TTGCTTCTCC  AATATGGTAG  CTTTTGCACA  CAACTAAATC
   23670       23680       23690       23700       23710       23720       23730

><  VneI
   ><  SduI
   ><  NspII
   ><  HgiAI                                  ><  PmlI
><  SnoI><  DdeI         ><  Sau3AI           ><  PmaCI
   ><  Bsp1286I          ><  NdeII            ><  MaeII
   ><  BmyI              ><  MboI             ><  Eco72I
   ><  BbvI              ><  DpnI             ><  BsaAI
><  ApaLI                ><  Bsp143I          ><  BbrPI
><  Alw44I               ><  DpnII  ><  AlwI
   ><  Alw21I    ><  Fnu4HI  ><  BspAI    ><  AflIII
GTGCACTCTC  AGGTATTGCT  GCTGAACAGG  ATCGAACAC  ACGTGAAGTG  TTCGCTCAAG  TCAAACAAAT
   23740       23750       23760       23770       23780       23790       23800
```

FIGURE 13.55

```
>< RsaI
>< Csp6I                              >< Tru9I
>< AfaI            >< SspI   >< MseI            >< SspI
GTACAAAACC CCAACTTTGA AATATTTTGG TGGTTTTAAT TTTTCACAAA TATTACCTGA CCCTCTAAAG
     23810      23820      23830      23840      23850      23860      23870

>< MnlI
>< MnlI                              >< Tru9I   >< SfaNI   >< HphI  NlaIII ><
     >< DdeI   >< MnlI               >< MseI >< MaeIII            BspHI ><
CCAACTAAGA GGTCTTTTAT TGAGGACTTG CTCTTTAATA AGGTGACACT CGCTGATGCT GGCTTCATGA
     23880      23890      23900      23910      23920      23930      23940

>< XhoII
                                              >< Sau3AI
                        >< StyI         >< RmaI
                        >< RmaI               >< NdeII
                        >< MaeI               >< MflI
                        >< EcoT14I            >< MboI        >< MstI
                        >< Eco130I        >< MaeI           >< HinP1I
                        >< BssTlI   >< VspI  >< DpnII        >< Hin6I
                        >< BsmI         >< HphI> < DpnI      >< HhaI
                   >< BscCI     >< Tru9I  >< BstYI           >< FspI
                        >< BsaJI   >< MseI  >< BspAI         >< FdiII
                        >< BlnI    >< AsnI   > < Bsp143I     >< CfoI
                        >< AvrII   >< AseI  >< BglII         >< AviII
AGCAATATGG CGAATGCCTA GGTGATATTA ATGCTAGAGA TCTCATTTGT GCGCAGAAGT TCAATGGACT
     23950      23960      23970      23980      23990      24000      24010

>< RmaIRsaI ><
                        >< MnlI      >< Fnu4HI    >< Fnu4HI Csp6I ><
               >< BspWI   >< BbvI    >< BbvI    >< BspWI   >< MaeIAfaI ><
TACAGTGTTG CCACCTCTGC TCACTGATGA TATGATTGCT GCCTACACTG CTGCTCTAGT TAGTGGTACT
     24020      24030      24040      24050      24060      24070      24080

>< MboII
                   >< HinP1I
                   >< Hin6I
                    >< HhaI
                    >< HaeII
                    >< Fnu4HI   >< Ksp632I
                    >< CfoI     >< EarI
               >< FokI  >< BspWI   >< Eam1104I
         >< BbvI       >< Bsp143II
GCCACTGCTG GATGGACATT TGGTGCTGGC GCTGCTCTTC AAATACCTTT TGCTATGCAA ATGGCATATA
     24090      24100      24110      24120      24130      24140      24150

Tru9I ><
                >< MaeIII                                        MseI ><
GGTTCAATGG CATTGGAGTT ACCCAAAATG TTCTCTATGA GAACCAAAAA CAAATCGCCA ACCAATTTAA
     24160      24170      24180      24190      24200      24210      24220

MaeII ><
                   >< TfiI                               >< Fnu4HI
                   >< HinfI              >< BbvI         >< AluI
CAAGGCGATT AGTCAAATTC AAGAATCACT TACAACAACA TCAACTGCAT TGGGCAAGCT GCAAGACGTT
     24230      24240      24250      24260      24270      24280      24290

>< Tru9I
>< MseI
>< HpaI                                        >< DdeI
>< HindII      >< BsmI  >< Tru9I     >< Tru9I >< BfrI
>< HincII>< BscCI       >< MseI      >< MseI          >< AluI
```

FIGURE 13. 56

```
GTTAACCAGA ATGCTCAAGC ATTAAACACA CTTGTTAAAC AACTTAGCTC TAATTTTGGT GCAATTTCAA
    24300      24310      24320      24330      24340      24350      24360

>< ThaI
                              >< SpoI
                              >< NruI
                              >< MvnI
                              >< BstUI         >< TthHB8I
                              >< Bsp68I        >< TaqI        >< RsaI
                    >< EcoRV  >< Bsp50I        >< MnlI        >< Csp6I           >< Tru9I
                    >< Eco32I >< AccII >< MnlI >< AciI>< AfaI                    >< MseI
GTGTGCTAAA TGATATCCTT TCGCGACTTG ATAAAGTCGA GGCGGAGGTA CAAATTGACA GGTTAATTAC
    24370      24380      24390      24400      24410      24420      24430

>< MaeIII >< BbvI           >< Fnu4HI   BbvI ><
AGGCAGACTT CAAAGCCTTC AAACCTATGT AACACAACAA CTAATCAGGG CTGCTGAAAT CAGGGCTTCT
    24440      24450      24460      24470      24480      24490      24500

>< Fnu4HI                                      >< HindII
     >< BspWI             >< DdeI                           >< HincII
GCTAATCTTG CTGCTACTAA AATGTCTGAG TGTGTTCTTG GACAATCAAA AAGAGTTGAC TTTTGTGGAA
    24510      24520      24530      24540      24550      24560      24570

> < NspI
                                                           > < NspHI
                                                           > < NlaIII
                                                           >< MaeIII
                                          >< NlaIII                >< MaeII
                                          >< MboII             >< FokI
                                >< Fnu4HI  >< BbsI         BsaAI ><
                                >< AciI>< BbvI        >< AflIII
AGGGCTACCA CCTTATGTCC TTCCCACAAG CAGCCCCGCA TGGTGTTGTC TTCCTACATG TCACGTATGT
    24580      24590      24600      24610      24620      24630      24640

>< ScrFI
>< MvaI
>< EcoRII
>< Ecl136I
>< BstOI
>< BstNI                           >< HinP1I
>< MnlI >< BslI                    >< Hin6I
>< DsaV>< BsiYI                    >< HhaI
>< BsiLI                           >< HaeII
>< BsaJI>< HphI                    >< CfoI         >< NlaIII
>< ApyI                            >< Bsp143II >< BspHI              EcoNI ><
GCCATCCCAG GAGAGGAACT TCACCACAGC GCCAGCAATT TGTCATGAAG GCAAAGCATA CTTCCCTCGT
    24650      24660      24670      24680      24690      24700      24710

>< MnlI
>< BslI
>< BsiYI          >< Tru9I
>< BsaJI>< HphI              >< MnlI
GAAGGTGTTT TTGTGTTTAA TGGCACTTCT TGGTTTATTA CACAGAGGAA CTTCTTTTCT CCACAAATAA
    24720      24730      24740      24750      24760      24770      24780

>< DdeI                         >< Tru9I
                       >< BsmAI                        >< SfaNI
   >< SfcI             >< Alw26I                       >< MseIAlwI ><
TTACTACAGA CAATACATTT GTCTCAGGAA ATTGTGATGT CGTTATTGGC ATCATTAACA ACACAGTTTA
    24790      24800      24810      24820      24830      24840      24850

>< Sau3AI
>< NdeII
```

FIGURE 13.57

```
><  MboI          ><  PleI                              >  <  ScaI
><  DpnII         ><  MnlI         >  <  Ksp632I        >  <  RsaI
  ><  DpnI        ><  DdeI  ><  HinfI                ><  MboII
><  BspAI         ><  BspWI        >  <  Eam1104I        ><  Csp6I
  ><  Bsp143I       ><  AluI   >  <  EarI   >  <  AluI  >  <  AfaI  >  <  HphI
TGATCCTCTG CAACCTGAGC TTGACTCATT CAAAGAAGAG CTGGACAAGT ACTTCAAAAA TCATACATCA
   24860      24870      24880      24890      24900      24910      24920

><  Sau3AI
          ><  NdeII
          ><  MboI
        ><  MamI
         ><  DpnII
            ><  DpnI
         ><  BspAI
            ><  Bsp143I
       ><  BsiBI                    ><  Tru9I        ><  HindII
       ><  BsaBI                    ><  MseI         ><  HincII              AciI  ><
CCAGATGTTG ATCTTGGCGA CATTTCAGGC ATTAACGCTT CTGTCGTCAA CATTCAAAAA GAAATTGACC
   24930      24940      24950      24960      24970      24980      24990

><  Tru9I
                        >  <  TfiI
              ><  MnlI     ><  SwaI
         ><  EcoNI        ><  MseI
           ><  BslI          >  <  HinfI
><  MnlI><  BsiYI           ><  DraI
GCCTCAATGA GGTCGCTAAA AATTTAAATG AATCACTCAT TGACCTTCAA GAATTGGGAA AATATGAGCA
   25000      25010      25020      25030      25040      25050      25060

><  StyI
              ><  PalI
              ><  HaeIII
                ><  EcoT14I
                ><  Eco130I
                ><  BsuRI
                ><  BssT1I                                            NlaIII  ><
    ><  Tru9I><  BshI                                                 MaeIII  ><
    ><  MseI   ><  BsaJI                                                ><  BstXI
ATATATTAAA TGGCCTTGGT ATGTTTGGCT CGGCTTCATT GCTGGACTAA TTGCCATCGT CATGGTTACA
   25070      25080      25090      25100      25110      25120      25130

>  <  SphI
                                                       >  <  PaeI
             ><  SpeI                                  >  <  NspI
              >  <  RmaI                               >  <  NspHI
             ><  NlaIII                                >  <  NlaIII
              >  <  MaeI                         ><  MnlI><  BbvI  Fnu4HI  ><
ATCTTGCTTT GTTGCATGAC TAGTTGTTGC AGTTGCCTCA AGGGTGCATG CTCTTGTGGT TCTTGCTGCA
   25140      25150      25160      25170      25180      25190      25200

><  FokI
             ><  DdeI
><  MnlI  ><  PleI><  Hinfl  ><  BsrI
AGTTTGATGA GGATGACTCT GAGCCAGTTC TCAAGGGTGT CAAATTACAT TACACATAAA CGAACTTATG
   25210      25220      25230      25240      25250      25260      25270

><  Sau3AI
                ><  NdeII
                ><  MboI
                ><  DpnII
                  >  <  DpnI
```

FIGURE 13.58

```
                                    >< BspAI
                                      > < Bsp143I
                        >< BsgI        >< AlwI     >< BsrI            BspWI >
GATTTGTTTA TGAGATTTTT TACTCTTGGA TCAATTACTG CACAGCCAGT AAAAATTGAC AATGCTTCTC
    25280      25290      25300      25310      25320      25330      25340

>< ScaI
         >< RsaI
         >< Csp6I     >< SfcI
         >< AfaI      >< NlaIII     >< AciI                >< MnlI      FokI >
CTGCAAGTAC TGTTCATGCT ACAGCAACGA TACCGCTACA AGCCTCACTC CCTTTCGGAT GGCTTGTTAT
    25350      25360      25370      25380      25390      25400      25410

> < HinPlI
                                  > < Hin6I
                                    >< HhaI                          RmaI ><
                                    >< HaeII      >< HinPlI          NheI ><
                                    >< Eco47III   >< Hin6I           MaeI ><
                                    >< CfoI       >< HhaI         Fnu4HI ><
               >< BspWI             >< Bsp143II   >< CfoI           AluI ><
TGGCGTTGCA TTTCTTGCTG TTTTTCAGAG CGCTACCAAA ATAATTGCGC TCAATAAAAG ATGGCAGCTA
    25420      25430      25440      25450      25460      25470      25480

>< EcoNI
         >< BslI
         >< BsiYI                                >< MaeIII
       >< BbvI    >< BsrI   >< BbvI    > < Fnu4HI           BbvI ><
GCCCTTTATA AGGGCTTCCA GTTCATTTGC AATTTACTGC TGCTATTTGT TACCATCTAT TCACATCTTT
    25490      25500      25510      25520      25530      25540      25550

Zsp2I ><
                                                                  Ppu10I ><
              > < SfcI       >< HinPlI                             NsiI ><
                 >< PstI     >< Hin6I      >< RsaI               Mph1103I ><
              > < Fnu4HI     >< HhaI       >< Csp6I               EcoT22I ><
   >< BspMI   >< MnlI        >< CfoI       >< AfaI     >< MnlI     AvaIII ><
TGCTTGTCGC TGCAGGTATG GAGGCGCAAT TTTTGTACCT CTATGCCTTG ATATATTTTC TACAATGCAT
    25560      25570      25580      25590      25600      25610      25620

>< SfaNI
         >< NspI
         >< NspHI
         ><·NlaIII                                                 >< SfaNI
CAACGCATGT AGAATTATTA TGAGATGTTG GCTTTGTTGG AAGTGCAAAT CCAAGAACCC ATTACTTTAT
    25630      25640      25650      25660      25670      25680      25690

>< Bst1107I
                                                 >< AccI  MaeIII ><
GATGCCAACT ACTTTGTTTG CTGGCACACA CATAACTATG ACTACTGTAT ACCATATAAC AGTGTCACAG
    25700      25710      25720      25730      25740      25750      25760

>< MboII
                                  >< HphI                           BstXI ><
  >< MunI  >< MaeIII >< MaeIII       >< Eco57I            >< BbsI MnlI >
ATACAATTGT CGTTACTGAA GGTGACGGCA TTTCAACACC AAAACTCAAA GAAGACTACC AAATTGGTGG
    25770      25780      25790      25800      25810      25820      25830

>< RsaI
                                                        > ·< NlaIII
                                                        >< HphI
                           >< Tru9I >< Tth111I>< Csp6I
  >< DdeI        >< DdeI   >< MseI>< AspI       >< AfaI
                              FIGURE 13.59
```

```
TTATTCTGAG GATAGGCACT CAGGTGTTAA AGACTATGTC GTTGTACATG GCTATTTCAC CGAAGTTTAC
    25840      25850      25860      25870      25880      25890      25900

Tru9I ><
         > < HinfI>< PleI          >< BsrI                          MseI ><
        >< AluI >< AccI       >< SfcI >< AlwNI         >< MboII       HindIII >
TACCAGCTTG AGTCTACACA AATTACTACA GACACTGGTA TTGAAAATGC TACATTCTTC ATCTTTAACA
    25910      25920      25930      25940      25950      25960      25970

> < TthHB8I
        >< Tru9I                    > < TaqI           >< Ksp632I
        >< MseI                     > < MboII          >< EarI BspWI ><
>< AluI                  >< Eco57I                     >< Eam1104I AlwI ><
AGCTTGTTAA AGACCCACCG AATGTGCAAA TACACACAAT CGACGGCTCT TCAGGAGTTG CTAATCCAGC
    25980      25990      26000      26010      26020      26030      26040

>< XhoII
>< Sau3AI
   >< NlaIV
>< NdeII
>< MflI
>< MboI
>< DpnII
   >< DpnI
>< BstYI
>< BstI
>< BspAI
   >< Bsp143I                                                         RsaI ><
   >< BscBI             >< RmaI                                       Csp6I ><
>< BamHI >< AlwI        >< MaeI                                       AfaI ><
AATGGATCCA ATTTATGATG AGCCGACGAC GACTACTAGC GTGCCTTTGT AAGCACAAGA AAGTGAGTAC
    26050      26060      26070      26080      26090      26100      26110

> < Tru9I
                                  >< RsaI
                                   > < MseI
                                  >< MboII
       > < RsaI                   >< MaeII          >< RsaI
         >< Csp6I                  >< Csp6I  >< Tru9I >< Csp6I
       > < AfaI                   >< AfaI    >< MseI >< AfaI
GAACTTATGT ACTCATTCGT TTCGGAAGAA ACAGGTACGT TAATAGTTAA TAGCGTACTT CTTTTTCTTG
    26120      26130      26140      26150      26160      26170      26180

>< TthHB8I
                                             >< TaqI
             >< RmaI                  >< HinP1I         > < RsaI
              > < MaeIII              >< Hin6I          Fnu4HI ><
              >< MaeI   >< RmaI       >< HhaI           >< Csp6I
              >< FokI   >< MaeI       >< CfoI >< BbvI  > < AfaI
CTTTCGTGGT ATTCTTGCTA GTCACACTAG CCATCCTTAC TGCGCTTCGA TTGTGTGCGT ACTGCTGCAA
    26190      26200      26210      26220      26230      26240      26250

>< Tru9I
        >< Tru9I                              >< ThaI
        >< MseI                               >< MvnI
>< SspI >< MaeII                                        >< MseI
        >< HpaI                               >< BstUI             Ksp632I >
        >< HindII                  >< MaeII   >< Bsp50I  >< MboII  EarI >
        >< HincII                  >< AccII >< AccII              Eam1104I >
TATTGTTAAC GTGAGTTTAG TAAAACCAAC GGTTTACGTC TACTCGCGTG TTAAAAATCT GAACTCTTCT
    26260      26270      26280      26290      26300      26310      26320
```

FIGURE 13.60

```
                        >< Sau3AI
                        >< NdeII
                        >< MboI
                        >< DpnII
               >< MboII >< DpnI
         >< XmnI  >< BspAI > < Eco57I                                                   >< Tru9I
         >< Asp700I >< Bsp143I                                                          >< MseI
         GAAGGAGTTC CTGATCTTCT GGTCTAAACG AACTAACTAT TATTATTATT CTGTTTGGAA CTTTAACATT
             26330      26340      26350      26360      26370      26380      26390

>< ScrFI
                                                                       >< MvaI
                                                                      >< EcoRII
                                                                       >< Ecl136I
                                                                      >< DsaV  NlaIV ><
                             >< RsaI                                   >< BstOI
                                  >< MnlI              >< Tru9I        >< BstNI    RmaI ><
                             >< Csp6I                  >< MseI         >< BsiLI    MaeI ><
            > < NlaIII       >< AfaI           > < AluI               >< ApyIBscBI ><
         GCTTATCATG GCAGACAACG GTACTATTAC CGTTGAGGAG CTTAAACAAC TCCTGGAACA ATGGAACCTA
             26400      26410      26420      26430      26440      26450      26460

>< ScrFI
                            >< RmaI
                               >< MvaI
                            >< MaeI
                              >< EcoRII
                              >< Ecl136I
                              >< DsaV
                                >< BstOI
                                >< BstNI
                                >< BsiLI
                                >< ApyI  >< MaeIII
         GTAATAGGTT TCCTATTCCT AGCCTGGATT ATGTTACTAC AATTTGCCTA TTCTAATCGG AACAGGTTTT
             26470      26480      26490      26500      26510      26520      26530

>< PalI
                                                    >< MscI
                                         >< MnlI    >< MaeIII
                                                  >< HaeIII
                                                  >< EaeI
                                                  >< BsuRI
                                                    >< BsrI
         >< RsaI                                  >< BspWI
         >< Csp6I   >< HindIII                    >< BshI
         >< AfaI    >< AluI                       >< BalI           >< BbvI Fnu4HI ><
         TGTACATAAT AAAGCTTGTT TTCCTCTGGC TCTTGTGGCC AGTAACACTT GCTTGTTTTG TGCTTGCTGC
             26540      26550      26560      26570      26580      26590      26600

>< VspI
                    >< Tru9I
                    >< MseI              >< HphI
         >< SfcI    >< AsnI              >< BsrI
         >< AccI    >< AseI >< MaeIII >< AciI
         TGTCTACAGA ATTAATTGGG TGACTGGCGG GATTGCGATT GCAATGGCTT GTATTGTAGG CTTGATGTGG
             26610      26620      26630      26640      26650      26660      26670

>< EspI
            >< Eco57I
         >< DdeI
         >< CelII                                          >< RsaI
         >< Bpu1102I                                       >< Csp6I
                                     FIGURE 13.61
```

```
                ><  BfrI                              ><  AfaI
    ><  AluI                                 ><  AciI                      MboII  >
CTTAGCTACT  TCGTTGCTTC  CTTCAGGCTG  TTTGCTCGTA  CCCGCTCAAT  GTGGTCATTC  AACCCAGAAA
    26680       26690       26700       26710       26720       26730       26740

><  ScrFI
                            ><  NciI
                            ><  MspI
                            ><  HpaII
                            ><  HapII
                            ><  DsaV><  MnlI
                            ><  BslI
                            ><  BsiYI
                            ><  BsaJI  ><  MunI            >  <  XcmI
                            ><  BcnI         ><  MaeIII ><  AciI  ><  NlaIII
CAAACATTCT  TCTCAATGTG  CCTCTCCGGG  GGACAATTGT  GACCAGACCG  CTCATGGAAA  GTGAACTTGT
    26750       26760       26770       26780       26790       26800       26810

Tru9I  ><
                                                                      SinI  >
                                                                    Sau96I  >
                                                                     PpuMI  >
                                                                     NspIV  >
                                                                     MseI  ><
                                                                    ><  MaeIII
            ><  Sau3AI                               >  <  RmaI  ><  HaeII
            ><  NdeII              ><  PalI          >  <  MaeI       EcoO109I  >
            ><  MboI               ><  MspI                    ><  HinPlI Eco47I  >
              ><  FbaI             ><  HpaII   ><  StyI><  Hin6I    DraII  >
            ><  DpnII              ><  HapII         ><  EcoT14I        Cfr13I  >
              ><  DpnI             ><  HaeIII  ><  Eco130I><  Bsp143II
            ><  BspAI              ><  GdiII         ><  BssT1I         BsiZI  >
              ><  Bsp143I          ><  EaeI          ><  BsaJI          Bme18I  >
            ><  BsiQI              ><  BsuRI         ><  BlnI   ><  HhaI  AvaII  >
            ><  BclI     ><  MaeIII  ><  BshI        ><  AvrII ><  CfoI   AsuI  >
CATTGGTGCT  GTGATCATTC  GTGGTCACTT  GCGAATGGCC  GGACACTCCC  TAGGGCGCTG  TGACATTAAG
    26820       26830       26840       26850       26860       26870       26880

><  Sau3AI
                    ><  NdeII
                    ><  MboI
                    ><  DpnII
                      ><  DpnI
    ><  PssI   ><  BspMI
    ><  Psp5II     ><  BspAI              ><  XmnI
    ><  NspHII     ><  Bsp143I            ><  Asp700I    >  <  HgaI     Fnu4HI  ><
GACCTGCCAA  AAGAGATCAC  TGTGGCTACA  TCACGAACGC  TTTCTTATTA  CAAATTAGGA  GCGTCGCAGC
    26890       26900       26910       26920       26930       26940       26950

><  TfiI
              ><  HinfI
              ><  BbvI                                                >  <  Tru9I
            ><  BbvI       ><  Fnu4HI  ><  AciI                       >  <  MseI
GTGTAGGCAC  TGATTCAGGT  TTTGCTGCAT  ACAACCGCTA  CCGTATTGGA  AACTATAAAT  TAAATACAGA
    26960       26970       26980       26990       27000       27010       27020

><  MspI                    ><  RsaI
    ><  HpaII                   ><  RmaI
    ><  HapII                   ><  Csp6I
    ><  Cfr10I                  ><  MaeI><  BcgI                 HindII  ><
    ><  BcgI/a      ><  SspI          ><  AfaI ><  MaeIII        HincII  ><
```

FIGURE 13.62

```
CCACGCCGGT AGCAACGACA ATATTGCTTT GCTAGTACAG TAAGTGACAA CAGATGTTTC ATCTTGTTGA
    27030      27040      27050      27060      27070      27080      27090

>< ScrFI
       >< MvaI
         >< MaeIII
   >< EcoRII
       >< Ecl136I
   >< DsaV
       >< BstOI
       >< BstNI
       >< BsiLI                                                       >< TfiI
       >< ApyI            >< MnlI                           HinfI ><
CTTCCAGGTT ACAATAGCAG AGATATTGAT TATCATTATG AGGACTTTCA GGATTGCTAT TTGGAATCTT
    27100      27110      27120      27130      27140      27150      27160

>< BsmAI        >< Tru9I      > < MnlI
 >< MaeII    >< Alw26I       >< MseI       >< DdeI              >< MboII
GACGTTATAA TAAGTTCAAT AGTGAGACAA TTATTTAAGC CTCTAACTAA GAAGAATTAT TCGGAGTTAG
    27170      27180      27190      27200      27210      27220      27230

>< Ksp632I
                                                 >< MboII         >< EarI
                   >< MboII                      >< NlaIIIEam1104I ><
ATGATGAAGA ACCTATGGAG TTAGATTATC CATAAAACGA ACATGAAAAT TATTCTCTTC CTGACATTGA
    27240      27250      27260      27270      27280      27290      27300

> < RsaI >< RsaI
                                                 >< Csp6I >< Csp6I
                 > < AluI         >< MnlI         > < AfaI >< AfaI
TTGTATTTAC ATCTTGCGAG CTATATCACT ATCAGGAGTG TGTTAGAGGT ACGACTGTAC TACTAAAAGA
    27310      27320      27330      27340      27350      27360      27370

>< MnlI   >< HphI >< HphI                >< MnlI
ACCTTGCCCA TCAGGAACAT ACGAGGGCAA TTCACCATTT CACCCTCTTG CTGACAATAA ATTTGCACTA
    27380      27390      27400      27410      27420      27430      27440

Sau3AI >
                                                                 > < PvuII
                                                                 > < Psp5I
                                                                 > < NspBII
                                                 >< TthHB8I        NdeII >
                                                 >< TaqI           MboI >
                                               >< RsaI             >< Fnu4HI
                                               >< Csp6I            DpnII >
           >< RmaI                               >< BbvI           BspAI >
           >< MaeI                             >< AfaI            > < AluI
ACTTGCACTA GCACACACTT TGCTTTTGCT TGTGCTGACG GTACTCGACA TACCTATCAG CTGCGTGCAA
    27450      27460      27470      27480      27490      27500      27510

>< SstI
                                                                >< SduI
                                                                >< SacI
                                                                >< NspII
                                                                >< HgiAI
                                                                >< Eco24I
                                                              > < Ecl136II
                                                                  >< BspWI
                                                                >< Bsp1286I
                                                                >< BmyI
>< HphI                                                         >< BanII
>< DpnI                           >< MnlI                       >< Alw21I
```

FIGURE 13. 63

```
           >< Bsp143I           >< MnlI                          >  < AluI      BbvI ><
           GATCAGTTTC ACCAAAACTT TTCATCAGAC AAGAGGAGGT TCAACAAGAG CTCTACTCGC CACTTTTTCT
                27520      27530      27540      27550      27560      27570      27580

SstI ><
                                                                                 SduI ><
                                                                                 SacI ><
                                                                                NspII ><
                                                                                HgiAI ><
                                                                                Eco24I ><
                                                                            Ecl136II ><
                                                                             Bsp1286I ><
                                                                                BmyI ><
                        >< RmaI     >< Tru9I                                     BanII ><
                        >< MaeI     >< MseI              >< Tru9I               Alw21I ><
            >< Fnu4HI              >< HphI               >< MseI                  AluI ><
           CATTGTTGCT GCTCTAGTAT TTTTAATACT TTGCTTCACC ATTAAGAGAA AGACAGAATG AATGAGCTCA
                27590      27600      27610      27620      27630      27640      27650

>< Tru9I                                     >< Tru9I
           >< MseI                                      >< MseI
           CTTTAATTGA CTTCTATTTG TGCTTTTTAG CCTTTCTGCT ATTCCTTGTT TTAATAATGC TTATTATATT
                27660      27670      27680      27690      27700      27710      27720

>< XhoII
                                     >< XbaI
                                    > < ScrFI
                                     >< Sau3AI
                                       >< RmaI
                                     >< NdeII
                                    > < MvaI
                                     >< MflI
                                     >< MboI
                                   >< EcoRII>< MaeI
                                    > < Ecl136I
                                     >< DpnII
                                      >< DpnI
                                     >< BstYI
                                    > < BstOI
                                    > < BstNI
                          >< TthHB8I >< BspAI          > < RsaI
                             >< DsaV>< Bsp143I           >< MboII
                            > < BsiLI               >< Csp6I
                        >< TaqI > < ApyI    > < AlwI    > < AfaI                >< NlaIII
           TTGGTTTTCA CTCGAAATCC AGGATCTAGA AGAACCTTGT ACCAAAGTCT AAACGAACAT GAAACTTCTC
                27730      27740      27750      27760      27770      27780      27790

>< HinPlI
                                                                                >< Hin6I
                                                                                 >< HhaI
                                                                       >< RsaI >< HaeII
                                                              >< SfcI         >< Eco47III
                                                                          >< Csp6I>< CfoI    SfaNI ><
                                                     >< NdeI          >< AfaI    >< Bsp143II
           ATTGTTTTGA CTTGTATTTC TCTATGCAGT TGCATATGCA CTGTAGTACA GCGCTGTGCA TCTAATAAAC
                27800      27810      27820      27830      27840      27850      27860

>< XhoII
                        >< Sau3AI
                        >< NdeII
                       > < MnlI
                        >< MflI
```

FIGURE 13.64

```
                        >< MboI
                        >< DpnII
                           >< DpnI        >< RsaI
                           >< BstYI    >< MboII
            >< NlaIII >< BspAI         >< Csp6I  >< RmaI
               >< AlwI  >< Bsp143I      >< AfaI  >< MaeI
     CTCATGTGCT TGAAGATCCT TGTAAGGTAC AACACTAGGG GTAATACTTA TAGCACTGCT TGGCTTTGTG
         27870      27880      27890      27900      27910      27920      27930

>< SduI
      >< RmaI
     >< NspII
      >< MaeI
     >< HgiAI
     >< Bsp1286I                                                  >< NspI
     >< BmyI                                                      >< NspHI
     >< Alw21I                                                    >< NlaIII  >< MaeIII
     CTCTAGGAAA GGTTTTACCT TTTCATAGAT GGCACACTAT GGTTCAAACA TGCACACCTA ATGTTACTAT
         27940      27950      27960      27970      27980      27990      28000

> < XhoII
               > < Sau3AI  > < Van91I                >< RsaI
                           >< PvuII                  >< NlaIV
                           >< Psp5I                    >< KpnI  >< NlaIII
               > < NdeII   > < PflMI               >< Eco64I        >< MaeIII
               > < MflI >< NspBII                   >< Csp6I >< HphI
               > < DpnII           >< HinP1I         >< BscBI        >< EcoO65I
                  >< Bsp143I       >< Hin6I          >< BanI  >< BspHI
               > < BstYI   > < BslI >< HhaI  >< RmaI >< Asp718       >< Eco91I
               > < BspAI   > < BsiYI >< CfoI  >< MaeI >< AfaI        >< BstPI
               > < MboI >< AluI >< BspWI  >< BspWI   >< AccB1I       >< BstEII
     >< AlwI >< DpnI > < AccB7I            >< AluI   >< Acc65I       >< BbvI
     CAACTGTCAA GATCCAGCTG GTGGTGCGCT TATAGCTAGG TGTTGGTACC TTCATGAAGG TCACCAAACT
         28010      28020      28030      28040      28050      28060      28070

>< SinI
                                                                      >< Sau96I
                                                                      >< NspIV
                                                                NspHII ><
                                                                 NlaIV ><
                                                                      >< Eco47I
                                                                      >< Cfr13I
                        >< RsaI                                       >< BsiZI
     >< Fnu4HI    >< MaeII                                       BscBI ><
         >< Esp3I     >< Csp6I    >< Tru9I                            >< Bme18I
         >< BsmAI     >< BsmBI    >< MseI         >< Tru9I            >< AvaII
         >< Alw26I    >< AfaI     >< DraI         >< MseI             >< AsuI
     GCTGCATTTA GAGACGTACT TGTTGTTTTA AATAAACGAA CAAATTAAAA TGTCTGATAA TGGACCCCAA
         28080      28090      28100      28110      28120      28130      28140

>< SinI
                                      >< Sau96I
                                      >< NspIV
                                       >< NspHII
                                        >< NlaIV
                                      >< Eco47I
                                      >< Cfr13I
                        >< SduI       >< BsiZI
                        >< NspII        >< BscBI
                        >< Bsp1286I     >< Bme18I
                        >< BmyI       >< AvaII    >< TfiI
          >< MaeII       >< AciI      >< AsuI     >< HinfI         >< MnlI
```

FIGURE 13.65

```
TCAAACCAAC GTAGTGCCCC CCGCATTACA TTTGGTGGAC CCACAGATTC AACTGACAAT AACCAGAATG
   28150      28160      28170      28180      28190      28200      28210
                              >< HinPlI >< StyI
                                     >< HaeII
                  > < PalI   >< Hin6I  >< EcoT14I
                  > < HaeIII    >< HhaI>< Eco130I
                        >< BspWI       >< BssT1I
                  > < BsuRI     >< Bsp143II
             >< HgaI> < BshI    >< CfoI>< BsaJI   >< HgaI
GAGGACGCAA TGGGGCAAGG CCAAAACAGC GCCGACCCCA AGGTTTACCC AATAATACTG CGTCTTGGTT
   28220      28230      28240      28250      28260      28270      28280
                                             >< TthHB8I
                                                  > < ScrFI
                                                 >< PalI
                                           >< PaeR7I
                                           >< NspIII
                                                  > < MvaI
                                                 >< HaeIII
                                                 >< EcoRII
                                           >< Eco88I
                                           >< XhoI  > < Ecl136I
                                                 >< DsaV
                                                 >< BsuRI
                                           >< SlaI  > < BstOI
                                      >< MnlI>< TaqI> < BstNI
                                                 >< CcrI  > < BsiLI
                                     >< HinfI      >< BshI
                                     >< TfiI>< BcoI>< BsaJI
              >< MnlI              >< DdeI     >< AvaI  > < ApyI
>< AluI  >< DdeI  > < NlaIII       >< BfrI     >< Ama87I >< MnlI
CACAGCTCTC ACTCAGCATG GCAAGGAGGA ACTTAGATTC CCTCGAGGCC AGGGCGTTCC AATCAACACC
   28290      28300      28310      28320      28330      28340      28350
      >< SinI
      >< Sau96I
      >< NspIV
       >< NspHII
      >< Eco47I
      >< Cfr13I
      >< Bsi2I
      >< Bme18I                > < Ksp632I
      >< AvaII                 > < Eam1104I
      >< AsuI                  > < EarI  > < AluI>< MboII       >< MaeIII
AATAGTGGTC CAGATGACCA AATTGGCTAC TACCGAAGAG CTACCCGACG AGTTCGTGGT GGTGACGGCA
   28360      28370      28380      28390      28400      28410      28420
         >< SstI
         >< SduI
         >< SacI
         >< NspII
         >< HgiAI
        >< EspI
         >< Eco24I                                    >< Sau96I
       >< Ecl136II                 >< StyI       >< PalI
         >< DdeI                   >< RmaI       >< NspIV
         >< CelII                  >< MaeI       >< HaeIII
          >< Bspl286I              >< EcoT14I >< Cfr13I
          >< Bpu1102I              >< Eco130I    >< BsuRI
         >< BmyI                   >< BssT1I     > < BsrI
         >< BanII      >< RsaI     >< BsaJI      >< Bsi2I
```

FIGURE 13.66

```
                  >< Alw21I      >< Csp6I        >< BlnI       >< BshI>< HindIII
    >< HphI    >< AluI           >< AfaI         >< AvrII      >< AsuI    >< AluI
  AAATGAAAGA GCTCAGCCCC AGATGGTACT TCTATTACCT AGGAACTGGC CCAGAAGCTT CACTTCCCTA
    28430      28440      28450      28460      28470      28480      28490

>< HinPlI
  >< Hin6I
    >< HhaI
      >< HaeII
    >< CfoI                        > < MnlI         >< NlaIV
    >< Bsp143II              >< SfaNI     >< DdeI >< BscBI
  CGGCGCTAAC AAAGAAGGCA TCGTATGGGT TGCAACTGAG GGAGCCTTGA ATACACCCAA AGACCACATT
    28500      28510      28520      28530      28540      28550      28560

>< NlaIV
  >< Eco64I
   >< BscBI
  >< BanI
    >< AciI
  >< AccBlI   >< BbvI       >< Fnu4HI                          >< MnlI
  GGCACCCGCA ATCCTAATAA CAATGCTGCC ACCGTGCTAC AACTTCCTCA AGGAACAACA TTGCCAAAAG
    28570      28580      28590      28600      28610      28620      28630

>< ThaI
                                                                    >< MnlI
                                                             >< MaeII >< MvnI
                                                    >< MnlI       BstUI ><
                                >< Fnu4HI           >< Ksp632I     Bsp50I ><
                                >< BspWI            >< EarI        >< BsaAI>< AciI
  >< MnlI     >< MnlI      >< AciI>< MboII     >< Eaml104I       AccII ><
  GCTTCTACGC AGAGGGAAGC AGAGGCGGCA GTCAAGCCTC TTCTCGCTCC TCATCACGTA GTCGCGGTAA
    28640      28650      28660      28670      28680      28690      28700

>< ScrFI
                  >< MvaI
                >< EcoRII                        >< TthHB8I
                  >< Ecl136I                         >< RmaI
                >< DsaV>< Fnu4HI                    >< NheI
                  >< BstOI                          >< MnlI
                  >< BstNI                          >< MaeI
                  >< BsiLI                        > < BspWI
                  >< ApyI       >< BbvI          >< TaqI     >< AciI
  TTCAAGAAAT TCAACTCCTG GCAGCAGTAG GGGAAATTCT CCTGCTCGAA TGGCTAGCGG AGGTGGTGAA
    28710      28720      28730      28740      28750      28760      28770

> < ThaI
            > < MvnI
         >< HphI    >< MnlI
            > < HinPlI
            > < Hin6I
               >< HhaI
          > < BstUI    >< RmaI                                        PalI ><
          > < Bsp50I   >< MaeI                                        HaeIII ><
  >< BbvI >< CfoI>< Fnu4HI                                            BsuRI ><
     > < AccII>< BspWI             >< AluI                            BshI ><
  ACTGCCCTCG CGCTATTGCT GCTAGACAGA TTGAACCAGC TTGAGAGCAA AGTTCTGGT AAAGGCCAAC
    28780      28790      28800      28810      28820      28830      28840

RsaI ><
          > < PalI>< MaeIII                                         >< MnlI
          > < HaeIII                  >< Fnu4HI                     MaeII ><
            > < BsuRI    >< DdeI      >< DdeI                       Csp6I ><
                              FIGURE 13.67
```

```
              > < BshI     > < BbvI      >< MnlI  >< BspWI         >< SfaNI       AfaI ><
            AACAACAAGG CCAAACTGTC ACTAAGAAAT CTGCTGCTGA GGCATCTAAA AAGCCTCGCC AAAAACGTAC
              28850      28860      28870      28880      28890      28900      28910
                                                  >< Tth111I
                                                  >< SinI
                                                  >< Sau96I
                                                  >< NspIV
                                                       >< NspHII
                                               > < MaeII
                                                  >< Eco47I
                                                  >< Cfr13I
                                                  >< BsmBI
                       >< Rsa.                    >< BsiZI          >< StyI
                        >< MaeIII                 >< Bme18I         >< EcoT14I
                         >< MaeII    >< Esp3I     >< AvaII          >< Eco130I
                       >< Csp6I      >< BsmAI     >< AsuI           >< BssT1I
                        >< AfaI      >< Alw26I> < AspI              >< BsaJI
            TGCCACAAAA CAGTACAACG TCACTCAAGC ATTTGGGAGA CGTGGTCCAG AACAAACCCA AGGAAATTTC
              28920      28930      28940      28950      28960      28970      28980

>< SinI
            >< Sau96I
            >< NspIV
             >< NspHII
             >< NlaIV                                  >< PalI
            >< Eco47I                                  >< HaeIII
            >< Cfr13I                                  >< GdiII
             >< BsiZI                                  >< Fnu4HI
             >< BscBI                                  >< EaeI
             >< Bme18I                                 >< BsuRI
             >< AvaII                                  >< BshI         BspWI >
             >< AsuI                                   >< AciI         >< BspWI
            GGGGACCAAG ACCTAATCAG ACAAGGAACT GATTACAAAC ATTGGCCGCA AATTGCACAA TTTGCTCCAA
              28990      29000      29010      29020      29030      29040      29050

>< BsmI                     >< NlaIII
             >< BscCI    >< MnlI    >< MaeIII          >< MaeIII                 >< NlaIII
            GTGCCTCTGC ATTCTTTGGA ATGTCACGCA TTGGCATGGA AGTCACACCT TCGGGAACAT GGCTGACTTA
              29060      29070      29080      29090      29100      29110      29120

>< XhoII
                                    >< Sau3AI
                                    >< NdeII
                                    >< MflI
                                    >< MboI
                                         >< FokI
                          >< Tru9I   >< DpnII
                      >< NlaIV       > < DpnI
                      >< NlaIII               >< BstYI          >< Tth111I
                               >< MseI        >< BspAI          >< MaeII
                      >< BscBI   >< BstXI>< AlwI> < Bsp143I      >< AspI         BspWI ><
            TCATGGAGCC ATTAAATTGG ATGACAAAGA TCCACAATTC AAAGACAACG TCATACTGCT GAACAAGCAC
              29130      29140      29150      29160      29170      29180      29190

EspI ><
                                                                                DdeI ><
                                                                                CelII ><
                                                                                Bpu1102I ><
                                         >< HgaI                                AluI ><
            ATTGACGCAT ACAAAACATT CCCACCAACA GAGCCTAAAA AGGACAAAAA GAAAAGAGACT GATGAAGCTC
              29200      29210      29220      29230      29240      29250      29260
```

FIGURE 13.68

```
                            >< PleI
      >< Fnu4HI             >< MboII
      >< BspWI              >< MboII         >< Ksp632I >< GsuI
      >< BsmAI              >< MaeIII        >< EarI>< Fnu4HI
      >< Alw26I                    >< HinfI >< Eaml104I>< BpmI
      >< AciI        >< Fnu4HI    >< BbvI           >< AciI      >< NlaIII
AGCCTTTGCC GCAGAGACAA AAGAAGCAGC CCACTGTGAC TCTTCTTCCT GCGGCTGACA TGGATGATTT
   29270      29280      29290      29300      29310      29320      29330

>< NlaIII         >< HinfI              NlaIII ><
    >< FokI                  >< AluI  >< TfiI>< DdeI                >< BspHI
CTCCAGACAA CTTCAAAATT CCATGAGTGG AGCTTCTGCT GATTCAACTC AGGCATAAAC ACTCATGATG
   29340      29350      29360      29370      29380      29390      29400

>< MaeII                        >< AccI
ACCACACAAG GCAGATGGGC TATGTAAACG TTTTCGCAAT TCCGTTTACG ATACATAGTC TACTCTTGTG
   29410      29420      29430      29440      29450      29460      29470

>< Tru9I
                                          >< Tru9I
                                            >< MseI
                                          >< MseI
    >< XmnI                                >< HpaI
    >< EcoRI>< MaeIII                      >< HindII                  Tru9I ><
    >< Asp700I    >< BsgI                  >< HincII                  MseI ><
CAGAATGAAT TCTCGTAACT AAACAGCACA AGTAGGTTTA GTTAACTTTA ATCTCACATA GCAATCTTTA
   29480      29490      29500      29510      29520      29530      29540

XorII >
                                                                TthHB8I >
                                                                   TaqI >
                                                                Sau3AI ><
                                                                 RsaI ><
                                                              >< ThaIPvuI >
                                                                 NdeII ><
                                                                    >< MnlI
                                                              >< MvnIMcrI >
                                                                  MboI ><
                                                                  DpnII ><
                                                                   DpnI ><
                                                                  Csp6I ><
                                                                  >< BstUI
                                                             >< HaeIII  BspCI >
                                                                     BspAI ><
                                                            >< TthHB8I >< Bsp50I
                                                                >< PalI Bsp143I ><
                                                                  >< BsuRI  BsiEI >
                                                                   >< BshIAfaI ><
    >< MnlI                                             >< TaqI       >< AciI
    >< MaeIII                                           >< MnlI       >< AccII
ATCAATGTGT AACATTAGGG AGGACTTGAA AGAGCCACCA CATTTTCATC GAGGCCACGC GGAGTACGAT
   29550      29560      29570      29580      29590      29600      29610

>< SduI
                                                      >< NspII
                                                           >< MboII    >< VspI
                                     >< Ksp632I       >< Eco24I        >< Tru9I
    >< RsaI       >< RmaI   >< Fnu4HI                 >< Bsp1286I      >< MseI
    >< Csp6I      >< MaeI       >< EarI               >< BmyI          >< AsnI
    >< AfaI       >< BbvI     > < AluI>< Eaml104I     >< BanII         >< AseI
```

FIGURE 13.69

```
CGAGGGTACA GTGAATAATG CTAGGGAGAG CTGCCTATAT GGAAGAGCCC TAATGTGTAA AATTAATTTT
    29620      29630      29640      29650      29660      29670      29680
                         >< Tru9I    >< DdeI
                         >< MseI     >< BfrI
              >< NlaIII     >  < AluI
AGTAGTGCTA TCCCCATGTG ATTTTAATAG CTTCTTAGGA GAATGACAAA AAAAAAAAAA AAAAAA
    29690      29700      29710      29720      29730      29740
```

FIGURE 13.70

A.
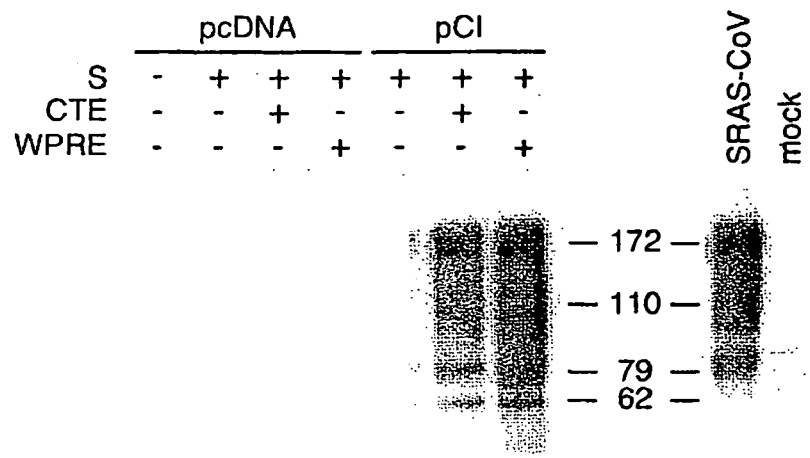
B.
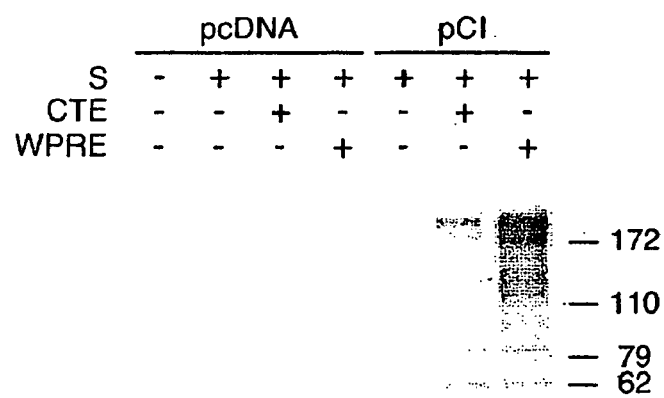
FIGURE 23

A.
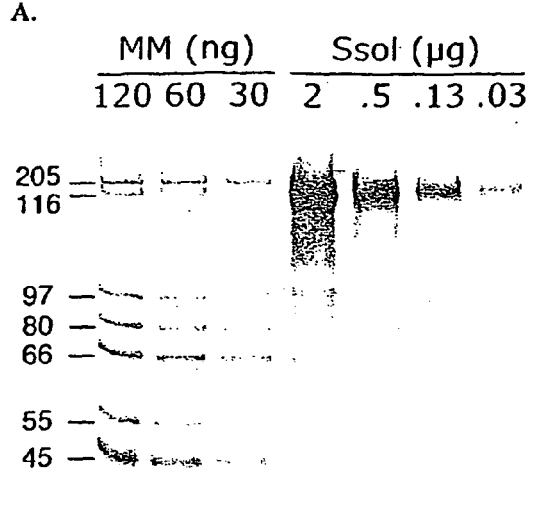
B.
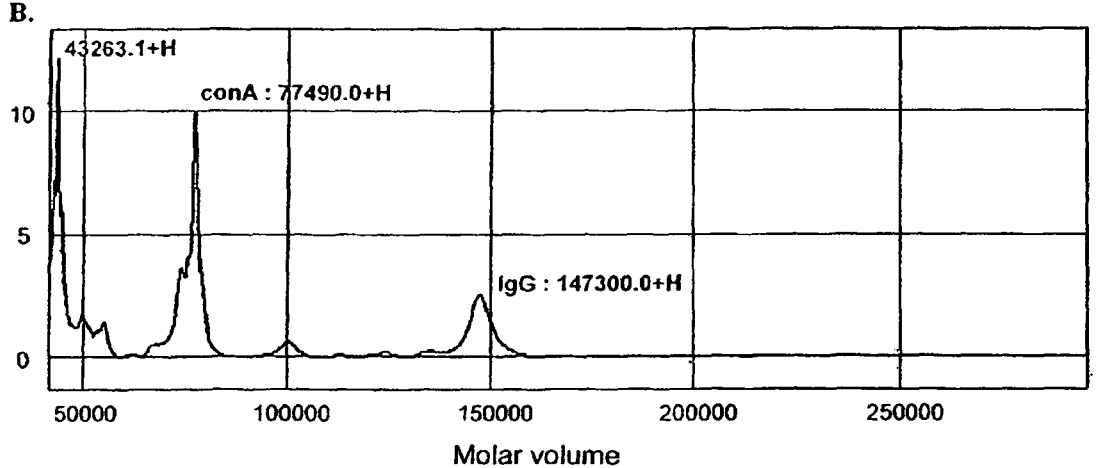
C.
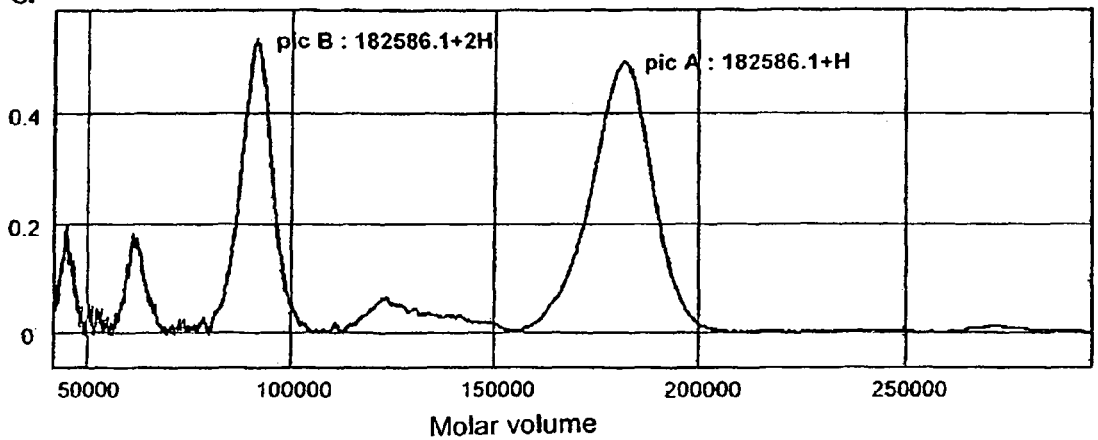
FIGURE 27 A-C

A.
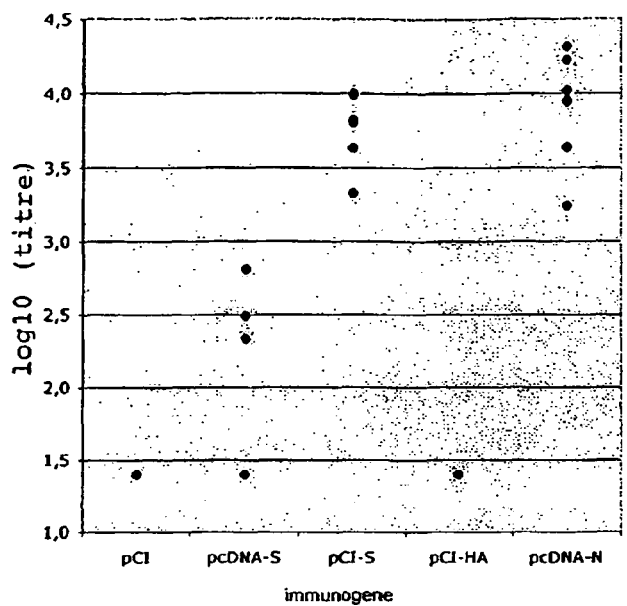
B.
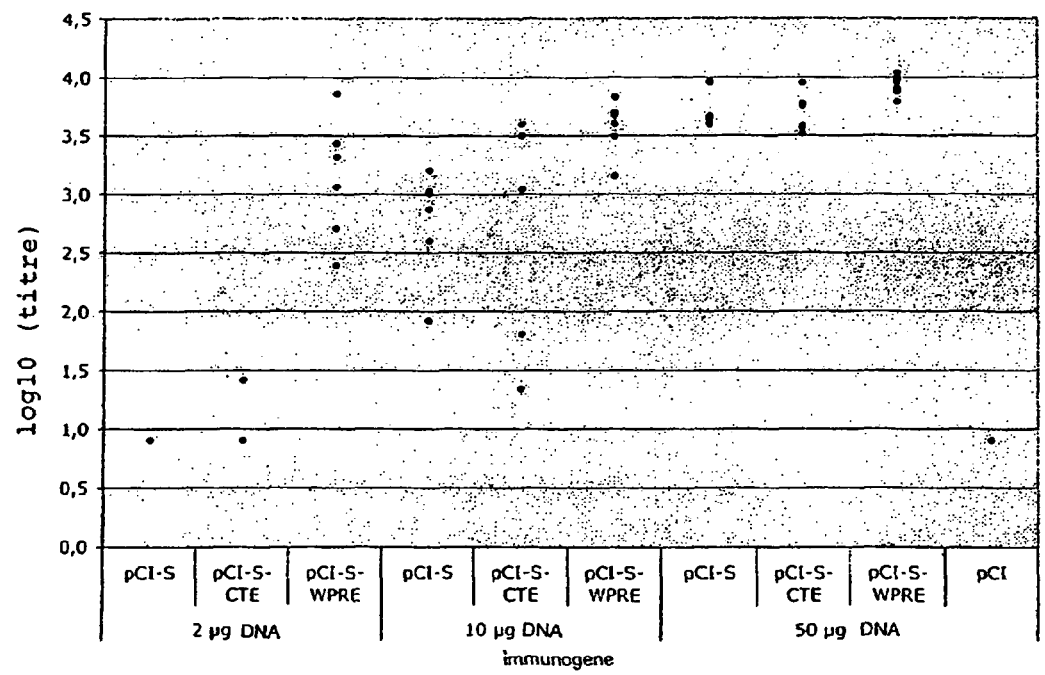
FIGURE 28

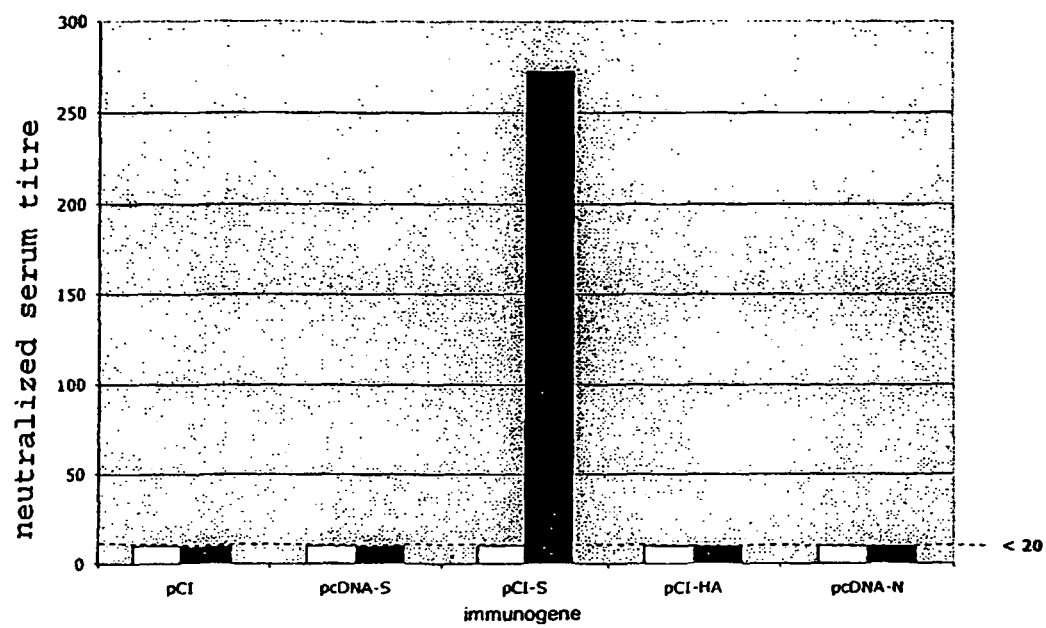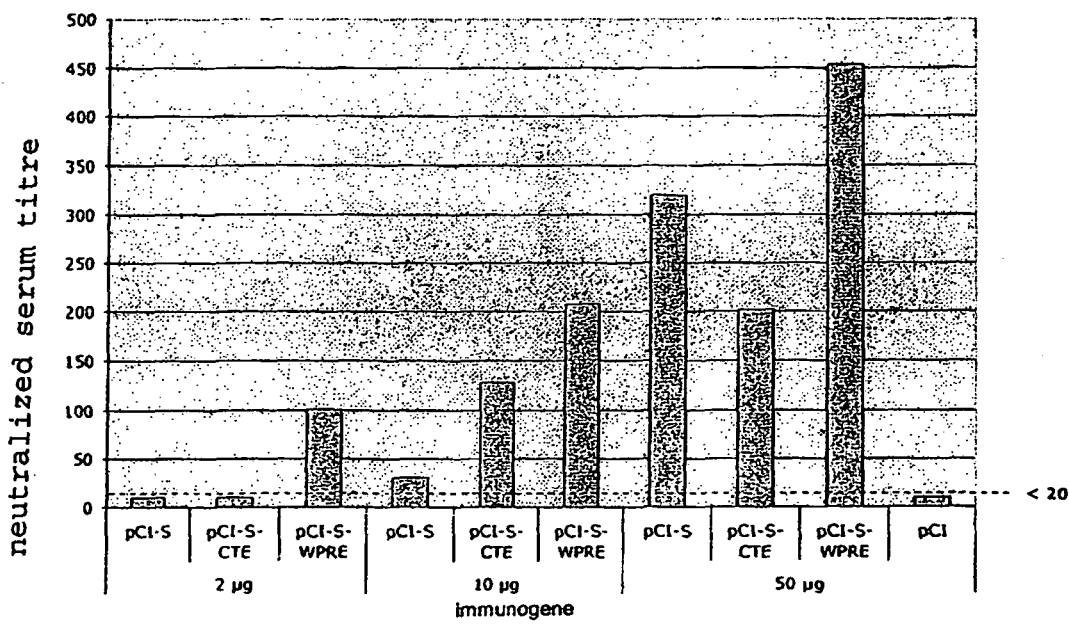
FIGURE 29

```
I-3059       1 CTCTTCTGGAAAAAGGTAGGCTTATCATTAGAGAAAACAACAGAGTTGTGGTTTCAAGTG
S-040530       _____

I-3059      61 ATATTCTTGTTAACAACTAAACGAACATGTTTATTTTCTTATTATTTCTTACTCTCACTA
S-040530     1 _____GG"T"C"C""""""C""C"""C"GC"G""C""G""C""G""C"

I-3059     121 GTGGTAGTGACCTTGACCGGTGCACCACTTTTGATGATGTTCAAGCTCCTAATTACACTC
S-040530    44 "C""""C""""""G"""""""""""""""C""C""C""C""G""G""C""C""C"""""C"

I-3059     181 AACATACTT_CATCTATGAGGGGGTTTACTATCCTGATGAAATTTTTAGATCAGACACT
S-040530   104 "G""C""CAG""G"_"""C"""""C""G""""""C""C""C""G""C"""C"GAGC""""""C

I-3059     240 CTTTATTTAACTCAGGATTTATTTCTTCCATTTTATTCTAATGTTACAGGGTTTCATACT
S-040530   163 """G""CC""G""C"""""CC""G""C""G""C""C""CAGC""""C""G""C""C""C""C""C

I-3059     300 ATTAATCATACGTTTGGCAACCCTGTCATACCTTTTAAGGATGGTATTTATTTTGCTGCC
S-040530   223 """C""C""C""C""C""C""""""""""C""G""C""C""C"""""""C""C""C""C""C""C"""

I-3059     360 ACAGAGAAATCAAATGTTGTCCGTGGTTGGTTTTTGGTTCTACCATGAACAACAAGTCA
S-040530   283 """C""""""GAGC""C""G""G""G""C"""""G""C""CAGC"""""""""""""""""AGC

I-3059     420 CAGTCGGTGATTATTATTAACAATTCTACTAATGTTGTTATACGAGCATGTAACTTTGAA
S-040530   343 """"AGC""""""C""C""C""""""CAGC""C""C""G""G""C""G""C""C"""""C""G

I-3059     480 TTGTGTGACAACCCTTTCTTTGCTGTTTCTAAACCCATGGGTACACAGACACATACTATG
S-040530   403 C""""""C"""""""""C""""""C""C""G""C""""""""""""""C""C""""""C""C""C"""

I-3059     540 ATATTCGATAATGCATTTAATTGCACTTTCGAGTACATATCTGATGCCTTTTCGCTTGAT
S-040530   463 """C"""""""C""C""C""C""C""""""C"""""""""""""""CAGC""C"""""CAGC""G""C

I-3059     600 GTTTCAGAAAAGTCAGGTAATTTTAAACACTTACGAGAGTTTGTGTTTAAAAAATAAAGAT
S-040530   523 ""GAGC""G""""AGC""C""C""C""G""""C""G""G""""""C""""""C""G""C""G""C

I-3059     660 GGGTTTCTCTATGTTTATAAGGGCTATCAACCTATAGATGTAGTTCGTGATCTACCTTCT
S-040530   583 """C""C""G""C""G""C""""""""""C""G""C""C""C""G""GA"A""C""G""CAGC

I-3059     720 GGTTTTAACACTTTGAAACCTATTTTTAAGTTGCCTCTTGGTATTAACATTACAAATTTT
S-040530   643 """C""C""""""CC""""G""C""C""C""C""""""C""G""C""C""""""C""C""C""C

I-3059     780 AGAGCCATTCTTACAGCCTTTTCACCTGCTCAAGACATTTGGGGCACGTCAGCTGCAGCC
S-040530   703 C"G""""""C""G""C""""""AGC""""""C""G""""""C""""""""CAGC""C""C"""

I-3059     840 TATTTTGTTGGCTATTTAAAGCCAACTACATTTATGCTCAAGTATGATGAAAATGGTACA
S-040530   763 """C""C""G""""""CC""G""""""T""C""C""C""""""G"""""C""C""G""C""C""C

I-3059     900 ATCACAGATGCTGTTGATTGTTCTCAAAATCCACTTGCTGAACTCAAATGCTCTGTTAAG
S-040530   823 """"""C""C""C""G""C""CAGC"""G""C""C""G""C""G""G""G"""AGC"""G"""

I-3059     960 AGCTTTGAGATTGACAAAGGAATTTACCAGACCTCTAATTTCAGGGTTGTTCCCTCAGGA
S-040530   883 """"""C""""""C""""""G""C""C""""""""AGC""C"""""A""G""G""TAGC""C

I-3059    1020 GATGTTGTGAGATTCCCTAATATTACAAACTTGTGTCCTTTTGGAGAGGTTTTTAATGCT
S-040530   943 """""G"""C""G""""""C"""""C""C""C""""C""C""C""C""A""G""C""C""C

I-3059    1080 ACTAAATTCCCTTCTGTCTATGCATGGGAGAGAAAAAAAATTTCTAATTGTGTTGCTGAT
S-040530  1003 """C""G"""""CAGC""G""C""C""""""C"G""G""G""CAGC""C""C""G""C""C

I-3059    1140 TACTCTGTGCTCTACAACTCAACATTTTTTTCAACCTTTAAGTGCTATGGGCGTTTCTGCC
S-040530  1063 """AGC""""""G""""""""""C""C""C""CAGC""""""C"""""""""C"""""GAGC"""

I-3059    1200 ACTAAGTTGAATGATCTTTGCTTCTCCAATGTCTATGCAGATTCTTTTGTAGTCAAGGGA
S-040530  1123 """C""C""""C""C""G""""""AG""C""G""C""C""CAGC""C""G""G""""""C

I-3059    1260 GATGATGTAAGACAAATAGCGCCAGGACAAACTGGTGTTATTGCTGATTATAATTATAAA
S-040530  1183 """C""C""G""""""G""C""C""T""C""G""C""C""G""C""C""C""C""C""G
```

FIGURE 32.1

```
I-3059     1320 TTGCCAGATGATTTCATGGGTTGTCTCCTTGCTTGGAATACTAGGAACATTGATGCTACT
S-040530   1243 C"""""C""C""C"""""""""C""C""G""G""C"""""C""CC"""""""""C""C""C""A

I-3059     1380 TCAACTGGTAATTATAATTATAAATATAGGTATCTTAGACATGGCAAGCTTAGGCCCTTT
S-040530   1303 AGC""C""C""C""C"""""C""G""CC"C""C""GC"G""C""""""""GC"""""""""C

I-3059     1440 GAGAGAGACATATCTAATGTGCCTTTCTCCCCTGATGGCAAACCTTGCACCCCACCTGCT
S-040530   1363 """C"G"""""C""C""C""""""C"""AG"""C""C"""""G""C"""""""""C""""""C

I-3059     1500 CTTAATTGTTATTGGCCATTAAATGATTATGGTTTTTACACCACTACTGGCATTGGCTAC
S-040530   1423 """G""C""C""C"""""CC"G""C""C""C""C""C"""""""""""C""C"""""C"""""T

I-3059     1560 CAACCTTACAGAGTTGTAGTACTTTCTTTTGAACTTTTAAATGCACCGGCCACGGTTTGT
S-040530   1483 """G""C"""""""""G""G""G""GAGC""C""G""GC"G""C""C""T"""""C""G""C

I-3059     1620 GGACCAAAATTATCCACTGACCTTATTAAGAACCAGTGTGTCAATTTTAATTTTAATGGA
S-040530   1543 """C""C""GC""GAG"""C"""""G""C""""""""""""C""G""C""C""C""C""C""C

I-3059     1680 CTCACTGGTACTGGTGTGTTAACTCCTTCTTCA__AAGAGATTTCAACCATTTCAACAAT
S-040530   1603 """G""C""C""C""C"""C""G""C"""__"AG""GC"""C""C""G""C""C""G""G"

I-3059     1738 TTGGCCGTGATGTCTCTGATTTCACTGATTCCGTTCGAGATCCTAAAACATCTGAAATAT
S-040530   1661 "C""""""G""""""GAGC""C"""""C""CAG"""G""G""C""C""G""CAGC""G""CC

I-3059     1798 TAGACATTTCACCTTGCTCTTTTGGGGGTGTAAGTGTAATTACACCTGGAACAAATGCTT
S-040530   1721 "G"""""CAGC""C"""AGC""C""C""C""GTCC""G""C""C""C""C""C""C""CA

I-3059     1858 _CATCTGAAGTTGCTGTTCTATATCAAGATGTTAACTGCACTGATGTTTCTACAGCAATC
S-040530   1781 G""G"_"""""G""C""G""G""C""G""C""G"""""""""C""C""GAGC""C""C"""

I-3059     1917 CATGCAGATCAACTCACACCAGCTTGGCGCATATATTCTACTGGAAACAATGTATTCCAG
S-040530   1840 """C""C""C""G""G""C""C""C"""""G""C""CAGC""C""G""""C""G"""""""

I-3059     1977 ACTCAAGCAGGCTGTCTTATAGGAGCTGAGCATGTCGACACTTCTTATGAGTGCGACATT
S-040530   1900 """C""G""C"""""C""G""C""C""C"""""C""G""""""CAGC""C"""""""""""C

I-3059     2037 CCTATTGGAGCTGGCATTTGTGCTAGTTACCATACAGTTTCTTTATTACGTAGTACTAGC
S-040530   1960 """C"""""""C""C""A""C""C""C""C"""""C""C""GAGCC"GC"G""G""C""C"""

I-3059     2097 CAAAAATCTATTGTGGCTTATACTATGTCTTTAGGTGCTGATAGTTCAATTGCTTACTCT
S-040530   2020 """G""G""C""C"""""C""C""C"""AGCC"G""C""C""C""CAGC""""C""C"""AGC

I-3059     2157 AATAACACCATTGCTATACCTACTAACTTTTCAATTAGCATTACTACAGAAGTAATGCCT
S-040530   2080 """C""""""""""C""C""C""C""C"""""CAGC""CTC"""""C""C""C"""""G""""""C

I-3059     2217 GTTTCTATGGCTAAAACCTCCGTAGATTGTAATATGTACATCTGCGGAGATTCTACTGAA
S-040530   2140 """GAGC"""""C""G""AAG"""G"""""C""C""""""""""""""""""C""CAGC""C""G

I-3059     2277 TGTGCTAATTTGCTTCTCCAATATGGTAGCTTTTGCACACAACTAAATCGTGCACTCTCA
S-040530   2200 """C"""C""CC"""""G""G""G""C""C"""""C"""""C""G""G""C""G""C""GAGC

I-3059     2337 GGTATTGCTGCTGAACAGGATCGCAACACACGTGAAGTGTTCGCTCAAGTCAAACAAATG
S-040530   2260 """C""C""C""C""C""G"""""C""G""""""CA"A"""""""""""C""""""G""G""G"""

I-3059     2397 TACAAAACCCCAACTTTGAAATATTTTGGTGGTTTTAATTTTTCACAAATATTACCTGAC
S-040530   2320 """T""G"""""C""CC""""G""C""C""G""C""C""C""C""T""G""CC"G""C"""

I-3059     2457 CCTCTAAAGCCAACTAAGAGGTCTTTTATTGAGGACTTGCTCTTTAATAAGGTGACACTC
S-040530   2380 """""G"""""C""C"""""C""C""C""C""C"""""""C"""""G""C""C""A"""""C""G

I-3059     2517 GCTGATGCTGGCTTCATGAAGCAATATGGCGAATGCCTAGGTGATATTAATGCTAGAGAT
S-040530   2440 """C"""C""C"""""T"""""""""G""C""""""G""""""G""C""C""C""C""CC"G""C

I-3059     2577 CTCATTTGTGCGCAGAAGTTCAATGGGCTTACAGTGTTGCCACCTCTGCTCACTGATGAT
S-040530   2500 """G""C""C""C"""""""""T""C"""""G""C""C"""""C""C"""""G""C""C""C

I-3059     2637 ATGATTGCTGCCTACACTGCTGCTCTAGTTAGTGGTACTGCCACTGCTGGATGGACATTT
S-040530   2560 """""""C""C""""""T""A""C""C""G""G""C""C""C"""""C""C""C"""""C""C
```

FIGURE 32.2

```
I-3059      2697 GGTGCTGGCGCTGCTCTTCAAATACCTTTTGCTATGCAAATGGCATATAGGTTCAATGGC
S-040530    2620 ""A""C""A""C""C""G""G""C""C""C""C"""""G"""""C""CC"""""""C"""

I-3059      2757 ATTGGAGTTACCCAAAATGTTCTCTATGAGAACCAAAAACAAATCGCCAACCAATTTAAC
S-040530    2680 """C""C""G"""""G""C""G""G""C"""""""""G""G""G"""""""""""G""C"""

I-3059      2817 AAGGCGATTAGTCAAATTCAAGAATCACTTACAACAACATCAACTGCATTGGGCAAGCTG
S-040530    2740 """""C""C""C""G""C""G""GAGC""G""C"""""CAGC""C""CC"""""""""""

I-3059      2877 CAAGACGTTGTTAACCAGAATGCTCAAGCATTAAACACACTTGTTAAACAACTTAGCTCT
S-040530    2800 ""G"""""G""G"""""""""C""C""G""CC""G"""""C""G""G""G""G""G"""AGC

I-3059      2937 AATTTTGGTGCAATTTCAAGTGTGCTAAATGATATCCTTTCGCGACTTGATAAAGTCGAG
S-040530    2860 """C""C""C""C""CAGCTC"""""G""C""C"""""GAGCA""G""G""C"""""G"""

I-3059      2997 GCGGAGGTACAAATTGACAGGCTAATTACAGGCAGACTTCAAAGCCTTCAAACCTATGTA
S-040530    2920 """C""A""G""G""C"""""G""C""C""AC""C""G""GTC"""G""G"""""C""G

I-3059      3057 ACACAACAACTAATCAGGGCTGCTGAAATCAGGGCTTCTGCTAATCTTGCTGCTACTAAA
S-040530    2980 """C""G""G""G"""""A""C""C""G"""C"""""CAGC""C"""""G""C""C""C""G

I-3059      3117 ATGTCTGAGTGTGTTCTTGGACAATCAAAAAGAGTTGACTTTTGTGGAAAGGGCTACCAC
S-040530    3040 """AGC"""""C""G""G""C""GAGC""G"""""G"""""C""C""C"""""""T"""

I-3059      3177 CTTATGTCCTTCCCACAAGCAGCCCCGCATGGTGTTGTCTTCCTACATGTCACGTATGTG
S-040530    3100 ""G"""AG"""""C""G""C"""""C""C""C""G""G"""""G""C""G""C""C"""

I-3059      3237 CCATCCCAGGAGAGGAACTTCACCACAGCGCCAGCAATTTGTCATGAAGGCAAAGCATAC
S-040530    3160 """TAG"""""""C"""""""""""C""C"""""C""C""C""C""G"""""G""C"""

I-3059      3297 TTCCCTCGTGAAGGTGTTTTTGTGTTTAATGGCACTTCTTGGTTTATTACACAGAGGAAC
S-040530    3220 """""C""G""G""C""G""C""""""""C"""""CAGC"""""C""C""C"""C""C"""

I-3059      3357 TTCTTTTCTCCACAAATAATTACTACAGACAATACATTTGTCTCAGGAAATTGTGATGTC
S-040530    3280 """""CAGC""C""G""C""C""C""""""""""C""C""C""G""C""C""C"""""""G

I-3059      3417 GTTATTGGCATCATTAACAACACAGTTTATGATCCTCTGCAACCTGAGCTTGACTCATTC
S-040530    3340 """G""C""""""""C""T"""""C""G""C""C""C"""""G""C"""""G"""AGC"""

I-3059      3477 AAAGAAGAGCTGGACAAGTACTTCAAAAATCATACATCACCAGATGTTGATCTTGGCGAC
S-040530    3400 """G""G"""""""""""A"""""""""G""C""C""C""C""C""C""G""C""G"""""T

I-3059      3537 ATTTCAGGCATTAACGCTTCTGTCGTCAACATTCAAAAAGAAATTGACCGCCTCAATGAG
S-040530    3460 """CAGC"""""C""""""C""C""G""G"""""C""G""G""G""C"""A""A""G""C""A

I-3059      3597 GTCGCTAAAAATTTAAATGAATCACTCATTGACCTTCAAGAATTGGGAAAATATGAGCAA
S-040530    3520 """G""C""G""CC""G""C""GAGC""G""C"""""G""G""GC"""""C""G""C"""""G

I-3059      3657 TATATTAAATGGCCTTGGTATGTTTGGCTCGGCTTCATTGCTGGACTAATTGCCATCGTC
S-040530    3580 """C""C""G"""""C"""""C""G"""""G""""""""""C""C""C""G""C"""""""G

I-3059      3717 ATGGTTACAATCTTGCTTTGTTGCATGACTAGTTGTTGCAGTTGCCTCAAGGGTGCATGC
S-040530    3640 """""G""C"""C""""G""C""""""""C""C""C""T""C"""""G""A""C""C"""

I-3059      3777 TCTTGTGGTTCTTGCTGCAAGTTTGATGAGGATGACTCTGAGCCAGTTCTCAAGGGTGTC
S-040530    3700 AGC"""""CAGC"""""""""""C""C"""""C"""AGC"""""C""G""G"""""C""G

I-3059      3837 AAATTACATTACACATAAACGAACTTATGGATTTGTTTATGAGATTTTTTACTCTTGGAT
S-040530    3760 ""GC"G""C"""""C"G"T__"""""CGA"

I-3059      3897 CAATTACTGCACAGCCAGTAAAAATTGACAATGCTTCTCCTGCAAGT
S-040530
```

FIGURE 32.3

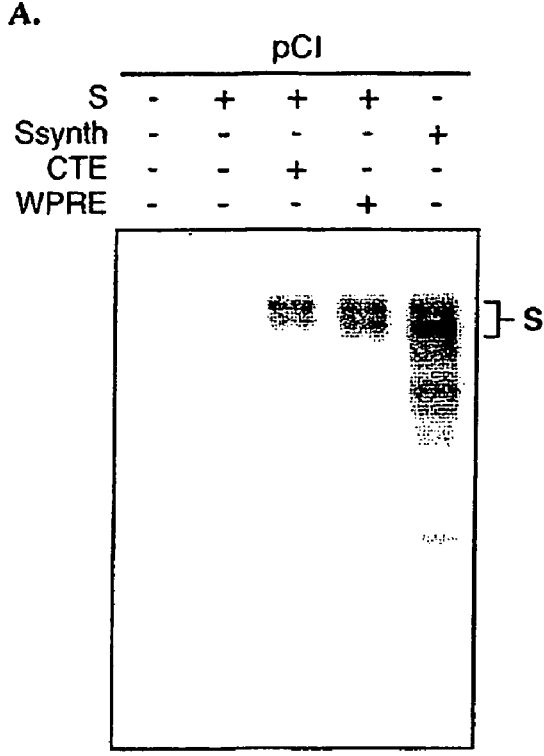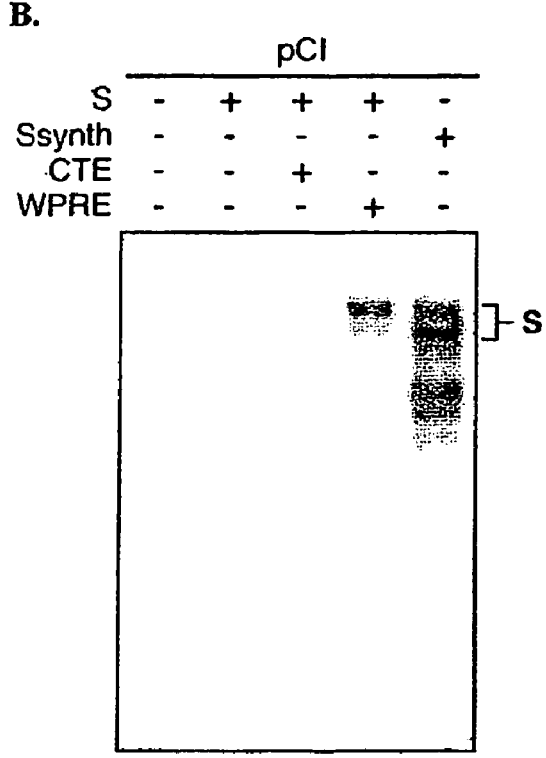
FIGURE 33

A.
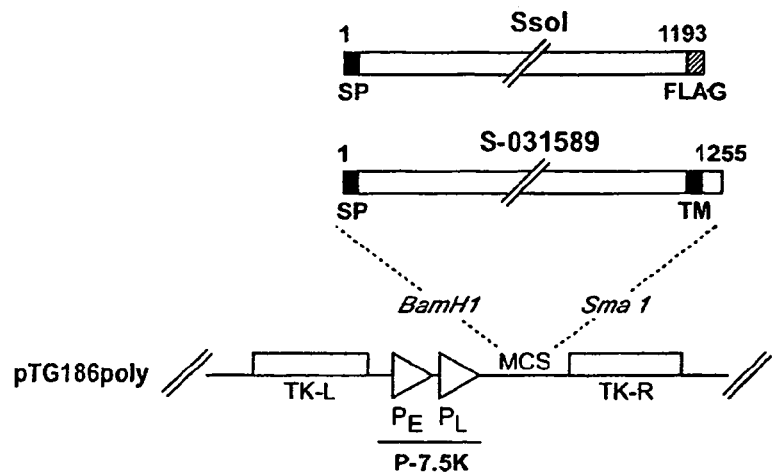
B.
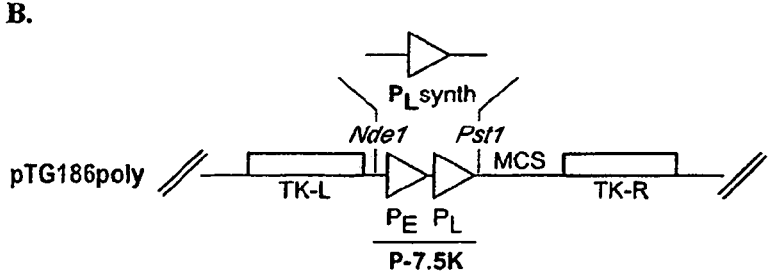
C.
<u>CATATG</u> AGC [T]$_{20}$<u>GGCATATAAATA</u> GACTC <u>GGCGCGCC</u> AT <u>CTGCAG</u>
<u>NdeI</u>　　　　promoteur 480　　　　<u>AscI</u>　　<u>PstI</u>
FIGURE 34 A-C A.
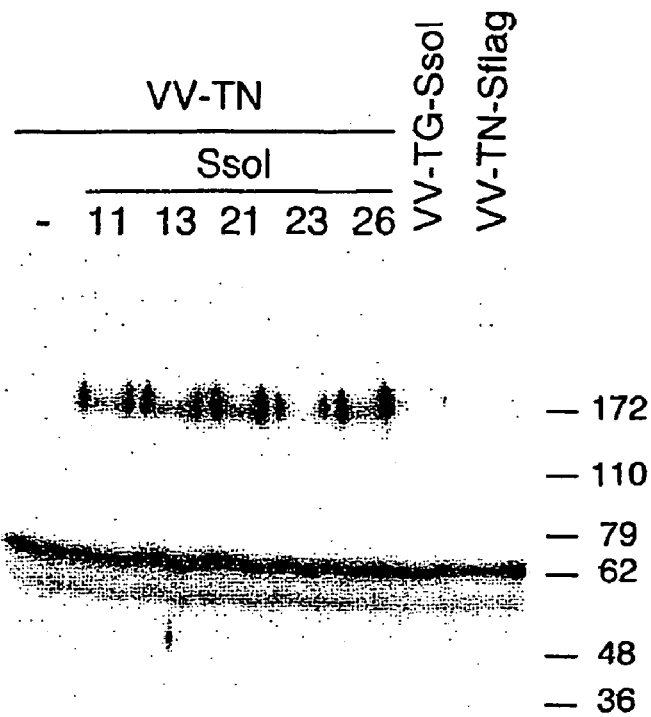
B.
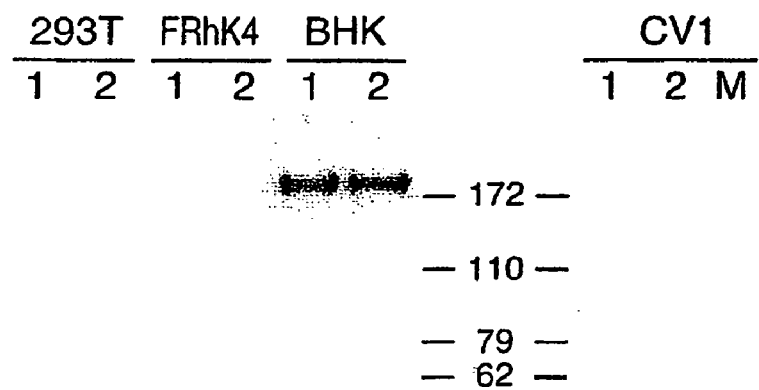
FIGURE 36

A.
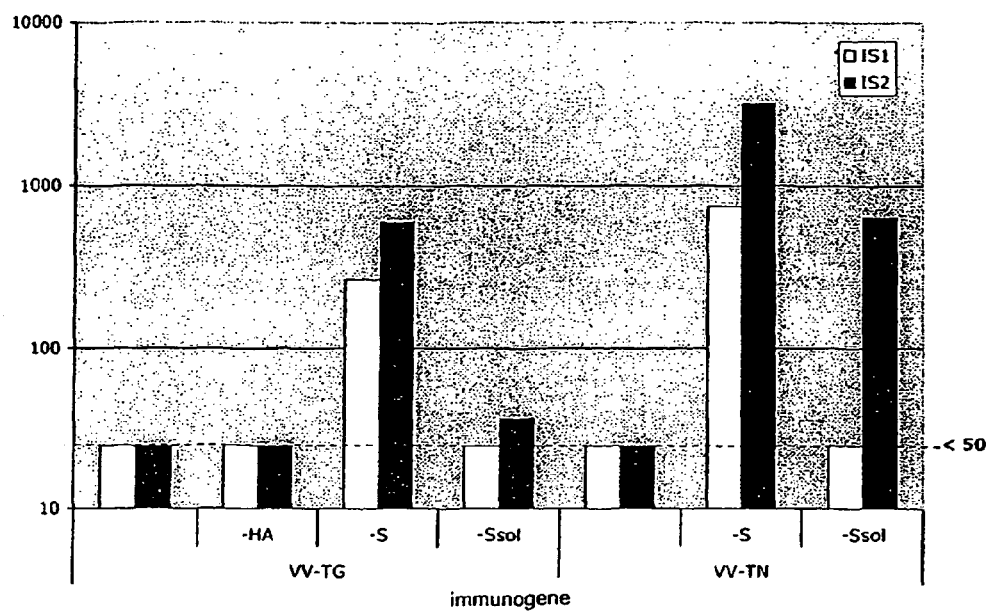
B.
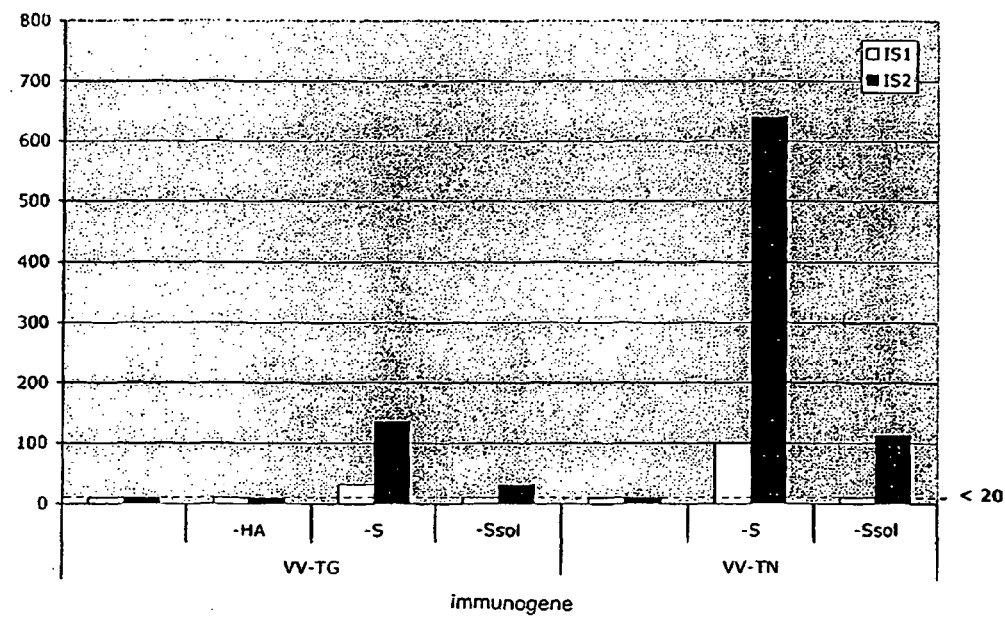
FIGURE 39

STRAIN OF SARS-ASSOCIATED CORONAVIRUS AND APPLICATIONS THEREOF

The present invention relates to a novel strain of severe acute respiratory syndrome (SARS)-associated coronavirus derived from a sample recorded under No. 031589 and collected in Hanoi (Vietnam), to nucleic acid molecules derived from its genome, to the proteins and peptides encoded by said nucleic acid molecules and to their applications, in particular as diagnostic reagents and/or as vaccine.

Coronavirus is a virus containing single-stranded RNA, of positive polarity, of approximately 30 kilobases which replicates in the cytoplasm of the host cells; the 5' end of the genome has a capped structure and the 3' end contains a polyA tail. This virus is enveloped and comprises, at its surface, peplomeric structures called spicules.

The genome comprises the following open reading frames or ORFs, from its 5' end to its 3' end: ORF1a and ORF1b corresponding to the proteins of the transcription-replication complex, and ORF-S, ORF-E, ORF-M and ORF-N corresponding to the structural proteins S, E, M and N. It also comprises ORFs corresponding to proteins of unknown function encoded by: the region situated between ORF-S and ORF-E and overlapping the latter, the region situated between ORF-M and ORF-N, and the region included in ORF-N.

The S protein is a membrane glycoprotein (200-220 kDa) which exists in the form of spicules or spikes emerging from the surface of the viral envelope. It is responsible for the attachment of the virus to the receptors of the host cell and for inducing the fusion of the viral envelope with the cell membrane.

The small envelope protein (E), also called sM (small membrane), which is a nonglycosylated transmembrane protein of about 10 kDa, is the protein present in the smallest quantity in the virion. It plays a powerful role in the coronavirus budding process which occurs at the level of the intermediate compartment in the endoplasmic reticulum and the Golgi apparatus.

The M protein or matrix protein (25-30 kDa) is a more abundant membrane glycoprotein which is integrated into the viral particle by an M/E interaction, whereas the incorporation of S into the particles is directed by an S/M interaction. It appears to be important for the viral maturation of coronaviruses and for the determination of the site where the viral particles are assembled.

The N protein or nucleocapsid protein (45-50 kDa) which is the most conserved among the coronavirus structural proteins is necessary for encapsidating the genomic RNA and then for directing its incorporation into the virion. This protein is probably also involved in the replication of the RNA.

When the host cell is infected, the reading frame (ORF) situated in 5' of the viral genome is translated into a polyprotein which is cleaved by the viral proteases and then releases several nonstructural proteins such as the RNA-dependent RNA polymerase (Rep) and the ATPase helicase (Hel). These two proteins are involved in the replication of the viral genome and in the generation of transcripts which are used in the synthesis of the viral proteins. The mechanisms by which these subgenomic mRNAs are produced are not completely understood; however, recent facts indicate that the sequences for regulation of transcription at the 5' end of each gene represent signals which regulate the discontinuous transcription of the subgenomic mRNAs.

The proteins of the viral membrane (S, E and M proteins) are inserted into the intermediate compartment, whereas the replicated RNA (+ strand) is assembled with the N (nucleocapsid) protein. This protein-RNA complex then combines with the M protein contained in the membranes of the endoplasmic reticulum and the viral particles form when the nucleocapsid complex buds into the endoplasmic reticulum. The virus then migrates across the Golgi complex and eventually leaves the cell, for example by exocytosis. The site of attachment of the virus to the host cell is at the level of the S protein.

Coronaviruses are responsible for 15 to 30% of colds in humans and for respiratory and digestive infections in animals, especially cats (FIPV: Feline infectious peritonitis virus), poultry (IBV: Avian infectious bronchitis virus), mice (MHV: Mouse hepatitis virus), pigs (TGEV: Transmissible gastroenteritis virus, PEDV: Porcine Epidemic diarrhea virus, PRCoV: Porcine Respiratory Coronavirus, HEV: Hemagglutinating encephaloinyelitis Virus) and bovines (BCoV: Bovine coronavirus).

In general, each coronavirus affects only one species; in immunocompetent individuals, the infection induces optionally neutralizing antibodies and cell immunity, capable of destroying the infected cells.

An epidemy of atypical pneumonia, called severe acute respiratory syndrome (SARS) has spread in various countries (Vietnam, Hong Kong, Singapore, Thailand and Canada) during the first quarter of 2003, from an initial focus which appeared in China in the last quarter of 2002. The severity of this disease is such that its mortality rate is about 3 to 6%. The determination of the causative agent of this disease is underway by numerous laboratories worldwide.

In March 2003, a new coronavirus (SARS-CoV or SARS virus) was isolated, in association with cases of severe acute respiratory syndrome (T. G. KSIAZEK et al., The New England Journal of Medicine, 2003, 348, 1319-1330; C. DROSTEN et al., The New England Journal of Medicine, 2003, 348, 1967-1976; Peiris et al., Lancet, 2003, 361, 1319).

Genomic sequences of this new coronavirus have thus been obtained, in particular those of the Urbani isolate (Genbank accession No. AY274119.3 and A. MARRA et al., Science, May 1, 2003, 300, 1399-1404) and the Toronto isolate (Tor2, Genbank accession No. AY278741 and A. ROTA et al., Science, 2003, 300, 1394-1399).

The organization of the genome is comparable with that of other known coronaviruses, thus making it possible to confirm that SARS-CoV belongs to the Coronaviridae family; open reading frames ORF1a and 1b and open reading frames corresponding to the S, E, M and N proteins, and to proteins encoded by: the region situated between ORF-S and ORF-E (ORF3), the region situated between ORF-S and ORF-E and overlapping ORF-E (ORF4), the region situated between ORF-M and ORF-N (ORF7 to ORF11) and the region corresponding to ORF-N (ORF13 and ORF14), have in particular been identified.

Seven differences have been identified between the sequences of the Tor2 and Urbani isolates; 3 correspond to silent mutations (c/t at position 16622 and a/g at position 19064 of ORF1b, t/c at position 24872 of ORF-S) and 4 modify the amino acid sequence of respectively: the proteins encoded by ORF1a (c/t at position 7919 corresponding to the A/V mutation), the S protein (g/t at position 23220 corresponding to the A/S mutation), the protein encoded by ORF3 (a/g at position 25298 corresponding to the R/G mutation) and the M protein (t/c at position 26857 corresponding to the S/P mutation).

In addition, phylogenetic analysis shows that SARS-CoV is distant from other coronaviruses and that it did not appear by mutation of human respiratory coronaviruses nor by recombination between known coronaviruses (for a review, see Holmes, J. C. I., 2003, 111, 1605-1609).

The determination and the taking into account of new variants are important for the development of reagents for the detection and diagnosis of SARS which are sufficiently sensitive and specific, and immunogenic compositions capable of protecting populations against epidemics of SARS.

The inventors have now identified another strain of SARS-associated coronavirus which is distinguishable from the Tor2 and Urbani isolates.

The subject of the present invention is therefore an isolated or purified strain of severe acute respiratory syndrome-associated human coronavirus, characterized in that its genome has, in the form of complementary DNA, a serine codon at position 23220-23222 of the gene for the S protein or a glycine codon at position 25298-25300 of the gene for ORF3, and an alanine codon at position 7918-7920 of ORF1a or a serine codon at position 26857-26859 of the gene for the M protein, said positions being indicated in terms of reference to the Genbank sequence AY274119.3.

According to an advantageous embodiment of said strain, the DNA equivalent of its genome has a sequence corresponding to the sequence SEQ ID No: 1; this coronavirus strain is derived from the sample collected from the bronchoalveolar washings from a patient suffering from SARS, recorded under the No. 031589 and collected at the Hanoi (Vietnam) French hospital.

In accordance with the invention, said sequence SEQ ID No: 1 is that of the deoxyribonucleic acid corresponding to the ribonucleic acid molecule of the genome of the isolated coronavirus strain as defined above.

The sequence SEQ ID No: 1 is distinguishable from the Genbank sequence AY274119.3 (Tor2 isolate) in that it possesses the following mutations:

- g/t at position 23220; the alanine codon (gct) at position 577 of the amino acid sequence of the Tor2 S protein is replaced by a serine codon (tct),
- a/g at position 25298; the arginine codon (aga) at position 11 of the amino acid sequence of the protein encoded by the Tor2 ORF3 is replaced by a glycine codon (gga).

In addition, the sequence SEQ ID No: 1 is distinguishable from the Genbank sequence AY278741 (Urbani isolate) in that it possesses the following mutations:

- t/c at position 7919; the valine codon (gtt) in position 2552 of the amino acid sequence of the protein encoded by ORF1a is replaced by an alanine codon (gct),
- t/c at position 16622: this mutation does not modify the amino acid sequence of the proteins encoded by ORF1b (silent mutation),
- g/a at position 19064: this mutation does not modify the amino acid sequence of the proteins encoded by ORF1b (silent mutation),
- c/t at position 24872: this mutation does not modify the amino acid sequence of the S protein, and
- c/t at position 26857: the proline codon (ccc) at position 154 of the amino acid sequence of the M protein is replaced by a serine codon (tcc).

Unless otherwise stated, the positions of the nucleotide and peptide sequences are indicated with reference to the Genbank sequence AY274119.3.

The subject of the present invention is also an isolated or purified polynucleotide, characterized in that its sequence is that of the genome of the isolated coronavirus strain as defined above.

According to an advantageous embodiment of said polynucleotide, it has the sequence SEQ ID No: 1.

The subject of the present invention is also an isolated or purified polynucleotide, characterized in that its sequence hybridizes under high stringency conditions with the sequence of the polynucleotide as defined above.

The terms "isolated or purified" mean modified "by the hand of humans" from the natural state; in other words if an object exists in nature, it is said to be isolated or purified if it is modified or extracted from its natural environment or both. For example, a polynucleotide or a protein/peptide naturally present in a living organism is neither isolated nor purified; on the other hand, the same polynucleotide or protein/peptide separated from coexisting molecules in its natural environment, obtained by cloning, amplification and/or chemical synthesis is isolated for the purposes of the present invention. Furthermore, a polynucleotide or a protein/peptide which is introduced into an organism by transformation, genetic manipulation or by any other method, is "isolated" even if it is present in said organism. The term purified as used in the present invention means that the proteins/peptides according to the invention are essentially free of association with the other proteins or polypeptides, as is for example the product purified from the culture of recombinant host cells or the product purified from a nonrecombinant source.

For the purposes of the present invention, high stringency hybridization conditions are understood to mean temperature and ionic strength conditions chosen such that they make it possible to maintain the specific and selective hybridization between complementary polynucleotides.

By way of illustration, high stringency conditions for the purposes of defining the above polynucleotides are advantageously the following: the DNA-DNA or DNA-RNA hybridization is performed in two steps: (1) prehybridization at 42° C. for 3 hours in phosphate buffer (20 mM, pH 7.5) containing 5×SSC (1×SSC corresponds to a 0.15 M NaCl+0.015 M sodium citrate solution), 50% formamide, 7% sodium dodecyl sulfate (SDS), 10× Denhardt's, 5% dextran sulfate and 1% salmon sperm DNA; (2) hybridization for 20 hours at 42° C. followed by 2 washings of 20 minutes at 20° C. in 2×SSC+2% SDS, 1 washing of 20 minutes at 20° C. in 0.1×SSC+0.1% SDS. The final washing is performed in 0.1×SSC+0.1% SDS for 30 minutes at 60° C.

The subject of the present invention is also a representative fragment of the polynucleotide as defined above, characterized in that it is capable of being obtained either by the use of restriction enzymes whose recognition and cleavage sites are present in said polynucleotide as defined above, or by amplification with the aid of oligonucleotide primers specific for said polynuclectide as defined above, or by transcription in vitro, or by chemical synthesis.

According to an advantageous embodiment of said fragment, it is selected from the group consisting of: the cDNA corresponding to at least one open reading frame (ORF) chosen from: ORF1a, ORF1b, ORF-S, ORF-E, ORF-M, ORF-N, ORF3, ORF4, ORF7 to ORF11, ORF13 and ORF14 and the cDNA corresponding to the noncoding 5' or 3' ends of said polynucleotide.

According to an advantageous feature of this embodiment, said fragment has a sequence selected from the group consisting of:

- the sequences SEQ ID NO: 2 and 4 representing the cDNA corresponding to the ORF-S which encodes the S protein,
- the sequences SEQ ID NO: 13 and 15 representing the cDNA corresponding to the ORF-E which encodes the E protein, the sequences SEQ ID NO: 16 and 18 representing the cDNA corresponding to the ORF-M which encodes the M protein, the sequences SEQ ID NO: 36 and 38 representing the cDNA corresponding to the ORF-N which encodes the N protein, the sequences representing the cDNA corresponding respectively: to ORF1a and ORF1b (ORF1ab, SEQ ID NO: 31), to ORF3 and ORF4 (SEQ ID NO: 7, 8), to ORF7 to 11 (SEQ ID NO: 19, 20) to ORF13 (SEQ ID NO: 32) and to ORF14 (SEQ ID NO: 34), and the sequences representing the cDNAs corresponding respectively to the noncoding 5' (SEQ ID NO: 39 and 72) and 3' (SEQ ID NO: 40, 73) ends of said polynucleotide.

The subject of the present invention is also a cDNA fragment encoding the S protein, as defined above, characterized in that it has a sequence selected from the group consisting of the sequences SEQ ID NO: 5 and 6 (Sa and Sb fragments).

The subject of the present invention is also a cDNA fragment corresponding to ORF1a and ORF1b as defined above, characterized in that it has a sequence selected from the group consisting of the sequences SEQ ID NO: 41 to 54 (L0 to L12 fragments).

The subject of the present invention is also a polynucleotide fragment as defined above, characterized in that it has at least 15 consecutive bases or base pairs of the sequence of the genome of said strain including at least one of those situated in position 7979, 16622, 19064, 23220, 24872, 25298 and 26857. Preferably this is a fragment of 20 to 2500 bases or base pairs, preferably from 20 to 400.

According to an advantageous embodiment of said fragment, it includes at least one pair of bases or base pairs corresponding to the following positions: 7919 and 23220, 7919 and 25298, 16622 and 23220, 19064 and 23220, 16622 and 25298, 19064 and 25298, 23220 and 24872, 23220 and 26857, 24872 and 25298, 25298 and 26857.

The subject of the present invention is also primers of at least 18 bases capable of amplifying a fragment of the genome of a SARS-associated coronavirus or of the DNA equivalent thereof.

According to an embodiment of said primers, they are selected from the group consisting of:

the pair of primers No. 1 corresponding respectively to positions 28507 to 28522 (sense primer, SEQ ID NO: 60) and 28774 to 28759 (antisense primer, SEQ ID NO: 61) of the sequence of the polynucleotide as defined above, the pair of primers No. 2 corresponding respectively to positions 28375 to 28390 (sense primer, SEQ ID NO: 62) and 28702 to 28687 (antisense primer, SEQ ID NO: 63) of the sequence of the polynucleotide as defined above, and the pair of primers consisting of the primers SEQ ID Nos: 55 and 56.

The subject of the present invention is also a probe capable of detecting the presence of the genome of a SARS-associated coronavirus or of a fragment thereof, characterized in that it is selected from the group consisting of: the fragments as defined above and the fragments corresponding to the following positions of the polynucleotide sequence as defined above: 28561 to 28586, 28588 to 28608, 28541 to 28563 and 28565 to 28589 (SEQ ID NO: 64 to 67).

The probes and primers according to the invention may be labeled directly or indirectly with a radioactive or nonradioactive compound by methods well known to persons skilled in the art so as to obtain a detectable and/or quantifiable signal. Among the radioactive isotopes used, there may be mentioned $^{32}P$, $^{33}P$, $^{35}S$, $^{3}H$ or $^{125}I$. The nonradioactive entities are selected from ligands such as biotin, avidin, streptavidin, digoxygenin, haptens, dyes, luminescent agents such as radioluminescent, chemoluminescent, bioluminescent, fluorescent and phosphorescent agents.

The invention encompasses the labeled probes and primers derived from the preceding sequences.

Such probes and primers are useful for the diagnosis of infection by a SARS-associated coronavirus.

The subject of the present invention is also a method for the detection of a SARS-associated coronavirus, from a biological sample, which method is characterized in that it comprises at least:

(a) the extraction of nucleic acids present in said biological sample, (b) the amplification of a fragment of ORF-N by RT-PCR with the aid of a pair of primers as defined above, and (c) the detection, by any appropriate means, of the amplification products obtained in (b).

The amplification products (amplicons) in (b) are 268 bp for the pair of primers No. 1 and 328 bp for the pair of primers No. 2.

According to an advantageous embodiment of said method, the step (b) of detection is carried out with the aid of at least one probe corresponding to positions 28561 to 28586, 28588 to 28608, 28541 to 28563 and 28565 to 28589 of the sequence of the polynucleotide as defined above.

Preferably, the SARS-associated coronavirus genome is detected and optionally quantified by PCR in real time with the aid of the pair of primers No. 2 and probes corresponding to positions 28541 to 28563 and 28565 to 28589 labeled with different compounds, in particular different fluorescent agents.

The real time RT-PCR which uses this pair of primers and this probe is very sensitive since it makes it possible to detect $10^2$ copies of RNA and up to 10 copies of RNA; it is in addition reliable and reproducible.

The invention encompasses the single-stranded, double-stranded and triple-stranded polydeoxyribonucleotides and polyribonucleotides corresponding to the sequence of the genome of the isolated strain of coronavirus and its fragments as defined above, and to their sense or antisense complementary sequences, in particular the RNAs and cDNAs corresponding to the sequence of the genome and of its fragments as defined above.

The present invention also encompasses the amplification fragments obtained with the aid of primers specific for the genome of the purified or isolated strain as defined above, in particular with the aid of primers or pairs of primers as defined above, the restriction fragments formed by or comprising the sequence of fragments as defined above, the fragments obtained by transcription in vitro from a vector containing the sequence SEQ ID NO: 1 or a fragment as defined above, and fragments obtained by chemical synthesis. Examples of restriction fragments are deduced from the restriction map of the sequence SEQ ID NO: 1 illustrated by FIG. 13. In accordance with the invention, said fragments are either in the form of isolated fragments, or in the form of mixtures of fragments. The invention also encompasses fragments modified, in relation to the preceding ones, by removal or addition of nucleotides in a proportion of about 15%, relative to the length of the above fragments and/or modified in terms of the nature of the nucleotides, as long as the modified nucleotide fragments retain a capacity for hybridization with the genomic or antigenomic RNA sequences of the isolate as defined above.

The nucleic acid molecules according to the invention are obtained by conventional methods, known per se, following standard protocols such as those described in *Current Protocols in Molecular Biology* (Frederick M. AUSUBEL, 2000, Wiley and son Inc., Library of Congress, USA). For example, they may be obtained by amplification of a nucleic sequence by PCR or RT-PCR or alternatively by total or partial chemical synthesis.

The subject of the present invention is also a DNA or RNA chip or filter, characterized in that it comprises at least one polynucleotide or one of its fragments as defined above.

The DNA or RNA chips or filters according to the invention are prepared by conventional methods, known per se, such as for example chemical or electrochemical grafting of oligonucleotides on a glass or nylon support.

The subject of the present invention is also a recombinant cloning and/or expression vector, in particular a plasmid, a virus, a viral vector or a phage comprising a nucleic acid fragment as defined above. Preferably, said recombinant vector is an expression vector in which said nucleic acid fragment is placed under the control of appropriate elements for regulating transcription and translation. In addition, said vector may comprise sequences (tags) fused in phase with the 5' and/or 3' end of said insert, which are useful for the immobilization and/or detection and/or purification of the protein expressed from said vector.

These vectors are constructed and introduced into host cells by conventional recombinant DNA and genetic engineering methods which are known per se. Numerous vectors into which a nucleic acid molecule of interest may be inserted in order to introduce it and to maintain it in a host cell are known per se; the choice of an appropriate vector depends on the use envisaged for this vector (for example replication of the sequence of interest, expression of this sequence, maintenance of the sequence in extrachromosomal form or alternatively integration into the chromosomal material of the host), and on the nature of the host cell.

In accordance with the invention, said plasmid is selected in particular from the following plasmids:

the plasmid, called SARS-S, contained in the bacterial strain deposited under the No. I-3659, on Jun. 20, 2003, at the Collection Nationale de Cultures de Microorganismes, 25 rue du Docteur Roux, 75724 Paris Cedex 15; it contains the cDNA sequence encoding the S protein of the SARS-CoV strain derived from the sample recorded under the No. 031589, said sequence corresponding to the nucleotides at positions 21406 to 25348 (SEQ ID NO: 4), with reference to the Genbank sequence AY274119.3,
- the plasmid, called SARS-S1, contained in the bacterial strain deposited under the No. I-3020, on May 12, 2003, at the Collection Nationale de Cultures de Microorganismes, 25 rue du Docteur Roux, 75724 Paris Cedex 15; it contains a 5' fragment of the cDNA sequence encoding the S protein of the SARS-CoV strain derived from the sample recorded under the No. 031589, as defined above, said fragment corresponding to the nucleotides at positions 21406 to 23454 (SEQ ID NO: 5), with reference to the Genbank sequence AY274119.3 Tor2,
- the plasmid, called SARS-S2, contained in the bacterial strain deposited under the No. I-3019, on May 12, 2003, at the Collection Nationale de Cultures de Microorganismes, 25 rue du Docteur Roux, 75724 Paris Cedex 15; it contains a 3' fragment of the cDNA sequence encoding the S protein of the SARS-CoV strain derived from the sample recorded under the number No. 031589, as defined above, said fragment corresponding to the nucleotides at positions 23322 to 25348 (SEQ ID NO: 6), with reference to the Genbank sequence accession No. AY274119.3,
- the plasmid, called SARS-SE, contained in the bacterial strain deposited under the No. I-3126, on Nov. 13, 2003, at the Collection Nationale de Cultures de Microorganismes, 25 rue du Docteur Roux, 75724 Paris Cedex 15; it contains the cDNA corresponding to the region situated between ORF-S and ORF-E and overlapping ORF-E of the SARS-CoV strain derived from the sample recorded under the No. 031589, as defined above, said region corresponding to the nucleotides at positions 25110 to 26244 (SEQ ID NO: 8), with reference to the Genbank sequence accession No. AY274119.3,
- the plasmid, called SARS-E, contained in the bacterial strain deposited under the No. I-3046, on May 28, 2003, at the Collection Nationale de Cultures de Microorganismes, 25 rue du Docteur Roux, 75724 Paris Cedex 15; it contains the cDNA sequence encoding the E protein of the SARSCoV strain derived from the sample recorded under the No. 031589, as defined above, said sequence corresponding to the nucleotides at positions 26082 to 26413 (SEQ ID NO: 15), with reference to the Genbank sequence accession No. AY274119.3,
- the plasmid, called SARS-M, contained in the bacterial strain deposited under the No. I-3047, on May 28, 2003, at the Collection Nationale de Cultures de Microorganismes, 25 rue du Docteur Roux, 75724 Paris Cedex 15; it contains the cDNA sequence encoding the M protein of the SARS-CoV strain derived from the sample recorded under the No. 031589, as defined above; said sequence corresponding to the nucleotides at positions 26330 to 27098 (SEQ ID NO: 18), with reference to the Genbank sequence accession No. AY274119.3,
- the plasmid, called SARS-MN, contained in the bacterial sequence deposited under the No. I-3125, on Nov. 13, 2003, at the Collection Nationale de Cultures de Microorganismes, 25 rue du Docteur Roux, 75724 Paris Cedex 15; it contains the cDNA sequence corresponding to the region situated between ORF-M and ORF-N of the SARS-CoV strain derived from the sample recorded under the No. 031589 and collected in Hanoi, as defined above, said sequence corresponding to the nucleotides at positions 26977 to 28218 (SEQ ID NO: 20), with reference to the Genbank accession No. AY274119.3,
- the plasmid, called SARS-N, contained in the bacterial strain deposited under the No. I-3048, on Jun. 5, 2003, at the Collection Nationale de Cultures de Microorganismes, 25 rue du Docteur Roux, 75724 Paris Cedex 15; it contains the cDNA encoding the N protein of the SARS-CoV strain derived from the sample recorded under the No. 031589, as defined above, said sequence corresponding to the nucleotides at positions 28054 to 29430 (SEQ ID NO: 38), with reference to the Genbank sequence accession No. AY274119.3; thus, this plasmid comprises an insert of sequence SEQ ID NO: 38 and is contained in a bacterial strain which was deposited under the No. I-3048, on Jun. 5, 2003, at the Collection Nationale de Cultures de Microorganismes, 25 rue du Docteur Roux, 75724 Paris Cedex 15,
- the plasmid, called SARS-5'NC, contained in the bacterial strain deposited under the No. I-3124, on Nov. 7, 2003, at the Collection Nationale de Cultures de Microorganismes, 25 rue du Docteur Roux, 75724 Paris Cedex 15; it contains the cDNA corresponding to the noncoding 5' end of the genome of the SARS-CoV strain derived from the sample recorded under the No. 031589, as defined above, said sequence corresponding to the nucleotides at positions 1 to 204 (SEQ ID NO: 39), with reference to the Genbank sequence accession No. AY274119.3, the plasmid called SARS-3'NC, contained in the bacterial strain deposited under the No. I-3123 on Nov. 7, 2003, at the Collection Nationale de Cultures de Microorganismes, 25 rue du Docteur Roux, 75724 Paris Cedex 15; it contains the cDNA sequence corresponding to the non-coding 3' end of the genome of the SARS-CoV strain derived from the sample recorded under the No. 031589, as defined above, said sequence corresponding to that situated between the nucleotide and position 28933 to 29727 (SEQ ID NO: 40), with reference to the Genbank sequence accession No. AY274119.3, ends with a series of nucledtides a., the expression plasmid, called pIV2.3N, containing a cDNA fragment encoding a C-terminal fusion of the N protein (SEQ ID NO: 37) with a polyhistidine tag, the expression plasmid, called pIV2.3$S_C$, containing a cDNA fragment encoding a C-terminal fusion of the fragment corresponding to positions 475 to 1193 of the amino acid sequence of the S protein (SEQ ID NO: 3) with a polyhistidine tag, the expression plasmid, pIV2.3$S_L$, containing a cDNA fragment encoding a C-terminal fusion of the fragment corresponding to positions 14 to 1193 of the amino acid sequence of the S protein (SEQ ID NO: 3) with a polyhistidine tag, the expression plasmid, called pIV2.4N, containing a cDNA fragment encoding a N-terminal fusion of the N protein (SEQ ID NO: 3) with a polyhistidine tag, the expression plasmid, called pIV2.4$S_C$ or pIV2.4$S_1$, containing an insert encoding a N-terminal fusion of the fragment corresponding to positions 475 to 1193 of the amino acid sequence of the S protein (SEQ ID NO: 3) with a polyhistidine tag, and the expression plasmid, called pIV2.4$S_L$, containing a cDNA fragment encoding an N-terminal fusion of the fragment corresponding to positions 14 to 1193 of the amino acid sequence of the S protein (SEQ ID NO: 3) with a polyhistidine tag.

According to an advantageous feature of the expression plasmid as defined above, it is contained in a bacterial strain which was deposited under the No. I-3117, on Oct. 23, 2003, at the Collection Nationale de Cultures de Microorganismes, 25 rue du Docteur Roux, 75724 Paris Cedex 15.

According to another advantageous feature of the expression plasmid as defined above, it is contained in a bacterial strain which was deposited under the No. I-3118, on Oct. 23, 2003, at the Collection Nationale de Cultures de Microorganismes, 25 rue du Docteur Roux, 75724 Paris Cedex 15.

According to another feature of the expression plasmid as defined above, it is contained in a bacterial strain which was deposited at the CNCM, 25 rue du Docteur Roux, 75724 Paris Cedex 15 under the following numbers:

a) strain No. I-3118, deposited on Oct. 23, 2003,
b) strain No. I-3019, deposited on May 12, 2003,
c) strain No. I-3020, deposited on May 12, 2003,
d) strain No. I-3059, deposited on Jun. 20, 2003,
e) strain No. I-3323, deposited on Nov. 22, 2004,
f) strain No. I-3324, deposited on Nov. 22, 2004,
g) strain No. I-3326, deposited on Dec. 1, 2004,
h) strain No. I-3327, deposited on Dec. 1, 2004,
i) strain No. I-3332, deposited on Dec. 1, 2004,
j) strain No. I-3333, deposited on Dec. 1, 2004,
k) strain No. I-3334, deposited on Dec. 1, 2004,
l) strain No. I-3335, deposited on Dec. 1, 2004,
m) strain No. I-3336, deposited on Dec. 1, 2004,
n) strain No. I-3337, deposited on Dec. 1, 2004,
o) strain No. I-3338, deposited on Dec. 2, 2004,
p) strain No. I-3339, deposited on Dec. 2, 2004,
q) strain No. I-3340, deposited on Dec. 2, 2004,
r) strain No. I-3341, deposited on Dec. 2, 2004.

The subject of the present invention is also a nucleic acid insert of viral origin, characterized in that it is contained in any of the strains as defined above in a)-r).

The subject of the present invention is also a nucleic acid containing a synthetic gene allowing optimized expression of the S protein in eukaryotic cells, characterized in that it possesses the sequence SEQ ID NO: 140.

The subject of the present invention is also an expression vector containing a nucleic acid containing a synthetic gene allowing optimized expression of the S protein, which vector is contained in the bacterial strain deposited at the CNCM, on Dec. 1, 2004, under the No. I-3333.

According to one embodiment of said expression vector, it is a viral vector, in the form of a viral particle or in the form of a recombinant genome.

According to an advantageous feature of this embodiment, this is a recombinant viral particle or a recombinant viral genome capable of being obtained by transfection of a plasmid according to paragraphs g), h) and k) to r) as defined above, in an appropriate cellular system, that is to say, for example, cells transfected with one or more other plasmids intended to transcomplement certain functions of the virus that are deleted in the vector and that are necessary for the formation of the viral particles.

The expression "S protein family" is understood here to mean the complete S protein, its ectodomaine and fragments of this ectodomaine which are preferably produced in a eukaryotic system.

The subject of the present invention is also a lentiviral vector encoding a polypeptide of the S protein family, as defined above.

The subject of the present invention is also a recombinant measles virus encoding a polypeptide of the S protein family, as defined above.

The subject of the present invention is also a recombinant vaccinia virus encoding a polypeptide of the S protein family, as defined above.

The subject of the present invention is also the use of a vector according to paragraphs e) to r) as defined above, or of a vector containing a synthetic gene for the S protein, as defined above, for the production, in a eukaryotic system, of the SARS-associated coronavirus S protein or of a fragment of this protein.

The subject of the present invention is also a method for producing the S protein in a eukaryotic system, comprising a step of transfecting eukaryotic cells in culture with a vector chosen from the vectors contained in the bacterial strains mentioned in paragraphs e) to r) above or a vector containing a synthetic gene allowing optimized expression of the S protein.

The subject of the present invention is also a cDNA library characterized in that it comprises fragments as defined above, in particular amplification fragments or restriction fragments, cloned into a recombinant vector, in particular an expression vector (expression library).

The subject of the present invention is also cells, in particular prokaryotic cells, modified by a recombinant vector as defined above.

The subject of the present invention is also a genetically modified eukaryotic cell expressing a protein or a polypeptide as defined above. Quite obviously, the terms "genetically modified eukaryotic cell" do not denote a cell modified with a wild-type virus.

According to an advantageous embodiment of said cell, it is capable of being obtained by transfection with any of the vectors mentioned in paragraphs i) to l) above.

According to an advantageous feature of this embodiment, this is the cell FRhK4-Ssol-30, deposited at the CNCM on Nov. 22, 2004, under the No. I-3325.

The recombinant vectors as defined above and the cells transformed with said expression vectors are advantageously used for the production of the corresponding proteins and peptides. The expression libraries derived from said vectors, and the cells transformed with said expression libraries are advantageously used to identify the immunogenic epitopes (B and T epitopes) of the SARS-associated coronavirus proteins.

The subject of the present invention is also the purified or isolated proteins and peptides, characterized in that they are encoded by the polynucleotide or one of its fragments as defined above.

According to an advantageous embodiment of the invention, said protein is selected from the group consisting of:
the S protein having the sequence SEQ ID NO: 3 or its ectodomaine
the E protein having the sequence SEQ ID NO: 14
the M protein having the sequence SEQ ID NO: 17
the N protein having the sequence SEQ ID NO: 37
the proteins encoded by the ORFs: ORF1a, ORF1b, ORF3, ORF4 and ORF7 to ORF11, ORF13 and ORF14 and having the respective sequence, SEQ ID NO: 74, 75, 10, 12, 22, 24, 26, 28, 30, 33 and 35.

The terms "ectodomaine of the S protein" and "soluble form of the S protein" will be used interchangeably below.

According to an advantageous embodiment of the invention, said polypeptide consists of the amino acids corresponding to positions 1 to 1193 of the amino acid sequence of the S protein.

According to another advantageous embodiment of the invention, said peptide is selected from the group consisting of:
a) the peptides corresponding to positions 14 to 1193 and 475 to 1193 of the amino acid sequence of the S protein,
b) the peptides corresponding to positions 2 to 14 (SEQ ID NO: 69) and 100 to 221 of the amino acid sequence of the M protein; these peptides correspond respectively to the ectodomaine and to the endodomaine of the M protein, and
c) the peptides corresponding to positions 1 to 12 (SEQ ID NO: 70) and 53 to 76 (SEQ ID NO: 71) of the amino acid sequence of the E protein; these peptides correspond respectively to the ectodomaine and to the C-terminal end of the E protein, and
d) the peptides of 5 to 50 consecutive amino acids, preferably of 10 to 30 amino acids, inclusive or partially or completely overlapping the sequence of the peptides as defined in a), b) or c).

The subject of the present invention is also a peptide, characterized in that it has a sequence of 7 to 50 amino acids including an amino acid residue selected from the group consisting of:
the alanine situated at position 2552 of the amino acid sequence of the protein encoded by ORF1a,
the serine situated at position 577 of the amino acid sequence of the S protein of the SARS-CoV strain as defined above,
the glycine at position 11 of the amino acid sequence of the protein encoded by ORF3 of the SARS-CoV strain as defined above,
the serine at position 154 of the amino acid sequence of the M protein of the SARS-CoV strain as defined above.

The subject of the present invention is also an antibody or a polyclonal or monoclonal antibody fragment which can be obtained by immunization of an animal with a recombinant vector as defined above, a cDNA library as defined above or alternatively a protein or a peptide as defined above, characterized in that it binds to at least one of the proteins encoded by SARS-CoV as defined above.

The invention encompasses the polyclonal antibodies, the monoclonal antibodies, the chimeric antibodies such as the humanized antibodies, and fragments thereof (Fab, Fv, scFv).

A subject of the present invention is also a hybridoma producing a monoclonal antibody against the N protein, characterized in that it is chosen from the following hybridomas:
the hybridoma producing the monoclonal antibody 87, deposited at the CNCM on Dec. 1, 2004 under the number I-3328,
the hybridoma producing the monoclonal antibody 86, deposited at the CNCM on Dec. 1, 2004 under the number I-3329,
the hybridoma producing the monoclonal antibody 57, deposited at the CNCM on Dec. 1, 2004 under the number I-3330, and
the hybridoma producing the monoclonal antibody 156, deposited at the CNCM on Dec. 1, 2004 under the number I-3331.

The subject of the present invention is also a polyclonal or monoclonal antibody or antibody fragment directed against the N protein, characterized in that it is produced by a hybridoma as defined above.

For the purposes of the present invention, the expression chimeric antibody is understood to mean, in relation to an antibody of a particular animal species or of a particular class of antibody, an antibody comprising all or part of a heavy chain and/or of a light chain of an antibody of another animal species or of another class of antibody.

For the purposes of the present invention, the expression humanized antibody is understood to mean a human immunoglobulin in which the residues of the CDRs (Complementary Determining Regions) which form the antigen-binding site are replaced by those of a nonhuman monoclonal antibody possessing the desired specificity, affinity or activity. Compared with the nonhuman antibodies, the humanized antibodies are less immunogenic and possess a prolonged half-life in humans because they possess only a small proportion of nonhuman sequences given that practically all the residues of the FR (Framework) regions and of the constant (Fc) region of these antibodies are those of a consensus sequence of human immunoglobulins.

A subject of the present invention is also a protein chip or filter, characterized in that it comprises a protein, a peptide or alternatively an antibody as defined above.

The protein chips according to the invention are prepared by conventional methods known per se. Among the appropriate supports on which proteins may be immobilized, there may be mentioned those made of plastic or glass, in particular in the form of microplates.

The subject of the present invention is also reagents derived from the isolated strain of SARS-associated coronavirus, derived from the sample recorded under the No. 031589, which are useful for the study and diagnosis of the infection caused by a SARS-associated coronavirus, said reagents are selected from the group consisting of:

(a) a pair of primers, a probe or a DNA chip as defined above, (b) a recombinant vector or a modified cell as defined above, (c) an isolated coronavirus strain or a polynucleotide as defined above, (d) a protein or a peptide as defined above, (e) an antibody or an antibody fragment as defined above, and (f) a protein chip as defined above.

These various reagents are prepared and used according to conventional molecular biology and immunology techniques following standard protocols such as those described in *Current Protocols in Molecular Biology* (Frederick M. AUSUBEL, 2000, Wiley and Son Inc., Library of Congress, USA), in *Current Protocols in Immunology* (John E. Cologan, 2000, Wiley and Son Inc., Library of Congress, USA) and in *Antibodies: A Laboratory Manual* (E. Howell and D. Lane, Cold Spring Harbor Laboratory, 1988).

The nucleic acid fragments according to the invention are prepared and used according to conventional techniques as defined above. The peptides and proteins according to the invention are prepared by recombinant DNA techniques, known to persons skilled in the art, in particular with the aid of the recombinant vectors as defined above. Alternatively, the peptides according to the invention may be prepared by conventional techniques of solid or liquid phase synthesis, known to persons skilled in the art.

The polyclonal antibodies are prepared by immunizing an appropriate animal with a protein or a peptide as defined above, optionally coupled to KLH or to albumin and/or combined with an appropriate adjuvant such as (complete or incomplete) Freund's adjuvant or aluminum hydroxide; after obtaining a satisfactory antibody titer, the antibodies are harvested by collecting serum from the immunized animals and enriched with IgG by precipitation, according to conventional techniques, and then the IgGs specific for the SARS-CoV proteins are optionally purified by affinity chromatography on an appropriate column to which said peptide or said protein is attached, as defined above, so as to obtain a monospecific IgG preparation.

The monoclonal antibodies are produced from hybridomas obtained by fusion of B lymphocytes from an animal immunized with a protein or a peptide as defined above with myelomas, according to the Köhler and Milstein technique (Nature, 1975, 256, 495-497); the hybridomas are cultured in vitro, in particular in fermenters or produced in vivo, in the form of ascites; alternatively, said monoclonal antibodies are produced by genetic engineering as described in American U.S. Pat. No. 4,816,567.

The humanized antibodies are produced by general methods such as those described in International application WO 98/45332.

The antibody fragments are produced from the cloned $V_H$ and $V_L$ regions, from the mRNAs of hybridomas or splenic lymphocytes of an immunized mouse; for example, the Fv, scFv or Fab fragments are expressed at the surface of filamentous phages according to the Winter and Milstein technique (Nature, 1991, 349, 293-299); after several selection steps, the antibody fragments specific for the antigen are isolated and expressed in an appropriate expression system, by conventional techniques for cloning and expression of recombinant DNA.

The antibodies or fragments thereof as defined above are purified by conventional techniques known to persons skilled in the art, such as affinity chromatography.

The subject of the present invention is additionally the use of a product selected from the group consisting of: a pair of primers, a probe, a DNA chip, a recombinant vector, a modified cell, an isolated coronavirus strain, a polynucleotide, a protein or a peptide, an antibody or an antibody fragment and a protein chip as defined above, for the preparation of a reagent for the detection and optionally genotyping/serotyping of a SARS-associated coronavirus.

The proteins and peptides according to the invention, which are capable of being recognized and/or of inducing the production of antibodies specific for the SARS-associated coronavirus, are useful for the diagnosis of infection with such a coronavirus; the infection is detected, by an appropriate technique—in particular EIA, ELISA, RIA, immunofluorescence—, in a biological sample collected from an individual capable of being infected.

According to an advantageous feature of said use, said proteins are selected from the group consisting of the S, E, M and/or N proteins and the peptides as defined above.

The S, E, M and/or N proteins and the peptides derived from these proteins as defined above, for example the N protein, are used for the indirect diagnosis of a SARS-associated coronavirus infection (serological diagnosis; detection of an antibody specific for SARS-CoV), in particular by an immunoenzymatic method (ELISA).

The antibodies and antibody fragments according to the invention, in particular those directed against the S, E, M and/or N proteins and the derived peptides as defined above, are useful for the direct diagnosis of a SARS-associated coronavirus infection; the detection of the protein(s) of SARS-CoV is carried out by an appropriate technique, in particular EIA, ELISA, RIA, immunofluorescence, in a biological sample collected from an individual capable of being infected.

The subject of the present invention is also a method for the detection of a SARS-associated coronavirus, from a biological sample, which method is characterized in that it comprises at least:

(a) bringing said biological sample into contact with at least one antibody or one antibody fragment, one protein, one peptide or alternatively one protein or peptide chip or filter as defined above, and (b) visualizing by any appropriate means antigen-antibody complexes formed in (a), for example by EIA, ELISA, RIA, or by immunofluorescence.

According to one advantageous embodiment of said process, step (a) comprises:

($a_1$) bringing said biological sample into contact with at least a first antibody or an antibody fragment which is attached to an appropriate support, in particular a microplate, ($a_2$) washing the solid phase, and ($a_3$) adding at least a second antibody or an antibody fragment, different from the first, said antibody or antibody fragment being optionally appropriately labeled.

This method, which makes it possible to capture the viral particles present in the biological sample, is also called immunocapture method.

For example:

step ($a_1$) is carried out with at least a first monoclonal or polyclonal antibody or a fragment thereof, directed against the S, M and/or E protein, and/or a peptide corresponding to the ectodomaine of one of these proteins (M2-14 or E1-12 peptides)

step ($a_3$) is carried out with at least one antibody or an antibody fragment directed against another epitope of the same protein or preferably against another protein, preferably against an inner protein such as the N nucleoprotein or the endodomaine of the E or M protein, more preferably still these are antibodies or antibody fragments directed against the N protein which is very abundant in the viral particle; when an antibody or an antibody fragment directed against an inner protein (N) or against the endodomaine of the E or M proteins is used, said antibody is incubated in the presence of detergent, such as Tween 20 for example, at concentrations of the order of 0.1%.

step (b) for visualizing the antigen-antibody complexes formed is carried out, either directly with the aid of a second antibody labeled for example with biotin or an appropriate enzyme such as peroxidase or alkaline phosphatase, or indirectly with the aid of an anti-immunoglobulin serum labeled as above. The complexes thus formed are visualized with the aid of an appropriate substrate.

According to a preferred embodiment of this aspect of the invention, the biological sample is mixed with the visualizing monoclonal antibody prior to its being brought into contact with the capture monoclonal antibodies. Where appropriate, the serum-visualizing antibody mixture is incubated for at least 10 minutes at room temperature before being applied to the plate.

The subject of the present invention is also an immunocapture test intended to detect an infection by the SARS-associated coronavirus by detecting the native nucleoprotein (N protein), in particular characterized in that the antibody used for the capture of the native viral nucleoprotein is a monoclonal antibody specific for the central region and/or for a conformational epitope.

According to one embodiment of said test, the antibody used for the capture of the N protein is the monoclonal antibody mAb87, produced by the hybridoma deposited at the CNCM on Dec. 1, 2004 under the number I-3328.

According to another embodiment of said immunocapture test, the antibody used for the capture of the N protein is the monoclonal antibody mAb86, produced by the hybridoma deposited at the CNCM on Dec. 1, 2004 under the number I-3329.

According to another embodiment of said immunocapture test, the monoclonal antibodies mAb86 and mAb87 are used for the capture of the N protein.

In the immunocapture tests according to the invention, it is possible to use, for visualizing the N protein, the monoclonal antibody mAb57, produced by the hybridoma deposited at the CNCM on Dec. 1, 2004 under the number I-3330, said antibody being conjugated with a visualizing molecule or particle.

In accordance with said immunocapture test, a combination of the antibodies mAb57 and mAb87, conjugated with a visualizing molecule or particle, is used for the visualization of the N protein.

A visualizing molecule may be a radioactive atom, a dye, a fluorescent molecule, a fluorophore, an enzyme; a visualizing particle may be for example: colloidal gold, a magnetic particle or a latex bead.

The subject of the present invention is also a reagent for detecting a SARS-associated coronavirus, characterized in that it is selected from the group consisting of:
(a) a pair of primers or a probe as defined above,
(b) a recombinant vector as defined above or a modified cell as defined above,
(c) an isolated coronavirus strain as defined above or a polynucleotide as defined above,
(d) an antibody or an antibody fragment as defined above,
(e) a combination of antibodies comprising the monoclonal antibodies mAb86 and/or mAb87, and the monoclonal antibody mAb57, as defined above,
(f) a chip or a filter as defined above, The subject of the present invention is also a method for the detection of a SARS-associated coronavirus infection, from a biological sample, by indirect IgG ELISA using the N protein, which method is characterized in that the plates are sensitized with an N protein solution at a concentration of between 0.5 and 4 µg/ml, preferably to 2 µg/ml, in a 10 mM PBS buffer pH 7.2, phenol red at 0.25 ml/l.

The subject of the present invention is additionally a method for the detection of a SARS-associated coronavirus infection, from a biological sample, by double epitope ELSA, characterized in that the serum to be tested is mixed with the visualizing antigen, said mixture then being brought into contact with the antigen attached to a solid support.

According to one variant of the tests for detecting SARS-associated coronaviruses, these tests combine an ELSA using the N protein, and another ELSA using the S protein, as described below.

The subject of the present invention is also an immune complex formed of a polyclonal or monoclonal antibody or antibody fragment as defined above, and of a SARS-associated coronavirus protein or peptide.

The subject of the present invention is additionally a SARS-associated coronavirus detection kit, characterized in that it comprises at least one reagent selected from the group consisting of: a pair of primers, a probe, a DNA or RNA chip, a recombinant vector, a modified cell, an isolated coronavirus strain, a polynucleotide, a protein or a peptide, an antibody, and a protein chip as defined above.

The subject of the present invention is additionally an immunogenic composition, characterized in that it comprises at least one product selected from the group consisting of:
a) a protein or a peptide as defined above,
b) a polynucleotide of the DNA or RNA type or one of its representative fragments as defined above, having a sequence chosen from:
(i) the sequence SEQ ID NO: 1 or its RNA equivalent
(ii) the sequence hybridizing under high stringency conditions with the sequence SEQ ID NO: 1,
(iii) the sequence complementary to the sequence SEQ ID NO: 1 or to the sequence hybridizing under high stringency conditions with the sequence SEQ ID NO: 1,
(iv) the nucleotide sequence of a representative fragment of the polynucleotide as defined in (i), (ii) or (iii),
(v) the sequence as defined in (i), (ii), (iii) or (iv), modified, and
c) a recombinant expression vector comprising a polynucleotide as defined in b), and
d) a cDNA library as defined above, said immunogenic composition being capable of inducing protective humoral or cellular immunity specific for the SARS-associated coronavirus, in particular the production of an antibody directed against a specific epitope of the SARS-associated coronavirus.

The proteins and peptides as defined above, in particular the S, M, E and/or N proteins and the derived peptides, and the nucleic acid (DNA or RNA) molecules encoding said proteins or said peptides are good candidate vaccines and may be used in immunogenic compositions for the production of a vaccine against the SARS-associated coronavirus.

According to an advantageous embodiment of the compositions according to the invention, they additionally contain at least one pharmaceutically acceptable vehicle and optionally carrier substances and/or adjuvants.

The pharmaceutically acceptable vehicles, the carrier substances and the adjuvants are those conventionally used.

The adjuvants are advantageously chosen from the group consisting of oily emulsions, saponin, mineral substances, bacterial extracts, aluminum hydroxide and squalene.

The carrier substances are advantageously selected from the group consisting of unilamellar liposomes, multilamellar liposomes, micelles of saponin or solid microspheres of a saccharide or auriferous nature.

The compositions according to the invention are administered by the general route, in particular by the intramuscular or subcutaneous route or alternatively by the local, in particular nasal (aerosol) route.

The subject of the present invention is also the use of an isolated or purified protein or peptide having a sequence selected from the group consisting of the sequences SEQ ID NO: 3, 10, 12, 14, 17, 22, 24, 26, 28, 30, 33, 35, 37, 69, 70, 71, 74 and 75 to form an immune complex with an antibody specifically directed against an epitope of the SARS-associated coronavirus.

The subject of the present invention is also an immune complex consisting of an isolated or purified protein or peptide having a sequence selected from the group consisting of the sequences SEQ ID NO: 3, 10, 12, 14, 17, 22, 24, 26, 28, 30, 33, 35, 37, 69, 70, 71, 74 and 75, and of an antibody specifically directed against an epitope of the SARS-associated coronavirus.

The subject of the present invention is also the use of an isolated or purified protein or pep tide having a sequence selected from the group consisting of the sequences SEQ ID NO: 3, 10, 12, 14, 17, 22, 24, 26, 28, 30, 33, 35, 37, 69, 70, 71, 74 and 75 to induce the production of an antibody capable of specifically recognizing an epitope of the SARS-associated coronavirus.

The subject of the present invention is also the use of an isolated or purified polynucleotide having a sequence selected from the group consisting of the sequences SEQ ID NO: 1, 2, 4, 7, 8, 13, 15, 16, 18, 19, 20, 31, 36 and 38 to induce the production of an antibody directed against the protein encoded by said polynucleotide and capable of specifically recognizing an epitope of the SARS-associated coronavirus.

The subject of the present invention is also monoclonal antibodies recognizing the native S protein of a SARS-associated coronavirus.

The subject of the present invention is also the use of a protein or a polypeptide of the S protein family, as defined above, or of an antibody recognizing the native S protein, as defined above, to detect an infection by a SARS-associated coronavirus, in a biological sample.

The subject of the present invention is also a method for detecting an infection by a SARS-associated coronavirus, in a biological sample, characterized in that the detection is carried out by ELISA using the recombinant S protein, expressed in a eukaryotic system.

According to an advantageous embodiment of said method, it is a double epitope ELISA method, and the serum to be tested is mixed with the visualizing antigen, said mixture then being brought into contact with the antigen attached to a solid support.

The subject of the present invention is also an immune complex consisting of a monoclonal antibody or antibody fragment recognizing the native S protein, and of a protein or a peptide of the SARS-associated coronavirus.

The subject of the present invention is also an immune complex consisting of a protein or a polypeptide of the S protein family, as defined above, and of an antibody specifically directed against an epitope of the SARS-associated coronavirus.

The subject of the present invention is additionally a SARS-associated coronavirus detection kit or box, characterized in that it comprises at least one reagent selected from the group consisting of: a protein or polypeptide of the S protein family, as defined above, a nucleic acid encoding a protein or peptide of the S protein family, as defined above, a cell expressing a protein or polypeptide of the S protein family, as defined above, or an antibody recognizing the native S protein of a SARS-associated coronavirus.

The subject of the present invention is an immunogenic and/or vaccine composition, characterized in that it comprises a polypeptide or a recombinant protein of the S protein family, as defined above, obtained in a eukaryotic expression system.

The subject of the present invention is also an immunogenic and/or vaccine composition, characterized in that it comprises a vector or recombinant virus, expressing a protein or a polypeptide of the S protein family, as defined above.

In addition to the preceding features, the invention further comprises other features, which will emerge from the description which follows, which refers to examples of use of the polynucleotide representing the genome of the SARS-CoV strain derived from the sample recorded under the number 031589, and derived cDNA fragments which are the subject of the present invention, and to Table I presenting the sequence listing:

TABLE I

Sequence listing

| Identification number | Sequence | Position of the cDNA with reference to Genbank AY274119.3 | Deposit number at the of the CNCM corresponding plasmid |
|---|---|---|---|
| SEQ ID NO: 1 | genome of the strain derived from the sample 031589 | — | — |
| SEQ ID NO: 2 | ORF-S* | 21406-25348 | — |
| SEQ ID NO: 3 | S protein | — | — |
| SEQ ID NO: 4 | ORF-S** | 21406-25348 | I-3059 |
| SEQ ID NO: 5 | Sa fragment | 21406-23454 | I-3020 |
| SEQ ID NO: 6 | Sb fragment | 23322-25348 | I-3019 |
| SEQ ID NO: 7 | ORF-3 + ORF-4* | 25110-26244 | — |
| SEQ ID NO: 8 | ORF-3 + ORF-4** | 25110-26244 | I-3126 |

TABLE I-continued Sequence listing

| Identification number | Sequence | Position of the cDNA with reference to Genbank AY274119.3 | Deposit number at the of the CNCM corresponding plasmid |
|---|---|---|---|
| SEQ ID NO: 9 | ORF3 | — | — |
| SEQ ID NO: 10 | ORF-3 protein | — | — |
| SEQ ID NO: 11 | ORF4 | — | — |
| SEQ ID NO: 12 | ORF-4 protein | — | — |
| SEQ ID NO: 13 | ORF-E* | 26082-26413 | — |
| SEQ ID NO: 14 | E protein | — | — |
| SEQ ID NO: 15 | ORF-E** | 26082-26413 | I-3046 |
| SEQ ID NO: 16 | ORF-M* | 26330-27098 | — |
| SEQ ID NO: 17 | M protein | — | — |
| SEQ ID NO: 18 | ORF-M** | 26330-27098 | I-3047 |
| SEQ ID NO: 19 | ORF7 to 11* | 26977-28218 | — |
| SEQ ID NO: 20 | ORF7 to 11** | 26977-28218 | I-3125 |
| SEQ ID NO: 21 | ORF7 | — | — |
| SEQ ID NO: 22 | ORF7 protein | — | — |
| SEQ ID NO: 23 | ORF8 | — | — |
| SEQ ID NO: 24 | ORF8 protein | — | — |
| SEQ ID NO: 25 | ORF9 | — | — |
| SEQ ID NO: 26 | ORF9 protein | — | — |
| SEQ ID NO: 27 | ORF10 | — | — |
| SEQ ID NO: 28 | ORF10 protein | — | — |
| SEQ ID NO: 29 | ORF11 | — | — |
| SEQ ID NO: 30 | ORF11 protein | — | — |
| SEQ ID NO: 31 | OrF1ab | 265-21485 | — |
| SEQ ID NO: 32 | ORF13 | 28130-28426 | — |
| SEQ ID NO: 33 | ORF13 protein | — | — |
| SEQ ID NO: 34 | ORF14 | — | — |
| SEQ ID NO: 35 | ORF14 protein | 28583-28795 | — |
| SEQ ID NO: 36 | ORF-N* | 28054-29430 | — |
| SEQ ID NO: 37 | N protein | — | — |
| SEQ ID NO: 38 | ORF-N** | 28054-29430 | I-3048 |
| SEQ ID NO: 39 | noncoding 5'** | 1-204 | I-3124 |
| SEQ ID NO: 40 | noncoding 3'** | 28933-29727 | I-3123 |
| SEQ ID NO: 41 | ORF1ab Fragment L0 | 30-500 | — |
| SEQ ID NO: 42 | Fragment L1 | 211-2260 | — |
| SEQ ID NO: 43 | Fragment L2 | 2136-4187 | — |
| SEQ ID NO: 44 | Fragment L3 | 3892-5344 | — |
| SEQ ID NO: 45 | Fragment L4b | 4932-6043 | — |
| SEQ ID NO: 46 | Fragment L4 | 5305-7318 | — |
| SEQ ID NO: 47 | Fragment L5 | 7275-9176 | — |
| SEQ ID NO: 48 | Fragment L6 | 9032-11086 | — |
| SEQ ID NO: 49 | Fragment L7 | 10298-12982 | — |
| SEQ ID NO: 50 | Fragment L8 | 12815-14854 | — |
| SEQ ID NO: 51 | Fragment L9 | 14745-16646 | — |
| SEQ ID NO: 52 | Fragment L10 | 16514-18590 | — |
| SEQ ID NO: 53 | Fragment L11 | 18500-20602 | — |
| SEQ ID NO: 54 | Fragment L12 | 20319-22224 | — |
| SEQ ID NO: 55 | Sense N primer | — | — |
| SEQ ID NO: 56 | Antisense N primer | — | — |
| SEQ ID NO: 57 | Sense $S_C$ primer | — | — |
| SEQ ID NO: 58 | Sence $S_L$ primer | — | — |
| SEQ ID NO: 59 | Antisense $S_C$ and $S_L$ primer | — | — |
| SEQ ID NO: 60 | Sense primer series 1 | 28507-28522 | — |
| SEQ ID NO: 61 | Antisense primer series 1 | 28774-28759 | — |
| SEQ ID NO: 62 | Sense primer series 2 | 28375-28390 | — |
| SEQ ID NO: 63 | Antisense primer series 2 | 28702-28687 | — |
| SEQ ID NO: 64 | Probe 1/series 1 | 28561-28586 | — |
| SEQ ID NO: 65 | Probe 2/series 1 | 28588-28608 | — |
| SEQ ID NO: 66 | Probe 1/series 2 | 28541-28563 | — |
| SEQ ID NO: 67 | Probe 2/series 2 | 28565-28589 | — |
| SEQ ID NO: 68 | Anchor primer 14T | | |
| SEQ ID NO: 69 | Peptide M2-14 | — | — |
| SEQ ID NO: 70 | Peptide E1-12 | — | — |
| SEQ ID NO: 71 | Peptide E53-76 | — | — |
| SEQ ID NO: 72 | Noncoding 5'* | 1-204 | — |

TABLE I-continued

Sequence listing

| Identification number | Sequence | Position of the cDNA with reference to Genbank AY274119.3 | Deposit number at the of the CNCM corresponding plasmid |
|---|---|---|---|
| SEQ ID NO: 73 | Noncoding 3'* | 28933-29727 | — |
| SEQ ID NO: 74 | ORF1a protein | — | — |
| SEQ ID NO: 75 | ORF1b protein | — | — |
| SEQ ID NO: 76-139 | Primers | | |
| SEQ ID NO: 140 | Pseudogene of S | | |
| SEQ ID NO: 141-148 | Primers | | |
| SEQ ID NO: 149 | Aa1-13 of S | | |
| SEQ ID NO: 150 | Polypeptide | | |
| SEQ ID NO: 151-158 | Primers | | |

* PCR amplification product (amplicon)
** Insert cloned into the plasmid deposited at the CNCM and to the appended drawings in which:

FIG. 1 illustrates Western-blot analysis of the expression in vitro of the recombinant proteins N, $S_C$ and $S_L$ from the expression vectors pIVEX. Lane 1: pIV2.3N. Lane 2: pIV2.3$S_C$. Lane 3: pIV2.3$S_L$. Lane 4: pIV2.4N. Lane 5: pIV2.4$S_1$ or pIV2.4$S_C$. Lane 6: pIV2.4$S_L$. The expression of the GFP protein expressed from the same vector is used as a control.

FIG. 2 illustrates the analysis, by polyacrylamide gel electrophoresis under denaturing conditions (SDS-PAGE) and staining with Coomassie blue, of the expression in vivo of the N protein from the expression vectors pIVEX. The E. coli BL21(DE3)pDIA17 strain transformed with the recombinant vectors pIVEX is cultured at 30° C. in LB medium, in the presence or in the absence of inducer (IPTG 1 mM). Lane 1: pIV2.3N. Lane 2: pIV2.4N.

FIG. 3 illustrates the analysis, by polyacrylamide gel electrophoresis under denaturing conditions (SDS-PAGE) and staining with Coomassie blue, of the expression in vivo of the $S_L$ and $S_C$ polypeptides from the expression vectors pIVEX. The E. coli BL21(DE3)pDIA17 strain transformed with the recombinant vectors pIVEX is cultured at 30° C. in LB medium, in the presence or in the absence of inducer (IPTG 1 mM). Lane 1: pIV2.3$S_C$. Lane 2: pIV2.3$S_L$. Lane 3: pIV2.4$S_1$. Lane 4: pIV2.4$S_L$.

FIG. 4 illustrates the antigenic activity of the recombinant N, $S_L$ and $S_C$ proteins produced in the E. coli BL21(DE3)pDIA17 strain transformed with the recombinant vectors pIVEX. A: electrophoresis (SDS-PAGE) of the bacterial lysates. B and C: Western-blot with the sera, obtained from the same patient infected with SARS-CoV, collected 6 days (B: serum M12) and 29 days (C: serum M13) respectively after the onset of the SARS symptoms. Lane 1: pIV2.3N. Lane 2: pIV2.4N. Lane 3: pIV2.3$S_C$. Lane 4: pIV2.4$S_1$. Lane 5: pIV2.3$S_L$. Lane 6: pIV2.4$S_L$.

FIG. 5 illustrates the purification on an Ni-NTA agarose column of the recombinant N protein produced in the E. coli BL21(DE3)pDIA17 strain from the vector pIV2.3N. Lane 1: total bacterial extract. Lane 2: soluble extract. Lane 3: insoluble extract. Lane 4: extract deposited on the Ni-NTA column. Lane 5: unbound proteins. Lane 6: fractions of peak 1. Lane 7: fractions of peak 2.

FIG. 6 illustrates the purification of the recombinant $S_C$ protein from the inclusion bodies produced in the E. coli BL21(DE3)pDIA17 strain transformed with pIV2.4$S_1$. A. Treatment with Triton X-100 (2%): Lane 1: total bacterial extract. Lane 2: soluble extract. Lane 3: insoluble extract. Lane 4: supernatant after treatment with Triton X-100 (2%). Lanes 5 and 6: pellet after treatment with Triton X-100 (2%). B: Treatment with 4 M, 5 M, 6 M and 7 M urea of the soluble and insoluble extracts.

FIG. 7 represents the immunoblot produced with the aid of a lysate of cells infected with SARS-CoV and a serum from a patient suffering from atypical pneumopathy.

FIG. 8 represents immunoblots produced with the aid of a lysate of cells infected with SARS-CoV and rabbit immunosera specific for the nucleoprotein N (A) and for the spicule protein S (B). I.S.: immune serum. p.i.: preimmune serum. The anti-N immune serum was used at 1/50 000 and the anti-S immune serum at 1/10 000.

FIG. 9 illustrates the ELISA reactivity of the rabbit monospecific polyclonal sera directed against the N protein or the short fragment of the S protein ($S_C$), toward the corresponding recombinant proteins used for immunization. A: rabbits P13097, P13081 and P13031 immunized with the purified recombinant N protein. B: rabbits P11135, P13042 and P14001 immunized with a preparation of inclusion bodies corresponding to the short fragment of the S protein ($S_C$). I.S.: immune serum. p.i.: preimmune serum.

FIG. 10 illustrates the ELISA reactivity of the purified recombinant N protein, toward sera from patients suffering from atypical pneumonia caused by SARS-CoV. FIG. 10a: ELISA plates prepared with the N protein at the concentration of 4 µg/ml and 2 µg/ml. FIG. 10B: ELISA plate prepared with the N protein at the concentration of 1 µg/ml. The sera designated A, B, D, E, F, G, H correspond to those of Table IV.

FIG. 11 illustrates the amplification by RT-PCR of decreasing quantities of synthetic RNA of the SARS-CoV N gene ($10^7$ to 1 copy), with the aid of pairs of primers No. 1 (N/+/28507, N/−/28774) (A) and No. 2 (N/+/28375, N/−/28702) (B). T: amplification performed in the absence of RNA. MW: DNA marker.

FIG. 12 illustrates the amplification by RT-PCR in real time of synthetic RNA for the SARS-CoV N gene: decreasing quantities of synthetic RNA as replica (repli.; lanes 16 to 29) and of viral RNA diluted $1/20 \times 10^4$ (lane 32) were amplified by RT-PCR in real time with the aid of the kit "Light Cycler RNA Amplification Kit Hybridization Probes" and pairs of primers and probes of the No. 2 series, under the conditions described in Example 8.

FIG. 13 (FIGS. 13.1 to 13.70) represents the restriction map of the sequence SEQ ID NO: 1 corresponding to the DNA equivalent of the genome of the SARS-CoV strain derived from the sample recorded under the number 031589.

Figure 16:
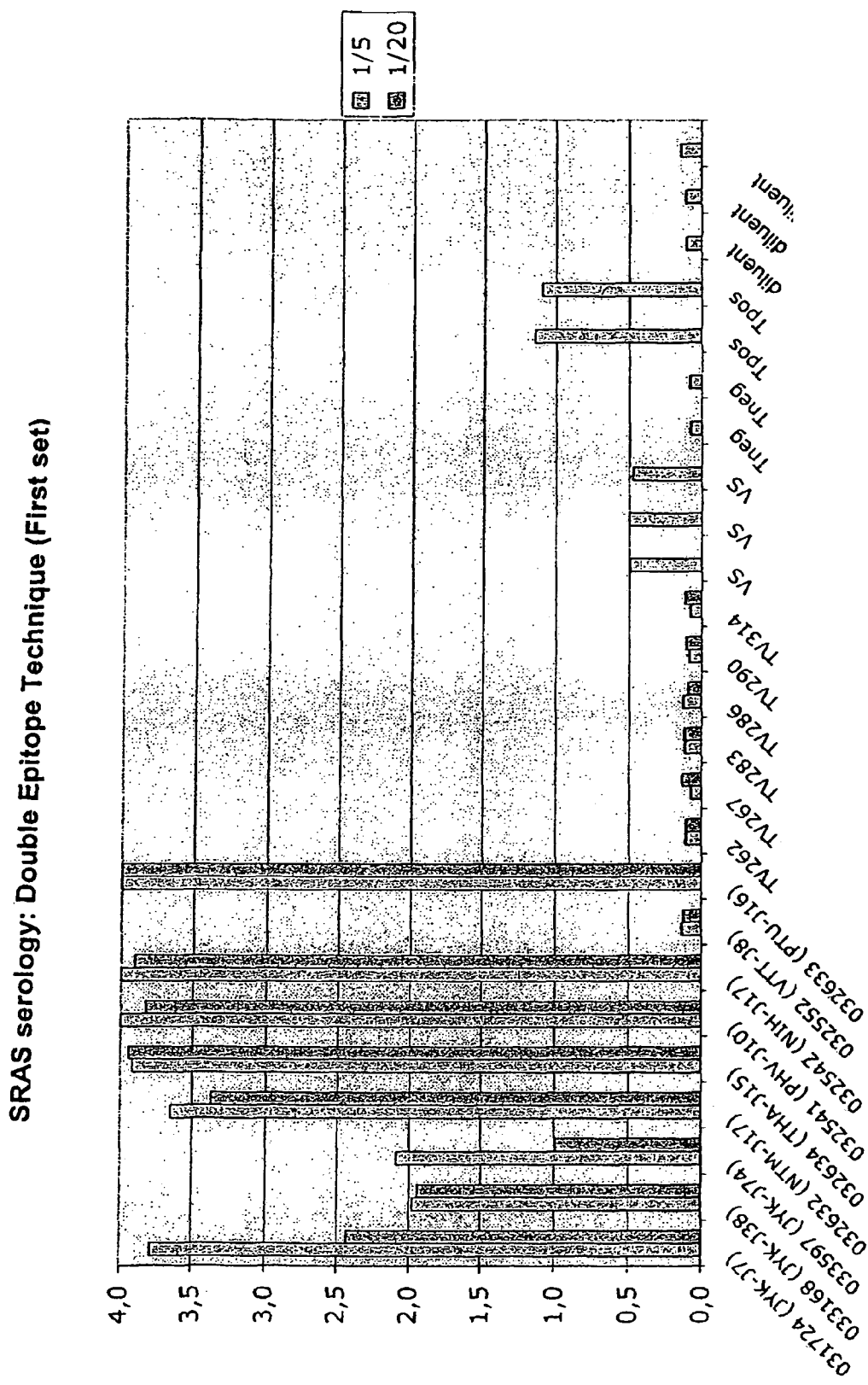

FIG. 16 presents the result of the SARS serology test by double epitope N ELISA (1st series of sera tested).

Figure 17:
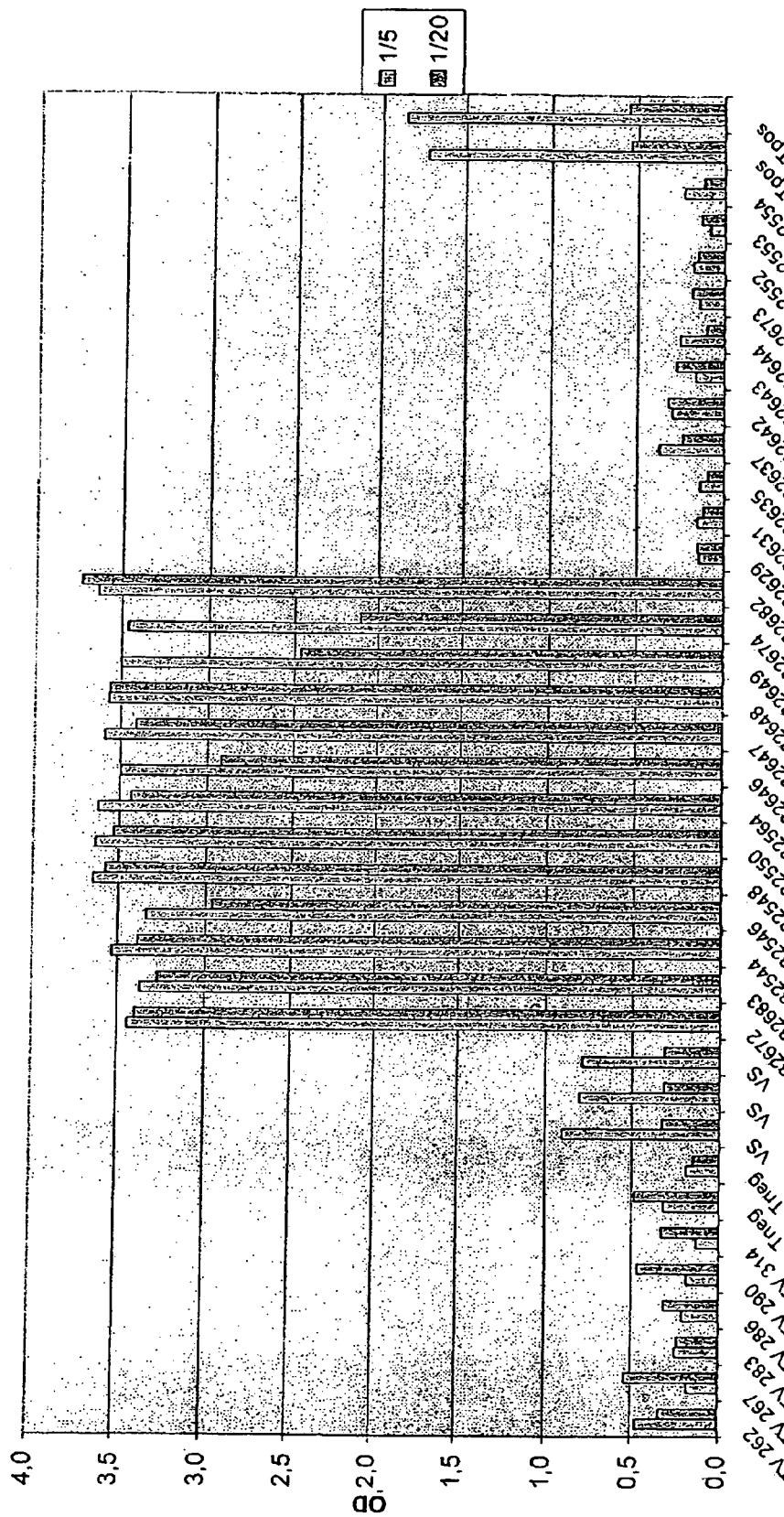

FIG. 17 shows the result of the SARS serology test by double epitope N ELISA (2nd series of sera tested).

Figure 18:
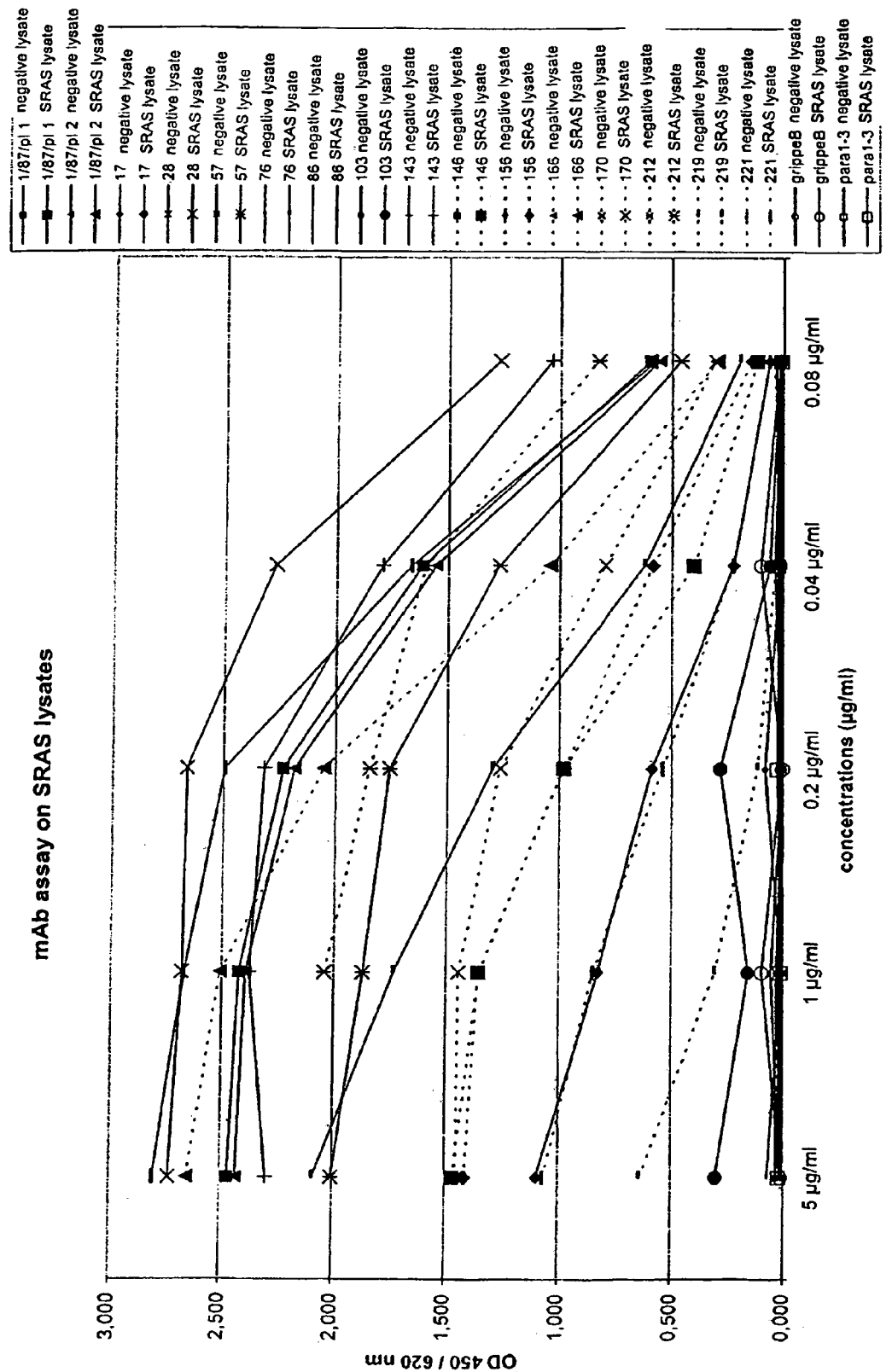

FIG. 18 illustrates the test of reactivity of the anti-N monoclonal antibodies by ELISA on the native nucleoprotein N of SARS-CoV. The antibodies were tested in the form of hybridoma culture supernatants by indirect ELISA using an irradiated lysate of VeroE6 cells infected with SARS-CoV as antigen (SARS lysate curves). A negative control for reactivity is performed for each antibody on a lysate of uninfected VeroE6 cells (negative lysate curves). Several monoclonal antibodies of known specificity were used as negative control antibodies: para1-3 directed against the antigens of the parainfluenza viruses type 1-3 (Bio-Rad) and influenza B directed against the antigens of the influenza virus type B (Bio-Rad).

Figure 19:
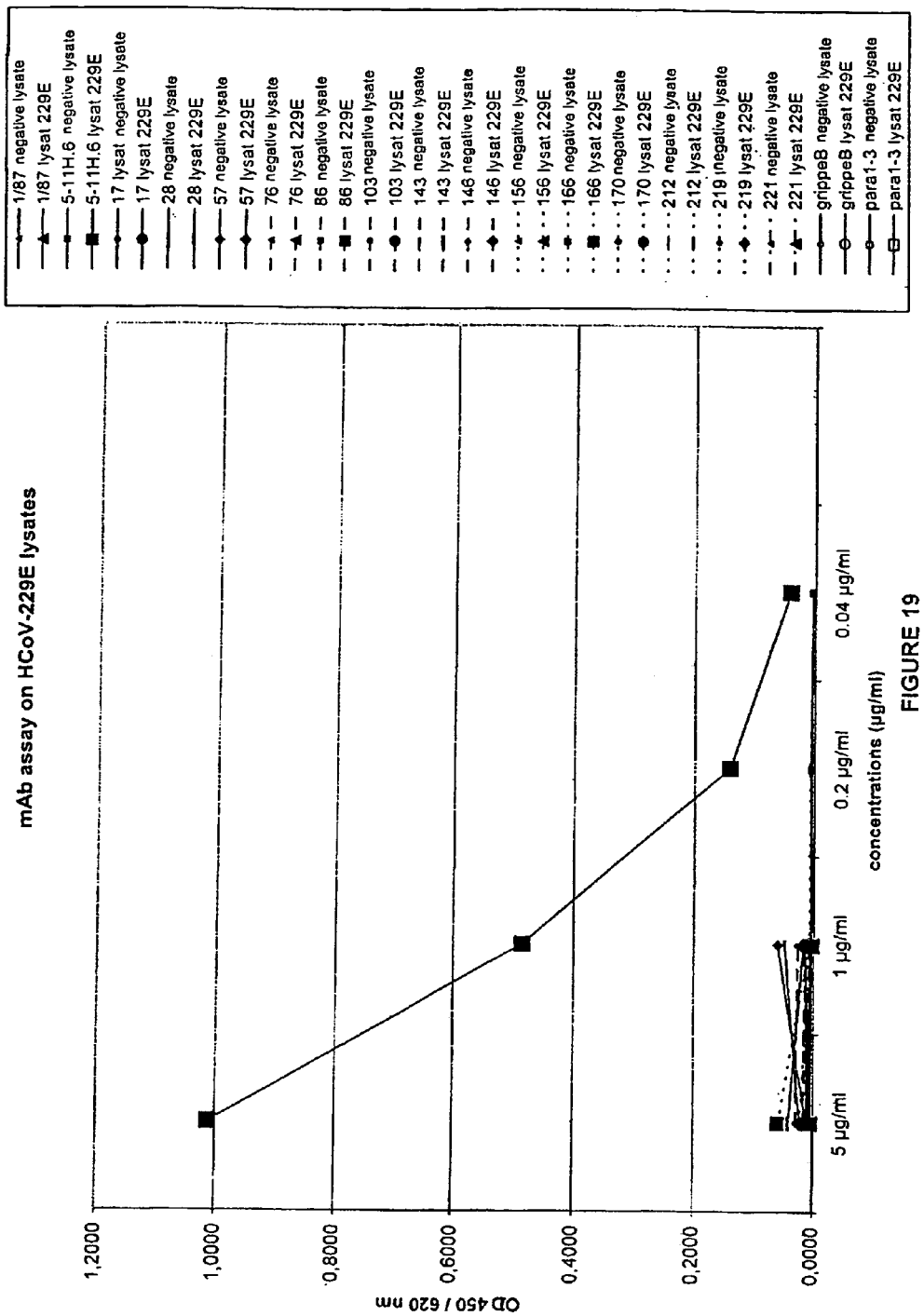

FIG. 19 illustrates the test of reactivity of the anti-N of SARS-CoV monoclonal antibodies by ELISA on the native antigens of the human coronavirus 229E (HCoV-229E). The antibodies were tested in the form of hybridoma culture supernatants by an indirect ELISA test using a lysate of MRC-5 cells infected with the human coronavirus 229E as antigen (229E lysate curves). A negative control for immunoreactivity was performed for each antibody on a lysate of noninfected MRC-5 cells (negative lysate curves). The monoclonal antibody 5-11H.6 directed against the S protein of the human coronavirus 229E (Sizun et al. 1998, J. Virol. Met. 72: 145-152) is used as positive control antibody. The antibodies para1-3 directed against the antigens of the parainfluenza virus type 1-3 (Bio-Rad) and influenza B directed against the antigens of the influenza virus type B (Bio-Rad) were added to the panel of monoclonal antibodies tested.

Figure 20:
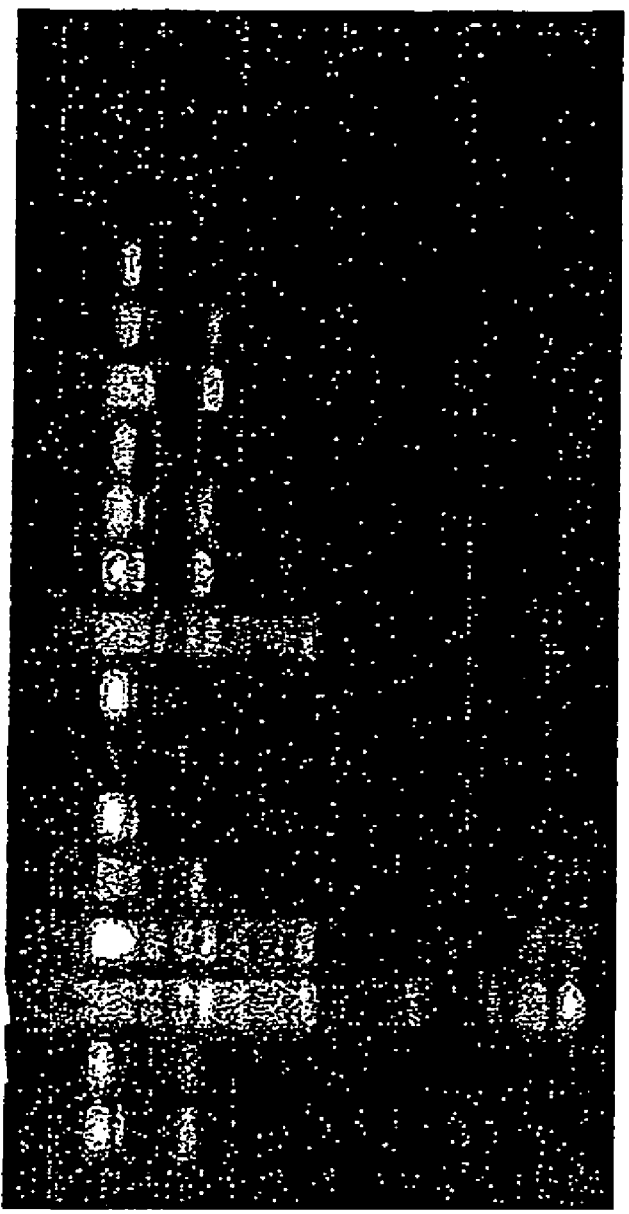

FIG. 20 shows a test of reactivity of the anti-N of SARS-CoV monoclonal antibodies by Western blotting on the denatured native nucleoprotein N of SARS-CoV. A lysate of VeroE6 cells infected with SARS-CoV was prepared in the loading buffer according to Laemmli and caused to migrate in a 12% SDS polyacrylamide gel and then the proteins were transferred onto PVDF membrane. The anti-N monoclonal antibodies tested were used for the immunoassay at the concentration of 0.05 µg/ml. The visualization is carried out with anti-mouse IgG(H+L) antibodies coupled to peroxidase (NA93IV, Amersham) and the ECL+ system. Two monoclonal antibodies were used as negative controls for reactivity: influenza B directed against the antigens of the influenza virus type B (Bio-Rad) and para1-3 directed against the antigens of the parainfluenza virus type 1-3 (Bio-Rad).

Figure 21:
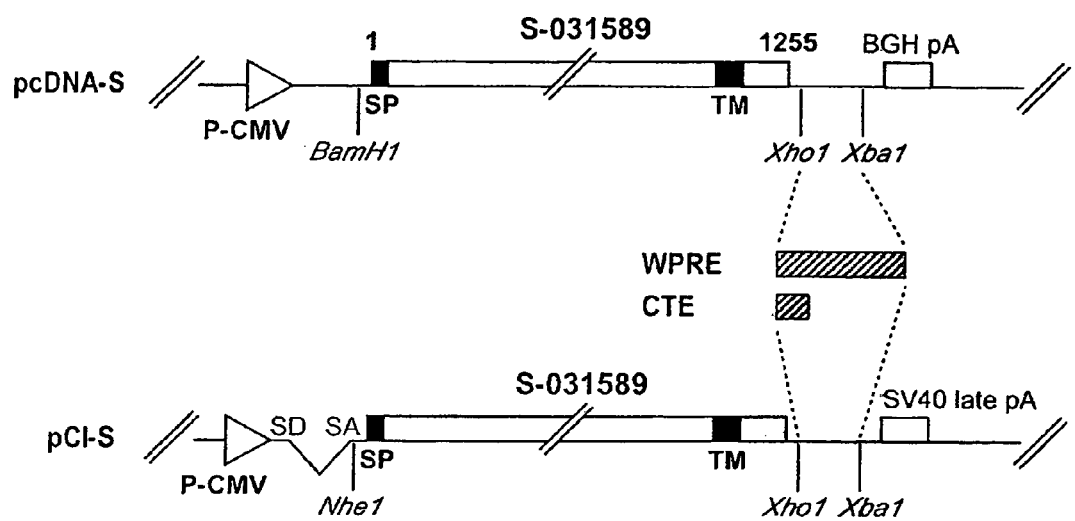

FIG. 21 presents the plasmids for expression in mammalian cells of the SARS-CoV S protein. The cDNA for the SARS-CoV S was inserted between the BamH1 and Xho1 sites of the expression plasmid pcDNA3.1(+) (Clontech) in order to obtain the plasmid pcDNA-S and between the Nhe1 and Xho1 sites of the expression plasmid pCI (Promega) in order to obtain the plasmid PCI-S. The WPRE and CTE sequences were inserted between each of the two plasmids pcDNA-S and pCI-S between the Xho1 and Xba1 sites in order to obtain the plasmids pcDNA-S-CTE, pcDNA-S-WPRE, pCI-S-CTE and pCI-S-WPRE, respectively.

SP: signal peptide predicted (aa 1-13) with the software signalP v2.0 (Nielsen et al., 1997, Protein Engineering, 10: 1-6)

TM: transmembrane region predicted (aa 1196-1218) with the software TMHMM v2.0 (Sonnhammer et al., 1998, Proc. of Sixth Int. Conf. on Intelligent Systems for Molecular Biology, pp. 175-182, AAAI Press). It should be noted that the amino acids W-1194 and P1195 are possibly part of the transmembrane region with the respective probabilities of 0.13 and 0.42

P-CMV: cytomegalovirus immediate/early promoter.

BGH pA: polyadenylation signal of the bovine growth hormone gene

SV40 late pA: SV40 virus late polyadenylation signal

SD/SA: splice donor and acceptor sites

Figure 22:
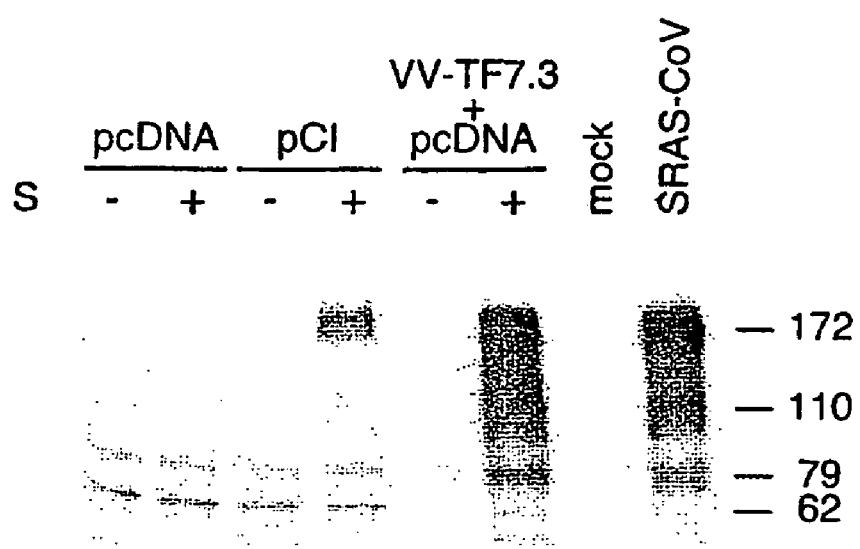

WPRE: sequences of the "Woodchuck Hepatitis Virus posttranscriptional regulatory element" of the woodchuck hepatitis virus CTE: sequences of the "constitutive transport element" of the Mason-Pfizer simian retrovirus FIG. 22 illustrates the expression of the S protein after transfection of VeroE6 cells. Cellular extracts were prepared 48 hours after transfection of VeroE6 cells with the plasmids pcDNA, pcDNA-S, pCI and pCI-S. Cellular extracts were also prepared 18 hours after infection with the recombinant vaccinia virus VV-TF7.3 and transfection with the plasmids pcDNA or pcDNA-S. As a control, extracts of VeroE6 cells were prepared 8 hours after infection with SARS-CoV at a multiplicity of infection of 3. They were separated on an 8% SDS acrylamide gel and analyzed by Western blotting with the aid of an anti-S rabbit polyclonal antibody and an anti-rabbit IgG(H+L) polyclonal antibody coupled to peroxidase (NA934V, Amersham). A molecular mass ladder (kDa) is presented in the figure.

SARS-CoV: extract of VeroE6 cells infected with SARS-CoV

Mock: control extract of noninfected cells

FIG. 23 illustrates the effect of the CTE and WPRE sequences on the expression of the S protein after transfection of VeroE6 and 293T cells. Cellular extracts were prepared 48 hours after transfection of VeroE6 cells (A) or 293T cells (B) with the plasmids pcDNA, pcDNA-S, pcDNA-S-CTE, pcDNA-S-WPRE, pCI-S, pCI-S-CTE and pCI-S-WPRE separated on 8% SDS polyacrylamide gel and analyzed by Western blotting with the aid of an anti-S rabbit polyclonal antibody and an anti-rabbit IgG(H+L) polyclonal antibody coupled to peroxidase (NA934V, Amersham). A molecular mass ladder (kDa) is presented in the figure.

SARS-CoV: extract of VeroE6 cells prepared 8 hours after infection with SARS-CoV at a multiplicity of infection of 3.

Mock: control extract of noninfected VeroE6 cells

Figure 24:
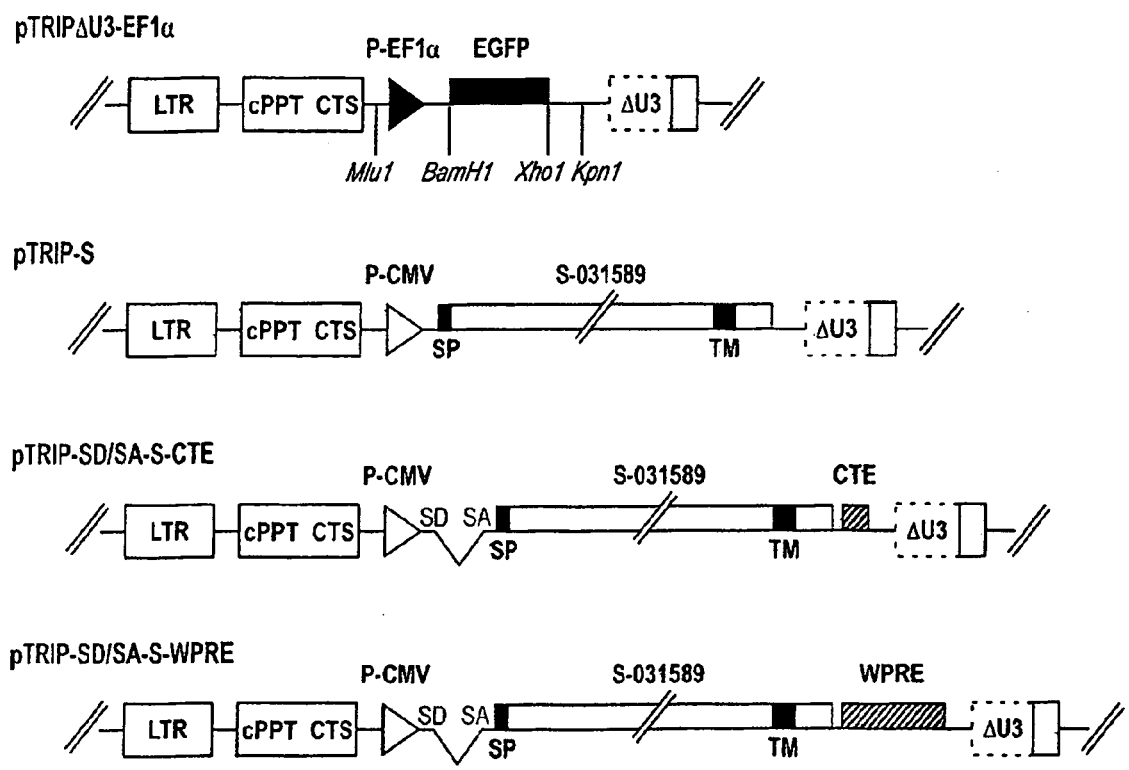

FIG. 24 presents defective lentiviral vectors with central DNA flap for the expression of SARS-CoV S. The cDNA for the SARS-CoV S protein was cloned in the form of a BamH1-Xho1 fragment into the plasmid pTRIPΔU3-CMV containing a defective lentiviral vector TRIP with central DNA flap (Sirven et al., 2001, Mol. Ther., 3.: 438-448) in order to obtain the plasmid pTRIP-S. The optimum expression cassettes consisting of the CMV virus immediate/early promoter, a splice signal, cDNA for S and either of the posttranscriptional signals CTE or WPRE were substituted for the cassette EF1α-EGFP of the defective lentiviral expression vector with central DNA flap TRIPΔU3-EF1α (Sirven et al., 2001, Mol. Ther., 3: 438-448) in order to obtain the plasmids pTRIP-SD/SA-S-CTE and pTRIP-SD/SA-S-WPRE.

SP: signal peptide

TM: transmembrane region

P-CMV: cytomegalovirus immediate/early promoter

P-EF1α: EF1α gene promoter

SD/SA: splice donor and acceptor sites

WPRE: sequences of the "Woodchuck Hepatitis Virus posttranscriptional regulatory element" of the woodchuck hepatitis virus CTE: sequences of the "constitutive transport element" of the Mason-Pfizer simian retrovirus LTR: long terminal repeat ΔU3: LTR deleted for the "promoter/enhancer"sequences cPPT: "polypurine tract cis-active sequence"

CTS: "central termination sequence"

Figure 25:
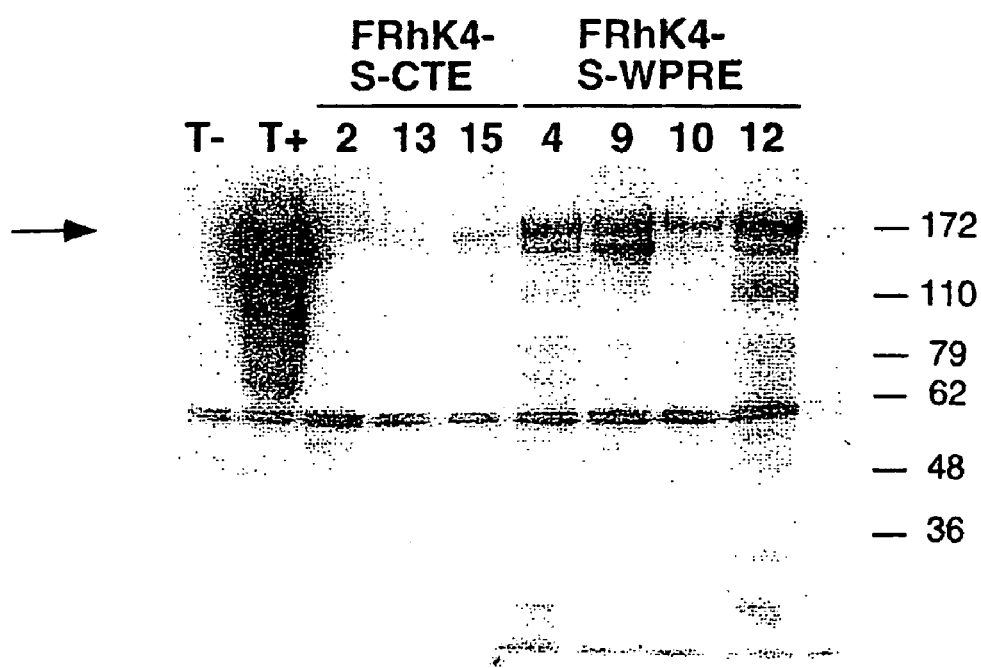

FIG. 25 shows the Western-blot analysis of the expression of the SARS-CoV S by cell lines transduced with the lentiviral vectors TRIP-SD/SA-S-WPRE and TRIP-SD/SA-S-CTE. Cellular extracts were prepared from established lines FrhK4-S-CTE and FrhK4-S-WPRE after transduction with the lentiviral vectors TRIP-SD/SA-S-CTE and TRIP-SD/SA-S-WPRE respectively. They were separated on an 8% SDS acrylamide gel and analyzed by Western blotting with the aid of an anti-S rabbit polyclonal antibody and an anti-rabbit IgG(H+L) conjugate coupled to peroxidase. A molecular mass ladder (kDa) is presented in the figure.

T−: control extract of FrhK-4 cells

T+: extract of FrhK-4 cells prepared 24 hours after infection with SARS-CoV at a multiplicity of infection of 3.

Figure 26:
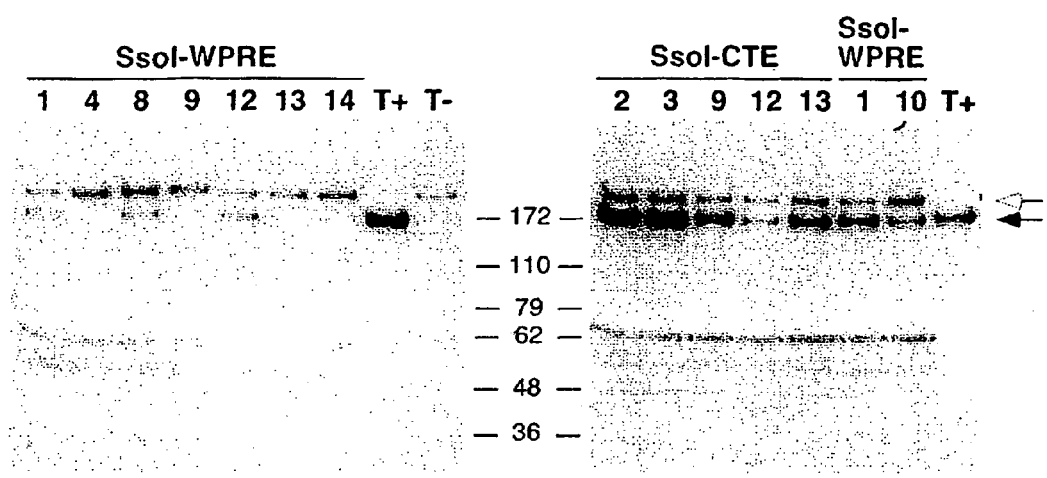

FIG. 26 relates to the analysis of the expression of Ssol polypeptide by cell lines transduced with the lentiviral vectors TRIP-SD/SA-Ssol-WPRE and TRIP-SD/SA-Ssol-CTE. The secretion of the Ssol polypeptide was determined in the supernatant of a series of cell clones isolated after transduction of FrhK-4 cells with the lentiviral vectors TRIP-SD/SA-Ssol-WPRE and TRIP-SD/SA-Ssol-CTE. 5 µl of supernatant, diluted 1/2 in loading buffer according to Laemmli, were analyzed by Western blotting, visualized with an anti-FLAG monoclonal antibody (M2, Sigma) and an anti-mouse IgG (H+L) conjugate coupled to peroxidase. T−: supernatant of the parental FRhK-4 line. T+: supernatant of BHK cells infected with a recombinant vaccinia virus expressing the Ssol polypeptide. The solid arrow indicates the Ssol polypeptide, while the empty arrow indicates a cross reaction with a protein of cellular origin.

Figure 27:
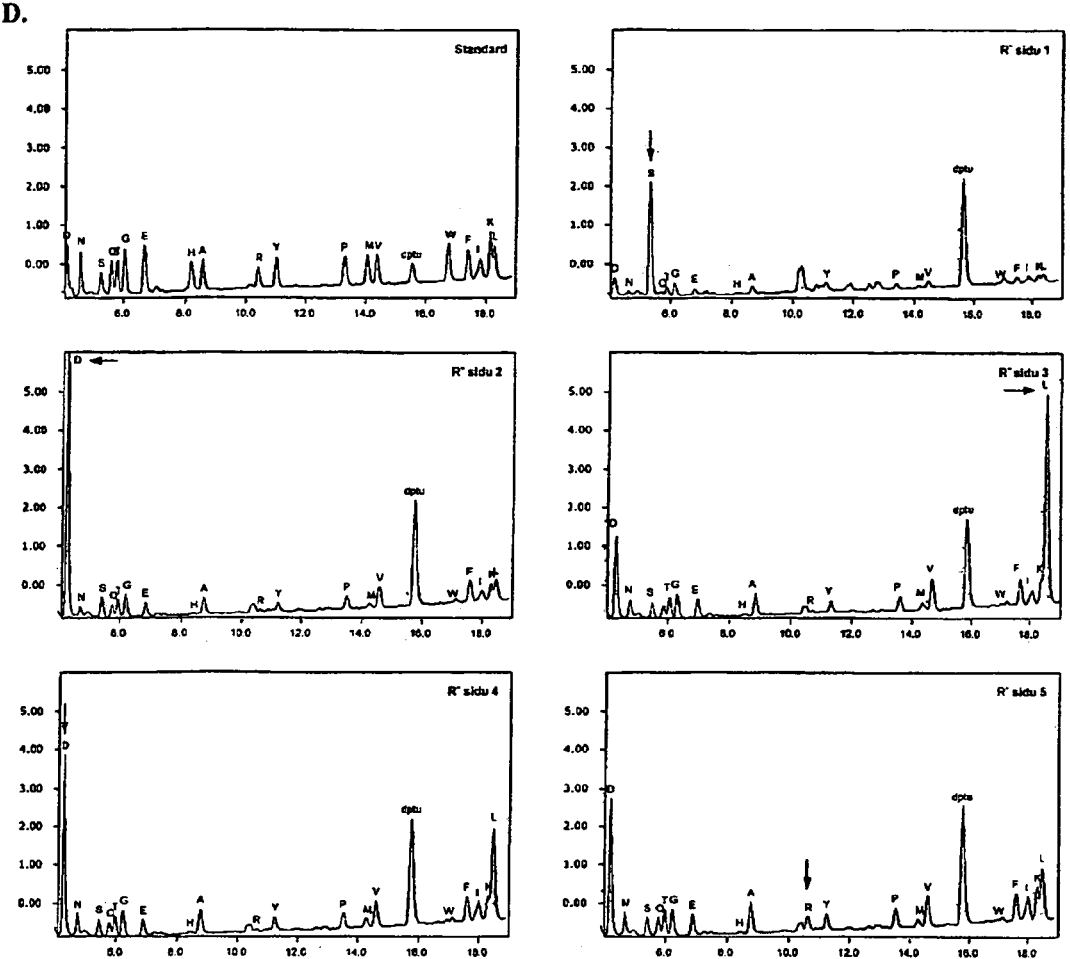

FIG. 27 shows the results relating to the analysis of the purified Ssol polypeptide A. 8, 2, 0.5 and 0.125 µg of recombinant Ssol polypeptide purified by anti-FLAG affinity chromatography and gel filtration (G75) were separated on 8% SDS polyacrylamide gel. The Ssol polypeptide and variable quantities of molecular mass markers (MM) were visualized by staining with silver nitrate (Gelcode SilverSNAP stain kit II, Pierce).

B. Standard markers for analysis by SELDI-TOF mass spectrometry

IgG: bovine IgG of MM 147300

ConA: conalbumin of MM 77490

HRP: horseradish peroxidase analyzed as a control and of MM 43240

C. Analysis by mass spectrometry (SELDI-TOF) of the recombinant Ssol polypeptide.

The peaks A and B correspond to the single and double charged Ssol polypeptide.

D. Sequencing of the N-terminal end of the recombinant Ssol polypeptide. 5 Edman degradation cycles in liquid phase were carried out on an ABI494 sequencer (Applied Biosystems).

FIG. 28 illustrates the influence of a splicing signal and of the CTE and WPRE sequences on the efficacy of the gene immunization with the aid of plasmid DNA encoding the SARS-CoV S A. Groups of 7 BALB/c mice were immunized twice at 4 weeks' interval with the aid of 50 µg of plasmid DNA of pCI, pcDNA-S, pCI-S, pcDNA-N and pCI-HA.

B. Groups of 6 BALB/c mice were immunized twice at 4 weeks' interval with the aid of 2 µg, 10 µg or 50 µg of plasmid DNA of pCI, pCI-S, pCI-S-CTE and pCI-S-WPRE.

The immune sera collected 3 weeks after the second immunization were analyzed by indirect ELISA using a lysate of VeroE6 cells infected with SARS-CoV as antigen. The anti-SARS-CoV antibody titers are calculated as the reciprocal of the dilution producing a specific OD of 0.5 after visualization with an anti-mouse IgG polyclonal antibody coupled to peroxidase (NA931V, Amersham) and TMB (KPL).

FIG. 29 shows the seroneutralization of the infectivity of SARS-CoV with the antibodies induced in mice after gene immunization with the aid of plasmid DNA encoding SARS-CoV S. Pools of immune sera collected 3 weeks after the second immunization were prepared for each of the groups of experiments described in FIG. 28 and evaluated for their capacity to seroneutralize the infectivity of 100 TCID50 of SARS-CoV on FRhK-4 cells. 4 points are produced for each of the 2-fold dilutions tested from 1/20. The seroneutralizing titer is calculated according to the Reed and Munsch method as the reciprocal of the dilution neutralizing the infectivity of 2 wells out of 4.

A. Groups by BALB/c mice immunized twice at 4 weeks' interval with the aid of 50 µg of plasmid DNA of pCI, pcDNA-S, pCI-S, pcDNA-N and pCI-HA. □: preimmune serum. ■: immune serum.

B. Groups of BALB/c mice immunized twice at 4 weeks' interval with the aid of 2 µg, 10 µg or 50 µg of plasmid DNA of pCI, pCI-S, pCI-S-CTE and pCI-S-WPRE.

Figure 30:
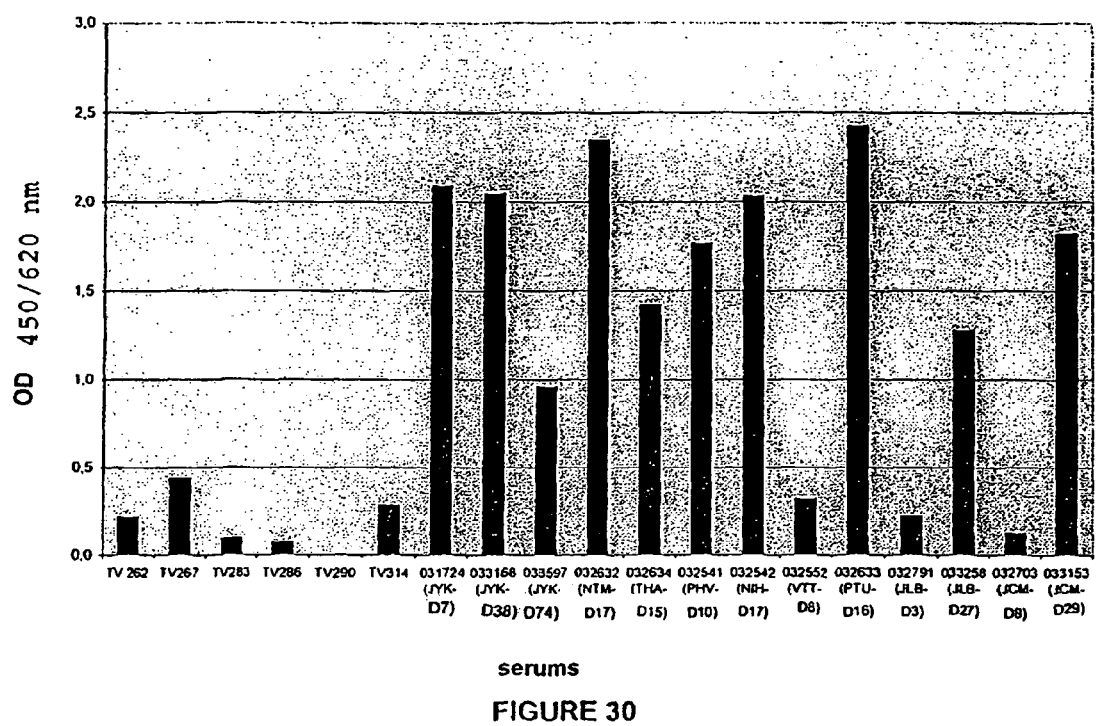

FIG. 30 illustrates the immunoreactivity of the recombinant Ssol polypeptide toward sera from patients suffering from SARS. The reactivity of sera from patients was analyzed by indirect ELISA test against solid phases prepared with the aid of the purified recombinant Ssol polypeptide. The antibodies from patients reacting with the solid phase at a dilution of 1/400 are visualized with a human anti-IgG(H+L) polyclonal antibody coupled to peroxidase (Amersham NA933V) and TMB plus, H2O2 (KPL). The sera of probable SARS cases are identified by a National Reference Center for Influenza Viruses serial number and by the initials of the patient and the number of days elapsed since the onset of symptoms, where appropriate. The TV sera are control sera from subjects which were collected in France before the SARS epidemic which occurred in 2003.

Figure 31:
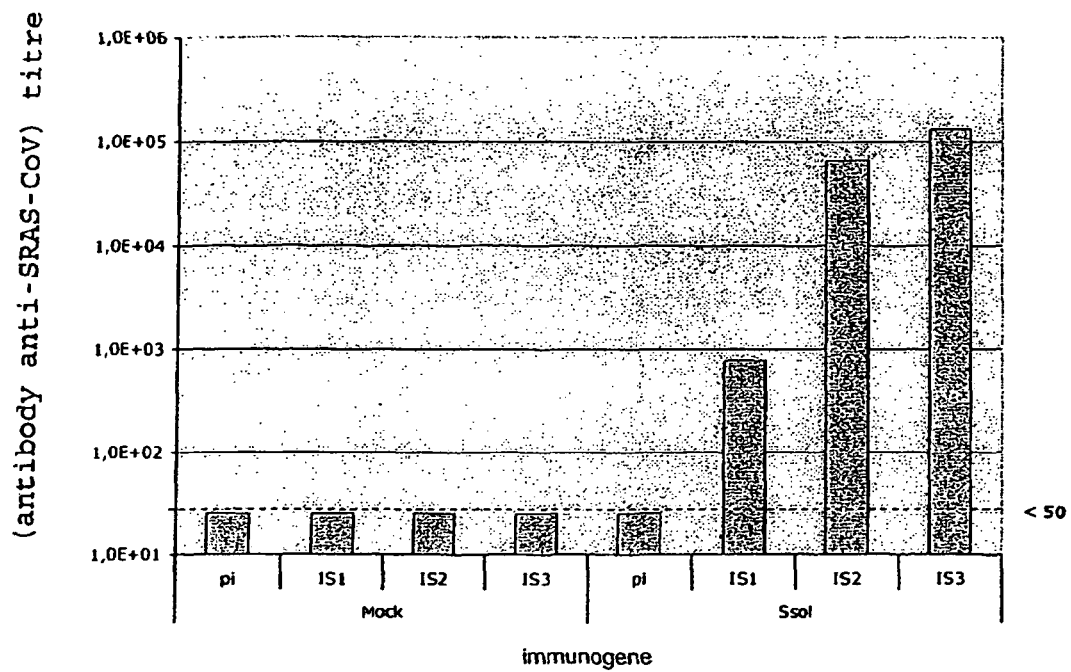

FIG. 31 shows the induction of antibodies directed against SARS-CoV after immunization with the recombinant Ssol polypeptide. Two groups of 6 mice were immunized at 3 weeks' interval with 10 µg of recombinant Ssol polypeptide (Ssol group) adjuvanted with aluminum hydroxide or, as a control, of adjuvant alone (mock group). Three successive immunizations were performed and the immune sera were collected 3 weeks after each of the three immunizations (IS1, IS2, IS3). The immune sera were analyzed per pool for each of the 2 groups by indirect ELISA using a lysate of VeroE6 cells infected with SARS CoV as antigen. The anti-SARS-CoV antibody titers are calculated as the reciprocal of the dilution producing a specific OD of 0.5 after visualization with an anti-mouse IgG polyclonal antibody coupled to peroxidase (Amersham) and TMB (KPL).

FIG. 32 presents the nucleotide alignment of the sequences of the synthetic gene 040530 with the sequence of the wild-type gene of the SARS-CoV isolate 031589. I-3059 corresponds to nucleotides 21406-25348 of the SARS-CoV isolate 031589 deposited at the C.N.C.M. under the number I-3059 (SEQ ID NO: 4, plasmid pSARS-S) S-040530 is the sequence of the synthetic gene 040530.

FIG. 33 illustrates the use of a synthetic gene for the expression of the SARS-CoV S. Cellular extracts prepared 48 hours after transfection of VeroE6 cells (A) or 293T cells (B) with the plasmids pCI, PCI-S, pCI-S-CTE, pCI-S-WPRE and pCI-Ssynth were separated on 8% SDS acrylamide gel and analyzed by Western blotting with the aid of an anti-S rabbit polyclonal antibody and an anti-rabbit IgG(H+L) polyclonal antibody coupled to peroxidase (NA934V, Amersham). The Western blot is visualized by luminescence (ECL+, Amersham) and acquisition on a digital imaging device (FluorS, BioRad). The levels of expression of the S protein were measured by quantifying the 2 predominant bands identified on the image.

Figure 34:
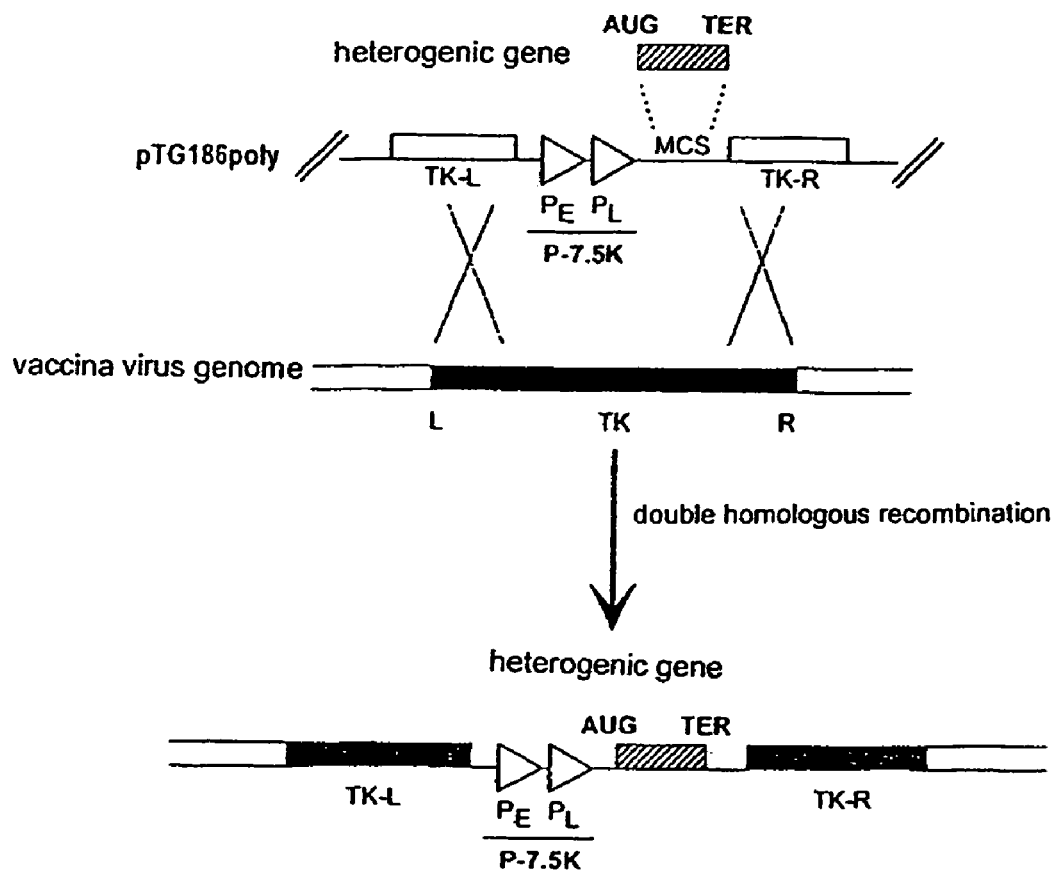

FIG. 34 presents a diagram for the construction of recombinant vaccinia viruses VV-TG-S, VV-TG-Ssol, VV-TN-S and VV-TN-Ssol A. The cDNAs for the S protein and the Ssol polypeptide of SARS-CoV were inserted between the BamH1 and Sma1 sites of the transfer plasmid pTG186 in order to obtain the plasmids pTG-S and pTG-Ssol.

B. The sequences of the synthetic promoter 480 were then substituted for those of the 7.5 promoter by exchange of the Nde1-Pst1 fragments of the plasmids pTG186poly, pTG-S and pTG-Ssol in order to obtain the transfer plasmids pTN480, pTN-S and pTN-Ssol.

C. Sequence of the synthetic promoter 480 as contained between the Nde1 and Pst1 sites of the transfer plasmids of the pTN series. An Asc1 site was inserted in order to facilitate subsequent handling. The restriction sites and the promoter sequence are underlined.

D. The recombinant vaccinia viruses are obtained by double homologous recombination in vivo between the TK cassette of the transfer plasmids of the pTG and pTN series and the TK gene of the Copenhagen strain of the vaccinia virus.

SP: signal peptide predicted (aa 1-13) with the software signalP v2.0 (Nielsen et al., 1997, Protein Engineering, 10: 1-6)

TM: transmembrane region predicted (aa 1196-1218) with the software TMHMM v2.0 (Sonnhammer et al., 1998, Proc. of Sixth Int. Conf. on Intelligent Systems for Molecular Biology, pp. 175-182, AAAI Press). It should be noted that the amino acids W1194 and P1195 possibly form part of the transmembrane region with respective probabilities of 0.13 and 0.42.

TK-L, TK-R: left- and right-hand parts of the vaccinia virus thymidine kinase gene MCS: multiple cloning site PE: early promoter PL: late promoter PL synth: synthetic late promoter 480

Figure 35:
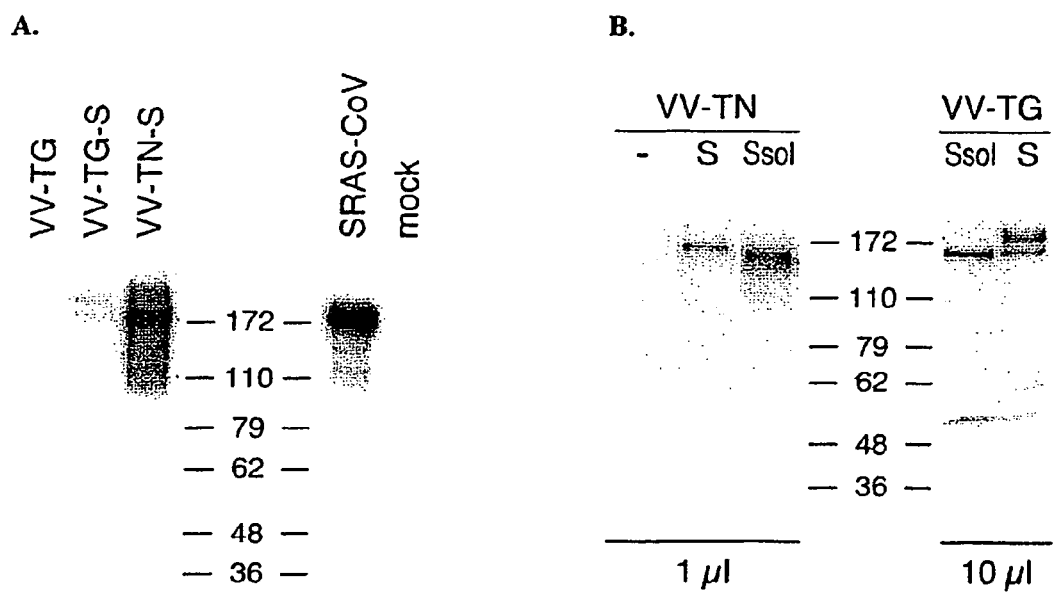

FIG. 35 illustrates the expression of the S protein by recombinant vaccinia viruses, analyzed by Western blotting. Cellular extracts were prepared 18 hours after infection of CV1 cells with the recombinant vaccinia viruses VV-TG, VV-TG-S and VV-TN-S at an M.O.I. of 2 (A). As a control, extracts of VeroE6 cells were prepared 8 hours after infection with SARS-CoV at a multiplicity of infection of 2. Cellular extracts were also prepared 18 hours after infection of CV1 cells with the recombinant vaccinia viruses VV-TG-S, VV-TG-Ssol, VV-TN, VV-TN-S and VV-TN-Ssol (B). They were separated on 8% SDS acrylamide gels and analyzed by Western blotting with the aid of an anti-S rabbit polyclonal antibody and an anti-rabbit IgG(H+L) polyclonal antibody coupled to peroxidase (NA934V, Amersham). "1 µl" and "10 µl" indicates the quantities of cellular extracts deposited on the gel. A molecular mass ladder (kDa) is presented in the figure.

SARS-CoV: extract of VeroE6 cells infected with SARS-CoV

Mock: control extract of noninfected cells

FIG. 36 shows the result of a Western-blot analysis of the secretion of the Ssol polypeptide by the recombinant vaccinia viruses.

A. Supernatants of CV1 cells infected with the recombinant vaccinia virus VV-TN, various clones of the VV-TN-Ssol virus and with the viruses VV-TG-Ssol or VV-TN-Sflag were harvested 18 hours after infection of CV1 cells at an M.O.I. of 2.

B. Supernatants of 293T, FRhK-4, BHK-21 and CV1 cells infected in duplicate (1.2) with the recombinant vaccinia virus VV-TN-Ssol at an M.O.I. of 2 were harvested 18 hours after infection. The supernatant of CV1 cells infected with the virus VV-TN was also harvested as a control (M).

All the supernatants were separated on 8% SDS acrylamide gel according to Laemmli and analyzed by Western blotting with the aid of an anti-FLAG mouse monoclonal antibody and an anti-mouse IgG(H+L) polyclonal antibody coupled to peroxidase (NA931V, Amersham) (A) or with the aid of an anti-S rabbit polyclonal antibody and an anti-rabbit IgG(H+L) polyclonal antibody coupled to peroxidase (NA934V, Amersham) (B).

A molecular mass ladder (kDa) is presented in the figure.

Figure 37:
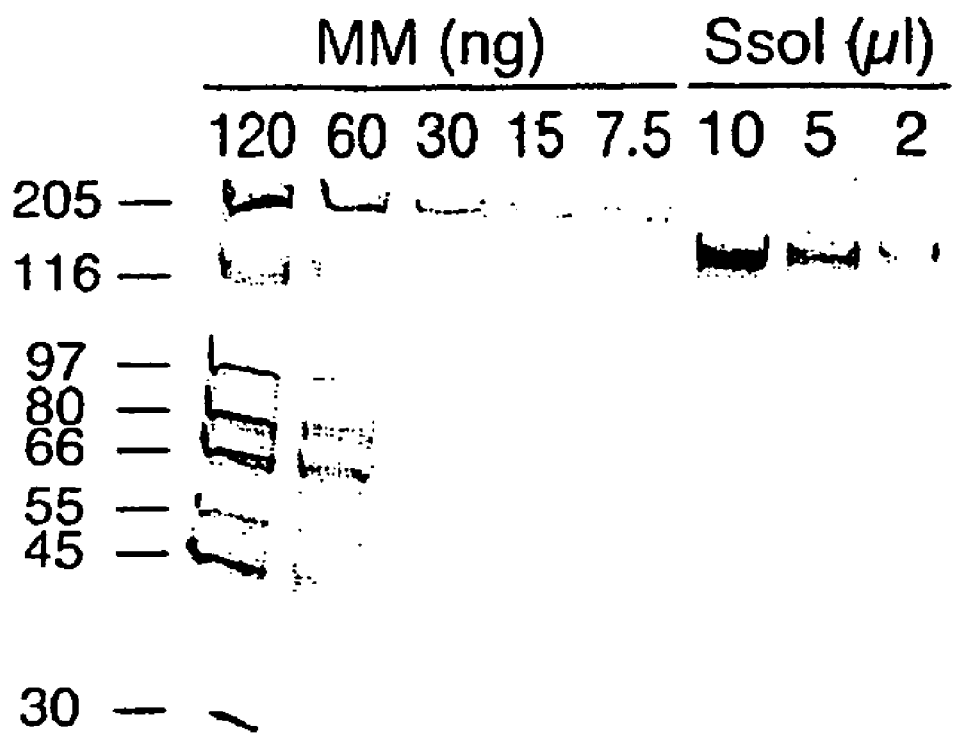

FIG. 37 shows the analysis of the Ssol polypeptide, purified on SDS polyacrylamide gel 10, 5 and 2 µl of recombinant Ssol polypeptide purified by anti-FLAG affinity chromatography were separated on 4 to 15% gradient SDS polyacrylamide gel. The Ssol polypeptide and variable quantities of molecular mass markers (MM) were visualized by staining with silver nitrate (Gelcode SilverSNAP stain kit II, Pierce).

Figure 38:
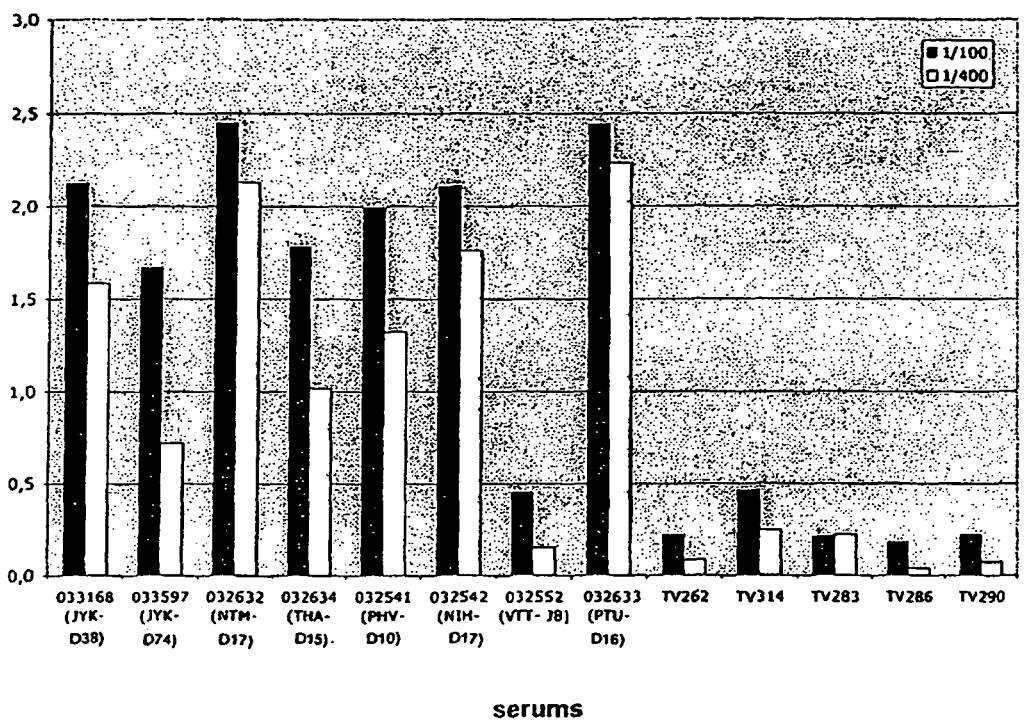

FIG. 38 illustrates the immunoreactivity of the recombinant Ssol polypeptide produced by the recombinant vaccinia virus VV-TN-Ssol toward sera of patients suffering from SARS. The reactivity of sera from patients was analyzed by indirect ELISA test against solid phases prepared with the aid of the purified recombinant Ssol polypeptide. The antibodies from patients reacting with the solid phase at a dilution of 1/100 and 1/400 are visualized with a human anti-IgG(H+L) polyclonal antibody coupled to peroxidase (Amersham NA933V) and TMB plus H202 (KPL). The sera of probable SARS cases are identified by a National Reference Center for Influenza Virus serial number and by the initials of the patient and the number of days elapsed since the onset of symptoms, where appropriate. The TV sera are control sera from subjects which were collected in France before the SARS epidemic which occurred in 2003.

FIG. 39 shows the anti-SARS-CoV antibody response in mice after immunization with the recombinant vaccinia viruses. Groups of 7 BALB/c mice were immunized by the i.v. route twice at 4 weeks' interval with 106 pfu of recombinant vaccinia viruses VV-TG, VV-TG-HA, VV-TG-S, W-TG-Ssol, VV-TN, VV-TN-S, VV-TN-Ssol.

A. Pools of immune sera collected 3 weeks after each of the two immunizations were prepared for each of the groups and were analyzed by indirect ELISA using a lysate of VeroE6 cells infected with SARS-CoV as antigen. The anti-SARS-CoV antibody titers are calculated as the reciprocal of the dilution producing a specific OD of 0.5 after visualization with an anti-mouse IgG polyclonal antibody coupled to peroxidase (NA931V, Amersham) and TMB (KPL).

B. The pools of immune sera were evaluated for their capacity to seroneutralize the infectivity of 100 TCID50 of SARS-CoV on FRhK-4 cells. 4 points are produced for each of the 2-fold dilutions tested from 1/20. The seroneutralizing titer is calculated according to the Reed and Munsch method as the reciprocal of the dilution neutralizing the infectivity of 2 wells out of 4.

Figures 40, 41:
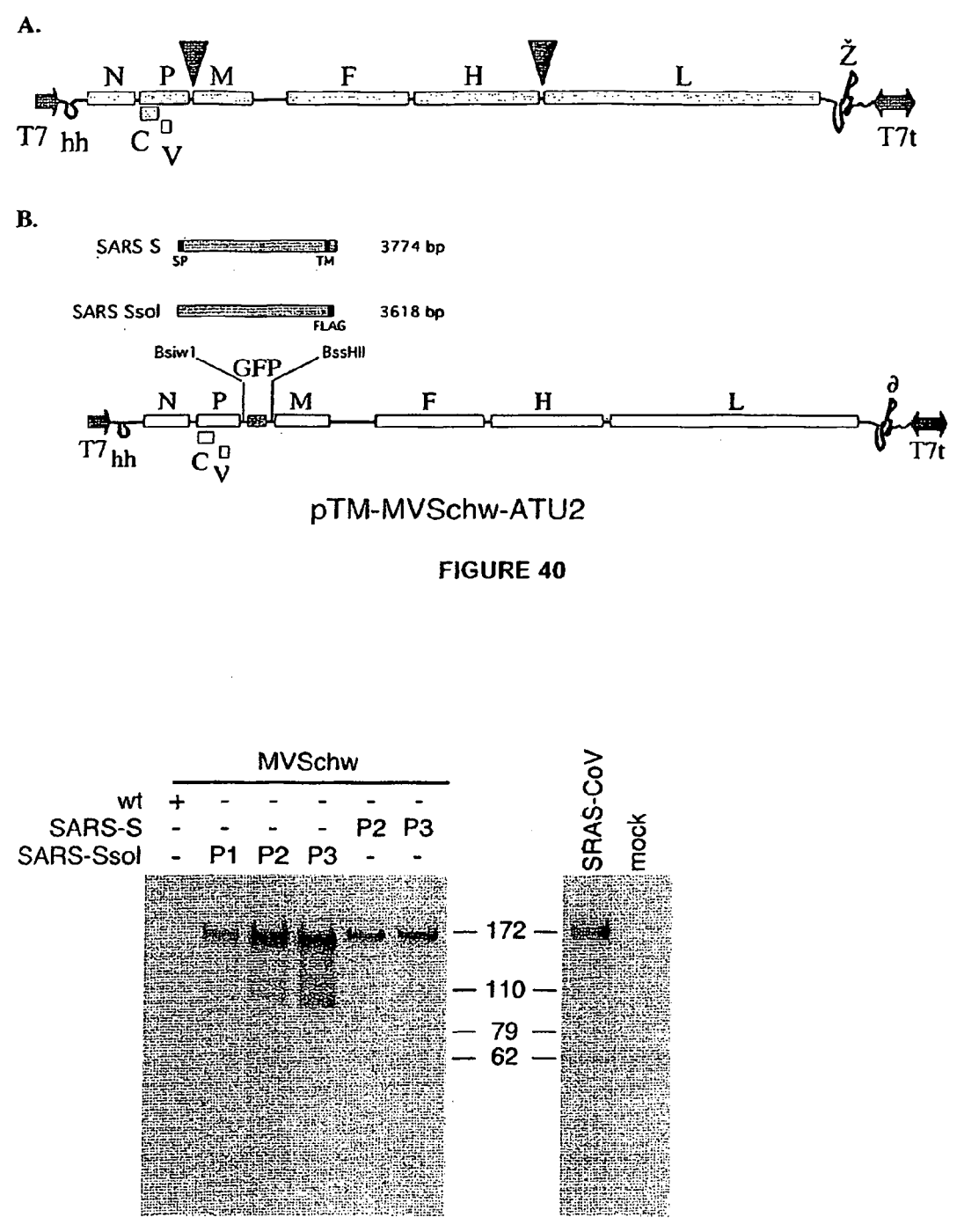

FIG. 40 describes the construction of the recombinant viruses MVSchw2-SARS-S and MVSchw2-SARS-Ssol.

A. The measles vector is a complete genome of the Schwarz vaccine strain of the measles virus (MV) into which an additional transcription unit has been introduced (Combredet, 2003, Journal of Virology, 77: 11546-11554). The expression of the additional open reading frames (ORF) is controlled by cis-acting elements necessary for the transcription, for the formation of the cap and for the polyadenylation of the transgene which were copied from the elements present at the N/P junction. 2 different vectors allow the insertion between the P (phosphoprotein) and M (matrix) genes on the one hand and the H (hemagglutinin) and L (polymerase) genes on the other hand.

B. The recombinant genomes MVSchw2-SARS-S and MVSchw2-SARS-Ssol of the measles virus were constructed by inserting the ORFs of the S protein and of the Ssol polypeptide into an additional transcription unit located between the P and M genes of the vector.

The various genes of the measles virus (MV) are indicated: N (nucleoprotein), PVC (V/C phosphoprotein and protein), M (matrix), F (fusion), H (hemagglutinin), L (polymerase). T7=T7 RNA polymerase promoter, hh=hammerhead ribozyme, T7t=T7 phage RNA polymerase terminator sequence, δ=ribozyme of the hepatitis δ virus, (2), (3)=additional transcription units (ATU).

Size of the MV genome: 15 894 nt.
SP: signal peptide
TM: transmembrane region
FLAG: FLAG tag FIG. 41 illustrates the expression of the S protein by the recombinant measles viruses, analyzed by Western blotting.

Cytoplasmic extracts were prepared after infection of Vero cells by different passages of the viruses MVSchw2-SARS-S and MVSchw2-SARS-Ssol and the wild-type virus MWSchw as control. Cellular extracts in loading buffer according to Laemmli were also prepared 8 hours after infection of VeroE6 cells with SARS-CoV at a multiplicity of infection of 3. They were separated on 8% SDS acrylamide gel and analyzed by Western blotting with the aid of an anti-S rabbit polyclonal antibody and an anti-rabbit IgG(H+L) polyclonal antibody coupled to peroxidase (NA934V, Amersham).

Figure 42:
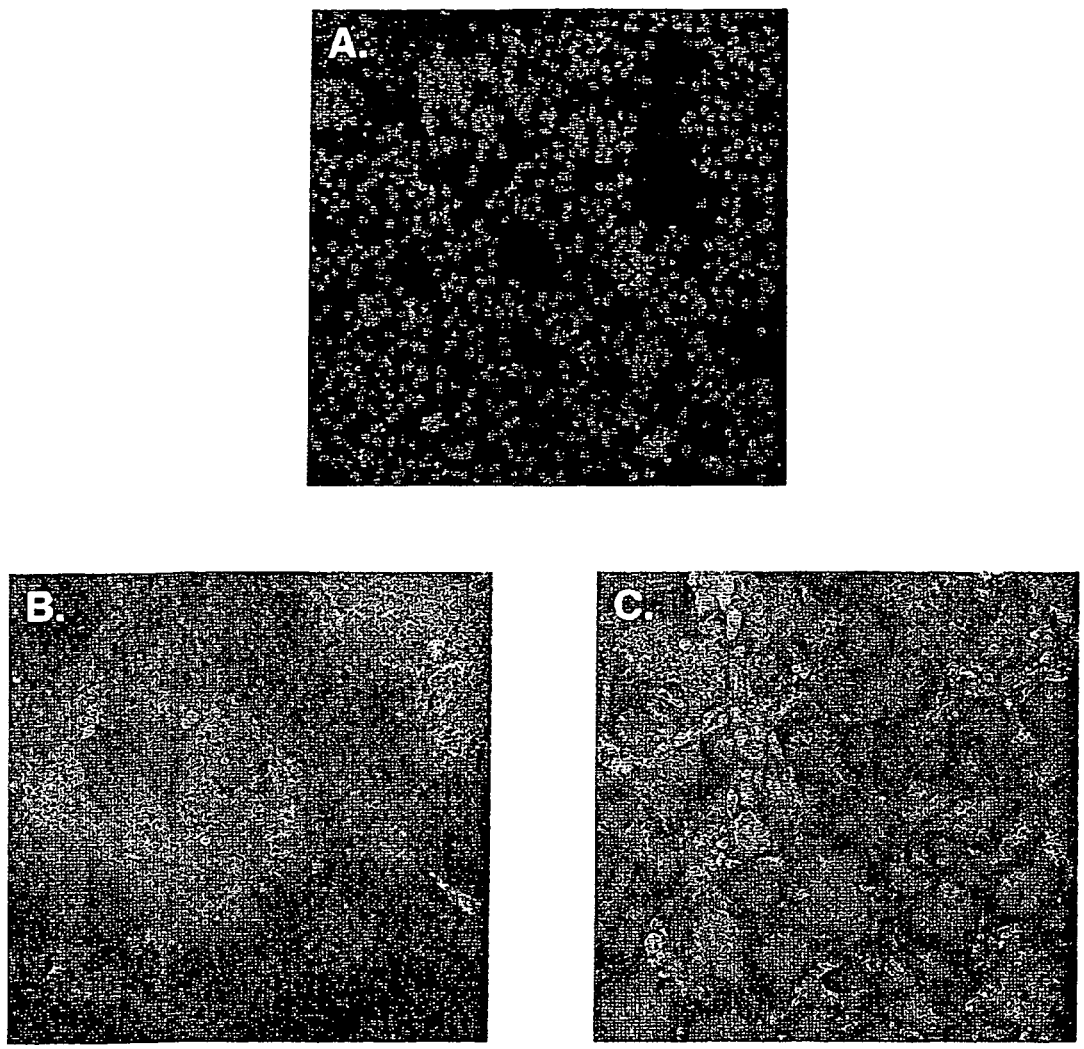

A molecular mass ladder (kDa) is presented in the figure.
Pn: nth passage of the virus after coculture of 293-3-46 and Vero cells
SARS-CoV: extract of VeroE6 cells infected with SARS-CoV
Mock: control extract of noninfected VeroE6 cells FIG. 42 shows the expression of the S protein by the recombinant measles viruses, analyzed by immunofluorescence Vero cells in monolayers on glass slides were infected with the wild-type virus MWSchw (A) or the viruses MVSchw2-SARS-S (B) and MVSchw2-SARS-Ssol (C). When the syncytia have reached 30 to 40% confluence (A., B.) or 90-100% (C), the cells were fixed, permeabilized and labeled with anti-SARS-CoV rabbit polyclonal antibodies and an anti-rabbit IgG(H+L) conjugate coupled to FITC (Jackson).

Figure 43:
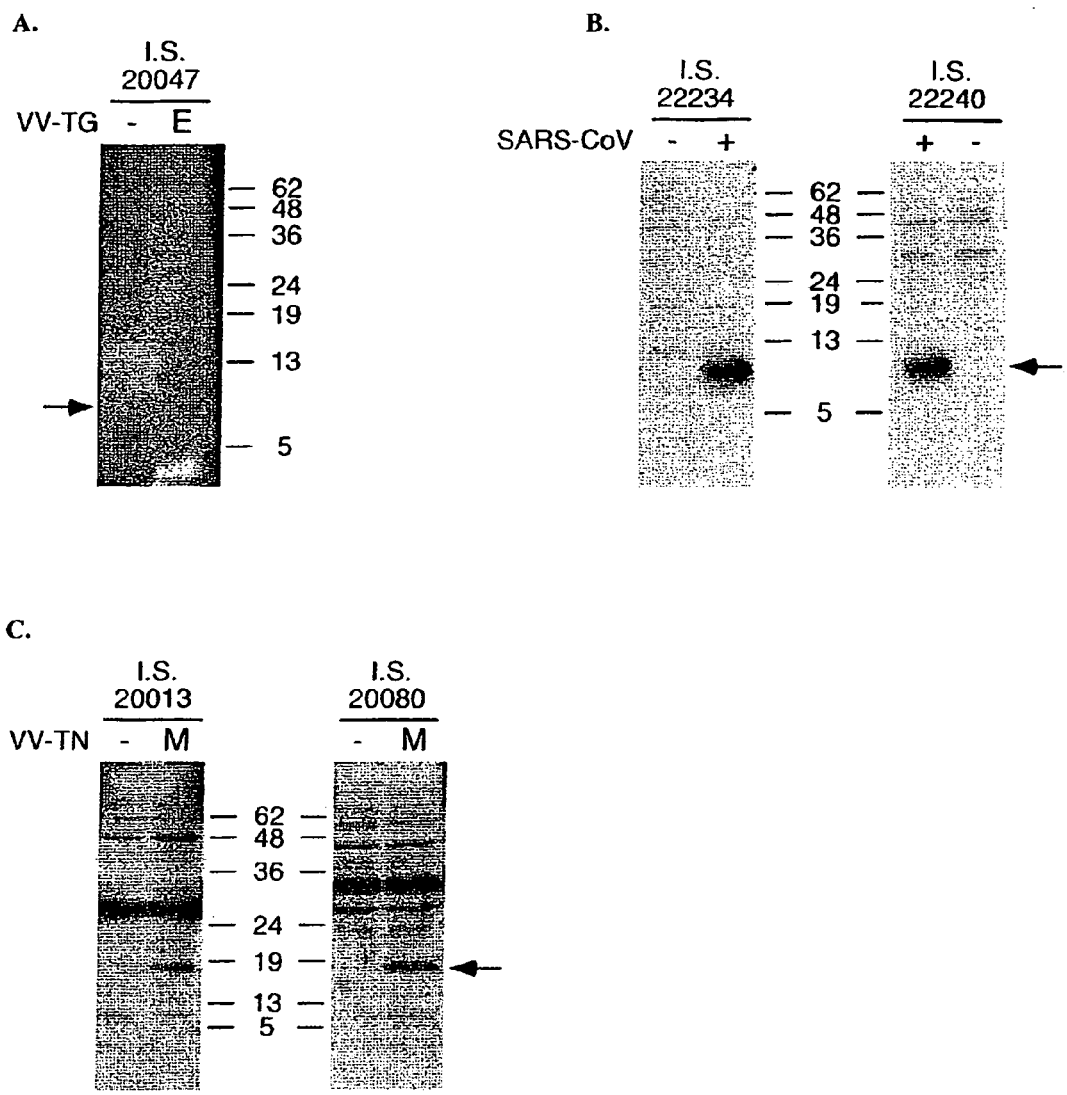

FIG. 43 illustrates the Western-blot analysis of the immunoreactivity of rabbit sera directed against the peptides E1-12, E53-76 and M2-14. The rabbit 20047 was immunized with the peptide E1-12 coupled to KLH. The rabbits 22234 and 22240 were immunized with the peptide E53-76 coupled to KLH. The rabbits 20013 and 20080 were immunized with the peptide M2-14 coupled to KLH. The immune sera were analyzed by Western blotting with the aid of extracts of cells infected with SARS-CoV (B) or with the aid of extracts of cells infected with a recombinant vaccinia virus expressing the protein E (A) or M (C) of the SARS-CoV 031589 isolate. The immunoblots were visualized with the aid of an anti-rabbit IgG(H+L) conjugate coupled to peroxidase (NA934V, Amersham).

The position of the E and M proteins is indicated by an arrow.

A molecular mass ladder (kDa) is presented in the figure.

It should be understood, however, that these examples are given solely by way of illustration of the subject of the invention, and do not constitute in any manner a limitation thereto.

EXAMPLE 1

Cloning and Sequencing of the Genome of the SARS-CoV Strain Derived from the Sample Recorded Under the Number 031589

The RNA of the SARS-CoV strain was extracted from the sample of bronchoalveolar washing recorded under the number 031589, performed on a patient at the Hanoi (Vietnam) French hospital suffering from SARS.

The isolated RNA was used as template to amplify the cDNAs corresponding to the various open reading frames of the genome (ORF1a, ORF1b, ORF-S, ORF-E, ORF-M, ORF-N (including ORF-13 and ORF-14), ORF3, ORF4, ORF7 to ORF11), and at the noncoding 5' and 3' ends. The sequences of the primers and of the probes used for the amplification/detection were defined based on the available SARS-CoV nucleotide sequence.

In the text which follows, the primers and the probes are identified by: the letter S, followed by a letter which indicates the corresponding region of the genome (L for the 5' end including ORF1a and ORF1b; S, M and N for ORF-S, ORF-M, ORF-N, SE and MN for the corresponding intergene regions), and then optionally by Fn, Rn, with n between 1 and 6 corresponding to the primers used for the nested PCR (F1+R1 pair for the first amplification, F2+R2 pair for the second amplication, and the like), and then by /+/ or /−/ corresponding to a sense or antisense primer and finally by the positions of the primers with reference to the Genbank sequence AY27411.3; for the sense and antisense S and N primers and the other sense primers only, when a single position is indicated, it corresponds to that of the 5' end of a probe or of a primer of about 20 bases; for the antisense primers other than the S and N primers, when a single position is indicated, it corresponds to that of the 3' end of a probe or of a primer of about 20 bases.

The amplification products thus generated were sequenced with the aid of specific primers in order to determine the complete sequence of the genome of the SARS-CoV strain derived from the sample recorded under the number 031589. These amplification products, with the exception of those corresponding to ORF1a and ORF1b, were then cloned into expression vectors in order to produce the corresponding viral proteins and the antibodies directed against these proteins, in particular by DNA-based immunization.

1. Extraction of the RNAs

The RNAs were extracted with the aid of the QIamp viral RNA extraction mini kit (QIAGEN) according to the manufacturer's recommendations. More specifically: 140 µl of the sample and 560 µl of AVL buffer were vigorously mixed for 15 seconds, incubated for 10 minutes at room temperature and then briefly centrifuged at maximum speed. 560 µl of 100% ethanol were added to the supernatant and the mixture thus obtained was very vigorously stirred for 15 sec. 630 µl of the mixture were then deposited on the column.

The column was placed on a 2 ml tube, centrifuged for 1 min at 8000 rpm, and then the remainder of the preceding mixture was deposited on the same column, centrifuged again, for 1 min at 8000 rpm, and the column was transferred over a clean 2 ml tube. Next, 500 µl of AW1 buffer were added to the column, and then the column was centrifuged for 1 min at 8000 rpm and the eluate was discarded. 500 µl of AW2 buffer were added to the column which was then centrifuged for 3 min at 14 000 rpm and transferred onto a 1.5 ml tube. Finally, 60 µl of AVE buffer were added to the column which was incubated for 1 to 2 min at room temperature and then centrifuged for 1 min at 8000 rpm. The eluate corresponding to the purified RNA was recovered and frozen at −20° C.

2. Amplification, Sequencing and Cloning of the cDNAs 2.1) cDNA Encoding the S Protein The RNAs extracted from the sample were subjected to reverse transcription with the aid of random sequence hexameric oligonucleotides (pdN6), so as to produce cDNA fragments.

The sequence encoding the SARS-CoV S glycoprotein was amplified in the form of two overlapping DNA fragments: 5' fragment (SARS-Sa, SEQ ID NO: 5) and 3' fragment (SARS-Sb, SEQ ID NO: 6), by carrying out two successive amplifications with the aid of nested primers. The amplicons thus obtained were sequenced, cloned into the PCR plasmid vector 2.1-TOPO™ (INVITROGEN), and then the sequence of the cloned cDNAs was determined.

a) Cloning and Sequencing of the Sa and Sb Fragments a.1) Synthesis of the cDNA

The reaction mixture containing: RNA (5 µl), $H_2O$ for injection (3.5 µl), 5× reverse transcriptase buffer (4 µl), 5 mM dNTP (2 µl), pdN6 100 µg/ml (4 µl), RNasin 40 IU/µl (0.5 µl) and reverse transcriptase AMV-RT, 10 IU/µl, PROMEGA (1 µl) was incubated in a thermocycler under the following conditions: 45 min at 42° C., 15 min at 55° C., 5 min at 95° C., and then the cDNA obtained was kept at +4° C.

a.2) First PCR Amplification

The 5' and 3' ends of the S gene were respectively amplified with the pairs of primers S/F1/+/21350-21372 and S/R1/−/23518-23498, S/F3/+/23258-23277 and S/R3/−/25382-25363. The 50 µl reaction mixture containing: cDNA (2 µl), 50 µM primers (0.5 µl), 10× buffer (5 µl), 5 mM dNTP (2 µl), Taq Expand High Fidelity, Roche (0.75 µl) and $H_2O$ (39, 75 µl) was amplified in a thermocycler, under the following conditions: an initial step of denaturation at 94° C. for 2 min was followed by 40 cycles comprising: a step of denaturation at 94° C. for 30 sec, a step of annealing at 55° C. for 30 sec and then a step of extension at 72° C. for 2 min 30 sec, with 10 sec of additional extension at each cycle, and then a final step of extension at 72° C. for 5 min.

a.3) Second PCR Amplification

The products of the first PCR amplification (5' and 3' amplicons) were subjected to a second PCR amplification step (nested PCR) under conditions identical to those of the first amplification, with the pairs of primers S/F2/+/21406-21426 and S/R2/−/23454-23435 and S/F4/+/23322-23341 and S/R4/−/25348-25329, respectively for the 5' amplicon and the 3' amplicon.

a.4) Cloning and Sequencing of the Sa and Sb Fragments

The Sa (5' end) and Sb (3' end) amplicons thus obtained were purified with the aid of the QIAquick PCR purification kit (QIAGEN), following the manufacturer's instructions, and then they were cloned into the vector PCR2. 1-TOPO (Invitrogen kit), to give the plasmids called SARS-S1 and SARS-S2.

The DNA of the Sa and Sb clones was isolated and then the corresponding insert was sequenced with the aid of the Big Dye kit, Applied Biosystem® and universal primers M13 forward and M13 reverse, and primers: S/S/+/21867, S/S/+/22353, S/S/+/22811, S/S/+/23754, S/S/+/24207, S/S/+/24699, S/S/+/24348, S/S/−/24209, S/S/−/23630, S/S/−/23038, S/S/−/22454, S/S/−/21815, S/S/−/24784, S/S/+/21556, S/S/+/23130 and S/S/+/24465 following the manufacturer's instructions; the sequences of the Sa and Sb fragments thus obtained correspond to the sequences SEQ ID NO: 5 and SEQ ID NO: 6 in the sequence listing appended as an annex.

The plasmid, called SARS-S1, was deposited under the No. I-3020, on May 12, 2003, at the Collection Nationale de Cultures de Microorganismes, 25 rue du Docteur Roux, 75724 Paris Cedex 15; it contains a 5' fragment of the sequence of the S gene of the SARS-CoV strain derived from the sample recorded under the No. 031589, as defined above, said fragment called Sa corresponding to the nucleotides at positions 21406 to 23454 (SEQ ID NO: 5), with reference to the Genbank sequence AY274119.3 Tor2.

The plasmid, called TOP10F'-SARS-S2, was deposited under the No. I-3019, on May 12, 2003, at the Collection Nationale de Cultures de Microorganismes, 25 rue du Docteur Roux, 75724 Paris Cedex 15; it contains a 3' fragment of the sequence of the S gene of the SARS-CoV strain derived from the sample recorded under the No. 031589, as defined above, said fragment called Sb corresponding to the nucleotides at positions 23322 to 25348 (SEQ ID NO: 6), with reference to the Genbank sequence accession No. AY274119.3.

b) Cloning and Sequencing of the Complete cDNA (SARS-S Clone of 4 kb)

The complete S cDNA was obtained from the abovementioned clones SARS-S1 and SARS-S2, in the following manner:

1) A PCR amplification reaction was carried out on a SARS-S2 clone in the presence of the abovementioned primer S/R4/−/25348-25329 and of the primer S/S/+/24696-24715: an amplicon of 633 bp was obtained,
2) Another PCR amplification reaction was carried out on another SARS-S2 clone, in the presence of the primers S/F4/+/23322-23341 mentioned above and S/S/−/24803-24784: an amplicon of 1481 bp was obtained.

The amplification reaction was carried out under the conditions as defined above for the amplification of the Sa and Sb fragments, with the exception that 30 amplification cycles comprising a step of denaturation at 94° C. for 20 sec and a step of extension at 72° C. for 2 min 30 sec were carried out.

3) The 2 amplicons (633 bp and 1481 bp) were purified under the conditions as defined above for the Sa and Sb fragments.
4) Another PCR amplification reaction with the aid of the abovementioned primers S/F4/+/23322-23341 and S/R4/−/$^{25}$348-25329 was carried out on the purified amplicons obtained in 3). The amplification reaction was carried out under the conditions as defined above for the amplification of the Sa and Sb fragments, except that 30 amplification cycles were performed.

The 2026 bp amplicon thus obtained was purified, cloned into the vector PCR2.1-TOPO and then sequenced as above, with the aid of the primers as-defined above for the Sa and Sb fragments. The clone thus obtained was called clone 3'.

5) The clone SARS-S1 obtained above and the clone 3"were digested with EcoR I, the bands of about 2 kb thus obtained were gel purified and then amplified by PCR with the abovementioned primers S/F2/+/21406-21426 and S/R4/−/25348-25329. The amplification reaction was carried out under the conditions as defined above for the amplification of the Sa and Sb fragments, except that 30 amplification cycles were performed. The amplicon of about 4 kb was purified and sequenced. It was then cloned into the vector PCR2.1-TOPO in order to give the plasmid, called SARS-S, and the insert obtained in this plasmid was sequenced as above, with the aid of the primers as defined above for the Sa and Sb fragments. The cDNA sequences of the insert and of the amplicon encoding the S protein correspond respectively to the sequences SEQ ID NO: 4 and SEQ ID NO: 2 in the sequence listing appended as an annex, they encode the S protein (SEQ ID NO: 3).

The sequence of the amplicon corresponding to the cDNA encoding the S protein of the SARS-CoV strain derived from the sample No. 031589 has the following two mutations compared with the corresponding sequences of respectively the Tor2 and Urbani isolates, the positions of the mutations being indicated with reference to the complete sequence of the genome of the Tor2 isolate (Genbank AY274119.3):

g/t in position 23220; the alanine codon (gct) in position 577 of the amino acid sequence of the S protein of Tor2 is replaced with a serine codon (tct), c/t in position 24872: this mutation does not modify the amino acid sequence of the S protein, and the plasmid, called SARS-S, was deposited under the No. I-3059, on Jun. 20, 2003, at the Collection Nationale de Cultures de Microorganismes, 25 rue du Docteur Roux, 75724 Paris Cedex 15; it contains the cDNA sequence encoding the S protein of the SARS-CoV strain derived from the sample recorded under the No. 031589, said sequence corresponding to the nucleotides at positions 21406 to 25348 (SEQ ID NO: 4), with reference to the Genbank sequence AY274119.3.

2.2) cDNA Encoding the M and E Proteins

The RNAs derived from the sample 031589, extracted as above, were subjected to a reverse transcription, combined, during the same step (Titan One Step RT-PCR® kit, Roche), with a PCR amplification reaction, with the aid of the pairs of primers:

S/E/F1/+/26051-26070 and S/E/R1/−/26455-26436 in order to amplify ORF-E, and

S/M/F1/+/26225-26244 and S/M/R1/−/27148-27129 in order to amplify ORF-M.

A first reaction mixture containing: 8.6 µl of $H_2O$ for injection, 1 µl of dNTP (5 mM), 0.2 µl of each of the primers (50 µM), 1.25 µl of DTT (100 mM) and 0.25 µl of RNAsin (40 IU/µl) was combined with a second reaction mixture containing: 1 µl of RNA, 7 µl of $H_2O$ for injection, 5 µl of 5× RT-PCR buffer and 0.5 µl of enzyme mixture and the combined mixtures were incubated in a thermocycler under the following conditions: 30 min at 42° C., 10 min at 55° C., 2 min at 94° C. followed by 40 cycles comprising a step of denaturation at 94° C. for 10 sec, a step of annealing at 55° C. for 30 sec and a step of extension at 68° C. for 45 sec, with 3 sec increment per cycle and finally a step of terminal extension at 68° C. for 7 min.

The amplification products thus obtained (M and E amplicons) were subjected to a second PCR amplification (nested PCR) using the Expand High-Fi® kit, Roche), with the aid of the pairs of primers:

S/E/F2/+/26082-26101 and S/E/R2/−/26413-26394 for the amplicon E, and

S/M/F2/+/26330-26350 and S/M/R2/−/27098-27078 for the amplicon M.

The reaction mixture containing: 2 µl of the product of the first PCR,. 39.25 µl of $H_2O$ for injection, 5 µl of 10× buffer containing $MgCl_2$, 2 µl of dNTP (5 mM), 0.5 µl of each of the primers (50 µM) and 0.75 µl of enzyme mixture was incubated in a thermocycler under the following conditions: a step of denaturation at 94° C. for 2 min was followed by 30 cycles comprising a step of denaturation at 94° C. for 15 sec, a step of annealing at 60° C. for 30 sec and a step of extension at 72° C. for 45 sec, with 3 sec increment per cycle, and finally a step of terminal extension at 72° C. for 7 min. The amplification products obtained corresponding to the cDNAs encoding the E and M proteins were sequenced as above, with the aid of the primers: S/E/F2/+/26082 and S/E/R2/−/26394, S/M/F2/+/26330, S/M/R2/−/27078 cited above and the primers S/M/+/26636-26655 and S/M/−/26567-26548. They were then cloned, as above, in order to give the plasmids called SARS-E and SARS-M. The DNA of these clones was then isolated and sequenced with the aid of the universal primers M13 forward and M13 reverse and the primers S/M/+/26636 and S/M/−/26548 mentioned above.

The sequence of the amplicon representing the cDNA encoding the E protein (SEQ ID NO: 13) of the SARS-CoV strain derived from the sample No. 031589 does not contain differences in relation to the corresponding sequences of the isolates AY274119.3-Tor2 and AY278741-Urbani. The sequence of the E protein of the SARS-CoV 031589 strain corresponds to the sequence SEQ ID NO: 14 in the sequence listing appended as an annex.

The plasmid, called SARS-E, was deposited under the No. I-3046, on May 28, 2003, at the Collection Nationale de Cultures de Microorganismes, 25 rue du Docteur Roux, 75724 Paris Cedex 15; it contains the cDNA sequence encoding the E protein of the SARS-CoV strain derived from the sample recorded under the No. 031589, as defined above, said sequence corresponding to the nucleotides at positions 26082 to 26413 (SEQ ID NO: 15), with reference to the Genbank sequence accession No. AY274119.3.

The sequence of the amplicon representing the cDNA encoding M (SEQ ID NO: 16) from the SARS-CoV strain derived from the sample No. 031589 does not contain differences in relation to the corresponding sequence of the isolate AY274119.3-Tor2. By contrast, at position 26857, the isolate AY278741-Urbani contains a c and the sequence of the SARS-CoV strain derived from the sample recorded under the No. 031589 contains a t. This mutation results in a modification of the amino acid sequence of the corresponding protein: at position 154, a proline (AY278741-Urbani) is changed to serine in the SARS-CoV strain derived from the sample recorded under the No. 031589. The sequence of the M protein of the SARS-CoV strain derived from the sample recorded under the No. 031589 corresponds to the sequence SEQ ID NO: 17 in the sequence listing appended as an annex.

The plasmid, called SARS-M, was deposited under the No. I-3047, on May 28, 2003, at the Collection Nationale de Cultures de Microorganismes, 25 rue du Docteur Roux, 75724 Paris Cedex 15; it contains the cDNA sequence encoding the M protein of the SARS-CoV strain derived from the sample recorded under the No. 031589, as defined above; said sequence corresponding to the nucleotides at positions 26330 to 27098 (SEQ ID NO: 18), with reference to the Genbank sequence accession No. AY274119.3.

2.3) cDNA Corresponding to ORF3, ORF4, ORF7 to ORF11

The same amplification, cloning and sequencing strategy was used to obtain the cDNA fragments corresponding respectively to the following ORFs: ORF3, ORF4, ORF7, ORF8, ORF9, ORF10 and ORF11. The pairs of primers used for the first amplification are:

ORF3 and ORF4: S/SE/F1/+/25069-25088 and S/SE/R1/−/26300-26281

ORF7 to ORF11: S/MN/F1/+/26898-26917 and S/MN/R1/−/28287-28266

The pairs of primers used for the second amplification are:

ORF3 and ORF4: S/SE/F2/+/25110-25129 and S/SE/R2/−/26244-26225

ORF7 to ORF11: S/MN/F2/+/26977-26996 and S/MN/R2/−/28218-28199

The conditions for the first amplification (RT-PCR) are the following: 45 min at 42° C., 10 min at 55° C., 2 min at 94° C. followed by 40 cycles comprising a step of denaturation at 94° C. for 15 sec, a step of annealing at 58° C. for 30 sec and a step of extension at 68° C. for 1 min, with 5 sec increment per cycle and finally a step of terminal extension at 68° C. for 7 min. The conditions for the nested PCR are the following: a step of denaturation at 94° C. for 2 min was followed by 40 cycles comprising a step of denaturation at 94° C. for 20 sec, a step of annealing at 58° C. for 30 sec and a step of extension at 72° C. for 50 sec, with 4 sec increment per cycle and finally a step of terminal extension at 72° C. for 7 min.

The amplification products obtained corresponding to the cDNAs containing respectively ORF3 and 4 and ORF7 to 11 were sequenced with the aid of the primers: S/SE/+/25363, S/SE/+/25835, S/SE/−/25494, S/SE/−/25875, S/MN/+/27839, S/MN/+/27409, S/MN/−/27836, S/MN/−/27799 and cloned as above for the other ORFs, to give the plasmids called SARS-SE and SARS-MN. The DNA of these clones was isolated and sequenced with the aid of these same primers and of the universal primers M13 sense and M13 antisense.

The sequence of the amplicon representing the cDNA of the region containing OFR3 and ORF4 (SEQ ID NO: 7) of the SARS-CoV strain derived from the sample No. 031589 contains a nucleotide difference in relation to the corresponding sequence of the isolate AY274119-Tor2. This mutation at position 25298 results in a modification of the amino acid sequence of the corresponding protein (ORF3): at position 11, an arginine (AY274119-Tor2) is changed to glycine in the SARS-CoV strain derived from the sample No. 031589. By contrast, no mutation was identified in relation to the corresponding sequence of the isolate AY278741-Urbani. The sequences of ORF3 and 4 of the SARS-CoV strain derived from the sample No. 031589 correspond respectively to the sequences SEQ ID NO: 10 and 12 in the sequence listing appended as an annex.

The plasmid, called SARS-SE, was deposited under the No. I-3126, on Nov. 13, 2003, at the Collection Nationale de Cultures de Microorganismes, 25 rue du Docteur Roux, 75724 Paris Cedex 15; it contains the cDNA corresponding to the region situated between ORF-S and ORF-E and overlapping ORF-E of the SARS-CoV strain derived from the sample recorded under the No. 031589, as defined above, said region corresponding to the nucleotides at positions 25110 to 26244 (SEQ ID NO: 8), with reference to the Genbank sequence accession No. AY274119.3.

The sequence of the amplicon representing the cDNA corresponding to the region containing ORF7 to ORF11 (SEQ ID NO: 19) of the SARS-CoV strain derived from the sample No. 031589 does not contain differences in relation to the corresponding sequences of the isolates AY274119-Tor2 and AY278741-Urbani. The sequences of ORF7 to 11 of the SARS-CoV strain derived from the sample No. 031589 correspond respectively to the sequences SEQ ID NO: 22, 24, 26, 28 and 30 in the sequence listing appended as an annex.

The plasmid, called SARS-MN, was deposited under the No. I-3125, on Nov. 13, 2003, at the Collection Nationale de Cultures de Microorganismes, 25 rue du Docteur Roux, 75724 Paris Cedex 15; it contains the cDNA sequence corresponding to the region situated between ORF-M and ORF-N of the SARS-CoV strain derived from the sample recorded under the No. 031589 and collected in Hanoi, as defined above, said sequence corresponding to the nucleotides at positions 26977 to 28218 (SEQ ID NO: 20), with reference to the Genbank sequence accession No. AY274119.3.

The sequence of the amplicon representing the cDNA corresponding to the region containing ORF7 to ORF11 (SEQ ID NO: 19) of the SARS-CoV strain derived from the sample No. 031589 does not contain differences in relation to the corresponding sequences of the isolates AY274119-Tor2 and AY278741-Urbani. The sequences of ORF7 to 11 of the SARS-CoV strain derived from the sample No. 031589 correspond respectively to the sequences SEQ ID NO: 22, 24, 26, 28 and 30 in the sequence listing appended as an annex.

2.4) cDNA Encoding the N Protein and Including ORF13 and ORF14

The cDNA was synthesized and amplified as described above for the fragments Sa and Sb. More specifically, the reaction mixture containing: 5 µl of RNA, 5 µl of $H_2O$ for injection, 4 µl of 5× reverse transcriptase buffer, 2 µl of dNTP (5 mM), 2 µl of oligo 20T (5 µM), 0.5 µl of RNasin (40 IU/µl) and 1.5 µl of AMV-RT (10 IU/µl Promega) was incubated in a thermocycler under the following conditions: 45 min at 42° C., 15 min at 55° C., 5 min at 95° C., and it was then kept at +4° C.

A first PCR amplification was performed with the pair of primers S/N/F3/+/28023 and S/N/R3/−/29480.

The reaction mixture as above for the amplification of the S1 and S2 fragments was incubated in a thermocycler, under the following conditions: an initial step of denaturation at 94° C. for 2 min was followed by 40 cycles comprising a step of denaturation at 94° C. for 20 sec, a step of annealing at 55° C. for 30 sec and then a step of extension at 72° C. for 1 min 30 sec with 10 sec of additional extension at each cycle, and then a final step of extension at 72° C. for 5 min.

The amplicon obtained at the first PCR amplification was subjected to a second PCR amplification step (nested PCR) with the pairs of primer S/N/F4/+/28054 and S/N/R4/−/29430 under conditions identical to those of the first amplification.

The amplification product obtained, corresponding to the cDNA encoding the N protein of the SARS-CoV strain derived from the sample No. 031589, was sequenced with the aid of the primers: S/N/F4/+/28054, S/N/R4/−/29430, S/N/+/28468, S/N/+/28918 and S/N/−/28607 and cloned as above for the other ORFs, to give the plasmid called SARS-N. The DNA of these clones was isolated and sequenced with the aid of the universal primers M13 sense and M13 antisense, and the primers S/N/+/28468, S/N/+/28918 and S/N/−/28607.

The sequence of the amplicon representing the cDNA corresponding to ORF-N and including ORF13 and ORF14 (SEQ ID NO: 36) of the SARS-CoV strain derived from the sample No. 031589 does not contain differences in relation to the corresponding sequences of the isolates AY274119.3-Tor2 and AY278741-Urbani. The sequence of the N protein of the SARS-CoV strain derived from the sample No. 031589 corresponds to the sequence SEQ ID NO: 37 in the sequence listing appended as an annex.

The sequences of ORF13 and 14 of the SARS-CoV strain derived from the sample No. 031589 correspond respectively to the sequences SEQ ID NO: 32 and 34 in the sequence listing appended as an annex.

The plasmid, called SARS-N, was deposited under the No. I-3048, on Jun. 5, 2003, at the Collection Nationale de Cultures de Microorganismes, 25 rue du Docteur Roux, 75724 Paris Cedex 15; it contains the cDNA encoding the N protein of the SARS-CoV strain derived from the sample recorded under the No. 031589, as defined above, said sequence corresponding to the nucleotides at positions 28054 to 29430 (SEQ ID NO: 38), with reference to the Genbank sequence accession No. AY274119.3.

2.5) Noncoding 5' and 3' Ends a) Noncoding 5' end (5'NC)

$a_1$) Synthesis of the cDNA

The RNAs derived from the sample 031589, extracted as above, were subjected to reverse transcription under the following conditions:

The RNA (15 μl) and the primer S/L/−/443 (3 μl at the concentration of 5 μm) were incubated for 10 min at 75° C.

Next, the 5× reverse transcriptase buffer (6 μl, INVITROGEN), 10 Mm dNTP (1 μl), 0.1 M DTT (3 μl) were added and the mixture was incubated at 50° C. for 3 min.

Finally, the reverse transcriptase (3 μl of Superscript®, INVITROGEN) was added to the preceding mixture which was incubated at 50° C. for 1 h 30 min and then at 90° C. for 2 min.

The cDNA thus obtained was purified with the aid of the QIAquick PCR purification kit (QIAGEN) according to the manufacturer's recommendations.

$b_1$) Terminal Transferase Reaction (TdT)

The cDNA (10 μl) is incubated for 2 min at 100° C., stored in ice, and the following are then added: $H_2O$ (2.5 μl), 5× TdT buffer (4 μl, AMERSHAM), 5 mM dATP (2 μl) and TdT (1.5 μl, AMERSHAM). The mixture thus obtained is incubated for 45 min at 37° C. and then for 2 min at 65° C.

The product obtained is amplified by a first PCR reaction with the aid of the primers: S/L/-225-206 and anchor 14T: 5'-AGATGAATTCGGTACCTTTTTTTTTTTTTT-3' (SEQ ID NO: 68). The amplification conditions are the following: an initial step of denaturation at 94° C. for 2 min is followed by 10 cycles comprising a step of denaturation at 94° C. for 10 sec, a step of annealing at 45° C. for 30 sec and then a step of extension at 72° C. for 30 sec and then by 30 cycles comprising a step of denaturation at 94° C. for 10 sec, a step of annealing at 50° C. for 30 sec and then a step of extension at 72° C. for 30 sec, and then a final step of extension at 72° C. for 5 min.

The product of the first PCR amplification was subjected to a second amplification step with the aid of the primers: S/L/−/204-185 and anchor 14T mentioned above under conditions identical to those of the first amplification. The amplicon thus obtained was purified, sequenced with the aid of the primer S/L/−/182-163 and it was then cloned as above for the different ORFs, to give the plasmid called SARS-5'NC. The DNA of this clone was isolated and sequenced with the aid of the universal primers M13 sense and M13 antisense and the primer S/L/−/182-163 mentioned above.

The amplicon representing the cDNA corresponding to the 5'NC end of the SARS-CoV strain derived from the sample recorded under the No. 031589 corresponds to the sequence SEQ ID NO: 72 in the sequence listing appended as an annex; this sequence does not contain differences in relation to the corresponding sequences of the isolates AY274119.3-Tor2 and AY278741-Urbani.

The plasmid, called SARS-5'NC, was deposited under the No. I-3124, on Nov. 7, 2003, at the Collection Nationale de Cultures de Microorganismes, 25 rue du Docteur Roux, 75724 Paris Cedex 15; it contains the cDNA corresponding to the noncoding 5' end of the genome of the SARS-CoV strain derived from the sample recorded under the No. 031589, as defined above, said sequence corresponding to the nucleotides at positions 1 to 204 (SEQ ID NO: 39), with reference to the Genbank sequence accession No. AY274119.3.

b) Noncoding 3' end (3'NC)

$a_1$) Synthesis of the cDNA

The RNAs derived from the sample 031589, extracted as above, were subjected to reverse transcription, according to the following protocol: the reaction mixture containing: RNA (5 μl), $H_2O$ (5 μl), 5× reverse transcriptase buffer (4 μl), 5 mM dNTP (2 μl), 5 μM Oligo 20T (2 μl), 40 U/μl RNasin (0.5 μl) and 10 IU/μl RT-AMV (1.5 μl, PROMEGA) was incubated in a thermocycler, under the following conditions: 45 min at 42° C., 15 min at 55° C., 5 min at 95° C., and it was then kept at +4° C.

The cDNA obtained was amplified by a first PCR reaction with the aid of the primers S/N/+/28468-28487 and anchor 14T mentioned above. The amplification conditions are the following: an initial step of denaturation at 94° C. for 2 min is followed by 10 cycles comprising a step of denaturation at 94° C. for 20 sec, a step of annealing at 45° C. for 30 sec and then a step of extension at 72° C. for 50 sec and then 30 cycles comprising a step of denaturation at 94° C. for 20 sec, a step of annealing at 50° C. for 30 sec and then a step of extension at 72° C. for 50 sec, and then a final step of extension at 72° C. for 5 min.

The product of the first PCR amplification was subjected to a second amplification step with the aid of the primers S/N/+/28933-28952 and anchor 14T mentioned above, under conditions identical to those of the first amplification. The amplicon thus obtained was purified, sequenced with the aid of the primer S/N/+/29257-29278 and cloned as above for the different ORFs, to give the plasmid called SARS-3'NC. The DNA of this clone was isolated and sequenced with the aid of the universal primers M13 sense and M13 antisense and the primer S/N/+/29257-29278 mentioned above.

The amplicon representing the cDNA corresponding to the 3'NC end of the SARS-CoV strain derived from the sample recorded under the No. 031589 corresponds to the sequence SEQ ID NO: 73 in the sequence listing appended as an annex; this sequence does not contain differences in relation to the corresponding sequences of the isolates AY274119.3-Tor2 and AY278741-Urbani.

The plasmid called SARS-3'NC was deposited under the No. I-3123 on Nov. 7, 2003, at the Collection Nationale de Cultures de Microorganismes, 25 rue du Docteur Roux, 75724 Paris Cedex 15; it contains the cDNA sequence corresponding to the noncoding 3' end of the genome of the SARS-CoV strain derived from the sample recorded under the No. 031589, as defined above, said sequence corresponding to that situated between the nucleotide at positions 28933 to 29727 (SEQ ID NO: 40), with reference to the Genbank sequence accession No. AY274119.3, ends with a series of nucleotides a.

2.6) ORF1a and ORF1b

The amplification of the 5' region containing ORF1a and ORF1b of the SARS-CoV genome derived from the sample 031589 was performed by carrying out RT-PCR reactions followed by nested PCRs according to the same principles as those described above for the other ORFs. The amplified fragments overlap over several tenths of bases, thus allowing computer reconstruction of the complete sequence of this part of the genome. On average, the amplified fragments are of two kilobases.

14 overlapping fragments, called L0 to L12, were thus amplified with the aid of the following primers:

TABLE II

Primers used for the amplification of the 5' region (ORF1a and ORF1b)

| REGION AMPLIFIED AND SEQUENCED (does not include the primers) | RT-PCR sense primer | RT-PCR antisense primer | Nested PCR sense primer | Nested PCR antisense primer |
|---|---|---|---|---|
| L0 50-480 | S/L0/F1/+30 | S/L0/R1/−481 | | |
| L1 231-2240 | S/L1/F1/+147 | S/L1/R1/−2336 | S/L1/F2/+211 | S/L1/R2/−2241 |
| L2 2156-4167 | S/L2/F1/+2033 | S/L2/R1/−4192 | S/L2/F2/+2136 | S/L2/R2/−4168 |
| L3 3913-5324 | S/L3bis/F1+3850 | S/L3bis/R1/−5365 | S/L3bis/F2+3892 | S/L3bis/R2/−5325 |
| L4b 4952-6023 | S/L4b/F1/+4878 | S/L4b/R1/−6061 | S/L4b/F2/+4932 | S/L4b/R2/−6024 |
| L4 5325-7318 | S/L4/F1/+5272 | S/L4/R1/−7392 | S/L4/F2/+5305 | S/L4/R2/−7323 |
| L5 7296-9156 | S/L5/F1/+7111 | S/L5/R1/−9253 | S/L5/F2/+7275 | S/L5/R2/−9157 |
| L6 9053-11066 | S/L6/F1/+8975 | S/L6/R1/−11151 | S/L6/F2/+9032 | S/L6/R2/−11067 |
| L7 10928-12962 | S/L7/F1/+10883 | S/L7/R1/−13050 | S/L7/F2/+10928 | S/L7/R2/−12963 |
| L8 12835-14834 | S/L8/F1/+12690 | S/L8/R1/−14857 | S/L8/F2/+12815 | S/L8/R2/−14835 |
| L9 14765-16624 | S/L9/F1/+14688 | S/L9/R1/−16678 | S/L9/F2/+14745 | S/L9/R2/−16625 |
| L10 16534-18570 | S/L10/F1/+16451 | S/L10/R1/−18594 | S/L10/F2/+16514 | S/L10/R2/−18571 |
| L11 18521-20582 | S/L11/F1/+18441 | S/L11/R1/−20612 | S/L11/F2/+18500 | S/L11/R2/−20583 |
| L12 20338-22205. | S/L12/F1/+20279 | S/L12/R1/−22229 | S/L12/F2/+20319 | S/L12/R2/−22206 |

All the fragments were amplified under the following conditions, except fragment L0 which was amplified as described above for ORF-M:

RT-PCR: 30 min at 42° C., 15 min at 55° C., 2 min at 94° C., and then the cDNA obtained is amplified under the following conditions: 40 cycles comprising: a step of denaturation at 94° C. for 15 sec, a step of annealing at 58° C. for 30 sec and then a step of extension at 68° C. for 1 min 30 sec, with 5 sec additional extension at each cycle, and then a final step of extension at 68° C. for 7 min.

Nested PCR: An initial step of denaturation at 94° C. for 2 min is followed by 35 cycles comprising: a step of denaturation at 94° C. for 15 sec, a step of annealing at 60° C. for 30 sec and then a step of extension at 72° C. for 1 min 30 sec, with 5 sec of additional extension at each cycle, and then a final step of extension at 72° C. for 7 min.

The amplification products were sequenced with the aid of the primers defined in table III below:

TABLE III

Primers used for the sequencing of the 5' region (ORF1a and ORF1b)

| Names | Sequences (SEQ ID NO: 76 to 139) |
|---|---|
| S/L3/+/4932 | 5'-CCACACACAGCTTGTGGATA-3' |
| S/L4/+/6401 | 5'-CCGAAGTTGTAGGCAATGTC-3' |

TABLE III-continued

Primers used for the sequencing of the 5' region (ORF1a and ORF1b)

| Names | Sequences (SEQ ID NO: 76 to 139) |
|---|---|
| S/L4/+/6964 | 5'-TTTGGTGCTCCTTCTTATTG-3' |
| S/L4/−/6817 | 5'-CCGGCATCCAAACATAATTT-3' |
| S/L5/−/7633 | 5'-TGGTCAGTAGGGTTGATTGG-3' |
| S/L5/−/8127 | 5'-CATCCTTTGTGTCAACATCG-3' |
| S/L5/−/8633 | 5'-GTCACGAGTGACACCATCCT-3' |

TABLE III-continued

Primers used for the sequencing of the 5' region (ORF1a and ORF1b)

| Names | Sequences (SEQ ID NO: 76 to 139) |
|---|---|
| S/L5/+/7839 | 5'-ATGCGACGAGTCTGCTTCTA-3' |
| S/L5/+/8785 | 5'-TTCATAGTGCCTGGCTTACC-3' |
| S/L5/+/8255 | 5'-ATCTTGGCGCATGTATTGAC-3' |
| S/L6/−/9422 | 5'-TGCATTAGCAGCAACAACAT-3' |
| S/L6/−/9966 | 5'-TCTGCAGAACAGCAGAAGTG-3' |

TABLE III-continued Primers used for the sequencing of the 5' region (ORF1a and ORF1b)

| Names | Sequences (SEQ ID NO: 76 to 139) |
|---|---|
| S/L6/−/10542 | 5'-CCTGTGCAGTTTGTCTGTCA-3' |
| S/L6/+/10677 | 5'-CCTTGTGGCAATGAAGTACA-3' |
| S/L6/+/10106 | 5'-ATGTCATTTGCACAGCAGAA-3' |
| S/L6/+/9571 | 5'-CTTCAATGGTTTGCCATGTT-3' |
| S/L7/−/11271 | 5'-TGCGAGCTGTCATGAGAATA-3' |
| S/L7/−/11801 | 5'-AACCGAGAGCAGTACCACAG-3' |
| S/L7/−/12383 | 5'-TTTGGCTGCTGTAGTCAATG-3' |
| S/L7/+/12640 | 5'-CTACGACAGATGTCCTGTGC-3' |
| S/L7/+/12088 | 5'-GAGCAGGCTGTAGCTAATGG-3' |
| S/L7/+/11551 | 5'-TTAGGCTATTGTTGCTGCTG-3' |
| S/L8/−/13160 | 5'-CAGACAACATGAAGCACCAC-3' |
| S/L8/−/13704 | 5'-CGCTGACGTGATATATGTGG-3' |
| S/L8/−/14284 | 5'-TGCACAATGAAGGATACACC-3' |
| S/L8/+/14453 | 5'-ACATAGCTCGCGTCTCAGTT-3' |
| S/L8/+/13968 | 5'-GGCATTGTAGGCGTACTGAC-3' |
| S/L8/+/13401 | 5'-GTTTGCGGTGTAAGTGCAG-3' |
| S/L9/−/15098 | 5'-TAGTGGCGGCTATTGACTTC-3' |
| S/L9/−/15677 | 5'-CTAAACCTTGAGCCGCATAG-3' |
| S/L9/−/16247 | 5'-CATGGTCATAGCAGCACTTG-3' |
| S/L9/+/16323 | 5'-CCAGGTTGTGATGTCACTGAT-3' |
| S/L9/+/15858 | 5'-CCTTACCCAGATCCATCAAG-3' |
| S/L9/+/15288 | 5'-CGCAAACATAACACTTGCTG-3' |
| S/L10/−/16914 | 5'-AGTGTTGGGTACAAGCCAGT-3' |
| S/L10/−/17466 | 5'-GTTCCAAGGAACATGTCTGG-3' |
| S/L10/−/18022 | 5'-AGGTGCCTGTGTAGGATGAA-3' |
| S/L10/+/18245 | 5'-GGGCTGTCATGCAACTAGAG-3' |
| S/L10/+/17663 | 5'-TCTTACACGCAATCCTGCTT-3' |
| S/L10/+/17061 | 5'-TACCCATCTGCTCGCATAGT-3' |
| S/L11/−/18877 | 5'-GCAAGCAGAATTAACCCTCA-3' |
| S/L11/−/19396 | 5'-AGCACCACCTAAATTGCATC-3' |
| S/L11/−/20002 | 5'-TGGTCCCTTTGAAGGTGTTA-3' |
| S/L11/+/20245 | 5'-TCGAACACATCGTTTATGGA-3' |
| S/L11/+/19611 | 5'-GAAGCACCTGTTTCCATCAT-3' |
| S/L11/+/19021 | 5'-ACGATGCTCAGCCATGTAGT-3' |
| SARS/L1/F3/+800 | 5'-GAGGTGCAGTCACTCGCTAT-3' |
| SARS/L1/F4/+1391 | 5'-CAGAGATTGGACCTGAGCAT-3' |
| SARS/L1/F5/+1925 | 5'-CAGCAAACCACTCAATTCCT-3' |
| SARS/L1/R3/−1674 | 5'-AAATGATGGCAACCTCTTCA-3' |
| SARS/L1/R4/−1107 | 5'-CACGTGGTTGAATGACTTTG-3' |
| SARS/L1/R5/−520 | 5'-ATTTCTGCAACCAGCTCAAC-3' |
| SARS/L2/F3/+2664 | 5'-CGCATTGTCTCCTGGTTTAC-3' |
| SARS/L2/F4/+3232 | 5'-GAGATTGAGCCAGAACCAGA-3' |
| SARS/L2/F5/+3746 | 5'-ATGAGCAGGTTGTCATGGAT-3' |
| SARS/L2/R3/−3579 | 5'-CTGCCTTAAGAAGCTGGATG-3' |
| SARS/L2/R4/−2991 | 5'-TTTCTTCACCAGCATCATCA-3' |
| SARS/L2/R5/−2529 | 5'-CACCGTTCTTGAGAACAACC-3' |
| SARS/L3/F3/+4708 | 5'-TCTTTGGCTGGCTCTTACAG-3' |
| SARS/L3/F4/+5305 | 5'-GCTGGTGATGCTGCTAACTT-3' |
| SARS/L3/F5/+5822 | 5'-CCATCAAGCCTGTGTCGTAT-3' |
| SARS/L3/R3/−5610 | 5'-CAGGTGGTGCAGACATCATA-3' |
| SARS/L3/R4/−4988 | 5'-AACATCAGCACCATCCAAGT-3' |
| SARS/L3/R5/−4437 | 5'-ATCGGACACCATAGTCAACG-3' |

The sequences of the fragments L0 to L12 of the SARS-CoV strain derived from the sample recorded under the No. 031589 correspond respectively to the sequences SEQ ID NO: 41 to SEQ ID NO: 54 in the sequence listing appended as an annex. Among these sequences, only that corresponding to the fragments L5 contains a nucleotide difference in relation to the corresponding sequence of the isolate AY278741-Urbani. This t/c mutation at position 7919 results in a modification of the amino acid sequence of the corresponding protein, encoded by ORF1a: at position 2552, a valine (gtt codon; AY278741) is changed to alanine (gct codon) in the SARS-CoV strain 031589. By contrast, no mutation was identified in relation to the corresponding sequence of the isolate AY274119.3-Urbani. The other fragments do not exhibit differences in relation to the corresponding sequences of the isolates Tor2 and Urbani.

EXAMPLE 2

Production and Purification of the Recombinant N and S Proteins of the SARS-CoV Strain Derived from the Sample Recorded Under the Number 031589

The entire N protein and two polypeptide fragments of the S protein of the SARS-CoV strain derived from the sample recorded under the number 031589 were produced in E. coli, in the form of fusion proteins comprising an N- or C-terminal polyhistidine tag. In the two S polypeptides, the N- and C-terminal hydrophobic sequences of the S protein (signal peptide: positions 1 to 13 and transmembrane helix: positions 1196 to 1218) were deleted whereas the β helix (positions 565 to 687) and the two motifs of the coiled-coil type (positions 895 to 980 and 1155 to 1186) of the S protein were preserved. These two polypeptides consist of: a long fragment ($S_L$) corresponding to positions 14 to 1193 of the amino acid sequence of the S protein and a short fragment ($S_C$) corresponding to positions 475 to 1193 of the amino acid sequence of the S protein.

1) Cloning of the cDNAs N, $S_L$ and $S_C$ into the Expression Vectors pIVEX2.3 and pIVEX2.4

The cDNAs corresponding to the N protein and to the $S_L$ and $S_C$ fragments were amplified by PCR under standard conditions, with the aid of the DNA polymerase Platinium Pfx® (INVITROGEN). The plasmids SRAS-N and SRAS-S were used as template and the following oligonucleotides as primers:

```
5'-CCCATATGTCTGATAATGGACCCCAATCAAA    (N sense,
C-3'                                   SEQ ID NO: 55)

5'-CCCCCGGGTGCCTGAGTTGAATCAGCAGAAG    (N antisense,
C-3'                                   SEQ ID NO: 56)

5'-CCCATATGAGTGACCTTGACCGGTGCACCA     (S_C sense,
C-3'                                   SEQ ID NO: 57)

5'-CCCATATGAAACCTTGCACCCCACCTGCT      (S_L sense,
C-3'                                   SEQ ID NO: 58)

5'-CCCCCGGGTTTAATATATTGCTCATATTTTCC   (S_C and S_L
C-3'.                                  anitsense,
                                       SEQ ID NO: 29)
```

The sense primers introduce an NdeI site (underlined) while the antisense primers introduce an XmaI or SmaI site (underlined). The 3 amplification products were column purified (QIAquick PCR Purification kit, QIAGEN) and cloned into an appropriate vector. The plasmid DNA purified from the 3 constructs (QIAFilter Midi Plasmid kit, QIAGEN) was verified by sequencing and digested with the enzymes NdeI and XmaI. The 3 fragments corresponding to the cDNAs N, $S_L$ and $S_C$ were purified on agarose gel and then inserted into the plasmids pIVEX2.3MCS (C-terminal polyhistidine tag) and pIVEX2.4d (N-terminal polyhistidine tag) digested beforehand with the same enzymes. After verification of the constructs, the 6 expression vectors thus obtained (pIV2.3N, pIV2.3$S_C$, pIV2.3$S_L$, pIV2.4N, pIV2.4$S_C$ also called pIV2.4$S_1$, pIV2.4$S_L$) were then used, on the one hand to test the expression of the proteins in vitro, and on the other hand to transform the bacterial strain BL21(DE3)pDIA17 (NOVAGEN). These constructs encode proteins whose expected molecular mass is the following: pIV2.3N (47174

Da), pIV2.3S$_C$ (82897 Da), pIV2.3S$_L$ (132056 Da), pIV2.4N (48996 Da), pIV2.4S$_1$ (81076 Da) and pIV2.4S$_L$ (133877 Da). Bacteria transformed with pIV2.3N were deposited at the CNCM on Oct. 23, 2003, under the number I-3117, and bacteria transformed with pIV2.4S$_1$ were deposited at the CNCM on Oct. 23, 2003, under the number I-3118.

2) Analysis of the Expression of the Recombinant Proteins In Vitro and In Vivo

Figure 1:
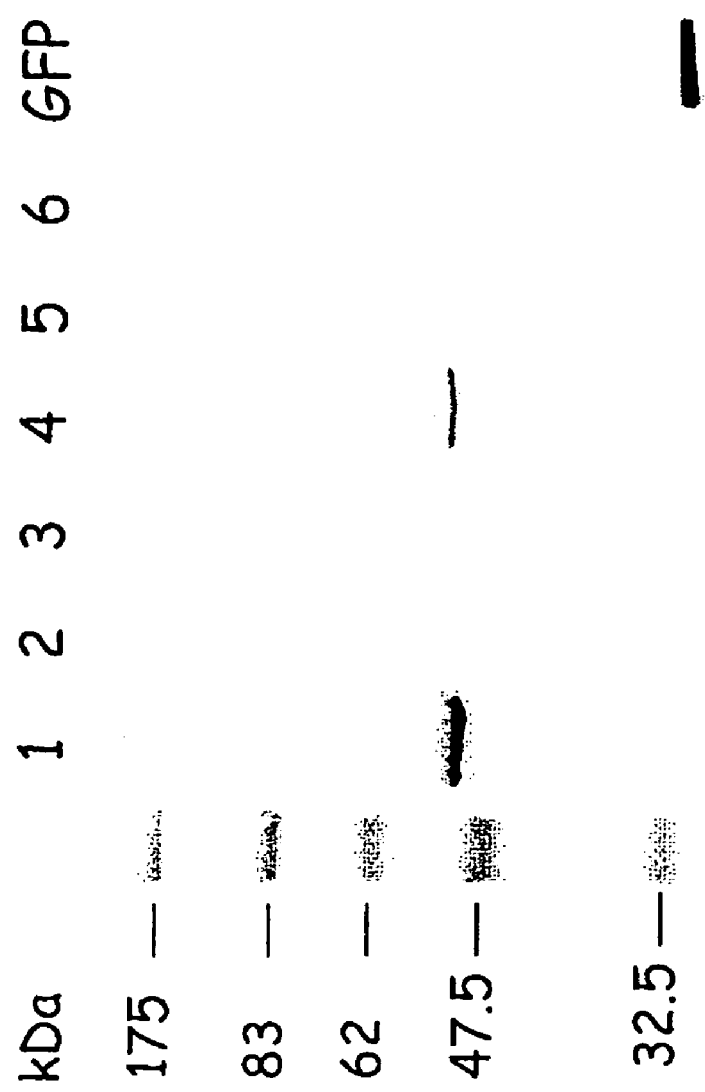
Figure 2:
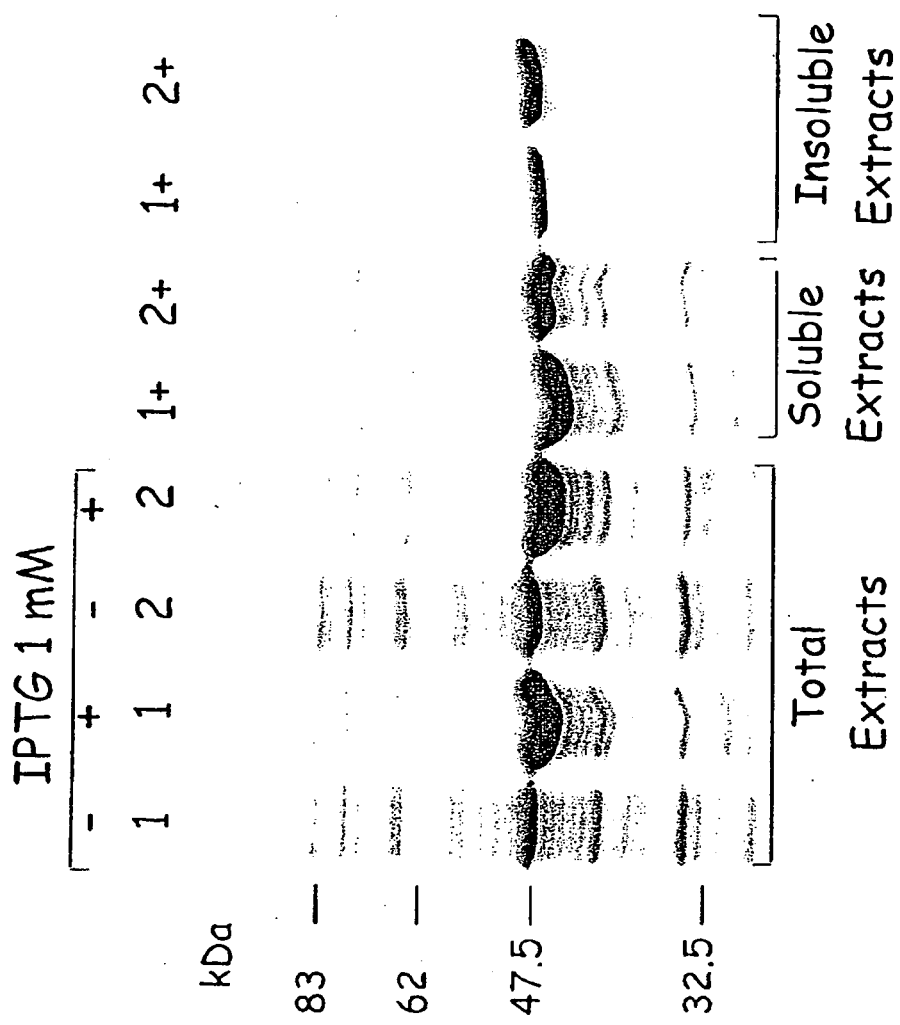
Figure 3:
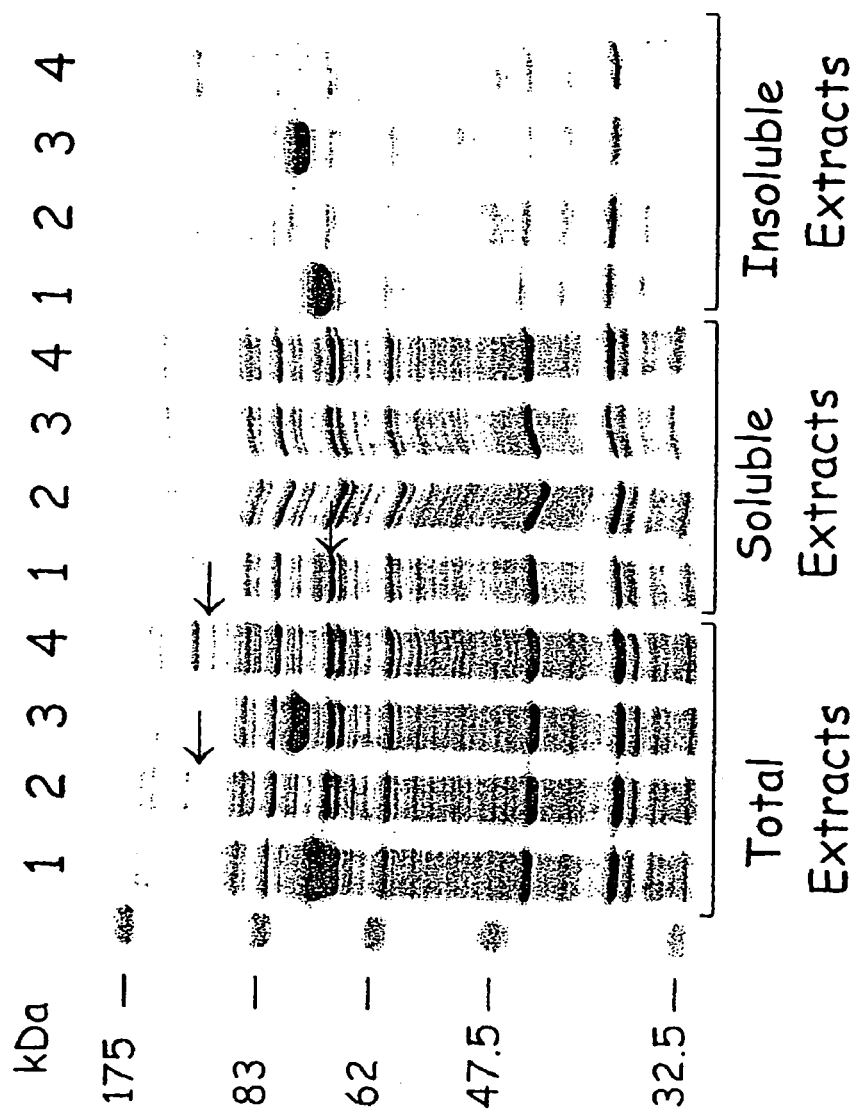

The expression of recombinant proteins from the 6 recombinant vectors was tested, in a first instance, in a system in vitro (RTS100, Roche). The proteins produced in vitro, after incubation of the recombinant vectors pIVEX for 4 h at 30° C., in the RTS100 system, were analyzed by Western blotting with the aid of an anti-(his)$_6$ antibody coupled to peroxidase. The result of expression in vitro (FIG. 1) shows that only the N protein is expressed in large quantities, regardless of the position, N- or C-terminal, of the polyhistidine tag. In a second step, the expression of the N and S proteins was tested in vivo at 30° C. in LB medium in the presence or in the absence of inducer (1 mM IPTG). The N protein is very well produced in this bacterial system (FIG. 2) and is found mainly in a soluble fraction after lysis of the bacteria. By contrast, the long version of S (S$_L$) is very weakly produced and is completely insoluble (FIG. 3). The short version (S$_C$) also exhibits a very weak solubility, but an expression level that is much higher than that of the long version. Moreover, the construct S$_C$ fused with a polyhistidine tag at the C-terminal position has a smaller size than that expected. An immunodetection experiment with an anti-polyhistidine antibody has shown that this construct was incomplete. In conclusion, the two constructs, pIV2.3N and pIV2.4S$_1$, which express respectively the entire N protein fused with the C-terminal polyhistidine tag and the short S protein fused with the N-terminal polyhistidine tag, were selected in order to produce the two proteins in a large quantity so as to purify them. The plasmids pIV2.3N and pIV2.4S$_1$ were deposited respectively under the No. I-3117 and I-3118 at the CNCM, 25 rue du Docteur Roux, 75724 PARIS 15, on Oct. 23, 2003.

3) Analysis of the Antigenic Activity of the Recombinant Proteins

Figure 4:
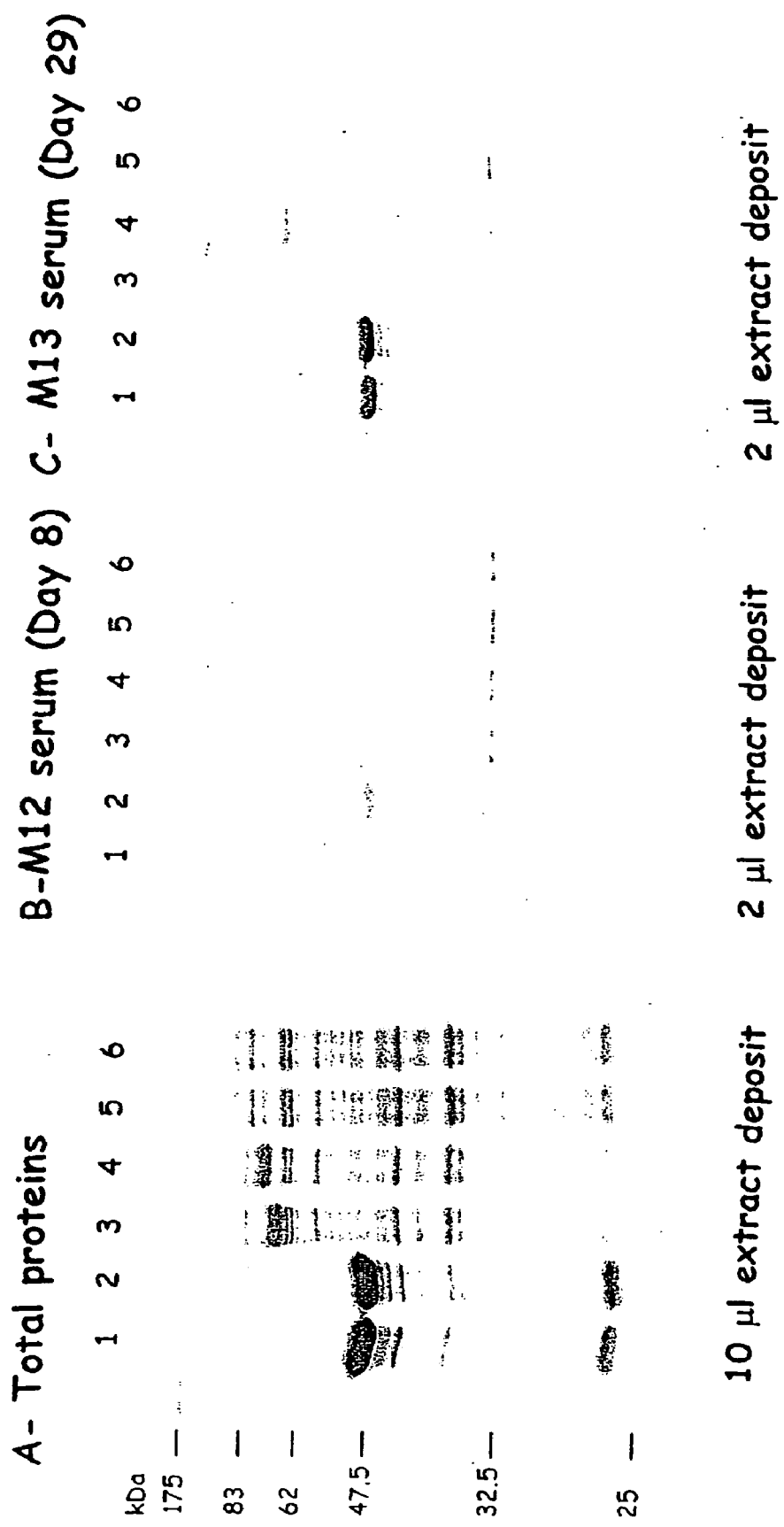

The antigenic activity of the N, S$_L$ and S$_C$ proteins was tested by Western blotting with the aid of two serum samples, obtained from the same patient infected with SARS-CoV, collected 8 days (M12) and 29 days (M13) after the onset of the SARS symptoms. The experimental protocol is as described in example 3. The results illustrated by FIG. 4 show (i) the seroconversion of the patient, and (ii) that the N protein possesses a higher antigenic reactivity than the short S protein.

4) Purification of the N Protein from pIV2.3N

Figure 5:
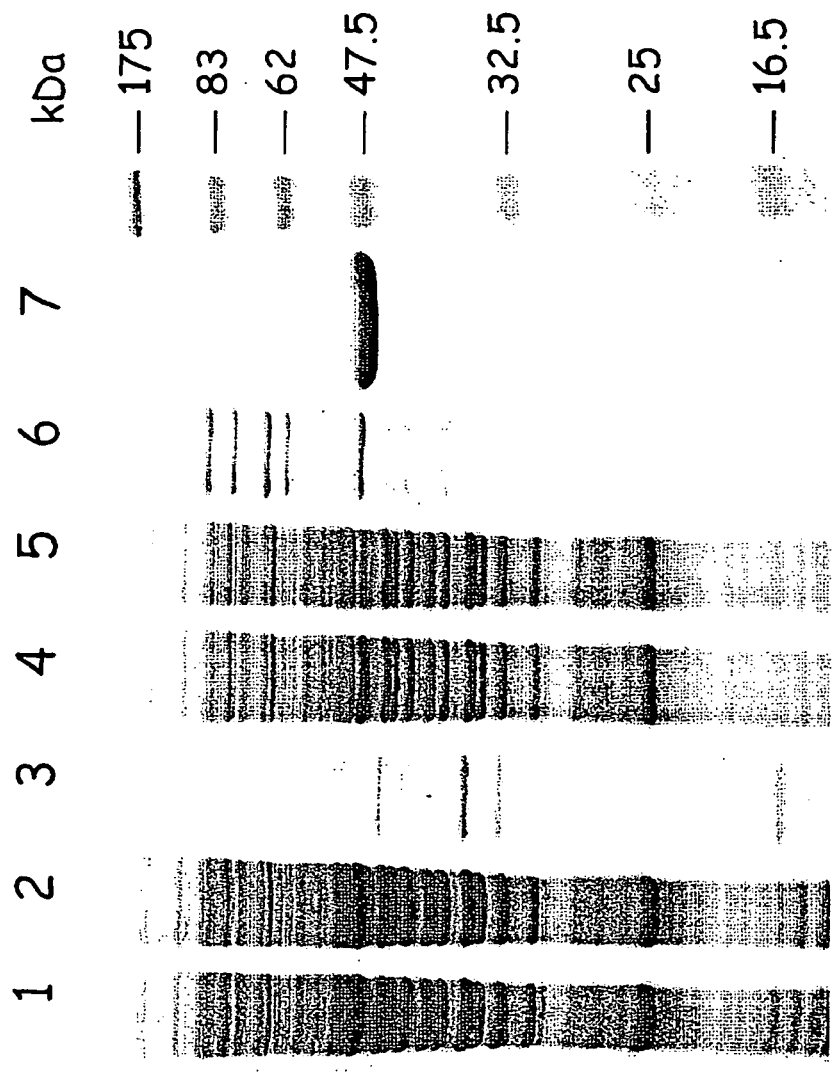

Several experiments for purifying the N protein, produced from the vector pIV2.3N, were carried out according to the following protocol. The bacteria BL21(DE3)pDIA17, transformed with the expression vector pIV2.3N, were cultured at 30° C. in 1 liter of culture medium containing 0.1 mg/ml of ampicillin, and induced with 1 mM IPTG when the cell density equivalent to A$_{600}$=0.8 is reached (about 3 hours). After 2 hours of culture in the presence of inducer, the cells were recovered by centrifugation (10 min at 5000 rpm), resuspended in the lysis buffer (50 mM NaH$_2$PO$_4$, 0.3 M NaCl, 20 mM imidazole, pH 8, containing the mixture of protease inhibitors Complete®, Roche), and lysed with the French press (12 000 psi). After centrifugation of the bacterial lysate (15 min at 12 000 rpm), the supernatant (50 ml) was deposited at a flow rate of 1 ml/min on a metal chelation column (15 ml) (Ni-NTA superflow, Qiagen), equilibrated with the lysis buffer. After washing the column with 200 ml of lysis buffer, the N protein was eluted with an imidazole gradient (20→250 mM) in 10 column volumes. The fractions containing the N protein were assembled and analyzed by polyacrylamide gel electrophoresis under denaturing conditions followed by staining with Coomassie blue. The results illustrated by FIG. 5 show that the protocol used makes it possible to purify the N protein with a very satisfactory homogeneity (95%) and a mean yield of 15 mg of protein per liter of culture.

5) Purification of the S$_C$ Protein from pIV2.4S$_C$ (pIV2.4S$_1$)

Figure 6:
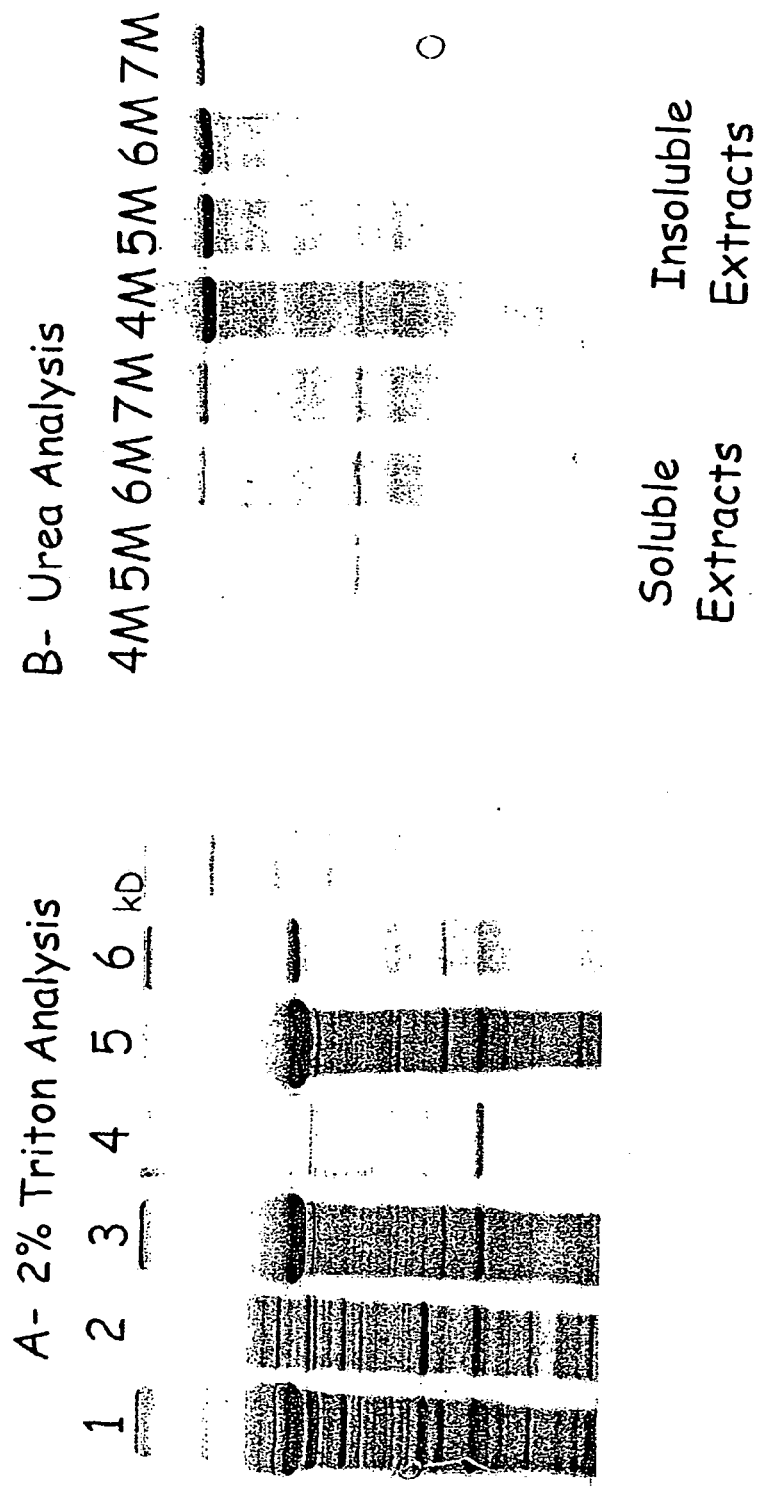

The protocol followed for purifying the short S protein is very different from that described above because the protein is highly aggregated in the bacterial system (inclusion bodies). The bacteria BL21(DE3)pDIA17, transformed with the expression vector pIV2.4S$_1$, were cultured at 30° C. in 1 liter of culture medium containing 0.1 mg/ml of ampicillin, and induced with 1 mM IPTG when the cell density equivalent to A$_{600}$=0.8 is reached (about 3 hours). After 2 hours of culture in the presence of inducer, the cells were recovered by centrifugation (10 min at 5000 rpm), resuspended in the lysis buffer (0.1 M Tris-HCl, 1 mM EDTA, pH 7.5), and lysed with the French press (1200 psi). After centrifugation of the bacterial lysate (15 min at 12 000 rpm), the pellet was resuspended in 25 ml of lysis buffer containing 2% Triton X100 and 10 mM β-mercaptoethanol, and then centrifuged for 20 min at 12 000 rpm. The pellet was resuspended in 10 mM Tris-HCl buffer containing 7 M urea, and gently stirred for 30 min at room temperature. This final washing of the inclusion bodies with 7 M urea is necessary in order to remove most of the *E. coli* membrane proteins which co-sediment with the aggregated S$_C$ protein. After a final centrifugation for 20 min at 12 000 rpm, the final pellet is resuspended in the 10 mM Tris-HCl buffer. The electrophoretic analysis of this preparation (FIG. 6) shows that the short S protein may be purified with a satisfactory homogeneity (about 90%) from the inclusion bodies (insoluble extract).

EXAMPLE 3

Immunodominance of the N Protein

The reactivity of the antibodies present in the serum of patients suffering from atypical pneumopathy caused by the SARS-associated coronavirus (SARS-CoV), toward the various proteins of this virus, was analyzed by Western blotting under the conditions described below.

1) Materials a) Lysate of Cells Infected with SARS-CoV

Vero E6 cells (2×10$^6$) were infected with SARS-CoV (isolate recorded under the number FFM/MA104) at a multiplicity of infection (M.O.I.) of 10$^{-1}$ or 10$^{-2}$ and then incubated in DMEM medium containing 2% FCS, at 35° C. in an atmosphere containing 5% Co$_2$. 48 hours later, the cellular lawn was washed with PBS and then lysed with 500 μl of loading buffer prepared according to Laemmli and containing β-mercaptoethanol. The samples were then boiled for 10 minutes and then sonicated for 3 times 20 seconds.

b) Antibodies b$_1$) Serum from a Patient Suffering from Atypical Pneumopathy

The serum designated by a reference at the National Reference Center for Influenza Viruses (Northern region) under the No. 20033168 is that from a French patient suffering from atypical pneumopathy caused by SARS-CoV collected on day 38 after the onset of the symptoms; the diagnosis of SARS-CoV infection was performed by nested RT-PCR and quantitative PCR.

b$_2$) Monospecific Rabbit Polyclonal Sera Directed Against the N Protein or the S Protein The sera are those produced from the recombinant N and S$_C$ proteins (example 2), according to the immunization protocol described in example 4; they are the rabbit P13097 serum (anti-N serum) and the rabbit P11135 serum (anti-S serum).

2) Method

20 µl of lysate of cells infected with SARS-CoV at M.O.I. values of $10^{-1}$ and $10^{-2}$ and, as a control, 20 µl of a lysate of noninfected cells (mock) were separated on 10% SDS polyacrylamide gel and then transferred onto a nitrocellulose membrane. After blocking in a solution of PBS/5% milk/ 0.1% Tween and washing in PBS/0.1% Tween, this membrane was hybridized overnight at 4° C. with: (i) the immune serum No. 20033168 diluted 1/300, 1/1000 and 1/3000 in the buffer PBS/1% BSA/0.1% Tween, (ii) the rabbit P13097 serum (anti-N serum) diluted 1/50 000 in the same buffer and (iii) the rabbit P11135 serum (anti-S serum) diluted 1/10 000 in the same buffer. After washing in PBS/Tween, a secondary hybridization was performed with the aid of either sheep polyclonal antibodies directed against the heavy and light chains of human G immunoglobulins and coupled with peroxidase (NA933V, Amersham), or of donkey polyclonal antibodies directed against the heavy and light chains of the rabbit G immunoglobulins and coupled with peroxidase (NA934V, Amersham). The bound antibodies were visualized with the aid of the ECL+ kit (Amersham) and of Hyperfilm MP autoradiography films (Amersham). A molecular mass ladder (kDa) is presented in the figure.

3) Results

Figure 7:
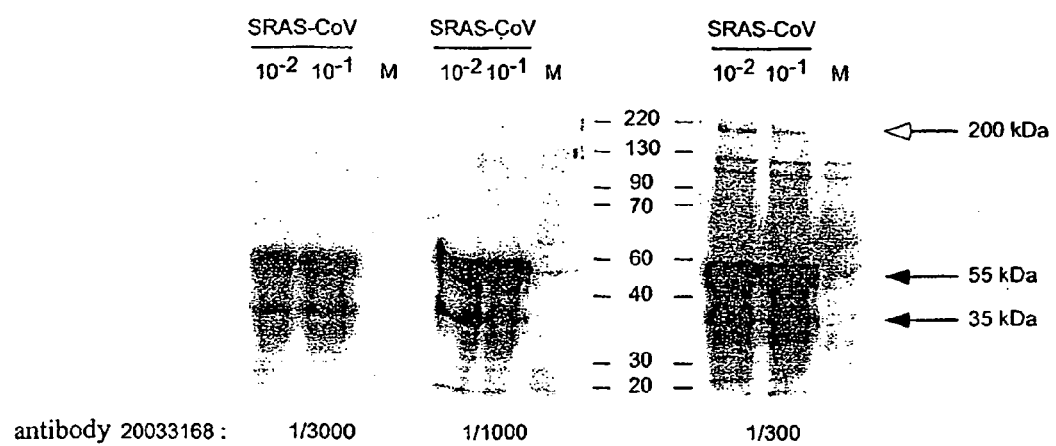

FIG. 7 shows that three polypeptides of apparent molecular mass 35, 55 and 200 kDa are specifically detected in the extracts of cells infected with SARS-CoV.

In order to identify these polypeptides, two other immunoblots (FIG. 8) were prepared on the same samples and under the same conditions with rabbit polyclonal antibodies specific for the nucleoprotein N (rabbit P13097, FIG. 8A) and for the spicule protein S (rabbit P11135, FIG. 8B). This experiment shows that the 200 kDa polypeptide corresponds to the SARS-CoV spicule glycoprotein S, that the 55 kDa polypeptide corresponds to the nucleoprotein N while the 35 kDa polypeptide probably represents a truncated or degraded form of N.

The data presented in FIG. 7 therefore show that the serum 20033168 strongly reacts with N and a lot more weakly with the SARS-CoV S since the 35 and 55 kDa polypeptides are visualized in the form of intense bands for 1/300, 1/1000 and 1/3000 dilutions of the immunoserum whereas the 200 kDa polypeptide is only weakly visualized for a dilution of 1/300. It is also possible to note that no other SARS-CoV polypeptide is detected for dilutions greater than 1/300 of the serum 20033168.

This experiment indicates that the antibody response specific for the SARS-CoV N dominates the antibody responses specific for the other SARS-CoV polypeptides and in particular the antibody response directed against the S glycoprotein.

It indicates an immuno-dominance of the nucleoprotein N during human infections with SARS-CoV.

EXAMPLE 4

Preparation of Monospecific Polyclonal Antibodies Directed Against the SRAS-associated Coronavirus (SARS-CoV) N and S Proteins 1) Materials and Method Three rabbits (P13097, P13081, P13031) were immunized with the purified recombinant polypeptide corresponding to the entire nucleoprotein (N), prepared according to the protocol described in example 2. After a first injection of 0.35 mg per rabbit of protein emulsified in complete Freund's adjuvant (intradermal route), the animals received 3 booster injections at 3 and then 4 weeks' interval, of 0.35 mg of recombinant protein emulsified in incomplete Freund's adjuvant.

Three rabbits (P11135, P13042, P14001) were immunized with the recombinant polypeptide corresponding to the short fragment of the S protein (S$_C$) produced as described in example 2. As this polypeptide is found mainly in the form of inclusion bodies in the bacterial cytoplasm, the animals received 4 intradermal injections at 3-4 weeks' interval of a preparation of inclusion bodies corresponding to 0.5 mg of recombinant protein emulsified in incomplete Freund's adjuvant. The first 3 injections were made with a preparation of inclusion bodies prepared according to the protocol described in example 2, while the fourth injection was made with a preparation of inclusion bodies which were prepared according to the protocol described in example 2 and then purified on sucrose gradient and washed in 2% Triton X100.

For each rabbit, a preimmune (p.i.) serum was prepared before the first immunization and an immune serum (I.S.) 5 weeks after the fourth immunization.

In a first instance, the reactivity of the sera was analyzed by ELISA test on preparations of recombinant proteins similar to those used for the immunizations; the ELISA tests were carried out according to the protocol and with the reagents as described in example 6.

In a second instance, the reactivity of the sera was analyzed by preparing an immunoblot (Western blot) of a lysate of cells infected with SARS-CoV, according to the protocol as described in example 3.

2) Results

The ELISA tests (FIG. 9) demonstrate that the preparations of recombinant N protein and of inclusion bodies of the short fragment of the S protein (S$_C$) are immunogenic in animals and that the titer of the immune sera is high (more than 1/25 000).

The immunoblot (FIG. 8) shows that the rabbit P13097 immune serum recognizes two polypeptides present in the lysates of cells infected with SARS-CoV: a polypeptide whose apparent molecular mass (50-55 kDa based on experiments) is compatible with that of the nucleo-protein N (422 residues, predicted molecular mass of 46 kDa) and a polypeptide of 35 kDa, which probably represents a truncated or degraded form of N.

This experiment also shows that the rabbit P11135 serum mainly recognizes a polypeptide whose apparent molecular mass (180-220 kDa based on experiments) is compatible with a glycosylated form of S (1255 residues, nonglycosylated polypeptide chain of 139 kDa), as well as lighter polypeptides, which probably represent truncated and/or nonglycosylated forms of S.

In conclusion, all these experiments demonstrate that the recombinant polypeptides expressed in *E. coli* and corresponding to the SARS-CoV N and S proteins make it possible to induce, in animals, polyclonal antibodies capable of recognizing the native forms of these proteins.

EXAMPLE 5

Preparation of Monospecific Polyclonal Antibodies Directed Against the SARS-associated Coronavirus (SARS-CoV) M and E Proteins 1) Analysis of the Structure of the M and E Proteins a) E Protein The structure of the SARS-CoV E protein (76 amino acids) was analyzed in silico, with the aid of various software packages such as signalP v1.1, NetNGlyc 1.0, THMM 1.0 and 2.0 (Krogh et al., 2001, J. Mol. Biol., 305(3):567-580) or alternatively TOPPRED (von Heijne, 1992, J. Mol. Biol. 225, 487-494). The analysis shows that this nonglycosylated polypeptide is a type 1 membrane protein, containing a single transmembrane helix (aa 12-34 according to THMM), and in which the majority of the hydrophilic domain (42 residues) is located at the C-terminal end and probably inside the viral particle (endodomain). It is possible to note an inversion in the topology predicted by versions 1.0 (N-ter is external) and 2.0 (N-ter is internal) of the THMM software, but that other algorithms, in particular TOPPRED and THUMBUP (Zhou et Zhou, 2003, Protein Science 12:1547-1555) confirm an external location of the N-terminal end of E.

b) M Protein

A similar analysis carried out on the SARS-CoV M protein (221 amino acids) shows that this polypeptide does not possess a signal peptide (according to the software signalP v1.1) but three transmembrane domains (residues 15-37, 50-72, 77-99 according to THMM2.0) and a large hydrophilic domain (aa 100-221) located inside the viral particle (endodomain). It is probably glycosylated on the asparagine at position 4 (according to NetNGlyc 1.0).

Thus, in agreement with the experimental data known for the other coronaviruses, it is remarkable that the two M and E proteins exhibit endodomains corresponding to the majority of the polypeptides and of the ectodomains that are very small in size.

The ectodomain of E probably corresponds to residues 1 to 11 or 1 to 12 of the protein: MYSFVSEETGT(L), SEQ ID NO: 70. Indeed, the probability associated with the transmembrane location of residue 12 is intermediate (0.56 according to THMM 2.0).

The ectodomain of M probably corresponds to residues 2 to 14 of the protein: ADNGTITVEELKQ, SEQ ID NO: 69. Indeed, the N-terminal methionine of M is very probably cleaved from the mature polypeptide because the residue at position 2 is an alanine (Varshavsky, 1996, 93:12142-12149).

Moreover, the analysis of the hydrophobicity (Kyte & Doolittle, Hopp & Woods) of the E protein demonstrates that the C-terminal end of the endodomain of E is hydrophilic and therefore probably exposed at the surface of this domain. Thus, a synthetic peptide corresponding to this end is a good immunogenic candidate for inducing, in animals, antibodies directed against the endodomain of E. Consequently, a peptide corresponding to 24 C-terminal residues of E was synthesized.

2) Preparation of Antibodies Directed Against the Ectodomain of the M and E Proteins and the Endodomain of the E Protein The peptides M2-14 (ADNGTITVEELKQ, SEQ ID NO: 69), E1-12 (MYSFVSEETGTL, SEQ ID NO: 70) and E53-76 (KPTVYVYSRV KNLNSSEGVP DLLV, SEQ ID NO: 71) were synthesized by Neosystem. They were coupled with KLH (Keyhole Limpet Hemocyanin) with the aid of MBS (m-maleimido-benzoyl-N-hydroxysuccinimide ester) via a cysteine added during the synthesis either at the N-terminus of the peptide (case for E53-76) or at the C-terminus (case of M2-14 and E1-12).

Two rabbits were immunized with each of the conjugates, according to the following immunization protocol: after a first injection of 0.5 mg of peptide coupled with KLH and emulsified in complete Freund's adjuvant (intradermal route), the animals receive 2 to 4 booster injections at 3 or 4 weeks' interval of 0.25 mg of peptide coupled to KLH and emulsified in incomplete Freund's adjuvant.

For each rabbit, a preimmune (p.i.) serum was prepared before the first immunization and an immune serum (I.S.) is prepared 3 to 5 weeks after the booster injections.

The reactivity of the sera was analyzed by Western blotting with the aid of extracts of cells infected with SARS-CoV (FIG. 43B) or with the aid of extracts of cells infected with a recombinant vaccinia virus expressing the protein E (VV-TG-E, FIG. 43A) or M (VV-TN-M, FIG. 43C) of the SARS-CoV 031589 isolate.

The immune sera of the rabbits 22234 and 22240, immunized with the conjugate KLH-E53-76, recognize a polypeptide of about 9 to 10 kD, which is present in the extracts of cells infected with SARS-CoV but absent from the extracts of noninfected cells (FIG. 43B). The apparent mass of this polypeptide is compatible with the predicted mass of the E protein, which is 8.4 kD. Similarly, the immune serum of the rabbit 20047, immunized with the conjugate KLH-E1-12, recognizes a polypeptide present in the extracts of cells infected with the VV-TG-E virus, whose apparent molar mass is compatible with that of the E protein (FIG. 43A).

The immune serum of the rabbits 20013 and 20080, immunized with the conjugate KLH-M2-14, recognizes a polypeptide present in the extracts of cells infected with the VV-TN-M virus (FIG. 43C), whose apparent molar mass (about 18 kD) is compatible with that of the glycoprotein M, which is 25.1 kD and has a high iso-electric point (9.1 for the naked polypeptide).

These results demonstrate that the peptides E1-12 and E53-76, on the one hand, and the peptide M2-14, on the other hand, make it possible to induce, in animals, polyclonal antibodies capable of recognizing the native forms of the SARS-CoV E and M proteins, respectively.

EXAMPLE 6

Analysis of the ELISA Reactivity of the Recombinant N Protein Toward Sera from Patients Suffering from SARS 1) Materials The antigen used to prepare the solid phases is the purified recombinant nucleoprotein N prepared according to the protocol described in example 2.

The sera to be tested (table IV) were chosen on the basis of the results of analysis of their reactivity by immunofluorescence (IF-SARS titer), toward cells infected with SARS-CoV.

TABLE IV

Sera tested by ELISA

| Reference | Serum No. | Type of serum | Date of the serum*** | IF-SARS titer |
|---|---|---|---|---|
| 3050 | A | Control | na* | nt** |
| 3048 | B | Control | na | nt |
| 033168 | D | Patient 1-SARS | Apr. 27, 2003 (D38) | 320 |
| 033397 | E | Patient-1 SARS | May 11, 2005 (D52) | 320 |
| 032632 | F | Patient-2 SARS | Mar. 21, 2003 (D17) | 2500 |
| 032791 | G | Patient-3 SARS | Apr. 04, 2003 (D3) | <40 |
| 033258 | H | Patient-3 SARS | Apr. 28, 2003 (D27) | 160 |

*na: not applicable.
**nt: not tested.
***the dates indicated correspond to the number of days after the onset of the SARS symptoms.

2) Method

The N protein (100 µl) diluted at various concentrations in 0.1 M carbonate buffer, pH 9.6 (1, 2 or 4 µg/ml) is distributed into the wells of ELISA plates, and then the plates are incubated overnight at laboratory temperature. The plates are washed with PBS-Tween buffer saturated with PBS-skimmed milk-sucrose (5%) buffer. The test sera (100 µl), diluted beforehand (1/50, 1/100, 1/200, 1/400, 1/800, 1/1600 and 1/3200) are added and then the plates are incubated for 1 h at 37° C. After 3 washings, the peroxidase-labeled anti-human IgG conjugate (reference 209-035-098, JACKSON) diluted 1/18 000 is added and then the plates are incubated for 1 h at 37° C. After 4 washings, the chromogen (TMB) and the substrate ($H_2O_2$) are added and the plates are incubated for 30 min at room temperature, protected from light. The reaction is then stopped and then the absorbance at 450 nm is measured with the aid of an automated reader.

3) Results

Figure 10A:
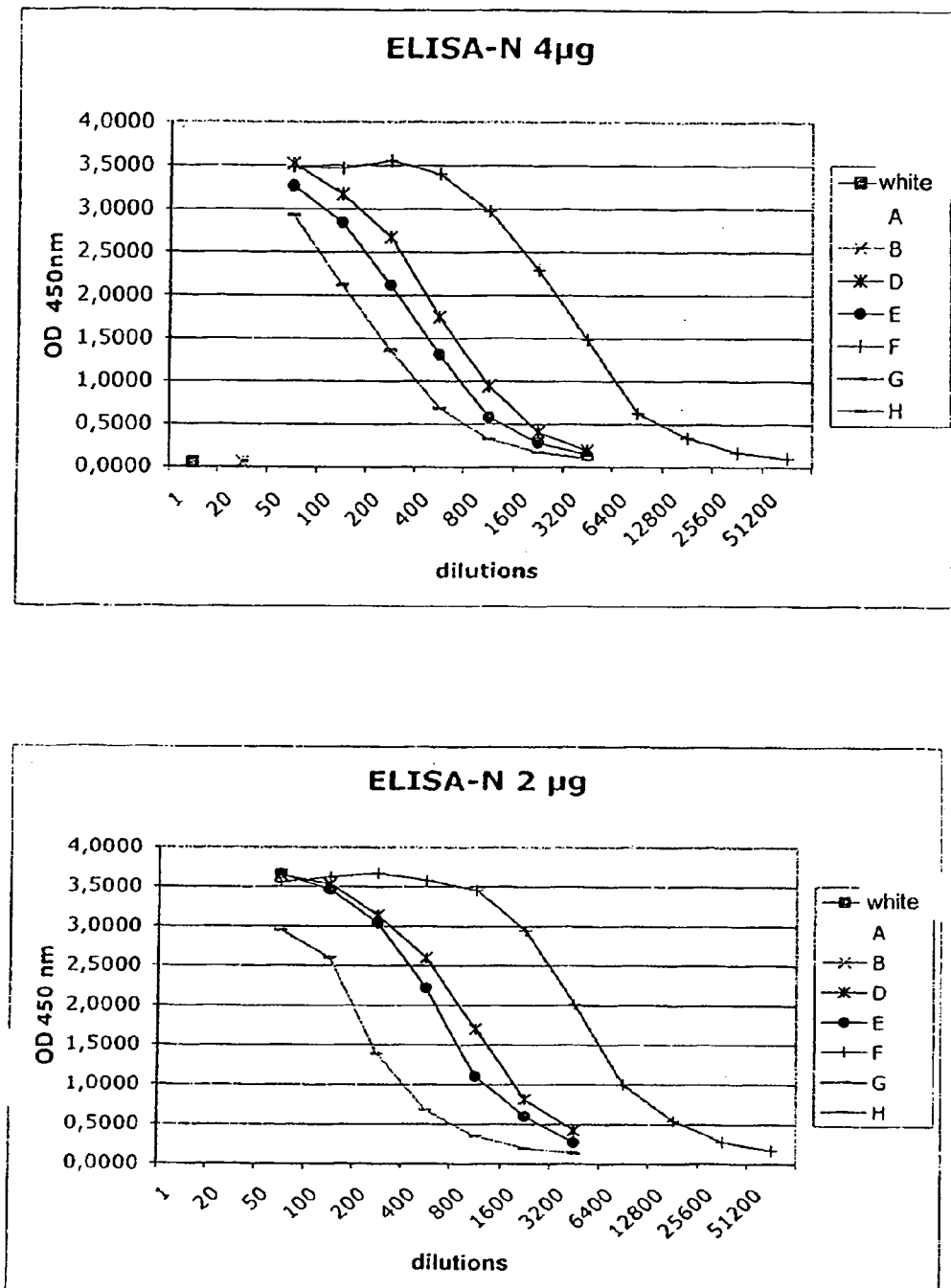
Figure 10B:
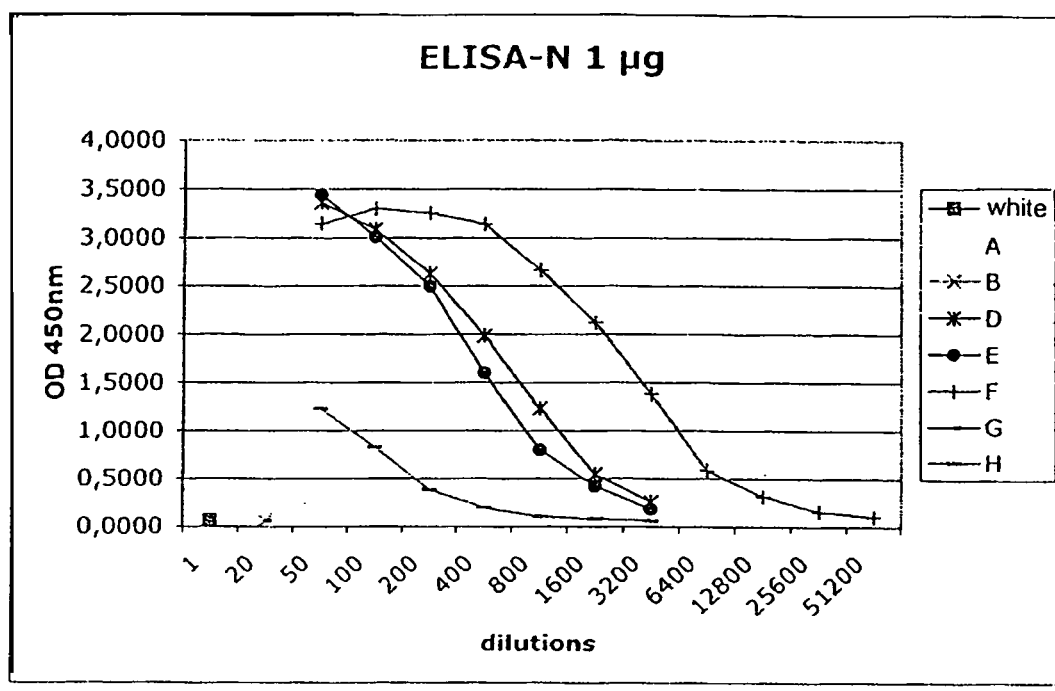
Figure 11:
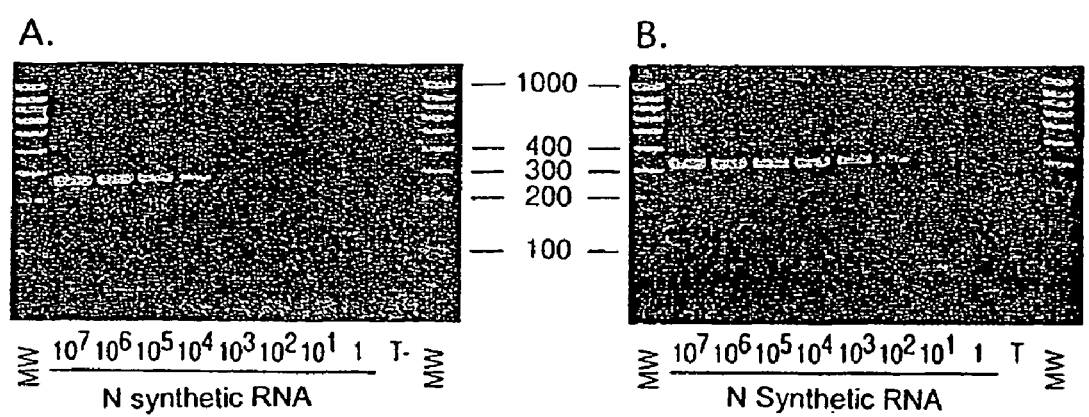

The ELISA tests (FIG. 10) demonstrate that the recombinant N protein preparation is specifically recognized by the antibodies of sera from patients suffering from SARS collected in the late phase of the infection ($\geq 17$ days after the onset of the symptoms) whereas it is not significantly recognized by the antibodies of a patient's serum collected in the early phase of the infection (3 days after the onset of the symptoms) or by control sera from subjects not suffering from SARS.

EXAMPLE 7

ELISA Tests Prepared for a Very Specific and Sensitive Detection of a SARS-associated Coronavirus Infection, from Sera of Patients 1) Indirect ELISA IgG Test a) Reagents Preparation of the Plates The plates are sensitized with a solution of N protein at 2 µg/ml in a 10 mM PBS buffer, pH 7.2, phenol red at 0.25 ml/l. 100 µl of solution are deposited in the wells and left to incubate at room temperature overnight. Saturation is obtained by prewashing in 10 mM PBS/0.1% Tween buffer, followed by washing with a saturation solution PBS, 25% milk/sucrose.

Diluent Sera

Buffer 0.48 g/l TRIS, 10 mM PBS, 3.7 g/l EDTA, 15% v/v milk, pH 6.7

Diluent Conjugate

Citrate buffer (15 g/l), 0.5% Tween, 25% bovine serum, 12% NaCl, 6% v/v skimmed milk pH 6.5

Conjugate

50× anti-human IgG conjugate, marketed by Bio-Rad: Platelia *H. pylori* kit ref 72778

Other Solutions:

Washing solution R2, solutions for visualizing with TMB R8 diluent, R9 chromogen, R10 stopping solution: reagents marketed by Bio-Rad (e.g.: *Platelia pylori* kit, ref 72778)

b) Procedure

Dilute the sera 1/200 in the sample diluent

Distribute 100 µl/well

Incubation 1 h at 37° C.

3 washings in 10× WASHING solution R2 diluted beforehand 10-fold in demineralized water (i.e., 1× washing solution)

Distribute 100 µl of conjugate (50× conjugate to be diluted immediately before use in the diluent conjugate provided)

Incubation 1 h at 37° C.

4 washings in 1× washing solution

Distribute 200 µl/well of visualization solution (to be diluted immediately before use e.g.: 1 ml of R9 in 10 ml of R8)

Incubation for 30 min at room temperature in the dark

Stop the reaction with 100 µl/well of R10

READING at 450/620 nm

The results can be interpreted by taking a THRESHOLD serum giving a response above which the sera tested would be considered as positive. This serum is chosen and diluted so as to give a significantly higher signal than the background noise.

2) Double Epitope ELISA Test a) Reagents

Preparation of the Plates

The plates are sensitized with a solution of N protein at 1 µg/ml in a 10 mM PBS buffer, pH 7.2, phenol red at 0.25 ml/l. 100 µl of solution are deposited in the wells and left to incubate at room temperature overnight. Saturation is obtained by prewashing in 10 mM PBS/0.1% Tween buffer, followed by washing with a saturation solution 10 mM PBS, 25% (V/V) milk.

Diluent Sera and Conjugate

Buffer 50 mM TRIS saline, pH 8, 2% milk

Conjugate

This is the purified recombinant N protein coupled with peroxidase according to the Nakane protocol (Nakane P. K. and Kawaoi A.; (1974): *Peroxydase-labeled antibody, a new method of conjugation. The Journal of Histochemistry and Cytochemistry* Vol. 22, N) 23, pp. 1084-1091), in respective molar ratios 1/2. This ProtN POD conjugate is used at a concentration of 2 µg/ml in serum/conjugate diluent.

Other Solutions:

Washing solution R2, solutions for visualization with TMB R8, diluent, R9 chromogen, R10 stopping solution: reagents marketed by Bio-Rad (e.g. *Platelia pylori* kit, ref 72778).

b) Procedure

1st Step in "Predilution" Plate

Dilute each serum 1/5 in the predilution plate (48 µl of diluent+12 µl of serum).

After having diluted all the sera, distribute 60 µl of conjugate.

Where appropriate, the serum+conjugate mix is left to incubate.

2nd Step in "Reaction" Plate
  Transfer 100 μl of mixture/well into the reaction plate
  Incubation 1 h 37° C.
  5 washings in 10× WASHING solution R2 diluted 10-fold beforehand in demineralized water (→1× washing solution)
  Distribute 200 μl/well of visualization solution (to be diluted immediately before use e.g.: 1 ml of R9 in 10 ml of R8)
  Incubation 30 min at room temperature and protected from light
  Stop the reaction with 100 μl/well of R10
  READING at 450/620 nm
  Likewise as for the indirect ELISA test, the results can be interpreted using a "threshold value" serum. Any serum having a response greater than the threshold value serum will be considered as positive.

2) Results

The sera of patients classified as probable cases of SARS from the French hospital of Hanoi, Vietnam or in relation with the French hospital of Hanoi (JYK) were analyzed using the indirect IgG-N test and the double epitope N test.

Figure 14:
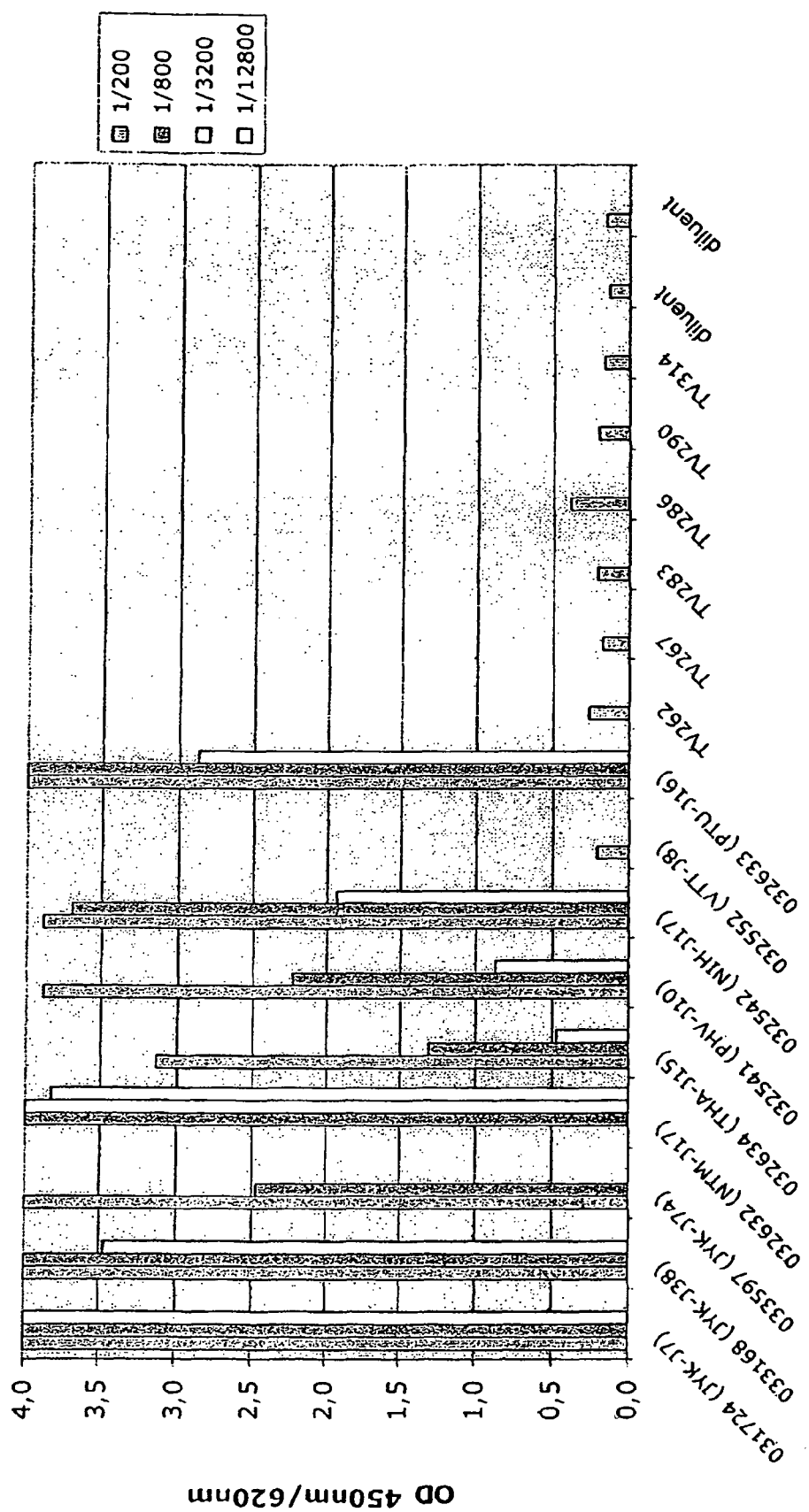
FIG. 14 shows the result of the SARS serology test by indirect N ELISA (1st series of sera tested).
Figure 15:
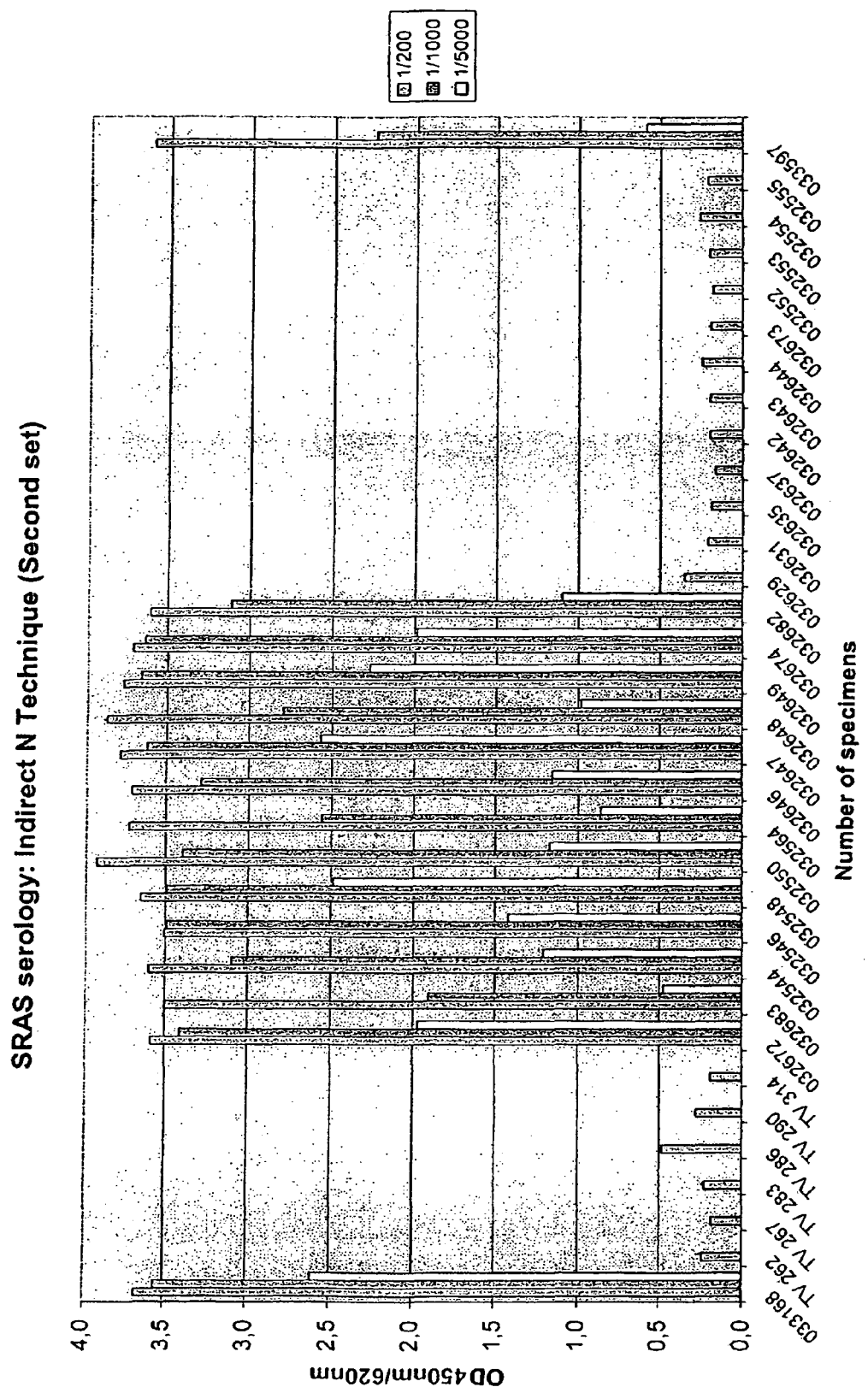
FIG. 15 shows the result of the SARS serology test by indirect N ELISA (2nd series of sera-tested).

The results of the indirect IgG-N test (FIGS. 14 and 15) and double epitope N test (FIGS. 16 and 17) show an excellent correlation between them and with an indirect ELISA test comparing the reactivity of the sera toward a lysate of VeroE6 cells infected or not infected with SARS-CoV (ELISA-SARS-CoV lysate; see table V below). All the sera collected 12 days or more after the onset of the symptoms were found to be positive, including in patients for whom it had not been possible to document the SARS-CoV virus infection by analyzing respiratory samples by RT-PCR, probably because of a sample being collected too late during the infection (≧D12). In the case of the patient TTH for whom a nasal sample collected on D7 was found to be negative by RT-PCR, the quality of the sample may be in question.

Some sera were found to be negative whereas the presence of SARS-CoV was detected by RT-PCR. They are in all cases early sera collected less than 10 days after the onset of the symptoms (e.g.: serum # 032637). In the case of a patient PTTH (serum # 032673), only a suspicion of SARS was raised at the, time the samples were collected.

In conclusion, the indirect IsG-N and N-double epitope serological tests make it possible to document the SARS-CoV infection in all the patients for the sera collected 12 days or more after the infection.

TABLE V

Results of the ELISA tests

| Sample Num | Patient | Day | PCR-SARS (1) | ELISA SARS-CoV lysate (2) | IgG-N (2nd series) | 2Xepitope (2nd series) |
|---|---|---|---|---|---|---|
| 033168 | JYK | 38 | POS | +++ | >5000 | NT |
| 033597 | JYK | 74 | POS | NT | ≈5000 | NT |
| 032552 | VTT | 8 | NEG-D3&D8&D12 | NEG | <200 | <5 |
| 032544 | CTP | 16 | NEG D16&D20 | ++ | >5000 | >>20 |
| 032546 | CJF | 15 | NEG D15&D19 | ++ | >5000 | >>20 |
| 032548 | PTL | 17 | NEG D17&D21 | ++ | >5000 | >>20 |
| 032550 | NTH | 17 | NEG-D17&D21 | ++ | >5000 | >>20 |
| 032553 | VTT | 8 | NEG-D3&D8&D12 | NEG | <200 | <5 |
| 032554 | NTBV | 4 | POS | NEG | <200 | <5 |
| 032555 | NTBV | 4 | POS | NEG | <200 | |
| 032564 | NTP | 15 | POS | ++ | >5000 | >>20 |
| 032629 | NVH | 4 | POS | NEG | <200 | <5 |
| 032631 | BTTX | 9 | POS | NEG | <200 | <5 |
| 032635 | NHH | 4 | POS | NEG | <200 | <5 |
| 032637 | NHB | 10 | POS | NEG | <200 | <5 |
| 032642 | BTTX | 9 | POS | NEG | <200 | <5 |
| 032643 | LTDH | 1 | POS | NEG | <200 | <5 |
| 032644 | NTBV | 4 | POS | NEG | <200 | <5 |
| 032646 | TTH | 12 | NEG D7&D12&D16 | ++ | >5000 | >>20 |
| 032647 | DTH | 17 | NEG D17&D21 | ++ | >5000 | >>20 |
| 032648 | NNT | 15 | NEG D15&D19 | ++ | >5000 | >>20 |
| 032649 | PTH | 17 | NEG D17&D21 | ++ | >5000 | >>20 |
| 032672 | LVV | 16 | NEG D16&D20 | + | >5000 | >>20 |
| 032673 | PTTH | NA | NEG | NEG | <200 | <5 |
| 032674 | PNB | 17 | NEG D17&D21 | ++ | >5000 | >>20 |

TABLE V-continued

Results of the ELISA tests

| Sample Num | Patient | Day | PCR-SARS (1) | ELISA SARS-CoV lysate (2) | IgG-N (2nd series) | 2Xepitope (2nd series) |
|---|---|---|---|---|---|---|
| 032682 | VTH | 12 | NEG D12&D16 | ++ | >5000 | >>20 |
| 032683 | DTV | 17 | NEG D17&D21 | + | >1000 | >>20 |

Remarks:
(1): The RT-PCR analyses were carried out by nested RT-PCR BNI, LC Artus and LC-N on nasal or pharyngeal swabs; POS means that at least one sample was found to be positive in this patient.
(2): The reactivity of the sera in the ELISA test using a lysate of cells infected with SARS-CoV was classified as very highly reactive (+++), highly reactive (++), reactive (+) and negative according to the OD value obtained at the dilutions tested.

EXAMPLE 8

Detection of SARS-associated Coronavirus (SARS-CoV) by RT-PCR

1) Real Time Development of RT-PCR Conditions with the Aid of Primers Specific for the Gene for the Nucleocapsid Protein—"Light Cycler N" Test a) Design of the Primers and Probes The primers and probes were designed from the sequence of the genome of the SARS-CoV strain derived from the sample recorded under the number 031589, with the aid of the programme "Light Cycler Probe Design (Roche)". Thus, the following two series of primers and probes were selected:

```
series 1 (SEQ ID NO: 60, 61, 64, 65):
sense primer:
N/+/28507:
5'-GGC ATC GTA TGG GTT G-3'                [28507-28522]

antisense primer:
N/-/28774:
5'-CAG TTT CAC CAC CTC C-3'                [28774-28759]

probe 1:
5'-GGC ACC CGC AAT CCT AAT AAC AAT         [28561-28586]
GC-fluorescein 3' probe 2:
5' Red705-GCC ACC GTG CTA CAA CTT          [28588-28608]
CCT-phosphate series 2 (SEQ ID NO: 62, 63, 66, 67)
sense primer:
N/+/28375:
5'-GGC TAC TAC CGA AGA G-3'                [28375-28390]

antisense primer:
N/-/28702:
5'-AAT TAC CGC GAC TAC G-3'                [28702-28687]

probe 1:
SARS/N/FL:
5'-ATA CAC CCA AAG ACC ACA TTG GC-         [28541-28563]
fluorescein 3' probe 2:
SARS/N/LC705:
5' Red705-CCC GCA ATC CTA ATA ACA ATG [28565-28589]
CTG C-phosphate 3'
``` b) Analysis of the Efficacy of the Two Primer Pairs

In order to test the respective efficacy of the two pairs of primers, an RT-PCR amplification was carried out on a synthetic RNA corresponding to nucleotides 28054-29430 of the genome of the SARS-CoV strain derived from the sample recorded under the number 031589 and containing the sequence of the N gene.

More specifically:

This synthetic RNA was prepared by in vitro transcription with the aid of the T7 phage RNA polymerase, of a DNA template obtained by linearization of the plasmid SRAS-N with the enzyme Bam H1. After eliminating the DNA template by digestion with the aid of DNAse 1, the synthetic RNAs are purified by a phenol-chloroform extraction, followed by two successive precipitations in ammonium acetate and isopropanol. They are then quantified by measuring the absorbance at 260 nm and their quality is checked by the ratio of the absorbances at 260 and 280 nm and by agarose gel electrophoresis. Thus, the concentration of the synthetic RNA preparation used for these studies is 1.6 mg/ml, which corresponds to $2.1\times10^{15}$ copies/ml of RNA.

Decreasing quantities of synthetic RNA were amplified by RT-PCR with the aid of the "Superscript™ One-Step RT-PCR with Platinum® Taq" kit and the pairs of primers No. 1 (N/+/28507, N/−/28774) (FIG. 1A) and No. 2 (N/+/28375, N/−/28702) (FIG. 1B), according to the supplier's instructions. The amplification conditions used are the following: the cDNA was synthesized by incubation for 30 min at 45° C., 15 min at 55° C. and then 2 min at 94° C. and it was then amplified by 5 cycles comprising: a step of denaturation at 94° C. for 15 sec, a step of annealing at 45° C. for 30 sec and then a step of extension at 72° C. for 30 sec, followed by 35 cycles comprising: a step of denaturation at 94° C. for 15 sec, a step of annealing at 55° C. for 30 sec and then a step of extension at 72° C. for 30 sec, with 2 sec of additional extension at each cycle, and a final step of extension at 72° C. for 5 min. The amplification products obtained were then kept at 10° C.

The results presented in FIG. 11 show that the pair of primers No. 2 (N/+/28375, N/−/28702) makes it possible to detect up to 10 copies of RNA (band of weak intensity) or $10^2$ copies (band of good intensity) against $10^4$ copies for the pair of primers No. 1 (N/+/28507, N/−/28774). The amplicons are respectively 268 bp (pair 1) and 328 bp (pair 2).

c) Development of Real Time RT-PCR

A real time RT-PCR was developed with the aid of the pair of primers No. 2 and of the pair of probes consisting of SRAS/N/FL and SRAS/N/LC705 (FIG. 2).

The amplification was carried out on a LightCycler™ (Roche) with the aid of the "Light Cycler RNA Amplification Kit Hybridization Probes" kit (reference 2 015 145, Roche) under the following optimized conditions. A reaction mixture containing: $H_2O$ (6.8 µl), 25 mM $MgCl_2$ (0.8 µl, 4 µM Mg2+ final), 5× reaction mixture (4 µl), 3 µm probe SRAS/N/FL (0.5 µl, 0.075 µM final), 3 µM probe SRAS/N/LC705 (0.5 µl, 0.075 µM final), 10 µM primer N/+/28375 (1 µl, 0.5 µM final), 10 µM primer N/−/28702 (1 µl, 0.5 µM final), enzyme mixture (0.4 µl) and sample (viral RNA, 5 µl) was amplified according to the following program:

| | | Reverse transcription: |
|---|---|---|
| 50° C. | 10:00 min | analysis mode: none |
| | | Denaturation: |
| 95° C. | 30 sec × 1 | analysis mode: none |
| | | Amplification: |
| 95° C. | 2 sec | |
| 50° C. | 15 sec | analysis mode: quantification* ×45 |
| 72° C. | 13 sec | thermal ramp 2.0° C./sec |
| | | Annealing: |
| 40° C. | 30 sec × 1 | analysis mode: none |

*The fluorescence is measured at the end of the annealing and at each cycle (in SINGLE mode).

Figure 12:
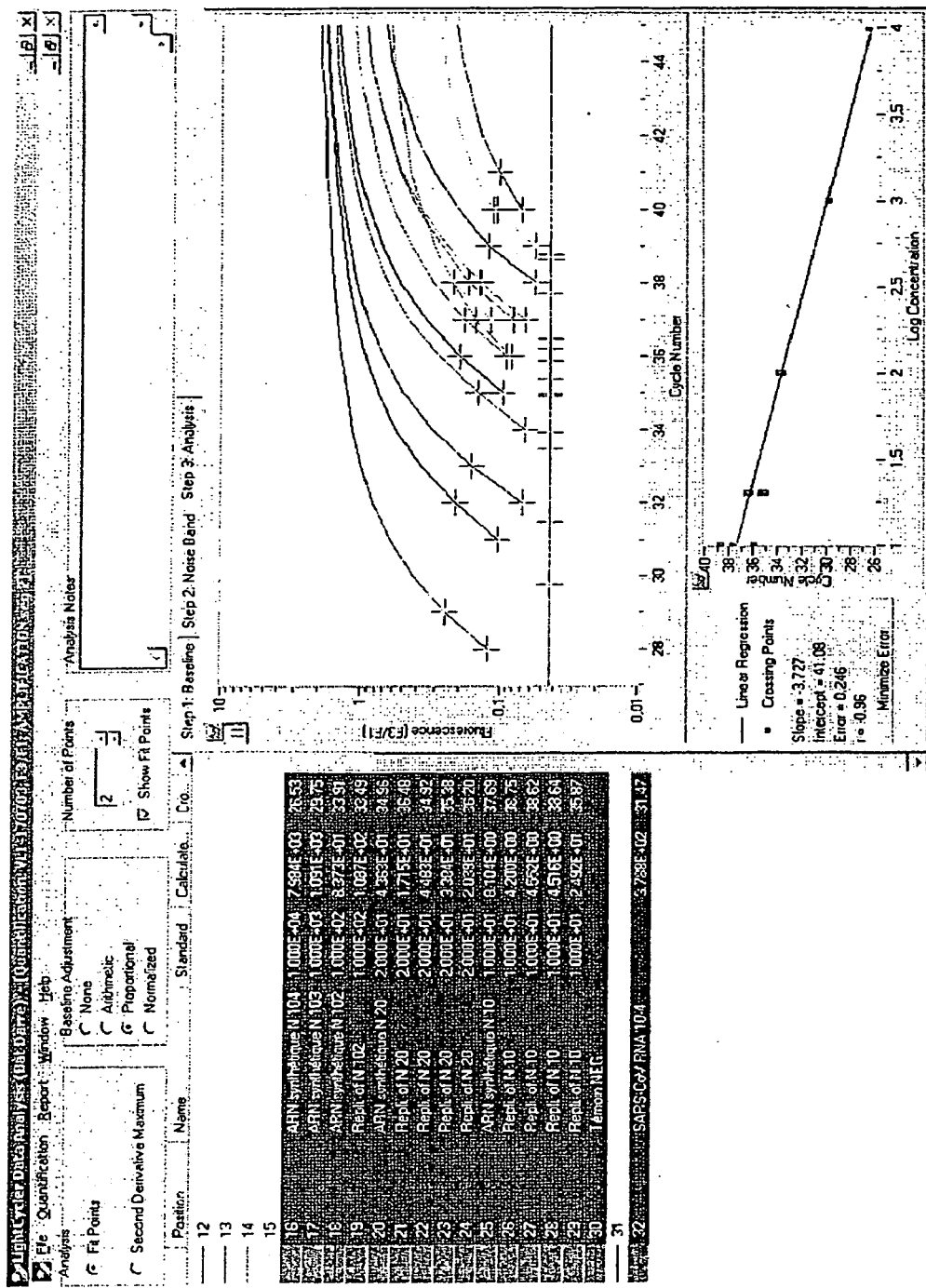

The results presented in FIG. 12 show that this real time RT-PCR is very sensitive since it makes it possible to detect $10^2$ copies of synthetic RNA in 100% of the 5 samples analyzed (29/29 samples in 8 experiments) and up to 10 copies of RNA in 100% of the 5 samples analyzed (40/45 samples in 8 experiments). It also shows that this RT-PCR makes it possible to detect the presence of the SARS-CoV genome in a sample and to quantify the number of genomes present. By way of example, the viral RNA of a SARS-CoV stock cultured on Vero E6 cells was extracted with the aid of the "Qiamp viral RNA extraction" kit (Qiagen), diluted to 0.05× $10^{-14}$ and analyzed by real time RT-PCR according to the protocol described above; the analysis presented in FIG. 12 shows that this virus stock contains $6.5 \times 10^9$ genome-equivalents/ml (geq/ml), which is entirely similar to the $1.0 \times 10^{10}$ geq/ml value measured with the aid of the "RealArt™ HPA-Coronavirus LC RT PCR Reagents" kit marketed by Artus.

2) Development of Nested RT-PCR Conditions Targeting the Gene for RNA Polymerase—"CDC (Centers for Disease Control and Prevention)/IP Nested RT-PCR" Test a) Extraction of the Viral RNA Clinical sample: QIAmp viral RNA Mini Kit (QIAGEN) according to the manufacturer's instructions, or an equivalent technique. The RNA is eluted in a volume of 60 µl.

b) "SNE/SAR" Nested RT-PCR

First Step: "SNE" Coupled RT-PCR

The Invitrogen "Superscript™ One-Step RT-PCR with Platinum® Taq" kit was used, but the "Titan" kit from Roche Boehringer can be used in its place with similar results.

Oligonucleotides:

```
SNE-S1
5' GGT TGG GAT TAT CCA AAA TGT GA 3'

SNE-AS1
5' GCA TCA TCA GAA AGA ATC ATC ATG 3'

→ Expected size: 440 bp
```

1. Prepare a mix:

| | |
|---|---|
| H2O | 6.5 µl |
| Reaction mix 2X | 12.5 µl |
| Oligo SNE-S1 50 µM | 0.2 µl |
| Oligo SNE-AS1 50 µM | 0.2 µl |
| RNAsin 40 U/µl | 0.12 µl |
| RT/Platinum Taq mix | 0.5 µl |

2. To 20 µl of the mix, add 5 µl of RNA and carry out the amplification on a thermocycler (ABI 9600 conditions):

| | | |
|---|---|---|
| 2.1 | 45° C. | 30 min. |
| | 55° C. | 15 min. |
| | 94° C. | 2 min. |
| 2.2. | 94° C. | 15 sec. |
| | 45° C. | 30 sec. ⎫ ×5 cycles |
| | 72° C. | 30 sec. ⎭ |
| 2.3. | 94° C. | 15 sec. |
| | 55° C. | 30 sec. ⎫ ×35 cycles |
| | 72° C. | 30 sec. + 2 sec./cycle ⎭ |
| 2.4. | 72° C. | 5 min. |
| 2.5 | 10° C. | ∞ |

Storage at +4° C.

The RNAsin (N2511/N2515) from Promega was used as RNase inhibitors.

Synthetic RNAs served as positive control. As the control, $10^3$, $10^2$ and 10 copies of synthetic RNA $R_{SNE}$ were amplified in each experiment.

Second Step: "SAR" Nested PCR

Oligonucleotides:

```
SAR1-S
5' CCT CTC TTG TTC TTG CTC GCA 3'

SAR1-AS
5' TAT AGT GAG CCG CCA CAC ATG 3'

→ Expected size: 121 bp
```

1. Prepare a mix:

| | |
|---|---|
| H2O | 35.8 µl |
| Taq buffer 10X | 5 µl |
| MgCl₂ 25 mM | 4 µl |
| Mix dNTPs 5 mM | 2 µl |
| Oligo SAR1-S 50 µM | 0.5 µl |
| Oligo SAR1-AS 50 µM | 0.5 µl |
| Taq DNA pol 5 U/µl | 0.25 µl |

AmpliTaq DNA Pol from Applied Biosystems was used (10× buffer without $MgCl_2$, ref 27216601).

2. To 48 μl of the mix, add 2 μl of the product from the first PCR and carry out the amplification (ABI 9600 conditions):

| 2.1. | 94° C. | 2 min. | |
|---|---|---|---|
| 2.2. | 94° C. | 30 sec. | |
| | 45° C. | 45 sec. | x5 cycles |
| | 72° C. | 30 sec. | |
| 2.3. | 94° C. | 30 sec. | |
| | 55° C. | 30 sec. | x35 cycles |
| | 72° C. | 30 sec. + 1 sec./cycle | |
| 2.4. | 72° C. | 5 min. | |
| 2.5 | 10° C. | ∞ | |

3. Analyze 10 μl of the reaction product on "low-melting" gel (Seakem GTG type) containing 3% agarose.

The sensitivity of the nested test is routinely, under the conditions described, 10 copies of RNA.

4. The fragments can then be purified on QIAquick PCR kit (QIAGEN) and sequenced with the oligos SAR1-S and SAR1-AS.

3) Detection of the SARS-CoV RNA by PCR from Respiratory Samples a) First Comparative Study A comparative study was carried out on a series of respiratory samples received by the National Reference Center for the Influenza Virus (Northern region) and likely to contain SARS-CoV. To do this, the RNA was extracted from the samples with the aid of the "Qiamp viral RNA extraction" kit (Qiagen) and analyzed by real time RT-PCR, on the one hand with the aid of the pairs of primers and probes of the No. 2 series under the conditions described above on the one hand, and on the other hand with the aid of the kit "LightCycler SARS-CoV quantification kit" marketed by Roche (reference 03 604 438). The results are summarized in table VI below. They show that 18 of the 26 samples are negative and 5 of the 26 samples are positive for the two kits, while one sample is positive for the Roche kit alone and two for the "series 2" N reagents alone. Additionally, for 3 samples (20032701, 20032712, 20032714) the quantities of RNA detected are markedly higher with the reagents (probes and primers) of the No. 2 series. These results indicate that the "series 2" N primers and probes are more sensitive for the detection of the SARS-CoV genome in biological samples than those of the kit currently available.

TABLE VI

Real time RT-PCR analysis of the RNAs extracted from a series of samples from 5 patients with the aid of the pairs of primers and probes of the No. 2 series ("series 2" N) or of the kit "Lightcycler SARS-CoV quantification kit" (Roche). The type of sample is indicated as well as the number of copies of viral genome measured in each of the two tests. NEG: negative RT-PCR.

| Sample No. | Patient | Type of sample | ROCHE KIT | "Series 2" N |
|---|---|---|---|---|
| 20033082 | K | nasal | NEG | NEG |
| 20033083 | K | pharyngeal | NEG | NEG |
| 20033086 | K | nasal | NEG | NEG |
| 20033087 | K | pharyngeal | NEG | NEG |
| 20032802 | M | nasal | NEG | NEG |
| 20032803 | M | expectoration | NEG | NEG |
| 20032806 | M | nasal or pharyngeal | NEG | NEG |
| 20031746ARN2 | C | pharyngeal | NEG | NEG |
| 20032711 | C | nasal or pharyngeal | 39 | NEG |
| 20032910 | B | nasal | NEG | NEG |

TABLE VI-continued

Real time RT-PCR analysis of the RNAs extracted from a series of samples from 5 patients with the aid of the pairs of primers and probes of the No. 2 series ("series 2" N) or of the kit "Lightcycler SARS-CoV quantification kit" (Roche). The type of sample is indicated as well as the number of copies of viral genome measured in each of the two tests. NEG: negative RT-PCR.

| Sample No. | Patient | Type of sample | ROCHE KIT | "Series 2" N |
|---|---|---|---|---|
| 20032911 | B | pharyngeal | NEG | NEG |
| 20033356 | V | expectoration | NEG | NEG |
| 20033357 | V | expectoration | NEG | NEG |
| 20031725 | K | endotracheal asp. | NEG | 150 |
| 20032657 | K | endotracheal asp. | NEG | NEG |
| 20032698 | K | endotracheal asp. | NEG | NEG |
| 20032720 | K | endotracheal asp. | 3 | 5 |
| 20033074 | K | stools | 115 | 257 |
| 20032701 | M | pharyngeal | 443 | 1676 |
| 20032702 | M | expectoration | NEG | 249 |
| 20031747ARN2 | C | pharyngeal | NEG | NEG |
| 20032712 | C | unknown | 634 | 6914 |
| 20032714 | C | pharyngeal | 17 | 223 |
| 20032800 | B | nasal | NEG | NEG |
| 20033353 | V | nasal | NEG | NEG |
| 20033384 | V | nasal | NEG | NEG | b) Second Comparative Study

The performance of various nested RT-PCR and real time RT-PCR methods were then compared for 121 respiratory samples from possible cases of SARS at the French hospital in Hanoi, Vietnam, taken between the 4th and the 17th day after the onset of the symptoms. Among these samples, 14 were found to be positive during a first test using the nested RT-PCR method targeting ORF1b (encoding replicase) as described initially by Bernhard Nocht Institute (BNI nested RT-PCR).

Information relating to this test is available on the internet, at the address http://www15.bni-hamburg.de/bni2/neu2/get-file.acgi?area engl=diagnostics&pid=4112.

The various tests compared in this study are:
the quantitative RT-PCR method according to the invention, with the "series 2" N primers and probes described above (LightCycler N column),
the nested RT-PCR test targeting the RNA polymerase gene described above, developed by the CDC, BNI and Institut Pasteur <CDC/IP nested RT-PCR),
the ARTUS kit with the reference "HPA Corona LC RT-PCR Kit # 5601-02", which is a real time RT-PCR test targeting the ORF1b gene,
the BNI nested RT-PCR test, also targeting the RNA polymerase gene mentioned above.

The inventors observed:
1) an inter-test variability for the same technique, linked to the degradation of the RNA preparation during repeated thawing, in particular for the samples containing the lowest quantities of RNA,
2) a reduced sensitivity of the CDC/IP nested RT-PCR compared with the BNI nested RT-PCR, and
3) a comparable sensitivity of the quantitative RT-PCR test according to the invention (Lightcycler N) compared with the Artus LightCycler (LC) test.

These results, which are presented in table VII below, show that the quantitative RT-PCR test according to the invention constitutes an excellent addition—or an alternative—to the tests currently available. Indeed, the SARS-linked coronavirus is an emergent virus which is capable of changing rapidly.

In particular, the gene for the RNA polymerase of the SARS-linked coronavirus, which is targeted in most of the tests currently available, can recombine with that of other coronaviruses not linked to SARS. The use of a test targeting this gene exclusively could then lead to the production of false-negatives.

The quantitative RT-PCR test according to the invention does not target the same genomic region as the ARTUS kit since it targets the gene encoding the N protein. By carrying out a diagnostic test targeting two different genes of the SARS-linked coronavirus, it can therefore be hoped to avoid false-negative type results which could be due to the genetic evolution of the virus.

Furthermore, it appears particularly advantageous to target the gene for the nucleocapsid protein because it is very stable because of the high selection pressure linked to the high structural constraints regarding this protein.

TABLE VII

Comparison of various methods of analysis by gene amplification, from 121 samples of probable cases of SARS at the French hospital in Hanoi, Vietnam (epidemic 2003)

| NRC No. | Sample type (1) | Sample collection day | Patient | CDC/IP nested RT-PCR | BNI nested RT-PCR | Artus Light Cycler kit | Light Cycler N (IP) |
|---|---|---|---|---|---|---|---|
| 107 samples | N and P | | | Negative | Negative | Negative | Negative |
| 032529 | P | 10 | NHB | Negative | Positive | Negative | Negative |
| 032530 | N | 10 | NHB | Positive | Positive | 3.10E+01 | 4.20E+01 |
| 032531 | P | 7 | LP | Positive | Positive | 7.70E+00 | 3.10E+00 |
| 032534 | N | 15 | BND | Positive | Positive | 1.60E+00 | Negative |
| 032600 | P | 4 | NHH | Negative | Positive | Negative | 1.30E+02 |
| 032612 | P | 17 | NTS | Negative | Positive | Negative | Negative |
| 032688 | P | 9 | BTX | Positive | Positive | Negative | Negative |
| 032689 | N | 4 | NVH | Positive | Positive | 1.20E+01 | 2.30E+02 |
| 032690 | P | 4 | NVH | Negative | Positive | 1.60E+00 | Negative |
| 032727 | P | 8 | NVH | Positive | Positive | 2.30E+02 | 4.00E+02 |
| 032728 | N | 8 | NVH | Positive | Positive | 1.10E+03 | 1.60E+04 |
| 032729 | P | 14 | NHB | Positive | Positive | 5.90E+00 | 3.40E+01 |
| 032730 | N | 14 | NHB | Positive | Positive | 1.30E+02 | 4.80E+02 |
| 032741 | P | 8 | NHH | Positive | Positive | 2.10E+02 | 1.30E+02 |
| positives | | | | 10 | 14 | 10 | 9 |
| fraction detected from the 14 positives | | | | 71.4% | 100.0% | 71.4% | 64.3% |

(1) P = pharyngeal swab N = nasal swab

EXAMPLE 9

Production and Characterization of Monoclonal Antibodies Directed Against the N Protein Balb C mice were immunized with the purified recombinant N protein and their spleen cells fused with an appropriate murine myeloma according to the Köhler and Milstein techniques.

Nineteen anti-N antibody secreting hybridomas were preselected and their immunoreactivities determined. These antibodies do indeed recognize the recombinant N protein (in ELISA) with variable intensities, and the natural viral N protein in ELISA and/or in Western blotting. FIGS. 18 to 20 show the results of these tests for 15 of these 19 monoclonal antibodies.

The highly reactive clones 12, 17, 28, 57, 72, 76, 86, 87, 98, 103, 146, 156, 166, 170, 199, 212, 218, 219 and 222 were subcloned. Specificity studies were carried out with the appropriate tools in order to determine the epitopes recognized and verify the absence of reactivity toward other human coronaviruses and certain respiratory viruses.

Epitope mapping studies (performed on spot membrane with the aid of overlapping peptides of 15 aa) and additional studies performed on the natural N protein in Western blotting revealed the existence of 4 groups of monoclonal antibodies:

1. Monoclonal antibodies specific for a major linear epitope at the N-ter position (75-81, sequence: INTNSVP).

The representative of this group is antibody 156. The hybridoma producing this antibody was deposited at the Collection Nationale de Cultures de Microorganismes (CNCM) of the Institut Pasteur (Paris, France) on Dec. 1, 2004, under the number I-3331. This same epitope is also recognized by a rabbit serum (anti-N polyclonal) obtained by conventional immunization with the aid of this same N protein.

2. Monoclonal antibodies specific for a major linear epitope located in a central position (position 217-224, sequence: ETALALL); the representatives of this group are the monoclonal antibodies 87 and 166. The hybridoma producing antibody 87 was deposited at the CNCM on Dec. 1, 2004, under the number I-3328.

3. Monoclonal antibodies specific for a major linear epitope located at the C-terminal position (position 403-408, sequence: DFFRQL), the representatives of this group are the antibodies 28, 57 and 143. The hybridoma producing antibody 57 was deposited at the CNCM on Dec. 1, 2004, under the number I-3330.

4. Monoclonal antibodies specific for a discontinuous conformational epitope. This group of antibodies does not recognize any of the peptides spanning the sequence of the N protein, but react strongly on the non-denatured natural protein. The representative of this final group is the antibody 86. The hybridoma producing this antibody was deposited at the CNCM on Dec. 1, 2004, under the number I-3329.

Table VIII below summarizes the epitope mapping results obtained:

TABLE VIII

Epitope mapping of the monoclonal antibodies

| Antibody | Epitope | Position | Region |
|---|---|---|---|
| 28 | DFSRQL Q | 403 ... 408 | C-Ter. |
| 143 | DFSRQL Q | | |
| 76 | DFSRQL Q | | |
| 57 | DFSRQL Q | | |
| | FFGMS RI | 315 ... 319 | |
| 146 | LPQRQ | 383 ... 387 | |
| 166 | ETALALLLL | 217 ... 224 | central |
| 87 | ETALALL | 217 ... 224 | |
| 156 | INTNSGP | 75 ... 81 | N-Ter. |
| 86 | Conformational | | |
| 212 | Conformational | | |
| 170 | Conformational | | |

In addition, as illustrated in particular in FIGS. 18 and 19, these antibodies exhibit no reactivity in ELISA and/or in WB toward the N protein of the human corona-virus 229 E.

EXAMPLE 10

Combinations of the Monoclonal Antibodies for the Development of a Sensitive Immunocapture Test Specific for the Viral N Antigen in the Serum or Biological Fluids of Patients Infected with the SARS-CoV Virus The antibodies listed below were selected because of their very specific properties for an additional capture and detection study of the viral N protein, in the serum of the subjects or patients.

These antibodies were produced in ascites on mice, purified by affinity chromatography and used alone or in combination, as capture antibodies and as signal antibodies.

List of the antibodies selected:
Ab anti-C-ter region (No. 28, 57, 143)
Ab anti-central region (No. 87, 166)
Ab anti-N-ter region (No. 156)
Ab anti-discontinuous conformational epitope 86)

1) Preparation of the Reagents:

a) Immunocapture ELISA plates

The plates are sensitized with the antibody solutions at 5 µg/ml in 0.1 M carbonate buffer, pH 9.6. The (monovalent or plurivalent) solutions are deposited in a volume of 100 µl in the wells and incubated overnight at room temperature. These plates are then washed with PBS buffer (10 mM pH 7.4 supplemented with 0.1% Tween 20) and then saturated with a PBS solution supplemented with 0.3% BSA and 5% sucrose). The plates are then dried and then packaged in a bag in the presence of a desiccant. They are ready to use.

b) Conjugates

The purified antibodies were coupled with peroxidase according to the Nakane protocol (Nakane et al. -1974, J. of Histo and cytochemistry, vol. 22, pp. 1084-1091) in a ratio of one molecule of IgG per 3 molecules of peroxidase. These conjugates were purified by exclusion chromatography and stored concentrated (concentration between 1 and 2 mg/ml) in the presence of 50% glycerol and at −20° C. They are diluted for their use in the assays at the final concentration of 1 or 2 µg/ml in PBS buffer (pH 7.4) supplemented with 1% BSA.

c) Other Reagents

Human sera negative for all the serum markers for the HIV, HBV, HCV and THLV viruses Pool of negative human sera supplemented with 0.5% Triton X 100

Inactivated viral Ag: viral culture supernatant inactivated by irradiation and inactivation verified after placing in culture on sensitive cells—titer of the suspension before inactivation about $10^7$ infectious particles per ml or alternatively about $5 \times 10^9$ physical viral particles per ml of antigen The Ag samples diluted in negative human serum: these samples were prepared by diluting 1:100 and then by 5-fold serial dilution.

These noninfectious samples mimic human samples thought to contain low to very low concentrations of viral nucleoprotein N. Such samples are not available for routine work.

Washing solution R2, solution for visualization TMB R8, chromogen R9 and stop solution R10, are the generic reagents marketed by Bio-Rad in its ELISA kits (e.g.: *Platelia pylori* kit ref. 72778).

2) Procedure

The samples of human sera overloaded with inactivated viral Ag are distributed in an amount of 100 µl per well, directly in the ready-to-use sensitized plates, and then incubated for 1 hour at 37° C. (Bio-Rad IPS incubation).

The material not bound to the solid phase is removed by 3 washings (washing with dilute R2 solution, automatic LP 35 washer).

The appropriate conjugates, diluted to the final concentration of 1 or 2 µg/ml, are distributed in an amount of 100 µl per well and the plates are again incubated for one hour at 37° C. (IPS incubation).

The excess conjugate is removed by 4 successive washings (dilute R2 solution—LP 35 washer).

The presence of conjugate attached to the plates is visualized after adding 100 µl of visualization solution prepared before use (1 ml of R9 and 10 ml of R8) and after incubation for 30 minutes, at room temperature and protected from light.

The enzymatic reaction is finally blocked by adding 100 µl of R10 reagent (1 N $H_2SO_4$) to all the wells.

The reading is carried out with the aid of an appropriate microplate reader at double wavelength (450/620 nm).

The results can be interpreted by using, as provisional threshold value, the mean of at least two negative controls multiplied by a factor of 2 or alternatively the mean of 100 negative sera supplemented with an increment corresponding to 6 SD (standard deviation calculated on the 100 individual measurements).

3) Results

Various capture antibody and signal antibody combinations were tested based on the properties of the antibodies selected, and avoiding the combinations of antibodies specific for the same epitopes in solid phase and as conjugates.

The best results were obtained with the 4 combinations listed below. These results are reproduced in table IX below.

1. Combination F/28

Solid phase (Ab 166+87 central region): conjugate antibody 28 (C-ter)

2. Combination G/28

Solid phase (Ab 86–conformational epitope): conjugate antibody 28 (C-ter)

3. Combination H/28

Solid phase (Ab 86, 166 and 87 central region and conformational epitope): conjugate antibody 28 (C-ter)

4. Combination H/28+87

Solid phase (Ab 86, 166 and 87 central region and conformational epitope): mixed conjugate antibodies 28 (C-ter) and 87 (central)

5. Combination G/87

Solid phase (Ab 86–conformational epitope): conjugate antibody 87 (central region)

The first 4 combinations exhibit equivalent and reproduced performance levels, greater than the other combinations used (such as for example the combination G/87). Of course, in these combinations, a monoclonal antibody may be replaced with another antibody recognizing the same epitope. Thus, the following variants may be mentioned:

6. Variant of the combination F/28

Solid phase (Ab 87 only): conjugate antibody 57 (C-ter)

7. Variant of the combination G/28

Solid phase (Ab 86–conformational epitope): conjugate antibody 57 (C-ter)

8. Variant of the combination H/28

Solid phase (Ab 86 and 87 central region and conformational epitope): conjugate antibody 57 (C-ter)

9. Variant of the combination H/28+87

Solid phase (Ab 86 and 87 central region and conformational epitope): mixed conjugate antibodies 57 (C-ter) and 87 (central)

TABLE IX

Test of immunoreactivity of the anti-SARS-CoV nucleoprotein Abs: optical densities measured with each combination of antibodies according to the dilutions of the inactivated viral antigen.

| No. | Dilution | F/28 | G/28 | G/87 | H/28 | H/28 + 87 |
|---|---|---|---|---|---|---|
| 0 | 1/100 | 5 | 5 | 3.495 | 3.900 | 5 |
| 1 | 1/500 | 3.795 | 3.814 | 1.379 | 3.702 | 3.804 |
| 2 | 1/2 500 | 2.815 | 2.950 | 0.275 | 3.268 | 2.680 |
| 3 | 1/12 500 | 0.987 | 1.038 | 0.135 | 1.374 | 0.865 |
| 4 | 1/62 500 | 0.404 | 0.348 | 0.125 | 0.480 | 0.328 |
| 5 | 1/312 500 | 0.285 | 0.211 | 0.123 | 0.240 | 0.215 |
| 6 | Control | 0.210 | 0.200 | 0.098 | 0.186 | 0.156 |
| 7 | Control | 0.269 | 0.153 | 0.104 | 0.193 | 0.202 |

The detection limit for these 4 experimental trials corresponds to the antigen dilution in negative serum 1:62 500. A rapid extrapolation suggests the detection of less than $10^3$ infectious particles per ml of sera.

From this study, it is evident that the most appropriate antibodies for the capture of the native viral nucleoprotein are the antibodies specific for the central region and/or for a conformational epitope, both being antibodies also selected for their high affinity for the native antigen.

Having determined the best antibodies for the composition of the solid phase, the antibodies to be selected as a priority for the detection of the antigens attached to the solid phase are the complementary antibodies specific for a dominant epitope in the C-ter region. The use of any other complementary antibody specific for epitopes located in the N-ter region of the protein leads to average or poor results.

EXAMPLE 11

Eukaryotic Expression Systems for the SARS-associated Coronavirus (SARS-CoV) Spicule (S) Protein 1) Optimization of the Conditions for Expression of the SARS-CoV S in Mammalian Cells The conditions for transient expression of the SARS-CoV spicule (S) protein were optimized in mammalian cells (293T, VeroE6).

For that, a DNA fragment containing the cDNA for SARS-CoV S was amplified by PCR with the aid of the oligonucleotides 5'-ATAGGATCCA CCATGTTTAT TTTCTTATTA TTTCTTACTC TCACT-3' and 5'-ATACTCGAGTT ATGT-GTAATG TAATTTGACA CCCTTG-3' from the plasmid pSARS-S (C.N.C.M. No. I-3059) and then inserted between the BamH1 and Xho1 sites of the plasmid pTRIPΔU3-CMV containing a lentiviral vector TRIP (Sirven, 2001, Mol. Ther., 3, 438-448) in order to obtain the plasmid pTRIP-S. The BamH1 and Xho1 fragment containing the cDNA for S was then subcloned between BamH1 and Xho1 of the eukaryotic expression plasmid pcDNA3.1(+) (Clontech) in order to obtain the plasmid pcDNA-S. The Nhe1 and Xho1 fragment containing the cDNA for S was then subcloned between the corresponding sites of the expression plasmid pCI (Promega) in order to obtain the plasmid pCI-S. The WPRE sequences of the woodchuck hepatitis virus ("Woodchuck Hepatitis Virus posttranscriptional regulatory element") and the CTE sequences ("constitutive transport element") of the simian retrovirus from Mason-Pfizer were inserted into each of the two plasmids pcDNA-S and pCI-S between the Xho1 and Xba1 sites in order to obtain respectively the plasmids pcDNA-S-CTE, pcDNA-S-WPRE, pCI-S-CTE and pCI-S-WPRE (FIG. 21). The plasmid pCI-S-WPRE was deposited at the CNCM, on Nov. 22, 2004, under the number I-3323. All the inserts were sequenced with the aid of a BigDye Terminator v1.1 kit (Applied Biosystems) and an automated sequencer ABI377.

The capacity of the plasmid constructs to direct the expression of SARS-CoV S in mammalian cells was assessed after transfection of VeroE6 cells (FIG. 22). In this experiment, monolayers of $5 \times 10^5$ VeroE6 cells in 35 mm Petri dishes were transfected with 2 μg of plasmids pcDNA (as control), pcDNA-S, pCI and pCI-S and 6 μl of Fugene6 reagent according to the manufacturer's instructions (Roche). After 48 hours of incubation at 37° C. and under 5% $CO_2$, cellular extracts were prepared in loading buffer according to Laemmli, separated on 8% SDS polyacrylamide gel, and then transferred onto a PVDF membrane (BioRad). The detection of this immunoblot (Western blot) was carried out with the aid of an anti-S rabbit polyclonal serum (immune serum from the rabbit P11135: cf. example 4 above) and donkey polyclonal antibodies directed against rabbit IgGs and coupled with peroxidase (NA934V, Amersham). The bound antibodies were visualized by luminescence with the aid of the ECL+ kit (Amersham) and autoradiography films Hyperfilm MP (Amersham).

This experiment (FIG. 22) shows that the plasmid pcDNA-S does not make it possible to direct the expression of SARS-CoV S at detectable levels whereas the plasmid pCI-S allows a weak expression, close to the limit of detection, which may be detected when the film is overexposed. Similar results were obtained when the expression of S was sought by immunofluorescence (data not shown). This impossibility to detect effective expression of S cannot be attributed to the detection techniques used since the S protein can be detected at the expected size (180 kDa) in an extract of cells infected with SARS-CoV or in an extract of VeroE6 cells infected with the recombinant vaccinia virus VV-TF7.3 and transfected with the plasmid pcDNA-S. In this latter experiment, the virus VV-TF7.3 expresses the RNA polymerase of the T7 phage and allows the cytoplasmic transcription of an uncapped RNA capable of being efficiently translated. This experiment suggests that the expression defects described above are due to an intrinsic inability of the cDNA for S to be efficiently expressed when the step for transcription to messenger RNA is carried out at the nuclear level.

In a second experiment, the effect of the CTE and WPRE signals on the expression of S was assessed after transfection of VeroE6 (FIG. 23A) and 293T (FIG. 23B) cells and according to a protocol similar to that described above. Whereas the expression of S cannot be detected after transfection of the plasmids pcDNA-S-CTE and pcDNA-S-WPRE derived from pcDNA-S, the insertion of the WPRE and CTE signals greatly improves the expression of S in the context of the expression plasmid pCI-S.

To specify this result, a second series of experiments were carried out where the immunoblot is quantitatively visualized by luminescence and acquisition on a digital imaging device (FluorS, BioRad). The analysis of the results obtained with the QuantityOne v4.2.3 software (BioRad) shows that the WPRE and CTE sequences increase respectively the expression of S by a factor of 20 to 42 and 10 to 26 in Vero E6 cells (table X). In 293T cells (table X), the effect of the CTE sequence is more moderate (4 to 5 times) whereas that of the WPRE sequence remains high (13 to 28 times).

TABLE X

Quantitative analysis of the effect of the CTE and WPRE signals on the expression of SARS-CoV S: Cellular extracts were prepared 48 hours after transfection of VeroE6 or 293T cells with the plasmid pCI, pCI-S, pCI-S-CTE and pCI-S-WPRE and analyzed by Western blotting as described in the legend to FIG. 22. The Western blot is visualized by luminescence (ECL+, Amersham) and acquisition on a digital imaging device (FluorS, BioRad). The expression levels are indicated according to an arbitrary scale where the value of 1 represents the level measured after transfection of the plasmid pCI-S. Two independent experiments were carried out for each of the two cell types. In experiment 1 on VeroE6 cells, the transfections were carried out in duplicate and the results are indicated in the form of the mean and standard deviation values for the expression levels measured.

| Plasmid | cell | exp. 1 | exp. 2 |
|---|---|---|---|
| PCI | VeroE6 | 0.0 | 0.0 |
| pCI-S | VeroE6 | 1.0 ± 0.1 | 1.0 |
| pCI-S-CTE | VeroE6 | 9.8 ± 0.9 | 26.4 |
| pCI-S-WPRE | VeroE6 | 20.1 ± 2.0 | 42.3 |
| PCI | 293T | 0.0 | 0.0 |
| PCI-S | 293T | 1.0 | 1.0 |
| PCI-S-CTE | 293T | 4.6 | 4.0 |
| PCI-S-WPRE | 293T | 27.6 | 12.8 |

In summary, all these results show that the expression, in mammalian cells, of the cDNA for the SARS-CoV S under the control of the RNA polymerase II promoter sequences requires, to be efficient, the expression of a splice signal and of either of the sequences WPRE and CTE.

2) Production of Stable Lines Allowing the Expression of SARS-CoV S

The cDNA for the SARS-CoV S protein was cloned in the form of a BamH1-Xho1 fragment into the plasmid pTRIPΔU3-CMV containing a defective lentiviral vector TRIP with central DNA flap (Sirven et al., 2001, Mol. Ther., 3: 438-448) in order to obtain the plasmid pTRIP-S (FIG. 24). Transient cotransfection according to Zennou et al. (2000, Cell, 101: 173-185) of this plasmid, of an encapsidation plasmid (p8.2) and of a plasmid for expression of the VSV envelope glycoprotein G (pHCMV-G) in 293T cells allowed the preparation of retroviral pseudoparticles containing the vector TRIP-S and pseudotyped with the envelope protein G. These pseudotyped TRIP-S vectors were used to translate 293T and FRhK-4 cells: no expression of the S protein could be detected by Western blotting and immunofluorescence in the transduced cells (data not presented).

The optimum expression cassettes consisting of the CMV virus immediate/early promoter, a splice signal, cDNA for S and either of the posttranscriptional signals WPRE or CTE described above were then substituted for the EF1α-EGFP cassette of the defective lentiviral expression vector with central DNA flap TRIPΔU3-EF1α (Sirven et al., 2001, Mol. Ther., 3: 438-448) (FIG. 25). These substitutions were carried out by a series of successive subclonings of the S expression cassettes which were excised from the plasmids PCT-S-CTE (BglII-Apa1) or respectively pCI-S-WPRE (BglII-Sal1) and then inserted between the Mlu1 and Kpn1 sites or respectively Mlu1 or Xho1 sites of the plasmid TRIPΔU3-EF1α in order to obtain the plasmids pTRIP-SD/SA-S-CTE and pTRIP-SD/SA-S-WPRE, deposited at the CNCM, on Dec. 1, 2004, under the numbers I-3336 and I-3334, respectively. Pseudotyped vectors were produced according to Zennou et al. (2000, Cell, 101: 173-185) and used to transduce 293T cells (10 000 cells) and FRhK-4 cells (15 000 cells) according to a series of 5 successive transduction cycles with a quantity of vectors corresponding to 25 ng (TRIP-SD/SA-S-CTE) or 22 ng TRIP-SD/SA-S-WPRE) of p24 per cycle.

The transduced cells were cloned by limiting dilution and a series of clones were qualitatively analyzed for the expression of SARS-CoV S by immunofluorescence (data not shown), and then quantitatively by Western blotting (FIG. 25) with the aid of an anti-S rabbit polyclonal serum. The results presented in FIG. 25 show that clones 2 and 15 of FrhK4-s-CTE cells transduced with TRIP-SD/SA-S-CTE and clones 4, 9 and 12 of FRhK4-S-WPRE cells transduced with TRIP-SD/SA-S-WPRE allow the expression of the SARS-CoV S at respectively low or moderate levels if they are compared to those which can be observed during infection with SARS-CoV.

In summary, the vectors TRIP-SD/SA-S-CTE and TRIP-SD/SA-S-WPRE allow the production of stable clones of FRhK-4 cells and similarly 293T cells expressing SARS-CoV S, whereas the assays carried out with the "parent" vector TRIP-S remained unsuccessful, which demonstrates the need for a splice signal and for either of the sequences CTE and WPRE for the production of stable cell clones expressing the S protein.

In addition, these modifications of the vector TRIP (insertion of a splice signal and of a post-transcriptional signal like CTE and WPRE) could prove advantageous for improving the expression of other cDNAs than that for S.

3) Production of Stable Lines Allowing the Expression of a Soluble Form of SARS-CoV S. Purification of this Recombinant Antigen.

A cDNA encoding a soluble form of the S protein (Ssol) was obtained by fusing the sequences encoding the ectodomain of the protein (amino acids 1 to 1193) with those of a tag (FLAG:DYKDDDDK) via a BspE1 linker encoding the SG dipeptide. Practically, in order to obtain the plasmid pcDNA-Ssol, a DNA fragment encoding the ectodomain of SARS-CoV S was amplified by PCR with the aid of the oligonucleotides 5,-ATAGGATCCA CCATGTTTAT TTTCTTATTA TTTCTTACTC TCACT-3' and 5'-ACCTC-CGGAT TTAATATATT GCTCATATTT TCCCAA-3' from the plasmid pcDNA-S, and then inserted between the unique BamH1 and BspE1 sites of a modified eukaryotic expression plasmid pcDNA3.1(+) (Clontech) containing the tag sequence FLAG between its BamH1 and Xho1 sites:

```
// GGATCC . . . nnn . . . TCC GGA GAT TAT AAA GAT
   BamH1                  S   G   D   Y   K   D GAC GAC GAT AAA TAA CTCGAG //
 D   D   D   K  ter Xho1
```

The Nhe1-Xho1 and BamH1-Xho1 fragments, containing the cDNA for S, were then excised from the plasmid pcDNA-Ssol, and subcloned between the corresponding sites of the plasmid pTRIP-SD/SA-S-CTE and of the plasmid pTRIP-SD-SA-S-WPRE, respectively, in order to obtain the plasmids pTRIP-SD/SA-Ssol-CTE and pTRIP-SD/SA-Ssol-WPRE, deposited at the CNCM, on Dec. 1, 2004, under the numbers I-3337 and I-3335, respectively.

Pseudotyped vectors were produced according to Zennou et al. (2000, Cell, 101:173-185) and used to transduce FRhK-4 cells (15 000 cells) according to a series of 5 successive transduction cycles (15 000 cells) with a quantity of vector corresponding to 24 ng (TRIP-SD/SA-Ssol-CTE) or 40 ng (TRIP-SD/SA-Ssol-WPRE) of p24 per cycle. The transduced cells were cloned by limiting dilution and a series of 16 clones transduced with TRIP-SD/SA-Ssol-CTE and of 15 clones with TRIP-SD/SA-Ssol-WPRE were analyzed for the expression of the Ssol polypeptide by Western blotting visualized with an anti-FLAG monoclonal antibody (FIG. 26 and data not presented), and by capture ELISA specific for the Ssol polypeptide which was developed for this purpose (table XI and data not presented). Part of the process for selecting the best secretory clones is shown in FIG. 26. Capture ELISA is based on the use of solid phases coated with polyclonal antibodies of rabbits immunized with purified and inactivated SARS-CoV. These solid phases allow the capture of the Ssol polypeptide secreted into the cellular supernatants, whose presence is then visualized with a series of steps successively involving the attachment of an anti-FLAG monoclonal antibody (M2, SIGMA), of anti-mouse IgG(H+L) biotinylated rabbit polyclonal antibodies (Jackson) and of a streptavidin-peroxidase conjugate (Amersham) and then the addition of chromogen and substrate (TMB+$H_2O_2$, KPL).

TABLE XI

Analysis of the expression of the Ssol polypeptide by cell lines transduced with the lentiviral vectors TRIP-SD/SA-Ssol-WPRE and TRIP-SD/SA-Ssol-CTE. The secretion of the Ssol polypeptide was assessed in the supernatant of a series of cell clones isolated after transduction of FRhK-4 cells with the lentiviral vectors TRIP-SD/SA-Ssol-WPRE and TRIP-SD/SA-Ssol-CTE. The supernatants diluted 1/50 were analyzed by a capture ELISA test specific for SARS-CoV S.

| Vector | Clone | OD (450 nm) |
|---|---|---|
| Control | — | 0.031 |
| TRIP-SD/SA-Ssol-CTE | CTE2 | 0.547 |
|  | CTE3 | 0.668 |
|  | CTE9 | 0.171 |
|  | CTE12 | 0.208 |
|  | CTE13 | 0.133 |
| TRIP-SD/SA-Ssol-WPRE | WPRE1 | 0.061 |
|  | WPRE10 | 0.134 |

The cell line secreting the highest quantities of Ssol polypeptide in the culture supernatant is the FRhK4-Ssol-CTE3 line. It was subjected to a second series of 5 cycles of transduction with the vector TRIP-SD/SA-Ssol-CTE under conditions similar to those described above and then cloned. The subclone secreting the highest quantities of Ssol was selected by a combination of Western blot and capture ELISA analysis: it is the subclone FRhK4-Ssol-30, which was deposited at the CNCM, on Nov. 22, 2004, under the name I-3325.

The FRhK4-Ssol-30 line allows the quantitative production and purification of the recombinant Ssol polypeptide. In a typical experiment where the experimental conditions for growth, production and purification were optimized, the cells of the FRhK4-Ssol-30 line are inoculated in standard culture medium (pyruvate-free DMEM containing 4.5 g/l of glucose and supplemented with 5% FCS, 100 U/ml of penicillin and 100 µg/ml of streptomycin) in the form of a subconfluent monolayer (1 million cells per each 100 $cm^2$ in 20 ml of medium). At confluence, the standard medium is replaced with the secretion medium where the quantity of FCS is reduced to 0.5% and the quantity of medium reduced to 16 ml per each 100 $cm^2$. The culture supernatant is removed after 4 to 5 days of incubation at 35° C. and under 5% $CO_2$. The recombinant polypeptide Ssol is purified from the supernatant by the succession of steps of filtration on 0.1 µm polyethersulfone (PES) membrane, concentration by ultrafiltration on a PES membrane with a 50 kD cut-off, affinity chromatography on anti-FLAG matrix with elution with a solution of FLAG peptide (DYKDDDDK) at 100 µg/ml in TBS (50 mM tris, pH 7.4, 150 mM NaCl) and then gel filtration chromatography in TBS on sephadex G-75 beads (Pharmacia). The concentration of the purified recombinant Ssol polypeptide was determined by micro-BCA test (Pierce) and then its biochemical characteristics analyzed.

Analysis by 8% SDS acrylamide gel stained with silver nitrate demonstrates a predominant polypeptide whose molecular mass is about 180 kD and whose degree of purity may be evaluated at 98% (FIG. 27A). Two main peaks are detected by SELDI-TOF mass spectrometry (Cyphergen): they correspond to single and double charged forms of a predominant polypeptide whose molecular mass is thus determined at 182.6±3.7 kD (FIGS. 27B and C). After transfer onto Prosorb membrane and rinsing in 0.1% TFA, the N-terminal end of the Ssol polypeptide was sequenced in liquid phase by Edman degradation on 5 residues (ABI494, Applied Biosystems) and determined as being SDLDR (FIG.

27D). This demonstrates that the signal peptide located at the N-terminal end of the SARS-CoV S protein, composed of aa 1 to 13 (MFIFLLFLTLTSG) according to an analysis carried out with the software signalP v2.0 (Nielsen et al., 1997, *Protein Engineering*, 10:1-6), is cleaved from the mature Ssol polypeptide. The recombinant Ssol polypeptide therefore consists of amino acids 14 to 1193 of the SARS-CoV S protein fused at the C-terminals with a sequence SG DYKDDDDK containing the sequence of the FLAG tag (underlined). The difference between the theoretical molar mass of the naked Ssol polypeptide (132.0 kD) and the real molar mass of the mature polypeptide (182.6 kD) suggests that the Ssol polypeptide is glycosylated.

A preparation of purified Ssol polypeptide, whose protein concentration was determined by micro-BCA test, makes it possible to prepare a calibration series in order to measure, with the aid of the capture ELISA test described above, the concentrations of Ssol present in the culture supernatants and to review the characteristics of the secretory lines. According to this test, the FRhK4-Ssol-CT3 line secretes 4 to 6 µg/ml of polypeptide Ssol while the FRhK4-Ssol-30 line secretes 9 to 13 µg/ml of Ssol after 4 to 5 days of culture at confluence. In addition, the purification scheme presented above makes it possible routinely to purify from 1 to 2 mg of Ssol polypeptide per liter of culture supernatant.

EXAMPLE 12

Gene Immunization Involving the SARS-associated Corona Virus (SARS-CoV) Spicule (S) Protein The effect of a splice signal and of the posttranscriptional signals WPRE and CTE was analyzed after gene immunization of BALB/c mice (FIG. 28).

For that, BALB/c mice were immunized at intervals of 4 weeks by injecting into the tibialis anterior a saline solution of 50 µg of plasmid DNA of pcDNA-S and pCI-S and, as a control, 50 µg of plasmid DNA of pcDNA-N (directing the expression of SARS-CoV N) or of pCI-HA (directing the expression of the HA of the influenza virus A/PR/8/34) and the immune sera collected 3 weeks after the $2^{nd}$ injection. The presence of antibodies directed against the SARS-CoV S was assessed by indirect ELISA using as antigen a lysate of VeroE6 cells infected with SARS-CoV and, as a control, a lysate of noninfected VeroE6 cells. The anti-SARS-CoV antibody titers (TI) are calculated as the reciprocal of the dilution producing a specific OD of 0.5 (difference between OD measured on a lysate of infected cells and OD measured on a lysate of noninfected cells) after visualization with an antimouse IgG polyclonal antibody coupled with peroxidase (NA931V, Amersham) and TMB supplemented with $H_2O_2$ (KPL) (FIG. 28A).

Under these conditions, the expression plasmid pcDNA-S only allows the induction of low antibody titers directed against SARS-CoV S in 3 mice out of 6 ($LOG_{10}(TI)=1.9\pm0.6$) whereas the plasmid pcDNA-N allows the induction of anti-N antibodies at high titers ($LOG_{10}(TI)=3.9\pm0.3$) in all the animals, and the control plasmids (pCI, pCI-HA) do not result in any detectable antibody ($LOG_{10}(TI)<1.7$). The plasmid pCI-S equipped with a splice signal allows the induction of antibodies at high titers ($LOG_{10}(TI)=3.7\pm0.2$), which are approximately 60 times higher than those observed after injection of the plasmid pcDNA-S ($p<10^{-5}$).

The efficiency of the posttranscriptional signals was studied by carrying out a dose-response study of the anti-S antibody titers induced in the BALB/c mouse as a function of the quantity of plasmid DNA used as immunogen (2 µg, 10 µg and 50 µg). This study (FIG. 28B) demonstrates that the posttranscriptional signal WPRE greatly improves the efficiency of gene immunization when small doses of DNA are used ($p<10^{-5}$ for a dose of 2 µg of DNA and $p<10^{-2}$ for a dose of 10 µg), whereas the effect of the CTE signal remains marginal (p=0.34 for a dose of 2 µg of DNA).

Finally, the antibodies induced in mice after gene immunization neutralize the infectivity of SARS-CoV in vitro (FIGS. 29A and 29B) at titers which are consistent with the titers measured by ELISA.

In summary, the use of a splice signal and of the posttranscriptional signal WPRE of the woodchuck hepatitis virus considerably improves the induction of neutralizing antibodies directed against SARS-CoV after gene immunization with the aid of plasmid DNA directing the expression of the cDNA for SARS-CoV S.

EXAMPLE 13

Diagnostic Applications of the S Protein

The ELISA reactivity of the recombinant Ssol polypeptide was analyzed with respect to sera from patients suffering from SARS.

The sera from probable cases of SARS tested were chosen on the basis of the results (positive or negative) of analysis of their specific reactivity toward the native antigens of SARS-CoV by immunofluorescence test on VeroE6 cells infected with SARS-CoV and/or by indirect ELISA test using as antigen a lysate of VeroE6 cells infected with SARS-CoV. The sera of these patients are identified by a serial number of the National Reference Center for Influenza Viruses and by the initials of the patient and the number of days elapsed since the onset of the symptoms. All the sera of probable cases (cf. Table XII) recognize the native antigens of SARS-CoV, with the exception of the serum 032552 of the patient VTT for whom infection with SARS-CoV could not be confirmed by RT-PCR performed on respiratory samples of days 3, 8 and 12. A panel of control sera was used as control (TV sera): they are sera collected in France before the SARS epidemic that occurred in 2003.

TABLE XII

Sera of probable cases of SARS

| Serum | Patient | Sample collection day |
|---|---|---|
| 031724 | JYK | 7 |
| 033168 | JYK | 38 |
| 033597 | JYK | 74 |
| 032632 | NTM | 17 |
| 032634 | THA | 15 |
| 032541 | PHV | 10 |
| 032542 | NIH | 17 |
| 032552 | VTT | 8 |
| 032633 | PTU | 16 |
| 032791 | JLB | 3 |
| 033258 | JLB | 27 |
| 032703 | JCM | 8 |
| 033153 | JCM | 29 |

Solid phases sensitized with the recombinant Ssol polypeptide were prepared by adsorption of a solution of purified Ssol polypeptide at 2 µg/ml in PBS in the wells of an ELISA plate, and then the plates are incubated overnight at 4° C. and washed with PBS-Tween buffer (PBS, 0.1% Tween 20). After saturating the ELISA plates with a solution of PBS-10% skimmed milk (weight/volume) and washing in PBS-Tween, the sera to be tested (100 µl) are diluted 1/400 in PBS skimmed milk-Tween buffer (PBS, 3% skimmed milk, 0.1% Tween) and then added to the wells of the sensitized ELISA plate. The plates are incubated for 1 h at 37° C. After 3 washings with PBS-Tween buffer, the anti-human IgG conjugate labeled with peroxidase (ref. NA933V, Amersham) diluted 1/4000 in PBS-skimmed milk-Tween buffer is added, and then the plates are incubated for 1 hour at 37° C. After 6 washings with PBS-Tween buffer, the chromogen (TMB) and the substrate ($H_2O_2$) are added and the plates are incubated for 10 minutes protected from light. The reaction is stopped by adding a 1 N $H_3PO_4$ solution, and then the absorbance is measured at 450 nm with a reference at 620 nm.

The ELISA tests (FIG. 30) demonstrate that the recombinant Ssol polypeptide is specifically recognized by the serum antibodies of patients suffering from SARS collected at the medium or late phase of infection ($\geq$10 days after the onset of the symptoms) whereas it is not significantly recognized by the serum antibodies of 2 patients (JLB and JCM) collected in the early phase of infection (3 to 8 days after the onset of the symptoms) or by control sera of subjects not suffering from SARS. The serum antibodies of patients JLB and JCM show a seroconversion between days 3 and 27 for the first and 8 and 29 for the second after the onset of the symptoms, which confirms the specificity of the reactivity of these sera toward the Ssol polypeptide.

In conclusion, these results demonstrate that the recombinant Ssol polypeptide may be used as an antigen for the development of an ELISA test for serological diagnosis of infection with SARS-CoV.

EXAMPLE 14

Vaccine Applications of the Recombinant Soluble S Protein

The immunogenicity of the recombinant Ssol polypeptide was studied in mice.

For that, a group of 6 mice was immunized at 3 weeks' interval with 10 µg of recombinant Ssol polypeptide adjuvanted with 1 mg of aluminum hydroxide (Alu-gel-S, Serva) diluted in PBS. Three successive immunizations were performed and the immune sera were collected 3 weeks after each of the immunizations (IS1, IS2, IS3). As a control, a group of mice (mock group) received aluminum hydroxide alone according to the same protocol.

The immune sera were analyzed per pool for each of the 2 groups by indirect ELISA using a lysate of VeroE6 cells infected with SARS-CoV as antigen and as a control a lysate of noninfected VeroE6 cells. The anti-SARS-CoV antibody titers are calculated as the reciprocal of the dilution producing a specific OD of 0.5 after visualization with an anti-mouse IgG (H+L) polyclonal antibody coupled with peroxidase (NA931V, Amersham) and TMB supplemented with $H_2O_2$ (KPL). This analysis (FIG. 31) shows that the immunization with the Ssol polypeptide induces in mice, from the first immunization, antibodies directed against the native form of the SARS-CoV spicule protein present in the lysate of infected VeroE6 cells. After 2 then 3 immunizations, the anti-S antibody titers become very high.

The immune sera were analyzed per pool for each of the two groups for their capacity to seroneutralize the infectivity of SARS-CoV. 4 points of seroneutralization on FRhK-4 cells (100 TCID50 of SARS-CoV) are produced for each of the 2-fold dilutions tested from 1/20. The seroneutralizing titer is calculated according to the Reed and Munsch method as the reciprocal of the dilution neutralizing the infectivity of 2 wells out of 4. This analysis shows that the antibodies induced in mice by the Ssol polypeptide are neutralizing: the titers observed are very high after 2 and then 3 immunizations (greater than 2560 and 5120 respectively, table XIII).

TABLE XIII

Induction of antibodies directed against SARS-CoV after immunization with the recombinant Ssol polypeptide. The immune sera were analyzed per pool for each of the two groups for their capacity to seroneutralize the infectivity of 100 TCID50 of SARS-CoV on FRhK-4 cells. 4 points are produced for each of the 2-fold dilutions tested from 1/20. The seroneutralizing titer is calculated according to the Reed and Munsch method as the reciprocal of the dilution neutralizing the infectivity of 2 wells out of 4.

| Group | Sera | Neutralizing Ab |
|---|---|---|
| Mock | pi | <20 |
|  | IS1 | <20 |
|  | IS2 | <20 |
|  | IS3 | <20 |
| Ssol | pi | <20 |
|  | IS1 | 57 |
|  | IS2 | >2560 |
|  | IS3 | >5120 |

The neutralizing titers observed in mice immunized with the Ssol polypeptide reach levels far greater than the titers observed by Yang et al. in mice (2004, Nature, 428:561-564) and those observed by Buchholz in the hamster (2004, PNAS 101:9804-9809) which protect respectively mice and hamsters from infection with SARS-CoV. It is therefore probable that the neutralizing antibodies induced in mice after immunization with the Ssol polypeptide protect these animals against infection with SARS-CoV.

EXAMPLE 15

Optimized Synthetic Gene for the Expression in Mammalian Cells of the SARS-associated Coronavirus (SARS-CoV) Spicule (S) Protein 1) Design of the Synthetic Gene A synthetic gene encoding the SARS-CoV spicule protein was designed from the gene of the isolate 031589 (plasmid pSARS-S, C.N.C.M. No. I-3059) so as to allow high levels of expression in mammalian cells and in particular in cells of human origin.

For that:
- the use of codons of the wild-type gene of the isolate 031589 was modified so as to become close to the bias observed in humans and to improve the efficiency of translation of the corresponding mRNA
- the overall GC content of the gene was increased so as to extend the half-life of the corresponding mRNA
- the optionally cryptic motifs capable of interfering with an efficient expression of the gene were deleted (splice donor and acceptor sites, polyadenylation signals, sequences very rich (>80%) or very low (<30%) in GC, repeat sequences, sequences involved in the formation of secondary RNA structures, TATA boxes)
- a second STOP codon was added to allow efficient termination of translation.

In addition, CpG motifs were introduced into the gene so as to increase its immunogenicity as DNA vaccine. In order to facilitate the manipulation of the synthetic gene, two BamH1 and Xho1 restriction sites were placed on either side of the open reading frame of the S protein, and the BamH1, Xho1, Nhe1, Kpn1, BspE1 and Sal1 restriction sites were avoided in the synthetic gene.

The sequence of the synthetic gene designed (gene 040530) is given in SEQ ID No: 140.

An alignment of the synthetic gene 040530 with the sequence of the wild-type gene of the isolate 031589 of SARS-CoV deposited at the C.N.C.M. under the number I-3059 (SEQ ID No: 4, plasmid pSRAS-S) is presented in FIG. 32.

2) Plasmid Constructs

The synthetic gene SEQ ID No: 140 was assembled from synthetic oligonucleotides and cloned between the Kpn1 and Sac1 sites of the plasmid pUC-Kana in order to give the plasmid 040530pUC-Kana. The nucleotide sequence of the insert of the plasmid 040530pUC-Kana was verified by automated sequencing (Applied).

A Kpn1-Xho1 fragment containing the synthetic gene 040530 was excised from the plasmid 040530pUC-Kana and subcloned between the Nhe1 and Xho1 sites of the expression plasmic pCI (Promega) in order to obtain the plasmid pCI-SSYNTH, deposited at the CNCM on Dec. 1, 2004, under the number I-3333.

A synthetic gene encoding the soluble form of the S protein was then obtained by fusing the synthetic sequences encoding the ectodomain of the S protein (amino acids 1 to 1193) with those of the tag (FLAG:DYKDDDDK) via a linker BspE1 encoding the dipeptide SG. Practically, a DNA fragment encoding the ectodomain of the SARS-CoV S was amplified by PCR with the aid of the oligonucleotides 5'-ACTA GCTAGC GGATCCACCATGTTCATCTT CCTG-3' and 5'-AGTATCCGGAC TTG ATGTACT GCTCGTACTTGC-3' from the plasmid 04053-0pUC-Kana, digested with Nhe1 and BspE1 and then inserted between the unique Nhe1 and BspE1 sites of the plasmid pCI-Ssol, to give the plasmid pCI-SCUBE, deposited at the CNCM on Dec. 1, 2004, under the number I-3332. The plasmids pCI-Ssol, pCI-Ssol-CTE, and pCI-Ssol-WPRE (deposited at the CNCM, on Nov. 22, 2004, under the number I-3324) had been previously obtained by subcloning the Kpn1-Xho1 fragment excised from the plasmid pcDNA-Ssol (see technical note of DI 2004-106) between the Nhe1 and Xho1 sites of the plasmids pCI, pCI-S-CTE and pCI-S-WPRE respectively.)

The plasmids pCI-Scube and pCI-Ssol encode the same recombinant Ssol polypeptide.

3) Results

The capacity of the synthetic gene encoding the S protein to efficiently direct the expression of the SARS-CoV S in mammalian cells was compared with that of the wild-type gene after transient transfection of primate cells (VeroE6) and of human cells (293T).

In the experiment presented in FIG. 33 and in table XIV, monolayers of 5×10⁵ VeroE6 cells or 7×10⁵ 293T cells in 35 mm Petri dishes were transfected with 2 µg of plasmids pCI (as control), pCI-S, pCI-S-CTE, pCI-S-WPRE and pCI-S-Ssynth and 6 µl of Fugene6 reagent according to the manufacturer's instructions (Roche). After 48 hours of incubation at 37° C. and under 5% $CO_2$, cell extracts were prepared in loading buffer according to Laemmli, separated on 8% SDS polyacrylamide gel and then transferred onto a PVDF membrane (BioRad). The detection of this immunoblot (Western blot) was carried out with the aid of an anti-S rabbit polyclonal serum (immune serum of the rabbit P11135: cf example 4 above) and of donkey polyclonal antibodies directed against rabbit IgGs and coupled with peroxidase (NA934V, Amersham). The immunoblot was quantitatively visualized by luminescence with the aid of the ECL+ kit (Amersham) and acquisition on a digital imaging device (FluorS, BioRad).

The analysis of the results obtained with the software QuantityOne v4.2.3 (BioRad) shows that in this experiment, the plasmid pCI-Synth allows the transient expression of the S protein at high levels in the VeroE6 and 293T cells, whereas the plasmid pCI-S does not make it possible to induce expression at sufficient levels to be detected. The expression levels observed are of the order of twice as high as those observed with the plasmid pCI-S-WPRE.

TABLE XIV

Use of a synthetic gene for the expression of the SARS-CoV S. Cell extracts prepared 48 hours after transfection of VeroE6 or 293T cells with the plasmids pCI, pCI-S, pCI-S-CTE, pCI-S-WPRE and pCI-S-Ssynth were separated on 8% SDS acrylamide gel and analyzed by Western blotting with the aid of an anti-S rabbit polyclonal antibody and an anti-rabbit IgG(H + L) polyclonal antibody coupled with peroxidase (NA934V, Amersham). The Western blot is visualized by luminescence (ECL+, Amersham) and acquisition on a digital imaging device (FluorS, BioRad). The expression levels of the S protein were measured by quantifying the two predominant bands identified on the image (see FIG. 33) and are indicated according to an arbitrary scale where the value 1 represents the level measured after transfection of the plasmid pCI-S-WPRE.

| Plasmid | VeroE6 | 293T |
| --- | --- | --- |
| pCI | 0.0 | 0.0 |
| pCI-S | ≦0.1 | ≦0.1 |
| pCI-S-CTE | 0.5 | ≦0.1 |
| pCI-S-WPRE | 1.0 | 1.0 |
| pCI-Ssynth | 1.8 | 1.9 |

In a second instance, the capacity of the synthetic gene Scube to efficiently direct the synthesis and the secretion of the Ssol polypeptide by mammalian cells was compared with that of the wild-type gene after transient transfection of hamster cells (BHK-21) and of human cells (293T).

In the experiment presented in table XV, monolayers of 6×10⁵ BHK-21 cells and 7×10⁵ 293T cells in 35 mm Petri dishes were transfected with 2 µg of plasmids pCI (as control), pCI-Ssol, pCI-Ssol-CTE, pCI-Ssol-WPRE and pCI-Scube and 6 µl of Fugene6 reagent according to the manufacturer's instructions (Roche). After 48 hours of incubation at 37° C. and under 5% $CO_2$, the cellular supernatants were collected and quantitatively analyzed for the secretion of the Ssol polypeptide by a capture ELISA test specific for the Ssol polypeptide.

Analysis of the results shows that, in this experiment, the plasmid pCI-Scube allows the expression of the Ssol polypeptide at levels 8 times (BHK-21 cells) to 20 times (293T cells) higher than the plasmid pCI-Ssol. The levels of expression observed are of the order of twice (293T cells) to 5 times (BHK-21 cells) as high as those observed with the plasmid pCI-Ssol-WPRE.

TABLE XV

Use of a synthetic gene for the expression of the Ssol polypeptide. The supernatants were harvested 48 hours after transfection of BHK or 293T cells with the plasmids pCI, pCI-Ssol, pCI-Ssol-CTE, pCI-Ssol-WPRE and pCI-Scube and quantitatively analyzed for the secretion of the Ssol polypeptide by an ELISA test specific for the Ssol polypeptide. The transfections were carried out in duplicate and the results are presented in the form of means and standard deviations of the concentrations of Ssol polypeptide (ng/ml) measured in the supernatants.

| Plasmid | BHK | 293T |
| --- | --- | --- |
| pci | <20 | <20 |
| pCI-Ssol | <20 | 56 ± 10 |
| pCI-Ssol-CTE | <20 | 63 ± 8 |
| pCI-Ssol-WPRE | 28 ± 1 | 531 ± 15 |
| pCI-Scube | 152 ± 6 | 1140 ± 20 |

In summary, these results show that the expression, in mammalian cells, of the synthetic gene 040530 encoding SARS-CoV S under the control of RNA polymerase II promoter sequences is much more efficient than that of the wild-type gene of the 031589 isolate. This expression is even more efficient than that directed by the wild-type gene in the presence of the WPRE sequences of the woodchuck hepatitis virus.

4) Applications

The use of the synthetic gene 040530 encoding SARS-CoV S or its Scube variant encoding the polypeptide Ssol is capable of advantageously replacing the wild-type gene in numerous applications where the expression of S is necessary at high levels. In particular in order to:

improve the efficiency of gene immunization with plasmids of the pCI-Ssynth or even pCI-Ssynth-CTE or pCI-Ssynth-WPRE type establish novel cell lines expressing higher quantities of the S protein or of the Ssol polypeptide with the aid of recombinant lentiviral vectors carrying the Ssynth gene or the Scube gene respectively improve the immunogenicity of the recombinant lentiviral vectors allowing the expression of the S protein or of the Ssol polypeptide improve the immunogenicity of live vectors allowing the expression of the S protein or of the Ssol polypeptide like recombinant vaccinia viruses or recombinant measles viruses (see examples 16 and 17 below)

EXAMPLE 16

Expression of the SARS-associated Coronavirus (SARS-CoV) Spicule (S) Protein with the Aid of Recombinant Vaccinia Viruses Vaccine Application Application to the Production of a Soluble Form of the Spicule (S) Protein and Design of a Serological Test for SARS 1) Introduction The aim of this example is to evaluate the capacity of recombinant vaccinia viruses (VV) expressing various SARS-associated coronavirus (SARS-CoV) antigens to constitute novel vaccine candidates against SARS and a means of producing recombinant antigens in mammalian cells.

For that, the inventors focused on the SARS-CoV spicule (S) protein which makes it possible to induce, after gene immunization in animals, antibodies neutralizing the infectivity of SARS-CoV, and a soluble and secreted form of this protein, the Ssol polypeptide, which is composed of the ectodomain (aa 1-1193) of S fused at its C-ter end with a tag FLAG (DYKDDDDK) via a BspE1 linker encoding the SG dipeptide. This Ssol polypeptide exhibits an antigenicity similar to that of the S protein and allows, after injection into mice in the form of a purified protein adjuvanted with aluminum hydroxide, the induction of high neutralizing antibody titers against SARS-CoV.

The various forms of the S gene were placed under the control of the promoter of the 7.5K gene and then introduced into the thymidine kinase (TK) locus of the Copenhagen strain of the vaccinia virus by double homologous recombination in vivo. In order to improve the immunogenicity of the recombinant vaccinia viruses, a synthetic late promoter was chosen in place of the 7.5K promoter, in order to increase the production of S and Ssol during the late phases of the viral cycle.

After having isolated the recombinant vaccinia viruses and verified their capacity to express the SARS-CoV S antigen, their capacity to induce in mice an immune response against SARS was tested. After having purified the Ssol antigen from the supernatant of infected cells, an ELISA test for serodiagnosis of SARS was designed, and its efficiency was evaluated with the aid of sera from probable cases of SARS.

2) Construction of the Recombinant Viruses

Recombinant vaccinia viruses directing the expression of the S glycoprotein of the 031589 isolate of SARS-CoV and of a soluble and secreted form of this protein, the Ssol polypeptide, under the control of the 7.5K promoter were obtained. With the aim of increasing the levels of expression of S and Ssol, recombinant viruses in which the cDNAs for S and for Ssol are placed under the control of a late synthetic promoter were also obtained.

The plasmid pTG186poly is a transfer plasmid for the construction of recombinant vaccinia viruses (Kieny, 1986, Biotechnology, 4:790-795). As such, it contains the VV thymidine kinase gene into which the promoter of the 7.5K gene has been inserted followed by a multiple cloning site allowing the insertion of heterologous genes (FIG. 34A). The promoter of the 7.5K gene in fact contains a tandem of two promoter sequences that are respectively active during the early ($P_E$) and late ($P_L$) phases of the vaccinia virus replication cycle. The BamH1-Xho1 fragments were excised from the plasmids pTRIP-S and pcDNA-Ssol respectively and inserted between the BamH1 and Sma1 sites of the plasmid pTG186poly in order to give the plasmids pTG-S and pTG-Ssol (FIG. 34A). The plasmids pTG-S and pTG-Ssol were deposited at the CNCM, on Dec. 2, 2004, under the numbers I-3338 and I-3339, respectively.

The plasmids pTN480, pTN-S and pTN-Ssol were obtained from the plasmids pTG186poly, pTG-S and pTG-Ssol respectively, by substituting the Nde1-Pst1 fragment containing the 7.5K promoter by a DNA fragment containing the synthetic late promoter 480, which was obtained by hybridization of the oligonucleotides 5'-TATGAGCTTT TTTTTTTTTT TTTTTTTGGC ATATAAATAG ACTCG-GCGCG CCATCTGCA-3' and 5'-GATGGCGCGC-CGAGTCTATT TATATGCCAA AAAAAAAAAA AAAAAAAAGC TCA-3' (FIG. 34B). The insert was sequenced with the aid of a BigDye Terminator v1.1 kit (Applied Biosystems) and an automated sequencer ABI377. The sequence of the late synthetic promoter 480 as cloned into the transfer plasmids of the pTN series is indicated in FIG. 34C. The plasmids PTN-S and pTN-Ssol were deposited at the CNCM, on Dec. 2, 2004, under the numbers I-3340 and I-3341, respectively.

The recombinant vaccinia viruses were obtained by double homologous recombination in vivo between the TK cassette of the transfer plasmids of the series pTG and pTN and the TK gene of the Copenhagen strain of the vaccinia virus according to a procedure described by Kieny et al. (1984, Nature, 312: 163-166). Briefly, CV-1 cells are transfected with the aid of DOTAP (Roche) with genomic DNA of the Copenhagen strain of the vaccinia virus and each of the transfer plasmids of the pTG and pTN series described above, and then super-infected with the helper vaccinia virus VV-ts7 for 24 hours at 33° C. The helper virus is counter-selected by incubation at 40° C. for 2 days and then the recombinant viruses (TK- phenotype) selected by two cloning cycles under agar medium on 143Btk- cells in the presence of BuDr (25 µg/ml). The 6 viruses VV-TG, VV-TG-S, VV-TG-Ssol, VV-TN, VV-TN-S, and VV-TN-Ssol are respectively obtained with the aid of the transfer plasmids pTG186poly, pT-G-S, pTG-Ssol, pTN480, pTN-S, pTN-Ssol. The viruses VV-TG and VV-TN do not express any heterologous gene and were used as TK- control in the experiments. The preparations of recombinant viruses were performed on monolayers of CV-1 or BHK-21 cells and the titer in plaque forming units (p.f.u) determined on CV-1 cells according to Earl and Moss (1998, Current Protocols in Molecular Biology, 16.16.1-16.16.13).

3) Characterization of the Recombinant Viruses

The expression of the transgenes encoding the S protein and the Ssol polypeptide was assessed by Western blotting.

Monolayers of CV-1 cells were infected at a multiplicity of 2 with various recombinant vaccinia viruses VV-TG, VV-TG-S, VV-TG-Ssol, VV-TN, VV-TN-S and VV-TN-Ssol. After 18 hours of incubation at 37° C. and under 5% CO2, cellular extracts were prepared in loading buffer according to Laemmli, separated on 8% SDS polyacrylamide gel and then transferred onto a PVDF membrane (BioRad). The detection of this immunoblot (Western blot) was performed with the aid of an anti-S rabbit polyclonal serum (immune serum from the rabbit P11135: cf. example 4) and donkey polyclonal antibodies directed against rabbit IgGs and coupled with peroxidase (NA934V, Amersham). The bound antibodies were visualized by luminescence with the aid of the ECL+kit (Amersham) and autoradiography films Hyperfilm MP (Amersham).

As shown in FIG. 35A, the recombinant virus VV-TN-S directs the expression of the S protein at levels which are comparable to those which can be observed 8 h after infection with SARS-CoV but which are much higher than those which can be observed after infection with VV-TG-S. In a second experiment (FIG. 35B), the analysis of variable quantities of cellular extracts shows that the levels of expression observed after infection with viruses of the TN series (VV-TN-S and VV-TN-Ssol) are about 10 times as high as those observed with the viruses of the TG series (VV-TG-S and VV-TG-Ssol, respectively); In addition, the Ssol polypeptide is secreted into the supernatant of CV-1 cells infected with the VV-TN-Ssol virus more efficiently than in the supernatant of cells infected with VV-TG-Ssol (FIG. 36A). In this experiment, the VV-TN-Sflag virus was used as a control because it expresses the membrane form of the S protein fused at its C-ter end with the FLAG tag. The Sflag protein is not detected in the supernatant of cells infected with VV-TN-Sflag, demonstrating that the Ssol polypeptide is indeed actively secreted after infection with VV-TN-Ssol.

These results demonstrate that the recombinant vaccinia viruses are indeed carriers of the transgenes and allow the expression of the SRAS glycoprotein in its membrane form (S) or in a soluble or secreted form (Ssol). The vaccinia viruses carrying the synthetic promoter 480 allow the expression of S and the secretion of Ssol at levels much higher than the viruses carrying the promoter of the 7.5K gene.

4) Application to the Production of a Soluble Form of SARS-CoV S. Purification of this Recombinant Antigen and Diagnostic Applications The BHK-21 line is the cell line which secretes the highest quantities of Ssol polypeptide after infection with the VV-TN-Ssol virus among the lines tested (BHK-21, CV1, 293T and FrhK-4, FIG. 36B); it allows the quantitative production and purification of the recombinant Ssol polypeptide. In a typical experiment where the experimental conditions for infection, production and purification were optimized, the BHK-21 cells are inoculated in standard culture medium (pyruvate-free DMEM containing 4.5 g/l of glucose and supplemented with 5% TPB, 5% FCS, 100 U/ml of penicillin and 100 µg/ml of streptomycin) in the form of a subconfluent monolayer (10 million cells for each 100 cm$^2$ in 25 ml of medium). After 24 h of incubation at 37° C. under 5% $CO_2$, the cells are infected at an M.O.I. of 0.03 and the standard medium replaced with the secretion medium where the quantity of FCS is reduced to 0.5% and the TPB eliminated. The culture supernatant is removed after 2.5 days of incubation at 35° C. and under 5% $CO_2$ and the vaccinia virus inactivated by addition of Triton X-100 (0.1%). After filtration on 0.1 µm polyethersulfone (PES) membrane, the recombinant Ssol polypeptide is purified by affinity chromatography on an anti-FLAG matrix with elution with a solution of FLAG peptide (DYKDDDDK) at 100 µg/ml in TBS (50 mM Tris, pH 7.4, 150 mM NaCl).

The analysis by 8% SDS acrylamide gel stained with silver nitrate identified a predominant polypeptide whose molecular mass is about 180 kD and whose degree of purity is greater than 90% (FIG. 37). The concentration of the purified Ssol recombinant polypeptide was determined by comparison with molecular mass markers and estimated at 24 ng/µl.

This purified Ssol polypeptide preparation makes it possible to produce a calibration series in order to measure, with the aid of a capture ELISA test, the Ssol concentrations present in the culture supernatants. According to this test, the BHK-21 line secretes about 1 µg/ml of Ssol polypeptide under the production conditions described above. In addition, the purification scheme presented makes it possible to purify of the order of 160 µg of Ssol polypeptide per liter of culture supernatant.

The ELISA reactivity of the recombinant Ssol polypeptide was analyzed toward sera from patients suffering from SARS.

The sera of probable cases of SARS tested were chosen on the basis of the results (positive or negative) of analysis of their specific reactivity toward the native antigens of SARS-CoV by immunofluorescence test on VeroE6 cells infected with SARS-CoV and/or by indirect ELISA test using, as antigen, a lysate of VeroE6 cells infected with SARS-CoV. The sera of these patients are identified by a serial number of the National Reference Center for Influenza Viruses and by the patient's initials and the number of days elapsed since the onset of the symptoms. All the sera of probable cases (cf. table XVI) recognize the native antigens of SARS-CoV with the exception of the serum 032552 of the patient VTT, for which infection with SARS-CoV could not be confirmed by RT-PCR performed on respiratory samples of days 3, 8 and 12. A panel of control sera was used as control (TV sera): they are sera collected in France before the SARS epidemic which occurred in 2003.

TABLE XVI

Sera of probable cases of SARS

| Serum | Patient | Sample collection day |
|---|---|---|
| 033168 | JYK | 38 |
| 033597 | JYK | 74 |
| 032632 | NTM | 17 |
| 032634 | THA | 15 |
| 032541 | PHV | 10 |
| 032542 | NIH | 17 |
| 032552 | VTT | 8 |
| 032633 | PTU | 16 |

Solid phases sensitized with the recombinant Ssol polypeptide were prepared by adsorption of a solution of purified Ssol polypeptide at 4 µg/ml in PBS in the wells of an ELISA plate. The plates are incubated overnight at 4° C. and then washed with PBS-Tween buffer (PBS, 0.1% Tween 20). After washing with PBS-Tween, the sera to be tested (100 µl) are diluted 1/100 and 1/400 in PBS-skimmed milk-Tween buffer (PBS, 3% skimmed milk, 0.1% Tween) and then added to the wells of the sensitized ELISA plate. The plates are then incubated for 1 h at 37° C. After 3 washings with PBS-Tween buffer, the anti-human IgG conjugate labeled with peroxidase (ref. NA933V, Amersham) diluted 1/4000 in PBS-skimmed milk-Tween buffer is added and then the plates are incubated for one hour at 37° C. After 6 washings with PBS-Tween buffer, the chromogen (TMB) and the substrate ($H_2O_2$) are added and the plates are incubated for 10 minutes protected from light. The reaction is stopped by adding a 1M solution of $H_3PO_4$ and then the absorbance is measured at 450 nm with a reference at 620 nm.

The ELISA tests (FIG. 38) demonstrate that the recombinant Ssol polypeptide is specifically recognized by the serum antibodies of patients suffering from SARS, collected at the middle or late phase of infection ($\geq$10 days after the onset of the symptoms), whereas it is not significantly recognized by the serum antibodies of the control sera of subjects not suffering from SARS.

In conclusion, these results demonstrate that the recombinant Ssol polypeptide can be purified from the supernatant of mammalian cells infected with the recombinant vaccinia virus VV-TN-Ssol and can be used as antigen for developing an ELISA test for serological diagnosis of infection with SARS-CoV.

5. Vaccine Applications

The immunogenicity of the recombinant vaccinia viruses was studied in mice.

For that, groups of 7 BALB/c mice were immunized by the i.v. route twice at 4 weeks' interval with $10^6$ p.f.u. of recombinant vaccinia viruses VV-TG, VV-T-G-S, VV-TG-Ssol, VV-TN, VV-TN-S and VV-TN-Ssol and, as a control, VV-TG-HA which directs the expression of hemagglutinin of the A/PR/8/34 strain of the influenza virus. The immune sera were collected 3 weeks after each of the immunizations (IS1, IS2).

The immune sera were analyzed per pool for each of the groups by indirect ELISA using a lysate of VeroE6 cells infected with SARS-CoV as antigen and, as control, a lysate of noninfected VeroE6 cells. The anti-SARS-CoV antibody titers (TI) are calculated as the reciprocal of the dilution producing a specific OD of 0.5 after visualization with an anti-mouse IgG(H+L) polyclonal antibody coupled with peroxidase (NA931V, Amersham) and TMB supplemented with $H_2O_2$ (KPL). This analysis (FIG. 39A) shows that immunization with the virus VV-TG-S and VV-TN-S induces in mice, from the first immunization, antibodies directed against the native form of the SARS-CoV spicule protein present in the lysate of infected VeroE6 cells. The responses induced by the VV-TN-S virus are higher than those induced by the VV-TG-S virus after the first (TI=740 and TI=270 respectively) and the second (TI=3230 and TI=600 respectively) immunization. The VV-TN-Ssol virus induces high anti-SARS-CoV antibody titers after two immunizations (TI=640), whereas the virus VV-TG-Ssol induces a response at the detection limit (TI=40).

The immune sera were analyzed per pool for each of the groups for their capacity to seroneutralize the infectivity of SARS-CoV. 4 seroneutralization points on FRhK-4 cells (100 TCID50 of SARS-CoV) are produced for each of the 2-fold dilutions tested from 1/20. The seroneutralizing titer is calculated according to the Reed and Munsch method as the reciprocal of the dilution neutralizing the infectivity of 2 wells out of 4. This analysis shows that the antibodies induced in mice by the vaccinia viruses expressing the S protein or the Ssol polypeptide are neutralizing and that the viruses with synthetic promoters are more efficient immunogens than the viruses carrying the 7.5K promoter: the highest titers (640) are observed after 2 immunizations with the virus VV-TN-S (FIG. 39B).

The protective power of the neutralizing antibodies induced in mice after immunization with the recombinant vaccinia viruses is evaluated with the aid of a challenge infection with SARS-CoV.

6) Other Applications

Third generation recombinant vaccinia viruses are constructed by substituting the wild-type sequences of the S and Ssol genes by synthetic genes optimized for the expression in mammalian cells, described above. These recombinant vaccinia viruses are capable of expressing larger quantities of S and Ssol antigens and therefore of exhibiting increased immunogenicity.

The recombinant vaccinia virus VV-TN-Ssol can be used for the quantitative production and purification of the Ssol antigen for diagnostic (serology by ELISA) and vaccine (subunit vaccine) applications.

EXAMPLE 17

Recombinant Measles Virus Expressing the SARS-associated Coronavirus (SARS-CoV) Spicule (S) Protein. Vaccine Applications.

1) Introduction

The measles vaccine (MV) induces a lasting protective immunity in humans after a single injection (Hilleman, 2002, Vaccine, 20: 651-665). The protection conferred is very robust and is based on the induction of an antibody response and of a CD4 and CD8 cell response. The MV genome is very stable and no reversion of the vaccine strains to virulence has ever been observed. The measles virus belongs to the genus *Morbillivirus* of the Paramyxoviridae family; it is an enveloped virus whose genome is a 16 kb single-stranded RNA of negative polarity (FIG. 40A) and whose exclusively cytoplasmic replication cycle excludes any possibility of integration into the genome of the host. The measles vaccine is thus one of the most effective and one of the safest live vaccines used in the human population. Frederic Tangy's team recently developed an expression vector on the basis of the Schwarz strain of the measles virus, which is the safest attenuated strain and the most widely used in humans as vaccine against measles. This vaccine strain may be isolated from an infectious molecular clone while preserving its immunogenicity in primates and in mice that are sensitive to the infection. It constitutes, after insertion of additional transcription units, a vector for the expression of heterologous sequences (Combredet, 2003, J. Virol. 77: 11546-11554). In addition, a recombinant MV Schwarz expressing the envelope glycoprotein of the West Nile virus (WNV) induces an effective and lasting antibody response which protects mice from a lethal challenge infection with WNV (Despres et al., 2004, J. Infect. Dis., in press). All these characteristics make the attenuated Schwarz strain of the measles virus an extremely promising candidate vector for the construction of novel recombinant live vaccines.

The aim of this example is to evaluate the capacity of recombinant measles viruses (MV) expressing various SARS-associated coronavirus (SARS-CoV) antigens to constitute novel candidate vaccines against SARS.

The inventors focused on the SARS-CoV spicule (S) protein, which makes it possible to induce, after gene immunization in animals, antibodies neutralizing the infectivity of SARS-CoV, and on a soluble and secreted form of this protein, the Ssol polypeptide, which is composed of the ectodomain (aa 1-1193) of S fused at its C-ter end with a FLAG tag (DYKDDDDK) via a BspE1 linker encoding the SG dipeptide. This Ssol polypeptide exhibits a similar antigenicity to that of the S protein and allows, after injection into mice in the form of a purified protein adjuvanted with aluminum hydroxide, the induction of high neutralizing antibody titers against SARS-CoV.

The various forms of the S gene were introduced in the form of an additional transcription unit between the P (phosphoprotein) and M (matrix) genes into the cDNA of the Schwarz strain of MV previously described (Combredet, 2003, J. Virol. 77: 11546-11554; EP application No. 02291551.6 of Jun. 20, 2002, and EP application No. 02291550.8 of Jun. 20, 2002). After having isolated the recombinant viruses MVSchw2-SARS-S and MVSchw2-SARS-Ssol and checked their capacity to express the SARS-CoV S antigen, their capacity to induce a protective immune response against SARS in mice and then in monkeys was tested.

2) Construction of the Recombinant Viruses

The plasmid pTM-MVSchw-ATU2 (FIG. 40B) contains an infectious cDNA corresponding to the antigenome of the Schwarz vaccine strain of the measles virus (MV) into which an additional transcription unit (ATU) has been introduced between the P (phosphoprotein) and M (matrix) genes (Combredet, 2003, Journal of Virology, 77: 11546-11554). Recombinant genomes MVSchw2-SARS-S and MVSchw2-SARS-Ssol of the measles virus were constructed by inserting ORFs of the S protein and of the Ssol polypeptide into the additional transcription unit of the MVSchw-ATU2 vector.

For that, a DNA fragment containing the SARS-CoV S cDNA was amplified by PCR with the aid of the oligonucleotides 5'-ATACGTACGA CCATGTTTAT TTTCTTATTA TTTCTTACTC TCACT-3' and 5'-ATAGCGCGCT CATTAT-GTGT AATGTAATTT GACACCCTTG-3' using the plasmid pcDNA-S as template and then inserted into the plasmid pCR®2.1-TOPO (Invitrogen) in order to obtain the plasmid pTOPO-S-MV. The two oligonucleotides used contain restriction sites BsiW1 and BssHII, so as to allow subsequent insertion into the measles vector, and were designed so as to generate a sequence of 3774 nt including the codons for initiation and termination, so as to observe the rule of 6 which stipulates that the length of the genome of a measles virus must be divisible by 6 (Calain & Roux, 1993, J. Virol., 67: 4822-4830; Schneider et al., 1997, Virology, 227: 314-322). The insert was sequenced with the aid of a BigDye Terminator v1.1 kit (Applied Biosystems) and an automated sequencer ABI377.

To express a soluble and secreted form of SARS-CoV S, a plasmid containing the cDNA of the Ssol polypeptide corresponding to the ectodomain (aa 1-1193) of SARS-CoV S fused at its C-ter end with the sequence of a FLAG tag (DYKDDDDK) via a BspE1 linker encoding the SG dipeptide was then obtained. For that, a DNA fragment was amplified with the aid of the oligonucleotides 5'-CCATTTCAAC AATTTGGCCG-3' and 5'-ATAGGATCCG CGCGCTCATT ATTTATCGTC GTCATCTTTA TAATC-3' from the plasmid pcDNA-Ssol and then inserted into the plasmid pTOPO-S-MV between the Sal1 and BamH1 sites in order to obtain the plasmid pTOPO-S-MV-SF. The sequence generated is 3618 nt long between the BsiW1 and BssHII sites and observes the rule of 6. The insert was sequenced as indicated above.

The BsiW1-BssHII fragments containing the cDNAs for the S protein and the Ssol polypeptide were then excised by digestion of the plasmids pTOPO-S-MV and pTOPO-S-MV-SF and then subcloned between the corresponding sites of the plasmid pTM-MVSchw-ATU2 in order to give the plasmids pTM-MVSchw2-SARS-S and pTM-MVSchw2-SARS-Ssol (FIG. 40B). These two plasmids were deposited at the C.N.C.M. on Dec. 1, 2004, under the numbers I-3326 and I-3327, respectively.

The recombinant measles viruses corresponding to the plasmids pTM-MVSchw2-SARS-S and pTM-MVSchw2-SARS-Ssol were obtained by reverse genetics according to the system based on the use of a helper cell line, described by Radecke et al. (1995, Embo J., 14: 5773-5784) and modified by Parks et al. (1999, J. Virol., 73: 3560-3566). Briefly, the helper cells 293-3-46 are transfected according to the calcium phosphate method with 5 µg of the plasmids pTM-MVSchw2-SARS-S or pTM-MVSchw2-SARS-Ssol and 0.02 µg of the plasmid pEMC-La directing the expression of the MV L polymerase (gift from M. A. Billeter). After incubating overnight at 37° C., a heat shock is produced for 2 hours at 43° C. and the transfected cells are transferred onto a monolayer of Vero cells. For each of the two plasmids, syncytia appeared after 2 to 3 days of coculture and were transferred successively onto monolayers of Vero cells at 70% confluence in 35 mm Petri dishes and then in 25 and 75 cm² flasks. When the syncytia have reached 80-90% confluence, the cells are recovered with the aid of a scraper and then frozen and thawed once. After low-speed centrifugation, the supernatant containing the virus is stored in aliquots at −80° C. The titers of the recombinant viruses MVSchw2-SARS-S and MVSchw2-SARS-Ssol were determined by limiting dilution on Vero cells and the titer as dose infecting 50% of the wells ($TCID_{50}$) calculated according to the Kärber method.

3) Characterization of the Recombinant Viruses

The expression of the transgenes encoding the S protein and the Ssol polypeptide was assessed by Western blotting and immunofluorescence.

Monolayers of Vero cells in T-25 flasks were infected at a multiplicity of 0.05 by various passages of the two viruses MVSchw2-SARS-S and MVSchw2-SARS-Ssol and the wild-type virus MWSchw as a control. When the syncytia had reached 80 to 90% confluence, cytoplasmic extracts were prepared in an extraction buffer (150 mM NaCl, 50 mM Tris-HCl, pH 7.2, 1% Triton X-100, 0.1% SDS, 1% DOC)

and then diluted in loading buffer according to Laemmli, separated on 8% SDS polyacrylamide gel and transferred onto a PVDF membrane (BioRad). The detection of this immunoblot (Western blot) was carried out with the aid of an anti-S rabbit polyclonal serum (immune serum of the rabbit P11135: cf. example 4 above) and donkey polyclonal antibodies directed against rabbit IgGs and coupled with peroxidase (NA934V, Amersham). The bound antibodies were visualized by luminescence with the aid of the ECL+kit (Amersham) and Hyperfilm MP autoradiography films (Amersham).

Vero cells in monolayers on glass slides were infected with the two viruses MVSchw2-SARS-S and MVSchw2-SARS-Ssol and the wild-type virus MWSchw as a control at multiplicities of infection of 0.05. When the syncytia had reached 90 to 100% (MVSchw2-SARS-Ssol virus) or 30 to 40% (MVSchw2-SARS-S, MWSchw) confluence, the cells were fixed in a 4% PBS-PFA solution, permeabilized with a PBS solution containing 0.2% Triton and then labeled with rabbit polyclonal antibodies hyperimmunized with purified and inactivated SARS-CoV virions and with an anti-rabbit IgG (H+L) goat antibody conjugate coupled with FITC (Jackson).

As shown in FIGS. 41 and 42, the recombinant viruses MVSchw2-SARS-S and MVSchw2-SARS-Ssol direct the expression of the S protein and the Ssol polypeptide respectively at levels comparable to those which can be observed 8 h after infection with SARS-CoV. The expression of these polypeptides is stable after 3 passages of the recombinant viruses in cell culture. These results demonstrate that the recombinant measles viruses are indeed carriers of the transgenes and allow the expression of the SARS glycoprotein in its membrane form (S) or in a soluble form (Ssol). The Ssol polypeptide is expected to be secreted by cells infected with the MVSchw2-SARS-Ssol virus as is the case when this same polypeptide is expressed in mammalian cells after transient transfection of the corresponding sequences (cf. example 11 above).

4) Applications

Having shown that the viruses MVSchw2-SARS-S and MVSchw2-SARS-Ssol allow the expression of the SARS-CoV S, their capacity to induce a protective immune response against SARS-CoV in CD46$^{+/-}$ IFN-$\bar{\alpha}\beta$R$^{-/-}$ mice, which is sensitive to infection by MV, is evaluated. The antibody response of the immunized mice is evaluated by ELISA test against the native antigens of SARS-CoV and for their capacity to neutralize the infectivity of SARS-CoV in vitro, using the methodologies described above. The protective power of the response will be evaluated by measuring the reduction in the pulmonary viral load 2 days after a nonlethal challenge infection with SARS-CoV.

Second generation recombinant measles viruses are constructed by substituting the wild-type sequences of the S and Sol genes by synthetic genes optimized for expression in mammalian cells, described in example 15 above. These recombinant measles viruses are capable of expressing larger quantities of the S and Ssol antigens and therefore of exhibiting increased immunogienicity.

Alternatively, the wild-type or synthetic genes encoding the S protein or the Ssol polypeptide may be inserted into the measles vector MVSchw-ATU3 in the form of an additional transcription unit located between the H and L genes, and then the recombinant viruses produced and characterized in a similar manner. This insertion is capable of generating recombinant viruses possessing different characteristics (multiplication of the virus, level of expression of the transgene) and possibly an improved immunogenicity compared with those obtained after insertion of the transgenes between the P and N genes.

The recombinant measles virus MVSchw2-SARS-Ssol may be used for the quantitative production and the purification of the Ssol antigen for diagnostic and vaccine applications.

EXAMPLE 18

Other Applications Linked to the S Protein a) The lentiviral vectors allowing the expression of S or Ssol (or even of fragments of S) can constitute a recombinant vaccine against SARS-CoV, to be used in human or veterinary prophylaxis. In order to demonstrate the feasibility of such a vaccine, the immunogenicity of the recombinant lentiviral vectors TRIP-SD/SA-S-WPRE and TRIP-SD/SA-Ssol-WPRE is studied in mice.

b) Monoclonal antibodies are produced with the aid of the recombinant Ssol polypeptide. According to the results presented in example 14 above, these antibodies or at least the majority of them will recognize the native form of the SARS-CoV S and will be capable of diagnostic and/or prophylactic applications.

c) A serological test for SARS is developed with the Ssol polypeptide used as antigen and the double epitope methodology.

The invention claimed is:

1. An isolated or purified strain of severe acute respiratory syndrome-associated human coronavirus, characterized in that its genome has, in the form of complementary DNA, a serine codon at position 23220-23222 of the gene for the S protein or a glycine codon at position 25298-25300 of the gene for ORF3, and an alanine codon at position 7918-7920 of ORF1a or a serine codon at position 26857-26859 of the gene for the M protein, said positions being indicated in terms of reference to the Genbank sequence AY274119.3.

2. The isolated or purified coronavirus strain as claimed in claim 1, characterized in that the DNA equivalent of its genome has a sequence corresponding to the sequence SEQ ID NO: 1.

3. An isolated or purified polynucleotide, characterized in that its sequence is that of the genome of the isolated coronavirus strain as claimed in claim 1 or claim 2.

4. The isolated or purified polynucleotide as claimed in claim 3, characterized in that its sequence is SEQ ID NO: 1.

5. A fragment of the polynucleotide as claimed in claim 3, characterized in that it includes at least one pair of bases or pairs of bases corresponding to the following positions: 7919 and 23220, 7919 and 25298, 16622 and 23220, 19064 and 23220, 16622 and 25298, 19064 and 25298, 23220 and 24872, 23220 and 26857, 24872 and 25298, 25298 and 26857.

* * * * *

SEQUENCE LISTING

```
<160> NUMBER OF SEQ ID NOS: 158

<210> SEQ ID NO 1
<211> LENGTH: 29746
<212> TYPE: DNA
<213> ORGANISM: CORONAVIRUS

<400> SEQUENCE: 1
atattaggtt tttacctacc caggaaaagc caaccaacct cgatctcttg tagatctgtt      60
ctctaaacga actttaaaat ctgtgtagct gtcgctcggc tgcatgccta gtgcacctac     120
gcagtataaa caataataaa ttttactgtc gttgacaaga aacgagtaac tcgtccctct     180
tctgcagact gcttacggtt tcgtccgtgt tgcagtcgat catcagcata cctaggtttc     240
```

```
gtccgggtgt gaccgaaagg taagatggag agccttgttc ttggtgtcaa cgagaaaaca    300
cacgtccaac tcagtttgcc tgtccttcag gttagagacg tgctagtgcg tggcttcggg    360
gactctgtgg aagaggccct atcggaggca cgtgaacacc tcaaaaatgg cacttgtggt    420
ctagtagagc tggaaaaagg cgtactgccc cagcttgaac agccctatgt gttcattaaa    480
cgttctgatg ccttaagcac caatcacggc cacaaggtcg ttgagctggt tgcagaaatg    540
gacggcattc agtacggtcg tagcggtata acactggagt actcgtgcc acatgtgggc     600 gaaaccccaa ttgcataccg caatgttctt cttcgtaaga acggtaataa gggagccggt    660
ggtcatagct atggcatcga tctaaagtct tatgacttag gtgacgagct tggcactgat    720
cccattgaag attatgaaca aaactggaac actaagcatg gcagtggtgc actccgtgaa    780
ctcactcgtg agctcaatgg aggtgcagtc actcgctatg tcgacaacaa tttctgtggc    840
ccagatgggt accctcttga ttgcatcaaa gattttctcg cacgcgcggg caagtcaatg    900
tgcactcttt ccgaacaact tgattacatc gagtcgaaga gaggtgtcta ctgctgccgt    960
gaccatgagc atgaaattgc ctggttcact gagcgctctg ataagagcta cgagcaccag   1020
acacccttcg aaattaagag tgccaagaaa tttgacactt tcaaagggga atgcccaaag   1080
tttgtgtttc ctcttaactc aaaagtcaaa gtcattcaac cacgtgttga aaagaaaaag   1140
actgagggtt tcatggggcg tatacgctct gtgtaccctg ttgcatctcc acaggagtgt   1200
aacaatatgc acttgtctac cttgatgaaa tgtaatcatt gcgatgaagt ttcatggcag   1260
acgtgcgact ttctgaaagc cacttgtgaa cattgtggca ctgaaaattt agttattgaa   1320
ggacctacta catgtgggta cctacctact aatgctgtag tgaaaatgcc atgtcctgcc   1380
tgtcaagacc cagagattgg acctgagcat agtgttgcag attatcacaa ccactcaaac   1440
attgaaactc gactccgcaa gggaggtagg actagatgtt ttggaggctg tgtgtttgcc   1500
tatgttggct gctataataa gcgtgcctac tgggttcctc gtgctagtgc tgatattggc   1560
tcaggccata ctggcattac tggtgacaat gtggagacct gaatgagga tctccttgag   1620 atactgagtc gtgaacgtgt taacattaac attgttggcg attttcattt gaatgaagag   1680
gttgccatca ttttggcatc tttctctgct tctacaagtg cctttattga cactataaag   1740
agtcttgatt acaagtcttt caaaaccatt gttgagtcct gcggtaacta taaagttacc   1800
aagggaaagc ccgtaaaagg tgcttggaac attggacaac agagatcagt tttaacacca   1860
ctgtgtggtt ttccctcaca ggctgctggt gttatcagat caattttgc gcgcacactt    1920 gatgcagcaa accactcaat tcctgatttg caaagagcag ctgtcaccat acttgatggt   1980
atttctgaac agtcattacg tcttgtcgac gccatggttt atacttcaga cctgctcacc   2040
aacagtgtca ttattatggc atatgtaact ggtggtcttg tacaacagac ttctcagtgg   2100
ttgtctaatc ttttgggcac tactgttgaa aaactcaggc ctatctttga atggattgag   2160
gcgaaactta gtgcaggagt tgaatttctc aaggatgctt gggagattct caaatttctc   2220
attacaggtg tttttgacat cgtcaagggt caaatacagg ttgcttcaga taacatcaag   2280
gattgtgtaa aatgcttcat tgatgttgtt aacaaggcac tcgaaatgtg cattgatcaa   2340
gtcactatcg ctggcgcaaa gttgcgatca ctcaacttag gtgaagtctt catcgctcaa   2400
agcaagggac tttaccgtca gtgtatacgt ggcaaggagc agctgcaact actcatgcct   2460
cttaaggcac caaaagaagt aaccttctt gaaggtgatt cacatgacac agtacttacc    2520
tctgaggagg ttgttctcaa gaacggtgaa ctcgaagcac tcgagacgcc cgttgatagc   2580
ttcacaaatg gagctatcgt tggcacacca gtctgtgtaa atggcctcat gctcttagag   2640
```

```
attaaggaca aagaacaata ctgcgcattg tctcctggtt tactggctac aaacaatgtc    2700
tttcgcttaa aagggggtgc accaattaaa ggtgtaacct ttggagaaga tactgtttgg    2760
gaagttcaag gttacaagaa tgtgagaatc acatttgagc ttgatgaacg tgttgacaaa    2820
gtgcttaatg aaaagtgctc tgtctacact gttgaatccg gtaccgaagt tactgagttt    2880
gcatgtgttg tagcagaggc tgttgtgaag actttacaac cagtttctga tctccttacc    2940
aacatgggta ttgatcttga tgagtggagt gtagctacat tctacttatt tgatgatgct    3000
ggtgaagaaa acttttcatc acgtatgtat tgttcctttt accctccaga tgaggaagaa    3060
gaggacgatg cagagtgtga ggaagaagaa attgatgaaa cctgtgaaca tgagtacggt    3120
acagaggatg attatcaagg tctccctctg gaatttggtg cctcagctga aacagttcga    3180
gttgaggaag aagaagagga agactggctg gatgatacta ctgagcaatc agagattgag    3240
ccagaaccag aacctacacc tgaagaacca gttaatcagt ttactggtta tttaaaactt    3300
actgacaatg ttgccattaa atgtgttgac atcgttaagg aggcacaaag tgctaatcct    3360 atggtgatig taaatgctgc taacatacac ctgaaacatg gtggtggtgt agcaggtgca    3420
ctcaacaagg caaccaatgg tgccatgcaa aaggagagtg atgattacat taagctaaat    3480
ggccctctta cagtaggagg gtcttgtttg ctttctggac ataatcttgc taagaagtgt    3540
ctgcatgttg ttggacctaa cctaaatgca ggtgaggaca tccagcttct taaggcagca    3600
tatgaaaatt tcaattcaca ggacatctta cttgcaccat tgttgtcagc aggcatattt    3660
ggtgctaaac cacttcagtc tttacaagtg tgcgtgcaga cggttcgtac acaggtttat    3720
attgcagtca atgacaaagc tctttatgag caggttgtca tggattatct tgataacctg    3780
aagcctagag tggaagcacc taaacaagag gagccaccaa acacagaaga ttccaaaact    3840
gaggagaaat ctgtcgtaca gaagcctgtc gatgtgaagc aaaaattaa ggcctgcatt    3900 gatgaggtta ccacaacact ggaagaaact aagtttctta ccaataagtt actcttgttt    3960
gctgatatca atggtaagct ttaccatgat tctcagaaca tgcttagagg tgaagatatg    4020
tcttttcctg agaaggatgc accttacatg gtaggtgatg ttatcactag tggtgatatc    4080
acttgtgttg taatacccctc caaaaaggct ggtggcacta ctgagatgct ctcaagagct    4140
ttgaagaaag tgccagttga tgagtatata accacgtacc ctggacaagg atgtgctggt    4200
tatacacttg aggaagctaa gactgctctt aagaaatgca aatctgcatt ttatgtacta    4260
ccttcagaag cacctaatgc taaggaagag attctaggaa ctgtatcctg gaatttgaga    4320
gaaatgcttg ctcatgctga agagacaaga aaattaatgc ctatatgcat ggatgttaga    4380
gccataatgg caaccatcca acgtaagtat aaaggaatta aaattcaaga gggcatcgtt    4440
gactatggtg tccgattctt ctttttatact agtaaagagc ctgtagcttc tattattacg    4500
aagctgaact ctctaaatga gccgcttgtc acaatgccaa ttggttatgt gacacatggt    4560
tttaatcttg aagaggctgc gcgctgtatg cgttctctta agctcctgc cgtagtgtca    4620 gtatcatcac cagatgctgt tactacatat aatggatacc tcacttcgtc atcaaagaca    4680
tctgaggagc actttgtaga aacagtttct ttggctggct cttacagaga ttggtcctat    4740
tcaggacagc gtacagagtt aggtgttgaa tttcttaagc gtggtgacaa aattgtgtac    4800
cacactctgg agagccccgt cgagtttcat cttgacggtg aggttctttc acttgacaaa    4860
ctaaagagtc tcttatccct gcgggaggtt aagactataa aagtgttcac aactgtggac    4920
aacactaatc tccacacaca gcttgtggat atgtctatga catatggaca gcagtttggt    4980
```

```
ccaacatact tggatggtgc tgatgttaca aaaattaaac ctcatgtaaa tcatgagggt    5040
aagactttct ttgtactacc tagtgatgac acactacgta gtgaagcttt cgagtactac    5100
catactcttg atgagagttt tcttggtagg tacatgtctg cttaaaacca cacaaagaaa    5160
tggaaatttc ctcaagttgg tggtttaact tcaattaaat gggctgataa caattgttat    5220
ttgtctagtg ttttattagc acttcaacag cttgaagtca aattcaatgc accagcactt    5280
caagaggctt attatagagc ccgtgctggt gatgctgcta cttttgtgc actcatactc    5340 gcttacagta ataaaactgt tggcgagctt ggtgatgtca gagaaactat gacccatctt    5400
ctacagcatg ctaatttgga atctgcaaag cgagttctta atgtggtgtg taaacattgt    5460
ggtcagaaaa ctactacctt aacgggtgta gaagctgtga tgtatatggg tactctatct    5520
tatgataatc ttaagacagg tgtttccatt ccatgtgtgt gtggtcgtga tgctacacaa    5580
tatctagtac aacaagagtc ttctttttgtt atgatgtctg caccacctgc tgagtataaa    5640
ttacagcaag gtacattctt atgtgcgaat gagtacactg gtaactatca gtgtggtcat    5700
tacactcata taactgctaa ggagaccctc tatcgtattg acggagctca ccttacaaag    5760
atgtcagagt acaaaggacc agtgactgat gttttctaca aggaaacatc ttacactaca    5820
accatcaagc ctgtgtcgta taaactcgat ggagttactt acacagagat tgaaccaaaa    5880
ttggatgggt attataaaaa ggataatgct tactatacag agcagccat agaccttgta    5940 ccaactcaac cattaccaaa tgcgagtttt gataatttca aactcacatg ttctaacaca    6000
aaatttgctg atgatttaaa tcaaatgaca ggcttcacaa agccagcttc acgagagcta    6060
tctgtcacat tcttcccaga cttgaatggc gatgtagtgg ctattgacta tagacactat    6120
tcagcgagtt tcaagaaagg tgctaaatta ctgcataagc caattgtttg gcacattaac    6180
caggctacaa ccaagacaac gttcaaacca aacacttggt gtttacgttg tctttggagt    6240
acaaagccag tagatacttc aaattcattt gaagttctgg cagtagaaga cacacaagga    6300
atggacaatc ttgcttgtga aagtcaacaa cccacctctg aagaagtagt ggaaaatcct    6360
accatacaga aggaagtcat agagtgtgac gtgaaaacta ccgaagttgt aggcaatgtc    6420 atacttaaaac catcagatga aggtgttaaa gtaacacaag agttaggtca tgaggatctt    6480
atggctgctt atgtgaaaaa cacaagcatt accattaaga aacctaatga gctttcacta    6540
gccttaggtt taaaaacaat tgccactcat ggtattgctg caattaatag tgttccttgg    6600
agtaaaattt tggcttatgt caaaccattc ttaggacaag cagcaattac aacatcaaat    6660
tgcgctaaga gattagcaca acgtgtgttt aacaattata tgccttatgt gtttacatta    6720
ttgttccaat tgtgtacttt tactaaaagt accaattcta gaattagagc ttcactacct    6780
acaactattg ctaaaaatag tgttaagagt gttgctaaat tatgtttgga tgccggcatt    6840
aattatgtga agtcacccaa attttctaaa ttgttcacaa tcgctatgtg ctattgttg    6900 ttaagtattt gcttaggttc tctaatctgt gtaactgctg cttttggtgt actcttatct    6960
aattttggtg ctccttctta ttgtaatggc gttagagaat tgtatcttaa ttcgtctaac    7020
gttactacta tggattctg tgaaggttct tttccttgca gcatttgttt aagtggatta    7080
gactcccttg attcttatcc agctcttgaa accattcagg tgacgatttc atcgtacaag    7140
ctagacttga caatttttagg tctggccgct gagtgggttt tggcatatat gttgttcaca    7200
aaattctttt atttattagg tctttcagct ataatgcagg tgttctttgg ctattttgct    7260
agtcatttca tcagcaattc ttggctcatg tggttatca ttagtattgt acaaatggca    7320
cccgtttctg caatggttag gatgtacatc ttctttgctt ctttctacta catatggaag    7380
```

```
agctatgttc atatcatgga tggttgcacc tcttcgactt gcatgatgtg ctataagcgc    7440
aatcgtgcca cacgcgttga gtgtacaact attgttaatg gcatgaagag atctttctat    7500
gtctatgcaa atggaggccg tggcttctgc aagactcaca attggaattg tctcaattgt    7560
gacacatttt gcactggtag tacattcatt agtgatgaag ttgctcgtga tttgtcactc    7620
cagtttaaaa gaccaatcaa ccctactgac cagtcatcgt atattgttga tagtgttgct    7680
gtgaaaaatg gcgcgcttca cctctacttt gacaaggctg gtcaaaagac ctatgagaga    7740
catccgctct cccatttttgt caatttagac aatttgagag ctaacaacac taaaggttca    7800
ctgcctatta atgtcatagt ttttgatggc aagtccaaat gcgacgagtc tgcttctaag    7860
tctgcttctg tgtactacag tcagctgatg tgccaaccta ttctgttgct tgaccaagct    7920
cttgtatcag acgttggaga tagtactgaa gtttccgtta agatgtttga tgcttatgtc    7980 gacaccttt cagcaacttt tagtgttcct atggaaaaac ttaaggcact tgttgctaca    8040
gctcacagcg agttagcaaa gggtgtagct ttagatggtg tcctttctac attcgtgtca    8100
gctgcccgac aaggtgttgt tgataccgat gttgacacaa aggatgttat tgaatgtctc    8160
aaactttcac atcactctga cttagaagtg acaggtgaca gttgtaacaa tttcatgctc    8220
acctataata aggttgaaaa catgacgccc agagatcttg gcgcatgtat tgactgtaat    8280
gcaaggcata tcaatgccca gtagcaaaa agtcacaatg tttcactcat ctggaatgta    8340
aaagactaca tgtctttatc tgaacagctg cgtaaacaaa ttcgtagtgc tgccaagaag    8400
aacaacatac cttttagact aacttgtgct acaactagac aggttgtcaa tgtcataact    8460
actaaaatct cactcaaggg tggtaagatt gttagtactt gttttaaact tatgcttaag    8520
gccacattat tgtgcgttct tgctgcattg gtttgttata tcgttatgcc agtcatacca    8580
ttgtcaatcc atgatggtta cacaaatgaa atcattggtt acaaagccat tcaggatggt    8640
gtcactcgtg acatcatttc tactgatgat tgttttgcaa ataaacatgc tggttttgac    8700
gcatggttta gccagcgtgg tggttcatac aaaaatgaca aaagctgccc tgtagtagct    8760
gctatcatta caagagagat tggtttcata gtgcctggct taccgggtac tgtgctgaga    8820
gcaatcaatg gtgacttctt gcatttttcta cctcgtgttt ttagtgctgt tggcaacatt    8880
tgctacacac cttccaaact cattgagtat agtgattttg ctacctctgc ttgcgttctt    8940
gctgctgagt gtacaatttt taaggatgct atgggcaaac ctgtgccata ttgttatgac    9000
actaatttgc tagagggttc tatttcttat agtgagcttc gtccagacac tcgttatgtg    9060
cttatggatg gttccatcat acagtttcct aacacttacc tggagggttc tgttagagta    9120
gtaacaactt tgatgctga gtactgtaga catggtacat gcgaaaggtc agaagtaggt    9180
atttgcctat ctaccagtgg tagatgggtt cttaataatg agcattacag agctctatca    9240
ggagttttct gtggtgttga tgcgatgaat ctcatagcta acatctttac tcctcttgtg    9300
caacctgtgg gtgctttaga tgtgtctgct tcagtagtgg ctggtggtat tattgccata    9360
ttggtgactt gtgctgccta ctactttatg aaattcagac gtgttttttgg tgagtacaac    9420 catgttgttg ctgctaatgc acttttgttt ttgatgtctt tcactatact ctgtctggta    9480
ccagcttaca gctttctgcc gggagtctac tcagtctttt acttgtactt gacattctat    9540
ttcaccaatg atgtttcatt cttggctcac cttcaatggt tgccatgtt ttctcctatt    9600 gtgccttttt ggataacagc aatctatgta ttctgtattt ctctgaagca ctgccattgg    9660
ttctttaaca actatcttag gaaaagagtc atgtttaatg gagttacatt tagtaccttc    9720
```

```
gaggaggctg ctttgtgtac cttttttgctc aacaaggaaa tgtacctaaa attgcgtagc    9780
gagacactgt tgccacttac acagtataac aggtatcttg ctctatataa caagtacaag    9840
tatttcagtg gagccttaga tactaccagc tatcgtgaag cagcttgctg ccacttagca    9900
aaggctctaa atgactttag caactcaggt gctgatgttc tctaccaacc accacagaca    9960
tcaatcactt ctgctgttct gcagagtggt tttaggaaaa tggcattccc gtcaggcaaa   10020
gttgaagggt gcatggtaca agtaacctgt ggaactacaa ctcttaatgg attgtggttg   10080
gatgacacag tatactgtcc aagacatgtc atttgcacag cagaagacat gcttaatcct   10140
aactatgaag atctgctcat tcgcaaatcc aaccatagct ttcttgttca ggctggcaat   10200
gttcaacttc gtgttattgg ccattctatg caaaattgtc tgcttaggct taaagttgat   10260
acttctaacc ctaagacacc caagtataaa tttgtccgta tccaacctgg tcaaacattt   10320
tcagttctag catgctacaa tggttcacca tctggtgttt atcagtgtgc catgagacct   10380
aatcatacca ttaaaggttc tttccttaat ggatcatgtg gtagtgttgg ttttaacatt   10440
gattatgatt gcgtgtcttt ctgctatatg catcatatgg agcttccaac aggagtacac   10500
gctggtactg acttagaagg taaattctat ggtccatttg ttgacagaca aactgcacag   10560
gctgcaggta cagacacaac cataacatta aatgttttgg catggctgta tgctgctgtt   10620
atcaatggtg ataggtggtt tcttaataga ttcaccacta ctttgaatga ctttaacctt   10680
gtggcaatga agtacaacta tgaacctttg acacaagatc atgttgacat attgggacct   10740 cttctctgctc aaacaggaat tgccgtctta gatatgtgtg ctgctttgaa agagctgctg   10800
cagaatggta tgaatggtcg tactatcctt ggtagcacta ttttagaaga tgagtttaca   10860
ccatttgatg ttgttagaca atgctctggt gttaccttcc aaggtaagtt caagaaaatt   10920
gttaagggca ctcatcattg gatgcttttta actttcttga catcactatt gattcttgtt   10980
caaagtacac agtggtcact gttttttcttt gtttacgaga atgctttctt gccatttact   11040
cttggtatta tggcaattgc tgcatgtgct atgctgcttg ttaagcataa gcacgcattc   11100
ttgtgcttgt ttctgttacc ttctcttgca acagttgctt actttaatat ggtctacatg   11160
cctgctagct gggtgatgcg tatcatgaca tggcttgaat tggctgacac tagcttgtct   11220
ggttataggc ttaaggattg tgttatgtat gcttcagctt tagttttgct tattctcatg   11280
acagctcgca ctgtttatga tgatgctgct agacgtgttt ggacactgat gaatgtcatt   11340
acacttgttt acaaagtcta ctatggtaat gctttagatc aagctatttc catgtgggcc   11400 ttagtttattt ctgtaacctc taactattct ggtgtcgtta cgactatcat gttttttagct   11460 agagctatag tgtttgtgtg tgttgagtat taccattgt tatttattac tggcaacacc   11520
ttacagtgta tcatgcttgt ttattgtttc ttaggctatt gttgctgctg ctactttggc   11580
ctttcttgtt tactcaaccg ttacttcagg cttactcttg gtgtttatga ctacttggtc   11640
tctacacaag aatttaggta tatgaactcc caggggcttt gcctcctaa gagtagtatt   11700 gatgctttca agcttaacat taagttgttg ggtattggag gtaaaccatg tatcaaggtt   11760
gctactgtac agtctaaaat gtctgacgta aagtgcacat ctgtggtact gctctcggtt   11820
cttcaacaac ttagagtaga gtcatcttct aaattgtggg cacaatgtgt acaactccac   11880
aatgatattc ttcttgcaaa agacacaact gaagctttcg agaagatggt ttctcttttg   11940
tctgttttgc tatccatgca gggtgctgta gacattaata ggttgtgcga ggaaatgctc   12000
gataaccgtg ctactcttca ggctattgct tcagaattta gttctttacc atcatatgcc   12060
gcttatgcca ctgcccagga ggcctatgag caggctgtag ctaatggtga ttctgaagtc   12120
```

```
gttctcaaaa agttaaagaa atctttgaat gtggctaaat ctgagtttga ccgtgatgct    12180
gccatgcaac gcaagttgga aaagatggca gatcaggcta tgacccaaat gtacaaacag    12240
gcaagatctg aggacaagag ggcaaaagta actagtgcta tgcaaacaat gctcttcact    12300
atgcttagga agcttgataa tgatgcactt aacaacatta tcaacaatgc gcgtgatggt    12360
tgtgttccac tcaacatcat accattgact acagcagcca aactcatggt tgttgtccct    12420
gattatggta cctacaagaa cacttgtgat ggtaacacct ttacatatgc atctgcactc    12480
tgggaaatcc agcaagttgt tgatgcggat agcaagattg ttcaacttag tgaaattaac    12540
atggacaatt caccaaattt ggcttggcct cttattgtta cagctctaag agccaactca    12600
gctgttaaac tacagaataa tgaactgagt ccagtagcac tacgacagat gtcctgtgcg    12660
gctggtacca cacaaacagc ttgtactgat gacaatgcac ttgcctacta taacaattcg    12720
aagggaggta ggtttgtgct ggcattacta tcagaccacc aagatctcaa atgggctaga    12780
ttccctaaga gtgatggtac aggtacaatt tacacagaac tggaaccacc ttgtaggttt    12840
gttacagaca caccaaaagg gcctaaagtg aaatacttgt acttcatcaa aggcttaaac    12900
aacctaaata gaggtatggt gctgggcagt ttagctgcta cagtacgtct tcaggctgga    12960
aatgctacag aagtacctgc caattcaact gtgctttcct tctgtgcttt tgcagtagac    13020
cctgctaaag catataagga ttacctagca agtggaggac aaccaatcac caactgtgtg    13080
aagatgttgt gtacacacac tggtacagga caggcaatta ctgtaacacc agaagctaac    13140
atggaccaag agtcctttgg tggtgcttca tgttgtctgt attgtagatg ccacattgac    13200
catccaaatc ctaaaggatt ctgtgacttg aaaggtaagt acgtccaaat acctaccact    13260
tgtgctaatg acccagtggg ttttacactt agaaacacag tctgtaccgt ctgcggaatg    13320
tggaaaggtt atggctgtag ttgtgaccaa ctccgcgaac ccttgatgca gtctgcggat    13380
gcatcaacgt tttaaacgg gtttgcggtg taagtgcagc ccgtcttaca ccgtgcggca    13440
caggcactag tactgatgtc gtctacaggg cttttgatat ttacaacgaa aaagttgctg    13500
gttttgcaaa gttcctaaaa actaattgct gtcgcttcca ggagaaggat gaggaaggca    13560
atttattaga ctcttacttt gtagttaaga ggcatactat gtctaactac aacatgaag    13620 agactattta taacttggtt aaagattgtc cagcggttgc tgtccatgac tttttcaagt    13680
ttagagtaga tggtgacatg gtaccacata tatcacgtca gcgtctaact aaatacacaa    13740
tggctgattt agtctatgct ctacgtcatt ttgatgaggg taattgtgat acattaaaag    13800
aaatactcgt cacatacaat tgctgtgatg atgattattt caataagaag gattggtatg    13860
acttcgtaga gaatcctgac atcttacgcg tatatgctaa cttaggtgag cgtgtacgcc    13920
aatcattatt aaagactgta caattctgcg atgctatgcg tgatgcaggc attgtaggcg    13980
tactgacatt agataataag gatcttaatg ggaactggta cgatttcggt gatttcgtac    14040
aagtagcacc aggctgcgga gttcctattg tggattcata ttactcattg ctgatgccca    14100
tcctcacttt gactagggca ttggctgctg agtcccatat ggatgctgat ctcgcaaaac    14160
cacttattaa gtgggatttg ctgaaatatg attttacgga agagagactt tgtctcttcg    14220
accgttattt taaatattgg gaccagacat accatcccaa ttgtattaac tgtttggatg    14280
ataggtgtat ccttcattgt gcaaacttta atgtgttatt ttctactgtg tttccaccta    14340
caagttttgg accactagta agaaaaatat ttgtagatgg tgttccttt gttgtttcaa    14400 ctggataccca ttttcgtgag ttaggagtcg tacataatca ggatgtaaac ttacatagct    14460
```

```
cgcgtctcag tttcaaggaa cttttagtgt atgctgctga tccagctatg catgcagctt   14520
ctggcaattt attgctagat aaacgcacta catgcttttc agtagctgca ctaacaaaca   14580
atgttgcttt tcaaactgtc aaacccggta attttaataa agactttat gactttgctg    14640 tgtctaaagg tttctttaag gaaggaagtt ctgttgaact aaaacacttc ttctttgctc   14700
aggatggcaa cgctgctatc agtgattatg actattatcg ttataatctg ccaacaatgt   14760
gtgatatcag acaactccta ttcgtagttg aagttgttga taaatacttt gattgttacg   14820
atggtggctg tattaatgcc aaccaagtaa tcgttaacaa tctggataaa tcagctggtt   14880
tcccatttaa taaatggggt aaggctagac tttattatga ctcaatgagt tatgaggatc   14940
aagatgcact tttcgcgtat actaagcgta atgtcatccc tactataact caaatgaatc   15000
ttaagtatgc cattagtgca aagaatagag ctcgcaccgt agctggtgtc tctatctgta   15060
gtactatgac aaatagacag tttcatcaga aattattgaa gtcaatagcc gccactagag   15120
gagctactgt ggtaattgga acaagcaagt tttacggtgg ctggcataat atgttaaaaa   15180
ctgtttacag tgatgtagaa actccacacc ttatgggttg ggattatcca aaatgtgaca   15240
gagccatgcc taacatgctt aggataatgg cctctcttgt tcttgctcgc aaacataaca   15300
cttgctgtaa cttatcacac cgtttctaca ggttagctaa cgagtgtgcg caagtattaa   15360
gtgagatggt catgtgtggc ggctcactat atgttaaacc aggtggaaca tcatccggtg   15420
atgctacaac tgcttatgct aatagtgtct ttaacatttg tcaagctgtt acagccaatg   15480
taaatgcact tctttcaact gatggtaata agatagctga caagtatgtc cgcaatctac   15540
aacacaggct ctatgagtgt ctctatagaa atagggatgt tgatcatgaa ttcgtggatg   15600
agttttacgc ttacctgcgt aaacatttct ccatgatgat tctttctgat gatgccgttg   15660
tgtgctataa cagtaactat gcggctcaag gtttagtagc tagcattaag aactttaagg   15720 cagttctttta ttatcaaaat aatgtgttca tgtctgaggc aaaatgttgg actgagactg   15780
accttactaa aggacctcac gaattttgct cacagcatac aatgctagtt aaacaaggag   15840
atgattacgt gtacctgcct tacccagatc catcaagaat attaggcgca ggctgttttg   15900
tcgatgatat tgtcaaaaca gatggtacac ttatgattga aaggttcgtg tcactggcta   15960
ttgatgctta cccacttaca aaacatccta atcaggagta tgctgatgtc tttcacttgt   16020
atttacaata cattagaaag ttacatgatg agcttactgg ccacatgttg gacatgtatt   16080
ccgtaatgct aactaatgat aacaccctca ggtactggga acctgagttt tatgaggcta   16140
tgtacacacc acatacagtc ttgcaggctg taggtgcttg tgtattgtgc aattcacaga   16200
cttcacttcg ttgcggtgcc tgtattagga ccattcct atgttgcaag tgctgctatg    16260
accatgtcat ttcaacatca cacaaattag tgttgtctgt taatccctat gtttgcaatg   16320
ccccaggttg tgatgtcact gatgtgacac aactgtatct aggaggtatg agctattatt   16380
gcaagtcaca taagcctccc attagttttc cattatgtgc taatggtcag gttttggttt   16440
tatacaaaaa cacatgtgta ggcagtgaca atgtcactga cttcaatgcg atagcaacat   16500
gtgattggac taatgctggc gattacatac ttgccaacac ttgtactgag agactcaagc   16560
ttttcgcagc agaaacgctc aaagccactg aggaaacatt taagctgtca tatggtattg   16620
ccactgtacg cgaagtactc tctgacagag aattgcatct tcatgggag gttggaaaac   16680 ctagaccacc attgaacaga aactatgtct ttactggtta ccgtgtaact aaaaatagta   16740
aagtacagat tggagagtac accttttgaaa aaggtgacta tggtgatgct gttgtgtaca   16800
gaggtactac gacatacaag ttgaatgttg gtgattactt tgtgttgaca tctcacactg   16860
```

```
taatgccact tagtgcacct actctagtgc cacaagagca ctatgtgaga attactggct    16920
tgtacccaac actcaacatc tcagatgagt tttctagcaa tgttgcaaat tatcaaaagg    16980
tcggcatgca aaagtactct acactccaag gaccacctgg tactggtaag agtcattttg    17040
ccatcggact tgctctctat tacccatctg ctcgcatagt gtatacggca tgctctcatg    17100
cagctgttga tgccctatgt gaaaaggcat taaaatattt gcccatagat aaatgtagta    17160
gaatcatacc tgcgcgtgcg cgcgtagagt gttttgataa attcaaagtg aattcaacac    17220
tagaacagta tgttttctgc actgtaaatg cattgccaga aacaactgct gacattgtag    17280
tctttgatga aatctctatg gctactaatt atgacttgag tgttgtcaat gctagacttc    17340
gtgcaaaaca ctacgtctat attggcgatc ctgctcaatt accagccccc cgcacattgc    17400
tgactaaagg cacactagaa ccagaatatt ttaattcagt gtgcagactt atgaaaacaa    17460
taggtccaga catgttcctt ggaacttgtc gccgttgtcc tgctgaaatt gttgacactg    17520
tgagtgcttt agtttatgac aataagctaa aagcacacaa ggataagtca gctcaatgct    17580
tcaaaatgtt ctacaaaggt gttattacac atgatgtttc atctgcaatc aacagacctc    17640
aaataggcgt tgtaagagaa tttcttacac gcaatcctgc ttggagaaaa gctgttttta    17700
tctcacctta taattcacag aacgctgtag cttcaaaaat cttaggattg cctacgcaga    17760
ctgttgattc atcacagggt tctgaatatg actatgtcat attcacacaa actactgaaa    17820
cagcacactc ttgtaatgtc aaccgcttca atgtggctat cacaagggca aaaattggca    17880
ttttgtgcat aatgtctgat agagatcttt atgacaaact gcaatttaca agtctagaaa    17940
taccacgtcg caatgtggct acattacaag cagaaatgt aactggactt tttaaggact    18000
gtagtaagat cattactggt cttcatccta cacaggcacc tacacacctc agcgttgata    18060
taaagttcaa gactgaagga ttatgtgttg acataccagg cataccaaag gacatgacct    18120
accgtagact catctctatg atgggtttca aaatgaatta ccaagtcaat ggttacccta    18180
atatgtttat cacccgcgaa gaagctattc gtcacgttcg tgcgtggatt ggctttgatg    18240
tagagggctg tcatgcaact agagatgctg tgggtactaa cctacctctc agctaggat    18300 tttctacagg tgttaactta gtagctgtac cgactggtta tgttgacact gaaaataaca    18360
cagaattcac cagagttaat gcaaaacctc caccaggtga ccagtttaaa catcttatac    18420
cactcatgta taaaggcttg ccctggaatg tagtgcgtat taagatagta caaatgctca    18480
gtgatacact gaaaggattg tcagacagag tcgtgttcgt cctttgggcg catggctttg    18540
agcttacatc aatgaagtac tttgtcaaga ttggacctga agaacgtgt tgtctgtgtg    18600 acaaacgtgc aacttgcttt tctacttcat cagatactta tgcctgctgg aatcattctg    18660
tgggttttga ctatgtctat aacccattta tgattgatgt tcagcagtgg ggctttacgg    18720
gtaaccttca gagtaaccat gaccaacatt gccaggtaca tggaaatgca catgtggcta    18780
gttgtgatgc tatcatgact agatgtttag cagtccatga gtgctttgtt aagcgcgttg    18840
attggtctgt tgaataccct attataggag atgaactgag ggttaattct gcttgcagaa    18900
aagtacaaca catggttgtg aagtctgcat tgcttgctga taagtttcca gttcttcatg    18960
acattggaaa tccaaaggct atcaagtgtg tgcctcaggc tgaagtagaa tggaagttct    19020
acgatgctca gccatgtagt gacaaagctt acaaaataga ggaactcttc tattcttatg    19080
ctacacatca cgataaattc actgatggtg tttgtttgtt ttggaattgt aacgttgatc    19140
gttacccagc caatgcaatt gtgtgtaggt ttgacacaag agtcttgtca aacttgaact    19200
```

```
taccaggctg tgatggtggt agtttgtatg tgaataagca tgcattccac actccagctt   19260
tcgataaaag tgcatttact aatttaaagc aattgccttt cttttactat tctgatagtc   19320
cttgtgagtc tcatggcaaa caagtagtgt cggatattga ttatgttcca ctcaaatctg   19380
ctacgtgtat tacacgatgc aatttaggtg gtgctgtttg cagacaccat gcaaatgagt   19440
accgacagta cttggatgca tataatatga tgatttctgc tggatttagc ctatggattt   19500
acaaacaatt tgatacttat aacctgtgga atacatttac caggttacag agtttagaaa   19560
atgtggctta taatgttgtt aataaaggac actttgatgg acacgccggc gaagcacctg   19620
tttccatcat taataatgct gtttacacaa aggtagatgg tattgatgtg gagatctttg   19680
aaaataagac aacacttcct gttaatgttg catttgagct tgggctaagc gtaacatta    19740
aaccagtgcc agagattaag atactcaata atttgggtgt tgatatcgct gctaatactg   19800
taatctggga ctacaaaaga gaagccccag cacatgtatc tacaataggt gtctgcacaa   19860
tgactgacat tgccaagaaa cctactgaga gtgcttgttc ttcacttact gtcttgtttg   19920
atggtagagt ggaaggacag gtagaccttt ttagaaacgc ccgtaatggt gttttaataa   19980
cagaaggttc agtcaaaggt ctaacacctt caaagggacc agcacaagct agcgtcaatg   20040
gagtcacatt aattggagaa tcagtaaaaa cacagtttaa ctactttaag aaagtagacg   20100
gcattattca acagttgcct gaaacctact ttactcagag cagagactta gaggatttta   20160
agcccagatc acaaatggaa actgactttc tcgagctcgc tatggatgaa ttcatacagc   20220
gatataagct cgagggctat gccttcgaac acatcgttta tggagatttc agtcatggac   20280
aacttggcgg tcttcattta atgataggct tagccaagcg ctcacaagat tcaccactta   20340
aattagagga ttttatccct atggacagca cagtgaaaaa ttacttcata acagatgcgc   20400
aaacaggttc atcaaaatgt gtgtgttctg tgattgatct tttacttgat gactttgtcg   20460
agataataaa gtcacaagat ttgtcagtga tttcaaaagt ggtcaaggtt acaattgact   20520
atgctgaaat ttcattcatg ctttggtgta aggatggaca tgttgaaacc ttctacccaa   20580
aactacaagc aagtcaagcg tggcaaccag gtgttgcgat gcctaacttg tacaagatgc   20640
aaagaatgct tcttgaaaag tgtgaccttc agaattatgg tgaaaatgct gttataccaa   20700
aaggaataat gatgaatgtc gcaaagtata ctcaactgtg tcaatactta aatacactta   20760
ctttagctgt accctacaac atgagagtta ttcactttgg tgctggctct gataaaggag   20820
ttgcaccagg tacagctgtg ctcagacaat ggttgccaac tggcacacta cttgtcgatt   20880
cagatcttaa tgacttcgtc tccgacgcag attctacttt aattggagac tgtgcaacag   20940
tacatacggc taataaatgg gaccttatta ttagcgatat gtatgaccct aggaccaaac   21000
atgtgacaaa agagaatgac tctaagaag ggttttttcac ttatctgtgt ggatttataa   21060
agcaaaaact agccctgggt ggttctatag ctgtaaagat aacagagcat tcttggaatg   21120
ctgacctta caagcttatg ggccatttct catggtggac agcttttgtt acaaatgtaa   21180
atgcatcatc atcggaagca ttttttaattg gggctaacta tcttggcaag ccgaaggaac   21240
aaattgatgg ctataccatg catgctaact acatttctg gaggaacaca aatcctatcc   21300
agttgtcttc ctattcactc tttgacatga gcaaatttcc tcttaaatta gaggaactg    21360
ctgtaatgtc tcttaaggag aatcaaatca atgatatgat ttattctctt ctggaaaaag   21420
gtaggcttat cattagagaa aacaacagag ttgtggtttc aagtgatatt cttgttaaca   21480
actaaacgaa catgttttat ttcttattat ttcttactct cactagtggt agtgaccttg   21540
accggtgcac cactttgat gatgttcaag ctcctaatta cactcaacat acttcatcta   21600
```

```
tgaggggggt tactatcct gatgaaattt ttagatcaga cactctttat ttaactcagg    21660
atttatttct tccattttat tctaatgtta cagggtttca tactattaat catacgtttg    21720
gcaaccctgt cataccttt aaggatggta tttattttgc tgccacagag aaatcaaatg    21780
ttgtccgtgg ttgggttttt ggttctacca tgaacaacaa gtcacagtcg gtgattatta    21840
ttaacaattc tactaatgtt gttatacgag catgtaactt tgaattgtgt gacaacccctt   21900 tctttgctgt ttctaaaccc atgggtacac agacacatac tatgatattc gataatgcat    21960
ttaattgcac tttcgagtac atatctgatg ccttttcgct tgatgtttca gaaaagtcag    22020
gtaattttaa acacttacga gagtttgtgt ttaaaaataa agatgggttt ctctatgttt    22080
ataagggcta tcaacctata gatgtagttc gtgatctacc ttctggtttt aacactttga    22140
aacctatttt taagttgcct cttggtatta acattacaaa ttttagagcc attcttacag    22200 cctttttcacc tgctcaagac atttggggca cgtcagctgc agcctatttt gttggctatt    22260
taaagccaac tacatttatg ctcaagtatg atgaaaatgg tacaatcaca gatgctgttg    22320
attgttctca aaatccactt gctgaactca aatgctctgt taagagcttt gagattgaca    22380
aaggaattta ccagacctct aatttcaggg ttgttccctc aggagatgtt gtgagattcc    22440
ctaatattac aaacttgtgt ccttttggag aggtttttaa tgctactaaa ttcccttctg    22500
tctatgcatg ggagagaaaa aaaatttcta attgtgttgc tgattactct gtgctctaca    22560
actcaacatt ttttcaacc tttaagtgct atggcgtttc tgccactaag ttgaatgatc    22620
tttgcttctc caatgtctat gcagattctt ttgtagtcaa gggagatgat gtaagacaaa    22680
tagcgccagg acaaactggt gttattgctg attataatta taaattgcca gatgatttca    22740
tgggttgtgt ccttgcttgg aatactagga acattgatgc tacttcaact ggtaattata    22800
attataaata taggtatctt agacatggca agcttaggcc ctttgagaga gacatatcta    22860
atgtgccttt ctcccctgat ggcaaaacctt gcacccccacc tgctcttaat tgttattggc    22920
cattaaatga ttatggtttt tacaccacta ctggcattgg ctaccaacct tacagagttg    22980
tagtactttc ttttgaactt ttaaatgcac cggccacggt ttgtggacca aaattatcca    23040
ctgaccttat taagaaccag tgtgtcaatt ttaattttaa tggactcact ggtactggtg    23100
tgttaactcc ttcttcaaag agatttcaac catttcaaca atttggccgt gatgtttctg    23160
atttcactga ttccgttcga gatcctaaaa catctgaaat attagacatt tcaccttgct    23220 cttttgggg tgtaagtgta attacacctg gaacaaatgc ttcatctgaa gttgctgttc    23280
tatatcaaga tgttaactgc actgatgttt ctacagcaat tcatgcagat caactcacac    23340
cagcttggcg catatattct actggaaaca atgtattcca gactcaagca ggctgtctta    23400
taggagctga gcatgtcgac acttcttatg agtgcgacat tccattggga ctggcattt    23460 gtgctagtta ccatacagtt tctttattac gtagtactag ccaaaaatct attgtggctt    23520
atactatgtc tttaggtgct gatagttcaa ttgcttactc taataacacc attgctatac    23580
ctactaactt ttcaattagc attactacag aagtaatgcc tgtttctatg gctaaaacct    23640
ccgtagattg taatatgtac atctgcggag attctactga atgtgctaat ttgcttctcc    23700
aatatggtag cttttgcaca caactaaatc gtgcactctc aggtattgct gctgaacagg    23760
atcgcaacac acgtgaagtg ttcgctcaag tcaaacaaat gtacaaaacc ccaactttga    23820
aatattttgg tggttttaat ttttcacaaa tattacctga ccctctaaag ccaactaaga    23880 ggtctttat tgaggacttg ctctttaata aggtgacact cgctgatgct ggcttcatga    23940
```

```
agcaatatgg cgaatgccta ggtgatatta atgctagaga tctcatttgt gcgcagaagt   24000
tcaatggact tacagtgttg ccacctctgc tcactgatga tatgattgct gcctacactg   24060
ctgctctagt tagtggtact gccactgctg gatggacatt tggtgctggc gctgctcttc   24120
aaataccttt tgctatgcaa atggcatata ggttcaatgg cattggagtt acccaaaatg   24180
ttctctatga gaaccaaaaa caaatcgcca accaatttaa caaggcgatt agtcaaattc   24240
aagaatcact tacaacaaca tcaactgcat tgggcaagct gcaagacgtt gttaaccaga   24300
atgctcaagc attaaacaca cttgttaaac aacttagctc taattttggt gcaatttcaa   24360
gtgtgctaaa tgatatcctt tcgcgacttg ataaagtcga ggcggaggta caaattgaca   24420
ggttaattac aggcagactt caaagccttc aaacctatgt aacacaacaa ctaatcaggg   24480
ctgctgaaat cagggcttct gctaatcttg ctgctactaa aatgtctgag tgtgttcttg   24540
gacaatcaaa aagagttgac ttttgtggaa agggctacca ccttatgtcc ttcccacaag   24600
cagccccgca tggtgttgtc ttcctacatg tcacgtatgt gccatcccag gagaggaact   24660
tcaccacagc gccagcaatt tgtcatgaag gcaaagcata cttccctcgt gaaggtgttt   24720
ttgtgtttaa tggcacttct tggtttatta cacagaggaa cttcttttct ccacaaataa   24780
ttactacaga caatacattt gtctcaggaa attgtgatgt cgttattggc atcattaaca   24840
acacagttta tgatcctctg caacctgagc ttgactcatt caaagaagag ctggacaagt   24900
acttcaaaaa tcatacatca ccagatgttg atcttggcga catttcaggc attaacgctt   24960
ctgtcgtcaa cattcaaaaa gaaattgacc gcctcaatga ggtcgctaaa aatttaaatg   25020
aatcactcat tgaccttcaa gaattgggaa aatatgagca atatattaaa tggccttggt   25080
atgtttggct cggcttcatt gctggactaa ttgccatcgt catggttaca atcttgcttt   25140
gttgcatgac tagttgttgc agttgcctca agggtgcatg ctcttgtggt tcttgctgca   25200
agtttgatga ggatgactct gagccagttc tcaagggtgt caaattacat acacataaa   25260 cgaacttatg gatttgttta tgagattttt tactcttgga tcaattactg cacagccagt   25320
aaaaattgac aatgcttctc ctgcaagtac tgttcatgct acagcaacga taccgctaca   25380
agcctcactc ccttttcggat ggcttgttat tggcgttgca tttcttgctg ttttttcagag   25440 cgctaccaaa ataattgcgc tcaataaaag atggcagcta gccctttata agggcttcca   25500
gttcatttgc aatttactgc tgctatttgt taccatctat tcacatcttt tgcttgtcgc   25560
tgcaggtatg gaggcgcaat ttttgtacct ctatgccttg atatattttc tacaatgcat   25620
caacgcatgt agaattatta tgagatgttg gctttgttgg aagtgcaaat ccaagaaccc   25680
attactttat gatgccaact actttgtttg ctggcacaca cataactatg actactgtat   25740
accatataac agtgtcacag atacaattgt cgttactgaa ggtgacggca tttcaacacc   25800
aaaactcaaa gaagactacc aaattggtgg ttattctgag gataggcact caggtgttaa   25860
agactatgtc gttgtacatg gctatttcac cgaagtttac taccagcttg agtctacaca   25920
aattactaca gacactggta ttgaaaatgc tacattcttc atctttaaca agcttgttaa   25980
agacccaccg aatgtgcaaa tacacacaat cgacggctct tcaggagttg ctaatccagc   26040
aatggatcca atttatgatg agccgacgac gactactagc gtgcctttgt aagcacaaga   26100
aagtgagtac gaactatgt actcattcgt ttcggaagaa acaggtacgt taatagttaa   26160
tagcgtactt cttttttcttg ctttcgtggt attcttgcta gtcacactag ccatccttac   26220
tgcgcttcga ttgtgtgcgt actgctgcaa tattgttaac gtgagtttag taaaaccaac   26280
ggtttacgtc tactcgcgtg ttaaaaatct gaactcttct gaaggagttc ctgatcttct   26340
```

```
ggtctaaacg aactaactat tattattatt ctgtttggaa ctttaacatt gcttatcatg   26400
gcagacaacg gtactattac cgttgaggag cttaaacaac tcctggaaca atggaaccta   26460
gtaataggtt tcctattcct agcctggatt atgttactac aatttgccta ttctaatcgg   26520
aacaggtttt tgtacataat aaagcttgtt ttcctctggc tcttgtggcc agtaacactt   26580
gcttgttttg tgcttgctgc tgtctacaga attaattggg tgactggcgg gattgcgatt   26640
gcaatggctt gtattgtagg cttgatgtgg cttagctact tcgttgcttc cttcaggctg   26700
tttgctcgta cccgctcaat gtggtcattc aacccagaaa caaacattct tctcaatgtg   26760
cctctccggg ggacaattgt gaccagaccg ctcatggaaa gtgaacttgt cattggtgct   26820
gtgatcattc gtggtcactt gcgaatggcc ggacactccc tagggcgctg tgacattaag   26880
gacctgccaa aagagatcac tgtggctaca tcacgaacgc tttcttatta caaattagga   26940
gcgtcgcagc gtgtaggcac tgattcaggt tttgctgcat acaaccgcta ccgtattgga   27000
aactataaat taaatacaga ccacgccggt agcaacgaca atattgcttt gctagtacag   27060
taagtgacaa cagatgtttc atcttgttga cttccaggtt acaatagcag agatattgat   27120
tatcattatg aggactttca ggattgctat ttggaatctt gacgttataa taagttcaat   27180
agtgagacaa ttatttaagc ctctaactaa gaagaattat tcggagttag atgatgaaga   27240
acctatggag ttagattatc cataaaacga acatgaaaat tattctcttc ctgacattga   27300
ttgtatttac atcttgcgag ctatatcact atcaggagtg tgttagaggt acgactgtac   27360
tactaaaaga accttgccca tcaggaacat acgagggcaa ttcaccattt caccctcttg   27420
ctgacaataa atttgcacta acttgcacta gcacacactt tgcttttgct tgtgctgacg   27480
gtactcgaca tacctatcag ctgcgtgcaa gatcagtttc accaaaactt ttcatcagac   27540
aagaggaggt tcaacaagag ctctactcgc cactttttct cattgttgct gctctagtat   27600
ttttaatact ttgcttcacc attaagagaa agacagaatg aatgagctca ctttaattga   27660
cttctatttg tgcttttttag cctttctgct attccttgtt ttaataatgc ttattatatt   27720
ttggttttca ctcgaaatcc aggatctaga agaaccttgt accaaagtct aaacgaacat   27780
gaaacttctc attgttttga cttgtatttc tctatgcagt tgcatatgca ctgtagtaca   27840
gcgctgtgca tctaataaac ctcatgtgct tgaagatcct tgtaaggtac aacactaggg   27900
gtaatactta tagcactgct tggctttgtg ctctaggaaa ggttttacct tttcatagat   27960
ggcacactat ggttcaaaca tgcacaccta atgttactat caactgtcaa gatccagctg   28020
gtggtgcgct tatagctagg tgttggtacc ttcatgaagg tcaccaaact gctgcattta   28080
gagacgtact tgttgtttta aataaacgaa caaattaaaa tgtctgataa tggaccccaa   28140
tcaaaccaac gtagtgcccc ccgcattaca tttggtggac ccacagattc aactgacaat   28200
aaccagaatg gaggacgcaa tgggncaagg ccaaaacagc gccgacccca aggtttaccc   28260
aataatactg cgtcttggtt cacagctctc actcagcatg gcaaggagga acttagattc   28320
cctcgaggcc agggcgttcc aatcaacacc aatagtggtc cagatgacca aattggctac   28380
taccgaagag ctacccgacg agttcgtggt ggtgacggca aaatgaaaga gctcagcccc   28440
agatggtact tctattacct aggaactggc ccagaagctt cacttcccta cggcgctaac   28500
aaagaaggca tcgtatgggt tgcaactgag ggagccttga atacacccaa agaccacatt   28560
ggcacccgca atcctaataa caatgctgcc accgtgctac aacttcctca aggaacaaca   28620
ttgccaaaag gcttctacgc agagggaagc agaggcggca gtcaagcctc ttctcgctcc   28680
```

-continued

```
tcatcacgta gtcgcggtaa ttcaagaaat tcaactcctg gcagcagtag gggaaattct    28740
cctgctcgaa tggctagcgg aggtggtgaa actgccctcg cgctattgct gctagacaga    28800
ttgaaccagc ttgagagcaa agtttctggt aaaggccaac aacaacaagg ccaaactgtc    28860
actaagaaat ctgctgctga ggcatctaaa aagcctcgcc aaaaacgtac tgccacaaaa    28920
cagtacaacg tcactcaagc atttgggaga cgtggtccag aacaaaccca aggaaatttc    28980
ggggaccaag acctaatcag acaaggaact gattacaaac attggccgca aattgcacaa    29040
tttgctccaa gtgcctctgc attctttgga atgtcacgca ttggcatgga agtcacacct    29100
tcgggaacat ggctgactta tcatggagcc attaaattgg atgacaaaga tccacaattc    29160
aaagacaacg tcatactgct gaacaagcac attgacgcat acaaaacatt cccaccaaca    29220
gagcctaaaa aggacaaaaa gaaaaagact gatgaagctc agccttttgcc gcagagacaa    29280 aagaagcagc ccactgtgac tcttcttcct gcggctgaca tggatgattt ctccagacaa    29340
cttcaaaatt ccatgagtgg agcttctgct gattcaactc aggcataaac actcatgatg    29400
accacacaag gcagatgggc tatgtaaacg ttttcgcaat tccgtttacg atacatagtc    29460
tactcttgtg cagaatgaat tctcgtaact aaacagcaca gtaggtttag ttaacttta    29520 atctcacata gcaatcttta atcaatgtgt aacattaggg aggacttgaa agagccacca    29580
cattttcatc gaggccacgc ggagtacgat cgagggtaca gtgaataatg ctagggagag    29640
ctgcctatat ggaagagccc taatgtgtaa aattaatttt agtagtgcta tccccatgtg    29700
attttaatag cttcttagga gaatgacaaa aaaaaaaaaa aaaaaa        29746
```

<210> SEQ ID NO 2
<211> LENGTH: 3945
<212> TYPE: DNA
<213> ORGANISM: CORONAVIRUS
<220> FEATURE:
<221> NAME/KEY: CDS
<222> LOCATION: (89)..(3853)
<223> OTHER INFORMATION:

<400> SEQUENCE: 2

```
ttctcttctg gaaaaggta ggcttatcat tagagaaaac aacagagttg tggtttcaag     60
tgatattctt gttaacaact aaacgaac atg ttt att ttc tta tta ttt ctt    112
                                Met Phe Ile Phe Leu Leu Phe Leu
                                  1               5 act ctc act agt ggt agt gac ctt gac cgg tgc acc act ttt gat gat    160
Thr Leu Thr Ser Gly Ser Asp Leu Asp Arg Cys Thr Thr Phe Asp Asp
     10                  15                  20 gtt caa gct cct aat tac act caa cat act tca tct atg agg ggg gtt    208
Val Gln Ala Pro Asn Tyr Thr Gln His Thr Ser Ser Met Arg Gly Val
 25                  30                  35                  40 tac tat cct gat gaa att ttt aga tca gac act ctt tat tta act cag    256
Tyr Tyr Pro Asp Glu Ile Phe Arg Ser Asp Thr Leu Tyr Leu Thr Gln
                 45                  50                  55 gat tta ttt ctt cca ttt tat tct aat gtt aca ggg ttt cat act att    304
Asp Leu Phe Leu Pro Phe Tyr Ser Asn Val Thr Gly Phe His Thr Ile
             60                  65                  70 aat cat acg ttt ggc aac cct gtc ata cct ttt aag gat ggt att tat    352
Asn His Thr Phe Gly Asn Pro Val Ile Pro Phe Lys Asp Gly Ile Tyr
         75                  80                  85 ttt gct gcc aca gag aaa tca aat gtt gtc cgt ggt tgg gtt ttt ggt    400
Phe Ala Ala Thr Glu Lys Ser Asn Val Val Arg Gly Trp Val Phe Gly
     90                  95                 100 tct acc atg aac aac aag tca cag tcg gtg att att att aac aat tct    448
```

| | | |
|---|---|---|
| Ser Thr Met Asn Asn Lys Ser Gln Ser Val Ile Ile Asn Asn Ser<br>105                                    110                              115                         120 | | |
| act aat gtt gtt ata cga gca tgt aac ttt gaa ttg tgt gac aac cct<br>Thr Asn Val Val Ile Arg Ala Cys Asn Phe Glu Leu Cys Asp Asn Pro<br>                        125                            130                         135 | | 496 |
| ttc ttt gct gtt tct aaa ccc atg ggt aca cag aca cat act atg ata<br>Phe Phe Ala Val Ser Lys Pro Met Gly Thr Gln Thr His Thr Met Ile<br>                        140                            145                         150 | | 544 |
| ttc gat aat gca ttt aat tgc act ttc gag tac ata tct gat gcc ttt<br>Phe Asp Asn Ala Phe Asn Cys Thr Phe Glu Tyr Ile Ser Asp Ala Phe<br>                        155                            160                         165 | | 592 |
| tcg ctt gat gtt tca gaa aag tca ggt aat ttt aaa cac tta cga gag<br>Ser Leu Asp Val Ser Glu Lys Ser Gly Asn Phe Lys His Leu Arg Glu<br>                     170                          175                       180 | | 640 |
| ttt gtg ttt aaa aat aaa gat ggg ttt ctc tat gtt tat aag ggc tat<br>Phe Val Phe Lys Asn Lys Asp Gly Phe Leu Tyr Val Tyr Lys Gly Tyr<br>185                                  190                            195                       200 | | 688 |
| caa cct ata gat gta gtt cgt gat cta cct tct ggt ttt aac act ttg<br>Gln Pro Ile Asp Val Val Arg Asp Leu Pro Ser Gly Phe Asn Thr Leu<br>                        205                            210                         215 | | 736 |
| aaa cct att ttt aag ttg cct ctt ggt att aac att aca aat ttt aga<br>Lys Pro Ile Phe Lys Leu Pro Leu Gly Ile Asn Ile Thr Asn Phe Arg<br>                    220                          225                       230 | | 784 |
| gcc att ctt aca gcc ttt tca cct gct caa gac att tgg ggc acg tca<br>Ala Ile Leu Thr Ala Phe Ser Pro Ala Gln Asp Ile Trp Gly Thr Ser<br>                   235                        240                       245 | | 832 |
| gct gca gcc tat ttt gtt ggc tat tta aag cca act aca ttt atg ctc<br>Ala Ala Ala Tyr Phe Val Gly Tyr Leu Lys Pro Thr Thr Phe Met Leu<br>250                                 255                         260 | | 880 |
| aag tat gat gaa aat ggt aca atc aca gat gct gtt gat tgt tct caa<br>Lys Tyr Asp Glu Asn Gly Thr Ile Thr Asp Ala Val Asp Cys Ser Gln<br>265                                 270                            275                       280 | | 928 |
| aat cca ctt gct gaa ctc aaa tgc tct gtt aag agc ttt gag att gac<br>Asn Pro Leu Ala Glu Leu Lys Cys Ser Val Lys Ser Phe Glu Ile Asp<br>                        285                            290                         295 | | 976 |
| aaa gga att tac cag acc tct aat ttc agg gtt gtt ccc tca gga gat<br>Lys Gly Ile Tyr Gln Thr Ser Asn Phe Arg Val Val Pro Ser Gly Asp<br>                   300                          305                       310 | | 1024 |
| gtt gtg aga ttc cct aat att aca aac ttg tgt cct ttt gga gag gtt<br>Val Val Arg Phe Pro Asn Ile Thr Asn Leu Cys Pro Phe Gly Glu Val<br>                   315                          320                       325 | | 1072 |
| ttt aat gct act aaa ttc cct tct gtc tat gca tgg gag aga aaa aaa<br>Phe Asn Ala Thr Lys Phe Pro Ser Val Tyr Ala Trp Glu Arg Lys Lys<br>330                                 335                         340 | | 1120 |
| att tct aat tgt gtt gct gat tac tct gtg ctc tac aac tca aca ttt<br>Ile Ser Asn Cys Val Ala Asp Tyr Ser Val Leu Tyr Asn Ser Thr Phe<br>345                        350                            355                       360 | | 1168 |
| ttt tca acc ttt aag tgc tat ggc gtt tct gcc act aag ttg aat gat<br>Phe Ser Thr Phe Lys Cys Tyr Gly Val Ser Ala Thr Lys Leu Asn Asp<br>                        365                            370                       375 | | 1216 |
| ctt tgc ttc tcc aat gtc tat gca gat tct ttt gta gtc aag gga gat<br>Leu Cys Phe Ser Asn Val Tyr Ala Asp Ser Phe Val Val Lys Gly Asp<br>                        380                            385                       390 | | 1264 |
| gat gta aga caa ata gcg cca gga caa act ggt gtt att gct gat tat<br>Asp Val Arg Gln Ile Ala Pro Gly Gln Thr Gly Val Ile Ala Asp Tyr<br>                   395                          400                       405 | | 1312 |
| aat tat aaa ttg cca gat gat ttc atg ggt tgt gtc ctt gct tgg aat<br>Asn Tyr Lys Leu Pro Asp Asp Phe Met Gly Cys Val Leu Ala Trp Asn<br>     410                                415                        420 | | 1360 |

-continued

| | | |
|---|---|---|
| act agg aac att gat gct act tca act ggt aat tat aat tat aaa tat<br>Thr Arg Asn Ile Asp Ala Thr Ser Thr Gly Asn Tyr Asn Tyr Lys Tyr<br>425                            430                                    435                            440 | 1408 | |
| agg tat ctt aga cat ggc aag ctt agg ccc ttt gag aga gac ata tct<br>Arg Tyr Leu Arg His Gly Lys Leu Arg Pro Phe Glu Arg Asp Ile Ser<br>                                    445                                    450                            455 | 1456 | |
| aat gtg cct ttc tcc cct gat ggc aaa cct tgc acc cca cct gct ctt<br>Asn Val Pro Phe Ser Pro Asp Gly Lys Pro Cys Thr Pro Pro Ala Leu<br>                     460                                    465                                    470 | 1504 | |
| aat tgt tat tgg cca tta aat gat tat ggt ttt tac acc act act ggc<br>Asn Cys Tyr Trp Pro Leu Asn Asp Tyr Gly Phe Tyr Thr Thr Thr Gly<br>                           475                                    480                                485 | 1552 | |
| att ggc tac caa cct tac aga gtt gta gta ctt tct ttt gaa ctt tta<br>Ile Gly Tyr Gln Pro Tyr Arg Val Val Val Leu Ser Phe Glu Leu Leu<br>490                            495                                    500 | 1600 | |
| aat gca ccg gcc acg gtt tgt gga cca aaa tta tcc act gac ctt att<br>Asn Ala Pro Ala Thr Val Cys Gly Pro Lys Leu Ser Thr Asp Leu Ile<br>505                            510                                    515                      520 | 1648 | |
| aag aac cag tgt gtc aat ttt aat ttt aat gga ctc act ggt act ggt<br>Lys Asn Gln Cys Val Asn Phe Asn Phe Asn Gly Leu Thr Gly Thr Gly<br>                         525                                    530                                535 | 1696 | |
| gtg tta act cct tct tca aag aga ttt caa cca ttt caa caa ttt ggc<br>Val Leu Thr Pro Ser Ser Lys Arg Phe Gln Pro Phe Gln Gln Phe Gly<br>                     540                                    545                                    550 | 1744 | |
| cgt gat gtt tct gat ttc act gat tcc gtt cga gat cct aaa aca tct<br>Arg Asp Val Ser Asp Phe Thr Asp Ser Val Arg Asp Pro Lys Thr Ser<br>                         555                                    560                            565 | 1792 | |
| gaa ata tta gac att tca cct tgc tct ttt ggg ggt gta agt gta att<br>Glu Ile Leu Asp Ile Ser Pro Cys Ser Phe Gly Gly Val Ser Val Ile<br>570                            575                                    580 | 1840 | |
| aca cct gga aca aat gct tca tct gaa gtt gct gtt cta tat caa gat<br>Thr Pro Gly Thr Asn Ala Ser Ser Glu Val Ala Val Leu Tyr Gln Asp<br>585                            590                                    595                      600 | 1888 | |
| gtt aac tgc act gat gtt tct aca gca att cat gca gat caa ctc aca<br>Val Asn Cys Thr Asp Val Ser Thr Ala Ile His Ala Asp Gln Leu Thr<br>                         605                                    610                            615 | 1936 | |
| cca gct tgg cgc ata tat tct act gga aac aat gta ttc cag act caa<br>Pro Ala Trp Arg Ile Tyr Ser Thr Gly Asn Asn Val Phe Gln Thr Gln<br>                     620                                    625                                    630 | 1984 | |
| gca ggc tgt ctt ata gga gct gag cat gtc gac act tct tat gag tgc<br>Ala Gly Cys Leu Ile Gly Ala Glu His Val Asp Thr Ser Tyr Glu Cys<br>                       635                                    640                            645 | 2032 | |
| gac att cct att gga gct ggc att tgt gct agt tac cat aca gtt tct<br>Asp Ile Pro Ile Gly Ala Gly Ile Cys Ala Ser Tyr His Thr Val Ser<br>650                            655                                    660 | 2080 | |
| tta tta cgt agt act agc caa aaa tct att gtg gct tat act atg tct<br>Leu Leu Arg Ser Thr Ser Gln Lys Ser Ile Val Ala Tyr Thr Met Ser<br>665                            670                                    675                      680 | 2128 | |
| tta ggt gct gat agt tca att gct tac tct aat aac acc att gct ata<br>Leu Gly Ala Asp Ser Ser Ile Ala Tyr Ser Asn Asn Thr Ile Ala Ile<br>                         685                                    690                            695 | 2176 | |
| cct act aac ttt tca att agc att act aca gaa gta atg cct gtt tct<br>Pro Thr Asn Phe Ser Ile Ser Ile Thr Thr Glu Val Met Pro Val Ser<br>                     700                                    705                            710 | 2224 | |
| atg gct aaa acc tcc gta gat tgt aat atg tac atc tgc gga gat tct<br>Met Ala Lys Thr Ser Val Asp Cys Asn Met Tyr Ile Cys Gly Asp Ser<br>                         715                                    720                            725 | 2272 | |
| act gaa tgt gct aat ttg ctt ctc caa tat ggt agc ttt tgc aca caa<br>Thr Glu Cys Ala Asn Leu Leu Leu Gln Tyr Gly Ser Phe Cys Thr Gln<br>730                            735                                    740 | 2320 | |

| | |
|---|---|
| cta aat cgt gca ctc tca ggt att gct gct gaa cag gat cgc aac aca<br>Leu Asn Arg Ala Leu Ser Gly Ile Ala Ala Glu Gln Asp Arg Asn Thr<br>745                        750                        755                    760 | 2368 |
| cgt gaa gtg ttc gct caa gtc aaa caa atg tac aaa acc cca act ttg<br>Arg Glu Val Phe Ala Gln Val Lys Gln Met Tyr Lys Thr Pro Thr Leu<br>                  765                        770                        775 | 2416 |
| aaa tat ttt ggt ggt ttt aat ttt tca caa ata tta cct gac cct cta<br>Lys Tyr Phe Gly Gly Phe Asn Phe Ser Gln Ile Leu Pro Asp Pro Leu<br>                780                        785                        790 | 2464 |
| aag cca act aag agg tct ttt att gag gac ttg ctc ttt aat aag gtg<br>Lys Pro Thr Lys Arg Ser Phe Ile Glu Asp Leu Leu Phe Asn Lys Val<br>795                        800                        805 | 2512 |
| aca ctc gct gat gct ggc ttc atg aag caa tat ggc gaa tgc cta ggt<br>Thr Leu Ala Asp Ala Gly Phe Met Lys Gln Tyr Gly Glu Cys Leu Gly<br>810                        815                        820 | 2560 |
| gat att aat gct aga gat ctc att tgt gcg cag aag ttc aat gga ctt<br>Asp Ile Asn Ala Arg Asp Leu Ile Cys Ala Gln Lys Phe Asn Gly Leu<br>825                        830                        835                        840 | 2608 |
| aca gtg ttg cca cct ctg ctc act gat gat atg att gct gcc tac act<br>Thr Val Leu Pro Pro Leu Leu Thr Asp Asp Met Ile Ala Ala Tyr Thr<br>                845                        850                        855 | 2656 |
| gct gct cta gtt agt ggt act gcc act gct gga tgg aca ttt ggt gct<br>Ala Ala Leu Val Ser Gly Thr Ala Thr Ala Gly Trp Thr Phe Gly Ala<br>                860                        865                        870 | 2704 |
| ggc gct gct ctt caa ata cct ttt gct atg caa atg gca tat agg ttc<br>Gly Ala Ala Leu Gln Ile Pro Phe Ala Met Gln Met Ala Tyr Arg Phe<br>                875                        880                        885 | 2752 |
| aat ggc att gga gtt acc caa aat gtt ctc tat gag aac caa aaa caa<br>Asn Gly Ile Gly Val Thr Gln Asn Val Leu Tyr Glu Asn Gln Lys Gln<br>890                        895                        900 | 2800 |
| atc gcc aac caa ttt aac aag gcg att agt caa att caa gaa tca ctt<br>Ile Ala Asn Gln Phe Asn Lys Ala Ile Ser Gln Ile Gln Glu Ser Leu<br>905                        910                        915                        920 | 2848 |
| aca aca aca tca act gca ttg ggc aag ctg caa gac gtt gtt aac cag<br>Thr Thr Thr Ser Thr Ala Leu Gly Lys Leu Gln Asp Val Val Asn Gln<br>                925                        930                        935 | 2896 |
| aat gct caa gca tta aac aca ctt gtt aaa caa ctt agc tct aat ttt<br>Asn Ala Gln Ala Leu Asn Thr Leu Val Lys Gln Leu Ser Ser Asn Phe<br>940                        945                        950 | 2944 |
| ggt gca att tca agt gtg cta aat gat atc ctt tcg cga ctt gat aaa<br>Gly Ala Ile Ser Ser Val Leu Asn Asp Ile Leu Ser Arg Leu Asp Lys<br>                955                        960                        965 | 2992 |
| gtc gag gcg gag gta caa att gac agg tta att aca ggc aga ctt caa<br>Val Glu Ala Glu Val Gln Ile Asp Arg Leu Ile Thr Gly Arg Leu Gln<br>970                        975                        980 | 3040 |
| agc ctt caa acc tat gta aca caa caa cta atc agg gct gct gaa atc<br>Ser Leu Gln Thr Tyr Val Thr Gln Gln Leu Ile Arg Ala Ala Glu Ile<br>985                        990                        995                 1000 | 3088 |
| agg gct tct gct aat   ctt gct gct act aaa   atg tct gag tgt gtt<br>Arg Ala Ser Ala Asn   Leu Ala Ala Thr Lys   Met Ser Glu Cys Val<br>                1005                        1010                        1015 | 3133 |
| ctt gga caa tca aaa   aga gtt gac ttt tgt   gga aag ggc tac cac<br>Leu Gly Gln Ser Lys   Arg Val Asp Phe Cys   Gly Lys Gly Tyr His<br>                1020                        1025                        1030 | 3178 |
| ctt atg tcc ttc cca   caa gca gcc ccg cat   ggt gtt gtc ttc cta<br>Leu Met Ser Phe Pro   Gln Ala Ala Pro His   Gly Val Val Phe Leu<br>                1035                        1040                        1045 | 3223 |
| cat gtc acg tat gtg   cca tcc cag gag agg   aac ttc acc aca gcg<br>His Val Thr Tyr Val   Pro Ser Gln Glu Arg   Asn Phe Thr Thr Ala | 3268 |

-continued

| | | | | | | | | | | | | | | |
|---|---|---|---|---|---|---|---|---|---|---|---|---|---|---|
| cca | gca | att | tgt | cat | gaa | ggc | aaa | gca | tac | ttc | cct | cgt | gaa | ggt | 3313 |
| Pro | Ala | Ile | Cys | His | Glu | Gly | Lys | Ala | Tyr | Phe | Pro | Arg | Glu | Gly | |
| | | | 1065 | | | | 1070 | | | | | 1075 | | | |

```
cca gca att tgt cat gaa ggc aaa gca tac ttc cct cgt gaa ggt    3313
Pro Ala Ile Cys His Glu Gly Lys Ala Tyr Phe Pro Arg Glu Gly
            1065            1070                1075 gtt ttt gtg ttt aat ggc act tct tgg ttt att aca cag agg aac    3358
Val Phe Val Phe Asn Gly Thr Ser Trp Phe Ile Thr Gln Arg Asn
            1080            1085                1090 ttc ttt tct cca caa ata att act aca gac aat aca ttt gtc tca    3403
Phe Phe Ser Pro Gln Ile Ile Thr Thr Asp Asn Thr Phe Val Ser
            1095            1100                1105 gga aat tgt gat gtc gtt att ggc atc att aac aac aca gtt tat    3448
Gly Asn Cys Asp Val Val Ile Gly Ile Ile Asn Asn Thr Val Tyr
            1110            1115                1120 gat cct ctg caa cct gag ctt gac tca ttc aaa gaa gag ctg gac    3493
Asp Pro Leu Gln Pro Glu Leu Asp Ser Phe Lys Glu Glu Leu Asp
            1125            1130                1135 aag tac ttc aaa aat cat aca tca cca gat gtt gat ctt ggc gac    3538
Lys Tyr Phe Lys Asn His Thr Ser Pro Asp Val Asp Leu Gly Asp
            1140            1145                1150 att tca ggc att aac gct tct gtc gtc aac att caa aaa gaa att    3583
Ile Ser Gly Ile Asn Ala Ser Val Val Asn Ile Gln Lys Glu Ile
            1155            1160                1165 gac cgc ctc aat gag gtc gct aaa aat tta aat gaa tca ctc att    3628
Asp Arg Leu Asn Glu Val Ala Lys Asn Leu Asn Glu Ser Leu Ile
            1170            1175                1180 gac ctt caa gaa ttg gga aaa tat gag caa tat att aaa tgg cct    3673
Asp Leu Gln Glu Leu Gly Lys Tyr Glu Gln Tyr Ile Lys Trp Pro
            1185            1190                1195 tgg tat gtt tgg ctc ggc ttc att gct gga cta att gcc atc gtc    3718
Trp Tyr Val Trp Leu Gly Phe Ile Ala Gly Leu Ile Ala Ile Val
            1200            1205                1210 atg gtt aca atc ttg ctt tgt tgc atg act agt tgt tgc agt tgc    3763
Met Val Thr Ile Leu Leu Cys Cys Met Thr Ser Cys Cys Ser Cys
            1215            1220                1225 ctc aag ggt gca tgc tct tgt ggt tct tgc tgc aag ttt gat gag    3808
Leu Lys Gly Ala Cys Ser Cys Gly Ser Cys Cys Lys Phe Asp Glu
            1230            1235                1240 gat gac tct gag cca gtt ctc aag ggt gtc aaa tta cat tac aca    3853
Asp Asp Ser Glu Pro Val Leu Lys Gly Val Lys Leu His Tyr Thr
            1245            1250                1255 taaacgaact tatggatttg tttatgagat tttttactct tggatcaatt actgcacagc    3913
cagtaaaaat tgacaatgct tctcctgcaa gt    3945
```

<210> SEQ ID NO 3
<211> LENGTH: 1255
<212> TYPE: PRT
<213> ORGANISM: CORONAVIRUS

<400> SEQUENCE: 3

```
Met Phe Ile Phe Leu Leu Phe Leu Thr Leu Thr Ser Gly Ser Asp Leu
1               5                   10                  15

Asp Arg Cys Thr Thr Phe Asp Asp Val Gln Ala Pro Asn Tyr Thr Gln
                20                  25                  30

His Thr Ser Ser Met Arg Gly Val Tyr Tyr Pro Asp Glu Ile Phe Arg
            35                  40                  45

Ser Asp Thr Leu Tyr Leu Thr Gln Asp Leu Phe Leu Pro Phe Tyr Ser
        50                  55                  60

Asn Val Thr Gly Phe His Thr Ile Asn His Thr Phe Gly Asn Pro Val
```

```
            65                  70                  75                  80
Ile Pro Phe Lys Asp Gly Ile Tyr Phe Ala Thr Glu Lys Ser Asn
                85                  90                  95
Val Val Arg Gly Trp Val Phe Gly Ser Thr Met Asn Asn Lys Ser Gln
                100                 105                 110
Ser Val Ile Ile Ile Asn Asn Ser Thr Asn Val Val Ile Arg Ala Cys
                115                 120                 125
Asn Phe Glu Leu Cys Asp Asn Pro Phe Phe Ala Val Ser Lys Pro Met
                130                 135                 140
Gly Thr Gln Thr His Thr Met Ile Phe Asp Asn Ala Phe Asn Cys Thr
145                 150                 155                 160
Phe Glu Tyr Ile Ser Asp Ala Phe Ser Leu Asp Val Ser Glu Lys Ser
                165                 170                 175
Gly Asn Phe Lys His Leu Arg Glu Phe Val Phe Lys Asn Lys Asp Gly
                180                 185                 190
Phe Leu Tyr Val Tyr Lys Gly Tyr Gln Pro Ile Asp Val Val Arg Asp
                195                 200                 205
Leu Pro Ser Gly Phe Asn Thr Leu Lys Pro Ile Phe Lys Leu Pro Leu
210                 215                 220
Gly Ile Asn Ile Thr Asn Phe Arg Ala Ile Leu Thr Ala Phe Ser Pro
225                 230                 235                 240
Ala Gln Asp Ile Trp Gly Thr Ser Ala Ala Ala Tyr Phe Val Gly Tyr
                245                 250                 255
Leu Lys Pro Thr Thr Phe Met Leu Lys Tyr Asp Glu Asn Gly Thr Ile
                260                 265                 270
Thr Asp Ala Val Asp Cys Ser Gln Asn Pro Leu Ala Glu Leu Lys Cys
                275                 280                 285
Ser Val Lys Ser Phe Glu Ile Asp Lys Gly Ile Tyr Gln Thr Ser Asn
                290                 295                 300
Phe Arg Val Val Pro Ser Gly Asp Val Val Arg Phe Pro Asn Ile Thr
305                 310                 315                 320
Asn Leu Cys Pro Phe Gly Glu Val Phe Asn Ala Thr Lys Phe Pro Ser
                325                 330                 335
Val Tyr Ala Trp Glu Arg Lys Lys Ile Ser Asn Cys Val Ala Asp Tyr
                340                 345                 350
Ser Val Leu Tyr Asn Ser Thr Phe Phe Ser Thr Phe Lys Cys Tyr Gly
                355                 360                 365
Val Ser Ala Thr Lys Leu Asn Asp Leu Cys Phe Ser Asn Val Tyr Ala
                370                 375                 380
Asp Ser Phe Val Val Lys Gly Asp Asp Val Arg Gln Ile Ala Pro Gly
385                 390                 395                 400
Gln Thr Gly Val Ile Ala Asp Tyr Asn Tyr Lys Leu Pro Asp Asp Phe
                405                 410                 415
Met Gly Cys Val Leu Ala Trp Asn Thr Arg Asn Ile Asp Ala Thr Ser
                420                 425                 430
Thr Gly Asn Tyr Asn Tyr Lys Tyr Arg Tyr Leu Arg His Gly Lys Leu
                435                 440                 445
Arg Pro Phe Glu Arg Asp Ile Ser Asn Val Pro Phe Ser Pro Asp Gly
                450                 455                 460
Lys Pro Cys Thr Pro Pro Ala Leu Asn Cys Tyr Trp Pro Leu Asn Asp
465                 470                 475                 480
Tyr Gly Phe Tyr Thr Thr Thr Gly Ile Gly Tyr Gln Pro Tyr Arg Val
                485                 490                 495
```

-continued

Val Val Leu Ser Phe Glu Leu Leu Asn Ala Pro Ala Thr Val Cys Gly
            500                 505                 510

Pro Lys Leu Ser Thr Asp Leu Ile Lys Asn Gln Cys Val Asn Phe Asn
            515                 520                 525

Phe Asn Gly Leu Thr Gly Thr Gly Val Leu Thr Pro Ser Ser Lys Arg
            530                 535                 540

Phe Gln Pro Phe Gln Gln Phe Gly Arg Asp Val Ser Asp Phe Thr Asp
545                 550                 555                 560

Ser Val Arg Asp Pro Lys Thr Ser Glu Ile Leu Asp Ile Ser Pro Cys
                565                 570                 575

Ser Phe Gly Gly Val Ser Val Ile Thr Pro Gly Thr Asn Ala Ser Ser
            580                 585                 590

Glu Val Ala Val Leu Tyr Gln Asp Val Asn Cys Thr Asp Val Ser Thr
            595                 600                 605

Ala Ile His Ala Asp Gln Leu Thr Pro Ala Trp Arg Ile Tyr Ser Thr
            610                 615                 620

Gly Asn Asn Val Phe Gln Thr Gln Ala Gly Cys Leu Ile Gly Ala Glu
625                 630                 635                 640

His Val Asp Thr Ser Tyr Glu Cys Asp Ile Pro Ile Gly Ala Gly Ile
                645                 650                 655

Cys Ala Ser Tyr His Thr Val Ser Leu Leu Arg Ser Thr Ser Gln Lys
            660                 665                 670

Ser Ile Val Ala Tyr Thr Met Ser Leu Gly Ala Asp Ser Ser Ile Ala
            675                 680                 685

Tyr Ser Asn Asn Thr Ile Ala Ile Pro Thr Asn Phe Ser Ile Ser Ile
            690                 695                 700

Thr Thr Glu Val Met Pro Val Ser Met Ala Lys Thr Ser Val Asp Cys
705                 710                 715                 720

Asn Met Tyr Ile Cys Gly Asp Ser Thr Glu Cys Ala Asn Leu Leu Leu
                725                 730                 735

Gln Tyr Gly Ser Phe Cys Thr Gln Leu Asn Arg Ala Leu Ser Gly Ile
            740                 745                 750

Ala Ala Glu Gln Asp Arg Asn Thr Arg Glu Val Phe Ala Gln Val Lys
            755                 760                 765

Gln Met Tyr Lys Thr Pro Thr Leu Lys Tyr Phe Gly Gly Phe Asn Phe
            770                 775                 780

Ser Gln Ile Leu Pro Asp Pro Leu Lys Pro Thr Lys Arg Ser Phe Ile
785                 790                 795                 800

Glu Asp Leu Leu Phe Asn Lys Val Thr Leu Ala Asp Ala Gly Phe Met
                805                 810                 815

Lys Gln Tyr Gly Glu Cys Leu Gly Asp Ile Asn Ala Arg Asp Leu Ile
            820                 825                 830

Cys Ala Gln Lys Phe Asn Gly Leu Thr Val Leu Pro Pro Leu Leu Thr
            835                 840                 845

Asp Asp Met Ile Ala Ala Tyr Thr Ala Ala Leu Val Ser Gly Thr Ala
850                 855                 860

Thr Ala Gly Trp Thr Phe Gly Ala Gly Ala Ala Leu Gln Ile Pro Phe
865                 870                 875                 880

Ala Met Gln Met Ala Tyr Arg Phe Asn Gly Ile Gly Val Thr Gln Asn
                885                 890                 895

Val Leu Tyr Glu Asn Gln Lys Gln Ile Ala Asn Gln Phe Asn Lys Ala
            900                 905                 910

```
Ile Ser Gln Ile Gln Glu Ser Leu Thr Thr Thr Ser Thr Ala Leu Gly
            915                 920                 925

Lys Leu Gln Asp Val Val Asn Gln Asn Ala Gln Ala Leu Asn Thr Leu
        930                 935                 940

Val Lys Gln Leu Ser Ser Asn Phe Gly Ala Ile Ser Ser Val Leu Asn
945                 950                 955                 960

Asp Ile Leu Ser Arg Leu Asp Lys Val Glu Ala Glu Val Gln Ile Asp
                965                 970                 975

Arg Leu Ile Thr Gly Arg Leu Gln Ser Leu Gln Thr Tyr Val Thr Gln
            980                 985                 990

Gln Leu Ile Arg Ala Ala Glu Ile Arg Ala Ser Ala Asn Leu Ala Ala
                995                 1000                1005

Thr Lys Met Ser Glu Cys Val Leu Gly Gln Ser Lys Arg Val Asp
    1010                1015                1020

Phe Cys Gly Lys Gly Tyr His Leu Met Ser Phe Pro Gln Ala Ala
    1025                1030                1035

Pro His Gly Val Val Phe Leu His Val Thr Tyr Val Pro Ser Gln
    1040                1045                1050

Glu Arg Asn Phe Thr Thr Ala Pro Ala Ile Cys His Glu Gly Lys
    1055                1060                1065

Ala Tyr Phe Pro Arg Glu Gly Val Phe Val Phe Asn Gly Thr Ser
    1070                1075                1080

Trp Phe Ile Thr Gln Arg Asn Phe Phe Ser Pro Gln Ile Ile Thr
    1085                1090                1095

Thr Asp Asn Thr Phe Val Ser Gly Asn Cys Asp Val Val Ile Gly
    1100                1105                1110

Ile Ile Asn Asn Thr Val Tyr Asp Pro Leu Gln Pro Glu Leu Asp
    1115                1120                1125

Ser Phe Lys Glu Glu Leu Asp Lys Tyr Phe Lys Asn His Thr Ser
    1130                1135                1140

Pro Asp Val Asp Leu Gly Asp Ile Ser Gly Ile Asn Ala Ser Val
    1145                1150                1155

Val Asn Ile Gln Lys Glu Ile Asp Arg Leu Asn Glu Val Ala Lys
    1160                1165                1170

Asn Leu Asn Glu Ser Leu Ile Asp Leu Gln Glu Leu Gly Lys Tyr
    1175                1180                1185

Glu Gln Tyr Ile Lys Trp Pro Trp Tyr Val Trp Leu Gly Phe Ile
    1190                1195                1200

Ala Gly Leu Ile Ala Ile Val Met Val Thr Ile Leu Leu Cys Cys
    1205                1210                1215

Met Thr Ser Cys Cys Ser Cys Leu Lys Gly Ala Cys Ser Cys Gly
    1220                1225                1230

Ser Cys Cys Lys Phe Asp Glu Asp Asp Ser Glu Pro Val Leu Lys
    1235                1240                1245

Gly Val Lys Leu His Tyr Thr
    1250                1255

<210> SEQ ID NO 4
<211> LENGTH: 3943
<212> TYPE: DNA
<213> ORGANISM: CORONAVIRUS

<400> SEQUENCE: 4
ctcttctgga aaaaggtagg cttatcatta gagaaaacaa cagagttgtg gtttcaagtg      60
```

```
atattcttgt taacaactaa acgaacatgt ttattttctt attatttctt actctcacta      120
gtggtagtga ccttgaccgg tgcaccactt ttgatgatgt tcaagctcct aattacactc      180
aacatacttc atctatgagg ggggtttact atcctgatga aatttttaga tcagacactc      240
tttatttaac tcaggattta tttcttccat tttattctaa tgttacaggg tttcatacta      300
ttaatcatac gtttggcaac cctgtcatac cttttaagga tggtatttat tttgctgcca      360
cagagaaatc aaatgttgtc cgtggttggg ttttggttc taccatgaac aacaagtcac       420
agtcggtgat tattattaac aattctacta atgttgttat acgagcatgt aactttgaat      480
tgtgtgacaa ccctttcttt gctgtttcta aacccatggg tacacagaca catactatga      540
tattcgataa tgcatttaat tgcactttcg agtacatatc tgatgccttt tcgcttgatg      600
tttcagaaaa gtcaggtaat tttaaacact tacgagagtt tgtgtttaaa aataaagatg      660
ggtttctcta tgtttataag ggctatcaac ctatagatgt agttcgtgat ctaccttctg      720
gttttaacac tttgaaacct attttttaagt tgcctcttgg tattaacatt acaaattta     780 gagccattct tacagccttt tcacctgctc aagacatttg gggcacgtca gctgcagcct      840
attttgttgg ctatttaaag ccaactacat ttatgctcaa gtatgatgaa aatggtacaa      900
tcacagatgc tgttgattgt tctcaaaatc cacttgctga actcaaatgc tctgttaaga      960
gctttgagat tgacaaagga atttaccaga cctctaattt cagggttgtt ccctcaggag     1020
atgttgtgag attccctaat attacaaact tgtgtccttt tggagaggtt tttaatgcta     1080
ctaaattccc ttctgtctat gcatgggaga gaaaaaaaat ttctaattgt gttgctgatt     1140
actctgtgct ctacaactca acattttttt caacctttaa gtgctatggc gtttctgcca     1200
ctaagttgaa tgatctttgc ttctccaatg tctatgcaga ttcttttgta gtcaagggag     1260
atgatgtaag acaaatagcg ccaggacaaa ctggtgttat tgctgattat aattataaat     1320
tgccagatga tttcatgggt tgtgtccttg cttggaatac taggaacatt gatgctactt     1380
caactggtaa ttataattat aaatataggt atcttagaca tggcaagctt aggccctttg     1440
agagagacat atctaatgtg cctttctccc ctgatggcaa accttgcacc ccacctgctc     1500
ttaattgtta ttggccatta aatgattatg gttttacac cactactggc attggctacc      1560
aaccttacag agttgtagta ctttcttttg aacttttaaa tgcaccggcc acggtttgtg     1620
gaccaaaatt atccactgac cttattaaga accagtgtgt caattttaat tttaatggac     1680
tcactggtac tggtgtgtta actccttctt caaagagatt tcaaccattt caacaatttg     1740
gccgtgatgt ctctgatttc actgattccg ttcgagatcc taaaacatct gaaatattag     1800
acatttcacc ttgctctttt gggggtgtaa gtgtaattac acctggaaca aatgcttcat     1860
ctgaagttgc tgttctatat caagatgtta actgcactga tgtttctaca gcaatccatg     1920
cagatcaact cacaccagct tggcgcatat attctactgg aaacaatgta ttccagactc     1980
aagcaggctg tcttatagga gctgagcatg tcgacacttc ttatgagtgc gacattccta     2040
ttggagctgg catttgtgct agttaccata cagtttcttt attacgtagt actagccaaa     2100
aatctattgt ggcttatact atgtctttag gtgctgatag ttcaattgct tactctaata     2160
acaccattgc tatacctact aacttttcaa ttagcattac tacagaagta atgcctgttt     2220
ctatggctaa aacctccgta gattgtaata tgtacatctg cggagattct actgaatgtg     2280
ctaatttgct tctccaatat ggtagctttt gcacacaact aaatcgtgca ctctcaggta     2340
ttgctgctga acaggatcgc aacacacgtg aagtgttcgc tcaagtcaaa caaatgtaca     2400 aaccccaac tttgaaatat tttggtggtt ttaattttc acaaatatta cctgaccctc      2460
```

| | |
|---|---:|
| taaagccaac taagaggtct tttattgagg acttgctctt taataaggtg acactcgctg | 2520 |
| atgctggctt catgaagcaa tatggcgaat gcctaggtga tattaatgct agagatctca | 2580 |
| tttgtgcgca gaagttcaat gggcttacag tgttgccacc tctgctcact gatgatatga | 2640 |
| ttgctgccta cactgctgct ctagttagtg gtactgccac tgctggatgg acatttggtg | 2700 |
| ctggcgctgc tcttcaaata ccttttgcta tgcaaatggc ataggttc aatggcattg | 2760 |
| gagttaccca aaatgttctc tatgagaacc aaaaacaaat cgccaaccaa tttaacaagg | 2820 |
| cgattagtca aattcaagaa tcacttacaa caacatcaac tgcattgggc aagctgcaag | 2880 |
| acgttgttaa ccagaatgct caagcattaa acacacttgt taaacaactt agctctaatt | 2940 |
| ttggtgcaat ttcaagtgtg ctaaatgata cctttcgcg acttgataaa gtcgaggcgg | 3000 |
| aggtacaaat tgacaggcta attacaggca gacttcaaag ccttcaaacc tatgtaacac | 3060 |
| aacaactaat cagggctgct gaaatcaggg cttctgctaa tcttgctgct actaaaatgt | 3120 |
| ctgagtgtgt tcttggacaa tcaaaaagag ttgacttttg tggaaagggc taccacctta | 3180 |
| tgtccttccc acaagcagcc ccgcatggtg ttgtcttcct acatgtcacg tatgtgccat | 3240 |
| cccaggagag gaacttcacc acagcgccag caatttgtca tgaaggcaaa gcatacttcc | 3300 |
| ctcgtgaagg tgttttttgtg tttaatggca cttcttggtt tattacacag aggaacttct | 3360 |
| tttctccaca ataattact acagacaata catttgtctc aggaaattgt gatgtcgtta | 3420 |
| ttggcatcat taacaacaca gtttatgatc ctctgcaacc tgagcttgac tcattcaaag | 3480 |
| aagagctgga caagtacttc aaaaatcata catcaccaga tgttgatctt ggcgacattt | 3540 |
| caggcattaa cgcttctgtc gtcaacattc aaaaagaaat tgaccgcctc aatgaggtcg | 3600 |
| ctaaaaattt aaatgaatca ctcattgacc ttcaagaatt gggaaaatat gagcaatata | 3660 |
| ttaaatggcc ttggtatgtt tggctcggct tcattgctgg actaattgcc atcgtcatgg | 3720 |
| ttacaatctt gctttgttgc atgactagtt gttgcagttg cctcaagggt gcatgctctt | 3780 |
| gtggttcttg ctgcaagttt gatgaggatg actctgagcc agttctcaag ggtgtcaaat | 3840 |
| tacattacac ataaacgaac ttatggattt gtttatgaga tttttactc ttggatcaat | 3900 |
| tactgcacag ccagtaaaaa ttgacaatgc ttctcctgca agt | 3943 |

```
<210> SEQ ID NO 5
<211> LENGTH: 2049
<212> TYPE: DNA
<213> ORGANISM: CORONAVIRUS

<400> SEQUENCE: 5
```

| | |
|---|---:|
| ctcttctgga aaaggtagg cttatcatta gagaaaacaa cagagttgtg gtttcaagtg | 60 |
| atattcttgt taacaactaa acgaacatgt ttattttctt attatttctt actctcacta | 120 |
| gtggtagtga ccttgaccgg tgcaccactt ttgatgatgt tcaagctcct aattacactc | 180 |
| aacatacttc atctatgagg gggtttact atcctgatga aatttttaga tcagacactc | 240 |
| tttatttaac tcaggattta tttcttccat tttattctaa tgttacaggg ttcatacta | 300 |
| ttaatcatac gtttggcaac cctgtcatac cttttaagga tggtatttat tttgctgcca | 360 |
| cagagaaatc aaatgttgtc cgtggttggg ttttttggttc taccatgaac aacaagtcac | 420 |
| agtcggtgat tattaattaac aattctacta atgttgttat acgagcatgt aactttgaat | 480 |
| tgtgtgacaa ccctttcttt gctgtttcta acccatggg tacacagaca catactatga | 540 |
| tattcgataa tgcatttaat tgcacttcg agtacatatc tgatgccttt tcgcttgatg | 600 |

```
tttcagaaaa gtcaggtaat tttaaacact tacgagagtt tgtgtttaaa aataaagatg      660
ggtttctcta tgtttataag ggctatcaac ctatagatgt agttcgtgat ctaccttctg      720
gttttaacac tttgaaacct attttttaagt tgcctcttgg tattaacatt acaaattta      780 gagccattct tacagccttt tcacctgctc aagacatttg gggcacgtca gctgcagcct     840 atttttgttgg ctatttaaag ccaactacat ttatgctcaa gtatgatgaa aatggtacaa     900
tcacagatgc tgttgattgt tctcaaaatc cacttgctga actcaaatgc tctgttaaga     960
gctttgagat tgacaaagga atttaccaga cctctaattt cagggttgtt ccctcaggag    1020
atgttgtgag attccctaat attacaaact gtgtccttt tggagaggtt tttaatgcta     1080
ctaaattccc ttctgtctat gcatgggaga gaaaaaaaat ttctaattgt gttgctgatt    1140
actctgtgct ctacaactca acattttttt caacctttaa gtgctatggc gtttctgcca    1200
ctaagttgaa tgatctttgc ttctccaatg tctatgcaga ttcttttgta gtcaagggag    1260
atgatgtaag acaaatagcg ccaggacaaa ctggtgttat tgctgattat aattataaat    1320
tgccagatga tttcatgggt tgtgtccttg cttggaatac taggaacatt gatgctactt    1380
caactggtaa ttataattat aaatataggt atcttagaca tggcaagctt aggccctttg    1440
agagagacat atctaatgtg cctttctccc ctgatggcaa accttgcacc ccacctgctc    1500
ttaattgtta ttggccatta aatgattatg gttttacac cactactggc attggctacc    1560
aaccttacag agttgtagta ctttcttttg aacttttaaa tgcaccggcc acggtttgtg    1620
gaccaaaatt atccactgac cttattaaga accagtgtgt caattttaat tttaatggac    1680
tcactggtac tggtgtgtta actccttctt caaagagatt tcaaccattt caacaatttg    1740
gccgtgatgt ctctgatttc actgattccg ttcgagatcc taaaacatct gaaatattag    1800
acatttcacc ttgctctttt gggggtgtaa gtgtaattac acctggaaca aatgcttcat    1860
ctgaagttgc tgttctatat caagatgtta actgcactga tgtttctaca gcaatccatg    1920
cagatcaact cacaccagct tggcgcatat attctactgg aaacaatgta ttccagactc    1980
aagcaggctg tcttatagga gctgagcatg tcgacacttc ttatgagtgc gacattccta    2040
ttggagctg                                                              2049
```

<210> SEQ ID NO 6
<211> LENGTH: 2027
<212> TYPE: DNA
<213> ORGANISM: CORONAVIRUS

<400> SEQUENCE: 6

```
catgcagatc aactcacacc agcttggcgc atatattcta ctggaaacaa tgtattccag       60
actcaagcag gctgtcttat aggagctgag catgtcgaca cttcttatga gtgcgacatt      120
cctattggag ctggcatttg tgctagttac catacagttt ctttattacg tagtactagc     180
caaaaatcta ttgtggctta tactatgtct ttaggtgctg atagttcaat tgcttactct     240
aataacacca ttgctatacc tactaacttt tcaattagca ttactacaga agtaatgcct     300
gtttctatgg ctaaaacctc cgtagattgt aatatgtaca tctgcggaga ttctactgaa    360
tgtgctaatt tgcttctcca atatggtagc ttttgcacac aactaaatcg tgcactctca    420
ggtattgctc tgaacagga tcgcaacaca cgtgaagtgt tcgctcaagt caaacaaatg    480
tacaaaaccc caactttgaa atattttggt ggttttaatt tttcacaaat attacctgac    540
cctctaaagc caactaagag gtctttttatt gaggacttgc tctttaataa ggtgacactc    600
gctgatgctg gcttcatgaa gcaatatggc gaatgcctag gtgatattaa tgctagagat    660
```

| | |
|---|---:|
| ctcatttgtg cgcagaagtt caatgggctt acagtgttgc cacctctgct cactgatgat | 720 |
| atgattgctg cctacactgc tgctctagtt agtggtactg ccactgctgg atggacattt | 780 |
| ggtgctggcg ctgctcttca aatacctttt gctatgcaaa tggcatatag gttcaatggc | 840 |
| attggagtta cccaaaatgt tctctatgag aaccaaaaac aaatcgccaa ccaatttaac | 900 |
| aaggcgatta gtcaaattca agaatcactt acaacaacat caactgcatt gggcaagctg | 960 |
| caagacgttg ttaaccagaa tgctcaagca ttaaacacac ttgttaaaca acttagctct | 1020 |
| aattttggtg caatttcaag tgtgctaaat gatatccttt cgcgacttga taaagtcgag | 1080 |
| gcggaggtac aaattgacag gttaattaca ggcagacttc aaagccttca acctatgta | 1140 |
| acacaacaac taatcagggc tgctgaaatc agggcttctg ctaatcttgc tgctactaaa | 1200 |
| atgtctgagt gtgttcttgg acaatcaaaa agagttgact tttgtggaaa gggctaccac | 1260 |
| cttatgtcct tcccacaagc agccccgcat ggtgttgtct tcctacatgt cacgtatgtg | 1320 |
| ccatcccagg agaggaactt caccacagcg ccagcaattt gtcatgaagg caaagcatac | 1380 |
| ttccctcgtg aaggtgtttt tgtgtttaat ggcacttctt ggtttattac acagaggaac | 1440 |
| ttcttttctc cacaaataat tactacagac aatacatttg tctcaggaaa ttgtgatgtc | 1500 |
| gttattggcg tcattaacaa cacagtttat gatcctctgc aacctgagct tgactcattc | 1560 |
| aaagaagagc tggacaagta cttcaaaaat catacatcac cagatgttga tcttggcgac | 1620 |
| atttcaggca ttaacgcttc tgtcgtcaac attcaaaaag aaattgaccg cctcaatgag | 1680 |
| gtcgctaaaa atttaaatga atcactcatt gaccttcaag aattgggaaa atatgagcaa | 1740 |
| tatattaaat ggccttggta tgtttggctc ggcttcattg ctggactaat tgccatcgtc | 1800 |
| atggttacaa tcttgctttg ttgcatgact agttgttgca gttgcctcaa gggtgcatgc | 1860 |
| tcttgtggtt cttgctgcaa gtttgatgag gatgactctg agccagttct caagggtgtc | 1920 |
| aaattacatt acacataaac gaacttatgg atttgtttat gagattttt actcttggat | 1980 |
| caattactgc acagccagta aaaattgaca atgcttctcc tgcaagt | 2027 |

<210> SEQ ID NO 7
<211> LENGTH: 1096
<212> TYPE: DNA
<213> ORGANISM: CORONAVIRUS

<400> SEQUENCE: 7

| | |
|---|---:|
| tcttgctttg ttgcatgact agttgttgca gttgcctcaa gggtgcatgc tcttgtggtt | 60 |
| cttgctgcaa gtttgatgag gatgactctg agccagttct caagggtgtc aaattacatt | 120 |
| acacataaac gaacttatgg atttgtttat gagattttt actcttggat caattactgc | 180 |
| acagccagta aaaattgaca atgcttctcc tgcaagtact gttcatgcta cagcaacgat | 240 |
| accgctacaa gcctcactcc ctttcggatg gcttgttatt ggcgttgcat tcttgctgt | 300 |
| ttttcagagc gctaccaaaa taattgcgct caataaaaga tggcagctag ccctttataa | 360 |
| gggcttccag ttcatttgca atttactgct gctatttgtt accatctatt cacatctttt | 420 |
| gcttgtcgct gcaggtatgg aggcgcaatt tttgtacctc tatgccttga tatattttct | 480 |
| acaatgcatc aacgcatgta gaattattat gagatgttgg ctttgttgga agtgcaaatc | 540 |
| caagaaccca ttactttatg atgccaacta ctttgtttgc tggcacacac ataactatga | 600 |
| ctactgtata ccatataaca gtgtcacaga tacaattgtc gttactgaag gtgacggcat | 660 |
| ttcaacacca aaactcaaag aagactacca aattggtggt tattctgagg ataggcactc | 720 |

```
aggtgttaaa gactatgtcg ttgtacatgg ctatttcacc gaagtttact accagcttga      780
gtctacacaa attactacag acactggtat tgaaaatgct acattcttca tctttaacaa      840
gcttgttaaa gacccaccga atgtgcaaat acacacaatc gacggctctt caggagttgc      900
taatccagca atggatccaa tttatgatga gccgacgacg actactagcg tgcctttgta      960
agcacaagaa agtgagtacg aacttatgta ctcattcgtt tcggaagaaa caggtacgtt     1020
aatagttaat agcgtacttc ttttcttgc tttcgtggta ttcttgctag tcacactagc      1080
catccttact gcgctt                                                    1096

<210> SEQ ID NO 8
<211> LENGTH: 1135
<212> TYPE: DNA
<213> ORGANISM: CORONAVIRUS

<400> SEQUENCE: 8
attgccatcg tcatggttac aatcttgctt tgttgcatga ctagttgttg cagttgcctc       60
aagggtgcat gctcttgtgg ttcttgctgc aagtttgatg aggatgactc tgagccagtt      120
ctcaagggtg tcaaattaca ttacacataa acgaacttat ggatttgttt atgagatttt      180
ttactcttgg atcaattact gcacagccag taaaaattga caatgcttct cctgcaagta      240
ctgttcatgc tacagcaacg ataccgctac aagcctcact ccctttcgga tggcttgtta      300
ttggcgttgc atttcttgct gtttttcaga gcgctaccaa ataattgcg ctcaataaaa       360 gatggcagct agccctttat aagggcttcc agttcatttg caatttactg ctgctatttg      420
ttaccatcta ttcacatctt tgcttgtcg ctgcaggtat ggaggcgcaa ttttttgtacc      480 tctatgcctt gatatatttt ctacaatgca tcaacgcatg tagaattatt atgagatgtt      540
ggctttgttg gaagtgcaaa tccaagaacc cattacttta tgatgccaac tactttgttt      600
gctggcacac acataactat gactactgta taccatataa cagtgtcaca gatacaattg      660
tcgttactga aggtgacggc atttcaacac caaaactcaa agaagactac caaattggtg      720
gttattctga ggataggcac tcaggtgtta agactatgt cgttgtacat ggctatttca      780
ccgaagttta ctaccagctt gagtctacac aaattactac agacactggt attgaaaatg      840
ctacattctt catcttaac aagcttgtta agacccacc gaatgtgcaa atacacacaa       900
tcgacggctc ttcaggagtt gctaatccag caatggatcc aattatgat gagccgacga      960 cgactactag cgtgcctttg taagcacaag aaagtgagta cgaacttatg tactcattcg     1020
tttcggaaga acaggtacg ttaatagtta atagcgtact tcttttctt gctttcgtgg      1080 tattcttgct agtcacacta gccatcctta ctgcgcttcg attgtgtgcg tactg          1135

<210> SEQ ID NO 9
<211> LENGTH: 1096
<212> TYPE: DNA
<213> ORGANISM: CORONAVIRUS
<220> FEATURE:
<221> NAME/KEY: CDS
<222> LOCATION: (137)..(958)
<223> OTHER INFORMATION:

<400> SEQUENCE: 9
tcttgctttg ttcatgact agttgttgca gttgcctcaa gggtgcatgc tcttgtggtt       60
cttgctgcaa gtttgatgag gatgactctg agccagttct caagggtgtc aaattacatt     120
acacataaac gaactt atg gat ttg ttt atg aga ttt ttt act ctt gga tca     172
              Met Asp Leu Phe Met Arg Phe Phe Thr Leu Gly Ser
              1               5                  10
```

```
att act gca cag cca gta aaa att gac aat gct tct cct gca agt act       220
Ile Thr Ala Gln Pro Val Lys Ile Asp Asn Ala Ser Pro Ala Ser Thr
        15                  20                  25 gtt cat gct aca gca acg ata ccg cta caa gcc tca ctc cct ttc gga       268
Val His Ala Thr Ala Thr Ile Pro Leu Gln Ala Ser Leu Pro Phe Gly
    30                  35                  40 tgg ctt gtt att ggc gtt gca ttt ctt gct gtt ttt cag agc gct acc       316
Trp Leu Val Ile Gly Val Ala Phe Leu Ala Val Phe Gln Ser Ala Thr
45                  50                  55                  60 aaa ata att gcg ctc aat aaa aga tgg cag cta gcc ctt tat aag ggc       364
Lys Ile Ile Ala Leu Asn Lys Arg Trp Gln Leu Ala Leu Tyr Lys Gly
                65                  70                  75 ttc cag ttc att tgc aat tta ctg ctg cta ttt gtt acc atc tat tca       412
Phe Gln Phe Ile Cys Asn Leu Leu Leu Leu Phe Val Thr Ile Tyr Ser
            80                  85                  90 cat ctt ttg ctt gtc gct gca ggt atg gag gcg caa ttt ttg tac ctc       460
His Leu Leu Leu Val Ala Ala Gly Met Glu Ala Gln Phe Leu Tyr Leu
        95                 100                 105 tat gcc ttg ata tat ttt cta caa tgc atc aac gca tgt aga att att       508
Tyr Ala Leu Ile Tyr Phe Leu Gln Cys Ile Asn Ala Cys Arg Ile Ile
    110                 115                 120 atg aga tgt tgg ctt tgt tgg aag tgc aaa tcc aag aac cca tta ctt       556
Met Arg Cys Trp Leu Cys Trp Lys Cys Lys Ser Lys Asn Pro Leu Leu
125                 130                 135                 140 tat gat gcc aac tac ttt gtt tgc tgg cac aca cat aac tat gac tac       604
Tyr Asp Ala Asn Tyr Phe Val Cys Trp His Thr His Asn Tyr Asp Tyr
                145                 150                 155 tgt ata cca tat aac agt gtc aca gat aca att gtc gtt act gaa ggt       652
Cys Ile Pro Tyr Asn Ser Val Thr Asp Thr Ile Val Val Thr Glu Gly
            160                 165                 170 gac ggc att tca aca cca aaa ctc aaa gaa gac tac caa att ggt ggt       700
Asp Gly Ile Ser Thr Pro Lys Leu Lys Glu Asp Tyr Gln Ile Gly Gly
        175                 180                 185 tat tct gag gat agg cac tca ggt gtt aaa gac tat gtc gtt gta cat       748
Tyr Ser Glu Asp Arg His Ser Gly Val Lys Asp Tyr Val Val Val His
    190                 195                 200 ggc tat ttc acc gaa gtt tac tac cag ctt gag tct aca caa att act       796
Gly Tyr Phe Thr Glu Val Tyr Tyr Gln Leu Glu Ser Thr Gln Ile Thr
205                 210                 215                 220 aca gac act ggt att gaa aat gct aca ttc ttc atc ttt aac aag ctt       844
Thr Asp Thr Gly Ile Glu Asn Ala Thr Phe Phe Ile Phe Asn Lys Leu
                225                 230                 235 gtt aaa gac cca ccg aat gtg caa ata cac aca atc gac ggc tct tca       892
Val Lys Asp Pro Pro Asn Val Gln Ile His Thr Ile Asp Gly Ser Ser
            240                 245                 250 gga gtt gct aat cca gca atg gat cca att tat gat gag ccg acg acg       940
Gly Val Ala Asn Pro Ala Met Asp Pro Ile Tyr Asp Glu Pro Thr Thr
        255                 260                 265 act act agc gtg cct ttg taagcacaag aaagtgagta cgaacttatg              988
Thr Thr Ser Val Pro Leu
    270 tactcattcg tttcggaaga aacaggtacg ttaatagtta atagcgtact tcttttttctt   1048 gctttcgtgg tattcttgct agtcacacta gccatcctta ctgcgctt                 1096

<210> SEQ ID NO 10
<211> LENGTH: 274
<212> TYPE: PRT
<213> ORGANISM: CORONAVIRUS
```

<400> SEQUENCE: 10

```
Met Asp Leu Phe Met Arg Phe Phe Thr Leu Gly Ser Ile Thr Ala Gln
1               5                   10                  15

Pro Val Lys Ile Asp Asn Ala Ser Pro Ala Ser Thr Val His Ala Thr
            20                  25                  30

Ala Thr Ile Pro Leu Gln Ala Ser Leu Pro Phe Gly Trp Leu Val Ile
        35                  40                  45

Gly Val Ala Phe Leu Ala Val Phe Gln Ser Ala Thr Lys Ile Ile Ala
    50                  55                  60

Leu Asn Lys Arg Trp Gln Leu Ala Leu Tyr Lys Gly Phe Gln Phe Ile
65                  70                  75                  80

Cys Asn Leu Leu Leu Leu Phe Val Thr Ile Tyr Ser His Leu Leu Leu
                85                  90                  95

Val Ala Ala Gly Met Glu Ala Gln Phe Leu Tyr Leu Tyr Ala Leu Ile
            100                 105                 110

Tyr Phe Leu Gln Cys Ile Asn Ala Cys Arg Ile Ile Met Arg Cys Trp
        115                 120                 125

Leu Cys Trp Lys Cys Lys Ser Lys Asn Pro Leu Leu Tyr Asp Ala Asn
130                 135                 140

Tyr Phe Val Cys Trp His Thr His Asn Tyr Asp Tyr Cys Ile Pro Tyr
145                 150                 155                 160

Asn Ser Val Thr Asp Thr Ile Val Val Thr Glu Gly Asp Gly Ile Ser
                165                 170                 175

Thr Pro Lys Leu Lys Glu Asp Tyr Gln Ile Gly Gly Tyr Ser Glu Asp
            180                 185                 190

Arg His Ser Gly Val Lys Asp Tyr Val Val His Gly Tyr Phe Thr
        195                 200                 205

Glu Val Tyr Tyr Gln Leu Glu Ser Thr Gln Ile Thr Thr Asp Thr Gly
    210                 215                 220

Ile Glu Asn Ala Thr Phe Phe Ile Phe Asn Lys Leu Val Lys Asp Pro
225                 230                 235                 240

Pro Asn Val Gln Ile His Thr Ile Asp Gly Ser Ser Gly Val Ala Asn
                245                 250                 255

Pro Ala Met Asp Pro Ile Tyr Asp Glu Pro Thr Thr Thr Thr Ser Val
            260                 265                 270

Pro Leu
```

<210> SEQ ID NO 11
<211> LENGTH: 1096
<212> TYPE: DNA
<213> ORGANISM: CORONAVIRUS
<220> FEATURE:
<221> NAME/KEY: CDS
<222> LOCATION: (558)..(1019)
<223> OTHER INFORMATION:

<400> SEQUENCE: 11

```
tcttgctttg ttgcatgact agttgttgca gttgcctcaa gggtgcatgc tcttgtggtt      60
cttgctgcaa gtttgatgag gatgactctg agccagttct caagggtgtc aaattacatt    120
acacataaac gaacttatgg atttgtttat gagattttt actcttggat caattactgc      180
acagccagta aaaattgaca atgcttctcc tgcaagtact gttcatgcta cagcaacgat    240
accgctacaa gcctcactcc ctttcggatg gcttgttatt ggcgttgcat ttcttgctgt    300
ttttcagagc gctaccaaaa taattgcgct caataaaaga tggcagctag ccctttataa    360
```

```
gggcttccag ttcatttgca atttactgct gctatttgtt accatctatt cacatctttt        420
gcttgtcgct gcaggtatgg aggcgcaatt tttgtacctc tatgccttga tatattttct        480
acaatgcatc aacgcatgta gaattattat gagatgttgg ctttgttgga agtgcaaatc        540
caagaaccca ttacttt atg atg cca act act ttg ttt gct ggc aca cac          590
                    Met Met Pro Thr Thr Leu Phe Ala Gly Thr His
                     1               5                  10 ata act atg act act gta tac cat ata aca gtg tca cag ata caa ttg          638
Ile Thr Met Thr Thr Val Tyr His Ile Thr Val Ser Gln Ile Gln Leu
            15                  20                  25 tcg tta ctg aag gtg acg gca ttt caa cac caa aac tca aag aag act          686
Ser Leu Leu Lys Val Thr Ala Phe Gln His Gln Asn Ser Lys Lys Thr
        30                  35                  40 acc aaa ttg gtg gtt att ctg agg ata ggc act cag gtg tta aag act          734
Thr Lys Leu Val Val Ile Leu Arg Ile Gly Thr Gln Val Leu Lys Thr
    45                  50                  55 atg tcg ttg tac atg gct att tca ccg aag ttt act acc agc ttg agt          782
Met Ser Leu Tyr Met Ala Ile Ser Pro Lys Phe Thr Thr Ser Leu Ser
60                  65                  70                  75 cta cac aaa tta cta cag aca ctg gta ttg aaa atg cta cat tct tca          830
Leu His Lys Leu Leu Gln Thr Leu Val Leu Lys Met Leu His Ser Ser
                80                  85                  90 tct tta aca agc ttg tta aag acc cac cga atg tgc aaa tac aca caa          878
Ser Leu Thr Ser Leu Leu Lys Thr His Arg Met Cys Lys Tyr Thr Gln
            95                  100                 105 tcg acg gct ctt cag gag ttg cta atc cag caa tgg atc caa ttt atg          926
Ser Thr Ala Leu Gln Glu Leu Leu Ile Gln Gln Trp Ile Gln Phe Met
        110                 115                 120 atg agc cga cga cga cta cta gcg tgc ctt tgt aag cac aag aaa gtg          974
Met Ser Arg Arg Arg Leu Leu Ala Cys Leu Cys Lys His Lys Lys Val
    125                 130                 135 agt acg aac tta tgt act cat tcg ttt cgg aag aaa cag gta cgt             1019
Ser Thr Asn Leu Cys Thr His Ser Phe Arg Lys Lys Gln Val Arg
140                 145                 150 taatagttaa tagcgtactt cttttctctg ctttcgtggt attcttgcta gtcacactag       1079
ccatccttac tgcgctt                                                      1096

<210> SEQ ID NO 12
<211> LENGTH: 154
<212> TYPE: PRT
<213> ORGANISM: CORONAVIRUS

<400> SEQUENCE: 12

Met Met Pro Thr Thr Leu Phe Ala Gly Thr His Ile Thr Met Thr Thr
1               5                   10                  15

Val Tyr His Ile Thr Val Ser Gln Ile Gln Leu Ser Leu Leu Lys Val
            20                  25                  30

Thr Ala Phe Gln His Gln Asn Ser Lys Lys Thr Thr Lys Leu Val Val
        35                  40                  45

Ile Leu Arg Ile Gly Thr Gln Val Leu Lys Thr Met Ser Leu Tyr Met
    50                  55                  60

Ala Ile Ser Pro Lys Phe Thr Thr Ser Leu Ser Leu His Lys Leu Leu
65                  70                  75                  80

Gln Thr Leu Val Leu Lys Met Leu His Ser Ser Ser Leu Thr Ser Leu
                85                  90                  95

Leu Lys Thr His Arg Met Cys Lys Tyr Thr Gln Ser Thr Ala Leu Gln
            100                 105                 110
```

```
Glu Leu Leu Ile Gln Gln Trp Ile Gln Phe Met Met Ser Arg Arg Arg
        115                 120                 125

Leu Leu Ala Cys Leu Cys Lys His Lys Lys Val Ser Thr Asn Leu Cys
    130                 135                 140

Thr His Ser Phe Arg Lys Lys Gln Val Arg
145                 150

<210> SEQ ID NO 13
<211> LENGTH: 332
<212> TYPE: DNA
<213> ORGANISM: CORONAVIRUS
<220> FEATURE:
<221> NAME/KEY: CDS
<222> LOCATION: (36)..(263)
<223> OTHER INFORMATION:

<400> SEQUENCE: 13
tgcctttgta agcacaagaa agtgagtacg aactt atg tac tca ttc gtt tcg        53
                                       Met Tyr Ser Phe Val Ser
                                         1               5 gaa gaa aca ggt acg tta ata gtt aat agc gta ctt ctt ttt ctt gct      101
Glu Glu Thr Gly Thr Leu Ile Val Asn Ser Val Leu Leu Phe Leu Ala
            10                  15                  20 ttc gtg gta ttc ttg cta gtc aca cta gcc atc ctt act gcg ctt cga      149
Phe Val Val Phe Leu Leu Val Thr Leu Ala Ile Leu Thr Ala Leu Arg
        25                  30                  35 ttg tgt gcg tac tgc tgc aat att gtt aac gtg agt tta gta aaa cca      197
Leu Cys Ala Tyr Cys Cys Asn Ile Val Asn Val Ser Leu Val Lys Pro
    40                  45                  50 acg gtt tac gtc tac tcg cgt gtt aaa aat ctg aac tct tct gaa gga      245
Thr Val Tyr Val Tyr Ser Arg Val Lys Asn Leu Asn Ser Ser Glu Gly
55                  60                  65                  70 gtt cct gat ctt ctg gtc taaacgaact aactattatt attattctgt             293
Val Pro Asp Leu Leu Val
                75 ttggaacttt aacattgctt atcatggcag acaacggta                           332

<210> SEQ ID NO 14
<211> LENGTH: 76
<212> TYPE: PRT
<213> ORGANISM: CORONAVIRUS

<400> SEQUENCE: 14

Met Tyr Ser Phe Val Ser Glu Glu Thr Gly Thr Leu Ile Val Asn Ser
  1               5                  10                  15

Val Leu Leu Phe Leu Ala Phe Val Val Phe Leu Leu Val Thr Leu Ala
                20                  25                  30

Ile Leu Thr Ala Leu Arg Leu Cys Ala Tyr Cys Cys Asn Ile Val Asn
            35                  40                  45

Val Ser Leu Val Lys Pro Thr Val Tyr Val Tyr Ser Arg Val Lys Asn
        50                  55                  60

Leu Asn Ser Ser Glu Gly Val Pro Asp Leu Leu Val
 65                 70                  75

<210> SEQ ID NO 15
<211> LENGTH: 332
<212> TYPE: DNA
<213> ORGANISM: CORONAVIRUS

<400> SEQUENCE: 15
tgcctttgta agcacaagaa agtgagtacg aacttatgta ctcattcgtt tcggaagaaa     60
```

-continued

```
caggtacgtt aatagttaat agcgtacttc tttttcttgc tttcgtggta ttcttgctag     120
tcacactagc catccttact gcgcttcgat tgtgtgcgta ctgctgcaat attgttaacg     180
tgagtttagt aaaaccaacg gtttacgtct actcgcgtgt taaaaatctg aactcttctg     240
aaggagttcc tgatcttctg gtctaaacga actaactatt attattattc tgtttggaac     300
tttaacattg cttatcatgg cagacaacgg ta                                   332

<210> SEQ ID NO 16
<211> LENGTH: 708
<212> TYPE: DNA
<213> ORGANISM: CORONAVIRUS
<220> FEATURE:
<221> NAME/KEY: CDS
<222> LOCATION: (41)..(703)
<223> OTHER INFORMATION:

<400> SEQUENCE: 16
tattattatt attctgtttg aactttaac attgcttatc atg gca gac aac ggt         55
                                              Met Ala Asp Asn Gly
                                              1               5 act att acc gtt gag gag ctt aaa caa ctc ctg gaa caa tgg aac cta       103
Thr Ile Thr Val Glu Glu Leu Lys Gln Leu Leu Glu Gln Trp Asn Leu
             10                  15                  20 gta ata ggt ttc cta ttc cta gcc tgg att atg tta cta caa ttt gcc      151
Val Ile Gly Phe Leu Phe Leu Ala Trp Ile Met Leu Leu Gln Phe Ala
         25                  30                  35 tat tct aat cgg aac agg ttt ttg tac ata ata aag ctt gtt ttc ctc      199
Tyr Ser Asn Arg Asn Arg Phe Leu Tyr Ile Ile Lys Leu Val Phe Leu
     40                  45                  50 tgg ctc ttg tgg cca gta aca ctt gct tgt ttt gtg ctt gct gct gtc      247
Trp Leu Leu Trp Pro Val Thr Leu Ala Cys Phe Val Leu Ala Ala Val
 55                  60                  65 tac aga att aat tgg gtg act ggc ggg att gcg att gca atg gct tgt      295
Tyr Arg Ile Asn Trp Val Thr Gly Gly Ile Ala Ile Ala Met Ala Cys
 70                  75                  80                  85 att gta ggc ttg atg tgg ctt agc tac ttc gtt gct tcc ttc agg ctg      343
Ile Val Gly Leu Met Trp Leu Ser Tyr Phe Val Ala Ser Phe Arg Leu
                 90                  95                 100 ttt gct cgt acc cgc tca atg tgg tca ttc aac cca gaa aca aac att      391
Phe Ala Arg Thr Arg Ser Met Trp Ser Phe Asn Pro Glu Thr Asn Ile
             105                 110                 115 ctt ctc aat gtg cct ctc cgg ggg aca att gtg acc aga ccg ctc atg      439
Leu Leu Asn Val Pro Leu Arg Gly Thr Ile Val Thr Arg Pro Leu Met
         120                 125                 130 gaa agt gaa ctt gtc att ggt gct gtg atc att cgt ggt cac ttg cga      487
Glu Ser Glu Leu Val Ile Gly Ala Val Ile Ile Arg Gly His Leu Arg
     135                 140                 145 atg gcc gga cac tcc cta ggg cgc tgt gac att aag gac ctg cca aaa      535
Met Ala Gly His Ser Leu Gly Arg Cys Asp Ile Lys Asp Leu Pro Lys
150                 155                 160                 165 gag atc act gtg gct aca tca cga acg ctt tct tat tac aaa tta gga      583
Glu Ile Thr Val Ala Thr Ser Arg Thr Leu Ser Tyr Tyr Lys Leu Gly
                 170                 175                 180 gcg tcg cag cgt gta ggc act gat tca ggt ttt gct gca tac aac cgc      631
Ala Ser Gln Arg Val Gly Thr Asp Ser Gly Phe Ala Ala Tyr Asn Arg
             185                 190                 195 tac cgt att gga aac tat aaa tta aat aca gac cac gcc ggt agc aac      679
Tyr Arg Ile Gly Asn Tyr Lys Leu Asn Thr Asp His Ala Gly Ser Asn
         200                 205                 210
```

```
gac aat att gct ttg cta gta cag taagt                              708
Asp Asn Ile Ala Leu Leu Val Gln
    215             220
```

<210> SEQ ID NO 17
<211> LENGTH: 221
<212> TYPE: PRT
<213> ORGANISM: CORONAVIRUS

<400> SEQUENCE: 17

```
Met Ala Asp Asn Gly Thr Ile Thr Val Glu Glu Leu Lys Gln Leu Leu
1               5                   10                  15

Glu Gln Trp Asn Leu Val Ile Gly Phe Leu Phe Leu Ala Trp Ile Met
            20                  25                  30

Leu Leu Gln Phe Ala Tyr Ser Asn Arg Asn Arg Phe Leu Tyr Ile Ile
        35                  40                  45

Lys Leu Val Phe Leu Trp Leu Leu Trp Pro Val Thr Leu Ala Cys Phe
    50                  55                  60

Val Leu Ala Ala Val Tyr Arg Ile Asn Trp Val Thr Gly Gly Ile Ala
65                  70                  75                  80

Ile Ala Met Ala Cys Ile Val Gly Leu Met Trp Leu Ser Tyr Phe Val
                85                  90                  95

Ala Ser Phe Arg Leu Phe Ala Arg Thr Arg Ser Met Trp Ser Phe Asn
            100                 105                 110

Pro Glu Thr Asn Ile Leu Leu Asn Val Pro Leu Arg Gly Thr Ile Val
        115                 120                 125

Thr Arg Pro Leu Met Glu Ser Glu Leu Val Ile Gly Ala Val Ile Ile
    130                 135                 140

Arg Gly His Leu Arg Met Ala Gly His Ser Leu Gly Arg Cys Asp Ile
145                 150                 155                 160

Lys Asp Leu Pro Lys Glu Ile Thr Val Ala Thr Ser Arg Thr Leu Ser
                165                 170                 175

Tyr Tyr Lys Leu Gly Ala Ser Gln Arg Val Gly Thr Asp Ser Gly Phe
            180                 185                 190

Ala Ala Tyr Asn Arg Tyr Arg Ile Gly Asn Tyr Lys Leu Asn Thr Asp
        195                 200                 205

His Ala Gly Ser Asn Asp Asn Ile Ala Leu Leu Val Gln
    210                 215                 220
```

<210> SEQ ID NO 18
<211> LENGTH: 769
<212> TYPE: DNA
<213> ORGANISM: CORONAVIRUS

<400> SEQUENCE: 18

```
cctgatcttc tggtctaaac gaactaacta ttattattat tctgtttgga actttaacat    60
tgcttatcat ggcagacaac ggtactatta ccgttgagga gcttaaacaa ctcctggaac   120
aatggaacct agtaataggt ttcctattcc tagcctggat tatgttacta caatttgcct   180
attctaatcg gaacaggttt ttgtacataa taaagcttgt tttcctctgg ctcttgtggc   240
cagtaacact tgcttgtttt gtgcttgctg ctgtctacag aattaattgg gtgactggcg   300
ggattgcgat tgcaatggct tgtattgtag gcttgatgtg gcttagctac ttcgttgctt   360
ccttcaggct gtttgctcgt acccgctcaa tgtggtcatt caacccagaa acaaacattc   420
ttctcaatgt gcctctccgg gggacaattg tgaccagacc gctcatggaa agtgaacttg   480
tcattggtgc tgtgatcatt cgtggtcact tgcgaatggc cggacactcc ctagggcgct   540
```

```
gtgacattaa ggacctgcca aaagagatca ctgtggctac atcacgaacg ctttcttatt      600
acaaattagg agcgtcgcag cgtgtaggca ctgattcagg ttttgctgca tacaaccgct      660
accgtattgg aaactataaa ttaaatacag accacgccgg tagcaacgac aatattgctt      720
tgctagtaca gtaagtgaca acagatgttt catcttgttg acttccagg                 769
```

<210> SEQ ID NO 19
<211> LENGTH: 1231
<212> TYPE: DNA
<213> ORGANISM: CORONAVIRUS

<400> SEQUENCE: 19

```
taccgtattg gaaactataa attaaataca gaccacgccg gtagcaacga caatattgct       60
ttgctagtac agtaagtgac aacagatgtt tcatcttgtt gacttccagg ttacaatagc      120
agagatattg attatcatta tgaggacttt caggattgct atttggaatc ttgacgttat      180
aataagttca atagtgagac aattatttaa gcctctaact aagaagaatt attcggagtt      240
agatgatgaa gaacctatgg agttagatta tccataaaac gaacatgaaa attattctct      300
tcctgacatt gattgtattt acatcttgcg agctatatca ctatcaggag tgtgttagag      360
gtacgactgt actactaaaa gaaccttgcc catcaggaac atacgagggc aattcaccat      420 tcaccctct tgctgacaat aaatttgcac taacttgcac tagcacacac tttgcttttg      480
cttgtgctga cggtactcga catacctatc agctgcgtgc aagatcagtt tcaccaaaac      540
ttttcatcag acaagaggag gttcaacaag agctctactc gccactttt ctcattgttg      600 ctgctctagt attttaata ctttgcttca ccattaagag aaagacagaa tgaatgagct      660
cactttaatt gacttctatt tgtgcttttt agcctttctg ctattccttg ttttaataat      720
gcttattata ttttggtttt cactcgaaat ccaggatcta aagaaccctt gtaccaaagt      780
ctaaacgaac atgaaacttc tcattgtttt gacttgtatt tctctatgca gttgcatatg      840
cactgtagta cagcgctgtg catctaataa acctcatgtg cttgaagatc cttgtaaggt      900
acaacactag gggtaatact tatagcactg cttggctttg tgctctagga aaggttttac      960
cttttcatag atggcacact atggttcaaa catgcacacc taatgttact atcaactgtc     1020
aagatccagc tggtggtgcg cttatagcta ggtgttggta ccttcatgaa ggtcaccaaa     1080
ctgctgcatt tagagacgta cttgttgttt taaataaacg aacaaattaa aatgtctgat     1140
aatggacccc aatcaaacca acgtagtgcc ccccgcatta catttggtgg acccacagat     1200
tcaactgaca ataaccagaa tggaggacgc a                                    1231
```

<210> SEQ ID NO 20
<211> LENGTH: 1242
<212> TYPE: DNA
<213> ORGANISM: CORONAVIRUS

<400> SEQUENCE: 20

```
gcatacaacc gctaccgtat tggaaactat aaattaaata cagaccacgc cggtagcaac       60
gacaatattg ctttgctagt acagtaagtg acaacagatg tttcatcttg ttgacttcca      120
ggttacaata gcagagatat tgattatcat tatgaggact ttcaggattg ctatttggaa      180
tcttgacgtt ataataagtt caatagtgag acagttattt aagcctctaa ctaagaagaa      240
ttattcggag ttagatgatg aagaacctat ggagttagat tatccataaa acgaacatga      300
aaattattct cttcctgaca ttgattgtat ttacatcttg cgagctatat cactatcagg      360
```

-continued

```
agtgtgttag aggtacgact gtactactaa aagaaccttg cccatcagga acatacgagg    420
gcaattcacc atttcaccct cttgctgaca ataaatttgc actaacttgc actagcacac    480
actttgcttt tgcttgtgct gacggtactc gacatacct atcagctgcgt gcaagatcag    540 tttcaccaaa acttttcatc agacaagagg aggttcaaca agagctctac tcgccacttt    600
ttctcattgt tgctgctcta gtattttaa tactttgctt caccattaag agaaagacag    660
aatgaatgag ctcactttaa ttgacttcta tttgtgcttt ttagcctttc tgctattcct    720
tgttttaata atgcttatta tattttggtt ttcactcgaa atccaggatc tagaagaacc    780
ttgtaccaaa gtctaaacga acatgaaact tctcattgtt ttgacttgta tttctctatg    840
cagttgcata tgcactgtag tacagcgctg tgcatctaat aaacctcatg tgcttgaaga    900
tccttgtaag gtacaacact aggggtaata cttatagcac tgcttggctt tgtgctctag    960
gaaaggtttt acctttcat agatggcaca ctatggttca aacatgcaca cctaatgtta   1020
ctatcaactg tcaagatcca gctggtggtg cgcttatagc taggtgttgg taccttcatg   1080
aaggtcacca aactgctgca tttagagacg tacttgttgt tttaaataaa cgaacgaatt   1140
aaaatgtctg ataatggacc ccaatcaaac caacgtagtg ccccccgcat tacatttggt   1200
ggacccacag attcaactga caataaccag aatggaggac gc                     1242
```

<210> SEQ ID NO 21
<211> LENGTH: 1231
<212> TYPE: DNA
<213> ORGANISM: CORONAVIRUS
<220> FEATURE:
<221> NAME/KEY: CDS
<222> LOCATION: (86)..(274)
<223> OTHER INFORMATION:

<400> SEQUENCE: 21

```
taccgtattg gaaactataa attaaataca gaccacgccg gtagcaacga caatattgct     60
ttgctagtac agtaagtgac aacag atg ttt cat ctt gtt gac ttc cag gtt      112
                             Met Phe His Leu Val Asp Phe Gln Val
                              1               5 aca ata gca gag ata ttg att atc att atg agg act ttc agg att gct      160
Thr Ile Ala Glu Ile Leu Ile Ile Ile Met Arg Thr Phe Arg Ile Ala
 10              15                  20                  25 att tgg aat ctt gac gtt ata ata agt tca ata gtg aga caa tta ttt      208
Ile Trp Asn Leu Asp Val Ile Ile Ser Ser Ile Val Arg Gln Leu Phe
         30                  35                  40 aag cct cta act aag aag aat tat tcg gag tta gat gat gaa gaa cct      256
Lys Pro Leu Thr Lys Lys Asn Tyr Ser Glu Leu Asp Asp Glu Glu Pro
     45                  50                  55 atg gag tta gat tat cca taaaacgaac atgaaaatta ttctcttcct             304
Met Glu Leu Asp Tyr Pro
         60 gacattgatt gtatttacat cttgcgagct atatcactat caggagtgtg ttagaggtac    364 gactgtacta ctaaaagaac cttgcccatc aggaacatac gagggcaatt caccatttca    424 ccctcttgct gacaataaat ttgcactaac ttgcactagc acacactttg cttttgcttg    484 tgctgacggt actcgacata cctatcagct gcgtgcaaga tcagtttcac caaaactttt    544 catcagacaa gaggaggttc aacaagagct ctactcgcca ttttttctca ttgttgctgc    604 tctagtattt ttaatacttt gcttcaccat taagagaaag acagaatgaa tgagctcact    664 ttaattgact ctatttgtg ctttttagcc tttctgctat tccttgtttt aataatgctt    724 attatatttt ggttttcact cgaaatccag gatctagaag aaccttgtac caaagtctaa    784
```

-continued

| | |
|---|---|
| acgaacatga aacttctcat tgttttgact tgtatttctc tatgcagttg catatgcact | 844 |
| gtagtacagc gctgtgcatc taataaacct catgtgcttg aagatccttg taaggtacaa | 904 |
| cactagggt aatacttata gcactgcttg gctttgtgct ctaggaaagg ttttaccttt | 964 |
| tcatagatgg cacactatgg ttcaaacatg cacacctaat gttactatca actgtcaaga | 1024 |
| tccagctggt ggtgcgctta tagctaggtg ttggtacctt catgaaggtc accaaactgc | 1084 |
| tgcatttaga gacgtacttg ttgttttaaa taaacgaaca aattaaaatg tctgataatg | 1144 |
| gaccccaatc aaaccaacgt agtgccccccc gcattacatt tggtggaccc acagattcaa | 1204 |
| ctgacaataa ccagaatgga ggacgca | 1231 |

<210> SEQ ID NO 22
<211> LENGTH: 63
<212> TYPE: PRT
<213> ORGANISM: CORONAVIRUS

<400> SEQUENCE: 22

Met Phe His Leu Val Asp Phe Gln Val Thr Ile Ala Glu Ile Leu Ile
1               5                   10                  15

Ile Ile Met Arg Thr Phe Arg Ile Ala Ile Trp Asn Leu Asp Val Ile
            20                  25                  30

Ile Ser Ser Ile Val Arg Gln Leu Phe Lys Pro Leu Thr Lys Lys Asn
        35                  40                  45

Tyr Ser Glu Leu Asp Asp Glu Glu Pro Met Glu Leu Asp Tyr Pro
    50                  55                  60

<210> SEQ ID NO 23
<211> LENGTH: 1231
<212> TYPE: DNA
<213> ORGANISM: CORONAVIRUS
<220> FEATURE:
<221> NAME/KEY: CDS
<222> LOCATION: (285)..(650)
<223> OTHER INFORMATION:

<400> SEQUENCE: 23

| | |
|---|---|
| taccgtattg gaaactataa attaaataca gaccacgccg gtagcaacga caatattgct | 60 |
| ttgctagtac agtaagtgac aacagatgtt tcatcttgtt gacttccagg ttacaatagc | 120 |
| agagatattg attatcatta tgaggacttt caggattgct atttggaatc ttgacgttat | 180 |
| aataagttca atagtgagac aattatttaa gcctctaact aagaagaatt attcggagtt | 240 |
| agatgatgaa gaacctatgg agttagatta tccataaaac gaac atg aaa att att | 296 |
| | Met Lys Ile Ile |
| | 1 |

| | |
|---|---|
| ctc ttc ctg aca ttg att gta ttt aca tct tgc gag cta tat cac tat | 344 |
| Leu Phe Leu Thr Leu Ile Val Phe Thr Ser Cys Glu Leu Tyr His Tyr | |
| 5                   10                  15                  20 | |

| | |
|---|---|
| cag gag tgt gtt aga ggt acg act gta cta cta aaa gaa cct tgc cca | 392 |
| Gln Glu Cys Val Arg Gly Thr Thr Val Leu Leu Lys Glu Pro Cys Pro | |
|             25                  30                  35 | |

| | |
|---|---|
| tca gga aca tac gag ggc aat tca cca ttt cac cct ctt gct gac aat | 440 |
| Ser Gly Thr Tyr Glu Gly Asn Ser Pro Phe His Pro Leu Ala Asp Asn | |
|         40                  45                  50 | |

| | |
|---|---|
| aaa ttt gca cta act tgc act agc aca cac ttt gct ttt gct tgt gct | 488 |
| Lys Phe Ala Leu Thr Cys Thr Ser Thr His Phe Ala Phe Ala Cys Ala | |
|     55                  60                  65 | |

| | |
|---|---|
| gac ggt act cga cat acc tat cag ctg cgt gca aga tca gtt tca cca | 536 |
| Asp Gly Thr Arg His Thr Tyr Gln Leu Arg Ala Arg Ser Val Ser Pro | |

```
                  70                  75                  80
aaa ctt ttc atc aga caa gag gag gtt caa caa gag ctc tac tcg cca    584
Lys Leu Phe Ile Arg Gln Glu Glu Val Gln Gln Glu Leu Tyr Ser Pro
 85                  90                  95                 100 ctt ttt ctc att gtt gct gct cta gta ttt tta ata ctt tgc ttc acc    632
Leu Phe Leu Ile Val Ala Ala Leu Val Phe Leu Ile Leu Cys Phe Thr
                    105                 110                 115 att aag aga aag aca gaa tgaatgagct cactttaatt gacttctatt           680
Ile Lys Arg Lys Thr Glu
                    120 tgtgctttt agcctttctg ctattccttg ttttaataat gcttattata ttttggtttt   740
cactcgaaat ccaggatcta aagaacctt gtaccaaagt ctaaacgaac atgaaacttc   800
tcattgtttt gacttgtatt tctctatgca gttgcatatg cactgtagta cagcgctgtg   860
catctaataa acctcatgtg cttgaagatc cttgtaaggt acaacactag gggtaatact   920
tatagcactg cttggctttg tgctctagga aaggttttac cttttcatag atggcacact   980
atggttcaaa catgcacacc taatgttact atcaactgtc aagatccagc tggtggtgcg  1040
cttatagcta ggtgttggta ccttcatgaa ggtcaccaaa ctgctgcatt tagagacgta  1100
cttgttgttt taaataaacg aacaaattaa aatgtctgat aatggacccc aatcaaacca  1160
acgtagtgcc ccccgcatta catttggtgg acccacagat tcaactgaca ataaccagaa  1220
tggaggacgc a                                                      1231

<210> SEQ ID NO 24
<211> LENGTH: 122
<212> TYPE: PRT
<213> ORGANISM: CORONAVIRUS

<400> SEQUENCE: 24

Met Lys Ile Ile Leu Phe Leu Thr Leu Ile Val Phe Thr Ser Cys Glu
 1               5                  10                  15

Leu Tyr His Tyr Gln Glu Cys Val Arg Gly Thr Thr Val Leu Leu Lys
                20                  25                  30

Glu Pro Cys Pro Ser Gly Thr Tyr Glu Gly Asn Ser Pro Phe His Pro
            35                  40                  45

Leu Ala Asp Asn Lys Phe Ala Leu Thr Cys Thr Ser Thr His Phe Ala
        50                  55                  60

Phe Ala Cys Ala Asp Gly Thr Arg His Thr Tyr Gln Leu Arg Ala Arg
 65                  70                  75                  80

Ser Val Ser Pro Lys Leu Phe Ile Arg Gln Glu Val Gln Gln Glu
                85                  90                  95

Leu Tyr Ser Pro Leu Phe Leu Ile Val Ala Ala Leu Val Phe Leu Ile
               100                 105                 110

Leu Cys Phe Thr Ile Lys Arg Lys Thr Glu
           115                 120

<210> SEQ ID NO 25
<211> LENGTH: 1231
<212> TYPE: DNA
<213> ORGANISM: CORONAVIRUS
<220> FEATURE:
<221> NAME/KEY: CDS
<222> LOCATION: (650)..(781)
<223> OTHER INFORMATION:

<400> SEQUENCE: 25
taccgtattg gaaactataa attaaataca gaccacgccg gtagcaacga caatattgct    60
```

```
ttgctagtac agtaagtgac aacagatgtt tcatcttgtt gacttccagg ttacaatagc    120
agagatattg attatcatta tgaggacttt caggattgct atttggaatc ttgacgttat    180
aataagttca atagtgagac aattatttaa gcctctaact aagaagaatt attcggagtt    240
agatgatgaa gaacctatgg agttagatta tccataaaac gaacatgaaa attattctct    300
tcctgacatt gattgtattt acatcttgcg agctatatca ctatcaggag tgtgttagag    360
gtacgactgt actactaaaa gaaccttgcc catcaggaac atacgagggc aattcaccat    420
ttcaccctct tgctgacaat aaatttgcac taacttgcac tagcacacac tttgcttttg    480
cttgtgctga cggtactcga catacctatc agctgcgtgc aagatcagtt tcaccaaaac    540 tttcatcag acaagaggag gttcaacaag agctctactc gccacttttt ctcattgttg    600
ctgctctagt atttttaata ctttgcttca ccattaagag aaagacaga atg aat gag    658
                                                      Met Asn Glu
                                                        1 ctc act tta att gac ttc tat ttg tgc ttt tta gcc ttt ctg cta ttc    706
Leu Thr Leu Ile Asp Phe Tyr Leu Cys Phe Leu Ala Phe Leu Leu Phe
    5                  10                  15 ctt gtt tta ata atg ctt att ata ttt tgg ttt tca ctc gaa atc cag    754
Leu Val Leu Ile Met Leu Ile Ile Phe Trp Phe Ser Leu Glu Ile Gln
 20                  25                  30                  35 gat cta gaa gaa cct tgt acc aaa gtc taaacgaaca tgaaacttct           801
Asp Leu Glu Glu Pro Cys Thr Lys Val
                40 cattgttttg acttgtattt ctctatgcag ttgcatatgc actgtagtac agcgctgtgc    861 atctaataaa cctcatgtgc ttgaagatcc ttgtaaggta caacactagg gtaatactt     921 atagcactgc ttggctttgt gctctaggaa aggttttacc ttttcataga tggcacacta    981 tggttcaaac atgcacacct aatgttacta tcaactgtca agatccagct ggtggtgcgc   1041 ttatagctag tgttggtac cttcatgaag gtcaccaaac tgctgcattt agagacgtac    1101 ttgttgtttt aaataaacga acaaattaaa atgtctgata atggacccca atcaaaccaa   1161 cgtagtgccc cccgcattac atttggtgga cccacagatt caactgacaa taaccagaat   1221 ggaggacgca                                                          1231

<210> SEQ ID NO 26
<211> LENGTH: 44
<212> TYPE: PRT
<213> ORGANISM: CORONAVIRUS

<400> SEQUENCE: 26

Met Asn Glu Leu Thr Leu Ile Asp Phe Tyr Leu Cys Phe Leu Ala Phe
 1               5                  10                  15

Leu Leu Phe Leu Val Leu Ile Met Leu Ile Ile Phe Trp Phe Ser Leu
                20                  25                  30

Glu Ile Gln Asp Leu Glu Glu Pro Cys Thr Lys Val
                35                  40

<210> SEQ ID NO 27
<211> LENGTH: 1231
<212> TYPE: DNA
<213> ORGANISM: CORONAVIRUS
<220> FEATURE:
<221> NAME/KEY: CDS
<222> LOCATION: (791)..(907)
<223> OTHER INFORMATION:

<400> SEQUENCE: 27
```

```
taccgtattg gaaactataa attaaataca gaccacgccg gtagcaacga caatattgct      60
ttgctagtac agtaagtgac aacagatgtt tcatcttgtt gacttccagg ttacaatagc     120
agagatattg attatcatta tgaggacttt caggattgct atttggaatc ttgacgttat     180
aataagttca atagtgagac aattatttaa gcctctaact aagaagaatt attcggagtt     240
agatgatgaa gaacctatgg agttagatta tccataaaac gaacatgaaa attattctct     300
tcctgacatt gattgtattt acatcttgcg agctatatca ctatcaggag tgtgttagag     360
gtacgactgt actactaaaa gaaccttgcc catcaggaac atacgagggc aattcaccat     420
ttcaccctct tgctgacaat aaatttgcac taacttgcac tagcacacac tttgcttttg     480
cttgtgctga cggtactcga catacctatc agctgcgtgc aagatcagtt tcaccaaaac     540
ttttcatcag acaagaggag gttcaacaag agctctactc gccactttt  ctcattgttg     600 ctgctctagt attttaata ctttgcttca ccattaagag aaagacagaa tgaatgagct     660
cactttaatt gacttctatt tgtgcttttt agcctttctg ctattccttg ttttaataat     720
gcttattata ttttggtttt cactcgaaat ccaggatcta aagaacctt  gtaccaaagt     780 ctaaacgaac atg aaa ctt ctc att gtt ttg act tgt att tct cta tgc       829
            Met Lys Leu Leu Ile Val Leu Thr Cys Ile Ser Leu Cys
              1               5                   10 agt tgc ata tgc act gta gta cag cgc tgt gca tct aat aaa cct cat      877
Ser Cys Ile Cys Thr Val Val Gln Arg Cys Ala Ser Asn Lys Pro His
    15                  20                  25 gtg ctt gaa gat cct tgt aag gta caa cac tagggggtaat acttatagca       927
Val Leu Glu Asp Pro Cys Lys Val Gln His
30                  35 ctgcttggct ttgtgctcta ggaaaggttt taccttttca tagatggcac actatggttc     987
aaacatgcac acctaatgtt actatcaact gtcaagatcc agctggtggt gcgcttatag    1047
ctaggtgttg gtaccttcat gaaggtcacc aaactgctgc atttagagac gtacttgttg    1107
ttttaaataa acgaacaaat taaaatgtct gataatggac cccaatcaaa ccaacgtagt    1167 gcccccccgca ttcatttggg tggacccaca gattcaactg acaataacca gaatggagga    1227
cgca                                                                 1231

<210> SEQ ID NO 28
<211> LENGTH: 39
<212> TYPE: PRT
<213> ORGANISM: CORONAVIRUS

<400> SEQUENCE: 28

Met Lys Leu Leu Ile Val Leu Thr Cys Ile Ser Leu Cys Ser Cys Ile
1               5                   10                  15

Cys Thr Val Val Gln Arg Cys Ala Ser Asn Lys Pro His Val Leu Glu
                20                  25                  30

Asp Pro Cys Lys Val Gln His
        35

<210> SEQ ID NO 29
<211> LENGTH: 1231
<212> TYPE: DNA
<213> ORGANISM: CORONAVIRUS
<220> FEATURE:
<221> NAME/KEY: CDS
<222> LOCATION: (876)..(1127)
<223> OTHER INFORMATION:

<400> SEQUENCE: 29
```

```
taccgtattg gaaactataa attaaataca gaccacgccg gtagcaacga caatattgct    60
ttgctagtac agtaagtgac aacagatgtt tcatcttgtt gacttccagg ttacaatagc   120
agagatattg attatcatta tgaggacttt caggattgct atttggaatc ttgacgttat   180
aataagttca atagtgagac aattatttaa gcctctaact aagaagaatt attcggagtt   240
agatgatgaa gaacctatgg agttagatta tccataaaac gaacatgaaa attattctct   300
tcctgacatt gattgtattt acatcttgcg agctatatca ctatcaggag tgtgttagag   360
gtacgactgt actactaaaa gaaccttgcc catcaggaac atacgagggc aattcaccat   420 tcaccctct  tgctgacaat aaatttgcac taacttgcac tagcacacac tttgcttttg    480
cttgtgctga cggtactcga catacctatc agctgcgtgc aagatcagtt tcaccaaaac   540
ttttcatcag acaagaggag gttcaacaag agctctactc gccacttttt ctcattgttg   600
ctgctctagt attttaata  ctttgcttca ccattaagag aaagacagaa tgaatgagct   660
cactttaatt gacttctatt tgtgcttttt agcctttctg ctattccttg ttttaataat   720
gcttattata ttttggtttt cactcgaaat ccaggatcta aagaacctt  gtaccaaagt   780 ctaaacgaac atgaaacttc tcattgtttt gacttgtatt tctctatgca gttgcatatg   840
cactgtagta cagcgctgtg catctaataa acctc atg tgc ttg aag atc ctt      893
                                   Met Cys Leu Lys Ile Leu
                                    1               5 gta agg tac aac act agg ggt aat act tat agc act gct tgg ctt tgt      941
Val Arg Tyr Asn Thr Arg Gly Asn Thr Tyr Ser Thr Ala Trp Leu Cys
         10                  15                  20 gct cta gga aag gtt tta cct ttt cat aga tgg cac act atg gtt caa      989
Ala Leu Gly Lys Val Leu Pro Phe His Arg Trp His Thr Met Val Gln
     25                  30                  35 aca tgc aca cct aat gtt act atc aac tgt caa gat cca gct ggt ggt     1037
Thr Cys Thr Pro Asn Val Thr Ile Asn Cys Gln Asp Pro Ala Gly Gly
 40                  45                  50 gcg ctt ata gct agg tgt tgg tac ctt cat gaa ggt cac caa act gct     1085
Ala Leu Ile Ala Arg Cys Trp Tyr Leu His Glu Gly His Gln Thr Ala
55                  60                  65                  70 gca ttt aga gac gta ctt gtt gtt tta aat aaa cga aca aat             1127
Ala Phe Arg Asp Val Leu Val Val Leu Asn Lys Arg Thr Asn
                 75                  80 taaaatgtct gataatggac cccaatcaaa ccaacgtagt gccccccgca ttacatttgg    1187
tggacccaca gattcaactg acaataacca gaatggagga cgca                    1231

<210> SEQ ID NO 30
<211> LENGTH: 84
<212> TYPE: PRT
<213> ORGANISM: CORONAVIRUS

<400> SEQUENCE: 30

Met Cys Leu Lys Ile Leu Val Arg Tyr Asn Thr Arg Gly Asn Thr Tyr
1               5                   10                  15

Ser Thr Ala Trp Leu Cys Ala Leu Gly Lys Val Leu Pro Phe His Arg
            20                  25                  30

Trp His Thr Met Val Gln Thr Cys Thr Pro Asn Val Thr Ile Asn Cys
        35                  40                  45

Gln Asp Pro Ala Gly Gly Ala Leu Ile Ala Arg Cys Trp Tyr Leu His
    50                  55                  60

Glu Gly His Gln Thr Ala Ala Phe Arg Asp Val Leu Val Val Leu Asn
65                  70                  75                  80
```

Lys Arg Thr Asn

<210> SEQ ID NO 31
<211> LENGTH: 21221
<212> TYPE: DNA
<213> ORGANISM: CORONAVIRUS

<400> SEQUENCE: 31

| | | | | | |
|---|---|---|---|---|---|
| atggagagcc | ttgttcttgg | tgtcaacgag | aaaacacacg | tccaactcag | tttgcctgtc | 60 |
| cttcaggtta | gagacgtgct | agtgcgtggc | ttcggggact | ctgtggaaga | ggccctatcg | 120 |
| gaggcacgtg | aacacctcaa | aaatggcact | tgtggtctag | tagagctgga | aaaaggcgta | 180 |
| ctgccccagc | ttgaacagcc | ctatgtgttc | attaaacgtt | ctgatgcctt | aagcaccaat | 240 |
| cacggccaca | aggtcgttga | gctggttgca | gaaatggacg | gcattcagta | cggtcgtagc | 300 |
| ggtataacac | tgggagtact | cgtgccacat | gtgggcgaaa | ccccaattgc | ataccgcaat | 360 |
| gttcttcttc | gtaagaacgg | taataaggga | gccggtggtc | atagctatgg | catcgatcta | 420 |
| aagtcttatg | acttaggtga | cgagcttggc | actgatccca | ttgaagatta | tgaacaaaac | 480 |
| tggaacacta | agcatggcag | tggtgcactc | cgtgaactca | ctcgtgagct | caatggaggt | 540 |
| gcagtcactc | gctatgtcga | caacaatttc | tgtggcccag | atgggtaccc | tcttgattgc | 600 |
| atcaaagatt | ttctcgcacg | cgcgggcaag | tcaatgtgca | ctctttccga | caacttgat | 660 |
| tacatcgagt | cgaagagagg | tgtctactgc | tgccgtgacc | atgagcatga | aattgcctgg | 720 |
| ttcactgagc | gctctgataa | gagctacgag | caccagacac | ccttcgaaat | taagagtgcc | 780 |
| aagaaatttg | acacttttca | aggggaatgc | ccaaagtttg | tgtttcctct | taactcaaaa | 840 |
| gtcaaagtca | ttcaaccacg | tgttgaaaag | aaaaagactg | agggtttcat | ggggcgtata | 900 |
| cgctctgtgt | accctgttgc | atctccacag | gagtgtaaca | atatgcactt | gtctaccttg | 960 |
| atgaaatgta | atcattgcga | tgaagtttca | tggcagacgt | gcgactttct | gaaagccact | 1020 |
| tgtgaacatt | gtggcactga | aaatttagtt | attgaaggac | ctactacatg | tgggtaccta | 1080 |
| cctactaatg | ctgtagtgaa | aatgccatgt | cctgcctgtc | aagacccaga | gattggacct | 1140 |
| gagcatagtg | ttgcagatta | tcacaaccac | tcaaacattg | aaactcgact | ccgcaaggga | 1200 |
| ggtaggacta | gatgttttgg | aggctgtgtg | tttgcctatg | ttggctgcta | taataagcgt | 1260 |
| gcctactggg | ttcctcgtgc | tagtgctgat | attggctcag | ccatactgg | cattactggt | 1320 |
| gacaatgtgg | agaccttgaa | tgaggatctc | cttgagatac | tgagtcgtga | acgtgttaac | 1380 |
| attaacattg | ttggcgattt | tcatttgaat | gaagaggttg | ccatcatttt | ggcatctttc | 1440 |
| tctgcttcta | caagtgccct | tattgacact | ataaagagtc | ttgattacaa | gtcttttcaaa | 1500 |
| accattgttg | agtcctgcgg | taactataaa | gttaccaagg | aaagcccgt | aaaaggtgct | 1560 |
| tggaacattg | gacaacagag | atcagttttt | acaccactgt | gtggttttcc | ctcacaggct | 1620 |
| gctggtgtta | tcagatcaat | ttttgcgcgc | acacttgatg | cagcaaacca | ctcaattcct | 1680 |
| gatttgcaaa | gagcagctgt | caccatactt | gatggtattt | ctgaacagtc | attacgtctt | 1740 |
| gtcgacgcca | tggtttatac | ttcagacctg | ctcaccaaca | gtgtcattat | tatggcatat | 1800 |
| gtaactggtg | tccttgtaca | acagactcct | cagtggttgt | ctaatctttt | gggcactact | 1860 |
| gttgaaaaac | tcaggcctat | ctttgaatgg | attgaggcga | aacttagtgc | aggagttgaa | 1920 |
| tttctcaagg | atgcttggga | gattctcaaa | tttctcatta | caggtgtttt | tgacatcgtc | 1980 |
| aagggtcaaa | tacaggttgc | ttcagataac | atcaaggatt | gtgtaaaatg | cttcattgat | 2040 |

```
gttgttaaca aggcactcga aatgtgcatt gatcaagtca ctatcgctgg cgcaaagttg    2100
cgatcactca acttaggtga agtcttcatc gctcaaagca agggacttta ccgtcagtgt    2160
atacgtggca aggagcagct gcaactactc atgcctctta aggcaccaaa agaagtaacc    2220
tttcttgaag gtgattcaca tgacacagta cttacctctg aggaggttgt tctcaagaac    2280
ggtgaactcg aagcactcga gacgcccgtt gatagcttca caaatggagc tatcgttggc    2340
acaccagtct gtgtaaatgg cctcatgctc ttagagatta aggacaaaga acaatactgc    2400
gcattgtctc ctggtttact ggctacaaac aatgtctttc gcttaaaagg gggtgcacca    2460
attaaaggtg taacctttgg agaagatact gtttgggaag ttcaaggtta caagaatgtg    2520
agaatcacat ttgagcttga tgaacgtgtt gacaaagtgc ttaatgaaaa gtgctctgtc    2580
tacactgttg aatccggtac cgaagttact gagtttgcat gtgttgtagc agaggctgtt    2640
gtgaagactt acaaccagt ttctgatctc cttaccaaca tgggtattga tcttgatgag    2700
tggagtgtag ctacattcta cttatttgat gatgctggtg aagaaaactt ttcatcacgt    2760
atgtattgtt ccttttaccc tccagatgag gaagaagagg acgatgcaga gtgtgaggaa    2820
gaagaaattg atgaaacctg tgaacatgag tacggtacag aggatgatta tcaaggtctc    2880
cctctggaat ttggtgcctc agctgaaaca gttcgagttg aggaagaaga gaggaagac    2940 tggctggatg atactactga gcaatcagag attgagccag aaccagaacc tacacctgaa    3000
gaaccagtta atcagtttac tggttattta aaacttactg acaatgttgc cattaaatgt    3060
gttgacatcg ttaaggaggc acaaagtgct aatcctatgg tgattgtaaa tgctgctaac    3120
atacacctga acatggtgg tggtgtagca ggtgcactca caaggcaac caatggtgcc    3180 atgcaaaagg agagtgatga ttacattaag ctaaatggcc ctcttacagt aggagggtct    3240
tgtttgcttt ctggacataa tcttgctaag aagtgtctgc atgttgttgg acctaaccta    3300
aatgcaggtg aggacatcca gcttcttaag gcagcatatg aaaatttcaa ttcacaggac    3360
atcttacttg caccattgtt gtcagcaggc atatttggtg ctaaaccact tcagtcttta    3420
caagtgtgcg tgcagacggt tcgtacacag gtttatattg cagtcaatga caaagctctt    3480
tatgagcagg ttgtcatgga ttatcttgat aacctgaagc ctagagtgga agcacctaaa    3540
caagaggagc caccaaacac agaagattcc aaaactgagg agaaatctgt cgtacagaag    3600
cctgtcgatg tgaagccaaa aattaaggcc tgcattgatg aggttaccac aacactggaa    3660
gaaactaagt tcttaccaa taagttactc ttgtttgctg atatcaatgg taagctttac    3720
catgattctc agaacatgct tagaggtgaa gatatgtctt tccttgagaa ggatgcacct    3780
tacatggtag gtgatgttat cactagtggt gatatcactt gtgttgtaat accctccaaa    3840
aaggctggtg gcactactga gatgctctca agagctttga gaaaagtgcc agttgatgag    3900
tatataacca cgtaccctgg acaaggatgt gctggttata cacttgagga agctaagact    3960
gctcttaaga aatgcaaatc tgcattttat gtactacctt cagaagcacc taatgctaag    4020
gaagagattc taggaactgt atcctggaat ttgagagaaa tgcttgctca tgctgaagag    4080
acaagaaaat taatgcctat atgcatggat gttagagcca taatggcaac catccaacgt    4140
aagtataaag gaattaaaat tcaagagggc atcgttgact atggtgtccg attcttcttt    4200
tatactagta aagagcctgt agcttctatt attacgaagc tgaactctct aaatgagccg    4260
cttgtcacaa tgccaattgg ttatgtgaca catggtttta atcttgaaga ggctgcgcgc    4320
tgtatgcgtt ctcttaaagc tcctgccgta gtgtcagtat catcaccaga tgctgttact    4380
acatataatg gatacctcac ttcgtcatca aagacatctg aggagcactt tgtagaaaca    4440
```

```
gtttctttgg ctggctctta cagagattgg tcctattcag gacagcgtac agagttaggt    4500
gttgaatttc ttaagcgtgg tgacaaaatt gtgtaccaca ctctggagag ccccgtcgag    4560
tttcatcttg acggtgaggt tctttcactt gacaaactaa agagtctctt atccctgcgg    4620
gaggttaaga ctataaaagt gttcacaact gtggacaaca ctaatctcca cacacagctt    4680
gtggatatgt ctatgacata tggacagcag tttggtccaa catacttgga tggtgctgat    4740
gttacaaaaa ttaaacctca tgtaaatcat gagggtaaga cttctttgt actacctagt     4800 gatgacacac tacgtagtga agcttcgag tactaccata ctcttgatga gagttttctt     4860
ggtaggtaca tgtctgcttt aaaccacaca aagaaatgga aatttcctca agttggtggt    4920
ttaacttcaa ttaaatgggc tgataacaat tgttatttgt ctagtgtttt attagcactt    4980
caacagcttg aagtcaaatt caatgcacca gcacttcaag aggcttatta tagagcccgt    5040
gctggtgatg ctgctaactt ttgtgcactc atactcgctt acagtaataa aactgttggc    5100
gagcttggtg atgtcagaga aactatgacc catcttctac agcatgctaa tttggaatct    5160
gcaaagcgag ttcttaatgt ggtgtgtaaa cattgtggtc agaaaactac taccttaacg    5220
ggtgtagaag ctgtgatgta tatgggtact ctatcttatg ataatcttaa gacaggtgtt    5280
tccattccat gtgtgtgtgg tcgtgatgct acacaatatc tagtacaaca agagtcttct    5340
tttgttatga tgtctgcacc acctgctgag tataaattac agcaaggtac attcttatgt    5400
gcgaatgagt acactggtaa ctatcagtgt ggtcattaca ctcatataac tgctaaggag    5460
accctctatc gtattgacgg agctcacctt acaaagatgt cagagtacaa aggaccagtg    5520
actgatgttt tctacaagga aacatcttac actacaacca tcaagcctgt gtcgtataaa    5580
ctcgatggag ttacttacac agagattgaa ccaaaattgg atgggtatta taaaaaggat    5640
aatgcttact atacagagca gcctatagac cttgtaccaa ctcaaccatt accaaatgcg    5700
agttttgata atttcaaact cacatgttct aacacaaaat tgctgatga tttaaatcaa    5760 atgacaggct tcacaaagcc agcttcacga gagctatctg tcacattctt cccagacttg    5820
aatggcgatg tagtggctat tgactataga cactattcag cgagtttcaa gaaggtgct   5880 aaattactgc ataagccaat tgtttggcac attaaccagg ctacaaccaa gacaacgttc    5940
aaaccaaaca cttggtgttt acgttgtctt tggagtacaa agccagtaga tacttcaaat    6000
tcatttgaag ttctggcagt agaagacaca caaggaatgg acaatcttgc ttgtgaaagt    6060
caacaaccca cctctgaaga agtagtggaa aatcctacca tacagaagga agtcatagag    6120
tgtgacgtga aaactaccga agttgtaggc aatgtcatac ttaaaccatc agatgaaggt    6180
gttaaagtaa cacaagagtt aggtcatgag gatcttatgg ctgcttatgt ggaaaacaca    6240
agcattacca ttaagaaacc taatgagctt tcactagcct taggtttaaa aacaattgcc    6300
actcatggta ttgctgcaat taataggtgtt ccttggagta aaattttggc ttatgtcaaa    6360
```

```
ggttcttttc cttgcagcat ttgtttaagt ggattagact cccttgattc ttatccagct    6840
cttgaaacca ttcaggtgac gatttcatcg tacaagctag acttgacaat tttaggtctg    6900
gccgctgagt gggttttggc atatatgttg ttcacaaaat tcttttattt attaggtctt    6960
tcagctataa tgcaggtgtt ctttggctat tttgctagtc atttcatcag caattcttgg    7020
ctcatgtggt ttatcattag tattgtacaa atggcacccg tttctgcaat ggttaggatg    7080
tacatcttct ttgcttcttt ctactacata tggaagagct atgttcatat catggatggt    7140
tgcacctctt cgacttgcat gatgtgctat aagcgcaatc gtgccacacg cgttgagtgt    7200
acaactattg ttaatggcat gaagagatct ttctatgtct atgcaaatgg aggccgtggc    7260
ttctgcaaga ctcacaattg gaattgtctc aattgtgaca cattttgcac tggtagtaca    7320
ttcattagtg atgaagttgc tcgtgatttg tcactccagt ttaaaagacc aatcaaccct    7380
actgaccagt catcgtatat tgttgatagt gttgctgtga aaaatggcgc gcttcacctc    7440
tactttgaca aggctggtca aaagacctat gagagacatc cgctctccca ttttgtcaat    7500
ttagacaatt tgagagctaa caacactaaa ggttcactgc ctattaatgt catagttttt    7560
gatggcaagt ccaaatgcga cgagtctgct tctaagtctg cttctgtgta ctacagtcag    7620
ctgatgtgcc aacctattct gttgcttgac caagctcttg tatcagacgt tggagatagt    7680
actgaagttt ccgttaagat gttgatgct tatgtcgaca cctttcagc aacttttagt    7740 gttcctatgg aaaaacttaa ggcacttgtt gctacagctc acagcgagtt agcaaagggt    7800
gtagctttag atggtgtcct ttctacattc gtgtcagctg cccgacaagg tgttgttgat    7860
accgatgttg acacaaagga tgttattgaa tgtctcaaac tttcacatca ctctgactta    7920
gaagtgacag gtgacagttg taacaatttc atgctcacct ataataaggt tgaaaacatg    7980
acgcccagag atcttggcgc atgtattgac tgtaatgcaa ggcatatcaa tgcccaagta    8040
gcaaaaagtc acaatgtttc actcatctgg aatgtaaaag actacatgtc tttatctgaa    8100
cagctgcgta acaaaattcg tagtgctgcc aagaagaaca ataccctttt tagactaact    8160
tgtgctacaa ctagacaggt tgtcaatgtc ataactacta aaatctcact caagggtggt    8220
aagattgtta gtacttgttt taaacttatg cttaaggcca cattattgtg cgttcttgct    8280
gcattggttt gttatatcgt tatgccagta catacattgt caatccatga tggttacaca    8340
aatgaaatca ttggttacaa agccattcag gatggtgtca ctcgtgacat catttctact    8400
gatgattgtt ttgcaaataa acatgctggt tttgacgcat ggtttagcca gcgtggtggt    8460
tcatacaaaa atgacaaaag ctgccctgta gtagctgcta tcattacaag agagattggt    8520
ttcatagtgc ctggcttacc gggtactgtg ctgagagcaa tcaatggtga cttcttgcat    8580
tttctacctc gtgtttttag tgctgttggc aacatttgct acacaccttc caaactcatt    8640
gagtatagtg attttgctac ctctgcttgc gttcttgctg ctgagtgtac aattttaag    8700 gatgctatgg gcaaacctgt gccatattgt tatgacacta atttgctaga gggttctatt    8760
tcttatagtg agcttcgtcc agacactcgt tatgtgctta tggatggttc catcatacag    8820
tttcctaaca cttacctgga gggttctgtt agagtagtaa caactttga tgctgagtac    8880 tgtagacatg gtacatgcga aaggtcagaa gtaggtattt gcctatctac cagtggtaga    8940
tgggttctta ataatgagca ttacagagct ctatcaggag ttttctgtgg tgttgatgcg    9000
atgaatctca tagctaacat ctttactcct cttgtgcaac ctgtgggtgc tttagatgtg    9060
tctgcttcag tagtggctgg tggtattatt gccatattgg tgacttgtgc tgcctactac    9120
tttatgaaat tcagacgtgt ttttggtgag tacaaccatg ttgttgctgc taatgcactt    9180
```

| | |
|---|---|
| ttgtttttga tgtctttcac tatactctgt ctggtaccag cttacagctt tctgccggga | 9240 |
| gtctactcag tctttactt gtacttgaca ttctatttca ccaatgatgt ttcattcttg | 9300 |
| gctcaccttc aatggtttgc catgttttct cctattgtgc cttttggat aacagcaatc | 9360 |
| tatgtattct gtatttctct gaagcactgc cattggttct ttaacaacta tcttaggaaa | 9420 |
| agagtcatgt ttaatggagt tacatttagt accttcgagg aggctgcttt gtgtaccttt | 9480 |
| ttgctcaaca aggaaatgta cctaaaattg cgtagcgaga cactgttgcc acttacacag | 9540 |
| tataacaggt atcttgctct atataacaag tacaagtatt tcagtggagc cttagatact | 9600 |
| accagctatc gtgaagcagc ttgctgccac ttagcaaagg ctctaaatga ctttagcaac | 9660 |
| tcaggtgctg atgttctcta ccaaccacca cagacatcaa tcacttctgc tgttctgcag | 9720 |
| agtggtttta ggaaaatggc attcccgtca ggcaaagttg aagggtgcat ggtacaagta | 9780 |
| acctgtggaa ctacaactct taatggattg tggttggatg acacagtata ctgtccaaga | 9840 |
| catgtcattt gcacagcaga agacatgctt aatcctaact atgaagatct gctcattcgc | 9900 |
| aaatccaacc atagctttct tgttcaggct ggcaatgttc aacttcgtgt tattggccat | 9960 |
| tctatgcaaa attgtctgct taggcttaaa gttgatactt ctaaccctaa gacacccaag | 10020 |
| tataaatttg tccgtatcca acctggtcaa acatttttcag ttctagcatg ctacaatggt | 10080 |
| tcaccatctg gtgtttatca gtgtgccatg agacctaatc ataccattaa aggttctttc | 10140 |
| cttaatggat catgtggtag tgttggtttt aacattgatt atgattgcgt gtctttctgc | 10200 |
| tatatgcatc atatggagct tccaacagga gtacacgctg gtactgactt agaaggtaaa | 10260 |
| ttctatggtc catttgttga cagacaaact gcacaggctg caggtacaga cacaaccata | 10320 |
| acattaaatg ttttggcatg gctgtatgct gctgttatca atggtgatag gtggtttctt | 10380 |
| aatagattca ccactacttt gaatgacttt aaccttgtgg caatgaagta caactatgaa | 10440 |
| cctttgacac aagatcatgt tgacatattg ggacctcttt ctgctcaaac aggaattgcc | 10500 |
| gtcttagata tgtgtgctgc tttgaaagag ctgctgcaga atggtatgaa tggtcgtact | 10560 |
| atccttggta gcactatttt agaagatgag tttacaccat tgatgttgt tagacaatgc | 10620 |
| tctggtgtta ccttccaagg taagttcaag aaaattgtta agggcactca tcattggatg | 10680 |
| cttttaactt tcttgacatc actattgatt cttgttcaaa gtacacagtg gtcactgttt | 10740 |
| ttctttgttt acgagaatgc tttcttgcca tttactcttg gtattatggc aattgctgca | 10800 |
| tgtgctatgc tgcttgttaa gcataagcac gcattcttgt gcttgttct gttaccttct | 10860 |
| cttgcaacag ttgcttactt taatatggtc tacatgcctg ctagctgggt gatgcgtatc | 10920 |
| atgacatggc ttgaattggc tgacactagc ttgtctggtt ataggcttaa ggattgtgtt | 10980 |
| atgtatgctt cagctttagt tttgcttatt ctcatgacag ctcgcactgt ttatgatgat | 11040 |
| gctgctagac gtgtttggac actgatgaat gtcattacac ttgttacaa agtctactat | 11100 |
| ggtaatgctt tagatcaagc tatttccatg tgggccttag ttatttctgt aacctctaac | 11160 |
| tattctggtg tcgttacgac tatcatgttt ttagctagag ctatagtgtt tgtgtgtgtt | 11220 |
| gagtattacc cattgttatt tattactggc aacaccttac agtgtatcat gcttgtttat | 11280 |
| tgtttcttag gctattgttg ctgctgctac tttggccttt tctgtttact caaccgttac | 11340 |
| ttcaggctta ctcttggtgt ttatgactac ttggtctcta cacaagaatt taggtatatg | 11400 |
| aactcccagg ggcttttgcc tcctaagagt agtattgatg ctttcaagct taacattaag | 11460 |
| ttgttgggta ttggaggtaa accatgtatc aaggttgcta ctgtacagtc taaaatgtct | 11520 |

```
gacgtaaagt gcacatctgt ggtactgctc tcggttcttc aacaacttag agtagagtca   11580
tcttctaaat tgtgggcaca atgtgtacaa ctccacaatg atattcttct tgcaaaagac   11640
acaactgaag ctttcgagaa gatggtttct cttttgtctg ttttgctatc catgcagggt   11700
gctgtagaca ttaataggtt gtgcgaggaa atgctcgata accgtgctac tcttcaggct   11760
attgcttcag aatttagttc tttaccatca tatgccgctt atgccactgc ccaggaggcc   11820
tatgagcagg ctgtagctaa tggtgattct gaagtcgttc tcaaaaagtt aaagaaatct   11880
ttgaatgtgg ctaaatctga gtttgaccgt gatgctgcca tgcaacgcaa gttggaaaag   11940
atggcagatc aggctatgac ccaaatgtac aaacaggcaa gatctgagga caagagggca   12000
aaagtaacta gtgctatgca aacaatgctc ttcactatgc ttaggaagct tgataatgat   12060
gcacttaaca acattatcaa caatgcgcgt gatggttgtg ttccactcaa catcatacca   12120
ttgactacag cagccaaact catggttgtt gtccctgatt atggtaccta caagaacact   12180
tgtgatggta acacctttac atatgcatct gcactctggg aaatccagca agttgttgat   12240
gcggatagca agattgttca acttagtgaa attaacatgg acaattcacc aaatttggct   12300
tggcctctta ttgttacagc tctaagagcc aactcagctg ttaaactaca gaataatgaa   12360
ctgagtccag tagcactacg acagatgtcc tgtgcggctg gtaccacaca aacagcttgt   12420
actgatgaca atgcacttgc ctactataac aattcgaagg gaggtaggtt tgtgctggca   12480
ttactatcag accaccaaga tctcaaatgg gctagattcc ctaagagtga tggtacaggt   12540
acaatttaca cagaactgga accaccttgt aggtttgtta cagacacacc aaaagggcct   12600
aaagtgaaat acttgtactt catcaaaggc ttaaacaacc taaatagagg tatggtgctg   12660
ggcagtttag ctgctacagt acgtcttcag gctggaaatg ctacagaagt acctgccaat   12720
tcaactgtgc tttccttctg tgcttttgca gtagaccctg ctaaagcata taggattac     12780 ctagcaagtg gaggacaacc aatcaccaac tgtgtgaaga tgttgtgtac acacactggt   12840
acaggacagg caattactgt aacaccagaa gctaacatgg accaagagtc ctttggtggt   12900
gcttcatgtt gtctgtattg tagatgccac attgaccatc caaatcctaa aggattctgt   12960
gacttgaaag gtaagtacgt ccaaatacct accacttgtg ctaatgaccc agtgggtttt   13020
acacttagaa acacagtctg taccgtctgc ggaatgtgga aaggttatgg ctgtagttgt   13080
gaccaactcc gcgaacccct tgatgcagtct gcggatgcat caacgttttt aaacgggttt   13140
gcggtgtaag tgcagcccgt cttacaccgt gcggcacagg cactagtact gatgtcgtct   13200
acagggcttt tgatatttac aacgaaaaag ttgctggttt tgcaaagttc ctaaaaacta   13260
attgctgtcg cttccaggag aaggatgagg aaggcaattt attagactct tactttgtag   13320
ttaagaggca tactatgtct aactaccaac atgaagagac tatttataac ttggttaaag   13380
attgtccagc ggttgctgtc catgacttttt caagtttag agtagatggt gacatggtac   13440
cacatatatc acgtcagcgt ctaactaaat acacaatggc tgatttagtc tatgctctac   13500
gtcattttga tgagggtaat tgtgatacat taaaagaaat actcgtcaca tacaattgct   13560
gtgatgatga ttatttcaat aagaaggatt ggtatgactt cgtagagaat cctgacatct   13620
tacgcgtata tgctaactta ggtgagcgtg tacgccaatc attattaaag actgtacaat   13680
tctgcgatgc tatgcgtgat gcaggcattg taggcgtact gacattagat aatcaggatc   13740
ttaatgggaa ctggtacgat ttcggtgatt tcgtacaagt agcaccaggc tgcggagttc   13800
ctattgtgga ttcatattac tcattgctga tgcccatcct cacttttgact agggcattgg   13860 ctgctgagtc ccatatggat gctgatctcg caaaaccact tattaagtgg gatttgctga   13920
```

```
aatatgattt tacggaagag agactttgtc tcttcgaccg ttattttaaa tattgggacc  13980
agacatacca tcccaattgt attaactgtt tggatgatag gtgtatcctt cattgtgcaa  14040
actttaatgt gttatttct  actgtgtttc cacctacaag ttttggacca ctagtaagaa  14100
aaatatttgt agatggtgtt cctttgttg  tttcaactgg ataccatttt cgtgagttag  14160
gagtcgtaca taatcaggat gtaaacttac atagctcgcg tctcagtttc aaggaacttt  14220
tagtgtatgc tgctgatcca gctatgcatg cagcttctgg caatttattg ctagataaac  14280
gcactacatg cttttcagta gctgcactaa caaacaatgt tgcttttcaa actgtcaaac  14340
ccggtaattt taataaagac ttttatgact ttgctgtgtc taaaggtttc tttaaggaag  14400
gaagttctgt tgaactaaaa cacttcttct ttgctcagga tggcaacgct gctatcagtg  14460
attatgacta ttatcgttat aatctgccaa caatgtgtga tatcagacaa ctcctattcg  14520
tagttgaagt tgttgataaa tactttgatt gttacgatgg tggctgtatt aatgccaacc  14580
aagtaatcgt taacaatctg gataaatcag ctggtttccc atttaataaa tggggtaagg  14640
ctagactta  ttatgactca atgagttatg aggatcaaga tgcacttttc gcgtatacta  14700
agcgtaatgt catccctact ataactcaaa tgaatcttaa gtatgccatt agtgcaaaga  14760
atagagctcg caccgtagct ggtgtctcta tctgtagtac tatgacaaat agacagtttc  14820
atcagaaatt attgaagtca atagccgcca ctagaggagc tactgtggta attggaacaa  14880
gcaagttta  cggtggctgg cataatatgt taaaaactgt ttacagtgat gtagaaactc  14940
cacaccttat gggttgggat tatccaaaat gtgacagagc catgcctaac atgcttagga  15000
taatggcctc tcttgttctt gctcgcaaac ataacacttg ctgtaactta tcacaccgtt  15060
tctacaggtt agctaacgag tgtgcgcaag tattaagtga gatggtcatg gtggcggct  15120
cactatatgt taaaccaggt ggaacatcat ccggtgatgc tacaactgct tatgctaata  15180
gtgtctttaa catttgtcaa gctgttacag ccaatgtaaa tgcacttctt tcaactgatg  15240
gtaataagat agctgacaag tatgtccgca atctacaaca caggctctat gagtgtctct  15300
atagaaatag ggatgttgat catgaattcg tggatgagtt ttacgcttac ctgcgtaaac  15360
atttctccat gatgattctt tctgatgatg ccgttgtgtg ctataacagt aactatgcgg  15420
ctcaaggttt agtagctagc attaagaact ttaaggcagt tctttattat caaaataatg  15480
tgttcatgtc tgaggcaaaa tgttggactg agactgacct tactaaagga cctcacgaat  15540
tttgctcaca gcatacaatg ctagttaaac aaggagatga ttacgtgtac ctgccttacc  15600
cagatccatc aagaatatta ggcgcaggct gttttgtcga tgatattgtc aaaacagatg  15660
gtacacttat gattgaaagg ttcgtgtcac tggctattga tgcttaccca cttacaaaac  15720
atcctaatca ggagtatgct gatgtctttc acttgtattt acaatacatt agaaagttac  15780
atgatgagct tactggccac atgttggaca tgtattccgt aatgctaact aatgataaca  15840
cctcacggta ctgggaacct gagttttatg aggctatgta cacaccacat acagtcttgc  15900
aggctgtagg tgcttgtgta ttgtgcaatt cacagacttc acttcgttgc ggtgcctgta  15960
ttaggagacc attcctatgt tgcaagtgct gctatgacca tgtcatttca acatcacaca  16020
aattagtgtt gtctgttaat ccctatgttt gcaatgcccc aggttgtgat gtcactgatg  16080
tgacacaact gtatcagga  ggtatgagct attattgcaa gtcacataag cctcccatta  16140
gttttccatt atgtgctaat ggtcaggttt ttggtttata caaaaacaca tgtgtaggca  16200
gtgacaatgt cactgacttc aatgcgatag caacatgtga ttggactaat gctggcgatt  16260
```

```
acatacttgc caacacttgt actgagagac tcaagctttt cgcagcagaa acgctcaaag   16320
ccactgagga aacatttaag ctgtcatatg gtattgccac tgtacgcgaa gtactctctg   16380
acagagaatt gcatctttca tgggaggttg gaaaacctag accaccattg aacagaaact   16440
atgtctttac tggttaccgt gtaactaaaa atagtaaagt acagattgga gagtacacct   16500
ttgaaaaagg tgactatggt gatgctgttg tgtacagagg tactacgaca tacaagttga   16560
atgttggtga ttactttgtg ttgacatctc acactgtaat gccacttagt gcacctactc   16620
tagtgccaca agagcactat gtgagaatta ctggcttgta cccaacactc aacatctcag   16680
atgagttttc tagcaatgtt gcaaattatc aaaaggtcgg catgcaaaag tactctacac   16740
tccaaggacc acctggtact ggtaagagtc attttgccat cggacttgct ctctattacc   16800
catctgctcg catagtgtat acggcatgct ctcatgcagc tgttgatgcc ctatgtgaaa   16860
aggcattaaa atatttgccc atagataaat gtagtagaat catacctgcg cgtgcgcgcg   16920
tagagtgttt tgataaattc aaagtgaatt caacactaga acagtatgtt ttctgcactg   16980
taaatgcatt gccagaaaca actgctgaca ttgtagtctt tgatgaaatc tctatggcta   17040
ctaattatga cttgagtgtt gtcaatgcta gacttcgtgc aaaacactac gtctatattg   17100
gcgatcctgc tcaattacca gccccccgca cattgctgac taaaggcaca ctagaaccag   17160
aatattttaa ttcagtgtgc agacttatga aaacaatagg tccagacatg ttccttggaa   17220
cttgtcgccg ttgtcctgct gaaattgttg acactgtgag tgctttagtt tatgacaata   17280
agctaaaagc acacaaggat aagtcagctc aatgcttcaa aatgttctac aaaggtgtta   17340
ttacacatga tgtttcatct gcaatcaaca gacctcaaat aggcgttgta agagaatttc   17400
ttacacgcaa tcctgcttgg agaaaagctg ttttatctc accttataat tcacagaacg   17460
ctgtagcttc aaaaatctta ggattgccta cgcagactgt tgattcatca cagggttctg   17520
aatatgacta tgtcatattc acacaaacta ctgaaacagc acactcttgt aatgtcaacc   17580
gcttcaatgt ggctatcaca agggcaaaaa ttggcatttt gtgcataatg tctgatagag   17640
atctttatga caaactgcaa tttacaagtc tagaaatacc acgtcgcaat gtggctacat   17700
tacaagcaga aaatgtaact ggacttttta aggactgtag taagatcatt actggtcttc   17760
atcctacaca ggcacctaca cacctcagcg ttgatataaa gttcaagact gaaggattat   17820
gtgttgacat accaggcata ccaaaggaca tgacctaccg tagactcatc tctatgatgg   17880
gtttcaaaat gaattaccaa gtcaatggtt accctaatat gtttatcacc cgcgaagaag   17940
ctattcgtca cgttcgtgcg tggattggct ttgatgtaga gggctgtcat gcaactagag   18000
atgctgtggg tactaaccta cctctccagc taggattttc tacaggtgtt aacttagtag   18060
ctgtaccgac tggttatgtt gacactgaaa ataacacaga attcaccaga gttaatgcaa   18120
aacctccacc aggtgaccag tttaaacatc ttataccact catgtataaa ggcttgccct   18180
ggaatgtagt gcgtattaag atagtacaaa tgctcagtga tactgaaaa ggattgtcag   18240 acagagtcgt gttcgtcctt tgggcgcatg gctttgagct tacatcaatg aagtactttg   18300
tcaagattgg acctgaaaga acgtgttgtc tgtgtgacaa acgtgcaact tgcttttcta   18360
cttcatcaga tacttatgcc tgctggaatc attctgtggg ttttgactat gtctataacc   18420
catttatgat tgatgttcag cagtggggct tacgggtaa ccttcagagt aaccatgacc   18480
aacattgcca ggtacatgga aatgcacatg tggctagttg tgatgctatc atgactagat   18540
gtttagcagt ccatgagtgc tttgttaagc gcgttgattg gtctgttgaa tacccctatta   18600 taggagatga actgagggtt aattctgctt gcagaaaagt acaacacatg gttgtgaagt   18660
```

```
ctgcattgct tgctgataag tttccagttc ttcatgacat tggaaatcca aaggctatca  18720
agtgtgtgcc tcaggctgaa gtagaatgga agttctacga tgctcagcca tgtagtgaca  18780
aagcttacaa aatagaggaa ctcttctatt cttatgctac acatcacgat aaattcactg  18840
atggtgtttg tttgttttgg aattgtaacg ttgatcgtta cccagccaat gcaattgtgt  18900
gtaggtttga cacaagagtc ttgtcaaact tgaacttacc aggctgtgat ggtggtagtt  18960
tgtatgtgaa taagcatgca ttccacactc cagctttcga taaaagtgca tttactaatt  19020
taaagcaatt gcctttcttt tactattctg atagtccttg tgagtctcat ggcaaacaag  19080
tagtgtcgga tattgattat gttccactca aatctgctac gtgtattaca cgatgcaatt  19140
taggtggtgc tgtttgcaga caccatgcaa atgagtaccg acagtacttg gatgcatata  19200
atatgatgat ttctgctgga tttagcctat ggatttacaa acaatttgat acttataacc  19260
tgtggaatac atttaccagg ttacagagtt tagaaaatgt ggcttataat gttgttaata  19320
aaggacactt tgatggacac gccggcgaag cacctgtttc catcattaat aatgctgttt  19380
acacaaaggt agatggtatt gatgtggaga tctttgaaaa taagacaaca cttcctgtta  19440
atgttgcatt tgagctttgg gctaagcgta acattaaacc agtgccagag attaagatac  19500
tcaataattt gggtgttgat atcgctgcta atactgtaat ctgggactac aaaagagaag  19560
ccccagcaca tgtatctaca ataggtgtct gcacaatgac tgacattgcc aagaaaccta  19620
ctgagagtgc ttgttcttca cttactgtct tgtttgatgg tagagtggaa ggacaggtag  19680
accttttttag aaacgcccgt aatggtgttt taataacaga aggttcagtc aaaggtctaa  19740
cacctccaaa gggaccagca caagctagcg tcaatggagt cacattaatt ggagaatcag  19800
taaaaacaca gtttaactac tttaagaaag tagacggcat tattcaacag ttgcctgaaa  19860
cctactttac tcagagcaga gacttagagg atttttaagcc cagatcacaa atggaaactg  19920
actttctcga gctcgctatg gatgaattca tacagcgata taagctcgag ggctatgcct  19980
tcgaacacat cgtttatgga gatttcagtc atggacaact tggcggtctt catttaatga  20040
taggcttagc caagcgctca caagattcac cacttaaatt agaggatttt atccctatgg  20100
acagcacagt gaaaaattac ttcataacag atgcgcaaac aggttcatca aaatgtgtgt  20160
gttctgtgat tgatctttta cttgatgact ttgtcgagat aataaagtca caagatttgt  20220
cagtgatttc aaaagtggtc aaggttacaa ttgactatgc tgaaatttca ttcatgcttt  20280
ggtgtaagga tggacatgtt gaaaccttct acccaaaact acaagcaagt caagcgtggc  20340
aaccaggtgt tgcgatgcct aacttgtaca agatgcaaag aatgcttctt gaaaagtgtg  20400
accttcagaa ttatggtgaa aatgctgtta taccaaaagg aataatgatg aatgtcgcaa  20460
agtatactca actgtgtcaa tacttaaata cacttacttt agctgtaccc tacaacatga  20520
gagttattca ctttggtgct ggctctgata aaggagttgc accaggtaca gctgcctca  20580
gacaatggtt gccaactggc acactacttg tcgattcaga tcttaatgac ttcgtctccg  20640
acgcagattc tactttaatt ggagactgtg aacagtaca tacggctaat aaatgggacc  20700
ttattattag cgatatgtat gaccctagga ccaaacatgt gacaaaagag aatgactcta  20760
aagaagggtt tttcacttat ctgtgtggat ttataaagca aaaactagcc ctgggtggtt  20820
ctatagctgt aaagataaca gagcattctt ggaatgctga cctttacaag cttatgggcc  20880
atttctcatg gtggacagct tttgttacaa atgtaaatgc atcatcatcg gaagcatttt  20940
taattggggc taactatctt ggcaagccga aggaacaaat tgatggctat accatgcatg  21000
```

```
ctaactacat tttctggagg aacacaaatc ctatccagtt gtcttcctat tcactctttg    21060
acatgagcaa atttcctctt aaattaagag gaactgctgt aatgtctctt aaggagaatc    21120
aaatcaatga tatgatttat tctcttctgg aaaaaggtag gcttatcatt agagaaaaca    21180
acagagttgt ggtttcaagt gatattcttg ttaacaacta a                        21221
```

<210> SEQ ID NO 32
<211> LENGTH: 297
<212> TYPE: DNA
<213> ORGANISM: CORONAVIRUS

<400> SEQUENCE: 32

```
atggacccca atcaaaccaa cgtagtgccc cccgcattac atttggtgga cccacagatt     60
caactgacaa taaccagaat ggaggacgca atggggcaag gccaaaacag cgccgacccc    120
aaggtttacc caataatact gcgtcttggt tcacagctct cactcagcat ggcaaggagg    180
aacttagatt ccctcgaggc cagggcgttc aatcaacac caatagtggt ccagatgacc    240
aaattggcta ctaccgaaga gctacccgac gagttcgtgg tggtgacggc aaaatga      297
```

<210> SEQ ID NO 33
<211> LENGTH: 98
<212> TYPE: PRT
<213> ORGANISM: CORONAVIRUS

<400> SEQUENCE: 33

Met Asp Pro Asn Gln Thr Asn Val Val Pro Pro Ala Leu His Leu Val
1               5                   10                  15

Asp Pro Gln Ile Gln Leu Thr Ile Thr Arg Met Glu Asp Ala Met Gly
            20                  25                  30

Gln Gly Gln Asn Ser Ala Asp Pro Lys Val Tyr Pro Ile Ile Leu Arg
        35                  40                  45

Leu Gly Ser Gln Leu Ser Leu Ser Met Ala Arg Arg Asn Leu Asp Ser
    50                  55                  60

Leu Glu Ala Arg Ala Phe Gln Ser Thr Pro Ile Val Val Gln Met Thr
65                  70                  75                  80

Lys Leu Ala Thr Thr Glu Glu Leu Pro Asp Glu Phe Val Val Val Thr
                85                  90                  95

Ala Lys

<210> SEQ ID NO 34
<211> LENGTH: 213
<212> TYPE: DNA
<213> ORGANISM: CORONAVIRUS

<400> SEQUENCE: 34

```
atgctgccac cgtgctacaa cttcctcaag gaacaacatt gccaaaaggc ttctacgcag     60
agggaagcag aggcggcagt caagcctctt ctcgctcctc atcacgtagt cgcggtaatt    120
caagaaattc aactcctggc agcagtaggg gaaattctcc tgctcgaatg gctagcggag    180
gtggtgaaac tgccctcgcg ctattgctgc tag                                  213
```

<210> SEQ ID NO 35
<211> LENGTH: 70
<212> TYPE: PRT
<213> ORGANISM: CORONAVIRUS

<400> SEQUENCE: 35

Met Leu Pro Pro Cys Tyr Asn Phe Leu Lys Glu Gln His Cys Gln Lys

```
1               5                  10                 15
Ala Ser Thr Gln Arg Glu Ala Glu Ala Ala Val Lys Pro Leu Leu Ala
               20                 25                 30

Pro His His Val Val Ala Val Ile Gln Glu Ile Gln Leu Leu Ala Ala
               35                 40                 45

Val Gly Glu Ile Leu Leu Leu Glu Trp Leu Ala Glu Val Val Lys Leu
         50                 55                 60

Pro Ser Arg Tyr Cys Cys
65              70

<210> SEQ ID NO 36
<211> LENGTH: 1377
<212> TYPE: DNA
<213> ORGANISM: CORONAVIRUS
<220> FEATURE:
<221> NAME/KEY: CDS
<222> LOCATION: (67)..(1335)
<223> OTHER INFORMATION:

<400> SEQUENCE: 36
atgaaggtca ccaaactgct gcatttagag acgtacttgt tgttttaaat aaacgaacaa      60 attaaa atg tct gat aat gga ccc caa tca aac caa cgt agt gcc ccc       108
       Met Ser Asp Asn Gly Pro Gln Ser Asn Gln Arg Ser Ala Pro
       1               5                  10 cgc att aca ttt ggt gga ccc aca gat tca act gac aat aac cag aat    156
Arg Ile Thr Phe Gly Gly Pro Thr Asp Ser Thr Asp Asn Asn Gln Asn
15              20                  25                  30 gga gga cgc aat ggg gca agg cca aaa cag cgc cga ccc caa ggt tta    204
Gly Gly Arg Asn Gly Ala Arg Pro Lys Gln Arg Arg Pro Gln Gly Leu
                35                  40                  45 ccc aat aat act gcg tct tgg ttc aca gct ctc act cag cat ggc aag    252
Pro Asn Asn Thr Ala Ser Trp Phe Thr Ala Leu Thr Gln His Gly Lys
            50                  55                  60 gag gaa ctt aga ttc cct cga ggc cag ggc gtt cca atc aac acc aat    300
Glu Glu Leu Arg Phe Pro Arg Gly Gln Gly Val Pro Ile Asn Thr Asn
        65                  70                  75 agt ggt cca gat gac caa att ggc tac tac cga aga gct acc cga cga    348
Ser Gly Pro Asp Asp Gln Ile Gly Tyr Tyr Arg Arg Ala Thr Arg Arg
    80                  85                  90 gtt cgt ggt ggt gac ggc aaa atg aaa gag ctc agc ccc aga tgg tac    396
Val Arg Gly Gly Asp Gly Lys Met Lys Glu Leu Ser Pro Arg Trp Tyr
95                  100                 105                 110 ttc tat tac cta gga act ggc cca gaa gct tca ctt ccc tac ggc gct    444
Phe Tyr Tyr Leu Gly Thr Gly Pro Glu Ala Ser Leu Pro Tyr Gly Ala
                115                 120                 125 aac aaa gaa ggc atc gta tgg gtt gca act gag gga gcc ttg aat aca    492
Asn Lys Glu Gly Ile Val Trp Val Ala Thr Glu Gly Ala Leu Asn Thr
            130                 135                 140 ccc aaa gac cac att ggc acc cgc aat cct aat aac aat gct gcc acc    540
Pro Lys Asp His Ile Gly Thr Arg Asn Pro Asn Asn Asn Ala Ala Thr
        145                 150                 155 gtg cta caa ctt cct caa gga aca aca ttg cca aaa ggc ttc tac gca    588
Val Leu Gln Leu Pro Gln Gly Thr Thr Leu Pro Lys Gly Phe Tyr Ala
    160                 165                 170 gag gga agc aga ggc ggc agt caa gcc tct tct cgc tcc tca tca cgt    636
Glu Gly Ser Arg Gly Gly Ser Gln Ala Ser Ser Arg Ser Ser Ser Arg
175                 180                 185                 190 agt cgc ggt aat tca aga aat tca act cct ggc agc agt agg gga aat    684
Ser Arg Gly Asn Ser Arg Asn Ser Thr Pro Gly Ser Ser Arg Gly Asn
                195                 200                 205
```

-continued

| | | |
|---|---|---|
| tct cct gct cga atg gct agc gga ggt ggt gaa act gcc ctc gcg cta<br>Ser Pro Ala Arg Met Ala Ser Gly Gly Gly Glu Thr Ala Leu Ala Leu<br>          210                    215                    220 | 732 |
| ttg ctg cta gac aga ttg aac cag ctt gag agc aaa gtt tct ggt aaa<br>Leu Leu Leu Asp Arg Leu Asn Gln Leu Glu Ser Lys Val Ser Gly Lys<br>          225                    230                    235 | 780 |
| ggc caa caa caa caa ggc caa act gtc act aag aaa tct gct gct gag<br>Gly Gln Gln Gln Gln Gly Gln Thr Val Thr Lys Lys Ser Ala Ala Glu<br>240                    245                    250 | 828 |
| gca tct aaa aag cct cgc caa aaa cgt act gcc aca aaa cag tac aac<br>Ala Ser Lys Lys Pro Arg Gln Lys Arg Thr Ala Thr Lys Gln Tyr Asn<br>255                    260                    265                    270 | 876 |
| gtc act caa gca ttt ggg aga cgt ggt cca gaa caa acc caa gga aat<br>Val Thr Gln Ala Phe Gly Arg Arg Gly Pro Glu Gln Thr Gln Gly Asn<br>                  275                    280                    285 | 924 |
| ttc ggg gac caa gac cta atc aga caa gga act gat tac aaa cat tgg<br>Phe Gly Asp Gln Asp Leu Ile Arg Gln Gly Thr Asp Tyr Lys His Trp<br>                  290                    295                    300 | 972 |
| ccg caa att gca caa ttt gct cca agt gcc tct gca ttc ttt gga atg<br>Pro Gln Ile Ala Gln Phe Ala Pro Ser Ala Ser Ala Phe Phe Gly Met<br>          305                    310                    315 | 1020 |
| tca cgc att ggc atg gaa gtc aca cct tcg gga aca tgg ctg act tat<br>Ser Arg Ile Gly Met Glu Val Thr Pro Ser Gly Thr Trp Leu Thr Tyr<br>320                    325                    330 | 1068 |
| cat gga gcc att aaa ttg gat gac aaa gat cca caa ttc aaa gac aac<br>His Gly Ala Ile Lys Leu Asp Asp Lys Asp Pro Gln Phe Lys Asp Asn<br>335                    340                    345                    350 | 1116 |
| gtc ata ctg ctg aac aag cac att gac gca tac aaa aca ttc cca cca<br>Val Ile Leu Leu Asn Lys His Ile Asp Ala Tyr Lys Thr Phe Pro Pro<br>                  355                    360                    365 | 1164 |
| aca gag cct aaa aag gac aaa aag aaa aag act gat gaa gct cag cct<br>Thr Glu Pro Lys Lys Asp Lys Lys Lys Lys Thr Asp Glu Ala Gln Pro<br>                  370                    375                    380 | 1212 |
| ttg ccg cag aga caa aag aag cag ccc act gtg act ctt ctt cct gcg<br>Leu Pro Gln Arg Gln Lys Lys Gln Pro Thr Val Thr Leu Leu Pro Ala<br>385                    390                    395 | 1260 |
| gct gac atg gat gat ttc tcc aga caa ctt caa aat tcc atg agt gga<br>Ala Asp Met Asp Asp Phe Ser Arg Gln Leu Gln Asn Ser Met Ser Gly<br>          400                    405                    410 | 1308 |
| gct tct gct gat tca act cag gca taa acactcatga tgaccacaca<br>Ala Ser Ala Asp Ser Thr Gln Ala<br>415                    420 | 1355 |
| aggcagatgg gctatgtaaa cg | 1377 |

<210> SEQ ID NO 37
<211> LENGTH: 422
<212> TYPE: PRT
<213> ORGANISM: CORONAVIRUS

<400> SEQUENCE: 37

Met Ser Asp Asn Gly Pro Gln Ser Asn Gln Arg Ser Ala Pro Arg Ile
1               5                    10                  15

Thr Phe Gly Gly Pro Thr Asp Ser Thr Asp Asn Asn Gln Asn Gly Gly
                  20                    25                    30

Arg Asn Gly Ala Arg Pro Lys Gln Arg Arg Pro Gln Gly Leu Pro Asn
          35                    40                    45

Asn Thr Ala Ser Trp Phe Thr Ala Leu Thr Gln His Gly Lys Glu Glu
50                    55                    60

| | | | | | | | | | | | | | | |
|---|---|---|---|---|---|---|---|---|---|---|---|---|---|---|
| Leu | Arg | Phe | Pro | Arg | Gly | Gln | Gly | Val | Pro | Ile | Asn | Thr | Asn | Ser | Gly |
| 65 | | | | 70 | | | | 75 | | | | 80 | | | |

Pro Asp Asp Gln Ile Gly Tyr Tyr Arg Arg Ala Thr Arg Arg Val Arg
                85                      90                      95

Gly Gly Asp Gly Lys Met Lys Glu Leu Ser Pro Arg Trp Tyr Phe Tyr
            100                     105                     110

Tyr Leu Gly Thr Gly Pro Glu Ala Ser Leu Pro Tyr Gly Ala Asn Lys
            115                     120                     125

Glu Gly Ile Val Trp Val Ala Thr Glu Gly Ala Leu Asn Thr Pro Lys
130                     135                     140

Asp His Ile Gly Thr Arg Asn Pro Asn Asn Asn Ala Ala Thr Val Leu
145                     150                     155                     160

Gln Leu Pro Gln Gly Thr Thr Leu Pro Lys Gly Phe Tyr Ala Glu Gly
                165                     170                     175

Ser Arg Gly Gly Ser Gln Ala Ser Ser Arg Ser Ser Ser Arg Ser Arg
            180                     185                     190

Gly Asn Ser Arg Asn Ser Thr Pro Gly Ser Ser Arg Gly Asn Ser Pro
            195                     200                     205

Ala Arg Met Ala Ser Gly Gly Gly Glu Thr Ala Leu Ala Leu Leu Leu
        210                     215                     220

Leu Asp Arg Leu Asn Gln Leu Glu Ser Lys Val Ser Gly Lys Gly Gln
225                     230                     235                     240

Gln Gln Gln Gly Gln Thr Val Thr Lys Lys Ser Ala Ala Glu Ala Ser
                245                     250                     255

Lys Lys Pro Arg Gln Lys Arg Thr Ala Thr Lys Gln Tyr Asn Val Thr
            260                     265                     270

Gln Ala Phe Gly Arg Arg Gly Pro Glu Gln Thr Gln Gly Asn Phe Gly
            275                     280                     285

Asp Gln Asp Leu Ile Arg Gln Gly Thr Asp Tyr Lys His Trp Pro Gln
290                     295                     300

Ile Ala Gln Phe Ala Pro Ser Ala Ser Ala Phe Phe Gly Met Ser Arg
305                     310                     315                     320

Ile Gly Met Glu Val Thr Pro Ser Gly Thr Trp Leu Thr Tyr His Gly
                325                     330                     335

Ala Ile Lys Leu Asp Asp Lys Asp Pro Gln Phe Lys Asp Asn Val Ile
            340                     345                     350

Leu Leu Asn Lys His Ile Asp Ala Tyr Lys Thr Phe Pro Pro Thr Glu
            355                     360                     365

Pro Lys Lys Asp Lys Lys Lys Thr Asp Glu Ala Gln Pro Leu Pro
        370                     375                     380

Gln Arg Gln Lys Lys Gln Pro Thr Val Thr Leu Leu Pro Ala Ala Asp
385                     390                     395                     400

Met Asp Asp Phe Ser Arg Gln Leu Gln Asn Ser Met Ser Gly Ala Ser
                405                     410                     415

Ala Asp Ser Thr Gln Ala
            420

<210> SEQ ID NO 38
<211> LENGTH: 1377
<212> TYPE: DNA
<213> ORGANISM: CORONAVIRUS

<400> SEQUENCE: 38
atgaaggtca ccaaactgct gcatttagag acgtacttgt tgttttaaat aaacgaacaa    60

```
attaaaatgt ctgataatgg accccaatca aaccaacgta gtgcccccg cattacattt    120 ggtggaccca cagattcaac tgacaataac cagaatggag gacgcaatgg ggcaaggcca    180
aaacagcgcc gaccccaagg tttacccaat aatactgcgt cttggttcac agctctcact    240
cagcatggca aggaggaact tagattccct cgaggccagg gcgttccaat caacaccaat    300
agtggtccag atgaccaaat tggctactac cgaagagcta cccgacgagt tcgtggtggt    360
gacggcaaaa tgaaagagct cagccccaga tggtacttct attacctagg aactggccca    420
gaagcttcac ttccctacgg cgctaacaaa gaaggcatcg tatgggttgc aactgaggga    480
gccttgaata cacccaaaga ccacattggc acccgcaatc ctaataacaa tgctgccacc    540
gtgctacaac ttcctcaagg aacaacattg ccaaaaggct tctacgcaga gggaagcaga    600
ggcggcagtc aagcctcttc tcgctcctca tcacgtagtc gcggtaattc aagaaattca    660
actcctggca gcagtagggg aaattctcct gctcgaatgg ctagcggagg tggtgaaact    720
gccctcgcgc tattgctgct agacagattg aaccagcttg agagcaaagt ttctggtaaa    780
ggccaacaac aacaaggcca aactgtcact aagaaatctg ctgctgaggc atctaaaaag    840
cctcgccaaa aacgtactgc cacaaaaacag tacaacgtca ctcaagcatt tgggagacgt    900
ggtccagaac aaacccaagg aaatttcggg gaccaagacc taatcagaca aggaactgat    960
tacaaacatt ggccgcaaat tgcacaattt gctccaagtg cctctgcatt ctttggaatg   1020
tcacgcattg gcatggaagt cacaccttcg ggaacatggc tgacttatca tggagccatt   1080
aaattggatg acaaagatcc acaattcaaa gacaacgtca tactgctgaa caagcacatt   1140
gacgcataca aaacattccc accaacagag cctaaaaagg acaaaaagaa aaagactgat   1200
gaagctcagc ctttgccgca gagacaaaag aagcagccca ctgtgactct tcttcctgcg   1260
gctgacatgg atgatttctc cagacaactt caaaattcca tgagtggagc ttctgctgat   1320
tcaactcagg cataaacact catgatgacc acacaaggca gatgggctat gtaaacg      1377

<210> SEQ ID NO 39
<211> LENGTH: 204
<212> TYPE: DNA
<213> ORGANISM: CORONAVIRUS

<400> SEQUENCE: 39
atattaggtt tttacctacc caggaaaagc caaccaacct cgatctcttg tagatctgtt    60
ctctaaacga actttaaaat ctgtgtagct gtcgctcggc tgcatgccta gtgcacctac   120
gcagtataaa caataataaa ttttactgtc gttgacaaga aacgagtaac tcgtccctct   180
tctgcagact gcttacggtt tcgt                                          204

<210> SEQ ID NO 40
<211> LENGTH: 809
<212> TYPE: DNA
<213> ORGANISM: CORONAVIRUS

<400> SEQUENCE: 40
actcaagcat ttgggagacg tggtccagaa caaacccaag gaaatttcgg ggaccaagac    60
ctaatcagac aaggaactga ttacaaacat tggccgcaaa ttgcacaatt tgctccaagt   120
gcctctgcat tctttggaat gtcacgcatt ggcatggaag tcacaccttc gggaacatgg   180
ctgacttatc atggagccat taaattggat gacaaagatc cacaattcaa agacaacgtc   240
atactgctga acaagcacat tgacgcatac aaaacattcc caccaacaga gcctaaaaag   300
gacaaaaaga aaaagactga tgaagctcag cctttgccgc agagacaaaa gaagcagccc   360
```

| | |
|---|---:|
| actgtgactc ttcttcctgc ggctgacatg gatgatttct ccagacaact tcaaaattcc | 420 |
| atgagtggag cttctgctga ttcaactcag gcataaacac tcatgatgac cacacaaggc | 480 |
| agatgggcta tgtaaacgtt ttcgcaattc cgtttacgat acatagtcta ctcttgtgca | 540 |
| gaatgaattc tcgtaactaa acagcacaag taggtttagt taactttaat ctcacatagc | 600 |
| aatctttaat caatgtgtaa cattaggagg gacttgaaag agccaccaca ttttcatcga | 660 |
| ggccacgcgg agtacgatcg agggtacagt gaataatgct agggagagct gcctatatgg | 720 |
| aagagcccta atgtgtaaaa ttaattttag tagtgctatc cccatgtgat tttaatagct | 780 |
| tcttaggaga atgacaaaaa aaaaaaaaa | 809 |

<210> SEQ ID NO 41
<211> LENGTH: 448
<212> TYPE: DNA
<213> ORGANISM: CORONAVIRUS

<400> SEQUENCE: 41

| | |
|---|---:|
| aatgaacaca tagggctgtt caagctgggg cagtacgcct ttttccagct ctactagacc | 60 |
| acaagtgcca tttttgaggt gttcacgtgc ctccgatagg gcctcttcca cagagtcccc | 120 |
| gaagccacgc actagcacgt tctaacctg aaggacaggc aaactgagtt ggacgtgtgt | 180 |
| tttctcgttg acaccaagaa caaggctctc catcttacct ttcggtcaca cccggacgaa | 240 |
| acctaggtat gctgatgatc gactgcaaca cggacgaaac cgtaagcagt ctgcagaaga | 300 |
| gggacgagtt actcgtttct tgtcaacgac agtaaaattt attattgttt atactgcgta | 360 |
| ggtgcactag gcatgcagcc gagcgacagc tacacagatt ttaaagttcg tttagagaac | 420 |
| agatctacaa gagatcgagg ttggttgg | 448 |

<210> SEQ ID NO 42
<211> LENGTH: 2033
<212> TYPE: DNA
<213> ORGANISM: CORONAVIRUS

<400> SEQUENCE: 42

| | |
|---|---:|
| atacctaggt ttcgtccggg tgtgaccgaa aggtaagatg gagagccttg ttcttggtgt | 60 |
| caacgagaaa acacacgtcc aactcagttt gcctgtcctt caggttagag acgtgctagt | 120 |
| gcgtggcttc ggggactctg tggaagaggc cctatcggag gcacgtgaac acctcaaaaa | 180 |
| tggcacttgt ggtctagtag agctggaaaa aggcgtactg ccccagcttg aacagcccta | 240 |
| tgtgttcatt aaacgttctg atgccttaag caccaatcac ggccacaagg tcgttgagct | 300 |
| ggttgcagaa atggacggca ttcagtacgg tcgtagcggt ataacactgg gagtactcgt | 360 |
| gccacatgtg ggcgaaaccc caattgcata ccgcaatgtt cttcttcgta agaacggtaa | 420 |
| taagggagcc ggtggtcata gctatggcat cgatctaaag tcttatgact taggtgacga | 480 |
| gcttggcact gatcccattg aagattatga acaaaactgg aacactaagc atggcagtgg | 540 |
| tgcactccgt gaactcactc gtgagctcaa tggaggtgca gtcactcgct atgtcgacaa | 600 |
| caatttctgt ggcccagatg gtaccctct tgattgcatc aaagattttc tcgcacgcgc | 660 |
| gggcaagtca atgtgcactc tttccgaaca acttgattac atcgagtcga agagaggtgt | 720 |
| ctactgctgc cgtgaccatg agcatgaaat tgcctggttc actgagcgct ctgataagag | 780 |
| ctacgagcac cagacaccct tcgaaattaa gagtgccaag aaatttgaca ctttcaaagg | 840 |
| ggaatgccca aagtttgtgt ttcctcttaa ctcaaaagtc aaagtcattc aaccacgtgt | 900 |

```
tgaaaagaaa aagactgagg gtttcatggg gcgtatacgc tctgtgtacc ctgttgcatc    960
tccacaggag tgtaacaata tgcacttgtc taccttgatg aaatgtaatc attgcgatga   1020
agtttcatgg cagacgtgcg actttctgaa agccacttgt gaacattgtg cactgaaaa    1080 tttagttatt gaaggaccta ctacatgtgg gtacctacct actaatgctg tagtgaaaat   1140
gccatgtcct gcctgtcaag acccagagat tggacctgag catagtgttg cagattatca   1200
caaccactca aacattgaaa ctcgactccg caagggaggt aggactagat gttttggagg   1260
ctgtgtgttt gcctatgttg gctgctataa taagcgtgcc tactgggttc ctcgtgctag   1320
tgctgatatt ggctcaggcc atactggcat tactggtgac aatgtggaga ccttgaatga   1380
ggatctcctt gagatactga gtcgtgaacg tgttaacatt aacattgttg gcgattttca   1440
tttgaatgaa gaggttgcca tcattttggc atctttctct gcttctacaa gtgcctttat   1500
tgacactata aagagtcttg attacaagtc tttcaaaacc attgttgagt cctgcggtaa   1560
ctataaagtt accaagggaa agcccgtaaa aggtgcttgg aacattggac aacagagatc   1620
agttttaaca ccactgtgtg gttttcctc acaggctgct ggtgttatca gatcaatttt    1680
tgcgcgcaca cttgatgcag caaccactc aattcctgat tgcaaagag cagctgtcac     1740 catacttgat ggtatttctg aacagtcatt acgtcttgtc gacgccatgg tttatacttc    1800
agacctgctc accaacagtg tcattattat ggcatatgta actggtggtc ttgtacaaca   1860
gacttctcag tggttgtcta atcttttggg cactactgtt gaaaaactca ggcctatctt   1920
tgaatggatt gaggcgaaac ttagtgcagg agttgaattt ctcaaggatg cttgggagat   1980
tctcaaattt ctcattacag gtgttttga catcgtcaag ggtcaaatac agg            2033

<210> SEQ ID NO 43
<211> LENGTH: 2018
<212> TYPE: DNA
<213> ORGANISM: CORONAVIRUS

<400> SEQUENCE: 43
ggattgaggc gaaacttagt gcaggagttg aatttctcaa ggatgcttgg gagattctca     60
aatttctcat tacaggtgtt tttgacatcg tcaagggtca aatacaggtt gcttcagata    120
acatcaagga ttgtgtaaaa tgcttcattg atgttgttaa caaggcactc gaaatgtgca    180
ttgatcaagt cactatcgct ggcgcaaagt tgcgatcact caacttaggt gaagtcttca    240
tcgctcaaag caagggactt taccgtcagt gtatacgtgg caaggagcag ctgcaactac    300
tcatgcctct taaggcacca aaagaagtaa cctttcttga aggtgattca catgacacag    360
tacttaccct ctgaggaggtt gttctcaaga acggtgaact cgaagcactc gagacgcccg   420
ttgatagctt cacaaatgga gctatcgttg cacaccagt ctgtgtaaat ggcctcatgc     480
tcttagagat taaggacaaa gaacaatact gcgcattgtc tcctggttta ctggctacaa   540
acaatgtctt tcgcttaaaa gggggtgcac caattaaagg tgtaaccttt ggagaagata   600
ctgtttggga agttcaaggt tacaagaatg tgagaatcac atttgagctt gatgaacgtg   660
ttgacaaagt gcttaatgaa aagtgctctg tctacactgt tgaatccggt accgaagtta   720
ctgagtttgc atgtgttgta gcagaggctg ttgtgaagac tttacaacca gtttctgatc   780
tccttaccaa catgggtatt gatcttgatg agtggagtgt agctacattc tacttatttg   840
atgatgctgg tgaagaaaac ttttcatcac gtatgtattg ttccttttac cctccagatg   900
aggaagaaga ggacgatgca gagtgtgagg aagaagaaat tgatgaaacc tgtgaacatg   960
agtacggtac agaggatgat tatcaaggtc tccctctgga atttggtgcc tcagctgaaa  1020
```

| | |
|---|---|
| cagttcgagt tgaggaagaa gaagaggaag actggctgga tgatactact gagcaatcag | 1080 |
| agattgagcc agaaccagaa cctacacctg aagaaccagt taatcagttt actggttatt | 1140 |
| taaaacttac tgacaatgtt gccattaaat gtgttgacat cgttaaggag cacaaagtg | 1200 |
| ctaatcctat ggtgattgta atgctgcta acatacacct gaaacatggt ggtggtgtag | 1260 |
| caggtgcact caacaaggca accaatggtg ccatgcaaaa ggagagtgat gattacatta | 1320 |
| agctaaatgg ccctcttaca gtaggagggt cttgtttgct ttctggacat aatcttgcta | 1380 |
| agaagtgtct gcatgttgtt ggacctaacc taaatgcagg tgaggacatc cagcttctta | 1440 |
| aggcagcata tgaaaatttc aattcacagg acatcttact tgcaccattg ttgtcagcag | 1500 |
| gcatatttgg tgctaaacca cttcagtctt tacaagtgtg cgtgcagacg gttcgtacac | 1560 |
| aggtttatat tgcagtcaat gacaaagctc tttatgagca ggttgtcatg gattatcttg | 1620 |
| ataacctgaa gcctagagtg gaagcaccta acaagagga gccaccaaac acagaagatt | 1680 |
| ccaaaactga ggagaaatct gtcgtacaga agcctgtcga tgtgaagcca aaaattaagg | 1740 |
| cctgcattga tgaggttacc acaacactgg aagaaactaa gtttcttacc aataagttac | 1800 |
| tcttgtttgc tgatatcaat ggtaagcttt accatgattc tcagaacatg cttagaggtg | 1860 |
| aagatatgtc tttccttgag aaggatgcac cttacatggt aggtgatgtt atcactagtg | 1920 |
| gtgatatcac ttgtgttgta ataccctcca aaaaggctgg tggcactact gagatgctct | 1980 |
| caagagcttt gaagaaagtg ccagttgatg agtatata | 2018 |

<210> SEQ ID NO 44
<211> LENGTH: 1442
<212> TYPE: DNA
<213> ORGANISM: CORONAVIRUS

<400> SEQUENCE: 44

| | |
|---|---|
| ttgatgaggt taccacaaca ctggaagaaa ctaagtttct taccaataag ttactcttgt | 60 |
| ttgctgatat caatggtaag ctttaccatg attctcagaa catgcttaga ggtgaagata | 120 |
| tgtctttcct tgagaaggat gcaccttaca tggtaggtga tgttatcact agtggtgata | 180 |
| tcacttgtgt tgtaataccc tccaaaaagg ctggtggcac tactgagatg ctctcaagag | 240 |
| ctttgaagaa agtgccagtt gatgagtata taaccacgta ccctggacaa ggatgtgctg | 300 |
| gttatacact tgaggaagct aagactgctc ttaagaaatg caaatctgca ttttatgtac | 360 |
| taccttcaga agcacctaat gctaaggaag agattctagg aactgtatcc tggaatttga | 420 |
| gagaaatgct tgctcatgct gaagagacaa gaaaattaat gcctatatgc atggatgtta | 480 |
| gagccataat ggcaaccatc aacgtaagt ataaaggaat taaaattcaa gagggcatcg | 540 |
| ttgactatgg tgtccgattc ttcttttata ctagtaaaga gcctgtagct tctattatta | 600 |
| cgaagctgaa ctctctaaat gagccgcttg tcacaatgcc aattggttat gtgacacatg | 660 |
| gttttaatct tgaagaggct gcgcgctgta tgcgttctct taagctcct gccgtagtgt | 720 |
| cagtatcatc accagatgct gttactacat ataatggata cctcacttcg tcatcaaaga | 780 |
| catctgagga gcactttgta gaaacagttt ctttggctgg ctcttacaga gattggtcct | 840 |
| attcaggaca gcgtacagag ttaggtgttg aatttcttaa gcgtggtgac aaaattgtgt | 900 |
| accacactct ggagagcccc gtcgagtttc atcttgacgg tgaggttctt tcacttgaca | 960 |
| aactaaagag tctcttatcc ctgcgggagg ttaagactat aaaagtgttc acaactgtgg | 1020 |
| acaacactaa tctccacaca cagcttgtgg atatgtctat gacatatgga cagcagtttg | 1080 |

```
gtccaacata cttggatggt gctgatgtta caaaaattaa acctcatgta aatcatgagg    1140
gtaagacttt ctttgtacta cctagtgatg acacactacg tagtgaagct ttcgagtact    1200
accatactct tgatgagagt tttcttggta ggtacatgtc tgctttaaac cacacaaaga    1260
aatggaaatt tcctcaagtt ggtggtttaa cttcaattaa atgggctgat aacaattgtt    1320
atttgtctag tgtttattta gcacttcaac agcttgaagt caaattcaat gcaccagcac    1380
ttcaagaggc ttattataga gcccgtgctg gtgatgctgc taacttttgt gcactcatac    1440
tc                                                                    1442

<210> SEQ ID NO 45
<211> LENGTH: 1050
<212> TYPE: DNA
<213> ORGANISM: CORONAVIRUS

<400> SEQUENCE: 45
atatgtctat gacatatgga cagcagtttg gtccaacata cttggatggt gctgatgtta      60
caaaaattaa acctcatgta aatcatgagg gtaagacttt ctttgtacta cctagtgatg     120
acacactacg tagtgaagct ttcgagtact accatactct tgatgagagt tttcttggta     180
ggtacatgtc tgctttaaac cacacaaaga atggaaatt tcctcaagtt ggtggtttaa      240
cttcaattaa atgggctgat aacaattgtt atttgtctag tgtttattta gcacttcaac     300
agcttgaagt caaattcaat gcaccagcac ttcaagaggc ttattataga gcccgtgctg     360
gtgatgctgc taacttttgt gcactcatac tcgcttacag taataaaact gttggcgagc     420
ttggtgatgt cagagaaact atgacccatc ttctacagca tgctaatttg aatctgcaa      480 agcgagttct taatgtggtg tgtaaacatt gtggtcagaa aactactacc ttaacgggtg     540
tagaagctgt gatgtatatg ggtactctat cttatgataa tcttaagaca ggtgtttcca     600
ttccatgtgt gtgtggtcgt gatgctacac aatatctagt acaacaagag tcttcttttg     660
ttatgatgtc tgcaccacct gctgagtata attacagca aggtacattc ttatgtgcga     720
atgagtacac tggtaactat cagtgtggtc attacactca taactgct aaggagaccc      780 tctatcgtat tgacggagct caccttacaa agatgtcaga gtacaaagga ccagtgactg     840
atgtttctca aggaaaca tcttacacta caaccatcaa gcctgtgtcg tataaactcg      900
atggagttac ttacacagag attgaaccaa aattggatgg gtattataaa aaggataatg     960
cttactatac agagcagcct atagacccttg taccaactca accattacca aatgcgagtt    1020
ttgataattt caaactcaca tgttctaaca                                     1050

<210> SEQ ID NO 46
<211> LENGTH: 1995
<212> TYPE: DNA
<213> ORGANISM: CORONAVIRUS

<400> SEQUENCE: 46
tttgtgcact catactcgct tacagtaata aaactgttgg cgagcttggt gatgtcagag      60
aaactatgac ccatcttcta cagcatgcta atttggaatc tgcaaagcga gttcttaatg     120
tggtgtgtaa acattgtggt cagaaaacta ctaccttaac gggtgtagaa gctgtgatgt     180
atatgggtac tctatcttat gataatctta agacaggtgt ttccattcca tgtgtgtgtg     240
gtcgtgatgc tacacaatat ctagtacaac aagagtcttc ttttgttatg atgtctgcac     300
cacctgctga gtataaatta cagcaaggta cattcttatg tgcgaatgag tacactggta     360
actatcagtg tggtcattac actcatataa ctgctaagga gaccctctat cgtattgacg     420
```

| | |
|---|---|
| gagctcacct tacaaagatg tcagagtaca aaggaccagt gactgatgtt ttctacaagg | 480 |
| aaacatctta cactacaacc atcaagcctg tgtcgtataa actcgatgga gttacttaca | 540 |
| cagagattga accaaaattg gatgggtatt ataaaaagga taatgcttac tatacagagc | 600 |
| agcctataga ccttgtacca actcaaccat taccaaatgc gagttttgat aatttcaaac | 660 |
| tcacatgttc taacacaaaa tttgctgatg atttaaatca aatgacaggc ttcacaaagc | 720 |
| cagcttcacg agagctatct gtcacattct tcccagactt gaatggcgat gtagtggcta | 780 |
| ttgactatag acactattca gcgagtttca agaaaggtgc taaattactg cataagccaa | 840 |
| ttgtttggca cattaaccag gctacaacca agacaacgtt caaaccaaac acttggtgtt | 900 |
| tacgttgtct ttggagtaca aagccagtag atacttcaaa ttcatttgaa gttctggcag | 960 |
| tagaagacac acaaggaatg gacaatcttg cttgtgaaag tcaacaaccc acctctgaag | 1020 |
| aagtagtgga aaatcctacc atacagaagg aagtcataga gtgtgacgtg aaaactaccg | 1080 |
| aagttgtagg caatgtcata cttaaaccat cagatgaagg tgttaaagta acacaagagt | 1140 |
| taggtcatga ggatcttatg gctgcttatg tggaaaacac aagcattacc attaagaaac | 1200 |
| ctaatgagct ttcactagcc ttaggtttaa aaacaattgc cactcatggt attgctgcaa | 1260 |
| ttaatagtgt tccttggagt aaaattttgg cttatgtcaa accattctta ggacaagcag | 1320 |
| caattacaac atcaaattgc gctaagagat tagcacaacg tgtgtttaac aattatatgc | 1380 |
| cttatgtgtt tacattattg ttccaattgt gtactttac taaaagtacc aattctagaa | 1440 |
| ttagagcttc actacctaca actattgcta aaaatagtgt taagagtgtt gctaaattat | 1500 |
| gtttggatgc cggcattaat tatgtgaagt cacccaaatt ttctaaattg ttcacaatcg | 1560 |
| ctatgtggct attgttgtta agtatttgct taggttctct aatctgtgta actgctgctt | 1620 |
| ttggtgtact cttatctaat tttggtgctc cttcttattg taatggcgtt agagaattgt | 1680 |
| atcttaattc gtctaacgtt actactatgg atttctgtga aggttctttt ccttgcagca | 1740 |
| tttgtttaag tggattagac tcccttgatt cttatccagc tcttgaaacc attcaggtga | 1800 |
| cgatttcatc gtacaagcta gacttgacaa ttttaggtct ggccgctgag tgggttttgg | 1860 |
| catatatgtt gttcacaaaa ttcttttatt tattaggtct ttcagctata atgcaggtgt | 1920 |
| tctttggcta ttttgctagt catttcatca gcaattcttg gctcatgtgg tttatcatta | 1980 |
| gtattgtaca aatgg | 1995 |

<210> SEQ ID NO 47
<211> LENGTH: 1884
<212> TYPE: DNA
<213> ORGANISM: CORONAVIRUS

<400> SEQUENCE: 47

| | |
|---|---|
| aattcttggc tcatgtggtt tatcattagt attgtacaaa tggcacccgt ttctgcaatg | 60 |
| gttaggatgt acatcttctt tgcttctttc tactacatat ggaagagcta tgttcatatc | 120 |
| atggatggtt gcacctcttc gacttgcatg atgtgctata gcgcaatcg tgccacacgc | 180 |
| gttgagtgta caactattgt taatggcatg aagagatctt tctatgtcta tgcaaatgga | 240 |
| ggccgtggct tctgcaagac tcacaattgg aattgtctca attgtgacac atttgcact | 300 |
| ggtagtacat tcattagtga tgaagttgct cgtgatttgt cactccagtt taaaagacca | 360 |
| atcaacccta ctgaccagtc atcgtatatt gttgatagtg ttgctgtgaa aaatggcgcg | 420 |
| cttcacctct actttgacaa ggctggtcaa aagacctatg agagacatcc gctctcccat | 480 |

```
tttgtcaatt tagacaattt gagagctaac aacactaaag gttcactgcc tattaatgtc      540 atagttttg atggcaagtc caaatgcgac gagtctgctt ctaagtctgc ttctgtgtac       600
tacagtcagc tgatgtgcca acctattctg ttgcttgacc aagctcttgt atcagacgtt      660
ggagatagta ctgaagtttc cgttaagatg tttgatgctt atgtcgacac cttttcagca      720
acttttagtg ttcctatgga aaacttaag gcacttgttg ctacagctca cagcgagtta      780
gcaaagggtg tagctttaga tggtgtcctt tctacattcg tgtcagctgc ccgacaaggt      840
gttgttgata ccgatgttga cacaaaggat gttattgaat gtctcaaact ttcacatcac      900
tctgacttag aagtgacagg tgacagttgt aacaatttca tgctcaccta ataataaggtt     960 gaaaacatga cgcccagaga tcttggcgca tgtattgact gtaatgcaag gcatatcaat     1020
gcccaagtag caaaaagtca caatgtttca ctcatctgga atgtaaaaga ctacatgtct     1080
ttatctgaac agctgcgtaa acaaattcgt agtgctgcca agaagaacaa catacctttt     1140
agactaactt gtgctacaac tagacaggtt gtcaatgtca taactactaa aatctcactc     1200
aagggtggta agattgttag tacttgtttt aaacttatgc ttaaggccac attattgtgc     1260
gttcttgctg cattggtttg ttatatcgtt atgccagtac atacattgtc aatccatgat     1320
ggttacacaa atgaaatcat tggttacaaa gccattcagg atggtgtcac tcgtgacatc     1380
atttctactg atgattgttt tgcaaataaa catgctggtt ttgacgcatg gtttagccag     1440
cgtggtggtt catacaaaaa tgacaaaagc tgccctgtag tagctgctat cattacaaga     1500
gagattggtt tcatagtgcc tggcttaccg ggtactgtgc tgagagcaat caatggtgac     1560
ttcttgcatt ttctacctcg tgtttttagt gctgttggca acatttgcta cacaccttcc     1620
aaactcattg agtatagtga ttttgctacc tctgcttgcg ttcttgctgc tgagtgtaca     1680
atttttaagg atgctatggg caaacctgtg ccatattgtt atgacactaa tttgctagag     1740
ggttctattt cttatagtga gcttcgtcca gacactcgtt atgtgcttat ggatggttcc     1800
atcatacagt ttcctaacac ttacctggag ggttctgtta gagtagtaac aacttttgat     1860
gctgagtact gtagacatgg taca                                            1884
```

<210> SEQ ID NO 48
<211> LENGTH: 2020
<212> TYPE: DNA
<213> ORGANISM: CORONAVIRUS

<400> SEQUENCE: 48

```
cactcgttat gtgcttatgg atggttccat catacagttt cctaacactt acctggaggg      60
ttctgttaga gtagtaacaa cttttgatgc tgagtactgt agacatggta catgcgaaag     120
gtcagaagta ggtatttgcc tatctaccag tggtagatgg ttcttaata atgagcatta     180 cagagctcta tcaggagttt tctgtggtgt tgatgcgatg aatctcatag ctaacatctt     240
tactcctctt gtgcaacctg tgggtgcttt agatgtgtct gcttcagtag tggctggtgg     300
tattattgcc atattggtga cttgtgctgc ctactacttt atgaaattca gacgtgtttt     360
tggtgagtac aaccatgttg ttgctgctaa tgcacttttg tttttgatgt ctttcactat     420
actctgtctg gtaccagctt acagcttcct gccgggagtc tactcagtct tttacttgta     480
cttgacattc tatttcacca atgatgtttc attcttggct caccttcaat ggtttgccat     540
gttttctcct attgtgcctt tttggataac agcaatctat gtattctgta tttctctgaa     600
gcactgccat tggttcttta caactatctc taggaaaaga gtcatgttta atggagttac     660
atttagtacc ttcgaggagg ctgctttgtg tacctttttg ctcaacaagg aaatgtacct     720
```

| | |
|---|---|
| aaaattgcgt agcgagacac tgttgccact tacacagtat aacaggtatc ttgctctata | 780 |
| taacaagtac aagtatttca gtggagcctt agatactacc agctatcgtg aagcagcttg | 840 |
| ctgccactta gcaaaggctc taaatgactt tagcaactca ggtgctgatg ttctctacca | 900 |
| accaccacag acatcaatca cttctgctgt tctgcagagt ggttttagga aaatggcatt | 960 |
| cccgtcaggc aaagttgaag ggtgcatggt acaagtaacc tgtggaacta caactcttaa | 1020 |
| tggattgtgg ttggatgaca cagtatactg tccaagacat gtcatttgca cagcagaaga | 1080 |
| catgcttaat cctaactatg aagatctgct cattcgcaaa tccaaccata gctttcttgt | 1140 |
| tcaggctggc aatgttcaac ttcgtgttat tggccattct atgcaaaatt gtctgcttag | 1200 |
| gcttaaagtt gatacttcta accctaagac acccaagtat aaatttgtcc gtatccaacc | 1260 |
| tggtcaaaca ttttcagttc tagcatgcta caatggttca ccatctggtg tttatcagtg | 1320 |
| tgccatgaga cctaatcata ccattaaagg ttctttcctt aatggatcat gtggtagtgt | 1380 |
| tggttttaac attgattatg attgcgtgtc tttctgctat atgcatcata tggagcttcc | 1440 |
| aacaggagta cacgctggta ctgacttaga aggtaaattc tatggtccat tgttgacag | 1500 |
| acaaactgca caggctgcag gtacagacac aaccataaca ttaaatgttt tggcatggct | 1560 |
| gtatgctgct gttatcaatg gtgataggtg gtttcttaat agattcacca ctactttgaa | 1620 |
| tgactttaac cttgtggcaa tgaagtacaa ctatgaacct ttgacacaag atcatgttga | 1680 |
| catattggga cctcttctg ctcaaacagg aattgccgtc ttagatatgt gtgctgcttt | 1740 |
| gaaagagctg ctgcagaatg gtatgaatgg tcgtactatc cttggtagca ctattttaga | 1800 |
| agatgagttt acaccatttg atgttgttag acaatgctct ggtgttacct tccaaggtaa | 1860 |
| gttcaagaaa attgttaagg gcactcatca ttggatgctt ttaactttct tgacatcact | 1920 |
| attgattctt gttcaaagta cacagtggtc actgtttttc tttgtttacg agaatgcttt | 1980 |
| cttgccattt actcttggta ttatggcaat tgctgcatgt | 2020 |

<210> SEQ ID NO 49
<211> LENGTH: 2040
<212> TYPE: DNA
<213> ORGANISM: CORONAVIRUS

<400> SEQUENCE: 49

| | |
|---|---|
| agcatttcca gcctgaagac gtactgtagc agctaaactg cccagcacca tacctctatt | 60 |
| taggttgttt aagcctttga tgaagtacaa gtatttcact ttaggccctt ttggtgtgtc | 120 |
| tgtaacaaac ctacaaggtg gttccagttc tgtgtaaatt gtacctgtac catcactctt | 180 |
| agggaatcta gcccatttga gatcttggtg gtctgatagt aatgccagca caaacctacc | 240 |
| tcccttcgaa ttgttatagt aggcaagtgc attgtcatca gtacaagctg tttgtgtggt | 300 |
| accagccgca caggacatct gtcgtagtgc tactggactc agttcattat tctgtagttt | 360 |
| aacagctgag ttggctctta gagctgtaac aataagaggc caagccaaat tggtgaatt | 420 |
| gtccatgtta atttcactaa gttgaacaat cttgctatcc gcatcaacaa cttgctggat | 480 |
| ttcccagagt gcagatgcat atgtaaaggt gttaccatca caagtgttct tgtaggtacc | 540 |
| ataatcaggg acaacaacca tgagtttggc tgctgtagtc aatggtatga tgttgagtgg | 600 |
| aacacaacca tcacgcgcat tgttgataat gttgttaagt gcatcattat caagcttcct | 660 |
| aagcatagtg aagagcattg tttgcatagc actagttact tttgccctct tgtcctcaga | 720 |
| tcttgcctgt ttgtacattt gggtcatagc ctgatctgcc atcttttcca acttgcgttg | 780 |

```
catggcagca tcacggtcaa actcagattt agccacattc aaagatttct ttaactttt      840 gagaacgact tcagaatcac cattagctac agcctgctca taggcctcct gggcagtggc      900
ataagcggca tatgatggta agaactaaa ttctgaagca atagcctgaa gagtagcacg       960
gttatcgagc atttcctcgc acaacctatt aatgtctaca gcaccctgca tggatagcaa     1020
aacagacaaa agagaaacca tcttctcgaa agcttcagtt gtgtcttttg caagaagaat     1080
atcattgtgg agttgtacac attgtgccca caatttagaa gatgactcta ctctaagttg     1140
ttgaagaacc gagagcagta ccacagatgt gcactttacg tcagacattt tagactgtac     1200
agtagcaacc ttgatacatg gtttacctcc aatacccaac aacttaatgt taagcttgaa     1260
agcatcaata ctactcttag gaggcaaaag ccctgggag ttcatatacc taaattcttg      1320
tgtagagacc aagtagtcat aaacaccaag agtaagcctg aagtaacggt tgagtaaaca     1380
gaaaaggcca agtagcagc agcaacaata gcctaagaaa caataaacaa gcatgataca     1440
ctgtaaggtg ttgccagtaa taataacaa tgggtaatac tcaacacaca caaacactat      1500
agctctagct aaaaacatga tagtcgtaac gacaccagaa tagttagagg ttacagaaat     1560
aactaaggcc cacatggaaa tagcttgatc taaagcatta ccatagtaga ctttgtaaac     1620
aagtgtaatg acattcatca gtgtccaaac acgtctagca gcatcatcat aaacagtgcg     1680
agctgtcatg agaataagca aaactaaagc tgaagcatac ataacacaat ccttaagcct     1740
ataaccagac aagctagtgt cagccaattc aagccatgtc atgatacgca tcacccagct     1800
agcaggcatg tagaccatat taagtaagc aactgttgca agagaaggta acagaaacaa      1860
gcacaagaat gcgtgcttat gcttaacaag cagcatagca catgcagcaa ttgccataat     1920
accaagagta atggcaaga agcattctc gtaaacaaag aaaaacagtg accactgtgt       1980
actttgaaca agaatcaata gtgatgtcaa gaaagttaaa agcatccaat gatgagtgca     2040
```

<210> SEQ ID NO 50
<211> LENGTH: 2012
<212> TYPE: DNA
<213> ORGANISM: CORONAVIRUS

<400> SEQUENCE: 50

```
cttgtaggtt tgttacagac acaccaaaag ggcctaaagt gaaatacttg tacttcatca       60
aaggcttaaa caacctaaat agaggtatgg tgctgggcag tttagctgct acagtacgtc      120
ttcaggctgg aaatgctaca gaagtacctg ccaattcaac tgtgctttcc ttctgtgctt      180
ttgcagtaga ccctgctaaa gcataaagg attacctagc aagtggagga caaccaatca      240
ccaactgtgt gaagatgttg tgtacacaca ctggtacagg acaggcaatt actgtaacac      300
cagaagctaa catggaccaa gagtcctttg gtggtgcttc atgttgtctg tattgtagat      360
gccacattga ccatccaaat cctaaaggat tctgtgactt gaaaggtaag tacgtccaaa      420
tacctaccac ttgtgctaat gacccagtgg gttttacact agaaacaca gtctgtaccg      480 tctgcggaat gtggaaaggt tatggctgta gttgtgacca actccgcgaa cccttgatgc      540
agtctgcgga tgcatcaacg ttttaaacg ggtttgcggt gtaagtgcag cccgtcttac       600
accgtgcggc acaggcacta gtactgatgt cgtctacagg gcttttgata tttacaacga      660
aaaagttgct ggttttgcaa agttcctaaa aactaattgc tgtcgcttcc aggaaagga      720 tgaggaaggc aatttattag actcttactt tgtagttaag aggcatacta tgtctaacta      780
ccaacatgaa gagactattt ataacttggt taaagattgt ccagcggttg ctgtcccatga     840 cttttttcaag tttagagtag atggtgacat ggtaccacat atatcacgtc agcgtctaac     900
```

```
taaatacaca atggctgatt tagtctatgc tctacgtcat tttgatgagg gtaattgtga    960
tacattaaaa gaaatactcg tcacatacaa ttgctgtgat gatgattatt tcaataagaa   1020
ggattggtat gacttcgtag agaatcctga catcttacgc gtatatgcta acttaggtga   1080
gcgtgtacgc caatcattat taaagactgt acaattctgc gatgctatgc gtgatgcagg   1140
cattgtaggc gtactgacat tagataatca ggatcttaat gggaactggt acgatttcgg   1200
tgatttcgta caagtagcac caggctgcgg agttcctatt gtggattcat attactcatt   1260
gctgatgccc atcctcactt tgactagggc attggctgct gagtcccata tggatgctga   1320
tctcgcaaaa ccacttatta agtgggattt gctgaaatat gattttacgg aagagagact   1380
ttgtctcttc gaccgttatt ttaaatattg gaccagaca taccatccca attgtattaa   1440
ctgtttggat gataggtgta tccttcattg tgcaaacttt aatgtgttat tttctactgt   1500
gtttccacct acaagttttg gaccactagt aagaaaaata tttgtagatg gtgttccttt   1560
tgttgtttca actggatacc attttcgtga gttaggagtc gtacataatc aggatgtaaa   1620
cttacatagc tcgcgtctca gtttcaagga acttttagtg tatgctgctg atccagctat   1680
gcatgcagct tctggcaatt tattgctaga taaacgcact acatgctttt cagtagctgc   1740
actaacaaac aatgttgctt ttcaaactgt caaacccggt aattttaata aagactttta   1800
tgactttgct gtgtctaaag gtttctttaa ggaaggaagt tctgttgaac taaaacactt   1860
cttctttgct caggatggca acgctgctat cagtgattat gactattatc gttataatct   1920
gccaacaatg tgtgatatca gacaactcct attcgtagtt gaagttgttg ataaatactt   1980
tgattgttac gatggtggct gtattaatgc ca                                 2012

<210> SEQ ID NO 51
<211> LENGTH: 1877
<212> TYPE: DNA
<213> ORGANISM: CORONAVIRUS

<400> SEQUENCE: 51
gtacttcgcg tacagtggca ataccatatg acagcttaaa tgtttcctca gtggctttga     60
gcgtttctgc tgcgaaaagc ttgagtctct cagtacaagt gttggcaagt atgtaatcgc    120
cagcattagt ccaatcacat gttgctatcg cattgaagtc agtgacattg tcactgccta    180
cacatgtgtt tttgtataaa ccaaaaacct gaccattagc acataatgga aaactaatgg    240
gaggcttatg tgacttgcaa taatagctca tacctcctag atacagttgt gtcacatcag    300
tgacatcaca acctggggca ttgcaaacat agggattaac agacaacact aatttgtgtg    360
atgttgaaat gacatggtca tagcagcact tgcaacatag gaatggtctc ctaatacagg    420
caccgcaacg aagtgaagtc tgtgaattgc acaatacaca agcacctaca gcctgcaaga    480
ctgtatgtgg tgtgtacata gcctcataaa actcaggttc ccagtaccgt gaggtgttat    540
cattagttag cattacggaa tacatgtcca acatgtggcc agtaagctca tcatgtaact    600
ttctaatgta ttgtaaatac aagtgaaaga catcagcata ctcctgatta ggatgttttg    660
taagtgggta agcatcaata gccagtgaca cgaacctttc aatcataagt gtaccatctg    720
ttttgacaat atcatcgaca aaacagcctg cgcctaatat tcttgatgga tctgggtaag    780
gcaggtacac gtaatcatct ccttgtttaa ctagcattgt atgctgtgag caaaattcgt    840
gaggtccttt agtaaggtca gtctcagtcc aacattttgc ctcagacatg aacacattat    900
tttgataata agaactgcc ttaaagttct taatgctagc tactaaacct tgagccgcat     960
```

```
agttactgtt atagcacaca acggcatcat cagaaagaat catcatgag  aaatgtttac    1020 gcaggtaagc gtaaaactca tccacgaatt catgatcaac atccctattt ctatagagac    1080
actcatagag cctgtgttgt agattgcgga catacttgtc agctatctta ttaccatcag    1140
ttgaaagaag tgcatttaca ttggctgtaa cagcttgaca aatgttaaag acactattag    1200
cataagcagt tgtagcatca ccggatgatg ttccacctgg tttaacatat agtgagccgc    1260
cacacatgac catctcactt aatacttgcg cacactcgtt agctaacctg tagaaacggt    1320
gtgataagtt acagcaagtg ttatgtttgc gagcaagaac aagagaggcc attatcctaa    1380
gcatgttagg catggctctg tcacattttg gataatccca acccataagg tgtggagttt    1440
ctacatcact gtaaacagtt tttaacatat tatgccagcc accgtaaaac ttgcttgttc    1500
caattaccac agtagctcct ctagtggcgg ctattgactt caataatttc tgatgaaact    1560
gtctatttgt catagtacta cagatagaga caccagctac ggtgcgagct ctattctttg    1620
cactaatggc atacttaaga ttcatttgag ttatagtagg gatgacatta cgcttagtat    1680
acgcgaaaag tgcatcttga tcctcataac tcattgagtc ataataaagt ctagccttac    1740
cccatttatt aaatgggaaa ccagctgatt tatccagatt gttaacgatt acttggttgg    1800
cattaataca gccaccatcg taacaatcaa agtatttatc aacaacttca actacgaata    1860
ggagttgtct gatatca                                                   1877

<210> SEQ ID NO 52
<211> LENGTH: 2051
<212> TYPE: DNA
<213> ORGANISM: CORONAVIRUS

<400> SEQUENCE: 52
tcaggtccaa tcttgacaaa gtacttcatt gatgtaagct caaagccatg cgcccaaagg      60
acgaacacga ctctgtctga caatcctttc agtgtatcac tgagcatttg tactatctta    120
atacgcacta cattccaggg caagccttta tacatgagtg gtataagatg tttaaactgg    180
tcacctggtg gaggttttgc attaactctg gtgaattctg tgttatttc agtgtcaaca    240 taaccagtcg gtacagctac taagttaaca cctgtagaaa atcctagctg agagaggtagg    300 ttagtaccca cagcatctct agttgcatga cagccctcta catcaaagcc aatccacgca    360
cgaacgtgac gaatagcttc ttcgcgggtg ataaacatat tagggtaacc attgacttgg    420
taattcattt tgaaacccat catagagatg agtctacggt aggtcatgtc ctttggtatg    480
cctggtatgt caacacataa tccttcagtc ttgaacttta tatcaacgct gaggtgtgta    540
ggtgcctgtg taggatgaag accagtaatg atcttactac agtccttaaa aagtccagtt    600
acattttctg cttgtaatgt agccacattg cgacgtggta tttctagact tgtaaattgc    660
agtttgtcat aaagatctct atcagacatt atgcacaaaa tgccaatttt tgcccttgtg    720
atagccacat tgaagcggtt gacattacaa gagtgtgctg tttcagtagt ttgtgtgaat    780
atgacatagt catattcaga accctgtgat gaatcaacag tctgcgtagg caatcctaag    840 attttgaag ctcagcgtt ctgtgaatta taggtgaga taaaacagc ttttctccaa        900 gcaggattgc gtgtaagaaa ttctcttaca acgcctattt gaggtctgtt gattgcagat    960
gaaacatcat gtgtaataac acctttgtag aacattttga agcattgagc tgacttatcc   1020
ttgtgtgctt ttagcttatt gtcataaact aaagcactca cagtgtcaac aatttcagca   1080
ggacaacggc gacaagttcc aaggaacatg tctggaccta ttgttttcat aagtctgcac   1140
actgaattaa aatattctgg ttctagtgtg cctttagtca gcaatgtgcg gggggctggt   1200
```

```
aattgagcag gatcgccaat atagacgtag tgttttgcac gaagtctagc attgacaaca    1260
ctcaagtcat aattagtagc catagagatt tcatcaaaga ctacaatgtc agcagttgtt    1320
tctggcaatg catttacagt gcagaaaaca tactgttcta gtgttgaatt cactttgaat    1380
ttatcaaaac actctacgcg cgcacgcgca ggtatgattc tactacattt atctatgggc    1440
aaatatttta atgccttttc acatagggca tcaacagctg catgagagca tgccgtatac    1500
actatgcgag cagatgggta atagagagca agtccgatgg caaaatgact cttaccagta    1560
ccaggtggtc cttggagtgt agagtacttt tgcatgccga cctttgata atttgcaaca    1620 ttgctagaaa actcatctga gatgttgagt gttgggtaca agccagtaat tctcacatag    1680
tgctcttgtg gcactagagt aggtgcacta agtggcatta cagtgtgaga tgtcaacaca    1740
aagtaatcac caacattcaa cttgtatgtc gtagtacctc tgtacacaac agcatcacca    1800
tagtcacctt tttcaaaggt gtactctcca atctgtactt tactattttt agttacacgg    1860
taaccagtaa agacatagtt tctgttcaat ggtggtctag gttttccaac ctcccatgaa    1920
agatgcaatt ctctgtcaga gagtacttcg cgtacagtgg caataccata tgacagctta    1980
aatgtttcct cagtggcttt gagcgtttct gctgcgaaaa gcttgagtct ctcagtacaa    2040
gtgttggcaa g                                                          2051

<210> SEQ ID NO 53
<211> LENGTH: 2075
<212> TYPE: DNA
<213> ORGANISM: CORONAVIRUS

<400> SEQUENCE: 53
tgcttgtagt tttgggtaga aggtttcaac atgtccatcc ttacaccaaa gcatgaatga      60
aatttcagca tagtcaattg taaccttgac cacttttgaa atcactgaca aatcttgtga     120
ctttattatc tcgacaaagt catcaagtaa aagatcaatc acagaacaca cacattttga     180
tgaacctgtt tgcgcatctg ttatgaagta attttttcact gtgctgtcca tagggataaa     240
atcctctaat ttaagtggtg aatcttgtga gcgcttggct aagcctatca ttaaatgaag     300
accgccaagt tgtccatgac tgaaatctcc ataaacgatg tgttcgaagg catagccctc     360
gagcttatat cgctgtatga attcatccat agcgagctcg agaaagtcag tttccatttg     420
tgatctgggc ttaaaatcct ctaagtctct gctctgagta agtaggttt caggcaactg      480 ttgaataatg ccgtcttactt tcttaaagta gttaaactgt gttttttactg attctccaat    540 taatgtgact ccattgacgc tagcttgtgc tggtcccttt gaaggtgtta gacctttgac     600
tgaaccttct gttattaaaa caccattacg ggcgtttcta aaaaggtcta cctgtccttc     660
cactctacca tcaaacaaga cagtaagtga agaacaagca ctctcagtag gtttcttggc    720
aatgtcagtc attgtgcaga cacctattgt agatacatgt gctggggctt ctcttttgta    780
gtcccagatt acagtattag cagcgatatc aacacccaaa ttattgagta tcttaatctc    840
tggcactggt ttaatgttac gcttagccca agctcaaat gcaacattaa caggaagtgt    900
tgtcttattt tcaaagatct ccacatcaat accatctacc tttgtgtaaa cagcattatt    960
aatgatggaa acaggtgctt cgccggcgtg tccatcaaag tgtcctttat taacaacatt   1020
ataagccaca ttttctaaac tctgtaacct ggtaaatgta ttccacaggt tataagtatc   1080
aaattgtttg taaatccata ggctaaatcc agcagaaatc atcatattat atgcatccaa   1140
gtactgtcgg tactcatttg catggtgtct gcaaacagca ccacctaaat tgcatcgtgt   1200
```

```
aatacacgta gcagatttga gtggaacata atcaatatcc gacactactt gtttgccatg    1260
agactcacaa ggactatcag aatagtaaaa gaaaggcaat tgctttaaat tagtaaatgc    1320
acttttatcg aaagctggag tgtggaatgc atgcttattc acatacaaac taccaccatc    1380
acagcctggt aagttcaagt ttgacaagac tcttgtgtca aacctacaca caattgcatt    1440
ggctgggtaa cgatcaacgt tacaattcca aaacaaacaa acaccatcag tgaatttatc    1500
gtgatgtgta gcataagaat agaagagttc ctctattttg taagctttgt cactacatgg    1560
ctgagcatcg tagaacttcc attctacttc agcctgaggc acacacttga tagcctttgg    1620
atttccaatg tcatgaagaa ctggaaactt atcagcaagc aatgcagact tcacaaccat    1680
gtgttgtact tttctgcaag cagaattaac cctcagttca tctcctataa tagggtattc    1740
aacagaccaa tcaacgcgct taacaaagca ctcatggact gctaaacatc tagtcatgat    1800
agcatcacaa ctagccacat gtgcatttcc atgtacctgg caatgttggt catggttact    1860
ctgaaggtta cccgtaaagc cccactgctg aacatcaatc ataaatgggt tatagacata    1920
gtcaaaaccc acagaatgat tccagcaggc ataagtatct gatgaagtag aaaagcaagt    1980
tgcacgtttg tcacacagac aacacgttct ttcaggtcca atcttgacaa agtacttcat    2040
tgatgtaagc tcaaagccat gcgcccaaag gacga                               2075

<210> SEQ ID NO 54
<211> LENGTH: 1891
<212> TYPE: DNA
<213> ORGANISM: CORONAVIRUS

<400> SEQUENCE: 54
aagattcacc acttaaatta gaggatttta tccctatgga cagcacagtg aaaaattact      60
tcataacaga tgcgcaaaca ggttcatcaa aatgtgtgtg ttctgtgatt gatcttttac     120
ttgatgactt tgtcgagata taaaagtcac aagatttgtc agtgatttca aaagtggtca     180
aggttacaat tgactatgct gaaatttcat tcatgctttg gtgtaaggat ggacatgttg     240
aaaccttcta cccaaaaacta caagcaagtc aagcgtggca accaggtgtt gcgatgccta     300
acttgtacaa gatgcaaaga atgcttcttg aaaagtgtga ccttcagaat tatggtgaaa     360
atgctgttat accaaaagga ataatgatga atgtcgcaaa gtatactcaa ctgtgtcaat     420
acttaaatac acttacttta gctgtaccct acaacatgag agttattcac tttggtgctg     480
gctctgataa aggagttgca ccaggtacag ctgtgctcag acaatggttg ccaactggca     540
cactacttgt cgattcagat cttaatgact tcgtctccga cgcagattct actttaattg     600
gagactgtgc aacagtacat acggctaata atgggaccct tattattagc gatatgtatg     660
accctaggac caaacatgtg acaaaagaga atgactctaa agaagggttt ttcacttatc     720
tgtgtggatt tataaagcaa aaactagccc tgggtggttc tatagctgta aagataacag     780
agcattcttg gaatgctgac ctttacaagc ttatgggcca tttctcatgg tggacagctt     840
ttgttacaaa tgtaaatgca tcatcatcgg aagcattttt aattggggct aactatcttg     900
gcaagccgaa ggaacaaatt gatggctata ccatgcatgc taactacatt ttctggagga     960
acacaaatcc tatccagttg tcttcctatt cactctttga catgagcaaa tttcctctta    1020
aattaagagg aactgctgta atgtctctta aggagaatca aatcaatgat atgatttatt    1080
ctcttctgga aaaaggtagg cttatcatta gagaaaacaa cagagttgtg gtttcaagtg    1140
atattcttgt taacaactaa acgaacatgt ttatttctt attatttctt actctcacta    1200
gtggtagtga ccttgaccgg tgcaccactt ttgatgatgt tcaagctcct aattacactc    1260
```

-continued

```
aacatacttc atctatgagg ggggtttact atcctgatga aattttttaga tcagacactc    1320 tttatttaac tcaggattta tttcttccat tttattctaa tgttacaggg tttcatacta    1380
ttaatcatac gtttggcaac cctgtcatac cttttaagga tggtatttat tttgctgcca    1440
cagagaaatc aaatgttgtc cgtggttggg tttttggttc taccatgaac aacaagtcac    1500
agtcggtgat tattattaac aattctacta atgttgttat acgagcatgt aactttgaat    1560
tgtgtgacaa ccctttcttt gctgtttcta aacccatggg tacacagaca catactatga    1620
tattcgataa tgcatttaat tgcactttcg agtacatatc tgatgccttt tcgcttgatg    1680
tttcagaaaa gtcaggtaat tttaaacact tacgagagtt tgtgtttaaa aataaagatg    1740
ggtttctcta tgtttataag ggctatcaac ctatagatgt agttcgtgat ctaccttctg    1800
gttttaacac tttgaaacct attttttaagt tgcctcttgg tattaacatt acaaatttta    1860
gagccattct tacagccttt tcacctgctc a                                    1891
```

```
<210> SEQ ID NO 55
<211> LENGTH: 32
<212> TYPE: DNA
<213> ORGANISM: artificial sequence
<220> FEATURE:
<223> OTHER INFORMATION: N sens primer

<400> SEQUENCE: 55
cccatatgtc tgataatgga ccccaatcaa ac                                   32

<210> SEQ ID NO 56
<211> LENGTH: 32
<212> TYPE: DNA
<213> ORGANISM: artificial sequence
<220> FEATURE:
<223> OTHER INFORMATION: N antisens primer

<400> SEQUENCE: 56
cccccgggtg cctgagttga atcagcagaa gc                                   32

<210> SEQ ID NO 57
<211> LENGTH: 31
<212> TYPE: DNA
<213> ORGANISM: artificial sequence
<220> FEATURE:
<223> OTHER INFORMATION: Sc sens primer

<400> SEQUENCE: 57
cccatatgag tgaccttgac cggtgcacca c                                    31

<210> SEQ ID NO 58
<211> LENGTH: 30
<212> TYPE: DNA
<213> ORGANISM: artificial sequence
<220> FEATURE:
<223> OTHER INFORMATION: SL sens primer

<400> SEQUENCE: 58
cccatatgaa accttgcacc ccacctgctc                                      30

<210> SEQ ID NO 59
<211> LENGTH: 33
<212> TYPE: DNA
<213> ORGANISM: Sc and SL antisens primer

<400> SEQUENCE: 59
```

-continued

```
cccccgggtt taatatattg ctcatatttt ccc                              33

<210> SEQ ID NO 60
<211> LENGTH: 16
<212> TYPE: DNA
<213> ORGANISM: Sens set 1 primer

<400> SEQUENCE: 60
ggcatcgtat gggttg                                                 16

<210> SEQ ID NO 61
<211> LENGTH: 16
<212> TYPE: DNA
<213> ORGANISM: Antisens set 2 (28774-28759) primer

<400> SEQUENCE: 61
cagtttcacc acctcc                                                 16

<210> SEQ ID NO 62
<211> LENGTH: 16
<212> TYPE: DNA
<213> ORGANISM: Sens set 2 (28375-28390) primer

<400> SEQUENCE: 62
ggctactacc gaagag                                                 16

<210> SEQ ID NO 63
<211> LENGTH: 16
<212> TYPE: DNA
<213> ORGANISM: Antisens set 2 (28702-28687)primer

<400> SEQUENCE: 63
aattaccgcg actacg                                                 16

<210> SEQ ID NO 64
<211> LENGTH: 26
<212> TYPE: DNA
<213> ORGANISM: Probe 1/set 1 (28561-28586)

<400> SEQUENCE: 64
ggcacccgca atcctaataa caatgc                                      26

<210> SEQ ID NO 65
<211> LENGTH: 21
<212> TYPE: DNA
<213> ORGANISM: Probe 2/set 1 (28588-28608)

<400> SEQUENCE: 65
gccaccgtgc tacaacttcc t                                           21

<210> SEQ ID NO 66
<211> LENGTH: 23
<212> TYPE: DNA
<213> ORGANISM: Probe 1/set 2 /probe N/FL (28541-28563)

<400> SEQUENCE: 66
atacacccaa agaccacatt ggc                                         23

<210> SEQ ID NO 67
<211> LENGTH: 25
<212> TYPE: DNA
<213> ORGANISM: Probe 2/set 2/probe SARS/N/LC705 (28565-28589)

<400> SEQUENCE: 67
```
cccgcaatcc taataacaat gctgc					25

<210> SEQ ID NO 68
<211> LENGTH: 30
<212> TYPE: DNA
<213> ORGANISM: artificial sequence
<220> FEATURE:
<223> OTHER INFORMATION: Anchor primer 14T

<400> SEQUENCE: 68
agatgaattc ggtacctttt ttttttttt					30

<210> SEQ ID NO 69
<211> LENGTH: 13
<212> TYPE: PRT
<213> ORGANISM: artificial sequence
<220> FEATURE:
<223> OTHER INFORMATION: M2-14 peptide

<400> SEQUENCE: 69

Ala Asp Asn Gly Thr Ile Thr Val Glu Glu Leu Lys Gln
1               5                   10

<210> SEQ ID NO 70
<211> LENGTH: 12
<212> TYPE: PRT
<213> ORGANISM: artificial sequence
<220> FEATURE:
<223> OTHER INFORMATION: E1-12 peptide

<400> SEQUENCE: 70

Met Tyr Ser Phe Val Ser Glu Glu Thr Gly Thr Leu
1               5                   10

<210> SEQ ID NO 71
<211> LENGTH: 24
<212> TYPE: PRT
<213> ORGANISM: artificial sequence
<220> FEATURE:
<223> OTHER INFORMATION: E53-72 peptide

<400> SEQUENCE: 71

Lys Pro Thr Val Tyr Val Tyr Ser Arg Val Lys Asn Leu Asn Ser Ser
1               5                   10                  15

Glu Gly Val Pro Asp Leu Leu Val
            20

<210> SEQ ID NO 72
<211> LENGTH: 153
<212> TYPE: DNA
<213> ORGANISM: CORONAVIRUS

<400> SEQUENCE: 72
gatattaggt ttttacctac ccaggaaaag ccaaccaacc tcgatctctt gtagatctgt					60 tctctaaacg aactttaaaa tctgtgtagc tgtcgctcgg ctgcatgcct agtgcaccta					120 cgcagtataa acaataataa attttactgt cgt					153

<210> SEQ ID NO 73
<211> LENGTH: 410
<212> TYPE: DNA
<213> ORGANISM: CORONAVIRUS

<400> SEQUENCE: 73

```
ttctccagac aacttcaaaa ttccatgagt ggagcttctg ctgattcaac tcaggcataa      60
acactcatga tgaccacaca aggcagatgg gctatgtaaa cgttttcgca attccgttta     120
cgatacatag tctactcttg tgcagaatga attctcgtaa ctaaacagca caagtaggtt     180
tagttaactt taatctcaca tagcaatctt taatcaatgt gtaacattag ggaggacttg     240
aaagagccac cacattttca tcgaggccac gcggagtacg atcgagggta cagtgaataa     300
tgctagggag agctgcctat atggaagagc cctaatgtgt aaaattaatt ttagtagtgc     360
tatccccatg tgattttaat agcttcttag gagaatgaca aaaaaaaaa                 410
```

<210> SEQ ID NO 74
<211> LENGTH: 4382
<212> TYPE: PRT
<213> ORGANISM: CORONAVIRUS

<400> SEQUENCE: 74

```
Met Glu Ser Leu Val Leu Gly Val Asn Glu Lys Thr His Val Gln Leu
  1               5                  10                  15

Ser Leu Pro Val Leu Gln Val Arg Asp Val Leu Val Arg Gly Phe Gly
                 20                  25                  30

Asp Ser Val Glu Glu Ala Leu Ser Glu Ala Arg Glu His Leu Lys Asn
             35                  40                  45

Gly Thr Cys Gly Leu Val Glu Leu Glu Lys Gly Val Leu Pro Gln Leu
         50                  55                  60

Glu Gln Pro Tyr Val Phe Ile Lys Arg Ser Asp Ala Leu Ser Thr Asn
 65                  70                  75                  80

His Gly His Lys Val Val Glu Leu Val Ala Glu Met Asp Gly Ile Gln
                 85                  90                  95

Tyr Gly Arg Ser Gly Ile Thr Leu Gly Val Leu Val Pro His Val Gly
                100                 105                 110

Glu Thr Pro Ile Ala Tyr Arg Asn Val Leu Leu Arg Lys Asn Gly Asn
            115                 120                 125

Lys Gly Ala Gly Gly His Ser Tyr Gly Ile Asp Leu Lys Ser Tyr Asp
        130                 135                 140

Leu Gly Asp Glu Leu Gly Thr Asp Pro Ile Glu Asp Tyr Glu Gln Asn
145                 150                 155                 160

Trp Asn Thr Lys His Gly Ser Gly Ala Leu Arg Glu Leu Thr Arg Glu
                165                 170                 175

Leu Asn Gly Gly Ala Val Thr Arg Tyr Val Asp Asn Asn Phe Cys Gly
            180                 185                 190

Pro Asp Gly Tyr Pro Leu Asp Cys Ile Lys Asp Phe Leu Ala Arg Ala
        195                 200                 205

Gly Lys Ser Met Cys Thr Leu Ser Glu Gln Leu Asp Tyr Ile Glu Ser
    210                 215                 220

Lys Arg Gly Val Tyr Cys Cys Arg Asp His Glu His Glu Ile Ala Trp
225                 230                 235                 240

Phe Thr Glu Arg Ser Asp Lys Ser Tyr Glu His Gln Thr Pro Phe Glu
                245                 250                 255

Ile Lys Ser Ala Lys Lys Phe Asp Thr Phe Lys Gly Glu Cys Pro Lys
            260                 265                 270

Phe Val Phe Pro Leu Asn Ser Lys Val Lys Val Ile Gln Pro Arg Val
        275                 280                 285

Glu Lys Lys Lys Thr Glu Gly Phe Met Gly Arg Ile Arg Ser Val Tyr
    290                 295                 300
```

-continued

```
Pro Val Ala Ser Pro Gln Glu Cys Asn Asn Met His Leu Ser Thr Leu
305                 310                 315                 320

Met Lys Cys Asn His Cys Asp Glu Val Ser Trp Gln Thr Cys Asp Phe
            325                 330                 335

Leu Lys Ala Thr Cys Glu His Cys Gly Thr Glu Asn Leu Val Ile Glu
                340                 345                 350

Gly Pro Thr Thr Cys Gly Tyr Leu Pro Thr Asn Ala Val Val Lys Met
            355                 360                 365

Pro Cys Pro Ala Cys Gln Asp Pro Glu Ile Gly Pro Glu His Ser Val
        370                 375                 380

Ala Asp Tyr His Asn His Ser Asn Ile Glu Thr Arg Leu Arg Lys Gly
385                 390                 395                 400

Gly Arg Thr Arg Cys Phe Gly Gly Cys Val Phe Ala Tyr Val Gly Cys
                405                 410                 415

Tyr Asn Lys Arg Ala Tyr Trp Val Pro Arg Ala Ser Ala Asp Ile Gly
            420                 425                 430

Ser Gly His Thr Gly Ile Thr Gly Asp Asn Val Glu Thr Leu Asn Glu
        435                 440                 445

Asp Leu Leu Glu Ile Leu Ser Arg Glu Arg Val Asn Ile Asn Ile Val
450                 455                 460

Gly Asp Phe His Leu Asn Glu Glu Val Ala Ile Ile Leu Ala Ser Phe
465                 470                 475                 480

Ser Ala Ser Thr Ser Ala Phe Ile Asp Thr Ile Lys Ser Leu Asp Tyr
                485                 490                 495

Lys Ser Phe Lys Thr Ile Val Glu Ser Cys Gly Asn Tyr Lys Val Thr
            500                 505                 510

Lys Gly Lys Pro Val Lys Gly Ala Trp Asn Ile Gly Gln Gln Arg Ser
        515                 520                 525

Val Leu Thr Pro Leu Cys Gly Phe Pro Ser Gln Ala Ala Gly Val Ile
530                 535                 540

Arg Ser Ile Phe Ala Arg Thr Leu Asp Ala Ala Asn His Ser Ile Pro
545                 550                 555                 560

Asp Leu Gln Arg Ala Ala Val Thr Ile Leu Asp Gly Ile Ser Glu Gln
                565                 570                 575

Ser Leu Arg Leu Val Asp Ala Met Val Tyr Thr Ser Asp Leu Leu Thr
            580                 585                 590

Asn Ser Val Ile Ile Met Ala Tyr Val Thr Gly Gly Leu Val Gln Gln
        595                 600                 605

Thr Ser Gln Trp Leu Ser Asn Leu Leu Gly Thr Thr Val Glu Lys Leu
610                 615                 620

Arg Pro Ile Phe Glu Trp Ile Glu Ala Lys Leu Ser Ala Gly Val Glu
625                 630                 635                 640

Phe Leu Lys Asp Ala Trp Glu Ile Leu Lys Phe Leu Ile Thr Gly Val
                645                 650                 655

Phe Asp Ile Val Lys Gly Gln Ile Gln Val Ala Ser Asp Asn Ile Lys
            660                 665                 670

Asp Cys Val Lys Cys Phe Ile Asp Val Val Asn Lys Ala Leu Glu Met
        675                 680                 685

Cys Ile Asp Gln Val Thr Ile Ala Gly Ala Lys Leu Arg Ser Leu Asn
        690                 695                 700

Leu Gly Glu Val Phe Ile Ala Gln Ser Lys Gly Leu Tyr Arg Gln Cys
705                 710                 715                 720

Ile Arg Gly Lys Glu Gln Leu Gln Leu Leu Met Pro Leu Lys Ala Pro
```

-continued

```
                725                 730                 735
Lys Glu Val Thr Phe Leu Glu Gly Asp Ser His Asp Thr Val Leu Thr
                740                 745                 750
Ser Glu Glu Val Val Leu Lys Asn Gly Glu Leu Glu Ala Leu Glu Thr
                755                 760                 765
Pro Val Asp Ser Phe Thr Asn Gly Ala Ile Val Gly Thr Pro Val Cys
                770                 775                 780
Val Asn Gly Leu Met Leu Leu Glu Ile Lys Asp Lys Glu Gln Tyr Cys
785                 790                 795                 800
Ala Leu Ser Pro Gly Leu Leu Ala Thr Asn Asn Val Phe Arg Leu Lys
                805                 810                 815
Gly Gly Ala Pro Ile Lys Gly Val Thr Phe Gly Glu Asp Thr Val Trp
                820                 825                 830
Glu Val Gln Gly Tyr Lys Asn Val Arg Ile Thr Phe Glu Leu Asp Glu
                835                 840                 845
Arg Val Asp Lys Val Leu Asn Glu Lys Cys Ser Val Tyr Thr Val Glu
                850                 855                 860
Ser Gly Thr Glu Val Thr Glu Phe Ala Cys Val Val Ala Glu Ala Val
865                 870                 875                 880
Val Lys Thr Leu Gln Pro Val Ser Asp Leu Leu Thr Asn Met Gly Ile
                885                 890                 895
Asp Leu Asp Glu Trp Ser Val Ala Thr Phe Tyr Leu Phe Asp Asp Ala
                900                 905                 910
Gly Glu Glu Asn Phe Ser Ser Arg Met Tyr Cys Ser Phe Tyr Pro Pro
                915                 920                 925
Asp Glu Glu Glu Glu Asp Asp Ala Glu Cys Glu Glu Glu Glu Ile Asp
                930                 935                 940
Glu Thr Cys Glu His Glu Tyr Gly Thr Glu Asp Asp Tyr Gln Gly Leu
945                 950                 955                 960
Pro Leu Glu Phe Gly Ala Ser Ala Glu Thr Val Arg Val Glu Glu Glu
                965                 970                 975
Glu Glu Glu Asp Trp Leu Asp Asp Thr Thr Glu Gln Ser Glu Ile Glu
                980                 985                 990
Pro Glu Pro Glu Pro Thr Pro Glu Pro Val Asn Gln Phe Thr Gly
                995                1000                1005
Tyr Leu  Lys Leu  Thr Asp  Asn  Val  Ala  Ile  Lys  Cys  Val  Asp  Ile
                1010                 1015                1020
Val Lys  Glu Ala  Gln Ser  Ala  Asn  Pro  Met  Val  Ile  Val  Asn  Ala
                1025                 1030                1035
Ala Asn  Ile His  Leu Lys  His  Gly  Gly  Val  Ala  Gly  Ala  Leu
                1040                 1045                1050
Asn Lys  Ala Thr  Asn Gly  Ala  Met  Gln  Lys  Glu  Ser  Asp  Asp  Tyr
                1055                 1060                1065
Ile Lys  Leu Asn  Gly Pro  Leu  Thr  Val  Gly  Gly  Ser  Cys  Leu  Leu
                1070                 1075                1080
Ser Gly  His Asn  Leu Ala  Lys  Lys  Cys  Leu  His  Val  Val  Gly  Pro
                1085                 1090                1095
Asn Leu  Asn Ala  Gly Glu  Asp  Ile  Gln  Leu  Leu  Lys  Ala  Ala  Tyr
                1100                 1105                1110
Glu Asn  Phe Asn  Ser Gln  Asp  Ile  Leu  Leu  Ala  Pro  Leu  Leu  Ser
                1115                 1120                1125
Ala Gly  Ile Phe  Gly Ala  Lys  Pro  Leu  Gln  Ser  Leu  Gln  Val  Cys
                1130                 1135                1140
```

```
Val Gln Thr Val Arg Thr Gln Val Tyr Ile Ala Val Asn Asp Lys
    1145                1150                1155

Ala Leu Tyr Glu Gln Val Val Met Asp Tyr Leu Asp Asn Leu Lys
    1160                1165                1170

Pro Arg Val Glu Ala Pro Lys Gln Glu Pro Pro Asn Thr Glu
    1175                1180                1185

Asp Ser Lys Thr Glu Glu Lys Ser Val Val Gln Lys Pro Val Asp
    1190                1195                1200

Val Lys Pro Lys Ile Lys Ala Cys Ile Asp Glu Val Thr Thr Thr
    1205                1210                1215

Leu Glu Glu Thr Lys Phe Leu Thr Asn Lys Leu Leu Leu Phe Ala
    1220                1225                1230

Asp Ile Asn Gly Lys Leu Tyr His Asp Ser Gln Asn Met Leu Arg
    1235                1240                1245

Gly Glu Asp Met Ser Phe Leu Glu Lys Asp Ala Pro Tyr Met Val
    1250                1255                1260

Gly Asp Val Ile Thr Ser Gly Asp Ile Thr Cys Val Val Ile Pro
    1265                1270                1275

Ser Lys Lys Ala Gly Gly Thr Thr Glu Met Leu Ser Arg Ala Leu
    1280                1285                1290

Lys Lys Val Pro Val Asp Glu Tyr Ile Thr Thr Tyr Pro Gly Gln
    1295                1300                1305

Gly Cys Ala Gly Tyr Thr Leu Glu Glu Ala Lys Thr Ala Leu Lys
    1310                1315                1320

Lys Cys Lys Ser Ala Phe Tyr Val Leu Pro Ser Glu Ala Pro Asn
    1325                1330                1335

Ala Lys Glu Glu Ile Leu Gly Thr Val Ser Trp Asn Leu Arg Glu
    1340                1345                1350

Met Leu Ala His Ala Glu Glu Thr Arg Lys Leu Met Pro Ile Cys
    1355                1360                1365

Met Asp Val Arg Ala Ile Met Ala Thr Ile Gln Arg Lys Tyr Lys
    1370                1375                1380

Gly Ile Lys Ile Gln Glu Gly Ile Val Asp Tyr Gly Val Arg Phe
    1385                1390                1395

Phe Phe Tyr Thr Ser Lys Glu Pro Val Ala Ser Ile Ile Thr Lys
    1400                1405                1410

Leu Asn Ser Leu Asn Glu Pro Leu Val Thr Met Pro Ile Gly Tyr
    1415                1420                1425

Val Thr His Gly Phe Asn Leu Glu Glu Ala Ala Arg Cys Met Arg
    1430                1435                1440

Ser Leu Lys Ala Pro Ala Val Val Ser Val Ser Ser Pro Asp Ala
    1445                1450                1455

Val Thr Thr Tyr Asn Gly Tyr Leu Thr Ser Ser Ser Lys Thr Ser
    1460                1465                1470

Glu Glu His Phe Val Glu Thr Val Ser Leu Ala Gly Ser Tyr Arg
    1475                1480                1485

Asp Trp Ser Tyr Ser Gly Gln Arg Thr Glu Leu Gly Val Glu Phe
    1490                1495                1500

Leu Lys Arg Gly Asp Lys Ile Val Tyr His Thr Leu Glu Ser Pro
    1505                1510                1515

Val Glu Phe His Leu Asp Gly Glu Val Leu Ser Leu Asp Lys Leu
    1520                1525                1530
```

```
Lys Ser Leu Leu Ser Leu Arg Glu Val Lys Thr Ile Lys Val Phe
1535                1540                1545

Thr Thr Val Asp Asn Thr Asn Leu His Thr Gln Leu Val Asp Met
1550                1555                1560

Ser Met Thr Tyr Gly Gln Gln Phe Gly Pro Thr Tyr Leu Asp Gly
1565                1570                1575

Ala Asp Val Thr Lys Ile Lys Pro His Val Asn His Glu Gly Lys
1580                1585                1590

Thr Phe Phe Val Leu Pro Ser Asp Thr Leu Arg Ser Glu Ala
1595                1600                1605

Phe Glu Tyr Tyr His Thr Leu Asp Glu Ser Phe Leu Gly Arg Tyr
1610                1615                1620

Met Ser Ala Leu Asn His Thr Lys Lys Trp Lys Phe Pro Gln Val
1625                1630                1635

Gly Gly Leu Thr Ser Ile Lys Trp Ala Asp Asn Cys Tyr Leu
1640                1645                1650

Ser Ser Val Leu Leu Ala Leu Gln Gln Leu Glu Val Lys Phe Asn
1655                1660                1665

Ala Pro Ala Leu Gln Glu Ala Tyr Tyr Arg Ala Arg Ala Gly Asp
1670                1675                1680

Ala Ala Asn Phe Cys Ala Leu Ile Leu Ala Tyr Ser Asn Lys Thr
1685                1690                1695

Val Gly Glu Leu Gly Asp Val Arg Glu Thr Met Thr His Leu Leu
1700                1705                1710

Gln His Ala Asn Leu Glu Ser Ala Lys Arg Val Leu Asn Val Val
1715                1720                1725

Cys Lys His Cys Gly Gln Lys Thr Thr Thr Leu Thr Gly Val Glu
1730                1735                1740

Ala Val Met Tyr Met Gly Thr Leu Ser Tyr Asp Asn Leu Lys Thr
1745                1750                1755

Gly Val Ser Ile Pro Cys Val Cys Gly Arg Asp Ala Thr Gln Tyr
1760                1765                1770

Leu Val Gln Gln Glu Ser Ser Phe Val Met Met Ser Ala Pro Pro
1775                1780                1785

Ala Glu Tyr Lys Leu Gln Gln Gly Thr Phe Leu Cys Ala Asn Glu
1790                1795                1800

Tyr Thr Gly Asn Tyr Gln Cys Gly His Tyr Thr His Ile Thr Ala
1805                1810                1815

Lys Glu Thr Leu Tyr Arg Ile Asp Gly Ala His Leu Thr Lys Met
1820                1825                1830

Ser Glu Tyr Lys Gly Pro Val Thr Asp Val Phe Tyr Lys Glu Thr
1835                1840                1845

Ser Tyr Thr Thr Thr Ile Lys Pro Val Ser Tyr Lys Leu Asp Gly
1850                1855                1860

Val Thr Tyr Thr Glu Ile Glu Pro Lys Leu Asp Gly Tyr Tyr Lys
1865                1870                1875

Lys Asp Asn Ala Tyr Tyr Thr Glu Gln Pro Ile Asp Leu Val Pro
1880                1885                1890

Thr Gln Pro Leu Pro Asn Ala Ser Phe Asp Asn Phe Lys Leu Thr
1895                1900                1905

Cys Ser Asn Thr Lys Phe Ala Asp Asp Leu Asn Gln Met Thr Gly
1910                1915                1920

Phe Thr Lys Pro Ala Ser Arg Glu Leu Ser Val Thr Phe Phe Pro
```

-continued

```
        1925                1930                1935

Asp Leu Asn Gly Asp Val Val Ala Ile Asp Tyr Arg His Tyr Ser
        1940                1945                1950

Ala Ser Phe Lys Lys Gly Ala Lys Leu Leu His Lys Pro Ile Val
        1955                1960                1965

Trp His Ile Asn Gln Ala Thr Thr Lys Thr Thr Phe Lys Pro Asn
        1970                1975                1980

Thr Trp Cys Leu Arg Cys Leu Trp Ser Thr Lys Pro Val Asp Thr
        1985                1990                1995

Ser Asn Ser Phe Glu Val Leu Ala Val Glu Asp Thr Gln Gly Met
        2000                2005                2010

Asp Asn Leu Ala Cys Glu Ser Gln Gln Pro Thr Ser Glu Glu Val
        2015                2020                2025

Val Glu Asn Pro Thr Ile Gln Lys Glu Val Ile Glu Cys Asp Val
        2030                2035                2040

Lys Thr Thr Glu Val Val Gly Asn Val Ile Leu Lys Pro Ser Asp
        2045                2050                2055

Glu Gly Val Lys Val Thr Gln Glu Leu Gly His Glu Asp Leu Met
        2060                2065                2070

Ala Ala Tyr Val Glu Asn Thr Ser Ile Thr Ile Lys Lys Pro Asn
        2075                2080                2085

Glu Leu Ser Leu Ala Leu Gly Leu Lys Thr Ile Ala Thr His Gly
        2090                2095                2100

Ile Ala Ala Ile Asn Ser Val Pro Trp Ser Lys Ile Leu Ala Tyr
        2105                2110                2115

Val Lys Pro Phe Leu Gly Gln Ala Ala Ile Thr Thr Ser Asn Cys
        2120                2125                2130

Ala Lys Arg Leu Ala Gln Arg Val Phe Asn Asn Tyr Met Pro Tyr
        2135                2140                2145

Val Phe Thr Leu Leu Phe Gln Leu Cys Thr Phe Thr Lys Ser Thr
        2150                2155                2160

Asn Ser Arg Ile Arg Ala Ser Leu Pro Thr Thr Ile Ala Lys Asn
        2165                2170                2175

Ser Val Lys Ser Val Ala Lys Leu Cys Leu Asp Ala Gly Ile Asn
        2180                2185                2190

Tyr Val Lys Ser Pro Lys Phe Ser Lys Leu Phe Thr Ile Ala Met
        2195                2200                2205

Trp Leu Leu Leu Ser Ile Cys Leu Gly Ser Leu Ile Cys Val
        2210                2215                2220

Thr Ala Ala Phe Gly Val Leu Leu Ser Asn Phe Gly Ala Pro Ser
        2225                2230                2235

Tyr Cys Asn Gly Val Arg Glu Leu Tyr Leu Asn Ser Ser Asn Val
        2240                2245                2250

Thr Thr Met Asp Phe Cys Glu Gly Ser Phe Pro Cys Ser Ile Cys
        2255                2260                2265

Leu Ser Gly Leu Asp Ser Leu Asp Ser Tyr Pro Ala Leu Glu Thr
        2270                2275                2280

Ile Gln Val Thr Ile Ser Ser Tyr Lys Leu Asp Leu Thr Ile Leu
        2285                2290                2295

Gly Leu Ala Ala Glu Trp Val Leu Ala Tyr Met Leu Phe Thr Lys
        2300                2305                2310

Phe Phe Tyr Leu Leu Gly Leu Ser Ala Ile Met Gln Val Phe Phe
        2315                2320                2325
```

-continued

```
Gly Tyr Phe Ala Ser His Phe Ile Ser Asn Ser Trp Leu Met Trp
    2330            2335            2340

Phe Ile Ile Ser Ile Val Gln Met Ala Pro Val Ser Ala Met Val
    2345            2350            2355

Arg Met Tyr Ile Phe Phe Ala Ser Phe Tyr Tyr Ile Trp Lys Ser
    2360            2365            2370

Tyr Val His Ile Met Asp Gly Cys Thr Ser Thr Cys Met Met
    2375            2380            2385

Cys Tyr Lys Arg Asn Arg Ala Thr Arg Val Glu Cys Thr Thr Ile
    2390            2395            2400

Val Asn Gly Met Lys Arg Ser Phe Tyr Val Tyr Ala Asn Gly Gly
    2405            2410            2415

Arg Gly Phe Cys Lys Thr His Asn Trp Asn Cys Leu Asn Cys Asp
    2420            2425            2430

Thr Phe Cys Thr Gly Ser Thr Phe Ile Ser Asp Glu Val Ala Arg
    2435            2440            2445

Asp Leu Ser Leu Gln Phe Lys Arg Pro Ile Asn Pro Thr Asp Gln
    2450            2455            2460

Ser Ser Tyr Ile Val Asp Ser Val Ala Val Lys Asn Gly Ala Leu
    2465            2470            2475

His Leu Tyr Phe Asp Lys Ala Gly Gln Lys Thr Tyr Glu Arg His
    2480            2485            2490

Pro Leu Ser His Phe Val Asn Leu Asp Asn Leu Arg Ala Asn Asn
    2495            2500            2505

Thr Lys Gly Ser Leu Pro Ile Asn Val Ile Val Phe Asp Gly Lys
    2510            2515            2520

Ser Lys Cys Asp Glu Ser Ala Ser Lys Ser Ala Ser Val Tyr Tyr
    2525            2530            2535

Ser Gln Leu Met Cys Gln Pro Ile Leu Leu Leu Asp Gln Ala Leu
    2540            2545            2550

Val Ser Asp Val Gly Asp Ser Thr Glu Val Ser Val Lys Met Phe
    2555            2560            2565

Asp Ala Tyr Val Asp Thr Phe Ser Ala Thr Phe Ser Val Pro Met
    2570            2575            2580

Glu Lys Leu Lys Ala Leu Val Ala Thr Ala His Ser Glu Leu Ala
    2585            2590            2595

Lys Gly Val Ala Leu Asp Gly Val Leu Ser Thr Phe Val Ser Ala
    2600            2605            2610

Ala Arg Gln Gly Val Val Asp Thr Asp Val Asp Thr Lys Asp Val
    2615            2620            2625

Ile Glu Cys Leu Lys Leu Ser His His Ser Asp Leu Glu Val Thr
    2630            2635            2640

Gly Asp Ser Cys Asn Asn Phe Met Leu Thr Tyr Asn Lys Val Glu
    2645            2650            2655

Asn Met Thr Pro Arg Asp Leu Gly Ala Cys Ile Asp Cys Asn Ala
    2660            2665            2670

Arg His Ile Asn Ala Gln Val Ala Lys Ser His Asn Val Ser Leu
    2675            2680            2685

Ile Trp Asn Val Lys Asp Tyr Met Ser Leu Ser Glu Gln Leu Arg
    2690            2695            2700

Lys Gln Ile Arg Ser Ala Ala Lys Lys Asn Asn Ile Pro Phe Arg
    2705            2710            2715
```

```
Leu Thr Cys Ala Thr Thr Arg Gln Val Asn Val Ile Thr Thr
2720                2725                2730

Lys Ile Ser Leu Lys Gly Gly Lys Ile Val Ser Thr Cys Phe Lys
2735                2740                2745

Leu Met Leu Lys Ala Thr Leu Leu Cys Val Leu Ala Ala Leu Val
2750                2755                2760

Cys Tyr Ile Val Met Pro Val His Thr Leu Ser Ile His Asp Gly
2765                2770                2775

Tyr Thr Asn Glu Ile Ile Gly Tyr Lys Ala Ile Gln Asp Gly Val
2780                2785                2790

Thr Arg Asp Ile Ile Ser Thr Asp Asp Cys Phe Ala Asn Lys His
2795                2800                2805

Ala Gly Phe Asp Ala Trp Phe Ser Gln Arg Gly Gly Ser Tyr Lys
2810                2815                2820

Asn Asp Lys Ser Cys Pro Val Val Ala Ala Ile Ile Thr Arg Glu
2825                2830                2835

Ile Gly Phe Ile Val Pro Gly Leu Pro Gly Thr Val Leu Arg Ala
2840                2845                2850

Ile Asn Gly Asp Phe Leu His Phe Leu Pro Arg Val Phe Ser Ala
2855                2860                2865

Val Gly Asn Ile Cys Tyr Thr Pro Ser Lys Leu Ile Glu Tyr Ser
2870                2875                2880

Asp Phe Ala Thr Ser Ala Cys Val Leu Ala Ala Glu Cys Thr Ile
2885                2890                2895

Phe Lys Asp Ala Met Gly Lys Pro Val Pro Tyr Cys Tyr Asp Thr
2900                2905                2910

Asn Leu Leu Glu Gly Ser Ile Ser Tyr Ser Glu Leu Arg Pro Asp
2915                2920                2925

Thr Arg Tyr Val Leu Met Asp Gly Ser Ile Ile Gln Phe Pro Asn
2930                2935                2940

Thr Tyr Leu Glu Gly Ser Val Arg Val Val Thr Thr Phe Asp Ala
2945                2950                2955

Glu Tyr Cys Arg His Gly Thr Cys Glu Arg Ser Glu Val Gly Ile
2960                2965                2970

Cys Leu Ser Thr Ser Gly Arg Trp Val Leu Asn Asn Glu His Tyr
2975                2980                2985

Arg Ala Leu Ser Gly Val Phe Cys Gly Val Asp Ala Met Asn Leu
2990                2995                3000

Ile Ala Asn Ile Phe Thr Pro Leu Val Gln Pro Val Gly Ala Leu
3005                3010                3015

Asp Val Ser Ala Ser Val Val Ala Gly Gly Ile Ile Ala Ile Leu
3020                3025                3030

Val Thr Cys Ala Ala Tyr Tyr Phe Met Lys Phe Arg Arg Val Phe
3035                3040                3045

Gly Glu Tyr Asn His Val Val Ala Ala Asn Ala Leu Leu Phe Leu
3050                3055                3060

Met Ser Phe Thr Ile Leu Cys Leu Val Pro Ala Tyr Ser Phe Leu
3065                3070                3075

Pro Gly Val Tyr Ser Val Phe Tyr Leu Tyr Leu Thr Phe Tyr Phe
3080                3085                3090

Thr Asn Asp Val Ser Phe Leu Ala His Leu Gln Trp Phe Ala Met
3095                3100                3105

Phe Ser Pro Ile Val Pro Phe Trp Ile Thr Ala Ile Tyr Val Phe
```

-continued

```
             3110                3115                 3120
Cys Ile Ser Leu Lys His Cys His Trp Phe Phe Asn  Asn Tyr Leu
             3125                3130                 3135
Arg Lys Arg Val Met Phe Asn Gly Val Thr Phe Ser  Thr Phe Glu
             3140                3145                 3150
Glu Ala Ala Leu Cys Thr Phe Leu Leu Asn Lys Glu  Met Tyr Leu
             3155                3160                 3165
Lys Leu Arg Ser Glu Thr Leu Leu Pro Leu Thr Gln  Tyr Asn Arg
             3170                3175                 3180
Tyr Leu Ala Leu Tyr Asn Lys Tyr Lys Tyr Phe Ser  Gly Ala Leu
             3185                3190                 3195
Asp Thr Thr Ser Tyr Arg Glu Ala Ala Cys Cys His  Leu Ala Lys
             3200                3205                 3210
Ala Leu Asn Asp Phe Ser Asn Ser Gly Ala Asp Val  Leu Tyr Gln
             3215                3220                 3225
Pro Pro Gln Thr Ser Ile Thr Ser Ala Val Leu Gln  Ser Gly Phe
             3230                3235                 3240
Arg Lys Met Ala Phe Pro Ser Gly Lys Val Glu Gly  Cys Met Val
             3245                3250                 3255
Gln Val Thr Cys Gly Thr Thr Thr Leu Asn Gly Leu  Trp Leu Asp
             3260                3265                 3270
Asp Thr Val Tyr Cys Pro Arg His Val Ile Cys Thr  Ala Glu Asp
             3275                3280                 3285
Met Leu Asn Pro Asn Tyr Glu Asp Leu Leu Ile Arg  Lys Ser Asn
             3290                3295                 3300
His Ser Phe Leu Val Gln Ala Gly Asn Val Gln Leu  Arg Val Ile
             3305                3310                 3315
Gly His Ser Met Gln Asn Cys Leu Leu Arg Leu Lys  Val Asp Thr
             3320                3325                 3330
Ser Asn Pro Lys Thr Pro Lys Tyr Lys Phe Val Arg  Ile Gln Pro
             3335                3340                 3345
Gly Gln Thr Phe Ser Val Leu Ala Cys Tyr Asn Gly  Ser Pro Ser
             3350                3355                 3360
Gly Val Tyr Gln Cys Ala Met Arg Pro Asn His Thr  Ile Lys Gly
             3365                3370                 3375
Ser Phe Leu Asn Gly Ser Cys Gly Ser Val Gly Phe  Asn Ile Asp
             3380                3385                 3390
Tyr Asp Cys Val Ser Phe Cys Tyr Met His His Met  Glu Leu Pro
             3395                3400                 3405
Thr Gly Val His Ala Gly Thr Asp Leu Glu Gly Lys  Phe Tyr Gly
             3410                3415                 3420
Pro Phe Val Asp Arg Gln Thr Ala Gln Ala Ala Gly  Thr Asp Thr
             3425                3430                 3435
Thr Ile Thr Leu Asn Val Leu Ala Trp Leu Tyr Ala  Ala Val Ile
             3440                3445                 3450
Asn Gly Asp Arg Trp Phe Leu Asn Arg Phe Thr Thr  Thr Leu Asn
             3455                3460                 3465
Asp Phe Asn Leu Val Ala Met Lys Tyr Asn Tyr Glu  Pro Leu Thr
             3470                3475                 3480
Gln Asp His Val Asp Ile Leu Gly Pro Leu Ser Ala  Gln Thr Gly
             3485                3490                 3495
Ile Ala Val Leu Asp Met Cys Ala Ala Leu Lys Glu  Leu Leu Gln
             3500                3505                 3510
```

```
Asn Gly Met Asn Gly Arg Thr Ile Leu Gly Ser Thr Ile Leu Glu
    3515                3520                3525

Asp Glu Phe Thr Pro Phe Asp Val Val Arg Gln Cys Ser Gly Val
    3530                3535                3540

Thr Phe Gln Gly Lys Phe Lys Lys Ile Val Lys Gly Thr His His
    3545                3550                3555

Trp Met Leu Leu Thr Phe Leu Thr Ser Leu Leu Ile Leu Val Gln
    3560                3565                3570

Ser Thr Gln Trp Ser Leu Phe Phe Val Tyr Glu Asn Ala Phe
    3575                3580                3585

Leu Pro Phe Thr Leu Gly Ile Met Ala Ile Ala Ala Cys Ala Met
    3590                3595                3600

Leu Leu Val Lys His Lys His Ala Phe Leu Cys Leu Phe Leu Leu
    3605                3610                3615

Pro Ser Leu Ala Thr Val Ala Tyr Phe Asn Met Val Tyr Met Pro
    3620                3625                3630

Ala Ser Trp Val Met Arg Ile Met Thr Trp Leu Glu Leu Ala Asp
    3635                3640                3645

Thr Ser Leu Ser Gly Tyr Arg Leu Lys Asp Cys Val Met Tyr Ala
    3650                3655                3660

Ser Ala Leu Val Leu Leu Ile Leu Met Thr Ala Arg Thr Val Tyr
    3665                3670                3675

Asp Asp Ala Ala Arg Arg Val Trp Thr Leu Met Asn Val Ile Thr
    3680                3685                3690

Leu Val Tyr Lys Val Tyr Tyr Gly Asn Ala Leu Asp Gln Ala Ile
    3695                3700                3705

Ser Met Trp Ala Leu Val Ile Ser Val Thr Ser Asn Tyr Ser Gly
    3710                3715                3720

Val Val Thr Thr Ile Met Phe Leu Ala Arg Ala Ile Val Phe Val
    3725                3730                3735

Cys Val Glu Tyr Tyr Pro Leu Leu Phe Ile Thr Gly Asn Thr Leu
    3740                3745                3750

Gln Cys Ile Met Leu Val Tyr Cys Phe Leu Gly Tyr Cys Cys Cys
    3755                3760                3765

Cys Tyr Phe Gly Leu Phe Cys Leu Leu Asn Arg Tyr Phe Arg Leu
    3770                3775                3780

Thr Leu Gly Val Tyr Asp Tyr Leu Val Ser Thr Gln Glu Phe Arg
    3785                3790                3795

Tyr Met Asn Ser Gln Gly Leu Leu Pro Pro Lys Ser Ser Ile Asp
    3800                3805                3810

Ala Phe Lys Leu Asn Ile Lys Leu Leu Gly Ile Gly Gly Lys Pro
    3815                3820                3825

Cys Ile Lys Val Ala Thr Val Gln Ser Lys Met Ser Asp Val Lys
    3830                3835                3840

Cys Thr Ser Val Val Leu Leu Ser Val Leu Gln Gln Leu Arg Val
    3845                3850                3855

Glu Ser Ser Ser Lys Leu Trp Ala Gln Cys Val Gln Leu His Asn
    3860                3865                3870

Asp Ile Leu Leu Ala Lys Asp Thr Thr Glu Ala Phe Glu Lys Met
    3875                3880                3885

Val Ser Leu Leu Ser Val Leu Leu Ser Met Gln Gly Ala Val Asp
    3890                3895                3900
```

-continued

```
Ile Asn Arg Leu Cys Glu Glu Met Leu Asp Asn Arg Ala Thr Leu
    3905                3910                3915

Gln Ala Ile Ala Ser Glu Phe Ser Ser Leu Pro Ser Tyr Ala Ala
    3920                3925                3930

Tyr Ala Thr Ala Gln Glu Ala Tyr Glu Gln Ala Val Ala Asn Gly
    3935                3940                3945

Asp Ser Glu Val Val Leu Lys Lys Leu Lys Lys Ser Leu Asn Val
    3950                3955                3960

Ala Lys Ser Glu Phe Asp Arg Asp Ala Ala Met Gln Arg Lys Leu
    3965                3970                3975

Glu Lys Met Ala Asp Gln Ala Met Thr Gln Met Tyr Lys Gln Ala
    3980                3985                3990

Arg Ser Glu Asp Lys Arg Ala Lys Val Thr Ser Ala Met Gln Thr
    3995                4000                4005

Met Leu Phe Thr Met Leu Arg Lys Leu Asp Asn Asp Ala Leu Asn
    4010                4015                4020

Asn Ile Ile Asn Asn Ala Arg Asp Gly Cys Val Pro Leu Asn Ile
    4025                4030                4035

Ile Pro Leu Thr Thr Ala Ala Lys Leu Met Val Val Val Pro Asp
    4040                4045                4050

Tyr Gly Thr Tyr Lys Asn Thr Cys Asp Gly Asn Thr Phe Thr Tyr
    4055                4060                4065

Ala Ser Ala Leu Trp Glu Ile Gln Gln Val Val Asp Ala Asp Ser
    4070                4075                4080

Lys Ile Val Gln Leu Ser Glu Ile Asn Met Asp Asn Ser Pro Asn
    4085                4090                4095

Leu Ala Trp Pro Leu Ile Val Thr Ala Leu Arg Ala Asn Ser Ala
    4100                4105                4110

Val Lys Leu Gln Asn Asn Glu Leu Ser Pro Val Ala Leu Arg Gln
    4115                4120                4125

Met Ser Cys Ala Ala Gly Thr Thr Gln Thr Ala Cys Thr Asp Asp
    4130                4135                4140

Asn Ala Leu Ala Tyr Tyr Asn Asn Ser Lys Gly Gly Arg Phe Val
    4145                4150                4155

Leu Ala Leu Leu Ser Asp His Gln Asp Leu Lys Trp Ala Arg Phe
    4160                4165                4170

Pro Lys Ser Asp Gly Thr Gly Thr Ile Tyr Thr Glu Leu Glu Pro
    4175                4180                4185

Pro Cys Arg Phe Val Thr Asp Thr Pro Lys Gly Pro Lys Val Lys
    4190                4195                4200

Tyr Leu Tyr Phe Ile Lys Gly Leu Asn Asn Leu Asn Arg Gly Met
    4205                4210                4215

Val Leu Gly Ser Leu Ala Ala Thr Val Arg Leu Gln Ala Gly Asn
    4220                4225                4230

Ala Thr Glu Val Pro Ala Asn Ser Thr Val Leu Ser Phe Cys Ala
    4235                4240                4245

Phe Ala Val Asp Pro Ala Lys Ala Tyr Lys Asp Tyr Leu Ala Ser
    4250                4255                4260

Gly Gly Gln Pro Ile Thr Asn Cys Val Lys Met Leu Cys Thr His
    4265                4270                4275

Thr Gly Thr Gly Gln Ala Ile Thr Val Thr Pro Glu Ala Asn Met
    4280                4285                4290

Asp Gln Glu Ser Phe Gly Gly Ala Ser Cys Cys Leu Tyr Cys Arg
```

-continued

```
            4295                4300                4305
Cys His Ile Asp His Pro Asn Pro Lys Gly Phe Cys Asp Leu Lys
    4310                4315                4320

Gly Lys Tyr Val Gln Ile Pro Thr Thr Cys Ala Asn Asp Pro Val
    4325                4330                4335

Gly Phe Thr Leu Arg Asn Thr Val Cys Thr Val Cys Gly Met Trp
    4340                4345                4350

Lys Gly Tyr Gly Cys Ser Cys Asp Gln Leu Arg Glu Pro Leu Met
    4355                4360                4365

Gln Ser Ala Asp Ala Ser Thr Phe Leu Asn Gly Phe Ala Val
    4370                4375                4380

<210> SEQ ID NO 75
<211> LENGTH: 2695
<212> TYPE: PRT
<213> ORGANISM: CORONAVIRUS

<400> SEQUENCE: 75

Arg Val Cys Gly Val Ser Ala Ala Arg Leu Thr Pro Cys Gly Thr Gly
1               5                   10                  15

Thr Ser Thr Asp Val Val Tyr Arg Ala Phe Asp Ile Tyr Asn Glu Lys
                20                  25                  30

Val Ala Gly Phe Ala Lys Phe Leu Lys Thr Asn Cys Cys Arg Phe Gln
            35                  40                  45

Glu Lys Asp Glu Glu Gly Asn Leu Leu Asp Ser Tyr Phe Val Val Lys
        50                  55                  60

Arg His Thr Met Ser Asn Tyr Gln His Glu Glu Thr Ile Tyr Asn Leu
65                  70                  75                  80

Val Lys Asp Cys Pro Ala Val Ala Val His Asp Phe Phe Lys Phe Arg
                85                  90                  95

Val Asp Gly Asp Met Val Pro His Ile Ser Arg Gln Arg Leu Thr Lys
            100                 105                 110

Tyr Thr Met Ala Asp Leu Val Tyr Ala Leu Arg His Phe Asp Glu Gly
        115                 120                 125

Asn Cys Asp Thr Leu Lys Glu Ile Leu Val Thr Tyr Asn Cys Cys Asp
    130                 135                 140

Asp Asp Tyr Phe Asn Lys Lys Asp Trp Tyr Asp Phe Val Glu Asn Pro
145                 150                 155                 160

Asp Ile Leu Arg Val Tyr Ala Asn Leu Gly Glu Arg Val Arg Gln Ser
                165                 170                 175

Leu Leu Lys Thr Val Gln Phe Cys Asp Ala Met Arg Asp Ala Gly Ile
            180                 185                 190

Val Gly Val Leu Thr Leu Asp Asn Gln Asp Leu Asn Gly Asn Trp Tyr
        195                 200                 205

Asp Phe Gly Asp Phe Val Gln Val Ala Pro Gly Cys Gly Val Pro Ile
    210                 215                 220

Val Asp Ser Tyr Tyr Ser Leu Leu Met Pro Ile Leu Thr Leu Thr Arg
225                 230                 235                 240

Ala Leu Ala Ala Glu Ser His Met Asp Ala Asp Leu Ala Lys Pro Leu
                245                 250                 255

Ile Lys Trp Asp Leu Leu Lys Tyr Asp Phe Thr Glu Glu Arg Leu Cys
            260                 265                 270

Leu Phe Asp Arg Tyr Phe Lys Tyr Trp Asp Gln Thr Tyr His Pro Asn
        275                 280                 285
```

```
Cys Ile Asn Cys Leu Asp Asp Arg Cys Ile Leu His Cys Ala Asn Phe
    290                 295                 300
Asn Val Leu Phe Ser Thr Val Phe Pro Pro Thr Ser Phe Gly Pro Leu
305                 310                 315                 320
Val Arg Lys Ile Phe Val Asp Gly Val Pro Phe Val Val Ser Thr Gly
                325                 330                 335
Tyr His Phe Arg Glu Leu Gly Val Val His Asn Gln Asp Val Asn Leu
            340                 345                 350
His Ser Ser Arg Leu Ser Phe Lys Glu Leu Leu Val Tyr Ala Ala Asp
        355                 360                 365
Pro Ala Met His Ala Ala Ser Gly Asn Leu Leu Leu Asp Lys Arg Thr
370                 375                 380
Thr Cys Phe Ser Val Ala Ala Leu Thr Asn Asn Val Ala Phe Gln Thr
385                 390                 395                 400
Val Lys Pro Gly Asn Phe Asn Lys Asp Phe Tyr Asp Phe Ala Val Ser
                405                 410                 415
Lys Gly Phe Phe Lys Glu Gly Ser Ser Val Glu Leu Lys His Phe Phe
            420                 425                 430
Phe Ala Gln Asp Gly Asn Ala Ala Ile Ser Asp Tyr Asp Tyr Tyr Arg
        435                 440                 445
Tyr Asn Leu Pro Thr Met Cys Asp Ile Arg Gln Leu Leu Phe Val Val
450                 455                 460
Glu Val Val Asp Lys Tyr Phe Asp Cys Tyr Asp Gly Gly Cys Ile Asn
465                 470                 475                 480
Ala Asn Gln Val Ile Val Asn Asn Leu Asp Lys Ser Ala Gly Phe Pro
                485                 490                 495
Phe Asn Lys Trp Gly Lys Ala Arg Leu Tyr Tyr Asp Ser Met Ser Tyr
            500                 505                 510
Glu Asp Gln Asp Ala Leu Phe Ala Tyr Thr Lys Arg Asn Val Ile Pro
        515                 520                 525
Thr Ile Thr Gln Met Asn Leu Lys Tyr Ala Ile Ser Ala Lys Asn Arg
530                 535                 540
Ala Arg Thr Val Ala Gly Val Ser Ile Cys Ser Thr Met Thr Asn Arg
545                 550                 555                 560
Gln Phe His Gln Lys Leu Leu Lys Ser Ile Ala Ala Thr Arg Gly Ala
                565                 570                 575
Thr Val Val Ile Gly Thr Ser Lys Phe Tyr Gly Gly Trp His Asn Met
            580                 585                 590
Leu Lys Thr Val Tyr Ser Asp Val Glu Thr Pro His Leu Met Gly Trp
        595                 600                 605
Asp Tyr Pro Lys Cys Asp Arg Ala Met Pro Asn Met Leu Arg Ile Met
610                 615                 620
Ala Ser Leu Val Leu Ala Arg Lys His Asn Thr Cys Cys Asn Leu Ser
625                 630                 635                 640
His Arg Phe Tyr Arg Leu Ala Asn Glu Cys Ala Gln Val Leu Ser Glu
                645                 650                 655
Met Val Met Cys Gly Gly Ser Leu Tyr Val Lys Pro Gly Gly Thr Ser
            660                 665                 670
Ser Gly Asp Ala Thr Thr Ala Tyr Ala Asn Ser Val Phe Asn Ile Cys
        675                 680                 685
Gln Ala Val Thr Ala Asn Val Asn Ala Leu Leu Ser Thr Asp Gly Asn
690                 695                 700
Lys Ile Ala Asp Lys Tyr Val Arg Asn Leu Gln His Arg Leu Tyr Glu
```

```
                705                 710                 715                 720
Cys Leu Tyr Arg Asn Arg Asp Val Asp His Glu Phe Val Asp Glu Phe
                725                 730                 735

Tyr Ala Tyr Leu Arg Lys His Phe Ser Met Met Ile Leu Ser Asp Asp
                740                 745                 750

Ala Val Val Cys Tyr Asn Ser Asn Tyr Ala Ala Gln Gly Leu Val Ala
                755                 760                 765

Ser Ile Lys Asn Phe Lys Ala Val Leu Tyr Tyr Gln Asn Asn Val Phe
                770                 775                 780

Met Ser Glu Ala Lys Cys Trp Thr Glu Thr Asp Leu Thr Lys Gly Pro
785                 790                 795                 800

His Glu Phe Cys Ser Gln His Thr Met Leu Val Lys Gln Gly Asp Asp
                805                 810                 815

Tyr Val Tyr Leu Pro Tyr Pro Asp Pro Ser Arg Ile Leu Gly Ala Gly
                820                 825                 830

Cys Phe Val Asp Asp Ile Val Lys Thr Asp Gly Thr Leu Met Ile Glu
                835                 840                 845

Arg Phe Val Ser Leu Ala Ile Asp Ala Tyr Pro Leu Thr Lys His Pro
850                 855                 860

Asn Gln Glu Tyr Ala Asp Val Phe His Leu Tyr Leu Gln Tyr Ile Arg
865                 870                 875                 880

Lys Leu His Asp Glu Leu Thr Gly His Met Leu Asp Met Tyr Ser Val
                885                 890                 895

Met Leu Thr Asn Asp Asn Thr Ser Arg Tyr Trp Glu Pro Glu Phe Tyr
                900                 905                 910

Glu Ala Met Tyr Thr Pro His Thr Val Leu Gln Ala Val Gly Ala Cys
                915                 920                 925

Val Leu Cys Asn Ser Gln Thr Ser Leu Arg Cys Gly Ala Cys Ile Arg
                930                 935                 940

Arg Pro Phe Leu Cys Cys Lys Cys Cys Tyr Asp His Val Ile Ser Thr
945                 950                 955                 960

Ser His Lys Leu Val Leu Ser Val Asn Pro Tyr Val Cys Asn Ala Pro
                965                 970                 975

Gly Cys Asp Val Thr Asp Val Thr Gln Leu Tyr Leu Gly Gly Met Ser
                980                 985                 990

Tyr Tyr Cys Lys Ser His Lys Pro Pro Ile Ser Phe Pro Leu Cys Ala
                995                 1000                1005

Asn Gly Gln Val Phe Gly Leu Tyr Lys Asn Thr Cys Val Gly Ser
    1010                1015                1020

Asp Asn Val Thr Asp Phe Asn Ala Ile Ala Thr Cys Asp Trp Thr
    1025                1030                1035

Asn Ala Gly Asp Tyr Ile Leu Ala Asn Thr Cys Thr Glu Arg Leu
    1040                1045                1050

Lys Leu Phe Ala Ala Glu Thr Leu Lys Ala Thr Glu Glu Thr Phe
    1055                1060                1065

Lys Leu Ser Tyr Gly Ile Ala Thr Val Arg Glu Val Leu Ser Asp
    1070                1075                1080

Arg Glu Leu His Leu Ser Trp Glu Val Gly Lys Pro Arg Pro Pro
    1085                1090                1095

Leu Asn Arg Asn Tyr Val Phe Thr Gly Tyr Arg Val Thr Lys Asn
    1100                1105                1110

Ser Lys Val Gln Ile Gly Glu Tyr Thr Phe Glu Lys Gly Asp Tyr
    1115                1120                1125
```

```
Gly Asp Ala Val Val Tyr Arg Gly Thr Thr Thr Tyr Lys Leu Asn
    1130                1135                1140

Val Gly Asp Tyr Phe Val Leu Thr Ser His Thr Val Met Pro Leu
1145                1150                1155

Ser Ala Pro Thr Leu Val Pro Gln Glu His Tyr Val Arg Ile Thr
1160                1165                1170

Gly Leu Tyr Pro Thr Leu Asn Ile Ser Asp Glu Phe Ser Ser Asn
    1175                1180                1185

Val Ala Asn Tyr Gln Lys Val Gly Met Gln Lys Tyr Ser Thr Leu
1190                1195                1200

Gln Gly Pro Pro Gly Thr Gly Lys Ser His Phe Ala Ile Gly Leu
    1205                1210                1215

Ala Leu Tyr Tyr Pro Ser Ala Arg Ile Val Tyr Thr Ala Cys Ser
    1220                1225                1230

His Ala Ala Val Asp Ala Leu Cys Glu Lys Ala Leu Lys Tyr Leu
    1235                1240                1245

Pro Ile Asp Lys Cys Ser Arg Ile Ile Pro Ala Arg Ala Arg Val
    1250                1255                1260

Glu Cys Phe Asp Lys Phe Lys Val Asn Ser Thr Leu Glu Gln Tyr
    1265                1270                1275

Val Phe Cys Thr Val Asn Ala Leu Pro Glu Thr Thr Ala Asp Ile
    1280                1285                1290

Val Val Phe Asp Glu Ile Ser Met Ala Thr Asn Tyr Asp Leu Ser
    1295                1300                1305

Val Val Asn Ala Arg Leu Arg Ala Lys His Tyr Val Tyr Ile Gly
    1310                1315                1320

Asp Pro Ala Gln Leu Pro Ala Pro Arg Thr Leu Leu Thr Lys Gly
    1325                1330                1335

Thr Leu Glu Pro Glu Tyr Phe Asn Ser Val Cys Arg Leu Met Lys
    1340                1345                1350

Thr Ile Gly Pro Asp Met Phe Leu Gly Thr Cys Arg Arg Cys Pro
    1355                1360                1365

Ala Glu Ile Val Asp Thr Val Ser Ala Leu Val Tyr Asp Asn Lys
    1370                1375                1380

Leu Lys Ala His Lys Asp Lys Ser Ala Gln Cys Phe Lys Met Phe
    1385                1390                1395

Tyr Lys Gly Val Ile Thr His Asp Val Ser Ser Ala Ile Asn Arg
    1400                1405                1410

Pro Gln Ile Gly Val Val Arg Glu Phe Leu Thr Arg Asn Pro Ala
    1415                1420                1425

Trp Arg Lys Ala Val Phe Ile Ser Pro Tyr Asn Ser Gln Asn Ala
    1430                1435                1440

Val Ala Ser Lys Ile Leu Gly Leu Pro Thr Gln Thr Val Asp Ser
    1445                1450                1455

Ser Gln Gly Ser Glu Tyr Asp Tyr Val Ile Phe Thr Gln Thr Thr
    1460                1465                1470

Glu Thr Ala His Ser Cys Asn Val Asn Arg Phe Asn Val Ala Ile
    1475                1480                1485

Thr Arg Ala Lys Ile Gly Ile Leu Cys Ile Met Ser Asp Arg Asp
    1490                1495                1500

Leu Tyr Asp Lys Leu Gln Phe Thr Ser Leu Glu Ile Pro Arg Arg
    1505                1510                1515
```

```
Asn Val Ala Thr Leu Gln Ala Glu Asn Val Thr Gly Leu Phe Lys
1520                1525                1530

Asp Cys Ser Lys Ile Ile Thr Gly Leu His Pro Thr Gln Ala Pro
1535                1540                1545

Thr His Leu Ser Val Asp Ile Lys Phe Lys Thr Glu Gly Leu Cys
1550                1555                1560

Val Asp Ile Pro Gly Ile Pro Lys Asp Met Thr Tyr Arg Arg Leu
1565                1570                1575

Ile Ser Met Met Gly Phe Lys Met Asn Tyr Gln Val Asn Gly Tyr
1580                1585                1590

Pro Asn Met Phe Ile Thr Arg Glu Glu Ala Ile Arg His Val Arg
1595                1600                1605

Ala Trp Ile Gly Phe Asp Val Glu Gly Cys His Ala Thr Arg Asp
1610                1615                1620

Ala Val Gly Thr Asn Leu Pro Leu Gln Leu Gly Phe Ser Thr Gly
1625                1630                1635

Val Asn Leu Val Ala Val Pro Thr Gly Tyr Val Asp Thr Glu Asn
1640                1645                1650

Asn Thr Glu Phe Thr Arg Val Asn Ala Lys Pro Pro Pro Gly Asp
1655                1660                1665

Gln Phe Lys His Leu Ile Pro Leu Met Tyr Lys Gly Leu Pro Trp
1670                1675                1680

Asn Val Val Arg Ile Lys Ile Val Gln Met Leu Ser Asp Thr Leu
1685                1690                1695

Lys Gly Leu Ser Asp Arg Val Val Phe Val Leu Trp Ala His Gly
1700                1705                1710

Phe Glu Leu Thr Ser Met Lys Tyr Phe Val Lys Ile Gly Pro Glu
1715                1720                1725

Arg Thr Cys Cys Leu Cys Asp Lys Arg Ala Thr Cys Phe Ser Thr
1730                1735                1740

Ser Ser Asp Thr Tyr Ala Cys Trp Asn His Ser Val Gly Phe Asp
1745                1750                1755

Tyr Val Tyr Asn Pro Phe Met Ile Asp Val Gln Gln Trp Gly Phe
1760                1765                1770

Thr Gly Asn Leu Gln Ser Asn His Asp Gln His Cys Gln Val His
1775                1780                1785

Gly Asn Ala His Val Ala Ser Cys Asp Ala Ile Met Thr Arg Cys
1790                1795                1800

Leu Ala Val His Glu Cys Phe Val Lys Arg Val Asp Trp Ser Val
1805                1810                1815

Glu Tyr Pro Ile Ile Gly Asp Glu Leu Arg Val Asn Ser Ala Cys
1820                1825                1830

Arg Lys Val Gln His Met Val Val Lys Ser Ala Leu Leu Ala Asp
1835                1840                1845

Lys Phe Pro Val Leu His Asp Ile Gly Asn Pro Lys Ala Ile Lys
1850                1855                1860

Cys Val Pro Gln Ala Glu Val Glu Trp Lys Phe Tyr Asp Ala Gln
1865                1870                1875

Pro Cys Ser Asp Lys Ala Tyr Lys Ile Glu Glu Leu Phe Tyr Ser
1880                1885                1890

Tyr Ala Thr His His Asp Lys Phe Thr Asp Gly Val Cys Leu Phe
1895                1900                1905

Trp Asn Cys Asn Val Asp Arg Tyr Pro Ala Asn Ala Ile Val Cys
```

-continued

```
            1910                1915                1920
Arg Phe Asp Thr Arg Val Leu Ser Asn Leu Asn Leu Pro Gly Cys
    1925                1930                1935

Asp Gly Gly Ser Leu Tyr Val Asn Lys His Ala Phe His Thr Pro
    1940                1945                1950

Ala Phe Asp Lys Ser Ala Phe Thr Asn Leu Lys Gln Leu Pro Phe
    1955                1960                1965

Phe Tyr Tyr Ser Asp Ser Pro Cys Glu Ser His Gly Lys Gln Val
    1970                1975                1980

Val Ser Asp Ile Asp Tyr Val Pro Leu Lys Ser Ala Thr Cys Ile
    1985                1990                1995

Thr Arg Cys Asn Leu Gly Gly Ala Val Cys Arg His His Ala Asn
    2000                2005                2010

Glu Tyr Arg Gln Tyr Leu Asp Ala Tyr Asn Met Met Ile Ser Ala
    2015                2020                2025

Gly Phe Ser Leu Trp Ile Tyr Lys Gln Phe Asp Thr Tyr Asn Leu
    2030                2035                2040

Trp Asn Thr Phe Thr Arg Leu Gln Ser Leu Glu Asn Val Ala Tyr
    2045                2050                2055

Asn Val Val Asn Lys Gly His Phe Asp Gly His Ala Gly Glu Ala
    2060                2065                2070

Pro Val Ser Ile Ile Asn Asn Ala Val Tyr Thr Lys Val Asp Gly
    2075                2080                2085

Ile Asp Val Glu Ile Phe Glu Asn Lys Thr Thr Leu Pro Val Asn
    2090                2095                2100

Val Ala Phe Glu Leu Trp Ala Lys Arg Asn Ile Lys Pro Val Pro
    2105                2110                2115

Glu Ile Lys Ile Leu Asn Asn Leu Gly Val Asp Ile Ala Ala Asn
    2120                2125                2130

Thr Val Ile Trp Asp Tyr Lys Arg Glu Ala Pro Ala His Val Ser
    2135                2140                2145

Thr Ile Gly Val Cys Thr Met Thr Asp Ile Ala Lys Lys Pro Thr
    2150                2155                2160

Glu Ser Ala Cys Ser Ser Leu Thr Val Leu Phe Asp Gly Arg Val
    2165                2170                2175

Glu Gly Gln Val Asp Leu Phe Arg Asn Ala Arg Asn Gly Val Leu
    2180                2185                2190

Ile Thr Glu Gly Ser Val Lys Gly Leu Thr Pro Ser Lys Gly Pro
    2195                2200                2205

Ala Gln Ala Ser Val Asn Gly Val Thr Leu Ile Gly Glu Ser Val
    2210                2215                2220

Lys Thr Gln Phe Asn Tyr Phe Lys Lys Val Asp Gly Ile Ile Gln
    2225                2230                2235

Gln Leu Pro Glu Thr Tyr Phe Thr Gln Ser Arg Asp Leu Glu Asp
    2240                2245                2250

Phe Lys Pro Arg Ser Gln Met Glu Thr Asp Phe Leu Glu Leu Ala
    2255                2260                2265

Met Asp Glu Phe Ile Gln Arg Tyr Lys Leu Glu Gly Tyr Ala Phe
    2270                2275                2280

Glu His Ile Val Tyr Gly Asp Phe Ser His Gly Gln Leu Gly Gly
    2285                2290                2295

Leu His Leu Met Ile Gly Leu Ala Lys Arg Ser Gln Asp Ser Pro
    2300                2305                2310
```

-continued

```
Leu Lys Leu Glu Asp Phe Ile Pro Met Asp Ser Thr Val Lys Asn
    2315                2320                2325

Tyr Phe Ile Thr Asp Ala Gln Thr Gly Ser Ser Lys Cys Val Cys
    2330                2335                2340

Ser Val Ile Asp Leu Leu Leu Asp Asp Phe Val Glu Ile Ile Lys
    2345                2350                2355

Ser Gln Asp Leu Ser Val Ile Ser Lys Val Val Lys Val Thr Ile
    2360                2365                2370

Asp Tyr Ala Glu Ile Ser Phe Met Leu Trp Cys Lys Asp Gly His
    2375                2380                2385

Val Glu Thr Phe Tyr Pro Lys Leu Gln Ala Ser Gln Ala Trp Gln
    2390                2395                2400

Pro Gly Val Ala Met Pro Asn Leu Tyr Lys Met Gln Arg Met Leu
    2405                2410                2415

Leu Glu Lys Cys Asp Leu Gln Asn Tyr Gly Glu Asn Ala Val Ile
    2420                2425                2430

Pro Lys Gly Ile Met Met Asn Val Ala Lys Tyr Thr Gln Leu Cys
    2435                2440                2445

Gln Tyr Leu Asn Thr Leu Thr Leu Ala Val Pro Tyr Asn Met Arg
    2450                2455                2460

Val Ile His Phe Gly Ala Gly Ser Asp Lys Gly Val Ala Pro Gly
    2465                2470                2475

Thr Ala Val Leu Arg Gln Trp Leu Pro Thr Gly Thr Leu Leu Val
    2480                2485                2490

Asp Ser Asp Leu Asn Asp Phe Val Ser Asp Ala Asp Ser Thr Leu
    2495                2500                2505

Ile Gly Asp Cys Ala Thr Val His Thr Ala Asn Lys Trp Asp Leu
    2510                2515                2520

Ile Ile Ser Asp Met Tyr Asp Pro Arg Thr Lys His Val Thr Lys
    2525                2530                2535

Glu Asn Asp Ser Lys Glu Gly Phe Phe Thr Tyr Leu Cys Gly Phe
    2540                2545                2550

Ile Lys Gln Lys Leu Ala Leu Gly Gly Ser Ile Ala Val Lys Ile
    2555                2560                2565

Thr Glu His Ser Trp Asn Ala Asp Leu Tyr Lys Leu Met Gly His
    2570                2575                2580

Phe Ser Trp Trp Thr Ala Phe Val Thr Asn Val Asn Ala Ser Ser
    2585                2590                2595

Ser Glu Ala Phe Leu Ile Gly Ala Asn Tyr Leu Gly Lys Pro Lys
    2600                2605                2610

Glu Gln Ile Asp Gly Tyr Thr Met His Ala Asn Tyr Ile Phe Trp
    2615                2620                2625

Arg Asn Thr Asn Pro Ile Gln Leu Ser Ser Tyr Ser Leu Phe Asp
    2630                2635                2640

Met Ser Lys Phe Pro Leu Lys Leu Arg Gly Thr Ala Val Met Ser
    2645                2650                2655

Leu Lys Glu Asn Gln Ile Asn Asp Met Ile Tyr Ser Leu Leu Glu
    2660                2665                2670

Lys Gly Arg Leu Ile Ile Arg Glu Asn Asn Arg Val Val Val Ser
    2675                2680                2685

Ser Asp Ile Leu Val Asn Asn
    2690                2695
```

```
<210> SEQ ID NO 76
<211> LENGTH: 20
<212> TYPE: DNA
<213> ORGANISM: Artificial sequence
<220> FEATURE:
<223> OTHER INFORMATION: S/L3/+/4932 primer

<400> SEQUENCE: 76
ccacacacag cttgtggata                                                  20

<210> SEQ ID NO 77
<211> LENGTH: 20
<212> TYPE: DNA
<213> ORGANISM: Artificial sequence
<220> FEATURE:
<223> OTHER INFORMATION: S/L4/+/6401 primer

<400> SEQUENCE: 77
ccgaagttgt aggcaatgtc                                                  20

<210> SEQ ID NO 78
<211> LENGTH: 20
<212> TYPE: DNA
<213> ORGANISM: Artificial sequence
<220> FEATURE:
<223> OTHER INFORMATION: S/L4/+/6964 primer

<400> SEQUENCE: 78
tttggtgctc cttcttattg                                                  20

<210> SEQ ID NO 79
<211> LENGTH: 20
<212> TYPE: DNA
<213> ORGANISM: Artificial sequence
<220> FEATURE:
<223> OTHER INFORMATION: S/L4/-/6817 primer

<400> SEQUENCE: 79
ccggcatcca aacataattt                                                  20

<210> SEQ ID NO 80
<211> LENGTH: 20
<212> TYPE: DNA
<213> ORGANISM: Artificial sequence
<220> FEATURE:
<223> OTHER INFORMATION: S/L5/-/7633 primer

<400> SEQUENCE: 80
tggtcagtag ggttgattgg                                                  20

<210> SEQ ID NO 81
<211> LENGTH: 20
<212> TYPE: DNA
<213> ORGANISM: Artificial sequence
<220> FEATURE:
<223> OTHER INFORMATION: S/L5/-/8127 primer

<400> SEQUENCE: 81
catcctttgt gtcaacatcg                                                  20

<210> SEQ ID NO 82
<211> LENGTH: 20
<212> TYPE: DNA
<213> ORGANISM: Artificial sequence
<220> FEATURE:
<223> OTHER INFORMATION: S/L5/-/8633 primer
```

```
<400> SEQUENCE: 82
gtcacgagtg acaccatcct                                              20

<210> SEQ ID NO 83
<211> LENGTH: 20
<212> TYPE: DNA
<213> ORGANISM: Artificial sequence
<220> FEATURE:
<223> OTHER INFORMATION: S/L5/+/7839 primer

<400> SEQUENCE: 83
atgcgacgag tctgcttcta                                              20

<210> SEQ ID NO 84
<211> LENGTH: 20
<212> TYPE: DNA
<213> ORGANISM: Artificial sequence
<220> FEATURE:
<223> OTHER INFORMATION: S/L5/+/8785 primer

<400> SEQUENCE: 84
ttcatagtgc ctggcttacc                                              20

<210> SEQ ID NO 85
<211> LENGTH: 20
<212> TYPE: DNA
<213> ORGANISM: Artificial sequence
<220> FEATURE:
<223> OTHER INFORMATION: S/L5/+/8255 primer

<400> SEQUENCE: 85
atcttggcgc atgtattgac                                              20

<210> SEQ ID NO 86
<211> LENGTH: 20
<212> TYPE: DNA
<213> ORGANISM: Artificial sequence
<220> FEATURE:
<223> OTHER INFORMATION: S/L6/-/9422 primer

<400> SEQUENCE: 86
tgcattagca gcaacaacat                                              20

<210> SEQ ID NO 87
<211> LENGTH: 20
<212> TYPE: DNA
<213> ORGANISM: Artificial sequence
<220> FEATURE:
<223> OTHER INFORMATION: S/L6/-/9966 primer

<400> SEQUENCE: 87
tctgcagaac agcagaagtg                                              20

<210> SEQ ID NO 88
<211> LENGTH: 20
<212> TYPE: DNA
<213> ORGANISM: Artificial sequence
<220> FEATURE:
<223> OTHER INFORMATION: S/L6/-/10542 primer

<400> SEQUENCE: 88
cctgtgcagt ttgtctgtca                                              20

<210> SEQ ID NO 89
```

```
<211> LENGTH: 20
<212> TYPE: DNA
<213> ORGANISM: Artificial sequence
<220> FEATURE:
<223> OTHER INFORMATION: S/L6/+/10677 primer

<400> SEQUENCE: 89
ccttgtggca atgaagtaca                                              20

<210> SEQ ID NO 90
<211> LENGTH: 20
<212> TYPE: DNA
<213> ORGANISM: Artificial sequence
<220> FEATURE:
<223> OTHER INFORMATION: S/L6/+/10106 primer

<400> SEQUENCE: 90
atgtcatttg cacagcagaa                                              20

<210> SEQ ID NO 91
<211> LENGTH: 20
<212> TYPE: DNA
<213> ORGANISM: Artificial sequence
<220> FEATURE:
<223> OTHER INFORMATION: S/L6/+/9571 primer

<400> SEQUENCE: 91
cttcaatggt ttgccatgtt                                              20

<210> SEQ ID NO 92
<211> LENGTH: 20
<212> TYPE: DNA
<213> ORGANISM: Artificial sequence
<220> FEATURE:
<223> OTHER INFORMATION: S/L7/-/11271 primer

<400> SEQUENCE: 92
tgcgagctgt catgagaata                                              20

<210> SEQ ID NO 93
<211> LENGTH: 20
<212> TYPE: DNA
<213> ORGANISM: Artificial sequence
<220> FEATURE:
<223> OTHER INFORMATION: S/L7/-/11801 primer

<400> SEQUENCE: 93
aaccgagagc agtaccacag                                              20

<210> SEQ ID NO 94
<211> LENGTH: 20
<212> TYPE: DNA
<213> ORGANISM: Artificial sequence
<220> FEATURE:
<223> OTHER INFORMATION: S/L7/-/12383 primer

<400> SEQUENCE: 94
tttggctgct gtagtcaatg                                              20

<210> SEQ ID NO 95
<211> LENGTH: 20
<212> TYPE: DNA
<213> ORGANISM: Artificial sequence
<220> FEATURE:
<223> OTHER INFORMATION: S/L7/+/12640 primer

<400> SEQUENCE: 95
```

-continued ctacgacaga tgtcctgtgc                    20

<210> SEQ ID NO 96
<211> LENGTH: 20
<212> TYPE: DNA
<213> ORGANISM: Artificial sequence
<220> FEATURE:
<223> OTHER INFORMATION: S/L7/+/12088 primer

<400> SEQUENCE: 96
gagcaggctg tagctaatgg                    20

<210> SEQ ID NO 97
<211> LENGTH: 20
<212> TYPE: DNA
<213> ORGANISM: Artificial sequence
<220> FEATURE:
<223> OTHER INFORMATION: S/L7/+/11551 primer

<400> SEQUENCE: 97
ttaggctatt gttgctgctg                    20

<210> SEQ ID NO 98
<211> LENGTH: 20
<212> TYPE: DNA
<213> ORGANISM: Artificial sequence
<220> FEATURE:
<223> OTHER INFORMATION: S/L8/-/13160 primer

<400> SEQUENCE: 98
cagacaacat gaagcaccac                    20

<210> SEQ ID NO 99
<211> LENGTH: 20
<212> TYPE: DNA
<213> ORGANISM: Artificial sequence
<220> FEATURE:
<223> OTHER INFORMATION: S/L8/-/13704 primer

<400> SEQUENCE: 99
cgctgacgtg atatatgtgg                    20

<210> SEQ ID NO 100
<211> LENGTH: 20
<212> TYPE: DNA
<213> ORGANISM: Artificial sequence
<220> FEATURE:
<223> OTHER INFORMATION: S/L8/-/14284 primer

<400> SEQUENCE: 100
tgcacaatga aggatacacc                    20

<210> SEQ ID NO 101
<211> LENGTH: 20
<212> TYPE: DNA
<213> ORGANISM: Artificial sequence
<220> FEATURE:
<223> OTHER INFORMATION: S/L8/+/14453 primer

<400> SEQUENCE: 101
acatagctcg cgtctcagtt                    20

<210> SEQ ID NO 102
<211> LENGTH: 20
<212> TYPE: DNA

<213> ORGANISM: Artificial sequence
<220> FEATURE:
<223> OTHER INFORMATION: S/L8/+/13968 primer

<400> SEQUENCE: 102
ggcattgtag gcgtactgac                                         20

<210> SEQ ID NO 103
<211> LENGTH: 19
<212> TYPE: DNA
<213> ORGANISM: Artificial sequence
<220> FEATURE:
<223> OTHER INFORMATION: S/L8/+/13401 primer

<400> SEQUENCE: 103
gtttgcggtg taagtgcag                                          19

<210> SEQ ID NO 104
<211> LENGTH: 20
<212> TYPE: DNA
<213> ORGANISM: Artificial sequence
<220> FEATURE:
<223> OTHER INFORMATION: S/L9/-/15098 primer

<400> SEQUENCE: 104
tagtggcggc tattgacttc                                         20

<210> SEQ ID NO 105
<211> LENGTH: 20
<212> TYPE: DNA
<213> ORGANISM: Artificial sequence
<220> FEATURE:
<223> OTHER INFORMATION: S/L9/-/15677 primer

<400> SEQUENCE: 105
ctaaaccttg agccgcatag                                         20

<210> SEQ ID NO 106
<211> LENGTH: 20
<212> TYPE: DNA
<213> ORGANISM: Artificial sequence
<220> FEATURE:
<223> OTHER INFORMATION: S/L9/-/16247 primer

<400> SEQUENCE: 106
catggtcata gcagcacttg                                         20

<210> SEQ ID NO 107
<211> LENGTH: 21
<212> TYPE: DNA
<213> ORGANISM: Artificial sequence
<220> FEATURE:
<223> OTHER INFORMATION: S/L9/+/16323 primer

<400> SEQUENCE: 107
ccaggttgtg atgtcactga t                                       21

<210> SEQ ID NO 108
<211> LENGTH: 20
<212> TYPE: DNA
<213> ORGANISM: Artificial sequence
<220> FEATURE:
<223> OTHER INFORMATION: S/L9/+/15858 primer

<400> SEQUENCE: 108
ccttacccag atccatcaag                                         20

```
<210> SEQ ID NO 109
<211> LENGTH: 20
<212> TYPE: DNA
<213> ORGANISM: Artificial sequence
<220> FEATURE:
<223> OTHER INFORMATION: S/L9/+/15288 primer

<400> SEQUENCE: 109
cgcaaacata acacttgctg                                              20

<210> SEQ ID NO 110
<211> LENGTH: 20
<212> TYPE: DNA
<213> ORGANISM: Artificial sequence
<220> FEATURE:
<223> OTHER INFORMATION: S/L10/-/16914 primer

<400> SEQUENCE: 110
agtgttgggt acaagccagt                                              20

<210> SEQ ID NO 111
<211> LENGTH: 20
<212> TYPE: DNA
<213> ORGANISM: Artificial sequence
<220> FEATURE:
<223> OTHER INFORMATION: S/L10/-/17466 primer

<400> SEQUENCE: 111
gttccaagga acatgtctgg                                              20

<210> SEQ ID NO 112
<211> LENGTH: 20
<212> TYPE: DNA
<213> ORGANISM: Artificial sequence
<220> FEATURE:
<223> OTHER INFORMATION: S/L10/-/18022 primer

<400> SEQUENCE: 112
aggtgcctgt gtaggatgaa                                              20

<210> SEQ ID NO 113
<211> LENGTH: 20
<212> TYPE: DNA
<213> ORGANISM: Artificial sequence
<220> FEATURE:
<223> OTHER INFORMATION: S/L10/+/18245 primer

<400> SEQUENCE: 113
gggctgtcat gcaactagag                                              20

<210> SEQ ID NO 114
<211> LENGTH: 20
<212> TYPE: DNA
<213> ORGANISM: Artificial sequence
<220> FEATURE:
<223> OTHER INFORMATION: S/L10/+/17663 primer

<400> SEQUENCE: 114
tcttacacgc aatcctgctt                                              20

<210> SEQ ID NO 115
<211> LENGTH: 20
<212> TYPE: DNA
<213> ORGANISM: Artificial sequence
<220> FEATURE:
```

<223> OTHER INFORMATION: S/L10/+/17061 primer

<400> SEQUENCE: 115
tacccatctg ctcgcatagt                    20

<210> SEQ ID NO 116
<211> LENGTH: 20
<212> TYPE: DNA
<213> ORGANISM: Artificial sequence
<220> FEATURE:
<223> OTHER INFORMATION: S/L11/-/18877 primer

<400> SEQUENCE: 116
gcaagcagaa ttaaccctca                    20

<210> SEQ ID NO 117
<211> LENGTH: 20
<212> TYPE: DNA
<213> ORGANISM: Artificial sequence
<220> FEATURE:
<223> OTHER INFORMATION: S/L11/-/19396 primer

<400> SEQUENCE: 117
agcaccacct aaattgcatc                    20

<210> SEQ ID NO 118
<211> LENGTH: 20
<212> TYPE: DNA
<213> ORGANISM: Artificial sequence
<220> FEATURE:
<223> OTHER INFORMATION: S/L11/-/20002 primer

<400> SEQUENCE: 118
tggtcccttt gaaggtgtta                    20

<210> SEQ ID NO 119
<211> LENGTH: 20
<212> TYPE: DNA
<213> ORGANISM: Artificial sequence
<220> FEATURE:
<223> OTHER INFORMATION: S/L11/+/20245 primer

<400> SEQUENCE: 119
tcgaacacat cgtttatgga                    20

<210> SEQ ID NO 120
<211> LENGTH: 20
<212> TYPE: DNA
<213> ORGANISM: Artificial sequence
<220> FEATURE:
<223> OTHER INFORMATION: S/L11/+/19611 primer

<400> SEQUENCE: 120
gaagcacctg tttccatcat                    20

<210> SEQ ID NO 121
<211> LENGTH: 20
<212> TYPE: DNA
<213> ORGANISM: Artificial sequence
<220> FEATURE:
<223> OTHER INFORMATION: S/L11/+/19021 primer

<400> SEQUENCE: 121
acgatgctca gccatgtagt                    20

```
<210> SEQ ID NO 122
<211> LENGTH: 20
<212> TYPE: DNA
<213> ORGANISM: Artificial sequence
<220> FEATURE:
<223> OTHER INFORMATION: SARS/L1/F3/+/800 primer

<400> SEQUENCE: 122
gaggtgcagt cactcgctat                                               20

<210> SEQ ID NO 123
<211> LENGTH: 20
<212> TYPE: DNA
<213> ORGANISM: Artificial sequence
<220> FEATURE:
<223> OTHER INFORMATION: SARS/L1/F4/+/1391 primer

<400> SEQUENCE: 123
cagagattgg acctgagcat                                               20

<210> SEQ ID NO 124
<211> LENGTH: 20
<212> TYPE: DNA
<213> ORGANISM: Artificial sequence
<220> FEATURE:
<223> OTHER INFORMATION: SARS/L1/F5/+/1925 primer

<400> SEQUENCE: 124
cagcaaacca ctcaattcct                                               20

<210> SEQ ID NO 125
<211> LENGTH: 20
<212> TYPE: DNA
<213> ORGANISM: Artificial sequence
<220> FEATURE:
<223> OTHER INFORMATION: SARS/L1/R3/-/1674 primer

<400> SEQUENCE: 125
aaatgatggc aacctcttca                                               20

<210> SEQ ID NO 126
<211> LENGTH: 20
<212> TYPE: DNA
<213> ORGANISM: Artificial sequence
<220> FEATURE:
<223> OTHER INFORMATION: SARS/L1/R4/-/1107 primer

<400> SEQUENCE: 126
cacgtggttg aatgactttg                                               20

<210> SEQ ID NO 127
<211> LENGTH: 20
<212> TYPE: DNA
<213> ORGANISM: Artificial sequence
<220> FEATURE:
<223> OTHER INFORMATION: SARS/L1/R5/-/520 primer

<400> SEQUENCE: 127
atttctgcaa ccagctcaac                                               20

<210> SEQ ID NO 128
<211> LENGTH: 20
<212> TYPE: DNA
<213> ORGANISM: Artificial sequence
<220> FEATURE:
<223> OTHER INFORMATION: SARS/L2/F3/+/2664 primer
```

-continued

<400> SEQUENCE: 128
cgcattgtct cctggtttac                                        20

<210> SEQ ID NO 129
<211> LENGTH: 20
<212> TYPE: DNA
<213> ORGANISM: Artificial sequence
<220> FEATURE:
<223> OTHER INFORMATION: SARS/L2/F4/+/3232 primer

<400> SEQUENCE: 129
gagattgagc cagaaccaga                                        20

<210> SEQ ID NO 130
<211> LENGTH: 20
<212> TYPE: DNA
<213> ORGANISM: Artificial sequence
<220> FEATURE:
<223> OTHER INFORMATION: SARS/L2/F5/+/3746 primer

<400> SEQUENCE: 130
atgagcaggt tgtcatggat                                        20

<210> SEQ ID NO 131
<211> LENGTH: 20
<212> TYPE: DNA
<213> ORGANISM: Artificial sequence
<220> FEATURE:
<223> OTHER INFORMATION: SARS/L2/R3/-/3579 primer

<400> SEQUENCE: 131
ctgccttaag aagctggatg                                        20

<210> SEQ ID NO 132
<211> LENGTH: 20
<212> TYPE: DNA
<213> ORGANISM: Artificial sequence
<220> FEATURE:
<223> OTHER INFORMATION: SARS/L2/R4/-/2991 primer

<400> SEQUENCE: 132
tttcttcacc agcatcatca                                        20

<210> SEQ ID NO 133
<211> LENGTH: 20
<212> TYPE: DNA
<213> ORGANISM: Artificial sequence
<220> FEATURE:
<223> OTHER INFORMATION: SARS/L2/R5/-/2529 primer

<400> SEQUENCE: 133
caccgttctt gagaacaacc                                        20

<210> SEQ ID NO 134
<211> LENGTH: 20
<212> TYPE: DNA
<213> ORGANISM: Artificial sequence
<220> FEATURE:
<223> OTHER INFORMATION: SARS/L3/F3/+/4708 primer

<400> SEQUENCE: 134
tctttggctg gctcttacag                                        20

<210> SEQ ID NO 135
<211> LENGTH: 20

-continued

<212> TYPE: DNA
<213> ORGANISM: Artificial sequence
<220> FEATURE:
<223> OTHER INFORMATION: SRAS/L3/F4/+/5305 primer

<400> SEQUENCE: 135
gctggtgatg ctgctaactt 20

<210> SEQ ID NO 136
<211> LENGTH: 20
<212> TYPE: DNA
<213> ORGANISM: Artificial sequence
<220> FEATURE:
<223> OTHER INFORMATION: SARS/L3/F5/+/5822 primer

<400> SEQUENCE: 136
ccatcaagcc tgtgtcgtat 20

<210> SEQ ID NO 137
<211> LENGTH: 20
<212> TYPE: DNA
<213> ORGANISM: Artificial sequence
<220> FEATURE:
<223> OTHER INFORMATION: SARS/L3/R3/-/5610 primer

<400> SEQUENCE: 137
caggtggtgc agacatcata 20

<210> SEQ ID NO 138
<211> LENGTH: 20
<212> TYPE: DNA
<213> ORGANISM: Artificial sequence
<220> FEATURE:
<223> OTHER INFORMATION: SARS/L3/R4/-/4988 primer

<400> SEQUENCE: 138
aacatcagca ccatccaagt 20

<210> SEQ ID NO 139
<211> LENGTH: 20
<212> TYPE: DNA
<213> ORGANISM: Artificial sequence
<220> FEATURE:
<223> OTHER INFORMATION: SARS/L3/R5/-/4437 primer

<400> SEQUENCE: 139
atcggacacc atagtcaacg 20

<210> SEQ ID NO 140
<211> LENGTH: 7788
<212> TYPE: DNA
<213> ORGANISM: Artificial sequence
<220> FEATURE:
<223> OTHER INFORMATION: synthetic S gene

<400> SEQUENCE: 140
tcaatattgg ccattagcca tattattcat tggttatata gcataaatca atattggcta 60
ttggccattg catacgttgt atctatatca taatatgtac atttatattg gctcatgtcc 120
aatatgaccg ccatgttggc attgattatt gactagttat taatagtaat caattacggg 180
gtcattagtt catagcccat atatggagtt ccgcgttaca taacttacgg taaatggccc 240
gcctggctga ccgcccaacg acccccgccc attgacgtca ataatgacgt atgttcccat 300
agtaacgcca atagggactt tccattgacg tcaatgggtg gagtatttac ggtaaactgc 360

```
ccacttggca gtacatcaag tgtatcatat gccaagtccg cccctattg acgtcaatga      420 cggtaaatgg cccgcctggc attatgccca gtacatgacc ttacgggact ttcctacttg      480
gcagtacatc tacgtattag tcatcgctat taccatggtg atgcggtttt ggcagtacac      540
caatgggcgt ggatagcggt ttgactcacg gggatttcca agtctccacc ccattgacgt      600
caatgggagt ttgttttggc accaaaatca acgggacttt ccaaaatgtc gtaataaccc      660
cgccccgttg acgcaaatgg gcggtaggcg tgtacggtgg aggtctata taagcagagc      720 tcgtttagtg aaccgtcaga tcactagaag ctttattgcg gtagtttatc acagttaaat      780
tgctaacgca gtcagtgctt ctgacacaac agtctcgaac ttaagctgca gaagttggtc      840
gtgaggcact gggcaggtaa gtatcaaggt tacaagacag gtttaaggag accaatagaa      900
actgggcttg tcgagacaga gaagactctt gcgtttctga taggcaccta ttggtcttac      960
tgacatccac tttgcctttc tctccacagg tgtccactcc cagttcaatt acagctctta     1020
aggctagagt acttaatacg actcactata ggctagcgga tccaccatgt tcatcttcct     1080
gctgttcctg accctgacca gcggcagcga cctggaccgg tgcaccacct tcgacgacgt     1140
gcaggccccc aactcacccc agcacaccag cagcatgcgg ggcgtgtact accccgacga     1200
gatctttcgg agcgacaccc tgtacctgac ccaggacctg ttcctgccct tctacagcaa     1260
cgtgaccggc ttccacacca tcaaccacac cttcggcaac cccgtgatcc ccttcaagga     1320
cggcatctac ttcgccgcca ccgagaagag caacgtggtg cggggctggg tgttcggcag     1380
caccatgaac aacaagagcc agagcgtgat catcatcaac aacagcacca acgtggtgat     1440
ccgggcctgc aacttcgagc tgtgcgacaa ccccttcttc gccgtgtcca acccatgggg     1500
cacccagacc cacaccatga tcttcgacaa cgccttcaac tgcaccttcg agtacatcag     1560
cgacgccttc agcctggacg tgagcgagaa gagcggcaac ttcaagcacc tgcgggagtt     1620
cgtgttcaag aacaaggacg gcttcctgta cgtgtacaag ggctaccagc catcgacgt      1680 ggtgagagac ctgcccagcg gcttcaacac cctgaagccc atcttcaagc tgcccctggg     1740
catcaacatc accaacttcc gggccatcct gaccgccttt agccctgccc aggacatctg     1800
gggcaccagc gccgccgcct acttcgtggg ctacctgaag cctaccacct tcatgctgaa     1860
gtacgacgag aacggcacca tcaccgacgc cgtggactgc agccagaacc ccctggccga     1920
gctgaagtgc agcgtgaaga gcttcgagat cgacaagggc atctaccaga ccagcaactt     1980
cagagtggtg cctagcggcg atgtggtgcg gttcccaat atcaccaacc tgtgcccctt     2040
cggcgaagtg ttcaacgcca ccaagttccc cagcgtgtac gcctgggagc ggaagaagat     2100
cagcaactgc gtggccgact acagcgtgct gtacaactcc accttcttca gcaccttcaa     2160
gtgctacggc gtgagcgcca ccaagctgaa cgacctgtgt ttcagcaacg tgtacgccga     2220
cagcttcgtg gtgaagggcg acgacgtgag acagatcgcc cctggccaga ccggcgtgat     2280
cgccgactac aactacaagc tgcccgacga cttcatgggc tgcgtgctgg cctgaacac      2340 ccggaacatc gacgccacaa gcaccggcaa ctacaattac aagtaccgct acctgcggca     2400
cggcaagctc ggccccttcg agcgggacat ctccaacgtg cccttcagcc ccgacggcaa     2460
gccctgcacc cccctgcccc tgaactgcta ctggccctg aacgactacg cttctacac      2520 caccaccggc atcggctatc agcctacag agtggtggtg ctgagcttcg agctgctgaa     2580
cgcccctgcc accgtgtgcg gccccaagct gagcaccgac ctgatcaaga accagtgcgt     2640
gaacttcaac ttcaacggcc tgaccggcac cggcgtgctg acccccagca gcaagcgctt     2700
ccagcccttc cagcagttcg gccgggatgt gagcgacttc accgacagcg tgcgggaccc     2760
```

```
caagaccagc gagatcctgg acatcagccc ctgcagcttc ggcggcgtgt ccgtgatcac    2820
ccccggcacc aacgccagca gcgaagtggc cgtgctgtac caggacgtga actgcaccga    2880
cgtgagcacc gccatccacg ccgaccagct gaccccgcc tggcggatct acagcaccgg     2940
gaacaacgtg ttccagaccc aggccggctg cctgatcggc gccgagcacg tggacaccag    3000
ctacgagtgc gacatcccca ttggcgccgg aatctgcgcc agctaccaca ccgtgagcct    3060
gctgcggagc accagccaga agtccatcgt ggcctacacc atgagcctgg gcgccgacag    3120
cagcatcgcc tacagcaaca acaccatcgc catccccacc aacttcagca tctccatcac    3180
caccgaagtg atgcccgtga gcatggccaa gacaagcgtg gattgcaaca tgtacatctg    3240
cggcgacagc accgagtgcg ccaacctgct gctgcagtac ggcagcttct gcacccagct    3300
gaaccgggcc ctgagcggca tcgccgccga gcaggaccgg aacaccagag aagtgttcgc    3360
ccaagtgaag cagatgtata agaccccccac cctgaagtac ttcggggggct tcaacttctc    3420 tcagatcctg cccgacccctc tgaagcccac caagcgctcc ttcatcgagg acctgctgtt    3480
caacaaagtg accctggccg acgccggctt tatgaagcag tacggcgagt gcctgggcga    3540
catcaacgcc cgggacctga tctgcgccca gaagtttaac gggctgaccg tgctgccccc    3600
cctgctgacc gacgacatga tcgccgccta tacagccgcc ctggtgagcg gcaccgccac    3660
cgccggctgg accttcggag ccggagccgc cctgcagatc cccttcgcca tgcagatggc    3720
ctaccggttc aacggcatcg gcgtgaccca gaacgtgctg tacgagaacc agaagcagat    3780
cgccaaccag ttcaacaagg ccatcagcca gatccaggag agcctgacca accagcac    3840 cgccctgggc aagctgcagg acgtggtgaa ccagaacgcc caggccctga cacctggt     3900 gaagcagctg agcagcaact tcggcgcat cagctctgtg ctgaacgaca tcctgagcag    3960
gctggacaaa gtggaggccg aagtgcagat cgaccggctg atcaccggac gcctgcagtc    4020
cctgcagacc tacgtgaccc agcagctgat cagagccgcc gagatccggg ccagcgccaa    4080
tctggccgcc accaagatga gcgagtgcgt gctgggccag agcaagagag tggacttctg    4140
cggcaagggc tatcacctga tgagcttccc ccaggccgcc ccccacgcg tggtgttcct     4200 gcacgtgacc tacgtgccta gccaggagcg gaacttcacc accgccccag ccatctgcca    4260
cgagggcaag gcctacttcc ccggggaggg cgtgttcgtg tttaacggca ccagctggtt    4320
catcacccag cgcaacttct tcagcccccca gatcatcacc acagacaaca ccttcgtgtc    4380
cggcaactgt gatgtggtga tcggcatcat caataacacc gtgtacgacc ccctgcagcc    4440
cgagctggac agcttcaagg aggagctgga caaatacttc aagaaccaca cctcccccga    4500
cgtggacctg ggcgatatca gcggcatcaa cgcctccgtg gtgaacatcc agaaggagat    4560
cgacagactg aacgaagtgg ccaagaacct gaacgagagc ctgatcgacc tgcaggagct    4620
gggcaagtac gagcagtaca tcaagtggcc ctggtacgtg tggctgggct catcgccgg    4680 cctgatcgcc atcgtgatgg tgaccatcct gctgtgctgc atgaccagct gctgtagctg    4740
cctgaaaggc gcctgcagct gtggcagctg ctgcaagttc gacgaggacg acagcgagcc    4800
cgtgctgaag ggcgtgaagc tgcactacac ctgataactc gagaattcac gcgtggtacc    4860
tctagagtcg acccgggcgg ccgcttcgag cagacatgat aagatacatt gatgagtttg    4920
gacaaaccac aactagaatg cagtgaaaaa aatgctttat ttgtgaaatt tgtgatgcta    4980
ttgctttatt tgtaaccatt ataagctgca ataaacaagt taacaacaac aattgcattc    5040
attttatgtt tcaggttcag ggggagatgt gggaggtttt ttaaagcaag taaaacctct    5100
```

```
acaaatgtgg taaaatcgat aaggatccgg gctggcgtaa tagcgaagag gcccgcaccg   5160
atcgcccttc ccaacagttg cgcagcctga atggcgaatg gacgcgccct gtagcggcgc   5220
attaagcgcg gcgggtgtgg tggttacgcg cagcgtgacc gctacacttg ccagcgccct   5280
agcgcccgct cctttcgctt tcttcccttc ctttctcgcc acgttcgccg gctttccccg   5340
tcaagctcta atcgggggc tccctttagg gttccgattt agagctttac ggcacctcga   5400
ccgcaaaaaa cttgatttgg gtgatggttc acgtagtggg ccatcgccct gatagacggt   5460
ttttcgccct ttgacgttgg agtccacgtt ctttaatagt ggactcttgt tccaaactgg   5520
aacaacactc aaccctatct cggtctattc ttttgattta aagggatttt gccgatttc    5580 ggcctattgg ttaaaaaatg agctgattta acaaatattt aacgcgaatt ttaacaaaat   5640
attaacgttt acaatttcgc ctgatgcggt attttctcct tacgcatctg tgcggtattt   5700
cacaccgcat atggtgcact ctcagtacaa tctgctctga tgccgcatag ttaagccagc   5760
cccgacaccc gccaacaccc gctgacgcgc cctgacgggc ttgtctgctc ccggcatccg   5820
cttacagaca agctgtgacc gtctccggga gctgcatgtg tcagaggttt tcaccgtcat   5880
caccgaaacg cgcgagacga aagggcctcg tgatacgcct atttttatag gttaatgtca   5940
tgataataat ggtttcttag acgtcaggtg gcacttttcg gggaaatgtg cgcggaaccc   6000
ctatttgttt attttctaa atacattcaa atatgtatcc gctcatgaga caataaccct    6060
gataaatgct tcaataatat tgaaaaagga agagtatgag tattcaacat ttccgtgtcg   6120
cccttattcc cttttttgcg gcattttgcc ttcctgtttt tgctcaccca gaaacgctgg   6180
tgaaagtaaa agatgctgaa gatcagttgg gtgcacgagt gggttacatc gaactggatc   6240
tcaacagcgg taagatcctt gagagttttc gccccgaaga acgttttcca atgatgagca   6300
cttttaaagt tctgctatgt ggcgcggtat tatcccgtat tgacgccggg caagagcaac   6360
tcggtcgccg catacactat tctcagaatg acttggttga gtactcacca gtcacagaaa   6420
agcatcttac ggatggcatg acagtaagag aattatgcag tgctgccata accatgagtg   6480
ataacactgc ggccaactta cttctgacaa cgatcggagg accgaaggag ctaaccgctt   6540
ttttgcacaa catgggggat catgtaactc gccttgatcg ttgggaaccg gagctgaatg   6600
aagccatacc aaacgacgag cgtgacacca cgatgcctgt agcaatggca acaacgttgc   6660
gcaaactatt aactggcgaa ctacttactc tagcttcccg gcaacaatta atagactgga   6720
tggaggcgga taaagttgca ggaccacttc tgcgctcggc ccttccggct ggctggttta   6780
ttgctgataa atctggagcc ggtgagcgtg ggtctcgcgg tatcattgca gcactggggc   6840
cagatggtaa gccctcccgt atcgtagtta tctacacgac ggggagtcag gcaactatgg   6900
atgaacgaaa tagacagatc gctgagatag gtgcctcact gattaagcat tggtaactgt   6960
cagaccaagt ttactcatat atactttaga ttgatttaaa acttcatttt taatttaaaa   7020
ggatctaggt gaagatcctt tttgataatc tcatgaccaa aatcccttaa cgtgagtttt   7080
cgttccactg agcgtcagac cccgtagaaa agatcaaagg atcttcttga gatccttttt   7140
ttctgcgcgt aatctgctgc ttgcaaacaa aaaaaccacc gctaccagcg gtggtttgtt   7200
tgccggatca agagctacca actctttttc cgaaggtaac tggcttcagc agagcgcaga   7260
taccaaatac tgtccttcta gtgtagccgt agttaggcca ccacttcaag aactctgtag   7320
caccgcctac atacctcgct ctgctaatcc tgttaccagt ggctgctgcc agtggcgata   7380
agtcgtgtct taccgggttg gactcaagac gatagttacc ggataaggcg cagcggtcgg   7440
gctgaacggg gggttcgtgc acacagccca gcttggagcg aacgacctac accgaactga   7500
```

```
gatacctaca gcgtgagcta tgagaaagcg ccacgcttcc cgaagggaga aaggcggaca    7560
ggtatccggt aagcggcagg gtcggaacag gagagcgcac gagggagctt ccaggggaa     7620 acgcctggta tctttatagt cctgtcgggt ttcgccacct ctgacttgag cgtcgatttt    7680
tgtgatgctc gtcaggggg cggagcctat ggaaaaacgc cagcaacgcg gccttttac     7740 ggttcctggc cttttgctgg ccttttgctc acatggctcg acagatct                7788
```

```
<210> SEQ ID NO 141
<211> LENGTH: 23
<212> TYPE: DNA
<213> ORGANISM: Artificial sequence
<220> FEATURE:
<223> OTHER INFORMATION: SNE-S1 primer

<400> SEQUENCE: 141
ggttgggatt atccaaaatg tga                                            23

<210> SEQ ID NO 142
<211> LENGTH: 24
<212> TYPE: DNA
<213> ORGANISM: Artificial sequence
<220> FEATURE:
<223> OTHER INFORMATION: SNE-AS1 primer

<400> SEQUENCE: 142
gcatcatcag aaagaatcat catg                                           24

<210> SEQ ID NO 143
<211> LENGTH: 21
<212> TYPE: DNA
<213> ORGANISM: Artificial sequence
<220> FEATURE:
<223> OTHER INFORMATION: SAR1-S primer

<400> SEQUENCE: 143
cctctcttgt tcttgctcgc a                                              21

<210> SEQ ID NO 144
<211> LENGTH: 21
<212> TYPE: DNA
<213> ORGANISM: Artificial sequence
<220> FEATURE:
<223> OTHER INFORMATION: SAR1-AS primer

<400> SEQUENCE: 144
tatagtgagc cgccacacat g                                              21

<210> SEQ ID NO 145
<211> LENGTH: 45
<212> TYPE: DNA
<213> ORGANISM: Artificial sequence
<220> FEATURE:
<223> OTHER INFORMATION: PCR primer

<400> SEQUENCE: 145
ataggatcca ccatgtttat tttcttatta tttcttactc tcact                    45

<210> SEQ ID NO 146
<211> LENGTH: 37
<212> TYPE: DNA
<213> ORGANISM: Artificial sequence
<220> FEATURE:
<223> OTHER INFORMATION: PCR primer
```

-continued

<400> SEQUENCE: 146
atactcgagt tatgtgtaat gtaatttgac acccttg 37

<210> SEQ ID NO 147
<211> LENGTH: 45
<212> TYPE: DNA
<213> ORGANISM: Artificial sequence
<220> FEATURE:
<223> OTHER INFORMATION: PCR primer

<400> SEQUENCE: 147
ataggatcca ccatgtttat tttcttatta tttcttactc tcact 45

<210> SEQ ID NO 148
<211> LENGTH: 36
<212> TYPE: DNA
<213> ORGANISM: Artificial sequence
<220> FEATURE:
<223> OTHER INFORMATION: PCR primer

<400> SEQUENCE: 148
acctccggat ttaatatatt gctcatattt tcccaa 36

<210> SEQ ID NO 149
<211> LENGTH: 13
<212> TYPE: PRT
<213> ORGANISM: Artificial sequence
<220> FEATURE:
<223> OTHER INFORMATION: N-terminal end of SRAS-CoV S protein
(amino-acids 1 to 13)

<400> SEQUENCE: 149

Met Phe Ile Phe Leu Leu Phe Leu Thr Leu Thr Ser Gly
1 5 10

<210> SEQ ID NO 150
<211> LENGTH: 10
<212> TYPE: PRT
<213> ORGANISM: Artificial sequence
<220> FEATURE:
<223> OTHER INFORMATION: oligopeptide

<400> SEQUENCE: 150

Ser Gly Asp Tyr Lys Asp Asp Asp Asp Lys
1 5 10

<210> SEQ ID NO 151
<211> LENGTH: 34
<212> TYPE: DNA
<213> ORGANISM: Artificial sequence
<220> FEATURE:
<223> OTHER INFORMATION: PCR primer

<400> SEQUENCE: 151
actagctagc ggatccacca tgttcatctt cctg 34

<210> SEQ ID NO 152
<211> LENGTH: 33
<212> TYPE: DNA
<213> ORGANISM: Artificial sequence
<220> FEATURE:
<223> OTHER INFORMATION: PCR primer

<400> SEQUENCE: 152
agtatccgga cttgatgtac tgctcgtact tgc 33

<210> SEQ ID NO 153
<211> LENGTH: 59
<212> TYPE: DNA
<213> ORGANISM: Artificial sequence
<220> FEATURE:
<223> OTHER INFORMATION: oligonucleotid

<400> SEQUENCE: 153
tatgagcttt ttttttttt ttttttggc atataaatag actcggcgcg ccatctgca    59

<210> SEQ ID NO 154
<211> LENGTH: 53
<212> TYPE: DNA
<213> ORGANISM: Artificial sequence
<220> FEATURE:
<223> OTHER INFORMATION: oligonucleotid

<400> SEQUENCE: 154
gatggcgcgc cgagtctatt tatatgccaa aaaaaaaaa aaaaaaagc tca    53

<210> SEQ ID NO 155
<211> LENGTH: 45
<212> TYPE: DNA
<213> ORGANISM: Artificial sequence
<220> FEATURE:
<223> OTHER INFORMATION: PCR primer

<400> SEQUENCE: 155
atacgtacga ccatgtttat tttcttatta tttcttactc tcact    45

<210> SEQ ID NO 156
<211> LENGTH: 40
<212> TYPE: DNA
<213> ORGANISM: Artificial sequence
<220> FEATURE:
<223> OTHER INFORMATION: PCR primer

<400> SEQUENCE: 156
atagcgcgct cattatgtgt aatgtaattt gacacccttg    40

<210> SEQ ID NO 157
<211> LENGTH: 20
<212> TYPE: DNA
<213> ORGANISM: Artificial sequence
<220> FEATURE:
<223> OTHER INFORMATION: PCR primer

<400> SEQUENCE: 157
ccatttcaac aatttggccg    20

<210> SEQ ID NO 158
<211> LENGTH: 45
<212> TYPE: DNA
<213> ORGANISM: Artificial sequence
<220> FEATURE:
<223> OTHER INFORMATION: PCR primer

<400> SEQUENCE: 158
ataggatccg cgcgctcatt atttatcgtc gtcatcttta taatc    45